(12) United States Patent
Tamura et al.

(10) Patent No.: US 10,494,380 B2
(45) Date of Patent: Dec. 3, 2019

(54) NITROGEN-CONTAINING TRICYCLIC DERIVATIVES HAVING HIV REPLICATION INHIBITORY ACTIVITY

(71) Applicant: Shionogi & Co., Ltd., Osaka-shi (JP)

(72) Inventors: Yoshinori Tamura, Toyonaka (JP); Shuichi Sugiyama, Toyonaka (JP); Akira Matsumura, Toyonaka (JP); Toshiyuki Akiyama, Toyonaka (JP); Yutaka Tomida, Toyonaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 15/577,795

(22) PCT Filed: May 27, 2016

(86) PCT No.: PCT/JP2016/065702
§ 371 (c)(1),
(2) Date: Nov. 29, 2017

(87) PCT Pub. No.: WO2016/194806
PCT Pub. Date: Dec. 8, 2016

(65) Prior Publication Data
US 2018/0162876 A1    Jun. 14, 2018

(30) Foreign Application Priority Data

May 29, 2015   (JP) ................... 2015-109547
Aug. 31, 2015  (JP) ................... 2015-170222
Nov. 13, 2015  (JP) ................... 2015-223036
Mar. 17, 2016  (JP) ................... 2016-054215

(51) Int. Cl.
*C07D 487/06* (2006.01)
*C07D 513/06* (2006.01)
*A61P 31/18* (2006.01)

(52) U.S. Cl.
CPC ............ *C07D 513/06* (2013.01); *A61P 31/18* (2018.01); *C07D 487/06* (2013.01)

(58) Field of Classification Search
CPC ......................... C07D 487/06; C07D 513/06
See application file for complete search history.

(56) References Cited

U.S. PATENT DOCUMENTS

| | | | |
|---|---|---|---|
| 5,792,774 A | 8/1998 | Haughan et al. | |
| 8,841,331 B2 | 9/2014 | Yoakim et al. | |
| 9,102,614 B2 | 8/2015 | Babaoglu et al. | |
| 9,975,906 B2 * | 5/2018 | Kawasuji | A61K 31/519 |
| 2003/0139394 A1 | 7/2003 | Lubisch et al. | |
| 2006/0178359 A1 | 8/2006 | Shiraishi et al. | |
| 2007/0032469 A1 | 2/2007 | Isaac et al. | |
| 2008/0318999 A1 | 12/2008 | Isaac et al. | |
| 2010/0292227 A1 | 11/2010 | Yoakim et al. | |
| 2014/0031338 A1 | 1/2014 | Chasset et al. | |
| 2014/0249162 A1 | 9/2014 | Son et al. | |
| 2015/0361093 A1 | 12/2015 | Tomita et al. | |

FOREIGN PATENT DOCUMENTS

| | | |
|---|---|---|
| EP | 1593681 A1 | 11/2005 |
| EP | 2772480 A1 | 9/2014 |
| EP | 2952503 A1 | 12/2015 |
| EP | 3144311 A1 | 3/2017 |
| JP | 2000-505450 A | 5/2000 |
| JP | 2003-510324 A | 3/2003 |
| JP | 2004-256531 | 9/2004 |
| JP | 2005-516031 A | 6/2005 |
| JP | 2009-503069 A | 1/2009 |
| JP | 2012-526728 A | 11/2012 |
| JP | 2013-535426 A | 9/2013 |
| JP | 2014-511872 A | 5/2014 |
| WO | 1997/031000 A1 | 8/1997 |
| WO | 2001/023386 A2 | 4/2001 |
| WO | 2003/057699 A1 | 7/2003 |
| WO | WO 2006/072636 A2 | 7/2006 |
| WO | 2007/018998 A1 | 2/2007 |

(Continued)

OTHER PUBLICATIONS

International Preliminary Report on Patentability and Written Opinion dated Dec. 14, 2017 in PCT/JP2016/065702.

(Continued)

*Primary Examiner* — Bruck Kifle
(74) *Attorney, Agent, or Firm* — Oblon, McClelland, Maier & Neustadt, L.L.P.

(57) ABSTRACT

The present invention provides a novel compound having antiviral activity, especially HIV replication inhibitory activity and a medicament containing the same. The compound represented by the formula:

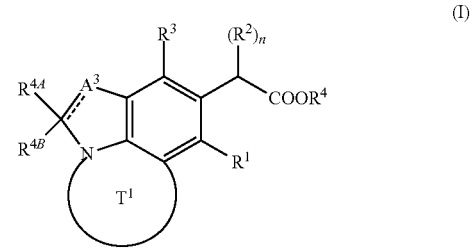

(I)

wherein $A^3$ is $CR^{3A}$, $CR^{3A}R^{3B}$, N or $NR^{3C}$; $R^{3A}$, $R^{3B}$, $R^{4A}$ and $R^{4B}$ are each independently a hydrogen atom, halogen, cyano, substituted or unsubstituted alkyl, substituted or unsubstituted alkynyl, or substituted or unsubstituted non-aromatic carbocyclyl; $R^{3C}$ is a hydrogen atom, substituted or unsubstituted alkyl, or substituted or unsubstituted non-aromatic carbocyclyl; ring $T^1$ is substituted or unsubstituted nitrogen-containing non-aromatic heterocycle; $R^1$ is a hydrogen atom, halogen, cyano, or substituted or unsubstituted alkyl; $R^2$ is each independently substituted or unsubstituted alkyl or the like: n is 1 or 2; $R^3$ is substituted or unsubstituted aromatic carbocyclyl or the like; $R^4$ is a hydrogen atom or a carboxy protecting group.

37 Claims, No Drawings

(56) References Cited

FOREIGN PATENT DOCUMENTS

| | | |
|---|---|---|
| WO | 2007/131350 A1 | 11/2007 |
| WO | 2009/062285 A1 | 5/2009 |
| WO | 2009/062288 A1 | 5/2009 |
| WO | 2009/062289 A1 | 5/2009 |
| WO | 2009/062308 A1 | 5/2009 |
| WO | 2010/130034 A1 | 11/2010 |
| WO | 2010/130842 A1 | 11/2010 |
| WO | 2011/015641 A1 | 2/2011 |
| WO | 2011/076765 A1 | 6/2011 |
| WO | 2012/003497 A1 | 1/2012 |
| WO | 2012/2003498 A1 | 1/2012 |
| WO | 2012/033735 A1 | 3/2012 |
| WO | 2012/065963 A2 | 5/2012 |
| WO | 2012/066442 A1 | 5/2012 |
| WO | 2012/102985 A1 | 8/2012 |
| WO | 2012/137181 A1 | 10/2012 |
| WO | 2012/140243 A1 | 10/2012 |
| WO | 2012/145728 A1 | 10/2012 |
| WO | 2013/002357 A1 | 1/2013 |
| WO | 2013/012649 A1 | 1/2013 |
| WO | 2013/025584 A1 | 2/2013 |
| WO | 2013/043553 A1 | 3/2013 |
| WO | 2013/062028 A1 | 5/2013 |
| WO | 2013/073875 A1 | 5/2013 |
| WO | 2013/103724 A1 | 7/2013 |
| WO | 2013/103738 A1 | 7/2013 |
| WO | 2013/123148 A1 | 8/2013 |
| WO | 2013/134113 A1 | 9/2013 |
| WO | 2013/134142 A1 | 9/2013 |
| WO | 2013/157622 A1 | 10/2013 |
| WO | 2013/159064 A1 | 10/2013 |
| WO | 2014/009794 A1 | 1/2014 |
| WO | 2014/028384 A1 | 2/2014 |
| WO | 2014/053665 A1 | 4/2014 |
| WO | 2014/053666 A1 | 4/2014 |
| WO | 2014/057103 A1 | 4/2014 |
| WO | 2014/119636 A1 | 8/2014 |
| WO | 2014/159959 A1 | 10/2014 |
| WO | 2014/164409 A1 | 10/2014 |
| WO | 2014/164467 A1 | 10/2014 |
| WO | 2015/126765 A1 | 8/2015 |
| WO | 2015/147247 A1 | 10/2015 |
| WO | 2015/174511 A1 | 11/2015 |
| WO | 2015/179448 A1 | 11/2015 |
| WO | 2016/005878 A1 | 1/2016 |
| WO | 2016/012930 A1 | 1/2016 |
| WO | 2016/033009 A1 | 3/2016 |
| WO | 2017/046707 A1 | 3/2017 |
| WO | 2017/093930 A1 | 6/2017 |
| WO | 2017/093932 A1 | 6/2017 |
| WO | 2017/093937 A1 | 6/2017 |
| WO | 2017/093938 A1 | 6/2017 |

OTHER PUBLICATIONS

Demeulemeester, Jonas, et al., "*LEDGiNs, non-catalytic site inhibitors of HIV-1 integrase: a patent review*", Expert Opinion on Therapeutic Patents, 2014, 24, 6, pp. 609-632.

Fader, Lee D., et al., "*Discovery of BI 224436, a Noncatalytic Site Integrase Inhibitor (NCINI) of HIV-1*", ACS Medicinal Chemistry Letters, 2014, 5, pp. 422-427.

Fader, Lee D., et al., "*Minimizing the Contribution of Enterohepatic Recirculation to Clearance in Rat for the NCINI Class of Inhibitors of HIV*", ACS Medicinal Chemistry Letters, 2014, 5, pp. 711-716.

International Search Report dated Aug. 23, 2016 in PCT/JP2016/065702, filed on May 27, 2016.

Extended European Search Report dated Nov. 30, 2017 in Patent Application No. 15793640.2.

\* cited by examiner

NITROGEN-CONTAINING TRICYCLIC DERIVATIVES HAVING HIV REPLICATION INHIBITORY ACTIVITY

TECHNICAL FIELD

The present invention relates to a novel compound having an antiviral activity, more particularly, an anti-HIV drug.

BACKGROUND ART

Among viruses, human immunodeficiency virus (hereinafter abbreviated as HIV) that is a type of retrovirus is known to be a cause of acquired immunodeficiency syndrome (hereinafter abbreviated as AIDS). As a therapeutic agent of the AIDS, reverse transcriptase inhibitors (AZT, 3TC, etc.), protease inhibitors (indinavir, etc.), and integrase inhibitor (raltegravir, etc.) are mainly used so far, but problems of side effects such as kidney problems and emergence of resistant viruses have been found, and development of anti-HIV drugs having a mechanism of action different from those is expected.

In addition, in the treatment of AIDS, because resistant viruses easily emerge, it is reported that, multiple drug therapy is currently effective. As the anti-HIV drugs, three types of reverse transcriptase inhibitors, protease inhibitors and integrase inhibitors have been used clinically, but the agents having the same mechanism of action often exhibit cross-resistance, or merely show additive effects, and there is a demand for the development of anti-HIV drugs having a different mechanism of action.

Anti-HIV drugs with a carboxyalkyl type side chain into a six-membered ring nucleus, such as benzene or pyridine, on their condensed ring, is described in Patent Document 1 to 32 and 36. In particular, five-membered heterocycle condensed with a benzene derivative is described in Patent Document 28 (WO2013/159064), Patent Document 29 (WO2012/145728) etc. Also in Patent Document 16 (WO2012/140243) and Patent Document 36 (WO2014/057103), benzene derivatives having various substituents are described. Moreover anti-HIV drugs having a carboxyalkyl type side chains at 5-membered ring nucleus are described in Patent Document 33 to 35. However, in any of the literature, tricyclic compounds of the present invention are not described.

Furthermore, patents relating to anti-HIV drugs, such as recent integrase inhibitors, have been introduced in Non-patent Document 1.

PRIOR ART DOCUMENTS

Patent Documents

Patent Document 1: WO2007/131350
Patent Document 2: WO2009/062285
Patent Document 3: WO2009/062288
Patent Document 4: WO2009/062289
Patent Document 5: WO2009/062308
Patent Document 6: WO2010/130034
Patent Document 7: WO2010/130842
Patent Document 8: WO2011/015641
Patent Document 9: WO2011/076765
Patent Document 10: WO2012/033735
Patent Document 11: WO2012/003497
Patent Document 12: WO2012/003498
Patent Document 13: WO2012/065963
Patent Document 14: WO2012/066442
Patent Document 15: WO2012/102985
Patent Document 16: WO2012/140243
Patent Document 17: WO2013/012649
Patent Document 18: WO2013/002357
Patent Document 19: WO2013/025584
Patent Document 20: WO2013/043553
Patent Document 21: WO2013/073875
Patent Document 22: WO2013/062028
Patent Document 23: WO2013/103724
Patent Document 24: WO2013/103738
Patent Document 25: WO2013/123148
Patent Document 26: WO2013/134113
Patent Document 27: WO2013/134142
Patent Document 28: WO2013/159064
Patent Document 29: WO2012/145728
Patent Document 30: WO2013/157622
Patent Document 31: WO2014/009794
Patent Document 32: WO2014/028384
Patent Document 33: WO2012/137181
Patent Document 34: WO2014/053665
Patent Document 35: WO2014/053666
Patent Document 36: WO2014/057103
Non-patent Document 1: Expert. Opin. Ther. Patents (2014) 24(6)

Furthermore, the patent application related to HIV replication inhibitors on the tricyclic derivative have been filed by the present applicant (WO2014/119636, WO2015/147247, WO2015/174511).

SUMMARY OF THE INVENTION

Problems to be Solved by the Invention

An object of the present invention is to provide a novel compound having an anti-viral activity. Preferably, the present invention provides an anti-HIV drug having an inhibitory effect on HIV replication. More preferably, the present invention also provides an effective new anti-HIV drug against mutant strains and resistant strains of HIV, having the core structure of which differs from that of traditional anti-HIV drugs. Furthermore, the present invention also provides its synthetic intermediates and manufacturing process thereof.

Means for Solving the Problem

As a result of intensive studies, the present inventors have found nitrogen-containing tricyclic derivatives useful as HIV replication inhibitors. In addition, the present inventors have found that the compounds of the present invention and the pharmaceutical composition containing the same are useful as an antiviral drugs (examples: antiretroviral drugs, anti-HIV drugs, anti-HTLV-1 (Human T cell leukemia virus type 1: human T-cell leukemia virus type 1) drugs, anti-FIV (Feline immunodeficiency virus: feline AIDS virus) drugs, anti-SIV (Simian immunodeficiency virus: Simian HIV virus) drugs), particularly anti-HIV drugs, anti-AIDS drugs, or therapeutic agents of the related diseases or the like, thereby accomplishing the present invention.

The present invention relates to the following (1) to (23), (1C) to (18C), (1B) to (16B) and (1A) to (21A).

(1) A compound represented by the following formula (I):

[Chemical formula 1]

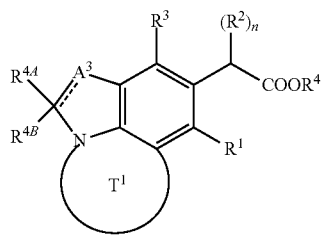

(I)

or its pharmaceutically acceptable salt,
wherein the broken line means the presence or absence of bond, $A^3$ is $CR^{3A}$, $CR^{3A}R^{3B}$, N or $NR^{3C}$;

$R^{3A}$, $R^{3B}$, $R^{4A}$ and $R^{4B}$ are each independently hydrogen, halogen, cyano, substituted or unsubstituted alkyl, substituted or unsubstituted alkynyl, or substituted or unsubstituted non-aromatic carbocyclyl;

$R^{3C}$ is hydrogen, substituted or unsubstituted alkyl, or substituted or unsubstituted non-aromatic carbocyclyl;

ring $T^1$ is substituted or unsubstituted nitrogen-containing non-aromatic heterocycle;

$R^1$ is hydrogen, halogen, cyano, or substituted or unsubstituted alkyl;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy;

n is 1 or 2;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and $R^4$ is hydrogen or carboxyl protecting group;

provided that the following compounds are excluded.

[Chemical formula 2]

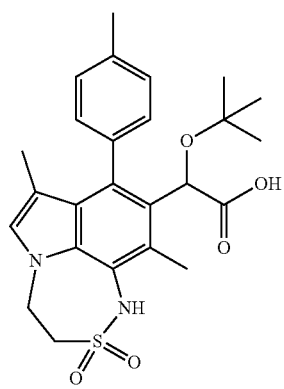

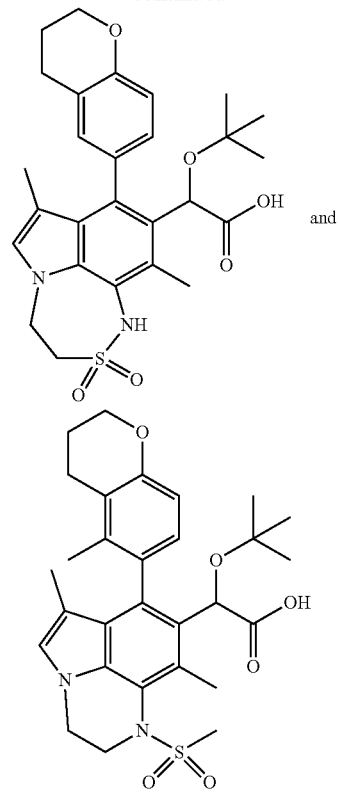

and (2) The compound or its pharmaceutically acceptable salt according to claim 1, represented by the following formula (I'):

[Chemical formula 3]

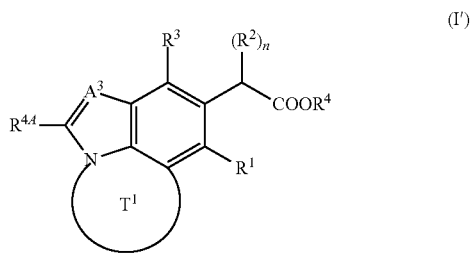

(I')

wherein $A^3$ is $CR^{3A}$ or N; $R^{3A}$ is hydrogen or halogen; the other symbols are the same as defined in (1).

(3) The compound or its pharmaceutically acceptable salt according to (1) or (2), wherein the substructure represented by the formula:

[Chemical formula 4]

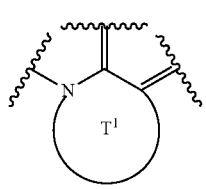

is the substructure represented by the following formula:

[Chemical formula 5]

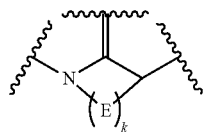

(T¹-I-1)

wherein E is each independently —NR$^a$—, —O—, —S—, —SO$_2$—, —SO—, or —CR$^b$R$^c$—;

R$^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —COOR$^{a1}$, —SOR$^{a2}$, —SO$_2$R$^{a3}$, —CONR$^{a4}$R$^{a5}$, —CSNR$^{a4}$R$^{a5}$, —COCONR$^{a4}$R$^{a5}$, or —C(NR$^{a6}$)NR$^{a4}$R$^{a5}$;

R$^{a1}$, R$^{a2}$ and R$^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a4}$ and R$^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^b$ is each independently hydrogen, halogen, substituted or unsubstituted alkyl, or substituted or unsubstituted aromatic carbocyclyl;

R$^c$ is each independently hydrogen, halogen, substituted or unsubstituted alkyl, or substituted or unsubstituted aromatic carbocyclyl; or R$^b$ and R$^c$ on the same carbon atom may be taken together with the bonded carbon atom to form carbonyl, substituted or unsubstituted non-aromatic carbocycle, or substituted or unsubstituted non-aromatic heterocycle; and/or two R$^b$s on adjacent carbon atoms may be taken together with each bonded carbon atom to form monocyclic substituted or unsubstituted non-aromatic carbocycle or monocyclic substituted or unsubstituted non-aromatic heterocycle; or two R$^b$s on adjacent carbon atoms may be taken together to form a bond; and/or the R$^a$ on a nitrogen atom and R$^b$ on a carbon atom which is adjacent to the nitrogen atom may be taken together with the nitrogen atom and the carbon atom to form monocyclic substituted or unsubstituted aromatic heterocycle or monocyclic substituted or unsubstituted non-aromatic heterocycle; or R$^a$ on a nitrogen atom and R$^b$ on a carbon atom which is adjacent to the nitrogen atom may be taken together to form a bond;

two R$^b$s on two carbon atoms which are not adjacent to each other may be taken together to form substituted or unsubstituted alkylene, substituted or unsubstituted alkylene containing one or more group(s) selected from —O—, —NR$^a$—, —S—, —CO—, —SO—, and —SO$_2$— at arbitrary position, substituted or unsubstituted alkenylene, or substituted or unsubstituted alkenylene containing one or more group(s) selected from —O—, —NR$^a$—, —S—, —CO—, —SO—, and —SO$_2$— at arbitrary position; or the R$^a$ on a nitrogen atom and R$^b$ on a carbon atom which is not adjacent to the nitrogen atom may be taken together to form substituted or unsubstituted alkylene, substituted or unsubstituted alkylene containing one or more group(s) selected from —O—, —NR$^a$—, —S—, —CO—, —SO—, and —SO$_2$— at arbitrary position, substituted or unsubstituted alkenylene, or substituted or unsubstituted alkenylene containing one or more group(s) selected from —O—, —NR$^a$—, —S—, —CO—, —SO—, —SO$_2$— at arbitrary position; and k is an integer of 2 to 7.

(4) The compound or its pharmaceutically acceptable salt according to (3), wherein the substructure represented by the formula:

[Chemical formula 6]

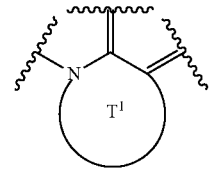

is the substructure represented by any one of the following formula:

[Chemical formula 7]

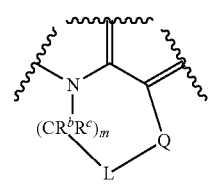

(T¹-3)

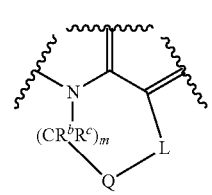

(T¹-4)

wherein
Q is —NR$^a$—, —O—, —S— or —CR$^b$R$^c$—,
L is —SO$_2$—, —SO—, or —CR$^b$R$^c$—;
m is an integer of 0 to 5; and
the other symbols are the same as defined in (3).

(5) The compound or its pharmaceutically acceptable salt according to (4), which is represented by the following formula (I-1-1) or (I-2-1):

[Chemical formula 8]

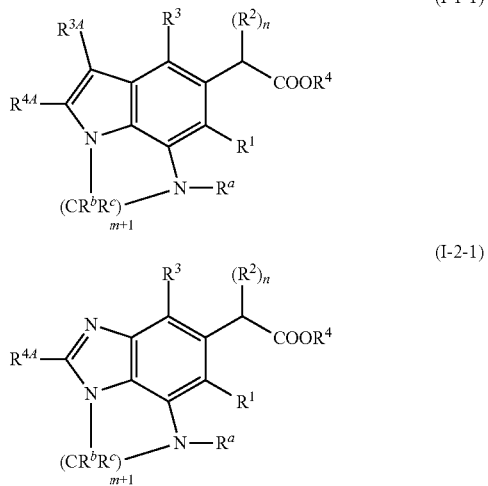

wherein $R^{3A}$ is hydrogen; $R^{4A}$, $R^1$, $R^2$, $R^3$, $R^4$ and n are the same as defined in (1); $R^a$, $R^b$ and $R^c$ are the same as defined in (3), and m is the same as defined in (4).

(6) The compound or its pharmaceutically acceptable salt according to any one of (1) to (5), wherein $R^{4A}$ is halogen, cyano, substituted or unsubstituted alkyl, substituted or unsubstituted alkynyl, or substituted or unsubstituted non-aromatic carbocyclyl.

(7) The compound or its pharmaceutically acceptable salt according to any one of (1) to (6), wherein $R^1$ is alkyl, cyano, or halogen.

(8) The compound or its pharmaceutically acceptable salt according to any one of (1) to (7), wherein n is 1; and $R^2$ is alkyloxy.

(9) The compound or its pharmaceutically acceptable salt according to any one of (1) to (8), wherein $R^4$ is hydrogen.

(10) The compound or its pharmaceutically acceptable salt according to any one of (1) to (6), wherein $R^1$ is alkyl or halogen; n is 1; $R^2$ is alkyloxy; and $R^4$ is hydrogen.

(11) The compound or its pharmaceutically acceptable salt according to (3), wherein $R^1$ is alkyl or halogen; n is 1; $R^2$ is alkyloxy; $R^4$ is hydrogen; $R^3$ is substituted or unsubstituted aromatic carbocyclyl or substituted or unsubstituted non-aromatic heterocyclyl; $R^a$ is hydrogen, substituted or unsubstituted alkyl, $-COR^{a1}$, $-CONR^{a4}R^{a5}$, $-SO_2R^{a3}$, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; $R^b$ is each independently hydrogen, halogen, substituted or unsubstituted alkyl, or substituted or unsubstituted aromatic carbocyclyl; $R^c$ is each independently hydrogen, halogen, substituted or unsubstituted alkyl, or substituted or unsubstituted aromatic carbocyclyl; or $R^a$ on a nitrogen atom and $R^b$ on a carbon atom which is adjacent to the nitrogen atom may be taken together with the nitrogen atom and carbon atom to form monocyclic substituted or unsubstituted aromatic heterocycle or monocyclic substituted or unsubstituted non-aromatic heterocycle, or two $R^b$s on adjacent carbon atoms are taken together with each bonded carbon atom to form monocyclic substituted or unsubstituted non-aromatic carbocycle or monocyclic substituted or unsubstituted non-aromatic heterocycle; and k is an integer of 3 to 5.

(12) The compound or its pharmaceutically acceptable salt according to any one of (4) to (6), wherein $R^a$ is hydrogen, substituted or unsubstituted alkyl, $-COR^{a1}$, $-CONR^{a4}R^{a5}$, or $-SO_2R^{a3}$; $R^b$ is independently hydrogen, halogen, or substituted or unsubstituted alkyl; $R^c$ is each independently hydrogen, halogen, or substituted or unsubstituted alkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

(13) The compound or its pharmaceutically acceptable salt according to any one of (4) to (6), wherein m is an integer of 1 to 3; $R^1$ is alkyl or halogen; n is 1; $R^2$ is alkyloxy; $R^4$ is hydrogen; $R^3$ is substituted or unsubstituted aromatic carbocyclyl, or substituted or unsubstituted non-aromatic heterocyclyl; $R^a$ and $R^b$ on the adjacent nitrogen atom and carbon atom are taken together with the each atom constituting the ring which binds to $R^a$ on a nitrogen atom and $R^b$ on a carbon atom which is adjacent to the nitrogen atom are taken together with each bonded atom to form substituted or unsubstituted monocyclic aromatic heterocycle or substituted or unsubstituted monocyclic non-aromatic heterocycle, two $R^b$s on adjacent carbon atoms are taken together with each carbon atoms to form substituted or unsubstituted monocyclic non-aromatic carbocycle or substituted or unsubstituted monocyclic non-aromatic heterocycle, or $R^b$ and $R^c$ on the same carbon atom are taken together with the bonded carbon atom to form carbonyl, substituted or unsubstituted non-aromatic carbocycle, or substituted or unsubstituted non-aromatic heterocycle.

(14) The compound or its pharmaceutically acceptable salt according to any one of (4) to (6), wherein $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

(15) The compound or its pharmaceutically acceptable salt according to any one of (4) or (5), wherein $R^{4A}$ is halogen, cyano, alkyl, or haloalkyl; $R^a$ is hydrogen, substituted or unsubstituted alkyl, $-COR^{a1}$, $-CONR^{a4}R^{a5}$, $-SO_2R^{a3}$; $R^b$ is each independently hydrogen, halogen, or substituted or unsubstituted alkyl; $R^c$ is each independently hydrogen, halogen, or substituted or unsubstituted alkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

(16) The compound or its pharmaceutically acceptable salt according to any one of (4) or (5), wherein $R^{4A}$ is halogen, cyano, alkyl, or haloalkyl; $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

(17) The compound or its pharmaceutically acceptable salt according to (1), which is any one of I-001, I-003, I-012, I-019, I-026, I-027, I-041, I-043, I-048, I-085, I-112, I-122, I-156, I-157, I-164, I-176, I-181, I-187, I-189, I-190, and I-197.

(18) The compound or its pharmaceutically acceptable salt according to (1), which is any one of I-220, I-244, I-257, I-258, I-260, I-262, I-267, I-270, I-278, I-292, I-293, I-303, I-304, I-305, I-306, I-307, I-308, and I-309.

(19) A pharmaceutical composition comprising the compound or its pharmaceutically acceptable salt according to any one of (1) to (18).

(20) The pharmaceutical composition according to (19), having anti-virus activity.

(21) The pharmaceutical composition according to (19), having anti-HIV activity.

(22) A method of treating or preventing a HIV infectious disease, which comprises administering the compound or its pharmaceutically acceptable salt according to any one of (1) to (18).

(23) The compound or its pharmaceutically acceptable salt according to any one of (1) to (18) for treating or preventing a HIV infectious disease.

(1C) A compound represented by the following formula (I):

[Chemical formula 9]

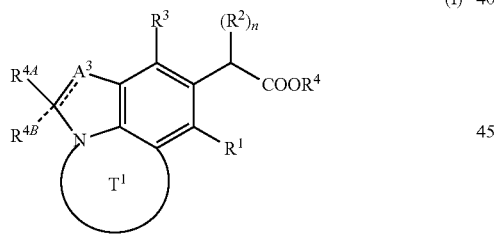

(I)

or its pharmaceutically acceptable salt,
wherein the broken line means the presence or absence of bond,
$A^3$ is $CR^{3A}$, $CR^{3A}R^{3B}$, N or $NR^{3C}$;
$R^{3A}$, $R^{3B}$, $R^{4A}$ and $R^{4B}$ are each independently hydrogen, halogen, cyano, substituted or unsubstituted alkyl, substituted or unsubstituted alkynyl, or substituted or unsubstituted non-aromatic carbocyclyl;
$R^{3C}$ is hydrogen, substituted or unsubstituted alkyl, or substituted or unsubstituted non-aromatic carbocyclyl;
ring $T^1$ is substituted or unsubstituted nitrogen-containing non-aromatic heterocycle;
$R^1$ is hydrogen, halogen, cyano, or substituted or unsubstituted alkyl;
$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy;

n is 1 or 2;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$ is hydrogen or carboxyl protecting group;

provided that the following compounds are excluded.

[Chemical formula 10]

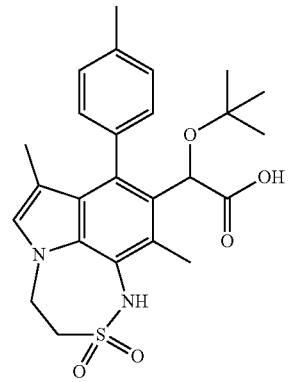

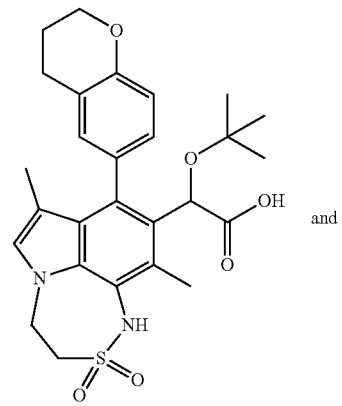

and

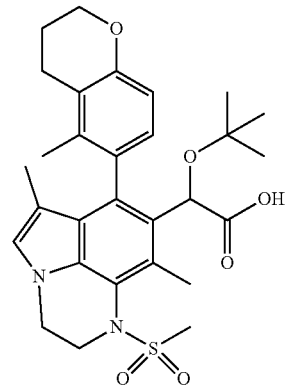

(2C) The compound or its pharmaceutically acceptable salt according to (1C), wherein the substructure represented by the formula:

[Chemical formula 11]

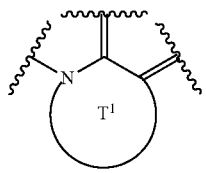

is the substructure represented by the following formula:

[Chemical formula 12]

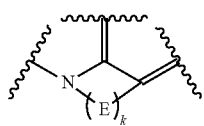

(T¹-I-1)

wherein E is each independently —NR$^a$—, —O—, —S—, —SO$_2$—, —SO—, or —CR$^b$R$^c$—;

R$^a$ is hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —COOR$^{a1}$, —SOR$^{a2}$, —SO$_2$R$^{a3}$, —CONR$^{a4}$R$^{a5}$, —CSNR$^{a4}$R$^{a5}$, —COCONR$^{a4}$R$^{a5}$, or —C(NR$^{a6}$)NR$^{a4}$R$^{a5}$;

R$^{a1}$, R$^{a2}$, and R$^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a4}$ and R$^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^b$ is each independently hydrogen, halogen, or substituted or unsubstituted alkyl;

R$^c$ is each independently hydrogen, halogen, or substituted or unsubstituted alkyl; or R$^b$ and R$^c$ on the same carbon atom may be taken together with the bonded carbon atom to form carbonyl, substituted or unsubstituted non-aromatic carbocycle, or substituted or unsubstituted non-aromatic heterocycle; and/or two R$^b$s on adjacent carbon atoms may be taken together with each bonded carbon atoms to form substituted or unsubstituted monocyclic non-aromatic carbocycle or substituted or unsubstituted monocyclic non-aromatic heterocycle; or R$^a$ on a nitrogen atom and R$^b$ on a carbon atom which is adjacent to the nitrogen atom may be taken together with each bonded annular atoms to form substituted or unsubstituted monocyclic aromatic heterocycle or substituted or unsubstituted monocyclic non-aromatic heterocycle; or two R$^b$s on two carbon atoms which are not adjacent to each other may be taken together to form substituted or unsubstituted alkylene, substituted or unsubstituted alkylene containing one or more group(s) selected from —O—, —NR$^a$—, —S—, —CO—, —SO—, —SO$_2$— at arbitrary position, substituted or unsubstituted alkenylene, or substituted or unsubstituted alkenylene containing on or more group(s) selected from —O—, —NR$^a$—, —S—, —CO—, —SO—, and —SO$_2$— at arbitrary position; or R$^a$ on a nitrogen atom and R$^b$ on a carbon atom which is adjacent to the nitrogen atom may be taken together to form substituted or unsubstituted alkylene, substituted or unsubstituted alkylene containing one or more group(s) selected from —O—, —NR$^a$—, —S—, —CO—, —SO—, and —SO$_2$— at arbitrary position, substituted or unsubstituted alkenylene, or substituted or unsubstituted alkenylene containing one or more group(s) selected from —O—, —NR$^a$—, —S—, —CO—, —SO—, —SO$_2$— at arbitrary position; and/or two R$^b$s on adjacent carbon atoms may be taken together to form a bond; or R$^a$ on a nitrogen atom and R$^b$ on a carbon atom which is adjacent to the nitrogen atom may be taken together to form a bond; and k is an integer of 2 to 7.

(3C) The compound or its pharmaceutically acceptable salt according to (2C), wherein the substructure represented by the formula:

[Chemical formula 13]

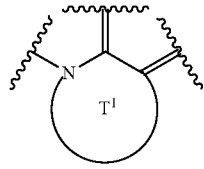

is the substructure represented by any one of the following formula:

[Chemical formula 14]

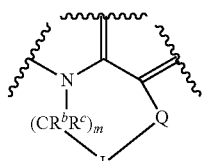

(T¹-3)

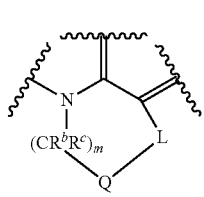

(T¹-4)

wherein Q is —NR$^a$—, —O—, —S— or —CR$^b$R$^c$—,
L is —SO$_2$—, —SO—, or —CR$^b$R$^c$—;
m is an integer of 0 to 5;
the other symbols are the same as defined above.

(4C) The compound or its pharmaceutically acceptable salt according to (2C) or (3C), which is represented by the following formula (I-1-1) or (I-2-1):

[Chemical formula 15]

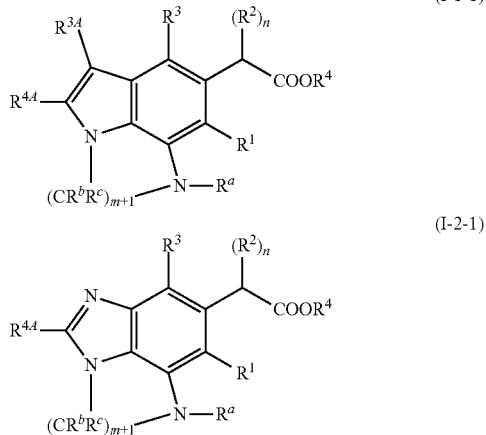

wherein each symbol is the same as defined above.

(5C) The compound or its pharmaceutically acceptable salt according to any one of (1C) to (4C), wherein either of R$^{4A}$ and R$^{5B}$ is halogen, cyano, substituted or unsubstituted alkyl, substituted or unsubstituted alkynyl, or substituted or unsubstituted non-aromatic carbocyclyl.

(6C) The compound or its pharmaceutically acceptable salt according to any one of (1C) to (5C), wherein R$^1$ is alkyl, cyano, or halogen.

(7C) The compound or its pharmaceutically acceptable salt according to any one of (1C) to (6C), wherein n is 1; R$^2$ is alkyloxy.

(8C) The compound or its pharmaceutically acceptable salt according to any one of (1C) to (7C), wherein R$^4$ is hydrogen.

(9C) The compound or its pharmaceutically acceptable salt according to any one of (1C) to (5C), wherein R$^1$ is alkyl or halogen; n is 1; R$^2$ is alkyloxy; and R$^4$ is hydrogen.

(10C) The compound or its pharmaceutically acceptable salt according to (2C), wherein R$^1$ is alkyl or halogen; n is 1; R$^2$ is alkyloxy; R$^4$ is hydrogen; R$^a$ is hydrogen, substituted or unsubstituted alkyl, —COR$^{a1}$, —CONR$^{a4}$R$^{a5}$, —SO$_2$R$^{a3}$, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; R$^b$ is each independently hydrogen, halogen, or substituted or unsubstituted alkyl; R$^c$ is each independently hydrogen, halogen, or substituted or unsubstituted alkyl; or R$^a$ on a nitrogen atom and R$^b$ on a carbon atom which is adjacent to the nitrogen atom are taken together with each bonded annular atoms to form substituted or unsubstituted monocyclic aromatic heterocycle or substituted or unsubstituted monocyclic non-aromatic heterocycle, or two R$^b$s on adjacent carbon atoms are taken together with each bonded carbon atoms to form substituted or unsubstituted monocyclic non-aromatic carbocycle or substituted or unsubstituted monocyclic non-aromatic heterocycle; and k is an integer of 3 to 5.

(11C) The compound or its pharmaceutically acceptable salt according to any one of (3C) to (5C), wherein R$^a$ is hydrogen, substituted or unsubstituted alkyl, —COR$^{a1}$, —CONR$^{a4}$R$^{a5}$, or —SO$_2$R$^{a3}$; R$^b$ is each independently hydrogen, halogen, or substituted or unsubstituted alkyl; R$^c$ is each independently hydrogen, halogen, or substituted or unsubstituted alkyl; m is an integer of 1 to 3; R$^1$ is alkyl or halogen; n is 1; R$^2$ is alkyloxy; and R$^4$ is hydrogen.

(12C) The compound or its pharmaceutically acceptable salt according to any one of (3C) to (5C), wherein m is an integer of 1 to 3; R$^1$ is alkyl or halogen; n is 1; R$^2$ is alkyloxy; R$^4$ is hydrogen, R$^a$ on a nitrogen atom and R$^b$ on a carbon atom which is adjacent to the nitrogen atom are taken together with each bonded annular atoms to form substituted or unsubstituted monocyclic aromatic heterocycle or substituted or unsubstituted monocyclic non-aromatic heterocycle, or two R$^b$ on adjacent carbon atoms are taken together with each bonded carbon atoms to form substituted or unsubstituted monocyclic non-aromatic carbocycle or substituted or unsubstituted monocyclic non-aromatic heterocycle.

(13C) The compound or its pharmaceutically acceptable salt according to any one of (3C) to (5C), wherein R$^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; R$^1$ is alkyl or halogen; n is 1; R$^2$ is alkyloxy; and R$^4$ is hydrogen.

(14C) The compound or its pharmaceutically acceptable salt according to (3C) or (4C), wherein R$^{3A}$ is hydrogen, halogen, alkyl, or haloalkyl; R$^{3B}$ is hydrogen; R$^{4A}$ is halogen, cyano, alkyl, haloalkyl, or non-aromatic carbocyclyl; R$^{4B}$ is hydrogen; R$^a$ is hydrogen, substituted or unsubstituted alkyl, —COR$^{a1}$, or —SO$_2$R$^{a3}$; R$^b$ is each independently hydrogen, halogen or substituted or unsubstituted alkyl; R$^c$ is each independently hydrogen, halogen or substituted or unsubstituted alkyl; m is an integer of 1 to 3; R$^1$ is alkyl or halogen; n is 1; R$^2$ is alkyloxy; and R$^4$ is hydrogen.

(15C) The compound or its pharmaceutically acceptable salt according to (3C) or (4C), wherein R$^{3A}$ is hydrogen, halogen, alkyl, or haloalkyl; R$^{4A}$ is halogen, cyano, alkyl, haloalkyl, or non-aromatic carbocyclyl; R$^a$ is hydrogen, substituted or unsubstituted alkyl, —CORa1, or —SO$_2$R$^{a3}$; Rb is each independently hydrogen, halogen or substituted or unsubstituted alkyl; Rc is each independently hydrogen, halogen or substituted or unsubstituted alkyl; m is an integer of 1 to 3; R$^1$ is alkyl; n is 1; R$^2$ is alkyloxy; and R$^4$ is hydrogen.

(16C) A pharmaceutical composition comprising the compound or its pharmaceutically acceptable salt according to any one of (1C) to (15C).

(17C) The pharmaceutical composition according to (16C), having anti-virus activity.

(18C) The pharmaceutical composition according to (16C), having anti-HIV activity.

(1B) A compound represented by the following formula (I):

[Chemical formula 16]

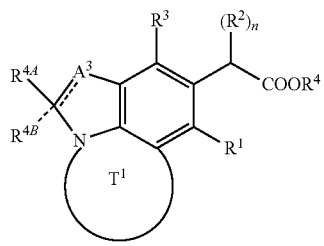

or its pharmaceutically acceptable salt, wherein the broken line means the presence or absence of bond, $A^3$ is $CR^{3A}$, $CR^{3A}R^{3B}$, N or $NR^{3C}$;

$R^{3A}$, $R^{3B}$, $R^{4A}$ and $R^{4B}$ are each independently hydrogen, halogen, cyano, substituted or unsubstituted alkyl, substituted or unsubstituted alkynyl, or substituted or unsubstituted non-aromatic carbocyclyl;

$R^{3C}$ is hydrogen, substituted or unsubstituted alkyl, or substituted or unsubstituted non-aromatic carbocyclyl;

ring $T^1$ is substituted or unsubstituted nitrogen-containing non-aromatic heterocycle;

$R^1$ is hydrogen, halogen, cyano, or substituted or unsubstituted alkyl;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy;

n is 1 or 2;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$ is hydrogen or carboxyl protecting group;

provided that the following compounds are excluded.

[Chemical formula 17]

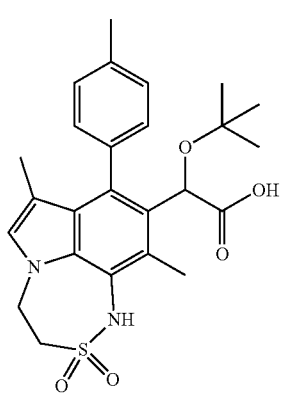

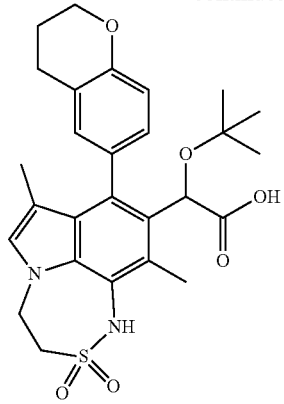

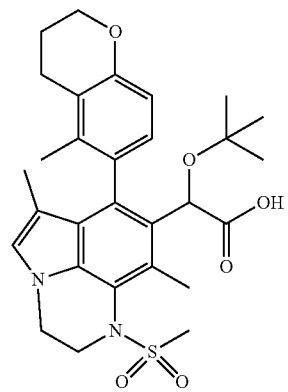

and (2B) The compound or its pharmaceutically acceptable salt according to the above (1B), wherein the substructure represented by the formula:

[Chemical formula 18]

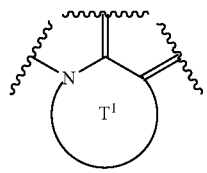

is the substructure represented by the following formula:

[Chemical formula 19]

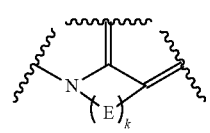

(T¹-I-1)

wherein E is each independently —$NR^a$—, —O—, —S—, —$SO_2$—, —SO—, or —$CR^bR^c$—;

Ra is hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —COOR$^{a1}$, —SOR$^{a2}$, —SO$_2$R$^{a3}$, —CONR$^{a4}$R$^{a5}$, —CSNR$^{a4}$R$^{a5}$, or —COCONR$^{a4}$R$^{a5}$;

R$^{a1}$, R$^{a2}$, and R$^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a4}$ and R$^{a5}$ are each independently hydrogen, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^b$ is each independently hydrogen, halogen, or substituted or unsubstituted alkyl;

R$^c$ is each independently hydrogen, halogen, or substituted or unsubstituted alkyl; or R$^b$ and R$^c$ on the same carbon atom may be taken together with the bonded carbon atom to form carbonyl, substituted or unsubstituted non-aromatic carbocycle, or substituted or unsubstituted non-aromatic heterocycle; and/or two R$^b$s on adjacent carbon atoms may be taken together with each bonded carbon atoms to form substituted or unsubstituted monocyclic non-aromatic carbocycle or substituted or unsubstituted monocyclic non-aromatic heterocycle; or R$^a$ on a nitrogen atom and R$^b$ on a carbon atom which is adjacent to the nitrogen atom may be taken together with each bonded annular atoms to form substituted or unsubstituted monocyclic aromatic heterocycle or substituted or unsubstituted monocyclic non-aromatic heterocycle; or two R$^b$s on carbon atoms which are not adjacent to each other may be taken together to form substituted or unsubstituted alkylene, substituted or unsubstituted alkylene containing one or more group(s) selected from —O—, —NR$^a$—, —S—, —CO—, —SO—, and —CO$_2$— at arbitrary position, substituted or unsubstituted alkenylene, or substituted or unsubstituted alkenylene containing one or more group(s) selected from —O—, —NR$^a$—, —S—, —CO—, —SO—, and —SO$_2$— at arbitrary position; or R$^a$ on a nitrogen atom and R$^b$ on a carbon atom which is adjacent to the nitrogen atom may be taken together to form substituted or unsubstituted alkylene, substituted or unsubstituted alkylene containing one or more group(s) selected from —O—, —NR$^a$—, —S—, —CO—, —SO—, and —SO$_2$— at arbitrary position, substituted or unsubstituted alkenylene, or substituted or unsubstituted alkenylene containing one or more group(s) selected from —O—, —NR$^a$—, —S—, —CO—, —SO—, and —SO$_2$— at arbitrary position;

two R$^b$ on adjacent carbon atoms may be taken together to form a bond; or

R$^a$ on a nitrogen atom and R$^b$ on a carbon atom which is adjacent to the nitrogen atom may be taken together to form a bond; and k is an integer of 2 to 7.

(3B) The compound or its pharmaceutically acceptable salt according to the above (2B), wherein the substructure represented by the formula:

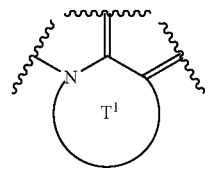

is the substructure represented by any one of the following formula:

[Chemical formula 21]

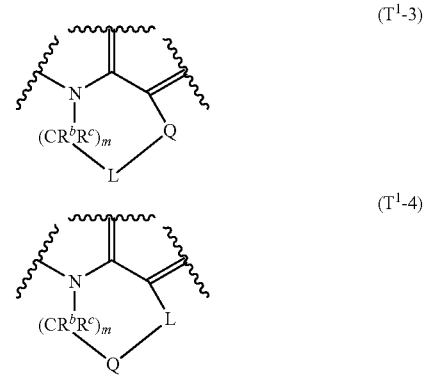

wherein
Q is —NR$^a$—, —O—, —S— or —CR$^b$R$^c$—,
L is —SO$_2$—, —SO—, or —CR$^b$R$^c$—;
m is an integer of 0 to 5;
the other symbols are the same as defined above.

(4B) The compound or its pharmaceutically acceptable salt according to the above (2B) or (3B), which is represented by the following formula (I-1-1) or (I-2-1):

[Chemical formula 22]

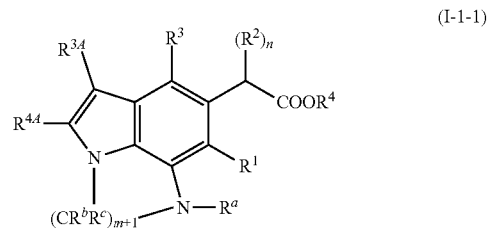

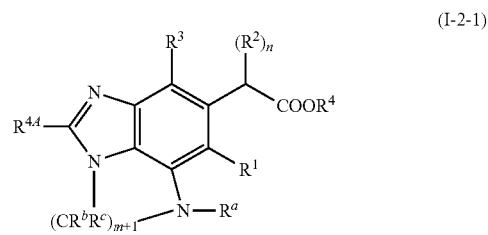

wherein each symbol is the same as defined above.

(5B) The compound or its pharmaceutically acceptable salt according to any one of the above (1B) to (4B), wherein R$^1$ is alkyl, cyano, or halogen.

(6B) The compound or its pharmaceutically acceptable salt according to any one of the above (1B) to (5B), wherein n is 1; and $R^2$ is alkyloxy.
(7B) The compound or its pharmaceutically acceptable salt according to any one of the above (1B) to (6B), wherein $R^4$ is hydrogen.
(8B) The compound or its pharmaceutically acceptable salt according to any one of the above (1B) to (4B), wherein $R^1$ is alkyl or halogen; n is 1; $R^2$ is alkyloxy; and $R^4$ is hydrogen.
(9B) The compound or its pharmaceutically acceptable salt according to any one of the above (2B) to (4B), wherein $R^a$ is hydrogen, substituted or unsubstituted alkyl, —$COR^{a1}$, —$CONR^{a4}R^{a5}$, or —$SO_2R^{a3}$; $R^b$ is each independently hydrogen, halogen, or substituted or unsubstituted alkyl; $R^c$ is each independently hydrogen, halogen, or substituted or unsubstituted alkyl; m is an integer of 1 to 3; $R^1$ is alkyl; n is 1; $R^2$ is alkyloxy; and $R^4$ is hydrogen.
(10B) The compound or its pharmaceutically acceptable salt according to any one of the above (2B) to (4B), wherein m is an integer of 1 to 3; $R^1$ is alkyl; n is 1; $R^2$ is alkyloxy; $R^4$ is hydrogen, $R^a$ on a nitrogen atom and $R^b$ on a carbon atom are taken together with each bonded annular atoms to form substituted or unsubstituted monocyclic aromatic heterocycle or substituted or unsubstituted monocyclic non-aromatic heterocycle or two $R^b$ on adjacent carbon atoms are taken together with each bonded carbon atoms to form substituted or unsubstituted monocyclic non-aromatic carbocycle or substituted or unsubstituted monocyclic non-aromatic heterocycle.
(11B) The compound or its pharmaceutically acceptable salt according to any one of the above (2B) to (4B), wherein $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl; n is 1; $R^2$ is alkyloxy; and $R^4$ is hydrogen.
(12B) The compound or its pharmaceutically acceptable salt according to the above (2B) or (3B), wherein $R^{3A}$ is hydrogen, halogen, alkyl, or haloalkyl; $R^{3B}$ is hydrogen; $R^{4A}$ is hydrogen, halogen, cyano, alkyl, haloalkyl, or non-aromatic carbocyclyl; $R^{4B}$ is hydrogen; $R^a$ is hydrogen, substituted or unsubstituted alkyl, —$COR^{a1}$, or —$SO_2R^{a3}$; $R^b$ is each independently hydrogen, halogen or substituted or unsubstituted alkyl; $R^c$ is each independently hydrogen, halogen or substituted or unsubstituted alkyl; m is an integer of 1 to 3; $R^1$ is alkyl; n is 1; $R^2$ is alkyloxy; and $R^4$ is hydrogen.
(13B) The compound or its pharmaceutically acceptable salt according to the above (2B) or (3B), wherein $R^{3A}$ is hydrogen, halogen, alkyl, or haloalkyl; $R^{4A}$ is hydrogen, halogen, cyano, alkyl, haloalkyl, or non-aromatic carbocyclyl; Ra is hydrogen, substituted or unsubstituted alkyl, —CORa1, or —$SO_2$R a 3; R b is each independently hydrogen, halogen or substituted or unsubstituted alkyl; Rc is each independently hydrogen, halogen or substituted or unsubstituted alkyl; m is an integer of 1 to 3; $R^1$ is alkyl; n is 1; $R^2$ is alkyloxy; and $R^4$ is hydrogen.
(14B) A pharmaceutical composition comprising the compound or its pharmaceutically acceptable salt according to any one of the above (1B) to (13B).
(15B) The pharmaceutical composition according to the above (14B), having anti-virus activity.
(16B) The pharmaceutical composition according to the above (14B), having anti-HIV activity.
(1A) A compound represented by the following formula (I):

[Chemical formula 23]

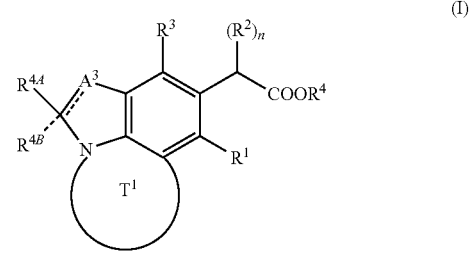

(I)

or its pharmaceutically acceptable salt,
wherein the broken line means the presence or absence of bond,
$A^3$ is $CR^{3A}$, $CR^{3A}R^{3B}$, N or $NR^{3C}$;
$R^{3A}$, $R^{3B}$, $R^{4A}$ and $R^{4B}$ are each independently hydrogen, halogen, cyano, substituted or unsubstituted alkyl, substituted or unsubstituted alkynyl, or substituted or unsubstituted non-aromatic carbocyclyl;
$R^{3C}$ is hydrogen, substituted or unsubstituted alkyl, or substituted or unsubstituted non-aromatic carbocyclyl;
ring $T^1$ is substituted or unsubstituted nitrogen-containing non-aromatic heterocycle, the two atoms which are not adjacent to one another constituting the heterocycle may be bridged with substituted or unsubstituted alkylene, substituted or unsubstituted alkenylene, or substituted or unsubstituted alkynylene;
$R^1$ is hydrogen, halogen, or substituted or unsubstituted alkyl;
$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy;
n is 1 or 2;
$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^4$ is hydrogen or carboxyl protecting group;
provided that the following compounds are excluded.

[Chemical formula 24]

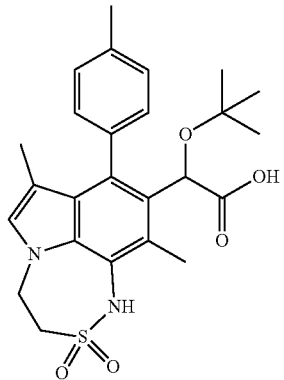

-continued

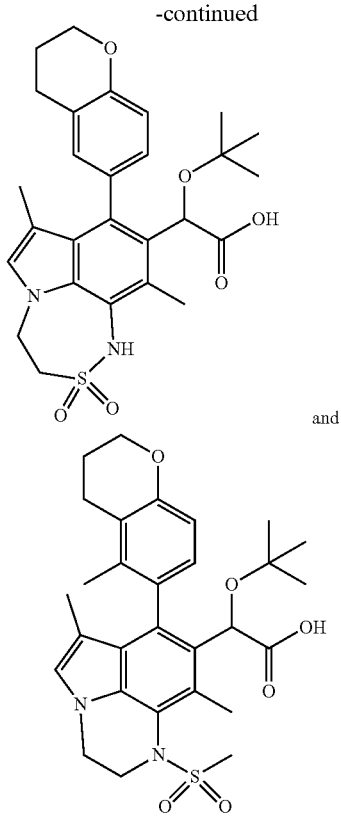

(1A') A compound represented by the following formula (I'):

[Chemical formula 25]

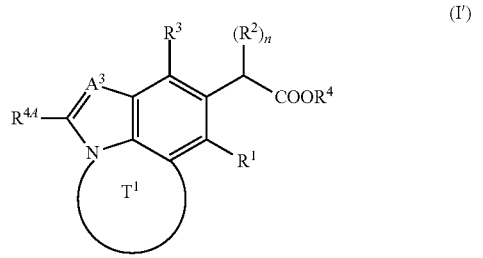

or its pharmaceutically acceptable salt,
wherein $A^3$ is $CR^{3A}$ or N;
$R^{3A}$ and $R^{4A}$ are each independently hydrogen, halogen, cyano, substituted or unsubstituted alkyl, or substituted or unsubstituted non-aromatic carbocyclyl;
ring $T^1$ is substituted or unsubstituted nitrogen-containing non-aromatic heterocycle, the two atoms which are not adjacent to one another constituting the heterocycle may be bridged with substituted or unsubstituted alkylene, substituted or unsubstituted alkenylene, or substituted or unsubstituted alkynylene;
$R^1$ is hydrogen, halogen, or substituted or unsubstituted alkyl;
$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy;
n is 1 or 2;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^4$ is hydrogen or carboxyl protecting group,
provided that the following compounds are excluded.

[Chemical formula 26]

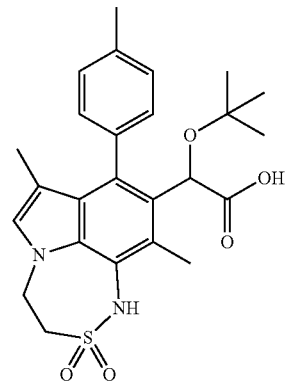

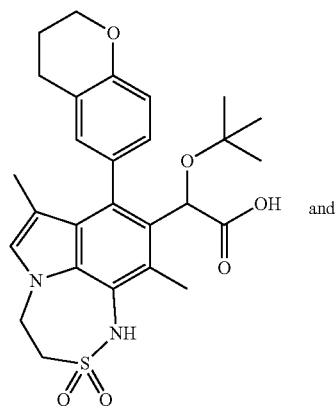
and

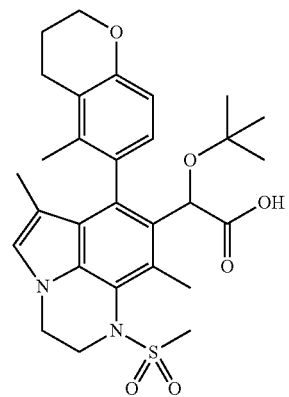

(2A) The compound or its pharmaceutically acceptable salt according to the above (1A), wherein the part represented by the formula:

is the structure represented by any one of the following formula:

[Chemical formula 27]
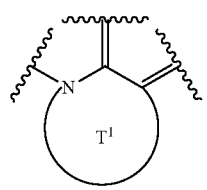

[Chemical formula 28]

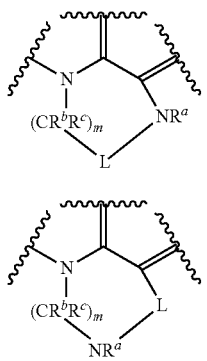

(T¹-1)

(T¹-2)

wherein
R$^a$ is hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —SOR$^{a2}$, or —SO$_2$R$^{a3}$;
R$^{a1}$, R$^{a2}$, and R$^{a3}$ are hydrogen, substituted or unsubstituted alkyl, substituted or unsubstituted alkenyl, substituted or unsubstituted alkyl oxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
m is an integer of 0 to 5;
L is —SO$_2$—, —SO—, —CO—, or —CR$^b$R$^c$—;
R$^b$ is each independently hydrogen, halogen, or substituted or unsubstituted alkyl;
R$^c$ is each independently hydrogen, halogen, or substituted or unsubstituted alkyl; or
R$^b$ and R$^c$ on the same carbon atom may be taken together to form oxo; or
R$^b$ and/or R$^c$ on adjacent carbon atoms may be taken together with the adjacent carbon atoms to form substituted or unsubstituted non-aromatic carbocycle or substituted or unsubstituted non-aromatic heterocycle; or
R$^a$ and R$^b$ and/or R$^c$ on adjacent carbon atom to the nitrogen atom bonded to R$^a$ may be taken together with the adjacent bonded nitrogen atom and carbon atom to form substituted or unsubstituted aromatic heterocycle or substituted or unsubstituted non-aromatic heterocycle.

(2A') The compound or its pharmaceutically acceptable salt according to the above (1A'), wherein the part represented by the formula:

[Chemical formula 29]
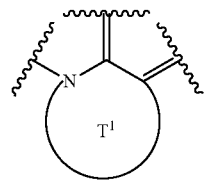

is the structure represented by any one of the following formula:

[Chemical formula 30]

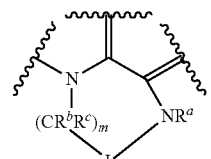

(T¹-1)

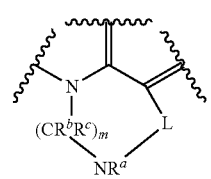

(T¹-2)

wherein R$^a$ is hydrogen, substituted or unsubstituted alkyl, substituted or unsubstituted alkenyl, —COR$^{a1}$, —SOR$^{a2}$, or —SO$_2$R$^{a3}$;
R$^{a1}$, R$^{a2}$, and R$^{a3}$ are hydrogen, substituted or unsubstituted alkyl, substituted or unsubstituted alkenyl, substituted or unsubstituted alkyl oxy, substituted or unsubstituted amino, or substituted or unsubstituted non-aromatic carbocyclyl;
m is an integer of 0 to 5;
L is —SO$_2$—, —SO—, —CO—, or —CR$^b$R$^c$—;
R$^b$ is each independently hydrogen, halogen, or substituted or unsubstituted alkyl;
R$^c$ is each independently hydrogen, halogen, or substituted or unsubstituted alkyl; or
R$^b$ and R$^c$ on the same carbon may be taken together to form oxo.

(3A) The compound or its pharmaceutically acceptable salt according to the above (2A) or (2A'), which is the following formula (I-1-1) or (I-2-1).

[Chemical formula 31]

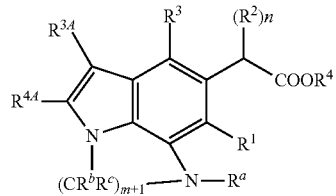

(I-1-1)

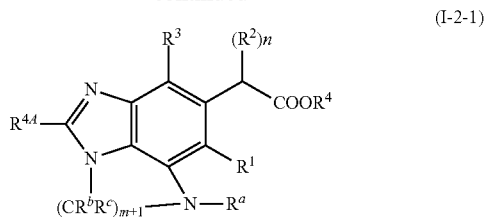

(I-2-1)

(4A) The compound or its pharmaceutically acceptable salt according to any one of the above (1A) to (3A) and (1A') to (2A'), wherein $R^1$ is alkyl.

(5A) The compound or its pharmaceutically acceptable salt according to any one of the above (1A) to (4A) and (1A') to (2A'), wherein n is 1; and $R^2$ is alkyloxy.

(6A) The compound or its pharmaceutically acceptable salt according to any one of the above (1A) to (5A), (1A') to (2A'), wherein $R^4$ is hydrogen.

(7A) The compound or its pharmaceutically acceptable salt according to any one of the above (1A) to (3A), (1A') to (2A'), wherein $R^1$ is alkyl; n is 1; $R^2$ is alkyloxy; and $R^4$ is hydrogen.

(8A) The compound or its pharmaceutically acceptable salt according to the above (2A), (2A') or (3A), wherein $R^a$ is hydrogen, substituted or unsubstituted alkyl, —$COR^{a1}$, or —$SO_2R^{a3}$; $R^b$ is each independently hydrogen, halogen or substituted or unsubstituted alkyl; $R^c$ is each independently hydrogen, halogen or substituted or unsubstituted alkyl; m is an integer of 1 to 3; $R^1$ is alkyl; n is 1; $R^2$ is alkyloxy; and $R^4$ is hydrogen.

(8A') The compound or its pharmaceutically acceptable salt according to the above (2A') or (3A), wherein $R^a$ is hydrogen, substituted or unsubstituted alkyl, —$COR^{a1}$, or —$SO_2R^{a3}$; $R^b$ and $R^c$ are each independently hydrogen, halogen or alkyl; m is an integer of 1 to 3; $R^1$ is alkyl; n is 1; $R^2$ is alkyloxy; and $R^4$ is hydrogen.

(9A) The compound or its pharmaceutically acceptable salt according to the above (2A) or (3A), wherein m is an integer of 1 to 3; $R^1$ is alkyl; n is 1; $R^2$ is alkyloxy; $R^4$ is hydrogen, $R^a$ and $R^b$ and/or $R^c$ on adjacent carbon atom to the nitrogen atom bonded to $R^a$ are taken together with the adjacent nitrogen atom and carbon atom to form substituted or unsubstituted monocyclic aromatic heterocycle or substituted or unsubstituted monocyclic non-aromatic heterocycle, or at least one of $R^b$ and/or $R^c$ on adjacent carbon atoms is taken together with the adjacent carbon atom to form substituted or unsubstituted monocyclic non-aromatic carbocycle or substituted or unsubstituted monocyclic non-aromatic heterocycle.

(10A) The compound or its pharmaceutically acceptable salt according to the above (2A) or (3A), wherein $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl; n is 1; $R^2$ is alkyloxy; and $R^4$ is hydrogen.

(11A) The compound or its pharmaceutically acceptable salt according to the above (2A), wherein $R^{3A}$ is hydrogen, halogen, alkyl, or haloalkyl; $R^{3B}$ is hydrogen; $R^{4A}$ is hydrogen, halogen, cyano, alkyl, haloalkyl, or non-aromatic carbocyclyl; $R^{4B}$ is hydrogen; $R^a$ is hydrogen, substituted or unsubstituted alkyl, —$COR^{a1}$, or —$SO_2R^{a3}$; $R^b$ is each independently hydrogen, halogen or alkyl; $R^c$ is each independently hydrogen, halogen or alkyl; m is an integer of 1 to 3; $R^1$ is alkyl; n is 1; $R^2$ is alkyloxy; and $R^4$ is hydrogen.

(11A') The compound or its pharmaceutically acceptable salt according to the above (2A') or (3A), wherein $R^{3A}$ is hydrogen, halogen, alkyl, or haloalkyl; $R^{4A}$ is hydrogen, halogen, cyano, alkyl, haloalkyl, or non-aromatic carbocyclyl; $R^a$ is hydrogen, substituted or unsubstituted alkyl, —$COR^{a1}$, or —$SO_2R^{a3}$; $R^b$ is each independently hydrogen, halogen or alkyl; $R^c$ is each independently hydrogen, halogen or alkyl; m is an integer of 1 to 3; $R^1$ is alkyl; n is 1; $R^2$ is alkyloxy; and $R^4$ is hydrogen.

(12A) The compound or its pharmaceutically acceptable salt according to the above (3A), wherein $R^{3A}$ is hydrogen, halogen, alkyl, or haloalkyl; $R^{4A}$ is hydrogen, halogen, cyano, alkyl, haloalkyl, or non-aromatic carbocyclyl; $R^a$ is hydrogen, substituted or unsubstituted alkyl, —$COR^{a1}$, or —$SO_2R^{a3}$; $R^b$ is each independently hydrogen, halogen or substituted or unsubstituted alkyl; $R^c$ is each independently hydrogen, halogen or substituted or unsubstituted alkyl; m is an integer of 1 to 3; $R^1$ is alkyl; n is 1; $R^2$ is alkyloxy; and $R^4$ is hydrogen.

(13A) A pharmaceutical composition comprising the compound or its pharmaceutically acceptable salt according to any one of the above (1A) to (12A), (1A'), (2A'), (8A'), and (11A').

(14A) The pharmaceutical composition according to the above (13A), having anti-virus activity.

(15A) The pharmaceutical composition according to the above (13A), having anti-HIV activity.

(16A) A pharmaceutical composition comprising the compound or its pharmaceutically acceptable salt according to any one of the above (1) to (16), (1A) to (12A), (1A'), (2A'), (8A'), and (11A'), for oral administration.

(17A) The pharmaceutical composition according to (16A), which is a tablet, powder, granule, capsule, pill, film, suspension, emulsion, elixir, syrup, lemonade, spirit, aromatic water, extract, decoction or tincture.

(18A) The pharmaceutical composition according to (17A), which is a sugarcoated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(19A) The pharmaceutical composition according to any one of the above (1) to (16), (1A) to (12A), (1A'), (2A'), (8A'), and (11A'), for parenteral administration.

(20A) The pharmaceutical composition according to (19A), for dermal, subcutaneous, intravenous, intra-arterial, intramuscular, intraperitoneal, transmucosal, inhalation, transnasal, ophathalmic, inner ear or vaginal administration.

(21A) The pharmaceutical composition according to (19A) or (20A), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(22A) A pharmaceutical composition comprising the compound or its pharmaceutically acceptable salt according to any one of the above (1) to (16), (1A) to (12A), (1A'), (2A'), (8A'), and (11A'), for a pediatric or geriatric patient.

(23A) A pharmaceutical composition comprising a combination of the compound or its pharmaceutically acceptable salt according to any one of the above (1) to (16), (1A)-(12A), (1A'), (2A'), (8A'), and (11A'), and a reverse transcriptase inhibitor, a protease inhibitor, integrase inhibitor or the other anti-HIV drug.

(24A) A pharmaceutical composition comprising the compound or its pharmaceutically acceptable salt according to any one of the above (1) to (16), (1A) to (12A), (1A'), (2A'), (8A'), and (11A'), for a combination treatment with a reverse transcriptase inhibitor, a protease inhibitor, a integrase inhibitor, or the other anti-HIV drug.

The present invention moreover provides the following invention.

A method for treatment or prevention of viral infection (example: HIV infection) characterized by administering to human the above compound or its pharmaceutically acceptable salt.

The above compound or its pharmaceutically acceptable salt, for the treatment or prevention of viral infection (example: HIV infection).

Effects of the Invention

The compound of the present invention has a replication inhibitory activity on a virus, particular HIV (example: HIV-1), a mutant virus thereof and a resistant virus thereof. Accordingly, the compound the present invention is useful in the prevention or treatment of viral infections (example: AIDS) and the like. Moreover, the present invention provides a synthetic intermediate for an antiviral drug.

MODE FOR CARRYING OUT THE INVENTION

Each meaning of terms used herein is described below. Each term, alone or in combination with another word, is used in the same meaning.

In the formula (I), the broken line means the presence or absence of a bond. Either of two broken lines in the formula (I) means the presence of a bond, the other means the absence of a bond. If the broken line in the ring means the presence of a bond, the broken line which binds to $R^{4B}$ means the absence of a bond, $A^3$ is $CR^{3,4}$ or N, and $R^{4B}$ is absence. If the broken line in the ring means the absence of a bond, the broken line which binds to $R^{4B}$ means the presence of a bond, $A^3$ means $CR^{3,4}R^{3B}$ or $NR^{3C}$. In this case, $R^{4B}$ is hydrogen, halogen, cyano, substituted or unsubstituted alkyl, substituted or unsubstituted alkynyl, or substituted or unsubstituted non-aromatic carbocyclyl.

"Halogen" includes a fluorine atom, a chlorine atom, a bromine atom, and an iodine atom. A fluorine atom and a chlorine atom are especially preferable.

"Alkyl" includes C1 to C15, preferably C1 to C10, more preferably C1 to C6, and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isopctyl, n-nonyl, n-decyl and the like.

A preferred embodiment of "alkyl" is methyl, ethyl, n-propyl, isopropyl, n-butyl, isobutyl, sec-butyl, tert-butyl, n-pentyl. A more preferred embodiment is methyl, ethyl, n-propyl, isopropyl, tert-butyl.

"Alkenyl" includes a C2 to C15, preferably C2 to C10, more preferably C2 to C6 and further preferably C2 to C4 linear or branched hydrocarbon group having one or more double bond(s) at any position(s). For example, vinyl, allyl, propenyl, isopropenyl, butenyl, isobutenyl, prenyl, butadieny, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl, butenyl.

"Alkynyl" includes a C2 to C10, preferably C2 to C8, more preferably C2 to C6, and further preferably C2 to C4 linear or branched hydrogen carbon group having one or more triple bond(s) at any position(s). For example, it includes ethynyl, propynyl, buthynyl, pentynyl, hexynyl, heptynyl, octynyl, nonynyl, decynyl and the like. These may have further a double bond at any available position.

A preferred embodiment of "alkynyl" is ethynyl, propynyl, buthynyl, or penthynyl.

"Alkylene" includes a C1 to C15, preferably C1 to C10, more preferably C1 to C6, and further preferably C1 to C4 linear or branched divalent hydrocarbon group. For example, it includes methylene, ethylene, trimethylene, propylene, tetramethylene, pentamethylene, hexamethylene and the like.

"Alkenylene" includes a C2 to C15, preferably C2 to C10, more preferably C2 to C6 and further preferably C2 to C4 linear or branched divalent hydrocarbon group having one or more double bond(s) at any position(s). For example, it includes vinylene, propenylene, butenylene, pentenylene and the like.

"Alkynylene" includes a C2 to C15, preferably C2 to C10, more preferably C2 to C6 and further preferably C2 to C4 linear or branched divalent hydrocarbon group having one or more triple bond(s) at any position(s). Furthermore, it may have double bond(s) at any position(s). For example, it includes ethynylene, propynylene, butynylene, pentynylene, hexynylene and the like.

"Alkyloxy" means a group wherein the above "alkyl" is bonded to an oxygen atom. For example, it includes methoxy, ethoxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methoxy, ethoxy, n-propyloxy, isopropyloxy, or tert-butyloxy.

"Alkenyloxy" means a group wherein the above "alkenyl" is bonded to an oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-butynyloxy, 2-pentynyloxy, 2-hexynyloxy, 2-heptynyloxy, 2-octynyloxy and the like.

"Aromatic carbocycle" includes a cyclic aromatic hydrocarbon ring which is monocyclic or polycyclic having two or more rings. For example, benzene ring, naphthalene ring, anthracene ring, phenanthrene ring or the like is exemplified.

An embodiment of "aromatic carbocycle" includes benzene ring, naphthalene ring. Another embodiment thereof includes benzene ring.

"Aromatic carbocyclyl" means a cyclic hydrocarbon group which is monocyclic or polycyclic having two or more rings. For example, phenyl, naphthyl, anthryl, phenanthryl or the like is exemplified.

A preferred embodiment of "aromatic carbocyclyl" includes phenyl.

"Non-aromatic carbocycle" includes a cyclic saturated hydrocarbon ring or a cyclic unsaturated non-aromatic hydrocarbon ring, which is monocyclic or polycyclic having two or more rings. "Non-aromatic carbocycle" which is polycyclic having two or more rings, includes a fused ring wherein a non-aromatic carbocycle, which is monocyclic or polycyclic having two or more rings, is fused with a ring of the above "aromatic carbocycle".

In addition, "non-aromatic carbocycle" also includes a ring having a bridge or a ring to form a spiro ring.

[Chemical formula 32]

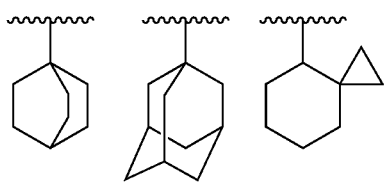

Monocyclic non-aromatic carbocycle is preferably C3 to C16, more preferably C3 to C12, and further preferably C3 to C8. For example, cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene or the like is exemplified.

Non-aromatic carbocycle which is polycyclic having two or more rings is preferably C8 to C13, more preferably C9 to C10. For example, indane, indene, acenaphthalene, tetrahydronephthalene, fluorene or the like is exemplified.

"Non-aromatic carbocyclyl" means a cyclic saturated hydrocarbon group or a cyclic unsaturated non-aromatic hydrocarbon, which is monocyclic or polycyclic having two or more rings. Non-aromatic carbocyclyl which is polycyclic having two or more rings includes a fused cyclic group wherein a non-aromatic carbocyclyl, which is monocyclic or polycyclic having two or more rings, is fused with a ring of the above "aromatic carbocyclyl".

In addition, "non-aromatic carbocyclyl" also includes a group having a bridge or a group to form a spiro ring as follows.

[Chemical formula 33]

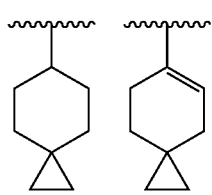

[Chemical formula 34]

Monocyclic non-aromatic carbocyclyl is preferably C3 to C16, more preferably C3 to C12, and further preferably C4 to C8. For example, cycloalkyl, cycloalkenyl or the like is exemplified.

"Cycloalkyl" is preferably C3 to C10, more preferably C3 to C7, and includes cyclopropyl, cyclobutyl, cyclopentyl, cyclohexyl, cycloheptyl, cyclooctyl, cyclononyl, cyclodecyl and the like.

"Cycloalkenyl" includes cyclopropenyl, cyclobutenyl, cyclopentenyl, cyclohexenyl, cycloheptenyl, cyclohexadienyl and the like.

Non-aromatic carbocyclyl which is polycyclic having two or more rings is preferably C8 to C13, more preferably C9 to 10. For example, indanyl, indenyl, acenaphthyl, tetrahydronaphthyl, fluorenyl, dihydroindenyl or the like is exemplified.

"Non-aromatic carbocyclyloxy" means a group wherein "non-aromatic carbocycle" is bonded to an oxygen atom. The part of "non-aromatic carbocycle" of the "non-aromatic carbocyclyloxy" is also the same as the above "non-aromatic carbocyclyl". For example, cyclopropyloxy, cyclohexyloxy, cyclohexenyloxy or the like is exemplified.

"Nitrogen-containing non-aromatic heterocycle" includes cyclic non-aromatic ring, which is monocyclic or polycyclic having two or more rings, having at least one nitrogen atom as an annular atom. Moreover, it may have same or different one or more hetero atom(s) selected from oxygen atom, sulfur atom, and nitrogen atom in the ring.

"Nitrogen-containing non-aromatic heterocycle which is polycyclic having two or more rings" includes nitrogen-containing non-aromatic heterocycle which is monocyclic or polycyclic having two or more rings fused each ring(s) in "aromatic carbocycle", "non-aromatic carbocycle", and/or "aromatic heterocycle".

Furthermore, "nitrogen-containing non-aromatic heterocycle" includes ring having a bridged structure or ring formed a spiro ring. That is, it also includes rings bridged by substituted or unsubstituted alkylene, substituted or unsubstituted alkylene containing one or more groups selected from —O—, —NR$^a$—, —S—, —CO—, —SO—, and —SO$_2$— at arbitrary position, and rings substituted or unsubstituted alkenylene, substituted or unsubstituted alkenylene containing one or more groups selected from —O—, —NR$^a$—, —S—, —CO—, —SO—, and —SO$_2$— at arbitrary position, substituted or unsubstituted alkynylene, or substituted or unsubstituted alkynylene containing one or more groups selected from —O—, —NR$^a$—, —S—, —CO—, —SO—, and —SO$_2$— at arbitrary position, and rings which are formed spiro ring with substituted or unsubstituted alkylene, substituted or unsubstituted alkylene containing one or more groups selected from —O—, —NR$^a$—, —S—, —CO—, —SO—, and —SO$_2$— at arbitrary position, substituted or unsubstituted alkenylene, substituted or unsubstituted alkenylene containing one or more groups selected from —O—, —NR$^a$—, —S—, —CO—, —SO—, and —SO$_2$— at arbitrary position, substituted or unsubstituted alkynylene or substituted or unsubstituted alkynylene containing one or more groups selected from —O—, —NR$^a$—, —S—, —CO—, —SO—, and —SO$_2$— at arbitrary position. For example, the following rings are exemplified.

[Chemical formula 35]

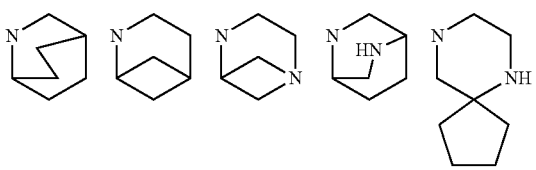

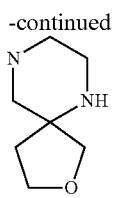

Monocyclic nitrogen-containing non-aromatic heterocycle is preferably 5 to 12-membered, more preferably 5 to 8-membered. For example, it includes thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, dihydrothiazoline, tetrahydrothiazoline, tetrahydroisothiazolin, dihydrooxazine, hexahydroazepine, tetrahydrodiazepine, tetrahydropyridazine, hexahydropyrimidine, thiazine, and the like.

Nitrogen-containing non-aromatic heterocycle which is polycyclic having two or more rings is preferably 9 to 20-membered, more preferably 8 to 16-membered. For example, it includes indoline, isoindoline and the like.

Preferable is nitrogen-containing non-aromatic heterocycle which is monocyclic or polycyclic having two or more rings, the bicyclic nitrogen-containing non-aromatic heterocycle includes fused ring, bridged ring, and spiro ring.

Preferable embodiment of bridged nitrogen-containing non-aromatic heterocycle is bicyclic nitrogen-containing non-aromatic heterocycle which is bridged by substituted or unsubstituted alkylene, substituted or unsubstituted alkenylene containing one or two groups selected from —O—, —NR$^a$—, —S—, —CO—, —SO—, —SO$_2$— at arbitrary position, substituted or unsubstituted alkylene, or substituted or unsubstituted alkenylene containing one or two groups selected from —O—, —NR$^a$—, —S—, —CO—, —SO—, —SO$_2$— at arbitrary position.

Preferable embodiment of nitrogen-containing non-aromatic heterocycle which is spiro ring is bicyclic nitrogen-containing non-aromatic heterocycle formed by substituted or unsubstituted alkylene consisting of two substituents on the same carbon atom as an annular atom of T$^1$ ring taken together, or bicyclic nitrogen-containing non-aromatic heterocycle formed by substituted or unsubstituted alkylene containing one or two groups selected from —O—, —NR$^a$—, —S—, —CO—, —SO—, and —SO$_2$.

Preferable embodiment of fused nitrogen-containing non-aromatic heterocycle is 9 or 10-membered bicyclic nitrogen-containing non-aromatic heterocycle.

"Aromatic heterocycle" includes aromatic ring, which is monocyclic or polycyclic having two or more rings, containing one or more and same or different of heteroatoms(s) selected from O, S and N arbitrarily.

"Aromatic heterocycle which is polycyclic having two or more rings" includes an aromatic heterocycle, which is monocyclic or polycyclic having two or more rings, fused the ring in the above "aromatic carbocycle".

Monocyclic aromatic heterocycle is preferably 5 to 8-membered ring, more preferably 5 or 6-membered ring. For example, pyrrole, imidazole, pyrazole, pyridine, pyridazine, pyrimidine, pyrazine, triazole, triazine, tetrazole, furan, thiophen, isoxazole, oxazole, oxadiazole, isothiazole, thiazole, thiadiazole or the like is exemplified.

Bicyclic aromatic heterocycle is preferably 8 to 18-membered ring, more preferably 9 or 10-membered ring. For example, indoline, isoindoline, indazoline, indolidine, quinoline, isoquinoline, cinnoline, phthalazine, quinazoline, naphthyridine, quinoxaline, purine, puteridine, benzimidazole, benzisoxazole, benzoxazole, benzoxadiazole, benzoisothiazole, benzothiazole, benzothiadiazole, benzofuran, isobenzofuran, benzothiophen, benzotriazole, imidazopyridine, triazolopyridine, imidazothiazole, pyrradinopyridazine, oxazolopyridine, thiazolopyridine or the like is exemplified.

Aromatic heterocycle which is polycyclic having three or more rings is preferably 11 to 26-membered ring, more preferably 13 or 14-membered ring. For example, carbazole, acridine, xanthene, phenothiazine, phenoxathiine, phenoxazine, dibenzofuran or the like is exemplified.

"Aromatic heterocyclyl" means an aromatic cyclic group, which is monocyclic or polycyclic having two or more rings, containing one or more and same or different heteroatom(s) selected from O, S, and N.

Aromatic heterocyclyl, which is polycyclic having two or more rings, includes aromatic heterocyclyl which is monocyclic or polycyclic having two or more rings fused the ring in the above "aromatic carbocyclyl".

Monocyclic aromatic heterocyclyl is preferably 5 to 10-membered ring, more preferably 5 or 6-membered ring. For example, pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like are exemplified.

Aromatic heterocyclyl which is polycyclic having two or more rings is preferably 8 to 18-membered ring, more preferably 9 or 10-membered ring. For example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradinopyridazinyl, oxazolopyridyl, thiazolopyridyl and the like are exemplified.

Aromatic heterocyclyl which is polycyclic having three or more rings is preferably 11 to 26-membered rings, more preferably 13 or 14-membered ring. For example, carbazolyl, acridinyl, xanthenyl, phenothiazinyl, phenoxathiinyl, phenoxazinyl, dibenzofuryl and the like are exemplified.

"Non-aromatic heterocycle" includes a non-aromatic ring, which is monocyclic or polycyclic having two or more rings, containing one or more and same or different of heteroatom(s) arbitrarily selected from O, S and N.

"Non-aromatic heterocycle which is polycyclic having two or more rings" includes a fused ring wherein a non-aromatic heterocycle, which is monocyclic or polycyclic having two or more ring(s), is fused with a ring of the above "aromatic carbocycle", "non-aromatic carbocycle", and/or "aromatic heterocycle".

In addition, the "non-aromatic heterocycle" also includes a ring having a bridge or a ring to form a spiro ring as follows.

[Chemical formula 36]

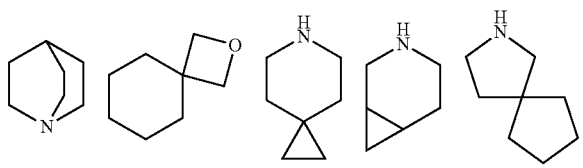

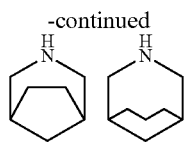

Monocyclic non-aromatic heterocycle is preferably 3 to 8 membered ring, more preferably 5 or 6-membered ring. For example, it includes dioxane, thiirane, oxyrane, oxetane, oxathiorane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazoline, tetrahydrothiazoline, tetrahydroisothiazoline, dihydrooxadine, hexahydroazepine, tetrahydrodiazepine, tetrahydropyridazine, hexahydropyrimidine, dioxolane, dioxazine, aziridine, dioxoline, oxepane, thiolane, thiazine and the like.

Non-aromatic heterocycle which is polycyclic having two or more rings is preferably 8 to 20 membered ring, more preferably 8 to 16 membered ring. For example, it includes indoline, isoindoline, chromane, isochromane and the like.

"Non-aromatic heterocyclyl" means a non-aromatic cyclic group, which is monocyclic or polycyclic having two or more rings, containing one or more and same or different heteroatom(s) arbitrarily selected from O, S and N.

"Non-aromatic heterocyclyl which is polycyclic having two or more rings, includes a fused cyclic group wherein a non-aromatic heterocyclyl, which is monocyclic or polycyclic having two or more rings, is fused with a ring of the above "aromatic carbocyclyl", "non-aromatic carbocyclyl", and/or "aromatic heterocyclyl".

In addition, the "non-aromatic heterocyclyl" also includes rings bridged by substituted or unsubstituted alkylene, substituted or unsubstituted alkylene containing one or more groups selected from —O—, —NR$^a$—, —S—, —CO—, —SO—, and —SO$_2$— at arbitrary position, substituted or unsubstituted alkenylene, substituted or unsubstituted alkenylene containing one or more groups selected from —O—, —NR$^a$—, —S—, —CO—, —SO—, and —SO$_2$— at arbitrary position, substituted or unsubstituted alkynylene or substituted or unsubstituted alkynylene containing one or more groups selected from —O—, —NR$^a$—, —S—, —CO—, —SO—, and —SO$_2$— at arbitrary position, and rings which are formed spiro ring with substituted or unsubstituted alkylene, substituted or unsubstituted alkylene containing one or more groups selected from —O—, —NR$^a$—, —S—, —CO—, —SO—, and —SO$_2$— at arbitrary position, substituted or unsubstituted alkenylene, substituted or unsubstituted alkenylene containing one or more groups selected from —O—, —NR$^a$—, —S—, —CO—, —SO—, and —SO$_2$— at arbitrary position, substituted or unsubstituted alkynylene or substituted or unsubstituted alkynylene containing one or more groups selected from —O—, —NR$^a$—, —S—, —CO—, —SO—, and —SO$_2$— at arbitrary position. For example, the following rings are exemplified.

[Chemical formula 37]

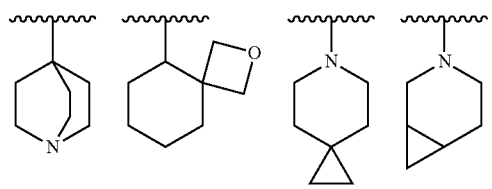

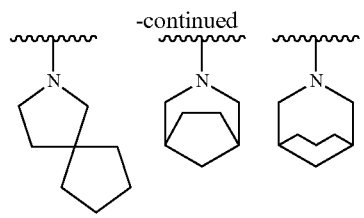

Monocyclic non-aromatic heterocyclyl is preferably 3 to 8-membered ring, more preferably 5 or 6-membered ring. For example, it includes dioxanyl, thiiranyl, oxyranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxadinyl, hexahidroazepinyl, tetrahydrodiazepinyl, tetrahydropyridazinyl, hexahydropyrimidinyl, dioxolanyl, dioxadinyl, aziridinyl, dioxolinyl, oxepanyl, thiolanyl, thiinyl, thiazinyl and the like.

Non-aromatic heterocyclyl which is polycyclic having two or more rings is preferably 8 to 20 membered ring, more preferably 8 to 16 membered ring. For example, it includes indolinyl, isoindolinyl, chromanyl, isochromanyl, dihydrobenzofuryl, benzodioxolyl, benzodioxanyl, benzomorpholinyl and the like.

"Carboxyl protecting group" means a protecting group which is converted to a carboxy group by hydrolysis or a deprotection reaction. Preferable examples as a carboxyl protecting group are alkyl (e.g.: methyl, ethyl, t-butyl) and aralkyl(e.g.: benzyl), more preferable example is C1 to C4 alkyl.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy". "substituted or unsubstituted alkylene", "substituted or unsubstituted alkenylene" and "substituted or unsubstituted alkynylene" include the following Substituent group. A carbon atom at any position(s) may be bended to the same or different and one or more group(s) selected from the following Substituent Group. The substituent(s) is(are) preferably 1 to 4, more preferably 1 to 3.

Substituent Group: halogen, hydroxy, carboxy, formyl, formyl oxy, sulfanyl, sulfino, sulfo, thioformyl, thiocarboxy, dithiocarboxy, thiocarbamoyl, cyano, nitro, nitroso, azido, hydradino, ureido, amidino, guadininno, trialkylsilyl, alkyloxy, alkenyloxy, alkynyloxy, haloalkyloxy, alkyl carbonyl, alkenyl carbonyl, alkynyl carbonyl, alkyl sulfonyl, alkenyl sulfonyl, alkynyl sulfonyl, alkyl carbonyl oxy, alkenyl carbonyl oxy, alkynyl carbonyl oxy, alkylsulfonyloxy, alkenyl sulfonyl oxy, alkynyl sulfonyl oxy, alkyl oxy carbonyl, alkenyloxycarbonyl, alkynyloxy carbonyl, alkyl sulfanyl, alkenyl sulfanyl, alkynyl sulfanyl, alkylsulfinyl, alkenyl sulfinyl, alkynyl sulfinyl, substituted or unsubstituted amino, substituted or unsubstituted imino, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycloxy, substituted or unsubstituted non-aromatic carbocycloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxy carbonyl, substituted or unsubstituted non-aromatic carbocyclyloxy carbonyl, substituted or unsubstituted aromatic heterocyclyloxy carbonyl, substituted or unsubstituted non-aromatic heterocyclyloxy carbonyl, substituted or unsubstituted aromatic carbocyclylalkyl oxy, substituted or unsubstituted non-aromatic carbocyclylalkyl oxy, substituted or unsubstituted aromatic heterocyclylalkyl oxy, substituted or unsubstituted non-aromatic heterocyclylalkyl oxy, substituted or unsubstituted aromatic carbocyclylalkyl sulfanyl, substituted or unsubstituted non-aromatic carbocyclylalkyl sulfanyl, substituted or unsubstituted aromatic heterocyclylalkyl sulfanyl, substituted or unsubstituted non-aromatic heterocyclylalkyl sulfanyl, substituted or unsubstituted aromatic carbocyclylalkyl oxy carbonyl, substituted or unsubstituted non-aromatic carbocyclylalkyl oxy carbonyl, substituted or unsubstituted aromatic heterocyclylalkyl oxy carbonyl, substituted or unsubstituted non-aromatic heterocyclylalkyl oxy carbonyl, substituted or unsubstituted aromatic carbocycle sulfanyl, substituted or unsubstituted non-aromatic carbocycle sulfanyl, substituted or unsubstituted aromatic heterocycle sulfanyl, substituted or unsubstituted non-aromatic heterocycle sulfanyl, substituted or unsubstituted aromatic carbocycle sulfonyl, substituted or unsubstituted non-aromatic carbocycle sulfonyl, substituted or unsubstituted aromatic heterocycle sulfonyl, and substituted or unsubstituted non-aromatic heterocycle sulfonyl.

The substituents on the ring of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted nitrogen-containing non-aromatic heterocycle", "substituted or unsubstituted aromatic carbocycle", "substituted or unsubstituted non-aromatic carbocycle", "substituted or unsubstituted aromatic heterocycle", "substituted or unsubstituted non-aromatic heterocycle", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", "substituted or unsubstituted non-aromatic heterocyclylcarbonyl", "substituted or unsubstituted aromatic carbocyclyloxy carbonyl", "substituted or unsubstituted non-aromatic carbocyclyloxy carbonyl", "substituted or unsubstituted aromatic heterocyclyloxy carbonyl", "substituted or unsubstituted non-aromatic heterocyclyloxy carbonyl", "substituted or unsubstituted aromatic carbocyclylalkyl oxy", "substituted or unsubstituted non-aromatic carbocyclylalkyl oxy", "substituted or unsubstituted aromatic heterocyclylalkyl oxy", "substituted or unsubstituted non-aromatic heterocyclylalkyl oxy", "substituted or unsubstituted aromatic carbocyclylalkyl sulfanyl", "substituted or unsubstituted non-aromatic carbocyclylalkyl sulfanyl", "substituted or unsubstituted aromatic heterocyclylalkyl sulfanyl", "substituted or unsubstituted non-aromatic heterocyclylalkyl sulfanyl", "substituted or unsubstituted aromatic carbocyclylalkyl oxy carbonyl", "substituted or unsubstituted non-aromatic carbocyclylalkyl oxy carbonyl", "substituted or unsubstituted aromatic heterocyclylalkyl oxy carbonyl", "substituted or unsubstituted non-aromatic heterocyclylalkyl oxy carbonyl", "substituted or unsubstituted aromatic carbocycle sulfanyl", "substituted or unsubstituted non-aromatic carbocycle sulfanyl", "substituted or unsubstituted aromatic heterocycle sulfanyl", "substituted or unsubstituted non-aromatic heterocycle sulfanyl", "substituted or unsubstituted aromatic carbocycle sulfonyl", "substituted or unsubstituted non-aromatic carbocycle sulfonyl", "substituted or unsubstituted aromatic heterocycle sulfonyl" and "substituted or unsubstituted non-aromatic heterocycle sulfonyl" include the following Substituent group. An atom at any position(s) on the ring may be bonded to the same or different and one or more group(s) selected form the following Substituent Group. The substituent(s) is(are) preferably 1 to 4, more preferably 1 to 3 group(s).

Substituent Group: halogen, hydroxy, carboxy, formyl, formyl oxy, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, substituted or unsubstituted alkyl, substituted or unsubstituted alkenyl, alkynyl, haloalkyl, hydroxyalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, alkylsulfonyl, alkenylsulfonyl, alkynylsulfonyl, alkylcarbonyloxy, alkenylcarbonyloxy, alkynylcarbonyloxy, alkylsulfonyloxy, alkenyl sulfonyl oxy, alkynyl sulfonyl oxy, alkyl oxy carbonyl, alkenyloxycarbonyl, alkynyloxy carbonyl, alkyl sulfanyl, alkenyl sulfanyl, alkynyl sulfanyl, alkylsulfinyl, alkenyl sulfinyl, alkynyl sulfinyl, substituted or unsubstituted amino, substituted or unsubstituted imino, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxy carbonyl, substituted or unsubstituted non-aromatic carbocyclyloxy carbonyl, substituted or unsubstituted aromatic heterocyclyloxy carbonyl, substituted or unsubstituted non-aromatic heterocyclyloxy carbonyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, substituted or unsubstituted aromatic carbocyclylalkyl oxy, substituted or unsubstituted non-aromatic carbocyclylalkyl oxy, substituted or unsubstituted aromatic heterocyclylalkyl oxy, substituted or unsubstituted non-aromatic heterocyclylalkyl oxy, substituted or unsubstituted aromatic carbocyclylalkyl sulfanyl, substituted or unsubstituted non-aromatic carbocyclylalkyl sulfanyl, substituted or unsubstituted aromatic heterocyclylalkyl sulfanyl, substituted or unsubstituted non-aromatic heterocyclylalkyl sulfanyl, substituted or unsubstituted aromatic carbocyclylalkyl oxy carbonyl, substituted or unsubstituted non-aromatic carbocyclylalkyl oxy carbonyl, substituted or unsubstituted aromatic heterocyclylalkyl oxy carbonyl, substituted or unsubstituted non-aromatic heterocyclylalkyl oxy carbonyl, substituted or unsubstituted aromatic carbocyclylalkyl oxy alkyl, substituted or unsubstituted non-aromatic carbocyclylalkyl oxy alkyl, substituted or unsubstituted aromatic heterocyclylalkyl oxy alkyl, substituted or unsubstituted non-aromatic heterocyclylalkyl oxy alkyl, substituted or unsubstituted aromatic carbocycle sulfanyl, substituted or unsubstituted non-aromatic carbocycle sulfanyl, substituted or unsubstituted aromatic heterocycle sulfanyl, substituted or unsubstituted non-aromatic heterocycle sulfanyl, substituted or unsubstituted aromatic carbocycle sulfonyl, substituted or unsubstituted non-aromatic carbocycle sulfonyl, substituted or unsubstituted aromatic heterocycle sulfonyl, substituted or unsubstituted non-aromatic heterocycle sulfonyl, —COR$^{a1}$, —COOR$^{a1}$, —SOSOR$^{a2}$, —SO$_2$R$^{a3}$, —CONR$^{a4}$R$^{a5}$, —CSNR$^{a4}$R$^{a5}$, —COCOCONR$^{a4}$R$^{a5}$, and —C(NR$^{a6}$)NR$^{a4}$R$^{a5}$, wherein R$^{a1}$, R$^{a2}$, and R$^{a3}$ are each dependently substituted or unsubstituted alkyl, substituted or unsubstituted alkenyl, substituted or unsubstituted alkyl oxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; R$^{a4}$ and R$^{a5}$ are each dependently hydrogen, hydroxy, substituted or unsubstituted alkyl, substituted or unsubstituted alkenyl, substituted or unsubstituted alkynyl, substituted or unsubstituted alkyl oxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; R$^{a6}$ is hydrogen, hydroxy, substituted or unsubstituted alkyl, substituted or unsubstituted alkenyl, substituted or unsubstituted alkynyl, substituted or unsubstituted alkyl oxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

"Substituted or unsubstituted non-aromatic carbocyclyl", "substituted or unsubstituted non-aromatic heterocyclyl" and "substituted or unsubstituted nitrogen-containing non-aromatic heterocycle" include the case substituted with "oxo".

[Chemical Formula 38]

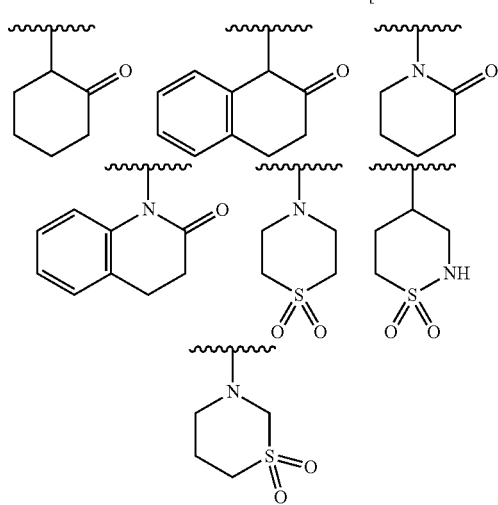

The non-aromatic carbocycle of "substituted or unsubstituted non-aromatic carbocyclyloxy" and the aromatic heterocycle of "substituted or unsubstituted nitrogen-containing non-aromatic heterocycle" also include the case optionally substituted with "oxo" as described above. For example, ring T$^1$ is optionally substituted with oxo as follows.

[Chemical Formula 39]

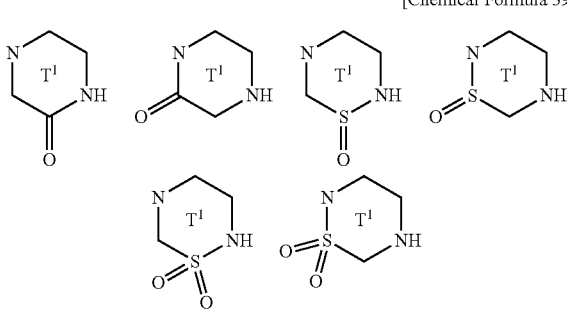

"Substituted or unsubstituted amino" includes an amino optionally substituted with one or two group(s) selected from the following Substituent Group.

Substituent Group: hydroxy, cyano, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkenylcarbonyl, alkynylcarbonyl, haloalkylcarbonyl, haloalkenylcarbonyl, haloalkynylcarbonyl, alkylsulfonyl, haloalkylsulfonyl, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, and substituted or unsubstituted non-aromatic heterocyclylcarbamoyl.

An embodiment of "substituted or unsubstituted amino" includes amino, methylamino, dimethylamino, ethylamino, diethylamino, ethylmethylamino, cyclopropylamino, cyclohexylamino, benzylamino, acetylamino, benzoylamino, methylsulfonylamino, tetrahydropyranylamino, tetrahydrofuranylamino, morpholinoamino, morpholinylamino, piperidinylamino, piperazinylamino and the like. Another embodiment thereof includes amino, methylamino, dimethylamino, ethylmethyl amino, diethylamino, acetylamino, methylsulfonylamino, tetrahydropyranylamino, tetrahydrofuranylamino, morpholinoamino, piperidinylamino and the like.

"Trialkylsilyl" means a group wherein three "alkyl" groups described above are bonded to a silicon atom. These three alkyl may be the same or different. For example, it includes trimethylsilyl, triethylsilyl, tert-butyldimethylsilyl and the like.

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl and the like.

A preferred embodiment of "haloalkyl" is trifluoromethyl, trichloromethyl or the like.

"Haloalkyloxy" means a group wherein the above "haloalkyl" is bonded to an oxygen atom. For example, it includes monofluoromethoxy, monofluoroethoxy, trifluoromethoxy, trichloromethoxy, trifluoroethoxy, trichloroethoxy and the like.

A preferred embodiment of "haloalkyloxy" is trifluoromethoxy or trichloromethoxy.

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl and the like.

A preferred embodiment of "alkylcarbonyl" is methylcarbonyl, ethylcarbonyl, or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynyl carbonyl" means a group wherein the above "alkynyl" is bonded to a carbonyl group. For example, it includes ethynylcarbonyl, propynylcarbonyl and the like.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

"Alkenylsulfonyl" means a group wherein the above "alkenyl" is bonded to a sulfonyl group. For example, it includes ethylenylsulfonyl, propenylsulfonyl and the like.

"Alkynylsulfonyl" means a group wherein the above "alkynyl" is bonded to a sulfonyl group. For example, it includes ethynylsulfonyl, propynylsulfonyl and the like.

"Alkylcarbonyloxy" means a group wherein the above "alkylcarbonyl" is bonded to an oxygen atom. For example, it includes methylcarbonyloxy, ethylcarbonyloxy, propylcarbonyloxy, isopropyncarbonyloxy, tert-butylcarbonyloxy, isobutylcarbonyloxy, sec-butylcarbonyloxy and the like.

A preferred embodiment of "alkylcarbonyloxy" is methylcarbonyloxy or ethylcarbonyloxy.

"Alkenylcarbonyloxy" means a group wherein the above "alkenylcarbonyl" is bonded to an oxygen atom. For example, it includes ethylenylcarbonyloxy, propenylcarbonyloxy and the like.

"Alkynylcarbonyloxy" means a group wherein the above "alkynylcarbonyl" is bonded to an oxygen atom. For example, it includes ethynylcarbonyloxy, propynylcarbonyloxy and the like.

"Alkylsulfonyloxy" means a group wherein the above "alkylsulfonyl" is bonded to an oxygen atom. For example, it includes methylsulfonyloxy, ethylsulfonyloxy, propylsulfonyloxy, isopropylsulfonyloxy, tert-butylsulfonyloxy, isobutylsulfonyloxy, sec-butylsulfonyloxy and the like.

A preferred embodiment of "alkylsulfonyloxy" is methylsulfonyloxy or ethylsulfonyloxy.

"Alkenylsulfonyloxy" means a group wherein the above "alkenylsulfonyl" is bonded to an oxygen atom. For example, it includes ethylenylsulfonyloxy, propenylsulfonyloxy and the like.

"Alkynylsulfonyloxy" means a group wherein the above "alkynylsulfonyl" is bonded to an oxygen atom. For example, it includes ethynylsulfonyloxy, propynylsulfonyloxy and the like.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like.

A preferred embodiment of "alkyloxycarbonyl" is methyloxycarbonyl, ethyloxycarbonyl, or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfanyl" means a group wherein a hydrogen atom attached to a sulfur atom of a sulfanyl group is replaced with the above "alkyl". For example, it includes methylsulfanyl, ethylsulfanyl, n-propylsulfanyl, isopropylsulfanyl and the like.

"Alkenylsulfanyl" means a group wherein a hydrogen atom attached to a sulfur atom of a sulfanyl group is replaced with the above "alkenyl". For example, it includes ethlenylsulfanyl, propenylsulfanyl and the like.

"Alkynylsulfanyl" means a group wherein a hydrogen atom attached to a sulfur atom of a sulfanyl group is replaced with the above "alkynyl". For example, it includes ethynylsulfanyl, propynylsulfanyl and the like.

"Alkylsulfinyl" means a group wherein the above "alkyl" is bonded to a sulfinyl group. For example, it includes methylsulfinyl, ethylsulfinyl, n-propylsulfinyl, isopropylsulfinyl and the like.

"Alkenylsulfinyl" means a group wherein the above "alkenyl" is bonded to a sulfinyl group. For example, it includes ethylenylsulfinyl, propenylsulfinyl and the like.

"Alkynylsulfinyl" means a group wherein the above "alkynyl" is bonded to a sulfinyl group. For example, it includes ethynylsulfinyl, propynylsulfinyl and the like.

"Substituted or unsubstituted imino" includes an imino optionally substituted with a group selected from the following Substituent Group.

Substituent Group: hydroxy, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkylcarbonyl, alkenylcarbonyl, alkynylcarbonyl, haloalkylcarbonyl, haloalkenylcarbonyl, haloalkynylcarbonyl, amino, alkylamino, haloalkylamino, substituted or unsubstituted aromatic carbocyclyl, substituted or unsubstituted non-aromatic carbocyclyl, substituted or unsubstituted aromatic heterocyclyl, and substituted or unsubstituted non-aromatic heterocyclyl.

An embodiment of "substituted or unsubstituted imino" includes imino, methylimino, ethylimino, cyclopropylimino, cyclohexylimino, acetylimino, tetrahydropyranylimino, tetrahydrofuranylimino, morpholino imino, morpholinyl imino, piperidinyl imino, piperazinyl imino and the like.

"Hydroxyalkyl" means a group wherein hydrogen atom(s) attached to a carbon atom of the above "alkyl" is replaced with one or more hydroxyl group(s). For example, it includes hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl.

"Alkyloxyalkyl" means a group wherein the above "alkyloxy" is bonded to the above "alkyl". For example, it includes methoxymethyl, methoxyethyl, ethoxymethyl and the like.

"Alkyloxyalkyloxy" means a group wherein the above "alkyloxy" is bonded to the above "alkyloxy". For example, it includes methoxymethoxy, methoxyethoxy, ethoxymethoxy, ethoxyethoxy and the like.

"Substituted or unsubstituted carbamoyl" includes a carbamoyl optionally substituted with one or more group(s) selected from the following Substituent Group.
Substituent Group: hydroxy, cyano, amino, alkyl, alkenyl, alkynyl, haloalkyl, haloalkenyl, haloalkynyl, hydroxyalkyl, alkylamino, alkylcarbonyl, alkenylcarbonyl, alkynylcarbonyl, alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, and substituted or unsubstituted non-aromatic heterocyclylalkyl.

An embodiment of "substituted or unsubstituted carbamoyl" includes carbamoyl, N-methylcarbamoyl, N,N-dimethylcarbamoyl, N-ethyl-N-methylcarbamoyl, N,N-diethylcarbamoyl, N-n-propylamino carbamoyl, N-isopropylcarbamoyl, N-morpholino carbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifluoroethyl)carbamoyl, N-(2-hydroxy-1-methylethyl)carbamoyl and the like. Another embodiment thereof includes carbamoyl, N-methyl carbamoyl, N, N-dimethylcarbamoyl, N-n-propylamino carbamoyl, N-isopropylcarbamoyl, N-morpholino carbamoyl, N-tetrahydrofuranyl carbamoyl, N-piperadylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl and the like.

"Substituted or unsubstituted sulfamoyl" includes an aminosulfonyl optionally substituted with one or more group(s) selected from the following Substituted Group.
Substituted Group: alkyl, alkenyl, alkynyl, haloalkyl, haloalkenyl, haloalkynyl, hydroxyalkyl, alkylcarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, and substituted or unsubstituted non-aromatic heterocyclylalkyl.

An embodiment of "substituted or unsubstituted sulfamoyl" includes sulfamoyl, N-methylsulfamoyl, N, N-dimethylsulfamoyl, N-ethyl-N-methylsulfamoyl, N, N-diethylsulfamoyl, N-n-propylamino sulfamoyl, N-isopropylsulfamoyl, N-morpholino sulfamoyl, N-tetrahydrofuranyl sulfamoyl, N-piperidylsulfamoyl, N-tetrahydropyranylsulfamoyl, N-benzylsulfamoyl, N-acetylsulfamoyl, N-methylsulfonylsulfamoyl and the like. Another embodiment thereof includes sulfamoyl, N-methylsulfamoyl, N, N-dimethylsulfamoyl, N-n-propylamino sulfamoyl, N-isopropylsulfamoyl, N-morpholino sulfamoyl, N-tetrahydrofuranylsulfamoyl, N-piperidylsulfamoyl, N-tetrahydropyranylsulfamoyl, N-methylsulfonylsulfamoyl and the like.

The "aromatic carbocycle" part of "aromatic carbocyclyloxy", "aromatic carbocyclylcarbonyl", "aromatic carbocyclyloxycarbonyl", "aromatic carbocycle sulfanyl", "aromatic carbocycle sulfonyl", "aromatic carbocyclylalkyl", "aromatic carbocyclylalkyloxy", "aromatic carbocyclylalkylsulfanyl", "aromatic carbocyclylalkyloxycarbonyl", "aromatic carbocyclylalkyloxyalkyl", "aromatic carbocyclylcarbamoyl is same as the above "aromatic carbocyclyl".

The substituent(s) on the "aromatic carbocycle" part of "substituted or unsubstituted aromatic carbocyclyloxy", "substituted or unsubstituted aromatic carbocyclylcarbonyl", "substituted or unsubstituted aromatic carbocyclyloxycarbonyl", "substituted or unsubstituted aromatic carbocycle sulfanyl", "substituted or unsubstituted aromatic carbocycle sulfonyl", "substituted or unsubstituted aromatic carbocyclylalkyl", "substituted or unsubstituted aromatic carbocyclylalkyloxy", "substituted or unsubstituted aromatic carbocyclylalkylsulfanyl", "substituted or unsubstituted aromatic carbocyclylalkyloxycarbonyl", "substituted or unsubstituted aromatic carbocyclylalkyloxyalkyl", and "substituted or unsubstituted aromatic carbocyclylcarbamoyl" is(are) same as the substituent(s) on the above "substituted or unsubstituted aromatic carbocyclyl".

The "non-aromatic carbocyclylalkyl" part of "non-aromatic carbocyclylalkyl", "non-aromatic carbocyclylcarbonyl", "non-aromatic carbocyclyloxycarbonyl", "non-aromatic carbocycle sulfanyl", "non-aromatic carbocycle sulfonyl", "non-aromatic carbocyclylalkyl", "non-aromatic carbocyclylalkyloxy", "non-aromatic carbocyclylalkylsulfanyl", "non-aromatic carbocyclylalkyloxycarbonyl", "non-aromatic carbocyclylalkyloxyalkyl", "non-aromatic carbocyclylcarbamoyl", "non-aromatic carbocycle amino" is same as the above "non-aromatic carbocyclyl".

The substituent(s) on the "non-aromatic carbocycle" part of "substituted or unsubstituted non-aromatic carbocyclyloxy", "substituted or unsubstituted non-aromatic carbocyclylcarbonyl", "substituted or unsubstituted non-aromatic carbocyclyloxycarbonyl", "substituted or unsubstituted non-aromatic carbocycle sulfanyl", "substituted or unsubstituted non-aromatic carbocycle sulfonyl", "substituted or unsubstituted non-aromatic carbocyclylalkyl", "substituted or unsubstituted non-aromatic carbocyclylalkyloxy", "substituted or unsubstituted non-aromatic carbocyclylalkylsulfanyl", "substituted or unsubstituted non-aromatic carbocyclylalkyloxycarbonyl", "substituted or unsubstituted non-aromatic carbocyclylalkyloxyalkyl", and "substituted or unsubstituted non-aromatic carbocyclylcarbamoyl" is(are) same as the substituent(s) on the above "substituted or unsubstituted non-aromatic carbocyclyl".

The "aromatic heterocycle" part of "aromatic heterocyclyloxy", "aromatic heterocyclylcarbonyl", "aromatic heterocyclyloxycarbonyl", "aromatic heterocycle sulfanyl", "aromatic heterocycle sulfonyl", "aromatic heterocyclylalkyl", "aromatic heterocyclylalkyloxy", "aromatic heterocyclylalkylsulfanyl", "aromatic heterocyclylalkyloxycarbonyl", "aromatic heterocyclylalkyloxyalkyl", and "aromatic heterocyclylcarbamoyl" is same as the above "aromatic heterocyclyl".

The substituent(s) on the "aromatic heterocycle" part of "substituted or unsubstituted aromatic heterocyclyloxy", "substituted or unsubstituted aromatic heterocyclylcarbonyl", "substituted or unsubstituted aromatic heterocyclyloxycarbonyl", "substituted or unsubstituted aromatic heterocycle sulfanyl", "substituted or unsubstituted aromatic heterocycle sulfonyl", "substituted or unsubstituted aromatic heterocyclylalkyl", "substituted or unsubstituted aromatic heterocyclylalkyloxy", "substituted or unsubstituted aromatic heterocyclylalkylsulfanyl", "substituted or unsubstituted aromatic heterocyclylalkyloxycarbonyl", "substituted or unsubstituted aromatic heterocyclylalkyloxyalkyl", and "substituted or unsubstituted aromatic heterocyclylcarbamoyl" is(are) same as the substituent(s) on the above "substituted or unsubstituted aromatic heterocyclyl".

The "non-aromatic heterocycle" part of "non-aromatic heterocyclyloxy", "non-aromatic heterocyclylcarbonyl", "non-aromatic heterocyclyloxycarbonyl", "non-aromatic heterocycle sulfanyl", "non-aromatic heterocycle sulfonyl", "non-aromatic heterocyclylalkyl", "non-aromatic heterocyclylalkyloxy", "non-aromatic heterocyclylalkylsulfanyl", "non-aromatic heterocyclylalkyloxycarbonyl", "non-aromatic heterocyclylalkyloxyalkyl", "non-aromatic heterocyclylcarbamoyl", and "non-aromatic heterocycle amino" is same as the above "non-aromatic heterocyclyl".

The substituent(s) on the "non-aromatic heterocycle" part of "substituted or unsubstituted non-aromatic heterocyclyloxy", "substituted or unsubstituted non-aromatic heterocyclylcarbonyl", "substituted or unsubstituted non-aromatic heterocyclyloxycarbonyl", "substituted or unsubstituted non-aromatic heterocycle sulfanyl", "substituted or unsubstituted non-aromatic heterocycle sulfonyl", "substituted or unsubstituted non-aromatic heterocyclylalkyl", "substituted or unsubstituted non-aromatic heterocyclylalkyloxy", "substituted or unsubstituted non-aromatic heterocyclylalkylsulfanyl", "substituted or unsubstituted non-aromatic heterocyclylalkyloxycarbonyl", "substituted or unsubstituted non-aromatic heterocyclylalkyloxyalkyl", and "substituted or unsubstituted non-aromatic heterocyclylcarbamoyl" is(are) same as the substituent(s) on the above "substituted or unsubstituted non-aromatic heterocyclyl".

The "alkyl" part of "aromatic carbocyclylalkyl", "non-aromatic carbocyclylalkyl", "aromatic heterocyclylalkyl", "non-aromatic heterocyclylalkyl", "aromatic carbocyclylalkyloxy", "non-aromatic carbocyclylalkyloxy", "aromatic heterocyclylalkyloxy", "non-aromatic heterocyclylalkyloxy", "aromatic carbocyclylalkylsulfanyl", "non-aromatic carbocyclylalkylsulfanyl", "aromatic heterocyclylalkylsulfanyl", "non-aromatic heterocyclylalkylsulfanyl", "aromatic carbocyclylalkyloxycarbonyl", "non-aromatic carbocyclylalkyloxycarbonyl", "aromatic heterocyclylalkyloxycarbonyl", "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl", and "non-aromatic heterocyclylalkyloxyalkyl" is same as the above "alkyl".

The substituent(s) of the "alkyl" part of "substituted or unsubstituted aromatic carbocyclylalkyl", "substituted or unsubstituted non-aromatic carbocyclylalkyl", "substituted or unsubstituted aromatic heterocyclylalkyl", "substituted or unsubstituted non-aromatic heterocyclylalkyl", "substituted or unsubstituted aromatic carbocyclylalkyloxy", "substituted or unsubstituted non-aromatic carbocyclylalkyloxy", "substituted or unsubstituted aromatic heterocyclylalkyloxy", "substituted or unsubstituted non-aromatic heterocyclylalkyloxy", "substituted or unsubstituted aromatic carbocyclylalkylsulfanyl", "substituted or unsubstituted non-aromatic carbocyclylalkylsulfanyl", "substituted or unsubstituted aromatic heterocyclylalkylsulfanyl", "substituted or unsubstituted non-aromatic heterocyclylalkylsulfa-nyl", "substituted or unsubstituted aromatic carbocyclylalkyloxycarbonyl", "substituted or unsubstituted non-aromatic carbocyclylalkyloxycarbonyl", "substituted or unsubstituted aromatic heterocyclylalkyloxycarbonyl", "substituted or unsubstituted non-aromatic heterocyclylalkyloxycarbonyl", "substituted or unsubstituted aromatic carbocyclylalkyloxyalkyl", "substituted or unsubstituted non-aromatic carbocyclylalkyloxyalkyl", "substituted or unsubstituted aromatic heterocyclylalkyloxyalkyl", and "substituted or unsubstituted non-aromatic heterocyclylalkyloxyalkyl" is(are) same as the substituent(s) on the above "substituted or unsubstituted alkyl".

"Aromatic carbocyclyloxy" means a group wherein "aromatic carbocycle" is bonded to an oxygen atom. For example, it includes phenyloxy, naphthyloxy and the like.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocyclyloxycarbonyl" means a group wherein the above "aromatic carbocyclyloxy" is bonded to a carbonyl group. For example, it includes phenyloxycarbonyl, naphthyloxycarbonyl and the like.

"Aromatic carbocycle sulfanyl" means a group wherein a hydrogen atom attached to a sulfur atom of a sulfanyl group is replaced with the above "aromatic carbocycle". For example, it includes phenylsulfanyl, naphthylsulfanyl and the like.

"Aromatic carbocycle sulfonyl" means a group wherein "aromatic carbocycle" is bonded to a sulfonyl group. For example, it includes phenylsulfonyl, naphthylsulfonyl and the like.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocyclyloxycarbonyl" means a group wherein the above "non-aromatic carbocyclyloxy" is bended to a carbonyl group. For example, it includes cyclopropyloxycarbonyl, cyclohexyloxycarbonyl, cyclohexenyloxycarbonyl and the like.

"Non-aromatic carbocycle sulfanyl" means a group wherein a hydrogen atom attached to a sulfur atom of a sulfanyl group is replaced with the above "non-aromatic carbocycle". For example, it includes cyclopropylsulfanyl, cyclohexylsulfanyl, cyclohexenylsulfanyl and the like.

"Non-aromatic carbocycle sulfonyl" means a group wherein "non-aromatic carbocycle" is bonded to a sulfonyl group. For example, it includes cyclopropylsulfonyl, cyclohexylsulfonyl, cyclohexenylsulfonyl and the like.

"Aromatic heterocyclyloxy" means a group wherein "aromatic heterocycle" is bonded to an oxygen atom. For example, it includes pyridyloxy, oxazolyloxy and the like.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocyclyloxycarbonyl" means a group wherein the above "aromatic heterocyclyloxy" is bonded to a carbonyl group. For example, it includes pyridyloxycarbonyl, oxazolyloxycarbonyl and the like.

"Non-aromatic heterocyclyloxy" means a group wherein "non-aromatic heterocycle" is bonded to an oxygen atom. For example, it includes piperidinyloxy, tetrahydrofuryloxy and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocyclyloxycarbonyl" means a group wherein the above "non-aromatic heterocyclyloxy" is bonded to a carbonyl group. For example, it includes piperidinyloxycarbonyl, tetrahydrofuryl oxycarbonyl and the like.

"Non-aromatic heterocycle sulfanyl" means a group wherein a hydrogen atom attached to a sulfer atom of a sulfanyl group is replaced with "non-aromatic heterocycle". For example, it includes piperidinylsulfanyl, tetrahydrofurylsulfanyl and the like.

"Non-aromatic heterocycle sulfonyl" means a group wherein "non-aromatic heterocycle" is bonded to a sulfonyl group. For example, it includes piperidinylsulfonyl, tetrahydrofurylsulfonyl and the like.

"Aromatic carbocyclylalkyl" or "aralkyl" means an alkyl substituted with one or more "aromatic carbocyclyl" described above. For example, it includes benzyl, phenethyl, phenylpropenyl, benzhydryl, trityl, naphthylmethyl, a group of the formula:

[Chemical formula 40]

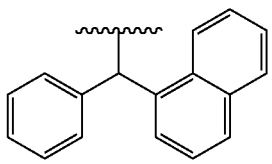

and the like.

A preferred embodiment of "aromatic carbocyclylalkyl" is benzyl, phenethyl or benzhydryl.

"Non-aromatic carbocyclylalkyl" means an alkyl substituted with one or more "non-aromatic carbocyclyl" described above. In addition, "non-aromatic carbocyclylalkyl" also includes "non-aromatic carbocyclylalkyl" wherein the alky part is substituted with the above "aromatic carbocyclyl". For example, it includes cyclopropylmethyl, cyclobutylmethyl, cyclopentylmethyl, cyclohexylmethyl, a group of the formula:

[Chemical formula 41]

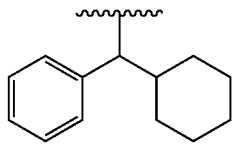

and the like.

"Aromatic heterocyclylalkyl" means an alkyl substituted with one or more "aromatic heterocyclyl" described above. in addition, "aromatic heterocyclylalkyl" also includes "aromatic heterocyclylalkyl" wherein the alkyl part is substituted with the above "aromatic carbocyclyl" and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula:

[Chemical formula 42]

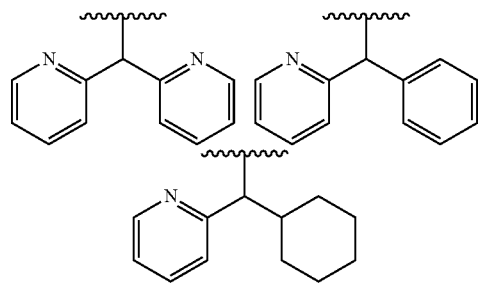

and the like.

"Non-aromatic heterocyclylalkyl" means an alkyl substituted with one or more "non-aromatic heterocyclyl" described above. In addition, "non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". For example, tetrahydropyranylmethyl, morpholinylethyl, piperidinylmethyl, piperazinylmethyl, groups of the formula:

[Chemical formula 43]

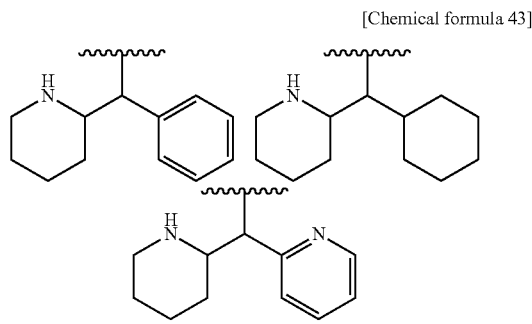

and the like.

"Aromatic carbocyclylalkyloxy" means an alkyloxy substituted with one or more "aromatic carbocyclyl" described above. For example, it includes benzyloxy, phenethyloxy, phenylpropenyloxy, benzhydryloxy, triryloxy, naphthylmethyloxy, a group of the formula:

[Chemical formula 44]

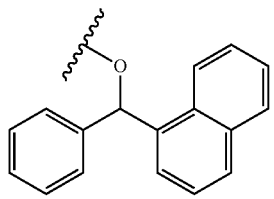

and the like.

"Non-aromatic carbocyclylalkyloxy" means an alkyloxy substituted with one or more "non-aromatic carbocyclyl" described above. In addition, "non-aromatic carbocyclylalkyloxy" also includes "non-aromatic carbocyclylalkyloxy" wherein the alkyl part is substituted with the above "aromatic carbocyclyl". For example, it includes cyclopropylmethyloxy, cyclobutylmethyloxy, cyclopentylmethyloxy, cyclohexylmethyloxy, a group of the formula:

[Chemical formula 45]

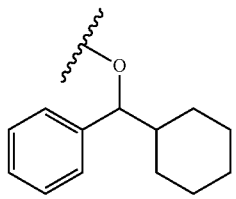

and the like.

"Aromatic heterocyclylalkyloxy" means an alkyloxy substituted with one or more "aromatic heterocyclyl" described above. In addition, "aromatic heterocyclylalkyloxy" also includes "aromatic heterocyclylalkyloxy" wherein the alkyl part is substituted with the above "aromatic carbocyclyl" and/or "non-aromatic carbocyclyl". For example, it includes pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, groups of the formula:

[Chemical formula 46]

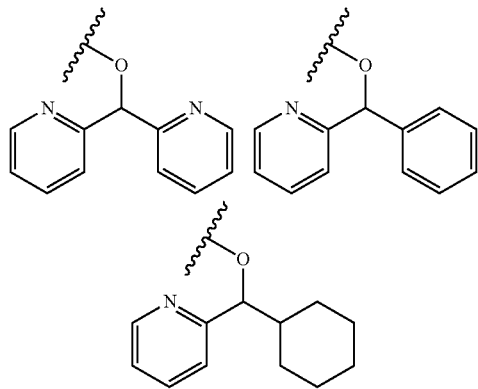

and the like.

"Non-aromatic heterocyclylalkyloxy" means an alkyloxy substituted with one or more "non-aromatic heterocyclyl" described above. In addition, "non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piperazinylmethyloxy, groups of the formula:

[Chemical formula 47]

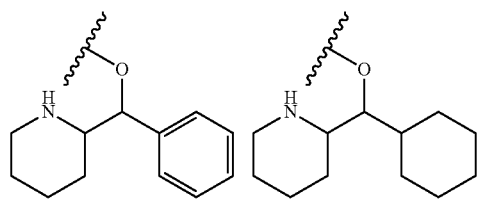

-continued

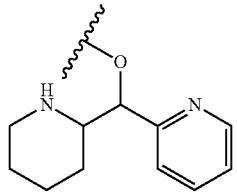

and the like.

"Aromatic carbocyclylalkylsulfanyl" means an alkylsulfanyl substituted with one or more "aromatic carbocyclyl" described above. For example, it includes benzylsulfanyl, phenethylsulfanyl, phenylpropynylsulfanyl, benzhydrylsulfanyl, tritylsulfanyl, naphthylmethylsulfanyl and the like.

"Non-aromatic carbocyclylalkylsulfanyl" means an alkylsulfanyl substituted with one or more "non-aromatic carbocyclyl" described above. In addition, "non-aromatic carbocyclylalkylsulfanyl" also includes "non-aromatic carbocyclylalkyl sulfanyl" wherein the alkyl part is substituted with the above "aromatic carbocyclyl". For example, it includes cyclopropylmethylsulfanyl, cyclobutylmethylsulfanyl, cyclopentylmethylsulfanyl, cyclohexylmethylsulfanyl and the like.

"Aromatic heterocyclylalkylsulfanyl" means an alkylsulfanyl substituted with one or more "aromatic heterocyclyl" described above. In addition, "aromatic heterocyclylalkylsulfanyl" also includes "aromatic heterocyclylalkylsulfanyl" wherein the alkyl part is substituted with the above "aromatic carbocyclyl" and/or "non-aromatic carbocyclyl". For example, it includes pyridylmethylsulfanyl, furanylmethylsulfanyl, imidazolylmethylsulfanyl, indolylmethylsulfanyl, benzothiophenylmethylsulfanyl, oxazolylmethylsulfanyl, isoxazolylmethylsulfanyl, thiazolylmethylsulfanyl, isothiazolylmethylsulfanyl, pyrazolylmethylsulfanyl, isopyrazolylmethylsulfanyl, pyrrolidinylmethylsulfanyl, benzoxazolylmethylsulfanyl and the like.

"Non-aromatic heterocyclylalkyl sulfanyl" means an alkylsulfanyl substituted with one or more "non-aromatic heterocyclyl" described above. In addition, "non-aromatic heterocyclylalkylsulfanyl" also includes "non-aromatic heterocyclylalkylsulfanyl" wherein the alkyl part is substituted with the above "aromatic carbocyclyl", "non-aromatic carbocyclyl" and/or "aromatic heterocyclyl". For example, it includes tetrahydropyranylmethylsulfanyl, morpholinylethylsulfanyl, piperidinylmethylsulfanyl, piperazinylmethylsulfanyl and the like.

"Aromatic carbocyclylalkyloxycarbonyl" means an alkyloxycarbonyl is substituted with one or more "aromatic carbocyclyl" described above. For example, it includes benzyloxycarbonyl, phenetyloxycarbonyl, phenylpropynyloxycarbonyl, benzhydryloxycarbonyl, trityloxycarbonyl, naphthylmethyloxycarbonyl, a group of the formula:

[Chemical formula 48]

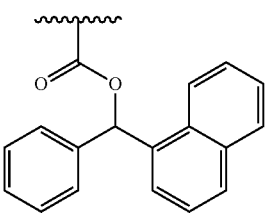

and the like.

"Non-aromatic carbocyclylalkyloxycarbonyl" means an alkyloxycarbonyl substituted with one or more "non-aromatic carbocyclyl" described above. In addition, "non-aromatic carbocyclylalkyloxycarbonyl" also includes "non-aromatic carbocyclylalkyloxycarbonyl" wherein the alkyl part is substituted with the above "aromatic carbocyclyl". For example, it includes cyclopropylmethyloxycarbonyl, cyclobutylmethyloxycarbonyl, cyclopentylmethyloxycarbonyl, cyclohexylmethyloxycarbonyl, a group of the formula:

[Chemical formula 49]

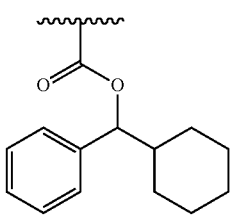

and the like.

"Aromatic heterocyclylalkyloxycarbonyl" means an alkyloxycarbonyl substituted with one or more "aromatic heterocyclyl" described above. In addition, "aromatic heterocyclylalkyloxycarbonyl" also includes "aromatic heterocyclylalkyloxycarbonyl" wherein the alkyl part is substituted with the above "aromatic carbocyclyl" and/or "non-aromatic carbocyclyl". For example, it includes pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, groups of the formula:

[Chemical formula 50]

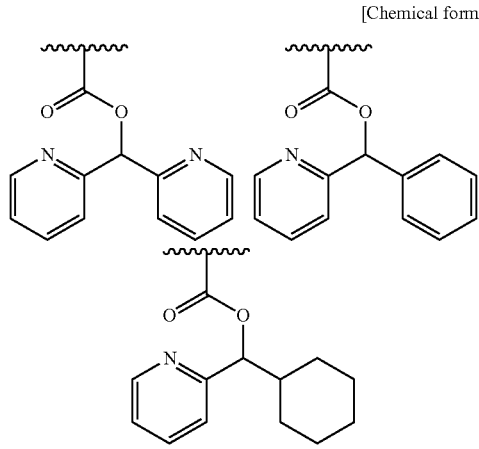

and the like.

"Non-aromatic heterocyclylalkyloxycarbonyl" means an alkyloxycarbonyl substituted with one or more "non-aromatic heterocyclyl" described above. In addition, "non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piperazinylmethyloxy, groups of formula:

[Chemical formula 51]

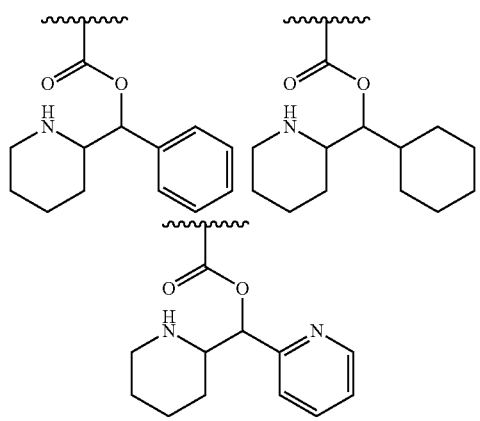

and the like.

"Aromatic carbocyclylalkyloxyalkyl" means an alkyloxyalkyl substituted with one or more "aromatic carbocyclyl". For example, it includes benzyloxymethyl, phenethyloxymethyl, phenylpropynyloxymethyl, benzhydryloxymethyl, trityloxymethyl, naphthylmethyloxymethyl, a group of the formula:

[Chemical formula 52]

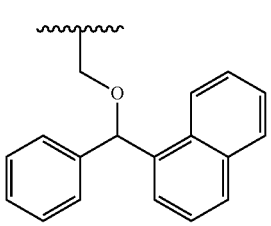

and the like.

"Non-aromatic carbocyclylalkyloxyalkyl" means an alkyloxyalkyl substituted with one or more "non-aromatic carbocyclyl". In addition, "non-aromatic carbocyclylalkyloxyalkyl" includes "non-aromatic carbocyclylalkyloxyalkyl" wherein the alkyl part is substituted with the above "aromatic carbocyclyl". For example, it includes cyclopropylmethyloxymethyl, cyclobutylmethyloxymethyl, cyclopentylmethyloxymethyl, cyclohexylmethyloxymethyl, a group of the formula:

[Chemical formula 53]

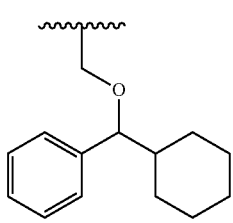

and the like.

"Aromatic heterocyclylalkyloxyalkyl" means an alkyloxyalkyl substituted with one or more "aromatic heterocyclyl" described above. In addition, "aromatic heterocyclylalkyloxyalkyl" also includes "aromatic heterocyclylalkyloxyalkyl" wherein the alkyl part attached to "non-aromatic carbocyclyl" is substituted with the above "aromatic carbocyclyl" and/or "non-aromatic carbocyclyl". For example, it includes pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups of the formula:

[Chemical formula 54]

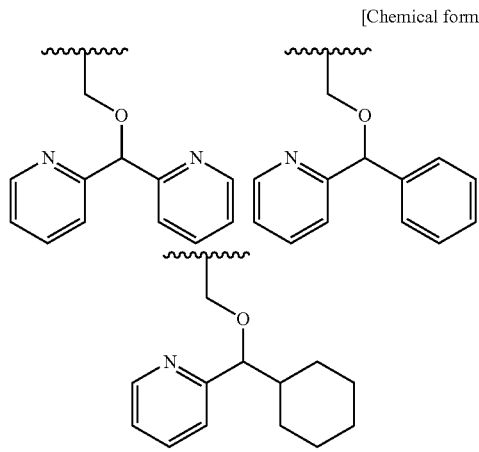

and the like.

"Non-aromatic heterocyclylalkyloxyalkyl" means an alkyloxyalkyl substituted with one or more "non-aromatic heterocyclyl" described above. In addition, "non-aromatic heterocyclylalkyloxy" also includes "non-aromatic heterocyclylalkyloxy" wherein the alkyl part attached to "non-aromatic heterocycle" is substituted with the above "aromatic carbocyclyl", "non-aromatic carbocyclyl" and/or "aromatic heterocyclyl". For example, tetrahydropyranylmethyloxymethyl, morpholinylethyloxymethyl, piperidinylmethyloxymethyl, piperazinylmethyloxymethyl, groups of the formula:

[Chemical formula 55]

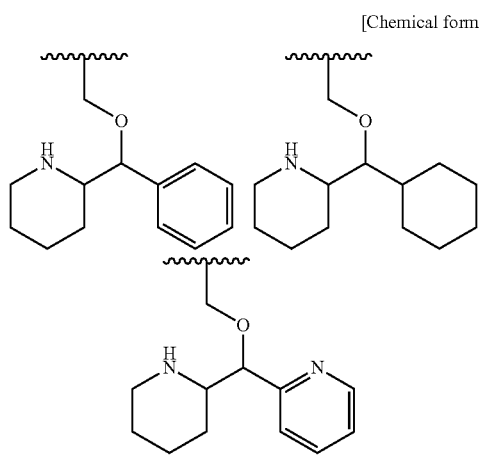

and the like.

The present invention provides a variety of compounds encompassed by the following compounds (I) or (I').

[Chemical formula 56]

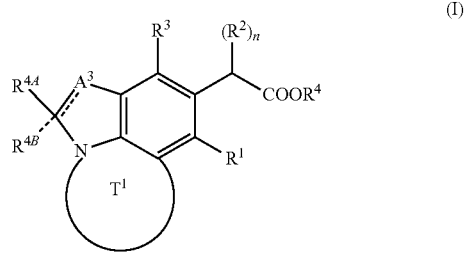

Preferred embodiments of each group are exemplified as follows. The compounds of the possible combinations as follows are preferred.

$R^1$ is hydrogen, halogen, or substituted or unsubstituted alkyl, more preferably halogen or alkyl, and further preferably alkyl.

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted non-aromatic carbocyclyloxy (preferably, substituted or unsubstituted cycloalkyloxy, or substituted or unsubstituted cycloalkenyloxy. Preferable is substituted or unsubstituted alkyl, substituted or unsubstituted alkenyl, substituted or unsubstituted alkyloxy, or substituted or unsubstituted alkenyloxy. More preferable is substituted or unsubstituted alkyloxy, substituted or unsubstituted alkenyloxy, particularly preferable is alkyloxy. Preferable alkyloxy is C1 to C6 or C1 to C4 linear or branched alkyloxy, more preferable is t-butyloxy. Preferred embodiment of the substituent(s) of "substituted or unsubstituted" in R2 include hydroxy, alkyloxy, halogen, haloalkyl, haloalkyloxy, amino, alkylamino and the like.

n is 1 or 2, preferably 1.

When n is 1, $R^2$ preferably takes the following steric structure.

[Chemical formula 57]

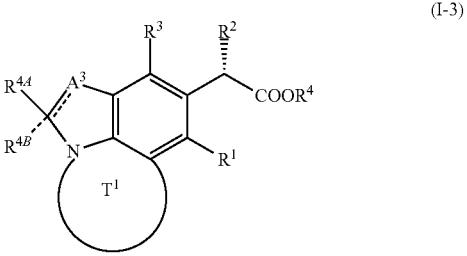

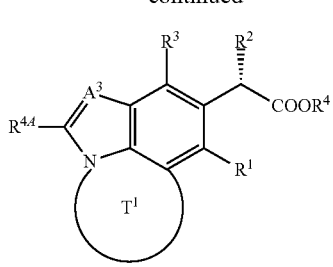

(I'-3)

R³ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. Preferably it is substituted or unsubstituted aromatic carbocyclyl. The substituent on these ring are exemplified by the following $R^{31}$ to $R^{35}$.

R³ is preferably substituted or unsubstituted aromatic carbocyclyl or substituted or unsubstituted non-aromatic cyclyl, preferably 5 to 7-membered ring, and may be fused and have a bridged structure. The part of fused ring is 5 to 10-membered, may be monocyclic or bicyclic. "Substituted or unsubstituted aromatic carbocyclyl" includes phenyl group exemplified by the following formula.

Another preferable embodiment of R³ is aromatic carbocyclyl which is optionally substituted with halogen, alkyl, and/or alkyloxy, non-aromatic carbocyclyl which is optionally substituted with halogen, alkyl, and/or alkyloxy, aromatic heterocyclyl which is optionally substituted with halogen, alkyl, and/or alkyloxy, or non-aromatic heterocyclyl which is optionally substituted with halogen, alkyl, and/or alkyloxy. More preferable embodiment of R³ is halogen, aromatic carbocyclyl which is optionally substituted with alkyl, and/or alkyloxy, or non-aromatic heterocyclyl which is optionally substituted with halogen, alkyl, and/or alkyloxy.

[Chemical formula 58]

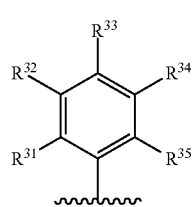

$R^{31}$, $R^{32}$, $R^{33}$, $R^{34}$ and $R^{35}$ are each independently, preferably hydrogen atom, halogen, hydroxy, amino, alkyl, cycloalkyl, alkenyl, alkynyl, haloalkyl, alkyloxy, alkenyloxy, alkynyloxy haloalkyl, haloalkyloxy, carboxy, carbamoyl, or alkylamino, more preferably hydrogen atom, halogen, hydroxy, amino, alkyl or alkyloxy, further preferably hydrogen atom, fluoro, chloro, bromo, hydroxy, amino, methyl, ethyl or methyloxy, particularly preferably hydrogen atom, halogen, hydroxy, methyl or ethyl.

$R^{31}$ and $R^{32}$, $R^{32}$ and $R^{33}$, $R^{33}$ and $R^{34}$, and $R^{34}$ and $R^{35}$ may be each independently, taken together with an adjacent atom to form substituted or unsubstituted aromatic carbocycle, substituted or unsubstituted non-aromatic carbocycle, substituted or unsubstituted aromatic heterocycle or substituted or unsubstituted non-aromatic heterocycle. These rings are preferably 5 to 8-membered ring, more preferably 5 or 6-membered ring, further preferably 6-membered ring.

Non-aromatic carbocycle and non-aromatic heterocycle in R³ is optionally substituted with "oxo" as same above.

The substituent(s) on the ring of "substituted or unsubstituted aromatic carbocycle", "substituted or unsubstituted non-aromatic carbocycle", "substituted or unsubstituted aromatic heterocycle", "substituted or unsubstituted non-aromatic heterocycle" in R³ include the substituent on the ring of the above "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl".

The two groups which are not adjacent to each other in $R^{31}$, $R^{32}$, $R^{33}$, $R^{34}$ and $R^{35}$ may be taken together to form a bridged structure. The bridged structure includes substituted or unsubstituted alkylene and substituted or unsubstituted alkenylene. The substituent(s) of "substituted or unsubstituted" is(are) preferably alkyl, cycloalkyl, cycloalkylalkyl, alkoxy, alkoxyalkyl, halogen, halogenated alkyl, amino, alkylamino, hydroxy, oxo, carboxy, carbamoyl or phenyl, more preferably halogen, alkyl, alkoxy, amino, hydroxy and/or oxo, further preferably methyl, ethyl, F, Br, amino, hydroxy and the like.

R³ is more preferably phenyl or non-aromatic carbocycle, which may be fused with one or two carbocycle or heterocycle (e.g.: 5 to 7-membered ring). More preferred example is cyclyl exemplified as below. The ring of carbocycle, heterocycle, phenyl, non-aromatic carbocycle, or the following cyclyl may have same or different 1 to 4 substituent(s) (e.g.: halogen, hydroxy, alkoxy, amino, mono- or di-alkylamino, alkyl, halogenated alkyl, hydroxy alkyl, amino alkyl, oxo, cyano).

R³ is further preferably the following groups.

[Chemical formula 59]

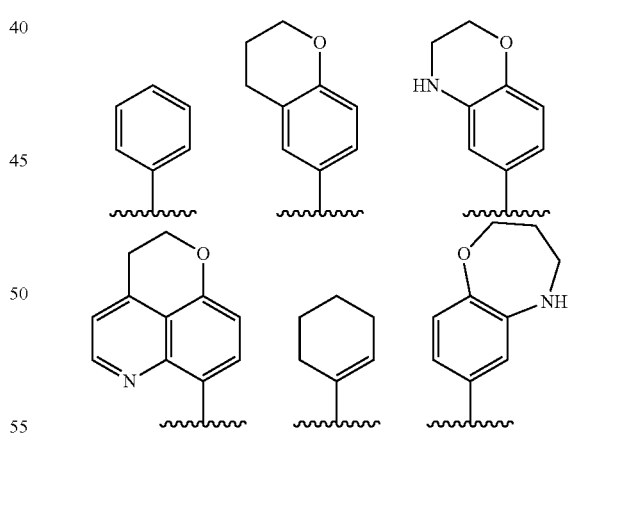

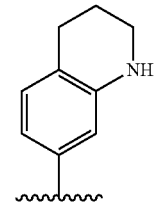

-continued

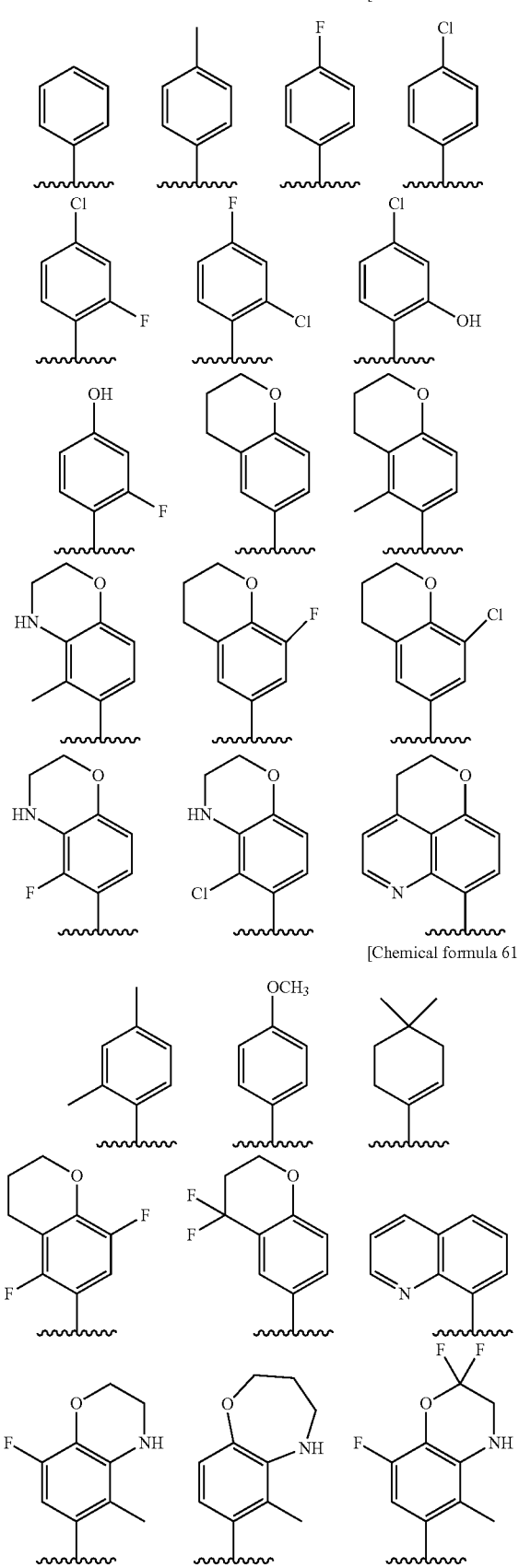

[Chemical formula 60]

[Chemical formula 61]

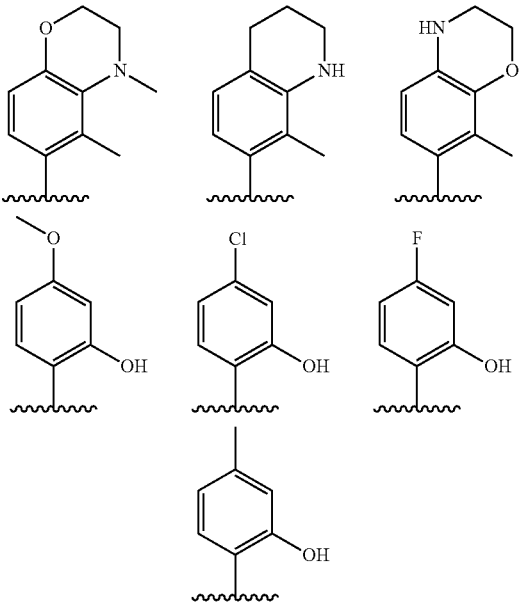

-continued $R^3$ may be a cyclic amine having a bond on the N atom, preferably saturated cyclic amine. The cyclic amine is 5 to 7-membered heterocycle which may be substituted, fused and/or bridged, and it may contain N atom, O atom and/or S atom as an annular atom. The substituent(s) is(are) preferably alkyl, cycloalkyl, oxo, hydroxy, halogen, alkoxy and the like. The cyclic amine is exemplified as follows.

[Chemical formula 62]

(1)

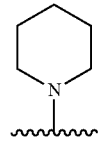

(2)

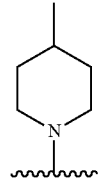

(3)

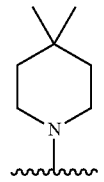

(4)

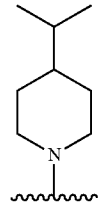

-continued (5) 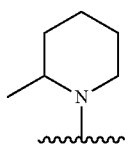

(6) 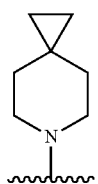

(7) 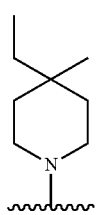

(8) 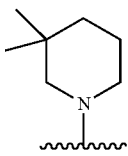

(9) 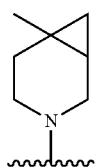

(10) 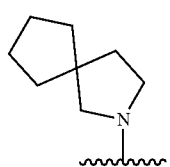

(11) 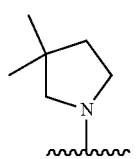

(12) 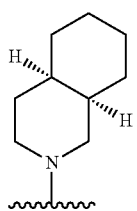

-continued

(13) 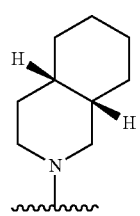

(14) 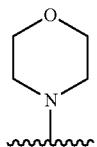

(15) 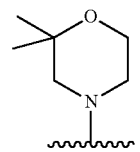

(16) 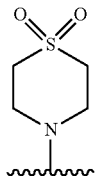

$R^3$ may be substituted or unsubstituted non-aromatic carbocyclyl having one or two double bond(s) in the ring, or substituted or unsubstituted non-aromatic heterocyclyl having one or two double bond(s) in the ring. The carbocyclyl or heterocyclyl is preferably 5 to 7-membered ring. The substituent(s) is(are) preferably alkyl, cycloalkyl, oxo, hydroxy, halogen, alkoxy and the like.

[Chemical formula 63]

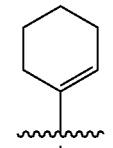

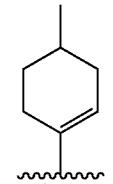

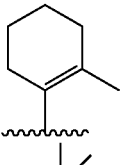

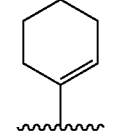

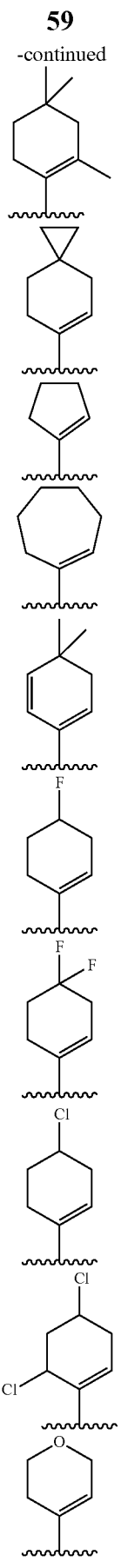
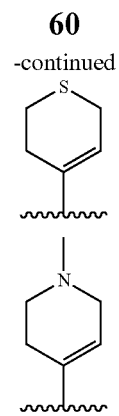
More preferably, R³ may be selected from the following groups.
[Chemical formula 64]
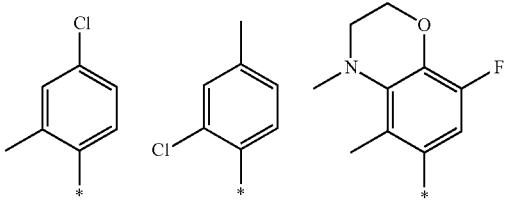
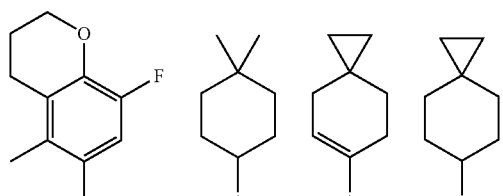
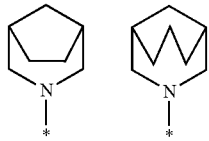
More preferable, R³ may be selected from the following groups.
[Chemical formula 65]
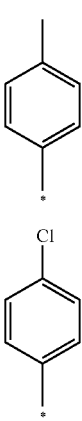

-continued

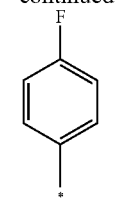
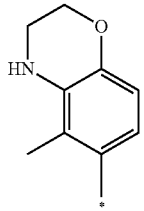
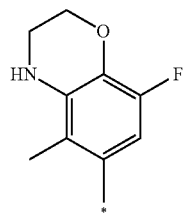
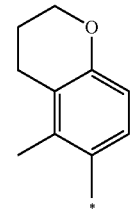
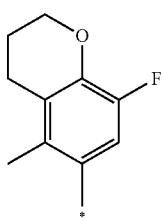
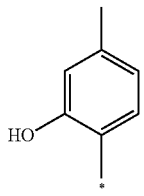
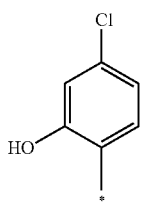
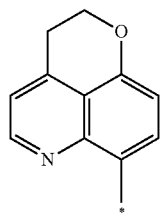

-continued

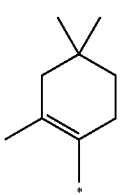
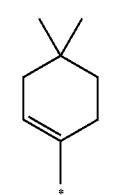

One embodiment of the isomers of the compound (I), (I'), (I-1), (I-2), (I-3), (I'-3), (I-1-1), (I-1A), (I-AA), (I'-1A), (A-1-1A), (I-1-1B), (I-1-1C), (I-1-1D), (I-1-1E) and (I-2-1) includes stereoisomers identified by the direction of $R^3$ ring, but the present invention includes all of those isomers and racemates.

$R^4$ is hydrogen or a carboxyl protecting group, preferably hydrogen. The compound, wherein $R^4$ is other than hydrogen and can be converted to hydrogen by hydrolysis or deprotection reaction of a carboxyl protecting group, is particularly useful as a synthetic intermediate. Also the compound, wherein $R^4$ is other than hydrogen and can be converted to hydrogen inside the body, is also useful as a prodrug. Examples of the carboxyl protecting group are preferably alkyl (e.g.: methyl, ethyl, t-butyl) and aralkyl (e.g.: benzyl), more preferably C1 to C4 alkyl.

$A^3$ is $CR^{3A}$, $CR^{3A}R^{3B}$, N or $NR^{3C}$, preferably $CR^{3A}$ or N, more preferably $CR^{3A}$.

In another embodiment, the following compounds are preferable.

[Chemical formula 66]

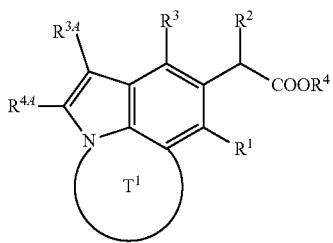

(I-1)

-continued

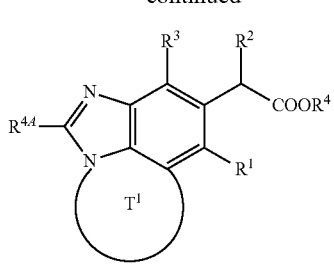
(I-2)

wherein each definition is the same as defined above.

$R^{3A}$, $R^{3B}$, $R^{4A}$ and $R^{4B}$ are each independently hydrogen, halogen, cyano, substituted or unsubstituted alkyl, substituted or unsubstituted alkynyl, or substituted or unsubstituted non-aromatic carbocyclyl (preferably substituted or unsubstituted cycloalkyl). Examples of the substituent(s) of "substituted or unsubstituted" are same or different 1 to 4, preferably 1 or 2 substituent(s) selected from alkyloxy, hydroxy, halogen, haloalkyl, haloalkyloxy, amino, alkylamino, and aromatic carbocyclylalkyloxy.

$R^{3C}$ is hydrogen, substituted or unsubstituted alkyl, or substituted or unsubstituted non-aromatic carbocyclyl.

More preferably, $R^{3A}$ is hydrogen, halogen, alkyl, or cyano, and $R^{4A}$ is alkyl substituted with hydrogen, halogen, cyano, alkyl, haloalkyl, hydroxy or alkyloxy, alkynyl, or 3 to 6-membered cycloalkyl.

$R^{3A}$ is more preferably hydrogen or halogen. $R^{3A}$ is particularly preferably hydrogen, fluoro or chloro. $R^{4A}$ is more preferably alkyl substituted with halogen, cyano, alkyl, haloalkyl, hydroxy or alkyloxy, alkynyl, or 3 to 6-membered cycloalkyl. $R^{4A}$ is particularly preferably halogen, cyano, C1-3 alkyl, haloC1-3 alkyl, C2-3 alkynyl, or 3 to 4-membered cycloalkyl.

In another embodiment, the following compounds are preferable.

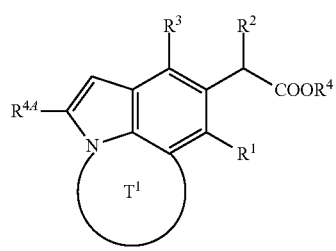
(I-1A)

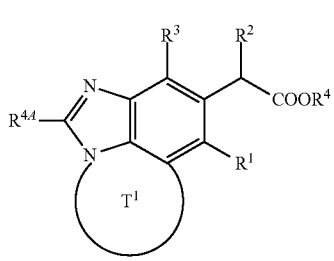
(I-2)

wherein each definition is the same as defined above.

$T^1$ ring is substituted or unsubstituted nitrogen-containing non-aromatic heterocycle. $T^1$ ring is preferably 5 to 12-membered ring, more preferably 5 to 10-membered ring. $T^1$ ring is further preferably 5 to 8-membered ring. The annular atoms of $T^1$ ring preferably contain one or two N atom(s), one or two N atom(s) and one O atom, or one or two N atom(s) and one S atom. Further preferably, the annular atoms of $T^1$ ring contain two N atoms, two N atoms and one S atom, or one N atom and one O atom. $T^1$ ring may be monocyclic, fused ring, or spiro ring, and further having a bridged structure. Preferable is 5 to 8-membered monocyclic ring, 9 to 12-membered fused ring, or 9 to 11-membered spiro ring, the ring may be further fused by C1-3 alkylene which optionally contain hetero atom(s).

The substituent(s) of $T^1$ ring are each independently oxo, hydroxy, halogen, amino, alkylamino, substituted or unsubstituted alkyl, substituted or unsubstituted alkenyl, substituted or unsubstituted alkynyl, —$COR^{a1}$, —$SOR^{a2}$, —$SO_2R^{a3}$, —$NR^{a4}R^{a5}$ ($R^{a1}$, $R^{a2}$, $R^{a3}$, $R^{a4}$ and $R^{a5}$ are each independently hydrogen, substituted or unsubstituted alkyl, substituted or unsubstituted alkenyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocycle sulfanyl, substituted or unsubstituted non-aromatic carbocycle sulfanyl, substituted or unsubstituted aromatic heterocycle sulfanyl, substituted or unsubstituted non-aromatic heterocycle sulfanyl, substituted or unsubstituted alkylcarbonyl, substituted or unsubstituted alkenylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, formyl, substituted or unsubstituted amino, or substituted or unsubstituted carbamoyl) or it is exemplified by same or different 1 to 4, preferably 1 to 2 substituent(s) selected from $R^a$, $R^b$, and $R^c$ described below.

Examples of the substituent(s) on the $T^1$ ring includes same or different 1 to 4, preferably 1 to 2 substituent(s) selected from alkyl, alkenyl, alkynyl, alkyloxy, hydroxy, alkyloxy alkyl, hydroxyalkyl, halogen, haloalkyl, haloalkyloxy, amino, alkylamino, dialkylamino, trialkylsilyl, non-aromatic carbocycle amino, substituted or unsubstituted phenyl (examples of the substituent(s): alkyl, alkyloxy, hydroxy, halogen), substituted or unsubstituted phenyloxy (examples of the substituent(s): alkyl, alkyloxy, hydroxy, halogen), substituted or unsubstituted benzyloxy (examples of the substituent: alkyl, alkyloxy, hydroxy, halogen), substituted or unsubstituted aromatic heterocyclyl (e.g.: 5 to 6-membered ring, (examples of the substituent(s): alkyl, alkyloxy, hydroxy, halogen)), substituted or unsubstituted non-aromatic heterocyclyl (e.g.: 4 to 6-membered ring, (examples of the substituent(s): alkyl, alkyloxy, hydroxy, halogen))), and non-aromatic heterocycle amino.

Another embodiment of the substituent(s) on the $T^1$ ring includes each independently same or different 1 to 4, preferably 1 to 2 substituent(s) selected from oxo, or $R^a$, $R^b$, and $R^c$ described below.

Another embodiment of the substituents on the $T^1$ ring are independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —$COR^{a1}$, —$COOR^{a1}$, —$SOR^{a2}$, —$SO_2R^{a3}$, —$CONR^{a4}R^{a5}$, —$CSNR^{a4}R^{a5}$, —$CCOONR^{a4}R^{a5}$, or —$C(NR^{a6})NR^{a4}R^{a5}$; wherein, $R^{a1}$, $R^{a2}$, and $R^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{a4}$ and $R^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

Two atoms constituting the nitrogen-containing non-aromatic heterocycle of $T^1$ ring, which are not adjacent to one another, may be bridged by substituted or unsubstituted alkylene containing one or more groups selected from —O—, —$NR^a$—, —S—, —CO—, —SO—, and —$SO_2$— at arbitrary position, substituted or unsubstituted alkenylene containing one or more groups selected from —O—, —$NR^a$—, —S—, —CO—, —SO—, and —$SO_2$— at arbitrary position, substituted or unsubstituted alkynylene, or substituted or unsubstituted alkynylene containing one or more groups selected from —O—, —$NR^a$—, —S—, —CO—, —SO—, and —$SO_2$— at arbitrary position. Examples of substituent(s) on the alkylene, alkenylene or alkynylene include methyl, ethyl, halogen, hydroxy, alkyloxy, haloalkyl, haloalkyloxy, amino, methylamino, carbamoyl, phenyl or the like.

$T^1$ ring preferably includes a structure which is exemplified below.

[Chemical formula 67]

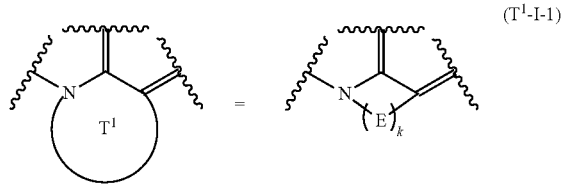

(T¹-I-1)

wherein each definition is the same as defined above.

E is each independently —$NR^a$—, —O—, —S—, —$SO_2$—, —SO—, or —$CR^bR^c$—. More preferred E is each independently —$NR^a$—, —O—, or —$CR^bR^c$—.

$R^a$ is hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —$COR^{a1}$, —$SOR^{a2}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$, wherein $R^{a1}$, $R^{a2}$, and $R^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^{a4}$ and $R^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. Examples of substituents of $R^a$ include alkyl, alkenyl, alkynyl, alkyloxy, hydroxy, alkyloxyalkyl, hydroxyalkyl, halogen, haloalkyl, haloalkyloxy, amino, alkylamino, dialkylamino, aminoalkyl, alkyloxyalkyl, alkylsulfonyl aminoalkyl, alkylcarbonylamino, alkylcarbonyl aminoalkyl, alkyloxyalkyloxycarbonylamino, alkylaminoalkyl, dialkyl aminoalkyl, amino alkyloxy, alkylamino alkyloxy, dialkylaminoalkyloxy, dialkylaminoalkyloxyalkyl, alkylcarbonylamino, carbamoyl, alkylcarbamoyl, dialkylcarbamoyl, benzyl, halogenated benzyl, aromatic carbocyclyl which is optionally substituted with halogen, alkyl, alkyloxy, cycloalkyl and/or haloalkyl, non-aromatic carbocyclyl which is optionally substituted with halogen, alkyl, alkyloxy, oxo and/or haloalkyl, aromatic heterocyclyl which is optionally substituted with halogen, alkyl, alkenyl, hydroxyalkyl, alkyloxy, cycloalkyl, non-aromatic carbocyclyl, non-aromatic heterocyclyl, and for haloalkyl, non-aromatic heterocyclyl which is optionally substituted with halogen, alkyl, alkyloxy, oxo and/or haloalkyl, aromatic carbocyclylalkyl which is optionally substituted with halogen, alkyl, and/or haloalkyl, non-aromatic carbocycle which is optionally substituted with halogen, alkyl, and/or haloalkyl, aromatic heterocyclylalkyl which is optionally substituted with halogen, alkyl, and/or haloalkyl, non-aromatic heterocyclylalkyl which is optionally substituted with halogen, alkyl, and/or haloalkyl, non-aromatic heterocyclyl which is optionally substituted with alkylhalogen, non-aromatic carbocycle amino, non-aromatic heterocyclylalkyl which is optionally substituted with oxo, halogen, and/or alkyl, trialkylsilyl. The substituents may be present one to four. When a number of the substituents are present, they may be same or different.

$R^a$ is preferably alkyl substituted with hydrogen, C1 to C6 alkyl, C1 to C6 haloalkyl, alkylamino or dialkylamino, substituted or unsubstituted aromatic heterocyclyl, substituted or unsubstituted non-aromatic heterocyclyl, substituted or unsubstituted non-aromatic heterocyclylalkyl, —$COR^{a1}$, or —$SO_2R^{a3}$. $R^{a1}$, $R^{a2}$, and $R^{a3}$ are each independently alkyl substituted with hydrogen, C1 to C6alkyl or alkylamino or dialkylamino. Preferred embodiments of $R^{a4}$ and $R^{a5}$ are each independently hydrogen, hydroxy, C1 to C6 alkyl, substituted or unsubstituted aromatic carbocyclyl (example of the substituent(s): halogen, alkyl, alkyloxy, haloalkyl, amino, monoalkylamino, dialkylamino etc.), or substituted or unsubstituted aromatic heterocyclyl (example of the substituent(s): halogen, alkyl, alkyloxy, haloalkyl, amino, monoalkylamino, dialkylamino etc.). Preferred embodiments of $R^{6a}$ are hydrogen or C1 to C6 alkyl.

Another embodiment of $R^a$ includes substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl. The substituent(s) of "substituted or unsubstituted" include(s) halogen, hydroxy, carboxy, cyano, ureido, substituted or unsubstituted amino, substituted or unsubstituted alkyl, substituted or unsubstituted alkyloxy, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted carbamoyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy and the like. Preferably it includes halogen, alkyl, alkyl oxy, haloalkyl, hydroxyalkyl, haloalkyloxy hydroxyalkyloxy, aminoalkyloxy, alkylsulfonylaminoalkyloxy, alkyloxyalkyloxy, trialkylsilyl alkyloxyalkyloxy, dialkylaminoalkyloxy, carbamoyl, monoalkyl carbamoyl which is optionally substituted with one or more group(s) selected from Substituent Group A, alkyloxycarbonylamino which is optionally substituted with one or more group(s) selected from Substituent Group A, dialkylcarbamoyl optionally substituted with one or more group(s) selected from Substituent Group A, alkylsulfonylamino optionally substituted with one or more group(s) selected from Substituent Group A, alkylcarbonylamino optionally substituted with one or more group(s) selected from Substituent Group A, aromatic carbocyclylalkyloxy optionally substituted with one or more group(s) selected from Substituent Group A, non-aromatic heterocyclylalkyloxy optionally substituted with one or more group(s) selected from Substituent Group A, aromatic heterocyclylalkyloxy optionally substituted with one or more group(s) selected from Substituent Group A, non-aromatic carbocyclyl optionally substituted with one or more group(s) selected from Substituent Group B, aromatic carbocyclyl optionally substituted with one or more group(s) selected from Substituent Group B, aromatic heterocyclyl optionally substituted with one or more group(s) selected from Substituent Group B, non-aromatic carbocyclyl optionally substituted with one or more group(s) selected from Substituent Group B, non-aromatic heterocyclyl optionally substituted with one or more group(s) selected from Substituent Group B, non-aromatic carbocyclyloxy optionally substituted with one or more group(s) selected from Substituent Group B, aromatic carbocyclyloxy optionally substituted with one or more group(s) selected from Substituent Group B, aromatic heterocyclyloxy optionally substituted with one or more group(s) selected from Substituent Group B, non-aromatic carbocyclyloxy optionally substituted with one or more group(s) selected from Substituent Group B, non-aromatic heterocyclyloxy optionally substituted with one or more group(s) selected from Substituent Group B and the like. When a number of the substituents are present, they may be same or different.

Substituent Group A: halogen, amino, hydroxy, carboxy, oxo, monoalkyl amino, dialkyl amino, carbamoyl, monoalkyl carbamoyl, dialkyl carbamoyl, alkyloxy, haloalkyloxy, sulfamoyl, monoalkyl sulfamoyl, dialkyl sulfamoyl, alkyloxyalkyloxy, haloalkyloxyalkyloxy, alkylcarbonyl, alkylsulfonyl, alkylcarbonylamino, alkylcarbonyl(alkyl)amino, alkylsulfonylamino, alkylsulfonyl(alkyl)amino, trialkylsilyl, alkyl and/or halogeno aromatic carbocyclyl, non-aromatic carbocyclyl optionally substituted with oxo, alkyl and/or halogen, alkyl and/or halogeno aromatic heterocyclyl, non-aromatic heterocyclyl optionally substituted with oxo, alkyl and/or halogen, alkyl and/or halogeno aromatic carbocyclyloxy, non-aromatic carbocyclyloxy optionally substituted with oxo, alkyl and/or halogen, alkyl and/or halogeno aromatic heterocyclyloxy, non-aromatic heterocyclyloxy optionally substituted with oxo, alkyl and/or halogen.

Substituent Group B: halogen, amino, hydroxy, carboxy, oxo, monoalkyl amino, dialkyl amino, carbamoyl, monoalkyl carbamoyl, dialkyl carbamoyl, alkyl, haloalkyl, alkyloxy, haloalkyloxy, hydroxyalkyl, amino alkyl, monoalkyl amino alkyl, dialkyl amino alkyl, sulfamoyl, monoalkyl sulfamoyl, dialkyl sulfamoyl, alkyl oxy alkyl, alkyl oxy alkyl oxy, haloalkyloxyalkyl, haloalkyloxyalkyloxy, alkylcarbonylamino, alkylcarbonyl(alkyl)amino, alkylsulfonylamino, alkylsulfonyl(alkyl)amino, alkyl and/or halogeno aromatic carbocyclyl, non-aromatic carbocyclyl optionally substituted with oxo, alkyl and/or halogen, alkyl and/or halogeno aromatic heterocyclyl, non-aromatic heterocyclyl optionally substituted with oxo, alkyl and/or halogen, alkyl and/or halogeno aromatic carbocyclyloxy, non-aromatic carbocyclyloxy optionally substituted with oxo, alkyl and/or halogen, alkyl and/or halogeno aromatic heterocyclyloxy, non-aromatic heterocyclyloxy optionally substituted with oxo, alkyl and/or halogen, alkyl and/or halogeno aromatic carbocyclylalkyl, non-aromatic carbocyclylalkyl optionally substituted with oxo, alkyl and/or halogen, alkyl and/or halogeno aromatic heterocyclylalkyl, non-aromatic heterocyclylalkyl optionally substituted with oxo, alkyl and/or halogen, alkyl and/or halogeno aromatic carbocyclylalkyloxy, non-aromatic carbocyclylalkyloxy optionally substituted with oxo, alkyl and/or halogen, alkyl and/or halogeno aromatic heterocyclylalkyloxy, non-aromatic heterocyclylalkyloxy optionally substituted with oxo, alkyl and/or halogen.

$R^b$ is each independently hydrogen, halogen, or substituted or unsubstituted alkyl, preferably hydrogen, halogen, or alkyl. Examples of the substituent(s) include halogen, hydroxy, alkyloxy, haloalkyl, haloalkyloxy, amino, alkylamino, carbamoyl, alkylcarbamoyl, phenyl, halogenated phenyl, aromatic carbocyclyl (e.g.: 6 or 10-membered ring), non-aromatic carbocyclyl (e.g.: 5 to 7-membered ring), aromatic heterocyclyl (e.g.: 5 or 6-membered ring), non-aromatic heterocyclyl (e.g.: 5 to 7-membered ring).

$R^c$ is each independently hydrogen, halogen, or substituted or unsubstituted alkyl, preferably hydrogen, halogen, or alkyl. Examples of the substituent(s) of "substituted or unsubstituted" are halogen, hydroxy, alkyloxy, haloalkyl, haloalkyloxy, amino, alkylamino, carbamoyl, alkyl carbamoyl, phenyl, halogenated phenyl, aromatic carbocyclyl (e.g.: 6 or 10-membered ring), non-aromatic carbocyclyl (e.g.: 5 to 7-membered ring), aromatic heterocyclyl (e.g.: 5 to 6-membered ring), non-aromatic heterocyclyl (e.g.: 5 to 7-membered ring) and the like.

$R^b$ and $R^c$ on the same carbon atom may be taken together with the bonding carbon atom to form carbonyl, substituted or unsubstituted non-aromatic carbocycle, or substituted or unsubstituted non-aromatic heterocycle;

two $R^b$s on adjacent carbon atoms may be taken together with the each bonded carbon atoms to form monocyclic substituted or unsubstituted non-aromatic carbocycle or monocyclic substituted or unsubstituted non-aromatic heterocycle;

$R^a$ on a nitrogen atom and $R^b$ on a carbon atom which is adjacent to the nitrogen atom may be taken together with each bonded annular atoms to form monocyclic substituted or unsubstituted aromatic heterocycle or monocyclic substituted or unsubstituted non-aromatic heterocycle;

two $R^b$s on two carbon atoms which are not adjacent to each other may be taken together to form substituted or unsubstituted alkylene, substituted or unsubstituted alkylene containing one or more group(s) selected from —O—, —$NR^a$—, —S—, —CO—, —SO—, and —$SO_2$— at arbitrary position, substituted or unsubstituted alkenylene, or substituted or unsubstituted alkenylene containing one or more group(s) selected from —O—, —$NR^a$—, —S—, —CO—, —SO—, and —$SO_2$— at arbitrary position;

$R^a$ and $R^b$ on the nitrogen atom and carbon atom which are not adjacent may be taken together to form substituted or unsubstituted alkylene, substituted or unsubstituted alkylene containing one or more group(s) selected from —O—, —$NR^a$—, —S—, —CO—, —SO—, and —$SO_2$— at arbitrary position, substituted or unsubstituted alkenylene, or substituted or unsubstituted alkenylene containing one or more group(s) selected from —O—, —$NR^a$—, —S—, —CO—, —SO—, and —$SO_2$— at arbitrary position;

two $R^b$s on adjacent carbon atoms may be taken together to form a bond;

$R^a$ on a nitrogen atom and $R^b$ on a carbon atom which is adjacent to the nitrogen atom may be taken together to form a bond.

$R^b$ and/or $R^c$ on adjacent carbon atoms in $T^1$ ring may be taken together with the adjacent carbon atoms to form substituted or unsubstituted non-aromatic carbocycle or substituted or unsubstituted non-aromatic heterocycle, preferably substituted or unsubstituted 5 or 6-membered non-aromatic heterocycle. Examples of the substituent(s) include halogen, alkyl, hydroxy, alkyloxy, haloalkyl, haloalkyloxy and the like.

$R^a$ on a nitrogen atom and $R^b$ on a carbon atom which is adjacent to the nitrogen atom may be taken together with the adjacent nitrogen atom and carbon atom to form substituted or unsubstituted aromatic heterocycle or substituted or unsubstituted non-aromatic heterocycle, preferably substituted or unsubstituted 5 or 6-membered aromatic heterocycle or substituted or unsubstituted 5 or 6-membered non-aromatic heterocycle. Examples of the substituent(s) include halogen, alkyl, alkyloxy, haloalkyl, haloalkyloxy and the like.

k is an integer of 2 to 7, preferably an integer of 3 to 5.

More preferably, $T^1$ ring includes a structure exemplified by the following formula:

[Chemical formula 68]

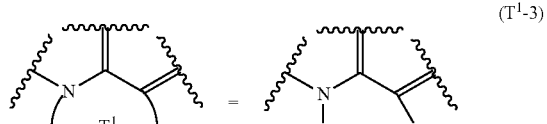

(T$^1$-3)

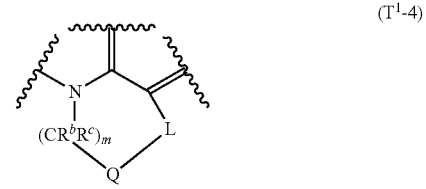

(T$^1$-4)

wherein each definition is the same as defined above.

L is —$SO_2$—, —SO—, or —$CR^bR^c$—, preferably —$SO_2$—, or —$CR^bR^c$.

Q is —$NR^a$—, —O—, —S— or —$CR^bR^c$—, preferably —$NR^a$—, —O—, or —$CR^bR^c$—.

m is an integer of 0 to 5, preferably an integer of 1 to 3.

Further preferably, $T^1$ ring includes a structure exemplified by the following formula:

[Chemical formula 69]

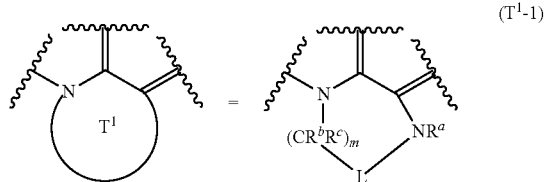

(T$^1$-1)

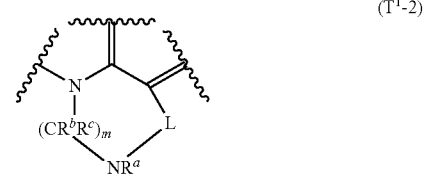

(T$^1$-2)

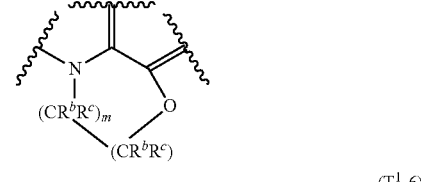

(T$^1$-5)

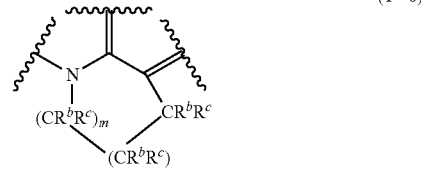

(T$^1$-6)

wherein each definition is the same as defined above.

Preferred embodiment of the present invention compounds are shown below. The compounds shown by the following embodiments are exemplified by all of the combination of these illustrative embodiments.

Embodiments 1

The formula (I) is the following formula (I'):

[Chemical formula 70]

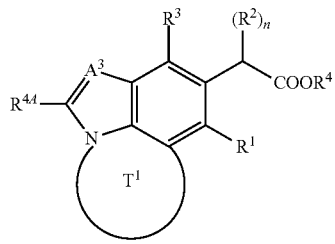

wherein $A^3$ is $CR^{3A}$ or N;
$R^{3A}$ is hydrogen or halogen;
$R^2$ is alkyloxy;
n is 1;
$R^4$ is hydrogen;
$R^1$ is halogen or alkyl;
$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^{4A}$ is alkyl optionally substituted with cyano, halogen, hydroxy or alkyloxy, halogen, alkynyl, or non-aromatic carbocyclyl; and
$T^1$ ring substituted or unsubstituted 5 to 12-membered nitrogen-containing non-aromatic heterocyclyl containing two N atoms, two N atoms and one S atom, or one N atom and one O atom.

Embodiment 2

The formula (I) is the following formula (I'-AA):

[Chemical formula 71]

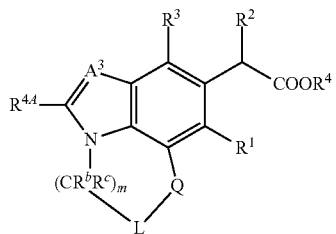

wherein $A^3$ is $CR^{3A}$ or N;
$R^{3A}$ is hydrogen or halogen; $R^1$ is alkyl or halogen;
$R^2$ is alkyloxy;
$R^3$ is aromatic carbocyclyl optionally substituted with halogen, alkyl and/or alkyloxy, non-aromatic carbocyclyl halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
Q is $-NR^a-$, $-O-$ or $-CR^bR^c-$;
L is $-SO_2-$, or $-CR^bR^c-$;
m is 1 or 2;
$R^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, $-COR^{a1}$, $-COOR^{a1}$, $-SOR^{a2}$, $-SO_2R^{a3}$, $-CONR^{a4}R^{a5}$, $-CSNR^{a4}R^{a5}$, $-COCONR^{a4}R^{a5}$, or $-C(NR^{a6})NR^{a4}R^{a5}$;
$R^{a1}$, $R^{a2}$, and $R^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{a4}$ and $R^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^b$ is each independently hydrogen, halogen, substituted or unsubstituted alkyl, or substituted or unsubstituted aromatic carbocycle;
$R^c$ is each independently hydrogen, halogen, substituted or unsubstituted alkyl, or substituted or unsubstituted aromatic carbocycle;
$R^b$ and $R^c$ on same carbon atom may be taken together with the bonded carbon atom to form carbonyl, substituted or unsubstituted non-aromatic carbocycle, or substituted or unsubstituted non-aromatic heterocycle;
two $R^b$s on adjacent carbon atoms may be taken together with the each bonded carbon atoms to form monocyclic substituted or unsubstituted non-aromatic carbocycle or monocyclic substituted or unsubstituted non-aromatic heterocycle;
two $R^b$s on adjacent carbon atoms may be taken together to form a bond;
$R^a$ and $R^b$ on the adjacent nitrogen atom and carbon atom may be taken together with the each bonding annular atoms to form monocyclic substituted or unsubstituted aromatic heterocycle or monocyclic substituted or unsubstituted non-aromatic heterocycle;
$R^a$ and $R^b$ on the adjacent nitrogen atom and carbon atom may be taken together to form a bond;
two $R^b$s on the carbon atoms which are not same and not adjacent may be taken together to form substituted or unsubstituted alkylene, substituted or unsubstituted alkylene containing one or more groups selected from —O—, —NR$^a$—, —S—, —CO—, —SO—, and —SO$_2$— at arbitrary position, substituted or unsubstituted alkenylene, or substituted or unsubstituted alkenylene containing one or more groups selected from —O—, —NR$^a$—, —S—, —CO—, —SO—, and —SO$_2$— at arbitrary position;

R$^a$ on a nitrogen atom and R$^b$ on a carbon atom which is not adjacent to the nitrogen atom may be taken together to form, substituted or unsubstituted alkylene, substituted or unsubstituted alkylene containing one or more groups selected from —O—, —NR$^a$—, —S—, —CO—, —SO—, and —SO$_2$— at arbitrary position, substituted or unsubstituted alkenylene, or substituted or unsubstituted alkenylene containing one or more groups selected from —O—, —NR$^a$—, —S—, —CO—, —SO—, and —SO$_2$— at arbitrary position;

two R$^b$s on adjacent carbon atoms may be taken together to form a bond; and/or R$^a$ on a nitrogen atom and R$^b$ on a carbon atom which is adjacent to the nitrogen atom may be taken together to form a bond.

Embodiment 3

The formula (I) is the following formula (I'-1A):

[Chemical formula 72]

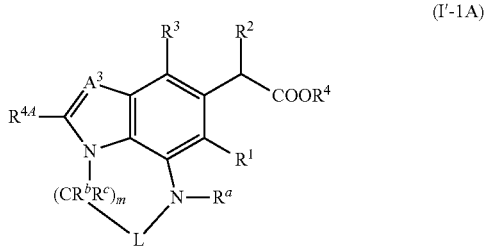

(I'-1A)

wherein A$^3$ is CR$^{3A}$ or N;

R$^{3A}$ is hydrogen or halogen; R$^1$ is alkyl or halogen;

R$^2$ is alkyloxy;

R$^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;

R$^4$ is hydrogen;

R$^{3A}$ is hydrogen or halogen;

R$^{4A}$ is alkyl optionally substituted with cyano, halogen, hydroxy or alkyloxy, halogen, alkynyl, or non-aromatic carbocyclyl;

L is —SO$_2$—, or —CR$^b$R$^c$—;

m is 1 or 2;

R$^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —COOR$^{a1}$, —SOR$^{a2}$, —SO$_2$R$^{a3}$, —CONR$^{a4}$R$^{a5}$, —CSNR$^{a4}$R$^{a5}$, —COCONR$^{a4}$R$^{a5}$, or —C(NR$^{a6}$)NR$^{a4}$R$^{a5}$;

R$^{a1}$, R$^{a2}$, and R$^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a4}$ and R$^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

R$^b$ is each independently hydrogen, halogen, substituted or unsubstituted alkyl, or substituted or unsubstituted aromatic carbocycle;

R$^c$ is each independently hydrogen, halogen, substituted or unsubstituted alkyl, or substituted or unsubstituted aromatic carbocycle; and/or R$^b$ and R$^c$ on the same carbon atom may be taken together with the bonding carbon atom to form carbonyl, substituted or unsubstituted non-aromatic carbocycle, or substituted or unsubstituted non-aromatic heterocycle;

two R$^b$s on the adjacent carbon atoms may be taken together with the each bonding carbon atoms to form monocyclic substituted or unsubstituted non-aromatic carbocycle or monocyclic substituted or unsubstituted non-aromatic heterocycle;

two R$^b$s on the adjacent carbon atoms may be taken together to form a bond;

R$^a$ on a nitrogen atom and R$^b$ on a carbon atom which is adjacent to the nitrogen atom may be taken together with the each bonded annular atoms to form monocyclic substituted or unsubstituted aromatic heterocycle or monocyclic substituted or unsubstituted non-aromatic heterocycle; or R$^a$ on a nitrogen atom and R$^b$ on a carbon atom may be taken together to form a bond;

two R$^b$s on two carbon atoms which are not adjacent to each other may be taken together to form substituted or unsubstituted alkylene, substituted or unsubstituted alkylene containing one or more group(s) selected from —O—, —NR$^a$—, —S—, —CO—, —SO—, and —SO$_2$— at arbitrary position, substituted or unsubstituted alkenylene, or substituted or unsubstituted alkenylene containing one or more group(s) selected from —O—, —NR$^a$—, —S—, —CO—, —SO—, and —SO$_2$— at arbitrary position;

R$^a$ on a nitrogen atom and R$^b$ on a carbon atom which is not adjacent to the nitrogen atom may be taken together to form substituted or unsubstituted alkylene, substituted or unsubstituted alkylene containing one or more group(s) selected form —O—, —NR$^a$—, —S—, —CO—, —SO—, and —SO$_2$— at arbitrary position, substituted or unsubstituted alkenylene, or substituted or unsubstituted alkenylene containing one or more group(s) selected form —O—, —NR$^a$—, —S—, —CO—, —SO—, and —SO$_2$— at arbitrary position;

two $R^b$s on adjacent carbon atoms may be taken together to form a bond; and/or $R^a$ on a nitrogen atom and $R^b$ on a carbon atom which is adjacent to the nitrogen atom may be taken together to form a bond.

Embodiment 4

The formula (I) is the following formula (I-1-1A):

[Chemical formula 73]

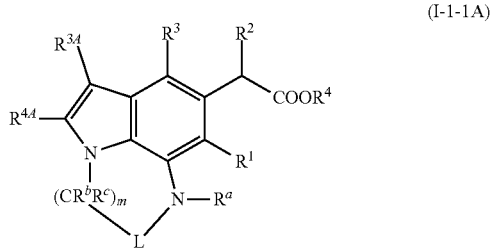

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is —$SO_2$—, or —$CR^bR^c$—;
m is 1 or 2;
$R^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —$COR^{a1}$, —$COOR^{a1}$, —$SOR^{a2}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;
$R^{a1}$, $R^{a2}$, and $R^{a3}$ are each independently substituted or unsubstituted alkyl, substituted or unsubstituted alkenyl, substituted or unsubstituted alkyloxy, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{a4}$ and $R^{a5}$ are each independently hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{a6}$ is hydrogen, hydroxy, substituted or unsubstituted alkyl, substituted or unsubstituted alkenyl, substituted or unsubstituted alkynyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^b$ is each independently hydrogen, halogen, substituted or unsubstituted alkyl, or substituted or unsubstituted aromatic carbocycle;
$R^c$ is each independently hydrogen, halogen, substituted or unsubstituted alkyl, or substituted or unsubstituted aromatic carbocycle; and/or
$R^b$ and $R^c$ on the same carbon atom may be taken together with the bonded carbon atom to form carbonyl, substituted or unsubstituted non-aromatic carbocycle, or substituted or unsubstituted non-aromatic heterocycle;
two $R^b$s on adjacent carbon atoms may be taken together to form a bond;
two $R^b$s on adjacent carbon atoms may be taken together with the each bonded carbon atoms to form monocyclic substituted or unsubstituted non-aromatic carbocycle or monocyclic substituted or unsubstituted non-aromatic heterocycle;
$R^a$ on a nitrogen atom and $R^b$ on a carbon atom which is adjacent to the nitrogen atom may be taken together to form a bond;
$R^a$ on a nitrogen atom and $R^b$ on a carbon atom which is adjacent to the nitrogen atom may be taken together with the each bonded annular atoms to form monocyclic substituted or unsubstituted aromatic heterocycle or monocyclic substituted or unsubstituted non-aromatic heterocycle;
two $R^b$s on two carbon atoms which are not adjacent may be taken together to form substituted or unsubstituted alkylene, substituted or unsubstituted alkylene containing one or more group(s) selected from —O—, —$NR^a$—, —S—, —CO—, —SO—, and —$SO_2$— at arbitrary position, substituted or unsubstituted alkenylene, or substituted or unsubstituted alkenylene containing one or more group(s) selected from —O—, —$NR^a$—, —S—, —CO—, —SO—, and —$SO_2$— at arbitrary position;
$R^a$ on a nitrogen atom and $R^b$ on a carbon atom which is not adjacent to the nitrogen atom may be taken together to form substituted or unsubstituted alkylene, substituted or unsubstituted alkylene containing with one or more group(s) selected from —O—, —$NR^a$—, —S—, —CO—, —SO—, and —$SO_2$— at arbitrary position, substituted or unsubstituted alkenylene, or substituted or unsubstituted alkenylene containing with one or more group(s) selected from —O—, —$NR^a$—, —S—, —CO—, —SO—, and —$SO_2$— at arbitrary position;
two $R^b$s on adjacent carbon atoms may be taken together to form a bond; and/or
$R^a$ on a nitrogen atom and $R^b$ on a carbon atom which is adjacent to the nitrogen atom may be taken together to form a bond.

Embodiment 5

The formula (I) is the following formula (I-1-1A):

[Chemical formula 74]

(I-1-1A)

wherein $R^1$ is alkyl or halogen;
$R^2$ is alkyloxy;
$R^3$ is aromatic carbocyclyl optionally substituted with optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is —$SO_2$—, or —$CR^bR^c$—;
m is 1 or 2;
$R^a$ is each independently hydrogen, substituted or unsubstituted alkyl, substituted or unsubstituted alkenyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —$COR^{a1}$, —$COOR^{a1}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;
$R^{a1}$, $R^{a2}$, and $R^{a3}$ are each independently substituted or unsubstituted alkyl, substituted or unsubstituted non-aromatic carbocyclyl, or substituted or unsubstituted aromatic heterocyclyl;
$R^{a4}$ and $R^{a5}$ are each independently hydrogen, substituted or unsubstituted alkyl, substituted or unsubstituted non-aromatic carbocyclyl, or substituted or unsubstituted aromatic heterocyclyl;
$R^{a6}$ is hydrogen; and
$R^b$ is each independently hydrogen, substituted or unsubstituted alkyl, or substituted or unsubstituted aromatic carbocycle;
$R^c$ is each independently hydrogen, substituted or unsubstituted alkyl, or substituted or unsubstituted aromatic carbocycle; and/or
$R^b$ and $R^c$ on the same carbon atom may be taken together with the bonded carbon atom to form carbonyl, substituted or unsubstituted non-aromatic carbocycle, or substituted or unsubstituted non-aromatic heterocycle;
two $R^b$s on adjacent carbon atoms may be taken together to form a bond;
two $R^b$s on adjacent carbon atoms may be taken together with the each bonded carbon atoms to form monocyclic substituted or unsubstituted non-aromatic heterocycle;
$R^a$ on a nitrogen atom and $R^b$ on a carbon atom which is adjacent to the nitrogen atom may be taken together to form a bond; and/or
$R^a$ on a nitrogen atom and $R^b$ on a carbon atom which is adjacent to the nitrogen atom may be taken together with the each bonded annular atoms to form monocyclic substituted or unsubstituted aromatic heterocycle or monocyclic substituted or unsubstituted non-aromatic heterocycle.

Embodiment 6

The formula (I) is the following formula (I-1-1A):

[Chemical formula 75]

(I-1-1A)

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl halogen optionally substituted with alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is —$SO_2$—, or —$CR^bR^c$—;
m is 1 or 2;
$R^a$ is each independently hydrogen, alkyl optionally substituted with one or more groups selected from Substituent Group A, alkenyl optionally substituted with one or more groups selected from Substituent Group A, aromatic heterocyclyl optionally substituted with one or more groups selected from Substituent Group B, non-aromatic heterocyclyl optionally substituted with one or more groups selected from Substituent Group B, aromatic carbocyclylalkyl optionally substituted with one or more groups selected from Substituent Group A, non-aromatic carbocyclylalkyl optionally substituted with one or more groups selected from Substituent Group A, aromatic heterocyclylalkyl optionally substituted with one or more groups selected from Substituent Group A, non-aromatic heterocyclylalkyl optionally substituted with one or more groups selected from Substituent Group A, —$COR^{a1}$, —$COOR^{a1}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;
$R^{a1}$, $R^{a2}$, and $R^{a3}$ are each independently alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;

$R^{a4}$ and $R^{a5}$ are each independently hydrogen, alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;

$R^{a6}$ is hydrogen; and $R^b$ is each independently hydrogen, alkyl optionally substituted with one or more groups selected from Substituent Group A, or aromatic carbocycle optionally substituted with one or more groups selected from Substituent Group B;

$R^c$ is each independently hydrogen, alkyl optionally substituted with one or more groups selected from Substituent Group A, or aromatic carbocycle optionally substituted with one or more groups selected from Substituent Group B; and/or $R^b$ and $R^c$ on the same carbon atom may be taken together with the bonded carbon atom to form carbonyl, non-aromatic carbocycle optionally substituted with one or more groups selected from Substituent Group B, or non-aromatic heterocycle optionally substituted with one or more groups selected from Substituent Group B;

two $R^b$s on adjacent carbon atoms may be taken together to form;

two $R^b$s on adjacent carbon atoms may be taken together with the each bonded carbon atoms to form monocyclic non-aromatic heterocycle optionally substituted with one or more groups selected from Substituent Group B;

$R^a$ on a nitrogen atom and $R^b$ on a carbon atom which is adjacent to the nitrogen atom may be taken together to form a bond; and/or $R^a$ on a nitrogen atom and $R^b$ on a carbon atom which is adjacent to the nitrogen atom may be taken together with the each bonded annular atoms to form monocyclic aromatic heterocycle optionally substituted with one or more groups selected from Substituent Group B or monocyclic non-aromatic heterocycle optionally substituted with one or more groups selected from Substituent Group B.

Embodiment 7

The formula (I) is the following formula:

[Chemical formula 76]

(I-1-1B)

(I-1-1C)

(I-1-1D)

or (I-1-1E)

wherein $R^1$ is alkyl or halogen;

$R^2$ is alkyloxy;

$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;

$R^4$ is hydrogen;

$R^{3A}$ is hydrogen or halogen;

$R^{4A}$ is alkyl optionally substituted with halogen, alkyl and/or alkyloxy, halogen, alkynyl, or non-aromatic carbocyclyl;

L is —$SO_2$—, or —$CR^bR^c$—;

m is 1 or 2;

$R^a$ is each independently hydrogen, alkyl optionally substituted with one or more groups selected from Substituent Group A, alkenyl optionally substituted with one or more groups selected from Substituent Group A, aromatic heterocyclyl optionally substituted with one or more groups selected from Substituent Group B, non-aromatic heterocyclyl optionally substituted with one or more groups selected from Substituent Group B, aromatic carbocyclylalkyl optionally substituted with one or more groups selected from Substituent Group A, non-aromatic carbocyclylalkyl optionally substituted with one or more groups selected from Substituent Group A, aromatic heterocyclylalkyl optionally substituted with one or more groups selected from Substituent Group A, non-aromatic heterocyclylalkyl optionally substituted with one or more groups selected from Substituent Group A, —$COR^{a1}$, —$COOR^1$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;

$R^{a1}$, $R^{a2}$, and $R^{a3}$ are each independently alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;

$R^{a4}$ and $R^{a5}$ are each independently hydrogen, alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^{a6}$ is hydrogen; and
$R^b$ is each independently hydrogen, alkyl optionally substituted with one or more groups selected from Substituent Group A, or aromatic carbocycle optionally substituted with one or more groups selected from Substituent Group B;
$R^c$ is each independently hydrogen, alkyl optionally substituted with one or more groups selected from Substituent Group A, or aromatic carbocycle optionally substituted with one or more groups selected from Substituent Group B; and/or
$R^b$ and $R^c$ on the same carbon atom may be taken together with the bonded carbon atom to form carbonyl, non-aromatic carbocycle optionally substituted with one or more groups selected from Substituent Group B, or non-aromatic heterocycle optionally substituted with one or more groups selected from Substituent Group B;
two $R^b$s on adjacent carbon atoms may be taken together to form a bond;
two $R^b$s on adjacent carbon atoms may be taken together with the each bonded carbon atoms to form monocyclic non-aromatic heterocycle optionally substituted with one or more groups selected from Substituent Group B;
$R^a$ on a nitrogen atom and $R^b$ on a carbon atom which is adjacent to the nitrogen atom may be taken together to form a bond; and/or
$R^a$ on a nitrogen atom and $R^b$ on a carbon atom which is adjacent to the nitrogen atom may be taken together with the bonded annular atoms to form monocyclic aromatic heterocycle optionally substituted with one or more groups selected from Substituent Group B or monocyclic non-aromatic heterocycle optionally substituted with one or more groups selected from Substituent Group B.

Embodiment 8

The formula (I) is the following formula:

[Chemical formula 77]

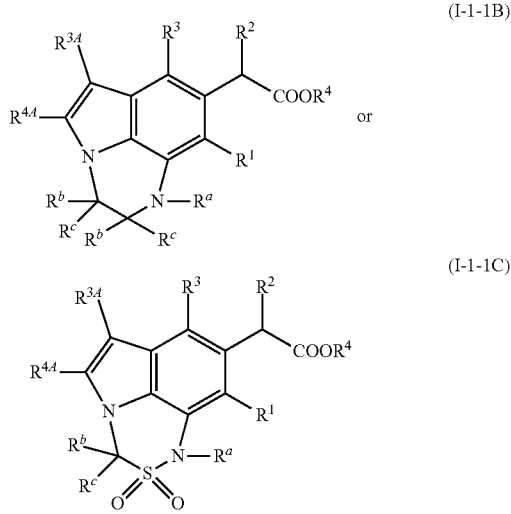

(I-1-1B) or (I-1-1C)

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3,4}$ is hydrogen or halogen;
$R^{4,4}$ is alkyl optionally substituted with cyano, halogen, hydroxy or alkyloxy, halogen, alkynyl, or non-aromatic carbocyclyl;
L is —$SO_2$—, or —$CR^bR^c$—;
m is 1 or 2;
$R^a$ is each independently hydrogen, alkyl optionally substituted with one or more groups selected from Substituent Group A, aromatic heterocyclyl optionally substituted with one or more groups selected from Substituent Group B, non-aromatic heterocyclyl optionally substituted with one or more groups selected from Substituent Group B, aromatic carbocyclylalkyl optionally substituted with one or more groups selected from Substituent Group A, non-aromatic carbocyclylalkyl optionally substituted with one or more groups selected from Substituent Group A, aromatic heterocyclylalkyl optionally substituted with one or more groups selected from Substituent Group A, non-aromatic heterocyclylalkyl optionally substituted with one or more groups selected from Substituent Group A, —$COOR^{a1}$, —$COOR^{a1}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;
$R^a$, $R^{a2}$, and $R^{a3}$ are each independently alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^{a4}$ and $R^{a5}$ are each independently hydrogen, alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^{a6}$ is hydrogen; and
$R^b$ is each independently hydrogen, alkyl optionally substituted with one or more groups selected from Substituent Group A, or aromatic carbocycle optionally substituted with one or more groups selected from Substituent Group B;
$R^c$ is each independently hydrogen, alkyl optionally substituted with one or more groups selected from Substituent Group A, or aromatic carbocycle optionally substituted with one or more groups selected from Substituent Group B; and/or
$R^b$ and $R^c$ on the same carbon atom may be taken together with the bonded carbon atom to form carbonyl, non-aromatic carbocycle optionally substituted with one or more groups selected from Substituent Group B, or non-aromatic heterocycle optionally substituted with one or more groups selected from Substituent Group B;
two $R^b$s on adjacent carbon atoms may be taken together with the each bonded carbon atom to form monocyclic non-aromatic heterocycle optionally substituted with one or more groups selected from Substituent Group B; and/or
$R^a$ on a nitrogen atom and $R^b$ on a carbon atom which is adjacent to the nitrogen atom may be taken together with the each bonded annular atoms to form monocyclic aromatic heterocycle optionally substituted with one or more groups selected from Substituent Group B or monocyclic non-aromatic heterocycle optionally substituted with one or more groups selected from Substituent Group B.

Embodiment 9

The formula (I) is the following formula:

[Chemical formula 78]

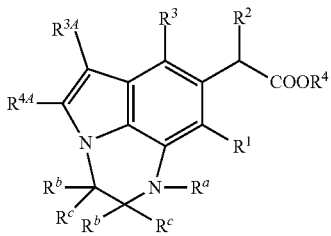

(I-1-1B)

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is $-SO_2-$, or $-CR^bR^c-$;
m is 1 or 2;
$R^a$ is each independently hydrogen, alkyl optionally substituted with one or more groups selected from Substituent Group A, $-COR^{a1}$, $-SO_2R^{a3}$, or $-CONR^{a4}R^{a5}$;
$R^{a1}$ and $R^{a3}$ are each independently alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^{a4}$ and $R^{a5}$ are each independently hydrogen, alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^b$ is each independently hydrogen or alkyl optionally substituted with one or more groups selected from Substituent Group A; and
$R^c$ is each independently hydrogen or alkyl optionally substituted with one or more groups selected from Substituent Group A.

Embodiment 10

The formula (I) is the following formula:

[Chemical formula 79]

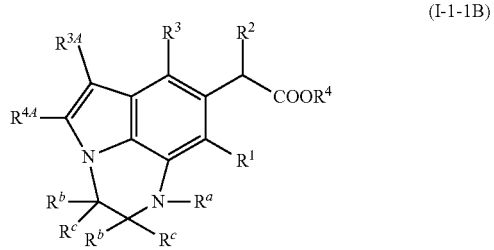

(I-1-1B)

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is $-SO_2-$, or $-CR^bR^c-$;
m is 1 or 2;
$R^a$ is each independently aromatic heterocyclyl optionally substituted with one or more groups selected from Substituent Group B, non-aromatic heterocyclyl optionally substituted with one or more groups selected from Substituent Group B, non-aromatic carbocyclylalkyl optionally substituted with one or more groups selected from Substituent Group A, or non-aromatic heterocyclylalkyl optionally substituted with one or more groups selected from Substituent Group A;
$R^b$ is each independently hydrogen or alkyl optionally substituted with one or more groups selected from Substituent Group A; and
$R^c$ is each independently hydrogen or alkyl optionally substituted with one or more groups selected from Substituent Group A.

Embodiment 11

The formula (I) is the following formula:

[Chemical formula 80]

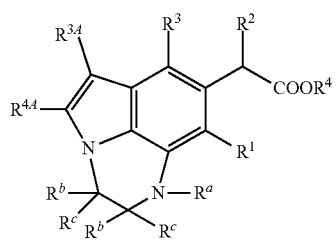

(I-1-1B)

wherein $R^1$ is alkyl or halogen;

$R^2$ is alkyloxy;

$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;

$R^4$ is hydrogen;

$R^{3A}$ is hydrogen or halogen;

$R^{4A}$ is alkyl optionally substituted with cyano, halogen, hydroxy or alkyloxy, halogen, alkynyl, or non-aromatic carbocyclyl;

L is —SO$_2$—, or —CR$^b$R$^c$—;

m is 1 or 2;

$R^b$ and $R^c$ on the same carbon atom may be taken together with the bonded carbon atom to form carbonyl, non-aromatic carbocycle optionally substituted with one or more groups selected from Substituent Group B, or non-aromatic heterocycle optionally substituted with one or more groups selected from Substituent Group B;

two $R^b$s on adjacent carbon atoms may be taken together with the each bonded carbon atoms to form monocyclic non-aromatic heterocycle optionally substituted with one or more groups selected from Substituent Group B; or $R^a$ on a nitrogen atom and $R^b$ on a carbon atom which is adjacent to the nitrogen atom may be taken together with the each bonded annular atoms to form monocyclic aromatic heterocycle optionally substituted with one or more groups selected from Substituent Group B or monocyclic non-aromatic heterocycle optionally substituted with one or more groups selected from Substituent Group B; and the other $R^a$, $R^b$ and $R^c$ are the same as defined the above Embodiment 8.

Embodiment 12

The formula (I) is the following formula:

[Chemical formula 81]

(I-1-1B)

wherein $R^1$ is alkyl or halogen;

$R^2$ is alkyloxy;

$R^3$ is aromatic carbocyclyl optionally substituted with halogen, alkyl and/or alkyloxy, non-aromatic carbocyclyl, halogen optionally substituted with halogen, alkyl and/or alkyloxy, aromatic heterocyclyl optionally substituted with alkyl and/or alkyloxy, or non-aromatic heterocyclyl optionally substituted with halogen, alkyl and/or alkyloxy;

$R^4$ is hydrogen;

$R^{3A}$ is hydrogen or halogen;

$R^{4A}$ is alkyl optionally substituted with cyano, halogen, hydroxy or alkyloxy, halogen, alkynyl, or non-aromatic carbocyclyl;

L is —SO$_2$—, or —CR$^b$R$^c$—;

m is 1 or 2;

$R^a$ is each independently hydrogen, alkyl, haloalkyl, aminoalkyl, alkylamino alkyl, dialkylamino alkyl, alkyloxyalkyl, alkylsulfonyl, or haloalkylsulfonyl;

$R^b$ is each independently hydrogen, alkyl, haloalkyl, or alkyloxyalkyl; and $R^c$ is each independently hydrogen, alkyl, haloalkyl, or alkyloxyalkyl.

Embodiment 13

The formula (I) is the following formula:

[Chemical formula 82]

(I-1-1B)

wherein $R^1$ is alkyl or halogen;

$R^2$ is alkyloxy;

$R^3$ is aromatic carbocyclyl optionally substituted with halogen, alkyl and/or alkyloxy, non-aromatic carbocyclyl optionally substituted with halogen, alkyl and/or alkyloxy, aromatic heterocyclyl optionally substituted with halogen, alkyl and/or alkyloxy, or non-aromatic heterocyclyl optionally substituted with halogen, alkyl and/or alkyloxy;

$R^4$ is hydrogen;

$R^{3A}$ is hydrogen or halogen;

$R^{4A}$ is alkyl optionally substituted with cyano, halogen, hydroxy or alkyloxy, halogen, alkynyl, or non-aromatic carbocyclyl;

L is —SO$_2$—, or —CR$^b$R$^c$—;

m is 1 or 2;

$R^a$ is each independently aromatic heterocyclyl optionally substituted with one or more groups selected from Substituent Group E or non-aromatic heterocyclyl optionally substituted with one or more groups selected from Substituent Group E; wherein Substituent Group E is alkyl, halogen, alkyloxy, dialkylamino alkyloxy, alkylamino alkyloxy, amino alkyloxy, non-aromatic heterocyclylalkyl oxy, non-aromatic heterocyclyloxy optionally substituted with alkyl and/or oxo, non-aromatic heterocyclyl optionally substituted with alkyl and/or oxo, dialkylamino alkyl, alkylamino alkyl, amino alkyl, non-aromatic heterocyclylalkyl, and aromatic heterocyclyl optionally substituted with alkyl;

$R^b$ is each independently hydrogen, alkyl, haloalkyl, or alkyloxyalkyl; and $R^c$ is each independently hydrogen, alkyl, haloalkyl, or alkyloxyalkyl.

Embodiment 14

The formula (I) is the following formula:

[Chemical formula 83]

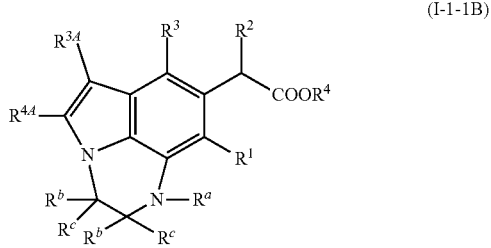

(I-1-1B)

wherein $R^1$ is alkyl or halogen;
$R^2$ is alkyloxy;
$R^3$ is aromatic carbocyclyl optionally substituted with halogen, alkyl and/or alkyloxy, non-aromatic carbocyclyl halogen, alkyl and/or alkyloxy, aromatic heterocyclyl optionally substituted with halogen, alkyl and/or alkyloxy, or non-aromatic heterocyclyl;
$R^4$ is hydrogen;
$R^{3A}$ is hydrogen or halogen;
$R^{4A}$ is alkyl optionally substituted with cyano, halogen, hydroxy or alkyloxy, halogen, alkynyl, or non-aromatic carbocyclyl;
L is —$SO_2$—, or —$CR^bR^c$—;
m is 1 or 2;
$R^a$ is each independently hydrogen, alkyl optionally substituted with one or more groups selected from Substituent Group A, —$COR^{a1}$, —$SO_2R^{a3}$, or —$CONR^{a4}R^{a5}$;
$R^{a1}$ and $R^{a3}$ are each independently alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^{a4}$ and $R^{a5}$ are each independently hydrogen, alkyl optionally substituted with one or more groups selected from Substituent Group A, non-aromatic carbocyclyl optionally substituted with one or more groups selected from Substituent Group B, or aromatic heterocyclyl optionally substituted with one or more groups selected from Substituent Group B;
$R^b$ is each independently hydrogen, alkyl optionally substituted with one or more groups selected from Substituent Group A or aromatic carbocyclyl optionally substituted with one or more groups selected from Substituent Group B; and
$R^c$ is each independently hydrogen, alkyl optionally substituted with one or more groups selected from Substituent Group A or aromatic carbocyclyl optionally substituted with one or more groups selected from Substituent Group B.

The compound of the present invention has a strong HIV replication inhibition activity. Also, it is excellent in various useful pharmacokinetics and/or safety and the like as a pharmaceutical. These profiles are remarkably improved by devising, for example, the type or position of heteroatoms on the ring or the type or position of substituents on the ring.

The compound of the present invention includes all possible isomers, preferably stereo isomers (e.g. keto-enol isomers, imine-enamine isomers, diastereoisomers, atropisomers, optical isomers, rotamers etc.), racemates or mixtures thereof. Although these isomers are often easily separated by optical resolution, crystallization, chromatographic separation and the like, these may be displayed in the same flat structural formula. Also, when these isomers can be separated by chromatographic separation, they are distinguishable by a peak time (RT).

One or more hydrogens, carbons and/or other atoms of the compounds represented by the formula (I), formula (I-1), formula (I-2), formula (I-1-1) and formula (I-2-1) may be substituted by an isotope of hydrogen, carbon and/or the other atom. Examples of the isotope include hydrogen, carbon, nitrogen, oxygen, phosphorus, sulfur, fluorine, iodine and chlorine, like $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound represented by the formula (I) also includes compounds substituted with the isotope. The compound substituted with the isotope is also useful as a pharmaceutical, and includes all radiolabeled materials of the compounds represented by the formula (I), formula (I-1), formula (I-2), formula (I-1-1) and formula (I-2-1). Also, a "radiolabeling method" for producing the "radiolabeled material" is also included in the present invention, and it is useful as a research and/or diagnostic tool in metabolism pharmacokinetic studies and binding assays.

The radiolabeled material of the compound represented by the formula (I) can be prepared by a method well known in the art. For example, a tritium-labeled compound represented by the formula (I) can be prepared, for example, by introducing tritium into a particular compound represented by the formula (I) by catalytic dehalogenation using tritium. This method includes reacting a precursor, in which the compound represented by the formula (I) is properly substituted with halogen, with tritium gas, in the presence of an appropriate catalyst, for example, Pd/C, in the presence or absence of a base. As the appropriate method for preparing other tritium-labeled compound, document of Isotopes in the Physical and Biomedical Sciences, Vol. 1, Labeled Compounds (Part A), Chapter 6 (1987) can be referred. A $^{14}C$-labeled compound can be prepared by using a raw material having a $^{14}C$ carbon.

Examples of the pharmaceutically acceptable salt of the compound represented by the formula (I) include salts of the compound represented by the formula (I) with an alkali metal (e.g., lithium, sodium, potassium, etc.), an alkaline earth metal (e.g., calcium, barium, etc.), magnesium, a transition metal (e.g., zinc, iron, etc.), ammonia, an organic base (e.g., trimethylamine, triethylamine, dicyclohexylamine, ethanolamine, diethanolamine, triethanolamine, meglumine, diethanolamine, ethylenediamine, pyridine, picoline, quinolone, etc.) and an amino acid, or salts with an inorganic acid (e.g., hydrochloric acid, sulfuric acid, nitric acid, carbonic acid, hydrobromic acid, phosphoric acid, hydroiodic acid, etc.) and an organic acid (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid, etc.). Examples include, particularly, salts with hydrochloric acid, sulfuric acid, phosphoric acid, tartaric acid, or methanesulfonic acid, and the like. These salts can be formed by a method usually carried out.

The compound of the present invention or its pharmaceutically acceptable salt may form a solvate (e.g., hydrate etc.) and/or a crystalline polymorph, and the present invention also includes such a variety of solvates and crystal polymorph. "Solvate" may be coordinated with solvent molecules (e.g. water molecules, etc.) in any number.

The compound of the present invention can be produced, for example, according to the general synthesis method described below. In addition, extraction, puridication and the like may be performed to carry out the usual organic chemistry experiments.

The synthesis of the compound of the present invention can be carried out while referring to the method known in the art. The present invention also provides intermediates and final compounds in the following general synthetic methods. The types of substituent(s) in each compounds and preferred embodiments are as described above.

(General Synthesis Method)

The compound represented by formula (I), formula (I-1), formula (I-2), formula (I-1-1) and formula (I-2-1) can be synthesized by appropriately combining known reactions to the person skilled in the art using compound known to the public or commercially available reagents. Preferably, a reaction for forming fused ring, a reaction for filming side chains, reduction reaction, oxidation reaction, hydrolysis reaction, Friedel-Crafts reaction, coupling reaction, protecting reaction, deprotection reaction and the like may be preformed as appropriate using benzene derivatives or pyridine derivatives having leaving group(s) such as halogen etc., nitro group(s), (substituted) amino group(s), (protected) amino group(s), alkyl group(s), (protected) hydroxy group(s), ester group(s) or the like as starting materials. Also each substituents ($R^3$, —$C(R^2)n$-$COOR^4$, $R^1$) on the 6-membered mother skeleton may be present in the compounds of the starting material, or be introduced after forming a $T^1$ ring.

As reaction solvents, for example, DMF, THF, dioxane, DME, tetrahydrofuran, acetone, acetonitrile, alcohol (e.g.: methanol, ethanol), ethyl acetate, DMSO, dichloromethane, dichloroethane, toluene, chloroform, benzene, toluene, xylene, water or a mixed solution selected from these solvents can be used as appropriate. As bases, for example, pyridine, lutidine, triethylamine, potassium carbonate, sodium carbonate, cesium carbonate, sodium hydride, N,N-diisopropyletylamine or the like can be used as appropriate.

[1] A Reaction Forming $T^1$ Ring $T^1$ ring is preferably formed after synthesized the respective bicyclic benzene derivatives. In one embodiment, when $T^1$ ring is $T^1$-1, the compound (I) or the compound (I-X) including the intermediates thereof ca be synthesized through the following steps. The reaction, for example, can be performed according to the method described in WO2004/094430.

[Chemical formula 84]

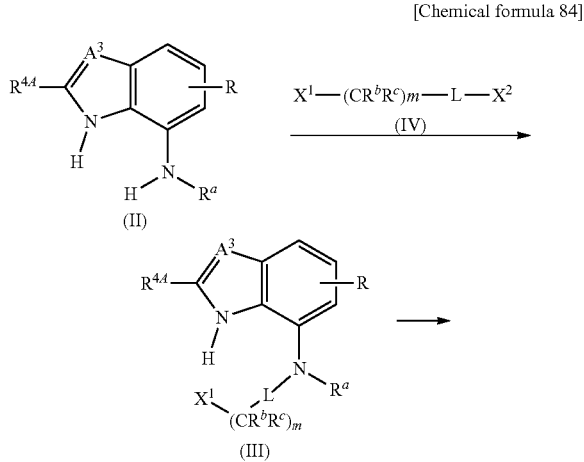

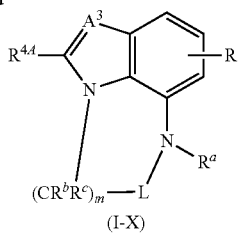
(I-X)

wherein $A^3$ is $CR^{3A}$ or N; R means one to three group(s) selected from the group consisting of $R^3$, —$C(R^2)nCOOR^4$, $R^1$, and a combination thereof, and the substituent that can be introduced these substituent(s) in the compound (I); $X^1$ is a leaving group (e.g.: halogen atom) or aldehyde group, or $X^1$ represents to be taken together with an adjacent ($CR^bR^c$) to form olefin or acetylene; $X^2$ is a leaving group (e.g.: a halogen atom); the other symbols are the same as defined above.

When the compound (I-X) is the compound (I), the compound (I-X) is represented by the following formula.

[Chemical formula 85]

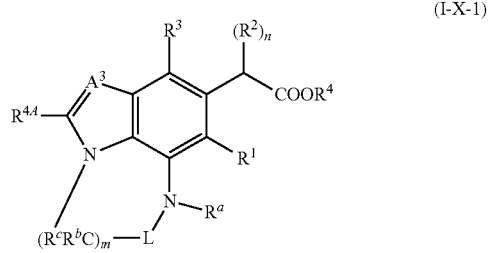
(I-X-1)

The above reactions in detail are as follows.
(1) In the case that L is C=O or $SO_2$,
(Step 1)

The compound (Ill) can be obtained by reacting the compound (II) with the compound (IV) in the presence of bases (e.g.: pyridine) and suitable reagent(s) (e.g.: DMAP) if necessary, in a solvent (e.g.: dichloromethane), at a suitable temperature (e.g.: 0 to 100° C., preferably room temperature), for suitable time (e.g.: a few minutes to several ten hours).

(Step 2)

The compound (I-X) can be obtained by reacting the compound (III) in the presence of deprotonating agents (e.g.: sodium hydride), in a solvent (e.g.: DMF), at a suitable temperature (e.g.: 0 to 150° C., preferably about 100° C.), when $A^5$ is N.

The compound (I-X) can be obtained by conducting the intramolecular Friedel-Crafts reaction using, for example, the compound (III), wherein $X^1$—($CR^bR^c$)— is Cl—C(O)—, in the presence of Lewis acid (e.g.: aluminium chloride, titanium tetraisopropoxide (IV)), when $A^5$ is C.

(2) In the case that L is —($CR^bR^c$)—:

(2-1) when $A^5$ is N, the compound (II) is reacted in the presence of bases (e.g.: cesium carbonate), in a solvent (e.g.: DMF), at a suitable temperature (e.g.: 0 to 100° C., preferably room temperature) in Step 1. In Step 2, the compound (I-X) can be obtained by reacting the compound (III) in the presence of deprotonating reagents (e.g.: sodium hydride) if necessary, at suitable temperature (e.g.: room temperature to 100° C.).

(2-2) When $A^5$ is C, the compound (I-X) can be obtained by reacting the compound (II), preferably wherein Ra is —$COR^{a1}$, —$SOR^{a2}$, or —$SO_2R^{a3}$, in the presence of bases (e.g.: cesium carbonate), in a solvent (e.g.: DMF, acetonitrile), at a suitable temperature (e.g.: 0 to 100° C., preferably room temperature) in Step 1. In Step 2, for example, the compound (I-X) can be obtained by conducting the intramolecular Friedel-Crafts reaction using the compound (III), wherein $X^1$—$(CR^bR^c)$— is Cl—C(O)—, and Lewis acid (e.g.: aluminium chloride, titanium chloride (IV)).

[2] Synthesis of the Compound (I-1)

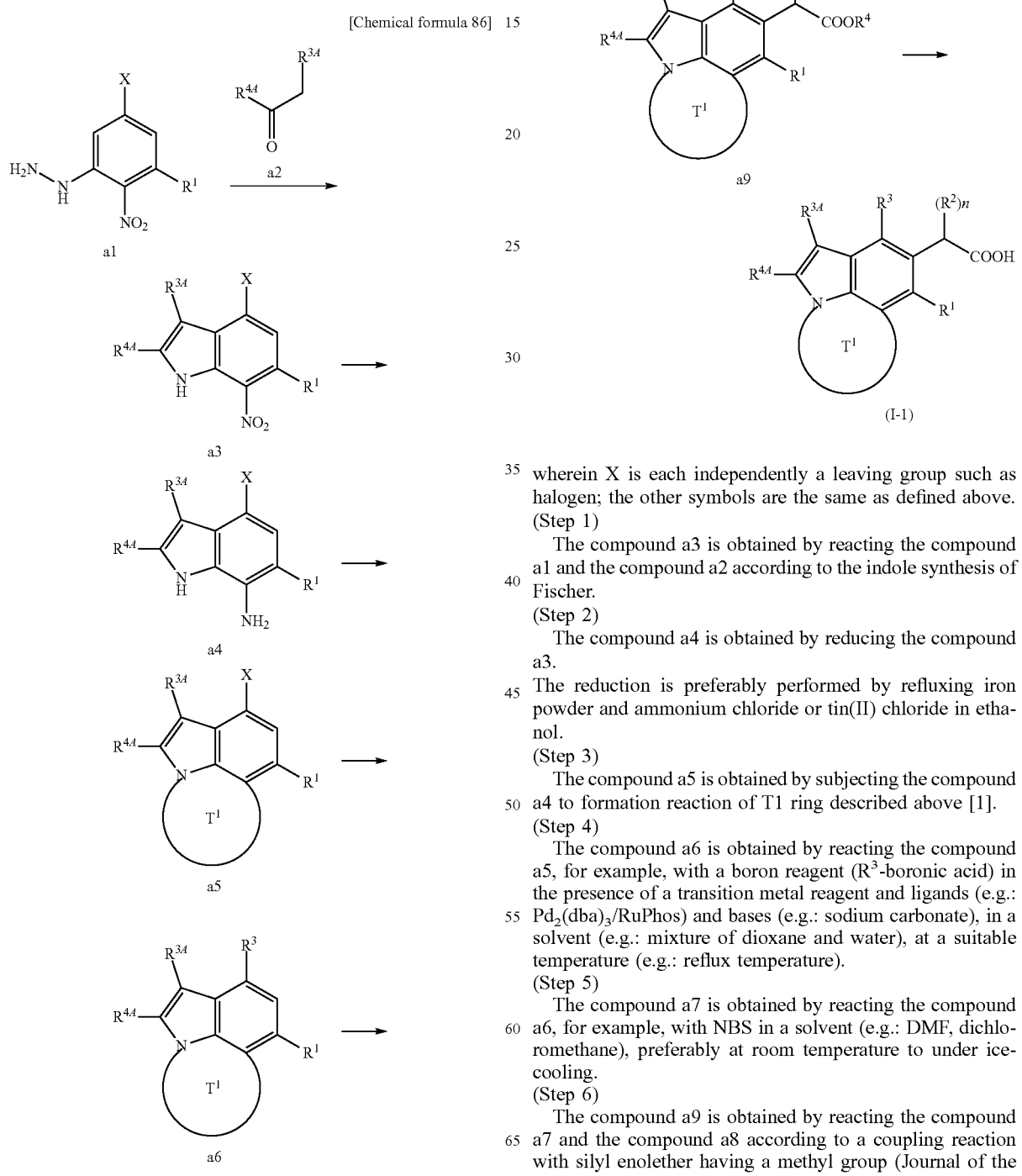

wherein X is each independently a leaving group such as halogen; the other symbols are the same as defined above.

(Step 1)
The compound a3 is obtained by reacting the compound a1 and the compound a2 according to the indole synthesis of Fischer.

(Step 2)
The compound a4 is obtained by reducing the compound a3.
The reduction is preferably performed by refluxing iron powder and ammonium chloride or tin(II) chloride in ethanol.

(Step 3)
The compound a5 is obtained by subjecting the compound a4 to formation reaction of T1 ring described above [1].

(Step 4)
The compound a6 is obtained by reacting the compound a5, for example, with a boron reagent ($R^3$-boronic acid) in the presence of a transition metal reagent and ligands (e.g.: $Pd_2(dba)_3$/RuPhos) and bases (e.g.: sodium carbonate), in a solvent (e.g.: mixture of dioxane and water), at a suitable temperature (e.g.: reflux temperature).

(Step 5)
The compound a7 is obtained by reacting the compound a6, for example, with NBS in a solvent (e.g.: DMF, dichloromethane), preferably at room temperature to under ice-cooling.

(Step 6)
The compound a9 is obtained by reacting the compound a7 and the compound a8 according to a coupling reaction with silyl enolether having a methyl group (Journal of the American Chemical Society, 2004, 126, 5182-5191.).

(Step 7)

The compound (I-A-1) is obtained by reacting the compound a9 in the presence of bases (e.g.: sodium hydroxide), in a solvent (e.g.: THF, mixture of methanol and water), at a suitable temperature (e.g.: about 50° C.). The compound (I-1) can be also converted into a variety of carboxylic acid equivalents or carboxylic acid derivatives by methods known to the skilled person in the art.

[2-1] Alternative Synthetic Method of the Compound (I-1) Type (Synthesis of the Compound (I-1'))

[Chemical formula 87]

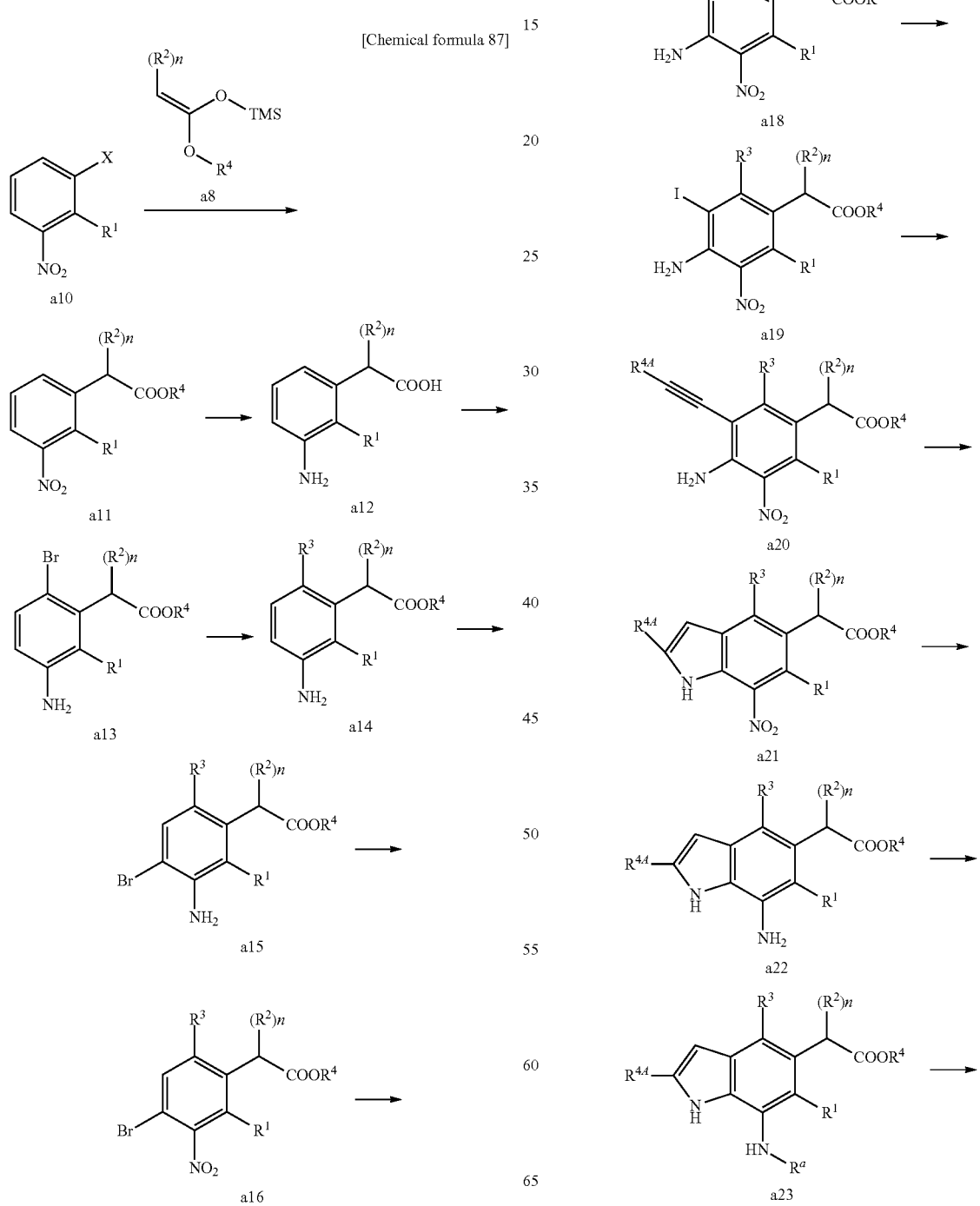

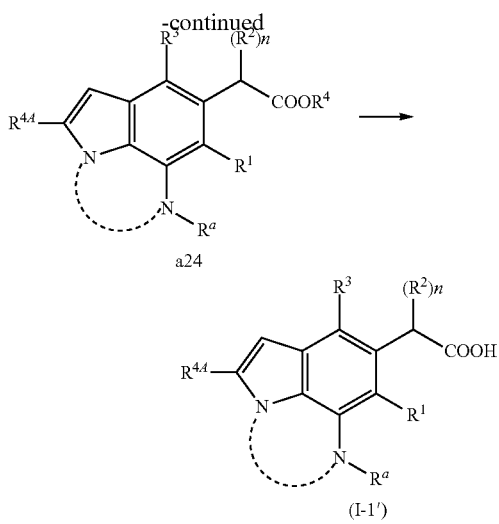

wherein the bow-shaped broken line means a ring formation, the ring is substituted or unsubstituted non-aromatic heterocycle, the other symbols are the same as defined above.
(Step 1)

The compound a11 can be obtained by reacting the compound a10 in DMF, DMA, THF, dioxane or the like or a mixture thereof, with a phosphine such as tri-t-butylphosphine, tricyclohexylphosphine, triphenylphosphine or the like, a catalyst such as dibenzylideneacetone palladium, palladium acetate, dichlorobistriphenylphosphine palladium or the like, zinc fluoride, and silyl enol ether a8 at 50° C. to 150° C., preferably 70° C. to 130° C., for 0.1 to 8 hours, preferably 0.5 to 2 hours.
(Step 2)

The compound a12 can be obtained by reacting the compound a11 in a solvent such as acetic acid, hydrochloric acid, sulfuric acid, or a mixture thereof, with a reductant such as zinc, iron, tin chloride or the like, at −20° C. to 80° C., preferably 0° C. to 60° C., for 0.1 to 8 hours, preferably 0.5 to 2 hours. Or the compound a12 can be obtained by reacting the compound a11 in a solvent such as methanol, ethyl acetate, acetic acid or the like, or a mixture thereof, in the presence of a catalyst such as Pd/C, Pd(OH)$_2$, Raney-Ni or the like, under hydrogen atmosphere, at −30° C. to 80° C., preferably 0° C. to 50° C., for 0.1 to 8 hours, preferably 0.5 to 2 hours.
(Step 3)

The compound a13 can be obtained by reacting the compound a12 in a solvent such as dichloromethane, chloroform, dichloroethane or the like, or a mixture thereof, with a brominating reagent such as bromine or NBS, at −50° C. to 50° C., preferably −30° C. to 30° C., for 0.1 to 4 hours, preferably 0.5 to 1 hour.
(Step 4)

The compound a14 can be obtained by coupling reaction of the compound a13 and $R^3$-L. Examples of the reaction is Suzuki cross-coupling, Ullmann cross-coupling, Negishi cross-coupling, Still coupling and the like.

The compound a14 can be obtained by reacting the compound a13 with substituted boronic acid, substituted borate, substituted tin alkyl, substituted halogenated zinc which is commercial available or synthesized in known methods in the presence of palladium catalyst such as Pd(PPh$_3$)$_4$, Pd(OAc)$_2$; Pd(PPh$_3$)$_2$Cl$_2$, Pd(dppf)$_2$ Cl$_2$ or the like and bases such as potassium carbonate, sodium carbonate, potassium phosphonate or the like in a solvent such as dioxane, DMF, DME, THF, water or the like, or a mixture thereof, added CuI, CsF or the like if necessary under a nitrogen atmosphere, at 0° C. to 150° C., preferably 60° C. to 120° C., for 0.5 to 24 hours, preferably 1 to 12 hours.
(Step 5)

The compound a15 can be obtained in the same manner as Step 3.
(Step 6)

The compound a16 can be obtained by reacting the compound a15 in a solvent such as dichloromethane, chloroform, dichloroethane or the like, or a mixture thereof with an oxidant such as mCPBA, peracetic acid, at 0° C. to 120° C., preferably 30° C. to 90° C., for 0.1 to 10 hours, preferably 0.5 to 4 hours.
(Step 7)

The compound a17 can be obtained by reacting the compound a16 in a solvent such as toluene, DMF, DMA, THF, dioxane or the like, or a mixture thereof, in the presence of a phosphine such as BINAP, xantphos or the like, a catalyst such as dibenzylideneacetone palladium, palladium acetate or the like, a base such as cesium carbonate, potassium carbonate or the like, and acetoamide, at 50° C. to 150° C., preferably 70° C. to 1300° C., for 0.1 to 8 hours, preferably 0.5 to 2 hours.
(Step 8)

The compound a18 can be obtained by reacting the compound a17 in a solvent such as methanol, ethanol or the like, or a mixture thereof, in the presence of a base such as cesium carbonate, potassium carbonate or the like, at 50° C. to 150° C., preferably 70° C. to 130° C., or 0.1 to 10 hours, preferably 0.5 to 4 hours.
(Step 9)

The compound a19 can be obtained by reacting the compound a18 with an iodinating reagent such as iodine and silver nitrate or NIS in a solvent such as methanol, ethanol or the like, or a mixture thereof, at −50° C. to 50° C., preferably −30° C. to 30° C.: for 0.1 to 4 hours, preferably 0.5 to 1 hour.
(Step 10)

The compound a20 can be obtained by reacting the compound a19 in a solvent such as DMF, DMA, THF, dioxane or the like, or a mixture thereof, with a base such as Et$_3$N, DIPEA or the like, substituted alkyne which is commercially available or synthesized in a known method, and a catalyst such as PdCl$_2$ (PPh$_3$)$_4$, Pd(PPh$_3$)$_4$, PdCl$_2$ (dppf) or the like at 50° C. to 150° C., preferably 70° C. to 130° C., for 0.1 to 8 hours, preferably 0.5 to 2 hours.
(Step 11)

The compound a21 can be obtained by reacting the compound a20 in a solvent such as DMF, THF or the like, or a mixture thereof, with a base such as t-BuOK, potassium carbonate or the like at −20° C. to 80° C., preferably 0° C. to 60° C., for 0.1 to 4 hours, preferably 0.5 to 1 hour.
(Step 12)

The compound a22 can be obtained in the same manner as in Step 2.
(Step 13)

The compound a23 can be obtained by reacting the compound a22 in a solvent such as dichloromethane, DMF, DMA or the like, or a mixture thereof, with a base such as cesium carbonate, pyridine, Et$_3$N or the like, alkylating reagent which is commercially available or synthesized in a known method such as methyl iodide, MsCl, AcCl, MeNCO or the like, sulfonylating reagent, acid chloride, isocyanate, at −50° C. to 50° C., preferably −30° C. to 30° C., for 0.1 to 4 hours, preferably 0.5 to 1 hour.

(Step 14)

The compound a24 can be obtained by reacting the compound a23 in a solvent such as DMF, DMF, THF or the like, or a mixture thereof, with a base such as cesium carbonate, potassium carbonate or the like, an alkylating reagent such as 1,2-dibromoethane, 1,3-dibromopropane, chloroacetylchloride, chloromethylsulfonyl chloride, oxalylchloride or the like which is commercially available or synthesized in a known method, at −20° C. to 80° C., preferably 0° C. to 60° C., for 0.1 to 8 hours, preferably 0.5 to 2 hours.

Alternatively, when $R^a$ is alkylsulfonyl or the like, the compound a24 can also be obtained by reacting with a base such as sodium hydroxide in a solvent such as DMF, DMA, THF or the like or a mixture thereof at 0° C. to 30° C., for 0.5 to 24 hours, preferably 1 to 5 hours after reacting in a solvent such as THF, toluene, dichloromethane or the like, added a Mitsunobu reagent such as DEAD, DIAD, or bis(2-methoxyethyl)azodicarbonate and triphenylphosohine, tri-n-butylphosphine, or tributylphosphine, and a diol, wherein one alcohol was protected, which is commercially available or synthesized in a known method at −20° C. to 100° C., preferably 0° C. to 30° C., for 0.5 to 24 hours, preferably 1 to 5 hours and then converted a resulting hydroxyl group to a general deprotecting group in a general deprotecting method.

(Step 15)

The compound (I-1') can be obtained by reacting the compound a24 with a base such as aqueous sodium hydroxide, aqueous potassium hydroxide, aqueous lithium hydroxide or the like in a solvent such as methanol, THF, dioxane or the like, or a mixture thereof, at 10° C. to 110° C., preferably 30° C. to 90° C., for 0.1 to 8 hours, preferably 0.5 to 1 hour.

[2-2] Alternative Synthesis of the Compound (I-1) Type (the Compound I-1")

[Chemical formula 88]

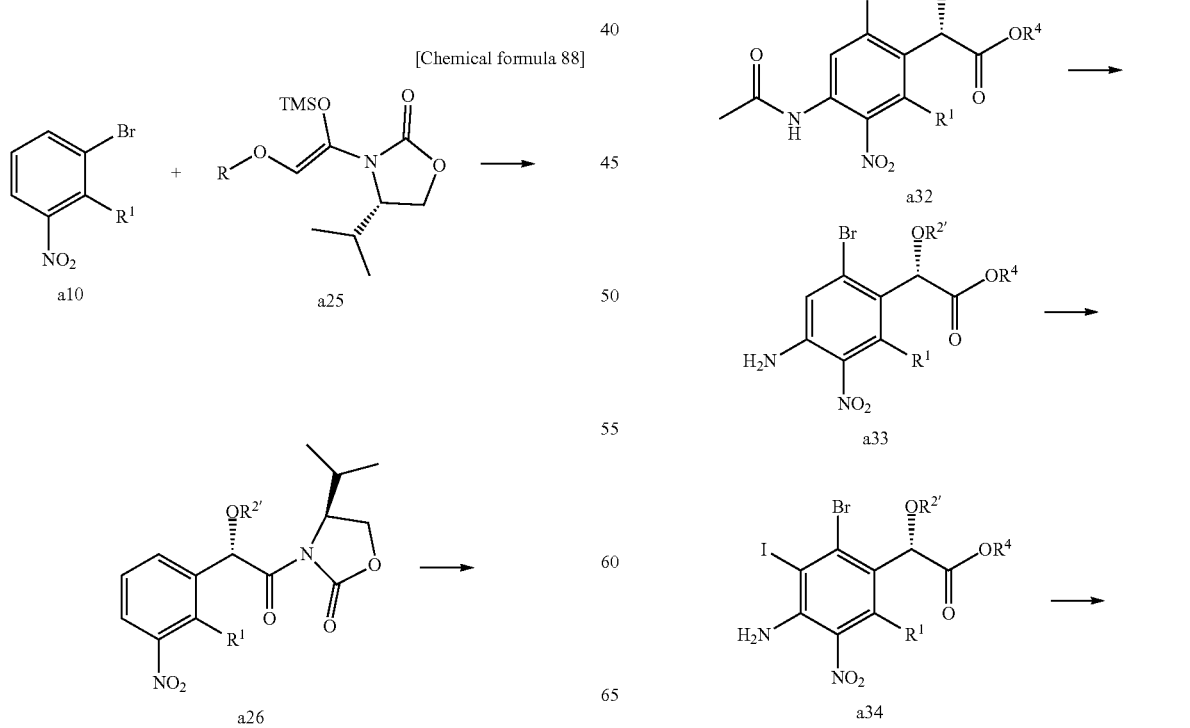

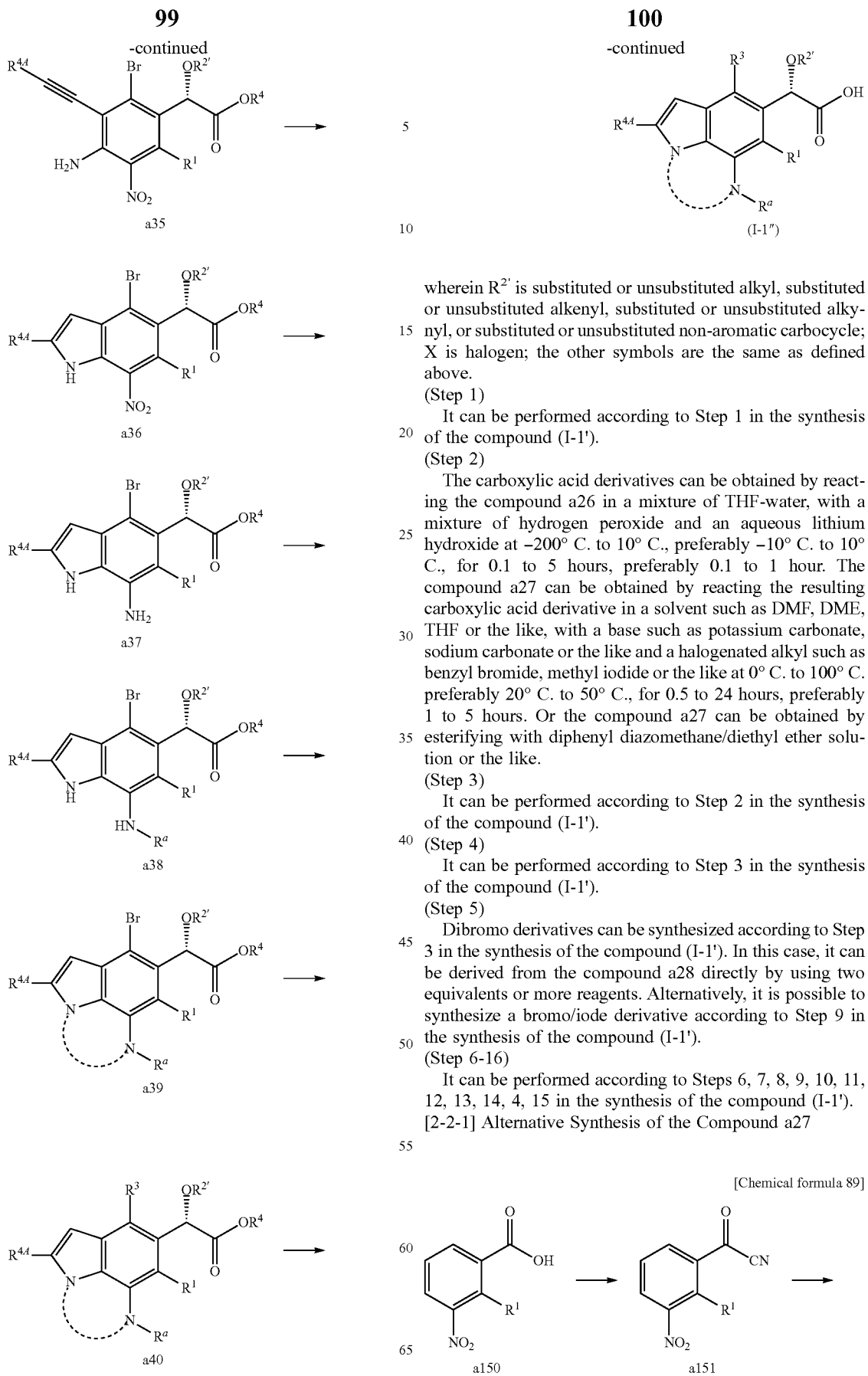

wherein $R^{2'}$ is substituted or unsubstituted alkyl, substituted or unsubstituted alkenyl, substituted or unsubstituted alkynyl, or substituted or unsubstituted non-aromatic carbocycle; X is halogen; the other symbols are the same as defined above.

(Step 1)

It can be performed according to Step 1 in the synthesis of the compound (I-1').

(Step 2)

The carboxylic acid derivatives can be obtained by reacting the compound a26 in a mixture of THF-water, with a mixture of hydrogen peroxide and an aqueous lithium hydroxide at −200° C. to 10° C., preferably −10° C. to 10° C., for 0.1 to 5 hours, preferably 0.1 to 1 hour. The compound a27 can be obtained by reacting the resulting carboxylic acid derivative in a solvent such as DMF, DME, THF or the like, with a base such as potassium carbonate, sodium carbonate or the like and a halogenated alkyl such as benzyl bromide, methyl iodide or the like at 0° C. to 100° C. preferably 20° C. to 50° C., for 0.5 to 24 hours, preferably 1 to 5 hours. Or the compound a27 can be obtained by esterifying with diphenyl diazomethane/diethyl ether solution or the like.

(Step 3)

It can be performed according to Step 2 in the synthesis of the compound (I-1').

(Step 4)

It can be performed according to Step 3 in the synthesis of the compound (I-1').

(Step 5)

Dibromo derivatives can be synthesized according to Step 3 in the synthesis of the compound (I-1'). In this case, it can be derived from the compound a28 directly by using two equivalents or more reagents. Alternatively, it is possible to synthesize a bromo/iode derivative according to Step 9 in the synthesis of the compound (I-1').

(Step 6-16)

It can be performed according to Steps 6, 7, 8, 9, 10, 11, 12, 13, 14, 4, 15 in the synthesis of the compound (I-1').

[2-2-1] Alternative Synthesis of the Compound a27

[Chemical formula 89]

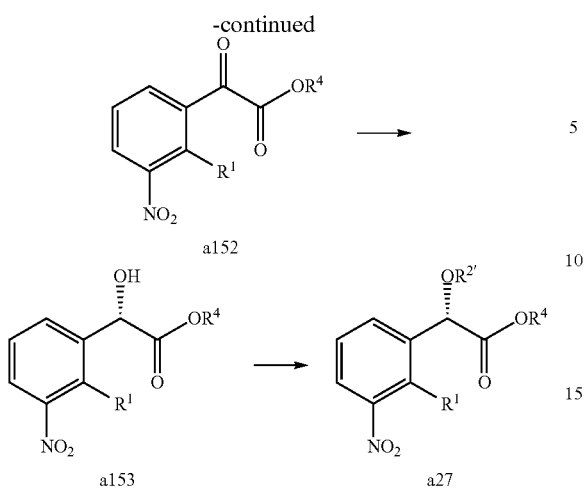

a152 a153  a27

(Step 1)

To a solution the compound a150, which is commercially available or synthesized in a known method, in a solvent such as dichloromethane, toluene, xylene, tetrahydrofuran or the like, or a mixture thereof is added thionyl chloride or oxalyl chloride, and the mixture is reacted at 0° C. to 150° C., preferably 50° C. to 120° C. for 0.5 to 24 hours, preferably 1 to 6 hours. Then, it is added sodium cyanide, potassium cyanide, copper cyanide, silicon cyanide or the like in a solvent such as dichloromethane, toluene, xylene, tetrahydrofuran, acetonitrile or the like and the mixture is reacted at 0° C. to 160° C., preferably 25° C. to 100° C. for 1 to 24 hours, preferably 1 to 5 hours to give the compound a151.

(Step 2)

The compound a151 is dissolved in $R^4OH$ and to a solution is added an acid such as concentrated sulfuric acid, concentrated hydrochloric acid or the like, and the mixture is reacted at 0° C. to 150° C., preferably 80° C. to 110° C., for 1 to 24 hours, preferably 6 to 12 hours, then converted a nitrile group to a carboxy group by hydrolysis and then esterified to give the compound a152.

(Step 3)

The compound a153 can be obtained by reacting a solution of the compound a152 in dichloromethane, toluene, methanol, DMSO, acetonitrile or the like with an asymmetric ruthenium catalyst, hydrogen donor compounds (e.g.: alcohol compound, formic acid, farmate salt etc.) and bases (e.g.: sodium carbonate, potassium carbonate, sodium methoxide, triethylamine, pyridine etc.), at −20° C. to 100° C., preferably 0° C. to 80° C., for 0.1 to 24 hours, preferably 0.1 to 5 hours.

(Step 4)

The compound a27 can be obtained by reacting a solution of the compound a153 in tetrahydrofuran, DMF, toluene or the like with bases (e.g.: sodium hydride, potassium tert-butoxide, sodium methoxide etc.) and $R^{2'}$—I, $R^{2'}$—Br, $R^{2'}$—Cl or the like which is commercially available or synthesized in a known method at −20° C. to 100° C., preferably 0° C. to 60° C., for 1 to 24 hours, preferably 3 to 12 hours.

Or, when $R^{2'}$ is tert-butyl ether, the corresponding compound a27 can be obtained by reacting the compound a153 in tert-butyl acetate with 0.2 to 3 equivalents of 70% aqueous solution of perchloric acid at 0° C. to 60° C., preferably 15° C. to 30° C., for 0.1 to 10 hours, preferably 0.5 to 2 hours.

[2-3] Synthesis of the Compound (I-1''')

[Chemical formula 90]

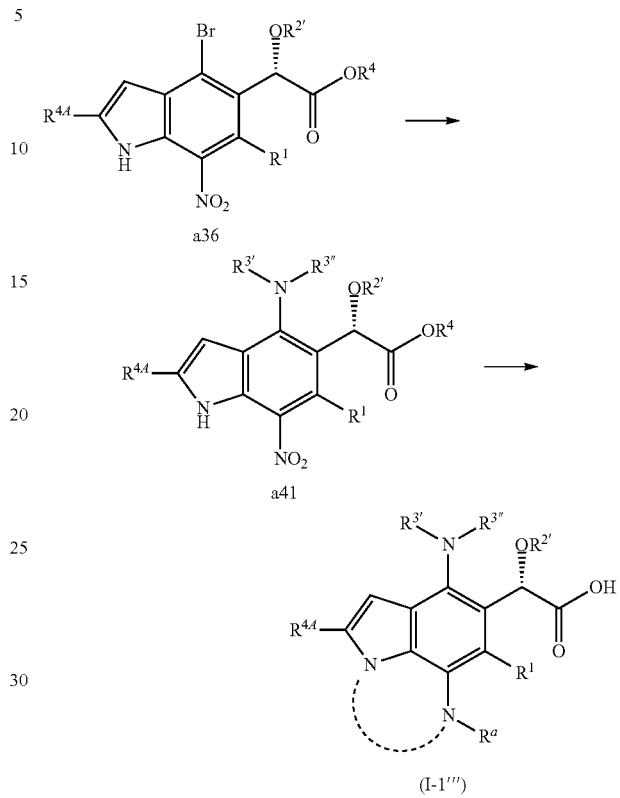

wherein $R^{3'}$ and $R^{3'''}$ are taken together with the adjacent nitrogen atom to form non-aromatic heterocycle; the other symbols are the same as defined above.

(Step 1)

The compound a41 can be obtained by reacting the compound a36 under solvent free condition or in DMSO, DMF, acetonitrile, methanol, butanol or the like with bases such as ammonium, cyclic amine, potassium carbonate, triethylamine, ethyl diisopropylamine, potassium t-butoxide or the like at 0° C. to 200° C., preferably 50° C. to 150° C., for 1 to 72 hours, preferably 1 to 24 hours.

(Step 2)

It can be carried out according to Step 12, 13, 14, 15 in the synthesis of the compound (I-1').

[2-4] Alternative Synthesis of the Compound (I-1) Type

[Chemical formula 91]

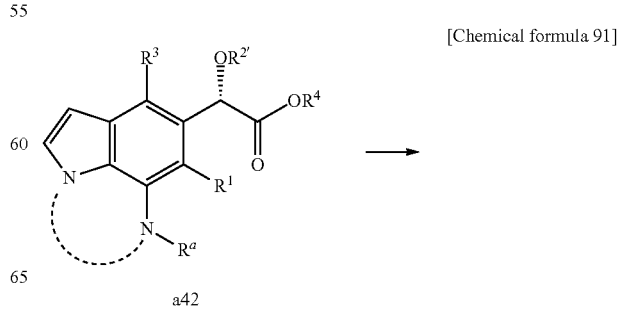

a42

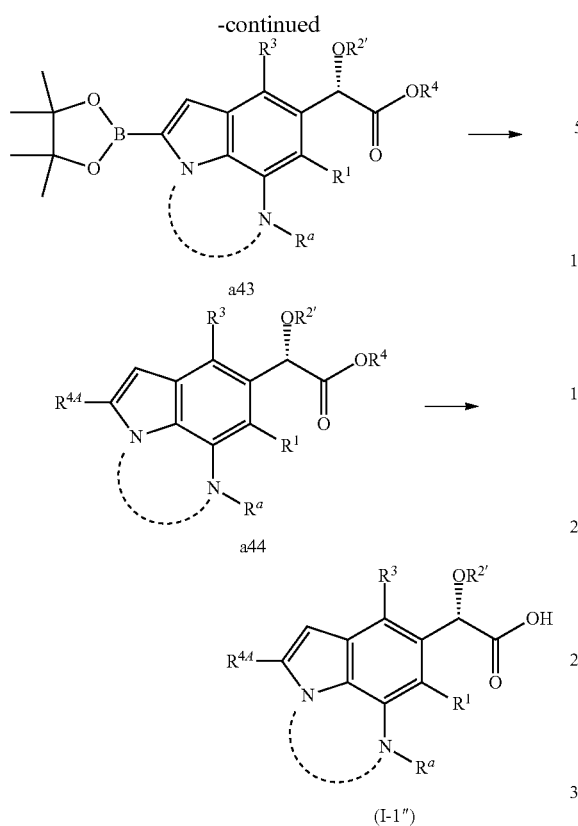

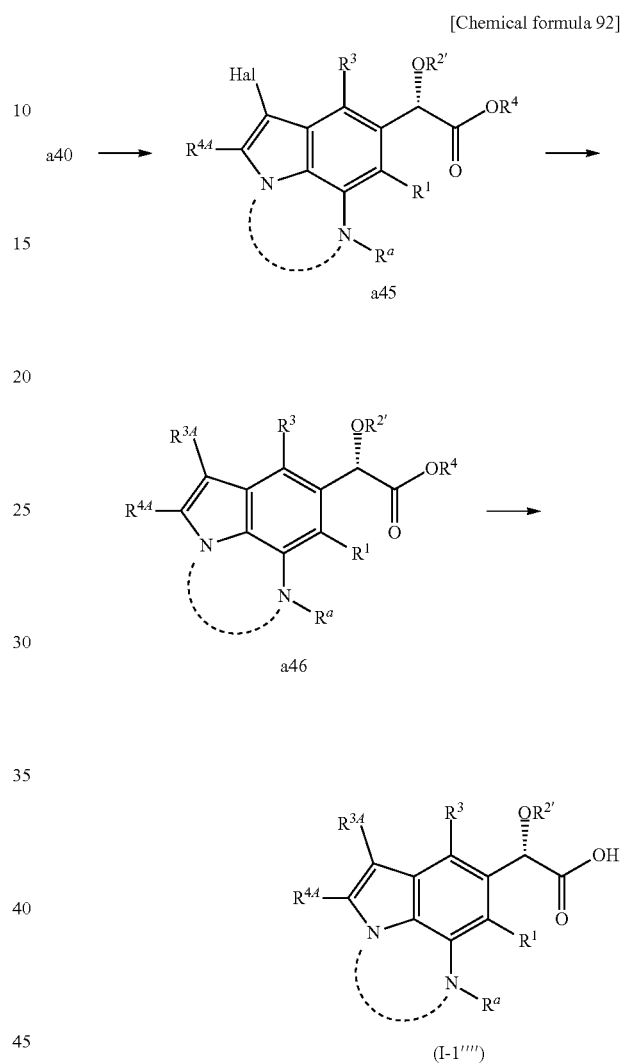

wherein each symbol is the same as defined above.

(Step 1)

The compound a43 can be obtained by reacting the compound a42 in a solvent such as hexane, THF, DMF or the like, or a mixture thereof, with 4,4'-di-tert-butyl-2,2'-bipyridine, bispinacol diborone and in iridium catalyst such as 1,5-cyclooctadiene methoxy iridium or the like at 50° C. to 150° C., preferably 70° C. to 130° C., for 0.1 to 8 hours, preferably 0.5 to 2 hours.

(Step 2)

The compound a44 can be obtained by reacting the compound a43 in a solvent such as DMF, DMA, THF, dioxane or the like, or a mixture thereof, with a aqueous solution of a base such as $K_2CO_3$, $Na_2CO_3$, $K_3PO_4$ or the like, alkenyl halide, aryl halide, alkyl halide, and a catalyst such as $PdCl_2$ (dtbpf), $Pd(PPh_3)_4$, $PdCl_2$ (dppf) or the like, at 50° C. to 150° C., preferably 70° C. to 130° C., for 0.1 to 8 hours, preferably 0.5 to 2 hours.

Or the halogenated compound can be obtained by reacting the compound a43 in a solvent such as DMF, DMA, THF, dioxane, methanol, water or the like, or a mixture thereof, with a halogenated metal such as copper(II) bromide, copper (II) chloride or the like at 50'C to 150° C., preferably 70° C. to 1300° C., for 0.1 to 8 hours, preferably 0.5 to 2 hours. Additionally, the compound a44 can be obtained by converting the introduced halo group to an aryl group or an alkynyl group by a coupling reaction generally known.

(Step 3)

The compound (I-1") can be obtained by reacting the compound a44 in a solvent such as methanol, THF, dioxane or the like, or a mixture thereof, with a base such as aqueous sodium hydroxide solution, aqueous potassium hydroxide solution, aqueous lithium hydroxide solution or the like at 10° C. to 110° C., preferably 30° C. to 90° C., for 0.1 to 8 hours, preferably 0.5 to 1 hour.

[2-5] Synthesis of the Compound (I-1"")

[Chemical formula 92]

wherein Hal is halogen; the other symbols are the same as defined above.

(Step 1)

The compound a45 can be obtained by reacting the compound a40 in a solvent such as DMF, DMA, THF, dioxane, acetic acid or the like, or a mixture thereof, with a halogenating reagent such as N-bromosuccinimide, 1-chloromethyl-4-fluoro-1,4-diazoniabicyclo[2,2,2]octane bis(tetrafluoroborate)(selectfluor (R)) or the like at −20° C. to 100° C., preferably 0° C. to 60° C., for 0.1 to 8 hours, preferably 0.5 to 2 hours.

(Step 2)

It is possible to convert the halogen group to an aryl group or an alkynyl group by a coupling reaction generally known.

(Step 3)

It can be carried out according to Step 15 in the synthesis of the compound (I-1').

[2-6] Synthesis of the Compound (I-x)

[Chemical formula 93]

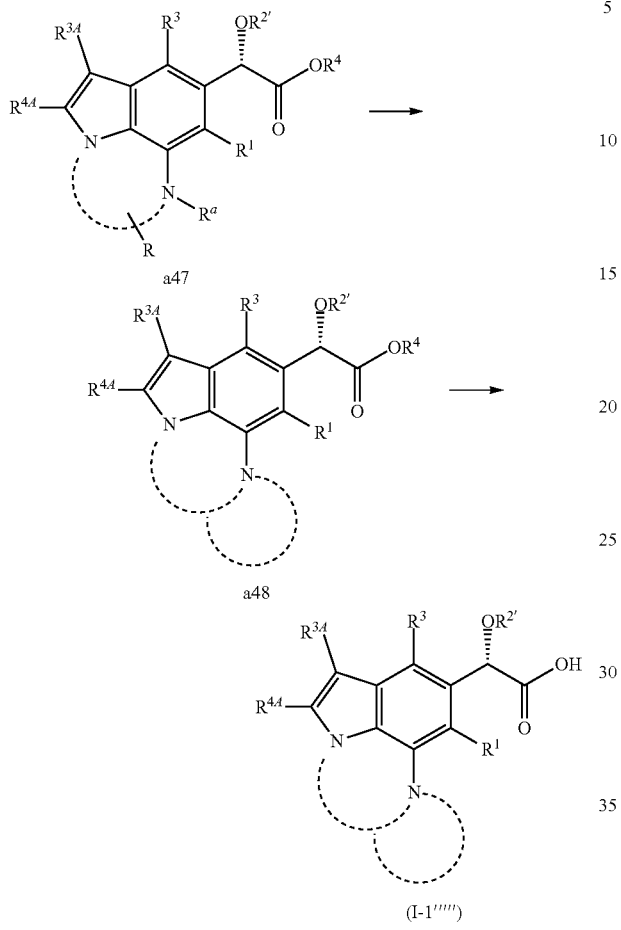

a47 a48

(I-1''''')

wherein R is alkyl etc.; the other symbols are the same as defined above.

(Step 1)

When $R^a$ of the compound a47 is hydrogen, or has a functional group such as amino group or hydroxyl group and R has a carboxy group, the compound a48 can be obtained by reacting the compound a47 in a solvent such as DMF, DMA, THF, dioxane, methylene chloride or the like, or a mixture thereof, with a condensing agent such as dicyclohexylcarbodiimide or O-(7-aza-benzotriazol-1-yl)-N,N,N', N'-tetramethyluronium hexafluorophosphate or the like, and additives such as 1-hydroxy-7-azabenzotriazole, 1-hydroxybenzotriazole or the like at −20° C. to 100° C., preferably 0° C. to 60° C., for 0.1 to 24 hours, preferably 0.5 to 6 hours. Or, when $R^a$ of the compound a47 is hydrogen, or has a functional group such as amino group or hydroxyl group and R has a functional group such as amino group or hydroxyl group, the compound a48 can be obtained by reacting the compound a47 in a solvent such as DMF, DMA, THF, dioxane, methylene chloride or the like, or a mixture thereof, with 1,1'-carbonyldiimidazole or oxalyl chloride etc. at −20° C. to 100° C., preferably 0° C. to 60° C. for 0.1 to 24 hours, preferably 0.5 to 6 hours.

Or, when Ra and R each has alkenyl group, the compound a48 can be obtained by reacting the compound a47 in a solvent such as DMF, DMA, THF, dioxane, methylene chloride or the like, or a mixture thereof, in the presence of a catalyst such as (1,3-bis(2,4,6-trimethylphenyl)-2-imidazolidinylidene)dichloro(phenylmethylene)(tricyclohexylphosphine)ruthenium or the like, at −20° C. to 100° C., preferably 0° C. to 60° C., for 0.1 to 48 hours, preferably 0.5 to 24 hours.

(Step 2)

It can be carried out according to Step 15 in the synthesis of the compound (I-1').

Alternative Synthesis of the Compound (I-1') Type

[Chemical formula 94]

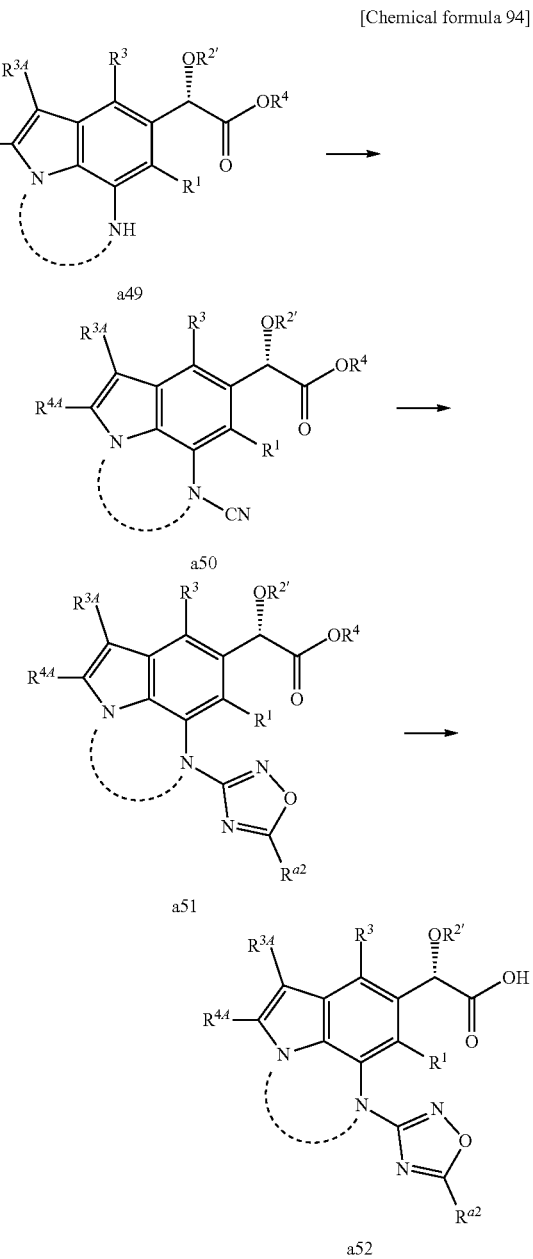

a49 a50 a51 a52 wherein $R^{a2}$ is substituted or unsubstituted alkyl; the other symbols are the same as defined above.

(Step 1)

The compound a51 can be obtained by reacting the compound a49 in a solvent such as DMF, DMA, DMSO or the like, or a mixture thereof, with a base such as potassium carbonate, cesium carbonate etc. and cyanogen bromide at 0° C. to 80° C., preferably 20° C. to 40° C., for 1 to 48 hours, preferably 6 to 24 hours.
(Step 2)

The hydroxyl guanidine derivative can be obtained by reacting the compound a50 in a solvent such as ethanol, methanol, THF or the like, or a mixture thereof with a base and hydroxylamine hydrochloride, at 0° C. to 100° C., preferably 60° C. to 80° C., for 0.1 to 24 hours, preferably 0.5 to 6 hours.
Then, the compound a51 can be obtained by reacting them in a solvent such as diglyme etc. with acid chloride shown by $R^{a2}COCl$ and bases, at 0° C. to 120° C., preferably 60° C. to 100° C., for 0.1 to 24 hours, preferably 0.5 to 6 hours. Preferred bases include triethylamine, pyridine and the like.
(Step 3)

It can be carried out according to Step 15 in the synthesis of the compound (I-1').

wherein $R^{a3}$ is hydrogen or substituted or unsubstituted alkyl; the other symbols are the same as defined above.
(Step 1)

The compound a53 can be obtained by reacting the compound a49 in a solvent such as dichloromethane, dichloroethane or the like, or a mixture thereof, with TMSNCS, at 25° C. to 120° C., preferably 60° C. to 100° C., for 1 to 48 hours, preferably 6 to 24 hours.
(Step 2)

Alternatively the compound a54 can be obtained by reacting the compound a53 in a solvent such as ethanol, methanol, THF or the like, or a mixture thereof, with a base and $R^{a3}COCH_2Cl$, at 0° C. to 100° C., preferably 60° C. to 90° C., for 0.1 to 24 hours, preferably 0.5 to 6 hours. Preferred bases include triethylamine, pyridine and the like.
(Step 3)

It can be carried out according to Step 15 in the synthesis of the compound (I-1').

[Chemical formula 95]

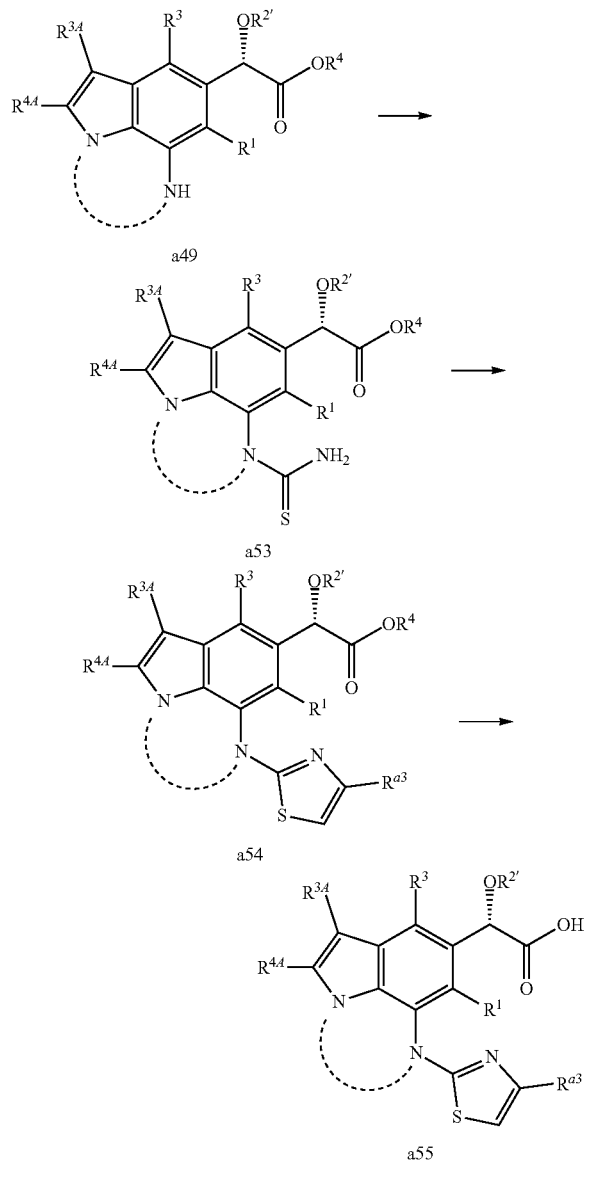

[Chemical formula 96]

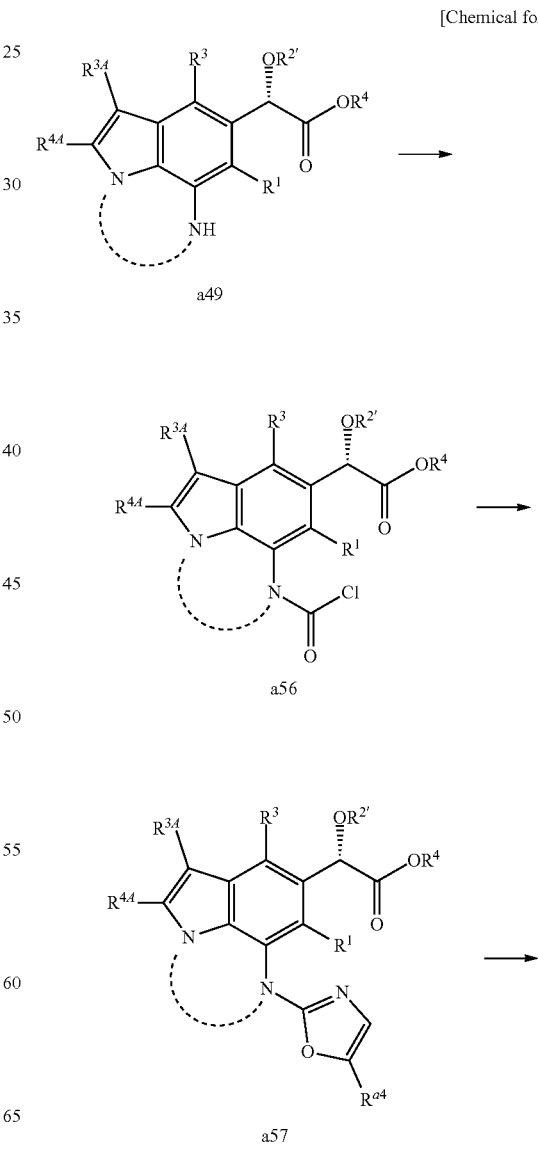

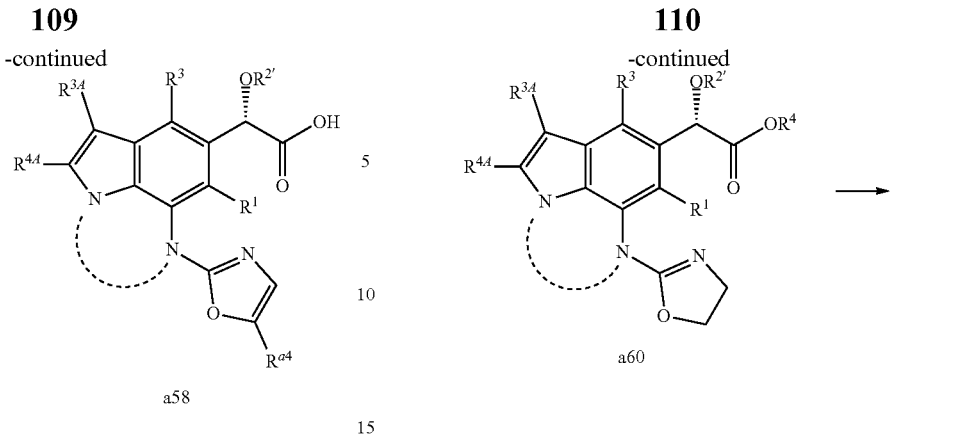

a58 a60 wherein $R^{a4}$ is hydrogen or substituted or unsubstituted alkyl; the other symbols are the same as defined above.

(Step 1)

The compound a56 can be obtained by reacting the compound a49 in a solvent such as dichloromethane, chloroform or the like, or a mixture thereof, with triphosgene, at 0° C. to 80° C., preferably 25° C. to 40° C., for 1 to 48 hours, preferably 6 to 24 hours.

(Step 2)

The urea derivative can be obtained by reacting the compound a56 in a solvent such as ethanol, methanol, THF, water or the like, or a mixture thereof, with a base and $R^{a4}COCH_2NH_2$, at 0° C. to 100° C., preferably 20° C. to 80° C., for 0.1 to 24 hours, preferably 0.5 to 6 hours. In addition, the compound a57 can be obtained by reacting in a solvent such as THF, toluene or the like, with Burgess reagent in sealed at 80° C. to 150° C., preferably 100° C. to 120° C., for 0.1 to 24 hours, preferably 0.5 to 6 hours. Preferred bases include sodium hydrogen carbonate or potassium hydrogen carbonate.

(Step 3)

It can be performed according to Step 15 in the synthesis of the compound (I-1').

(Step 1)

The compound a59 can be obtained by reacting the compound a49 in a solvent such as acetonitrile, propionitrile or the like, or a mixture thereof, with t-butyl(2-isothiocyanate ethoxy)dimethylsilane, at 25° C. to 120° C., preferably 60° C. to 100° C., for 1 to 48 hours, preferably 6 to 24 hours, and then reacting them in a solvent such as THF, dichloromethane or the like, or a mixture thereof, with TBAF, at 0° C. to 80° C., preferably 20° C. to 40° C., 1 to 48 hours, preferably 6 to 24 hours.

(Step 2)

The compound a60 can be obtained by reacting the compound a59 in a solvent such as ethanol, methanol, THF or the like, or a mixture thereof, with mercury oxide, at 0° C. to 60° C., preferably 20° C. to 40° C., for 1 to 7 days, preferably 3 to 5 days.

(Step 3)

It can be carried out according to Step 15 of the synthesis of the compound (I-1').

Synthesis of the Compound (I-1'-1)

[Chemical formula 97]

[Chemical formula 98]

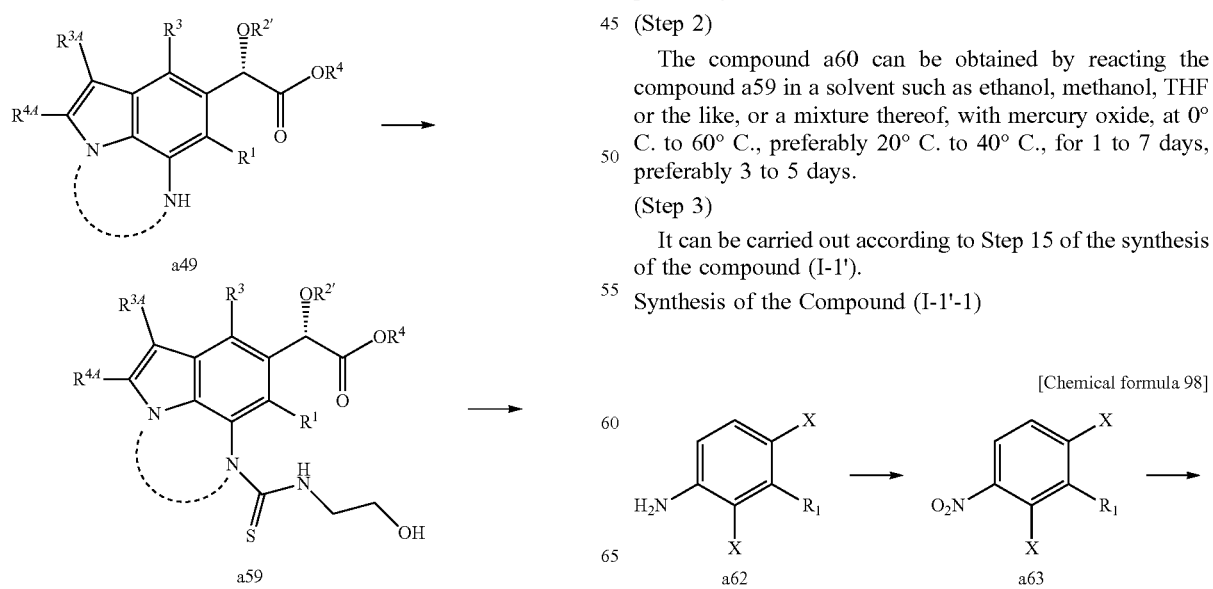

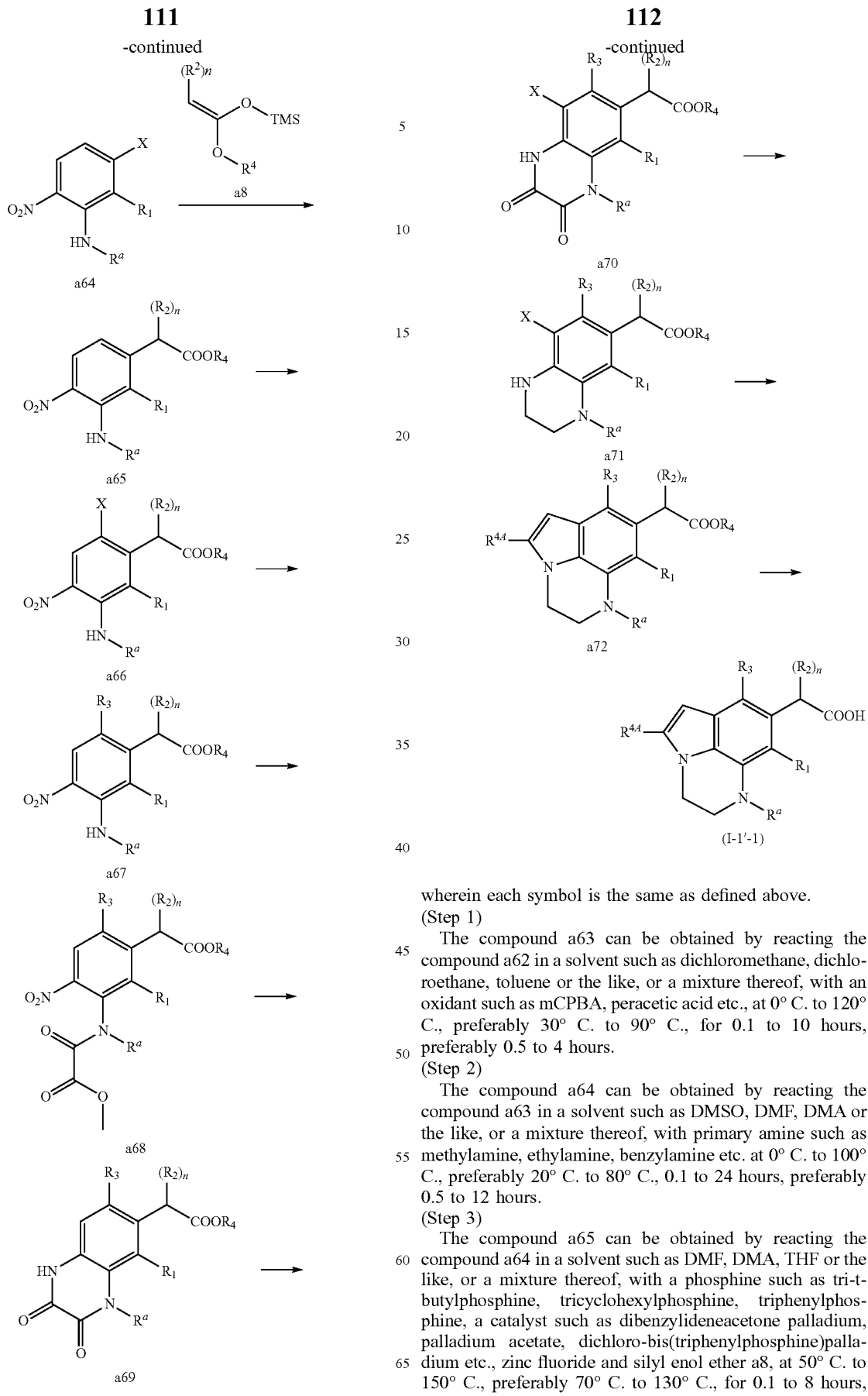

wherein each symbol is the same as defined above.
(Step 1)
The compound a63 can be obtained by reacting the compound a62 in a solvent such as dichloromethane, dichloroethane, toluene or the like, or a mixture thereof, with an oxidant such as mCPBA, peracetic acid etc., at 0° C. to 120° C., preferably 30° C. to 90° C., for 0.1 to 10 hours, preferably 0.5 to 4 hours.
(Step 2)
The compound a64 can be obtained by reacting the compound a63 in a solvent such as DMSO, DMF, DMA or the like, or a mixture thereof, with primary amine such as methylamine, ethylamine, benzylamine etc. at 0° C. to 100° C., preferably 20° C. to 80° C., 0.1 to 24 hours, preferably 0.5 to 12 hours.
(Step 3)
The compound a65 can be obtained by reacting the compound a64 in a solvent such as DMF, DMA, THF or the like, or a mixture thereof, with a phosphine such as tri-t-butylphosphine, tricyclohexylphosphine, triphenylphosphine, a catalyst such as dibenzylideneacetone palladium, palladium acetate, dichloro-bis(triphenylphosphine)palladium etc., zinc fluoride and silyl enol ether a8, at 50° C. to 150° C., preferably 70° C. to 130° C., for 0.1 to 8 hours, preferably 0.5 to 2 hours.

(Step 4)

The compound a66 can be obtained by reacting the compound a65 in a solvent such as dichloromethane, DMF, acetic acid or the like, or a mixture thereof, with a halogenating reagent such as NBS, NIS, iodine etc., at −50° C. to 50° C., preferably −30° C. to 30° C., for 0.1 to 8 hours, preferably 0.5 to 4 hours.

(Step 5)

The compound a67 can be obtained by reacting the compound a66 in a solvent such as DMF, DMA, dioxane, water or the like, or a mixture thereof, with a aqueous solution of base such as $K_2CO_3$, $Na_2CO_3$, $K_3PO_4$ etc., boronic acid which is commercially available or synthesized in a known method, borate, and a catalyst such as $PdCl_2$ (dtbpf), $Pd(PPh_3)_4$, $PdCl_2$ (dppf) tec., at 50° C. to 50° C., preferably 70° C. to 130° C., for 0.1 to 8 hours, preferably 0.5 to 2 hours.

(Step 6)

The compound a68 can be obtained by reacting the compound a67 in a solvent such as dichloromethane, DMF, DMA or the like, or a mixture thereof, with a base such as triethylamine, pyridine, DMAP or the like, and methyl chloroglyoxylate, at −40° C. to 40° C., preferably 0° C. to 20° C., for 0.1 to 4 hours, preferably 0.5 to 1 hour.

(Step 7)

The compound a69 can be obtained by reacting the compound a68 in a solvent such as ethanol, methanol, THF, water or the like, or a mixture thereof, with a reductant such as sodium hydrosulfite, iron, tin chloride or the like, at 0° C. to 100° C., preferably 20° C. to 80° C., for 0.1 to 12 hours, probably 0.5 to 6 hours.

(Step 8)

It can be performed according to Step 4 in the synthesis of the compound 70.

(Step 9)

The compound a71 can be obtained by the compound a70 in a solvent such as THF, diethyl ether, DME or the like, or a mixture thereof, with a reductant such as borane-tetrahydrofuran complex, borane dimethyl sulfide complex, at −20° C. to 50° C., preferably 0° C. to 30° C., for 0.1 to 8 hours, preferably 0.5 to 4 hours.

(Step 10)

The compound a72 can be obtained by the compound a71 in a solvent such as THF, DMF, toluene or the like, or a mixture thereof, with a phosphine such as tri-t-butylphosphine, tricyclohexylphosphine, triphenylphosphine, a catalyst such as dibenzylideneacetone palladium, palladium acetate, dichloro bis(triphenylphosphine)palladium and metal enolate which is commercially available or synthesized in known method, at 50° C. to 150° C., preferably 70° C. to 130° C., 0.1 to 8 hours, preferably 0.5 to 2 hours.

(Step 11)

The compound (I-1'-1) can be obtained by reacting the compound a72 in a solvent such as methanol, ethanol, THF or the like, or a mixture thereof, with a base such as aqueous solution of sodium hydroxide, aqueous solution of potassium hydroxide, aqueous solution of lithium hydroxide, at 10° C. to 110° C., preferably 30° C. to 90° C., for 0.1 to 8 hours, preferably 0.5 to 4 hours.

Synthesis of the Compound (I-1'-2)

[Chemical formula 99]

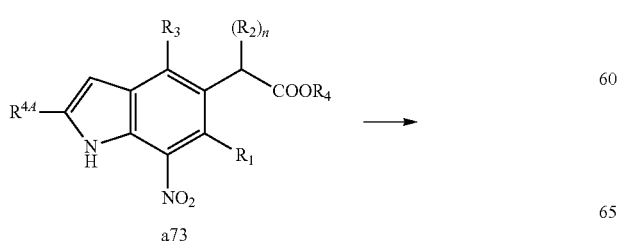

a73

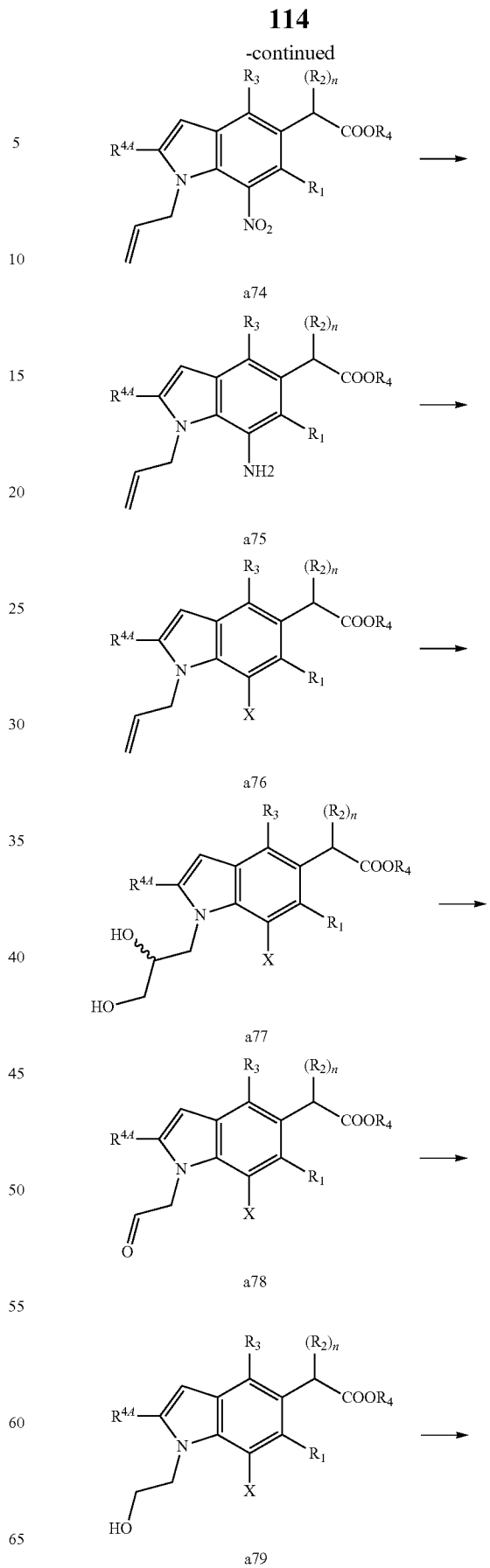

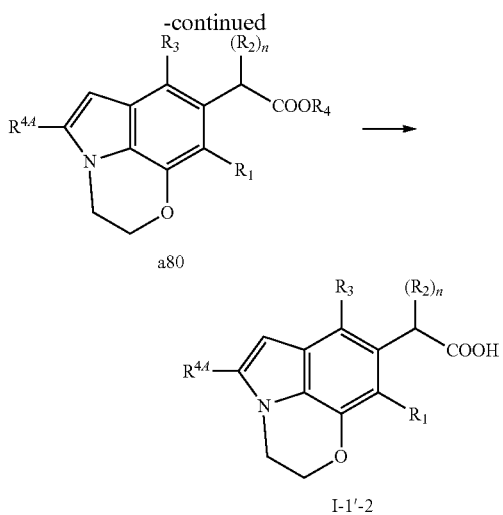

wherein each symbol is the same as defined above.

(Step 1)
The compound a74 can be obtained by reacting the compound a73 in a solvent such as DMF, DMA, THF or the like, or a mixture thereof, with a allylation reagent such as ally bromide, ally chloride and a base such as sodium hydride potassium-t-butoxide, cesium carbonate, at −20° C. to 50° C., preferably 0° C. to 30° C., for 0 to 4 hours, preferably 0.5 to 2 hours.

(Step 2)
The compound a75 can be obtained by reacting the compound a74 in a solvent such as ethanol, methanol, THF, water or the like, or a mixture thereof, with a reductant such as sodium hydrosulfite, iron, tin chloride, at 0° C. to 100° C., preferably 20° C. to 80° C., for 0.1 to 8 hours, preferably 0.5 to 4 hours.

(Step 3)
The compound a76 can be obtained by reacting the compound a75 in a solvent such as acetonitrile, ethyl acetate, dimethylsulfoxide or the like, or a mixture thereof, nitrite t-butyl, halogenated metal such as potassium iodide, copper(I) bromide, copper(I) chloride, at 0° C. to 80° C., preferably 20° C. to 60° C., 0.1 to 8 hours, preferably 0.5 to 4 hours.

(Step 4)
The compound a77 can be obtained by reacting the compound a76 in a solvent such as ethanol, THF, water or the like, or a mixture thereof, with osmium (VI) acid potassium and sodium per iodate, at −10° C. to 60° C., preferably 10° C. to 40° C., for 0.1 to 8 hours, preferably 0.5 to 4 hours.

(Step 5)
The compound a78 can be obtained by reacting the compound a77 in a solvent such as ethanol, THF, water or the like, or a mixture thereof, with sodium per iodate at −10° C. to 60° C., preferably 10° C. to 40° C., for 0.1 to 4 hours, preferably 0.5 to 2 hours.

(Step 6)
The compound a79 can be obtained by reacting the compound a78 in a solvent such as ethanol, methanol, water or the like, or a mixture thereof, with a reductant such as sodium borohydrate, lithium borohydrate, lithium aluminium hydride or the like, at −20° C. to 40° C., preferably 0° C. to 20° C., for 0.1 to 4 hours, preferably 0.5 to 2 hours.

(Step 7)
The compound a80 can be obtained by reacting the compound a79 in a solvent such as dioxane, DMF, toluene or the like, or a mixture thereof, with copper(I) iodide, a ligand such as 9,10-phenanthroline, 2,2'-bipyridyl, N,N-dimethylamino glycine or the like, a base such as potassium carbonate, cesium carbonate, potassium phosphate or the like, at 80° C. to 180° C., preferably 100° C. to 160° C., for 0.1 to 8 hours, preferably 0.5 to 4 hours.

(Step 8)
The compound (I-1'-2) can be obtained by reacting the compound a80 in a solvent such as methanol, ethanol, THF or the like, or a mixture thereof, with a base such as aqueous sodium hydroxide solution, aqueous potassium hydroxide solution, aqueous lithium hydroxide solution or the like, at 10° C. to 110° C., preferably 30° C. to 90° C., for 0.1 to 8 hours, preferably 0.5 to 4 hours.

Synthesis of the Compound (I-1'-3) and the Compound (I-1'-4)

[Chemical formula 100]

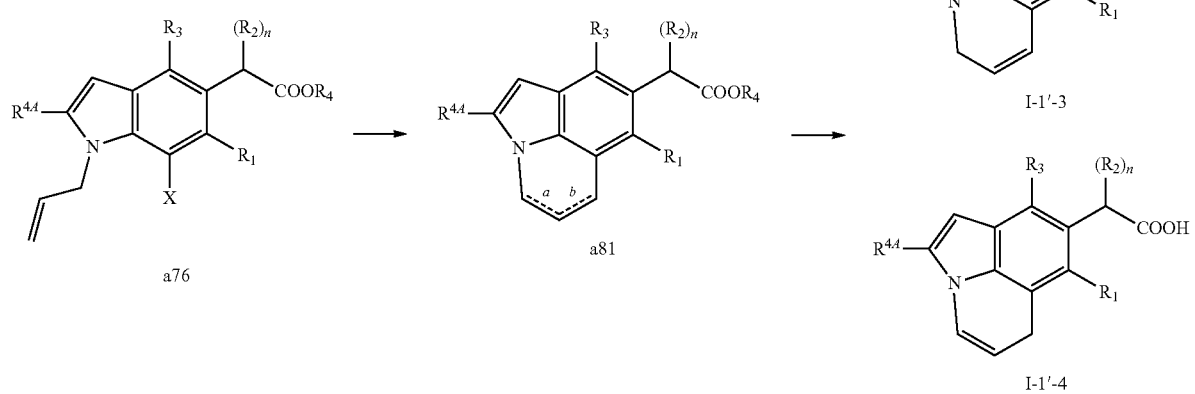

wherein the broken line means presence or absence of a bond, either of the broken line or the broken line b is only presence; each symbol is the same as defined above.

(Step 1)

The compound a81 can be obtained by reacting the compound a76 in a solvent such as DMF, dioxane, acetonitrile or the like, or a mixture thereof, with a base such as triethylamine, potassium acetate, sodium hydrogen carbonate or the like, a phosphine such as tri-t-butylphosphine, tricyclohexylphosphine, tri(o-tolyl)phosphine or the like, and a catalyst such as dibenzylideneacetone palladium, palladium acetate, dichloro bistriphenylphosphinepalladium, at 50° C. to 150° C., preferably 70° C. to 130° C., for 0.1 to 4 hours, preferably 0.5 to 2 hours.

(Step 2)

The compound (I-1'-4) can be obtained by reacting the compound a81 in a solvent such as methanol, ethanol, THF or the like, or a mixture thereof, with a base such as aqueous sodium hydroxide solution, aqueous potassium hydroxide solution, aqueous lithium hydroxide solution or the like, at 10° C. to 110° C., preferably 30° C. to 90° C., for 0.1 to 8 hours, preferably 0.5 to 4 hours and then separating by column chromatography etc.

[2-7] Another Synthesis of the Compound a40

[Chemical formula 101]

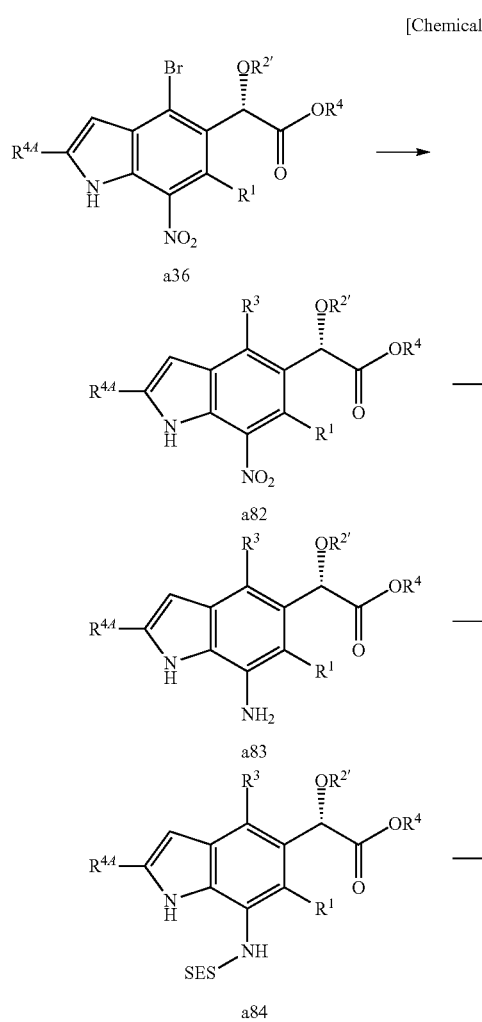

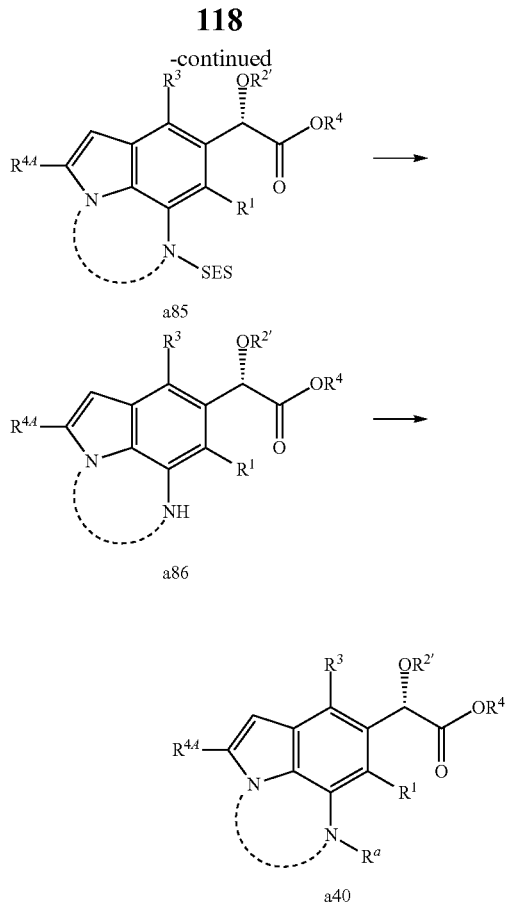

wherein each symbol is the same as defined above.

(Step 1)

It can be carried out according to Step 4 in the synthesis of the compound (I-1').

(Step 2)

It can be carried out according to Step 2 in the synthesis of the compound (I-1').

(Step 3)

The compound a84 can be obtained by reacting the compound a83 in a solvent such as dichloromethane, DMF, DMA or the like, or a mixture thereof, with a base such as pyridine, Et$_3$N or the like and 2-(trimethylsilyl)ethane sulfonyl chloride, at −20° C. to 60° C., preferably −0° C. to 30° C. for 1 to 24 hours, preferably 5 to 18 hours.

(Step 4)

It can be carried out according to Step 14 in the synthesis of the compound (I-1').

(Step 5)

The compound a86 can be obtained by reacting the compound a85 in a solvent such as THF, dioxane or the like, or a mixture thereof, with a fluorine ion such as tetrabutylammonium fluoride, Pyridine-HF, at 0° C. to 100° C., preferably 20° C. to 60° C., for 1 to 24 hours, preferably 10 to 20 hours.

(Step 6)

It can be carried out according to Step 13 in the synthesis of the compound (I-1'). Or it can be carried out according to Step 1 in the Synthesis of a113.

[2-8] Another Synthesis of the Compound a40

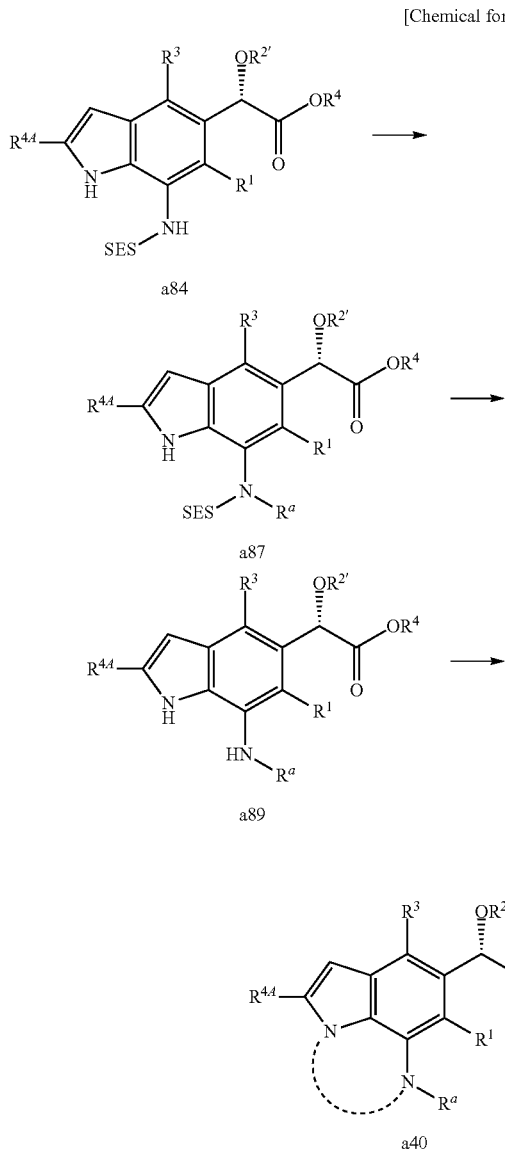

wherein each symbol is the same as defined above (Step 1)

The compound a87 can be obtained by reacting the compound a84 in a solvent such as dichloromethane, DMF, DMA or the like, or a mixture thereof, with a base such as cesium carbonate, pyridine, triethylamine or the like, an alkylating agent such as methyl iodide, ethyl bromoacetate etc. which is commercially available or synthesized in a known method, at −50° C. to 50° C., preferably −30° C. to 30° C., for 0.1 to 4 hours, preferably 0.5 to 1 hour.

(Step 2)

It can be carried out according to Step 5 in the [2-7] synthesis of the compound a40.

(Step 3)

It can be carried out according to Step 14 in the synthesis of the compound (I-1').

[2-9] Another Synthesis of the Compound a46

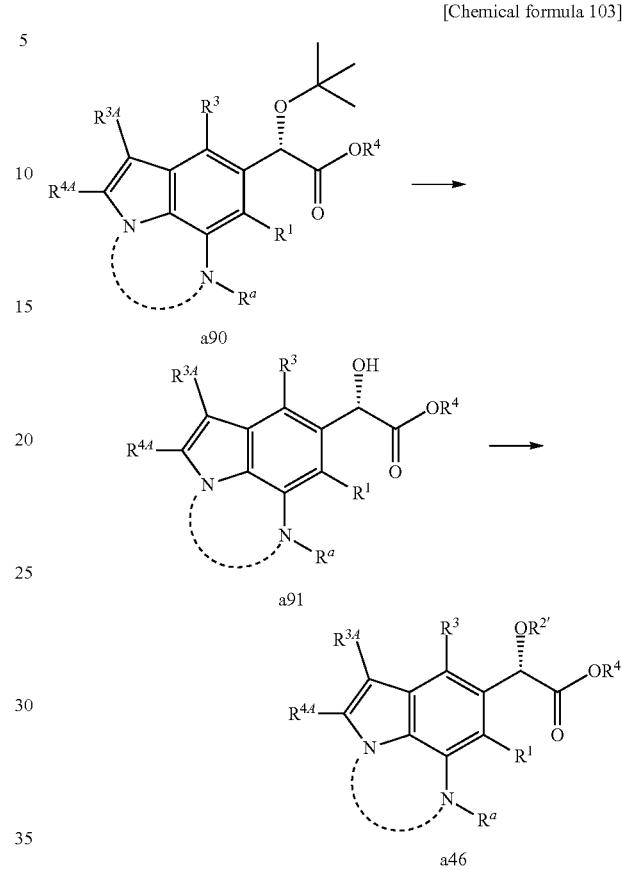

wherein each symbol is the same as defined above.

(Step 1)

The compound a91 can be obtained by reacting the compound a90 in a solvent such as dichloromethane, DMF, DMA or the like, or a mixture thereof, with an acid such as TFA, tosylate, hydrochloric acid or the like, at −20° C. to 60° C., preferably 0° C. to 40° C., for 0.1 to 4 hours, preferably 0.5 to 2 hours.

(Step 2)

The compound a46 can be obtained by reacting the compound a91 in a solvent such as THF, DMF, toluene or the like, or a mixture thereof, with a base such as sodium hydride, potassium tert-butoxide, sodium methoxide or the like, and an alkylating agent such as $R^{2'}$—I, $R^{2'}$—Br, $R^{2'}$—Cl or the like, at −20° C. to 100° C., preferably 0° C. to 60° C., for 1 to 24 hours, preferably 3 to 12 hours.

[2-10] Synthesis of the Compound (I-1'-5)

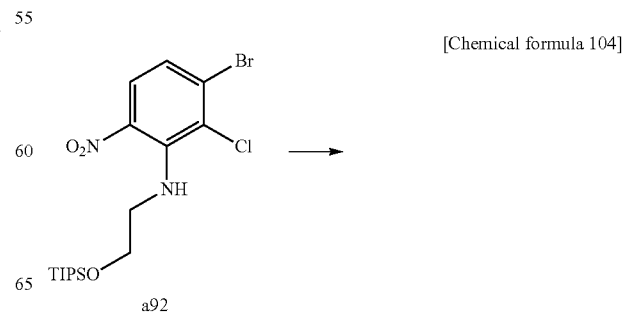

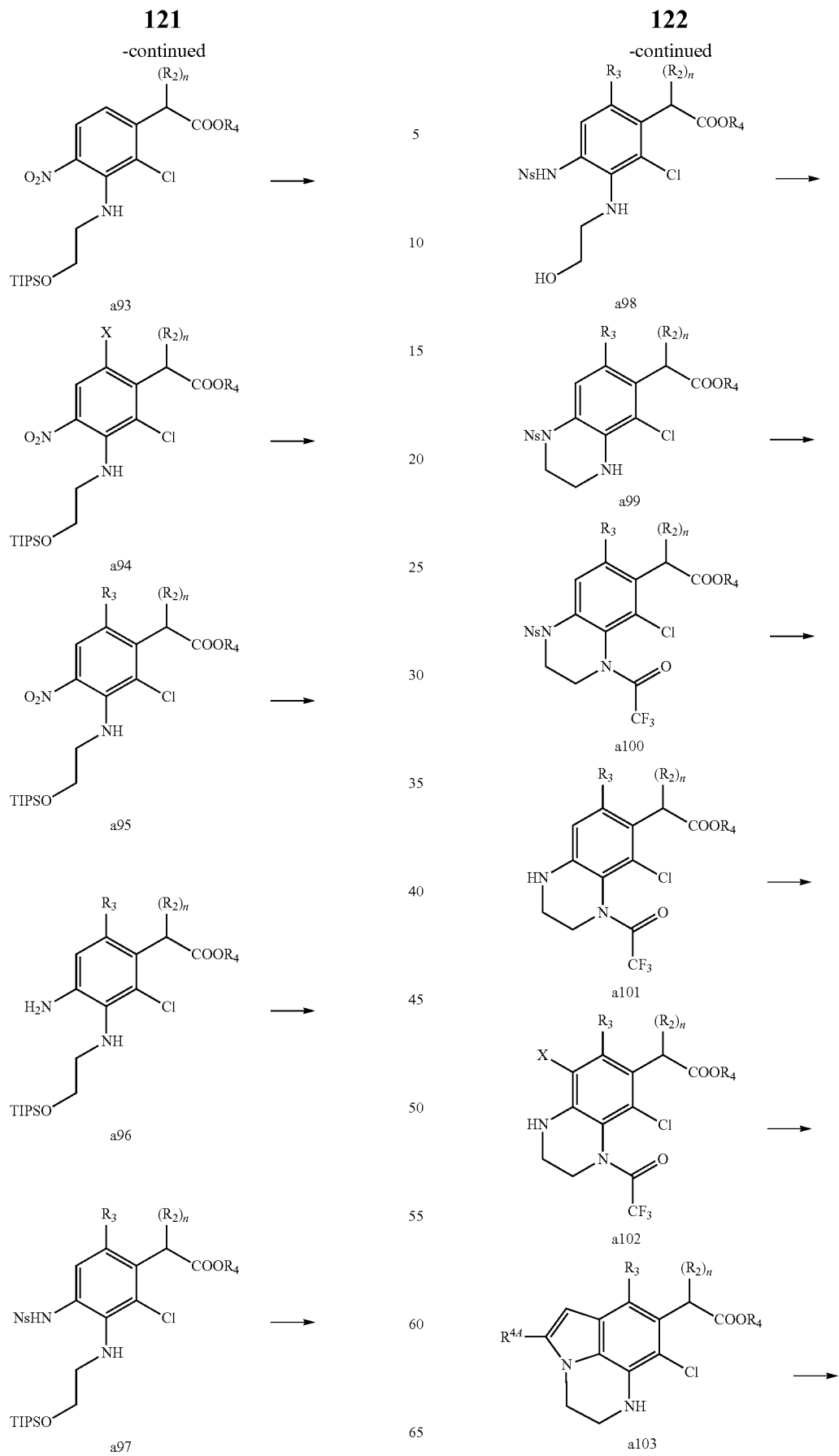

123

-continued

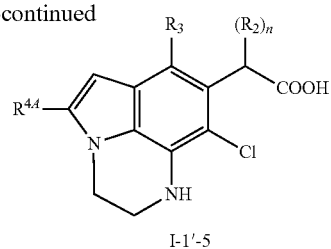

I-1'-5 wherein each symbol is the same as defined above.
(Step 1)
It can be carried out according to Step 3 in the synthesis of the compound (I-1'-1).
(Step 2)
It can be carried out according to Step 4 in the synthesis of the compound (I-1'-1).
(Step 3)
It can be carried out according to Step 5 in the synthesis of the compound (I-1'-1).
(Step 4)
It can be carried out according to Step 7 in the synthesis of the compound (I-1'-1).
(Step 5)
The compound a97 can be obtained by reacting the compound a96 in a solvent such as dichloromethane, DMF, DMA or the like, or a mixture thereof, with a base such as pyridine, triethylamine or the like, DMAP, and 2-nitrobenzenesulfonylchloride, at 0° C. to 80° C., preferably 20° C. to 40° C., for 0.5 to 24 hours, preferably 1 to 8 hours.
(Step 6)
It can be carried out according to Step 5 in the [2-7] another synthesis of the compound a40.
(Step 7)
The compound a99 can be obtained by reacting the compound a98 in a solvent such as toluene, THF, dichloromethane or the like, or a mixture thereof, with Mitsunobu reagent such as DEAD, DIAD or bis(2-methoxyethyl)azodicarboxylate and triphenylphosphine, tri-n-butylphosphine or tributylphosphine, at −20° C. to 70° C., preferably 0° C. to 30° C., for 0.1 to 12 hours, preferably 0.5 to 2 hours.
(Step 8)
The compound a100 can be obtained by reacting the compound a99 in a solvent such as pyridine, lutidine or the like, or a mixture thereof, with TFAA, at 0° C. to 80° C., preferably 20° C. to 40° C., for 0.5 to 24 hours, preferably 1 to 4 hours.
(Step 9)
The compound a101 can be obtained by reacting the compound a100 in a solvent such as DMF, DMA or the like, or a mixture thereof, with a base such as potassium carbonate, cesium carbonate or the like, and thiophenol, at −20° C. to 60° C., preferably 0° C. to 20° C., for 0.5 to 24 hours, preferably 1 to 8 hours.
(Step 10)
It can be carried out according to Step 4 in the synthesis of the compound (I-1'-1).
(Step 11)
It can be carried out according to Step 10 in the synthesis of the compound (I-1'-1).
(Step 12)
It can be carried out according to Step 11 in the synthesis of the compound (I-1'-1).

124

[2-11] Another Synthesis of the Compound (I-1''''-1)

[Chemical formula 105]

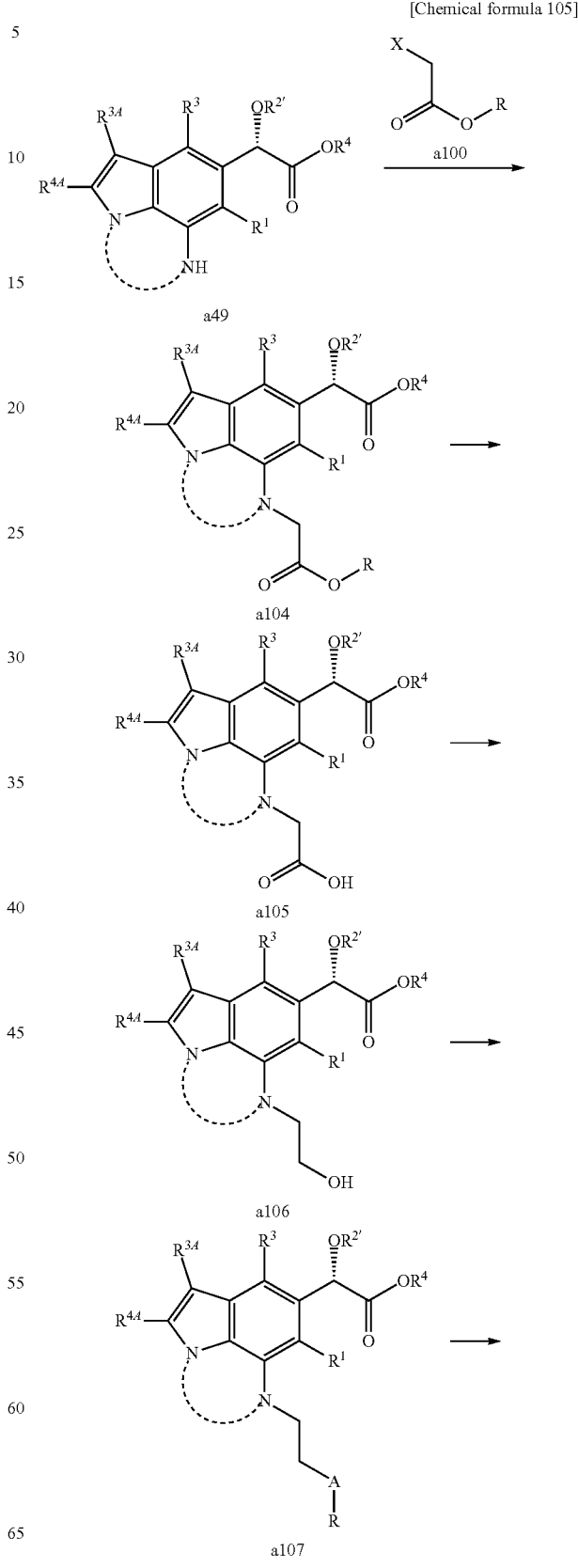

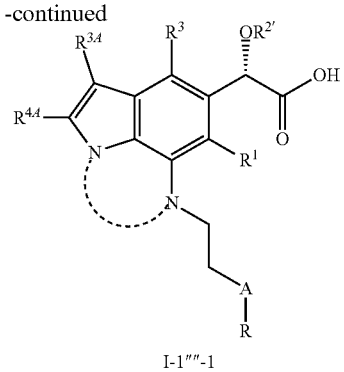

I-1''''-1 wherein A is a bond, —O—, or —NR$^a$, R is hydrogen, halogen, or substituted or unsubstituted alkyl, the other symbols are the same as defined above.

(Step 1)

The compound a104 can be obtained by reacting the compound a49 in a solvent such as dichloromethane, DMF, DMA or the like, or a mixture thereof, with a base such as cesium carbonate, pyridine, triethylamine or the like and the compound a100, at −50° C. to 50° C., preferably −30° C. to 30° C., for 0.1 to 4 hours, preferably 0.5 to 1 hour.

(Step 2)

The compound a105 can be obtained by reacting the compound a104 in a solvent such as methanol, ethanol, tetrahydrofuran DMSO or the like or a mixture thereof, with potassium hydroxide, sodium hydroxide or lithium hydroxide etc., at −20° C. to 50° C., preferably −5° C. to 20° C., for 0.1 to 24 hours, preferably 1 to 6 hours.

(Step 3)

The compound a106 can be obtained by reacting the compound a105 in a solvent such as THF, diethyl ether or the like, or a mixture thereof, with a reductant such as borane-tetrahydrofuran complex, boron dimethyl sulfide complex etc., at 0° C. to 100° C., preferably 50° C. to 80° C., for 0.5 to 24 hours, preferably 1 to 3 hours.

(Step 4)

The compound a107 can be obtained by reacting the compound a106 in a solvent such as DMF, DME, tetrahydrofuran, acetone, acetonitrile or the like, with a base potassium carbonate, sodium carbonate, cesium carbonate, sodium hydride or the like, and an alkylating agent which is commercially available or synthesized in a known method, at −30° C. to 100° C., preferably −10° C. to 50° C., for 0.5 to 24 hours, preferably 1 to 5 hours. Or, the compound a107 can be obtained by reacting it in a solvent such as dichloromethane, chloroform or the like, with an halogenating agent such as trifluoride N,N-diethylamino sulfur, at −30° C. to 100° C., preferably −10° C. to 50° C., for 0.5 to 24 hours, preferably 1 to 5 hours. Or, the compound a107 can be obtained by reacting them with substituted alcohol and substituted amine in the presence of bases at −30° C. to 50° C., preferably −10° C. to 20° C., for 0.5 to 12 hours, preferably 1 to 5 hours after activating the compound 218 with an activating agent such as methane sulfonyl chloride, p-toluene sulfonyl chloride etc.

(Step 5)

It can be carried out according to Step 15 in the synthesis of the compound (I-1').

[2-12] Synthesis of the Compound (I-1''''-2)

[Chemical formula 106]

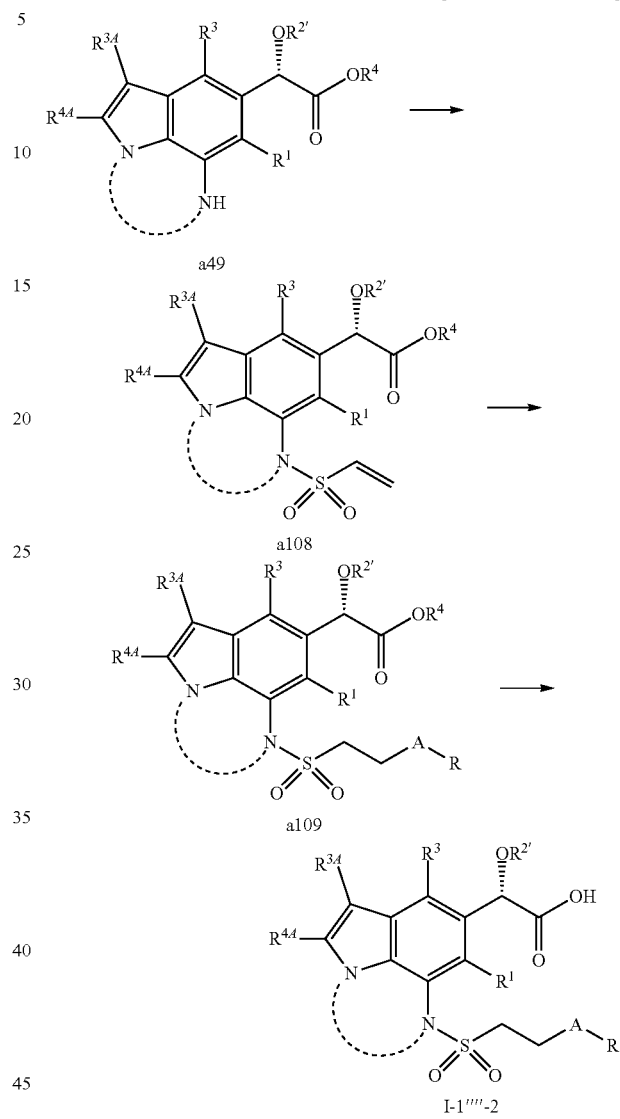

wherein each symbol is the same as defined above.

(Step 1)

The compound a108 can be obtained by reacting the compound a49 in a solvent such as pyridine, lutidine or the like, or a mixture thereof, with 2-chloroethane-1-sulfonyl chloride, at 0° C. to 80° C., preferably 20° C. to 40° C., for 1 to 8 hours, preferably 2 to 4 hours.

(Step 2)

The compound a109 can be obtained by reacting the compound a108 in a solvent such as THF, DMF or the like, or a mixture thereof, with aqueous tetrabutylammonium hydroxide solution or substituted amine, at 0° C. to 80° C., preferably 20° C. to 40° C., for 0.5 to 8 hours, preferably 1 to 4 hours.

(Step 3)

It can be carried out according to Step 15 in the synthesis of the compound (I-1').

[2-13] Synthesis of the Compound (I-1""-3)
(Synthesis of the Compound a113)

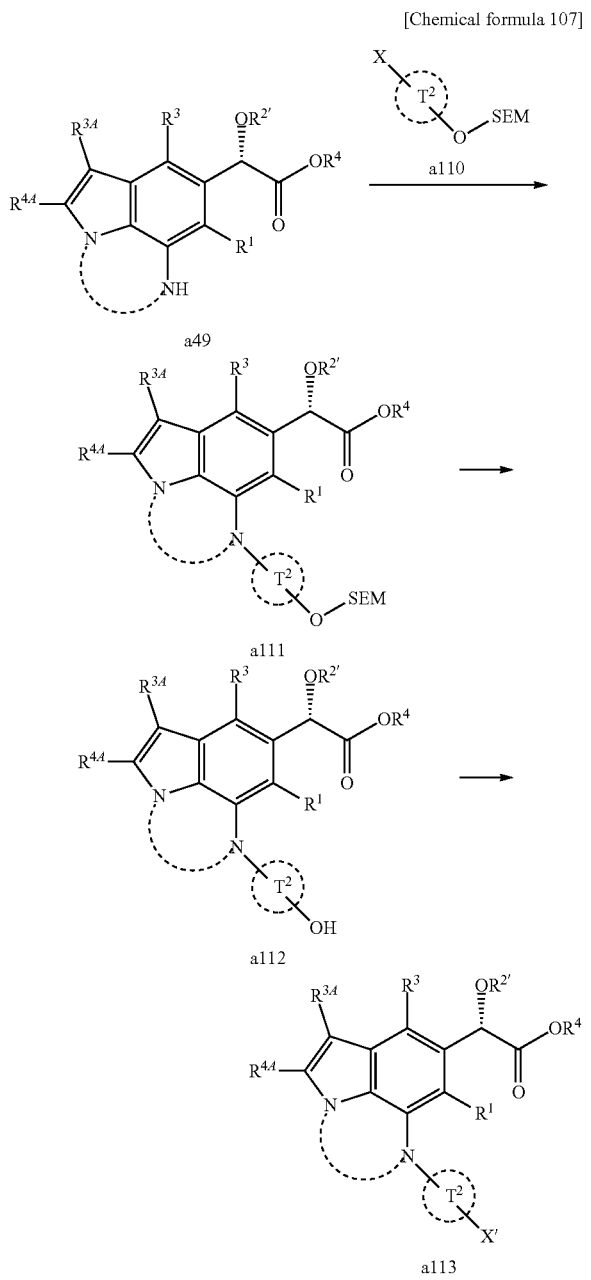

wherein $T^2$ ring is substituted or unsubstituted non-aromatic carbocycle, substituted or unsubstituted aromatic carbocycle, substituted or unsubstituted non-aromatic carbocycle, or substituted or unsubstituted aromatic carbocycle, X' is $C_{1-6}$ alkylsulfonyloxy, halo $C_{1-6}$ alkylsulfonyloxy or substituted or unsubstituted arylsulfonyloxy etc., the other symbols are the same as defined above.

(Step 1)
The compound a111 can be obtained by reacting the compound a49 in a solvent such as toluene, DMF, dioxane or the like, or a mixture thereof, with the compound a110, a phosphine such as BINAP, xantphos etc., a catalyst such as dibenzylideneacetone palladium, palladium acetate, etc., and a base such as cesium carbonate, sodium tert-butoxide etc., at 40° C. to 120° C., preferably 50° C. to 100° C., from 0.1 to 8 hours, preferably 0.5 to 4 hours.

(Step 2)
The compound a112 can be obtained by reacting the compound a111 in a solvent such as THF, dioxane or the like, or a mixture thereof, with a fluorine ion such as tetrabutylammonium fluoride, Pyridine-HF etc., at 40° C. to 100° C., preferably 50° C. to 80° C., for 1 to 24 hours, preferably 3 to 18 hours.

(Step 3)
The compound a113 can be obtained by reacting the compound a112 in a solvent such as toluene, DMF, dioxane or the like, or a mixture thereof, with a base such as pyridine, triethylamine or the like, a sulfonyl reagent such as triflate reagent (e.g.: N-phenyl-bis(trifluoromethane suldonimide), etc.), mesylating reagent (e.g.: methanesulfonyl chloride, methane sulfonic acid anhydride etc.) or the like, at −10° C. to 60° C., preferably 0° C. to 20° C., 5 minutes to 4 hours, preferably 10 minutes to 1 hour.

(Synthesis of the Compound (I-1""-3))

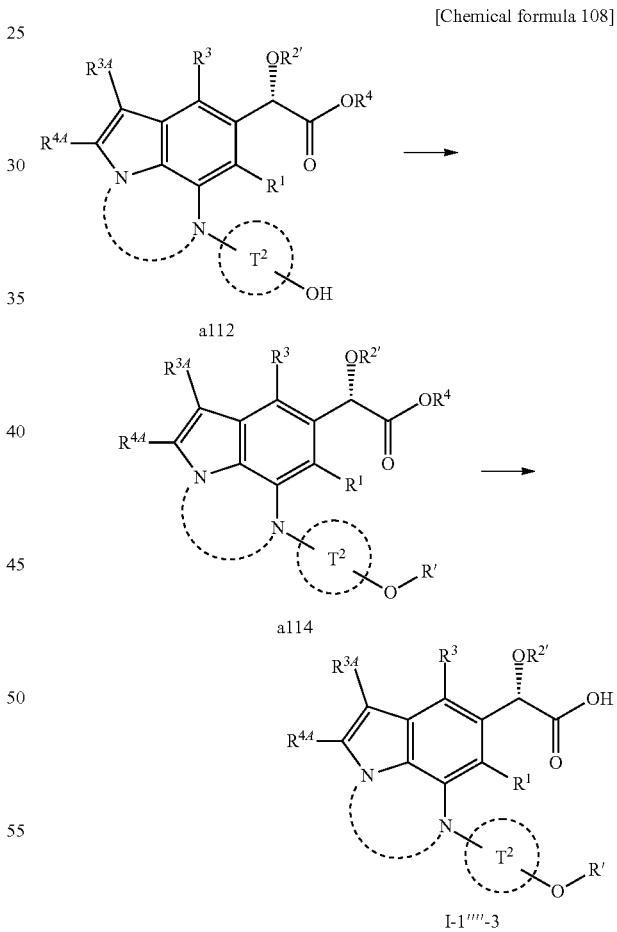

wherein R' is substituted or unsubstituted alkyl, substituted or unsubstituted alkenyl, substituted alkynyl, substituted or unsubstituted non-aromatic carbocycle, substituted or unsubstituted aromatic carbocycle, substituted or unsubstituted non-aromatic heterocycle, or substituted or unsubstituted aromatic heterocycle, the other symbols are the same as defined above.

(Step 1)

The compound a114 can be obtained by reacting the compound a112 in a solvent such as toluene, THF, dichloromethane or the like, or a mixture thereof, with Mitsunobu reagent such as DEAD, DIAD or bis(2-methoxyethyl)azodicalboxylate, triphenylphosphine, tri-n-butylphosphine or tributylphosphine, and alcohol substituted with R' which is commercially available or synthesized in a known method, at −20° C. to 100° C., preferably 0° C. to 30° C., for 0.5 to 24 hours, preferably 1 to 5 hours. Or, the compound a114 can be obtained by reacting it in a solvent such as DMF, DME, tetrahydrofuran, acetone, acetonitrile or the like, with a base such as potassium carbonate, sodium carbonate, cesium carbonate, sodium hydride or the like, and an alkylating agent which is commercially available or synthesized in a known method, at −30° C. to 100° C., preferably −10° C. to 50° C., for 0.5 to 24 hours, preferably 1 to 5 hours.

(Step 2)

It can be carried out according to Step 15 in the synthesis of the compound (I-1').

[2-14] Synthesis of the Compound (I-1''''-4)

[Chemical formula 109]

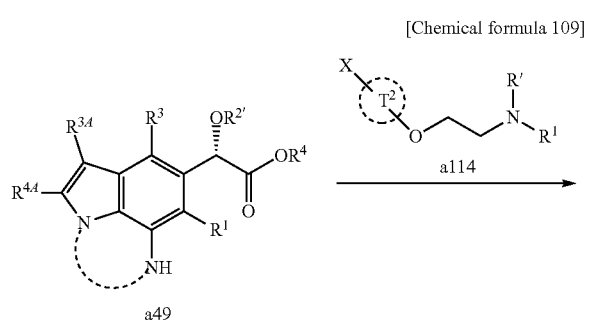

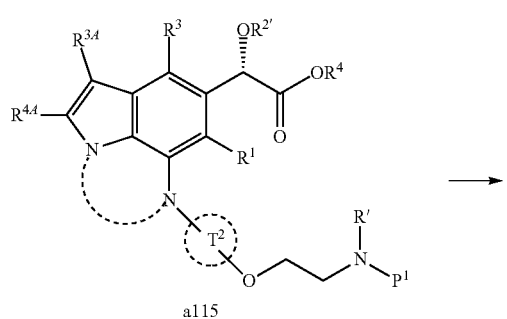

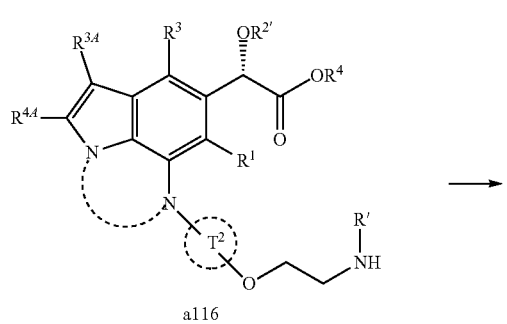

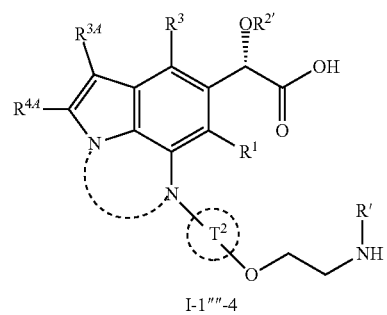

wherein $P^1$ is a protecting group of the amino group such as 9-fluorenylmethyloxycarbonyl group or benzyloxycarbonyl group, the other symbols are the same as defined above.

(Step 1)

It can be carried out according to Step 1 in the synthesis of the compound a113.

(Step 2)

The compound a116 can be obtained by deprotecting with the conventional method corresponding to each protection groups. For example, when $P^1$ is 9-fluorenylmethyloxycarbonyl group, the compound a116 can be obtained by reacting in a solvent such as dichloromethane, chloroform or the like, or a mixture thereof, with a base such as diethyl amine etc. at 0° C. to 100° C., preferably 20° C. to 50° C., for 0.5 to 24 hours, preferably 1 to 5 hours. Or, when $P^1$ is benzyloxycarbonyl group, the compound a116 can be obtained by reacting it in a solvent such as methanol, ethanol, ethyl acetate, tetrahydrofuran or the like, or a mixture thereof, with 5% or 10% palladium carbon, palladium hydroxide, platinum dioxide or the like, under hydrogen atmosphere, under 1 to 10 atm, preferably 1 to 3 atm, at 0° C. to 60° C., preferably 20° C. to 40° C., for 0.1 to 24 hours, preferably 1 to 12 hours.

(Step 3)

It can be carried out according to Step 15 in the synthesis of the compound (I-1').

[2-15] Synthesis of the Compound (I-1''''-5)

[Chemical formula 110]

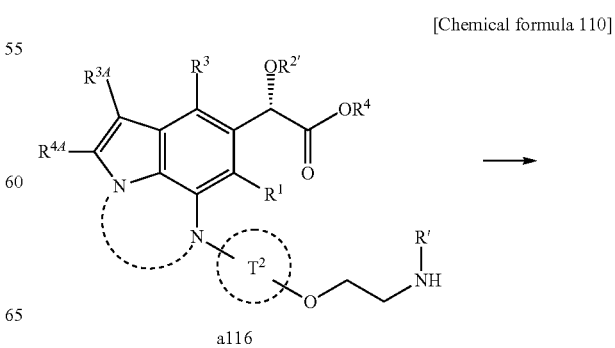

-continued

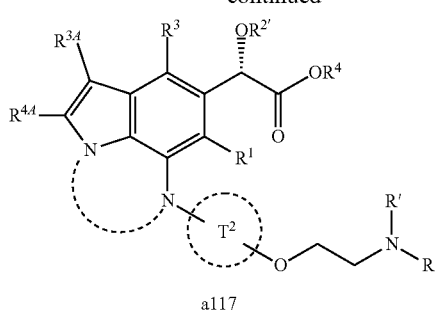

a117

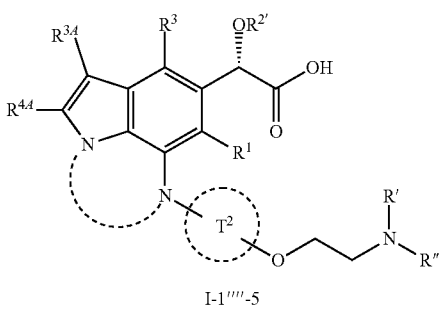

I-1''''-5 wherein R'' is substituted or unsubstituted alkyl, substituted or unsubstituted acyl, substituted or unsubstituted alkylsulfonyl, or substituted or unsubstituted carbamoyl, the other symbols are the same as defined above.

(Step 1)

It can be carried out according to Step 13 in the synthesis of the compound (I-1').

(Step 2)

It can be carried out according to Step 15 in the synthesis of the compound (I-1').

[2-16] Synthesis of the Compound (I-1''''-6)

[Chemical formula 111]

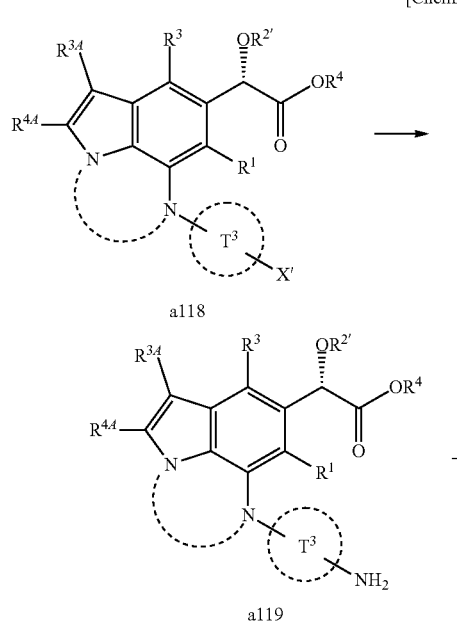

a118 a119

-continued

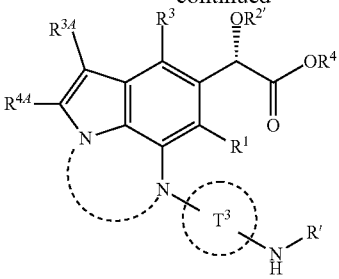

a120

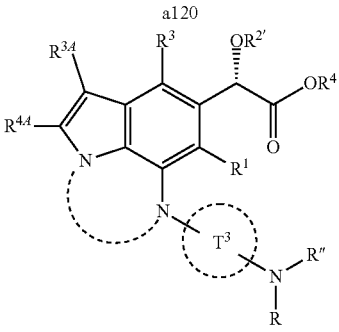

a121

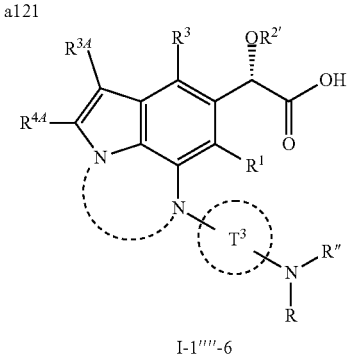

I-1''''-6 wherein $T^3$ ring is substituted or unsubstituted aromatic carbocycle or substituted or unsubstituted aromatic heterocycle, the other symbols are the same as defined above.

(Step 1)

[2-13] The compound a119 can be obtained by reacting the compound a118 in a solvent such as toluene, DMF, DMA, THF, dioxane or the like, or a mixture thereof, with a phosphine such as BINAP, xantphos etc., a catalyst such as dibenzylideneacetone palladium, palladium acetate etc., a base such as cesium carbonate, potassium carbonate etc. and diphenyl methane imine, at 50° C. to 150° C., preferably 70° C. to 130° C., for 0.5 to 12 hours, preferably 1 to 6 hours.

(Step 2)

The compound a120 can be obtained by reacting the compound a1119 in a solvent such as dichloromethane, DMF, DMA or the like, or a mixture thereof, with a base such as cesium carbonate, pyridine, triethylamine or the like, a sulfonyl reagent, acid chloride, isocyanate, alkylating agent or arylating agent etc. such as MsCl, AcCl, MeNCO or the like which is commercially available or synthesized in a known method, at −50° C. to 50° C., preferably −30° C. to 30° C., for 0.1 to 4 hours, preferably 0.5 to 1 hour.

(Step 3)

The compound a121 can be obtained by reacting the compound a120 in a solvent such as DMF, DME, tetrahydrofuran, acetone, acetonitrile or the like, with a base such as potassium carbonate, sodium carbonate, cesium carbonate, sodium hydride etc., and alkylating agent or arylating agent which is commercially available or synthesized in a known method at −30° C. to 100° C., preferably −10° C. to 50° C., for 0.5 to 24 hours, preferably 1 to 5 hours.

It can be synthesized even if Step 2 and Step 3 are replaced order.

(Step 4)

It can be carried out according to Step 15 in the synthesis of the compound (I-1').

[2-17] Synthesis of the Compound (I-1''''-7)

[Chemical formula 112]

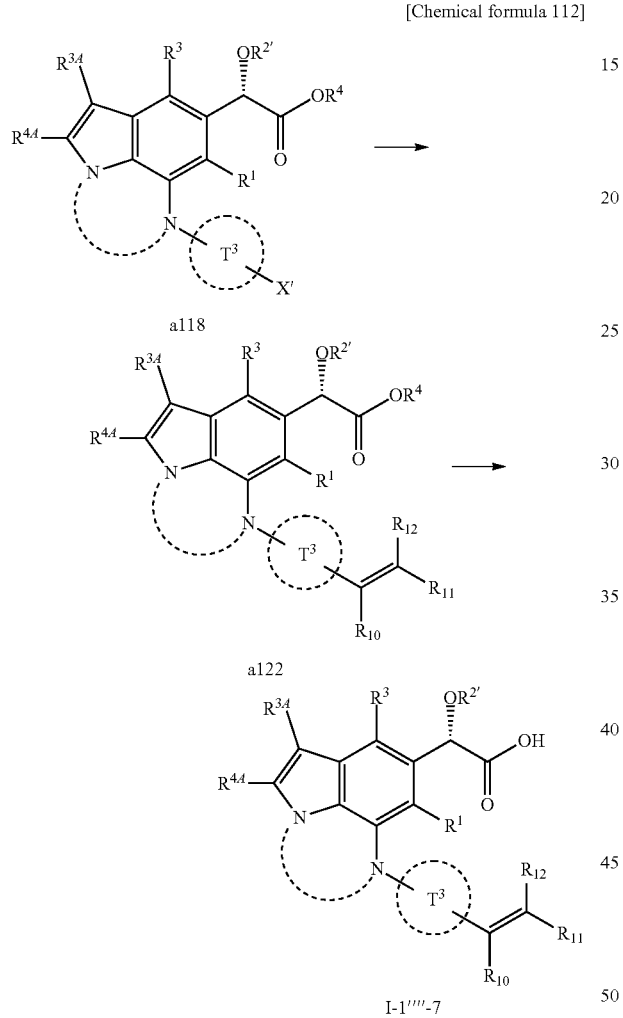

a118 a122

I-1''''-7

$R^{10}$, $R^{11}$ and $R^{12}$ are each independently hydrogen, hydroxy, substituted or unsubstituted alkyl, substituted or unsubstituted alkyloxy, substituted or unsubstituted non-aromatic carbocycle, substituted or unsubstituted aromatic carbocycle, substituted or unsubstituted non-aromatic heterocycle, or substituted or unsubstituted aromatic heterocycle, or $R^{10}$ and R11 may be taken together with the each bonding carbon atoms to form substituted or unsubstituted carbocycle or substituted or unsubstituted heterocycle, or $R^{11}$ and $R^{12}$ may be taken together with the each bonding carbon atoms to form substituted or unsubstituted carbocycle or substituted or unsubstituted heterocycle.

(Step 1)

It can be carried out according to Step 4 in the synthesis of the compound (I-1').

(Step 2)

It can be carried out according to Step 15 in the synthesis of the compound (I-1').

[2-18] Synthesis of the Compound (I-1''''-8)

[Chemical formula 113]

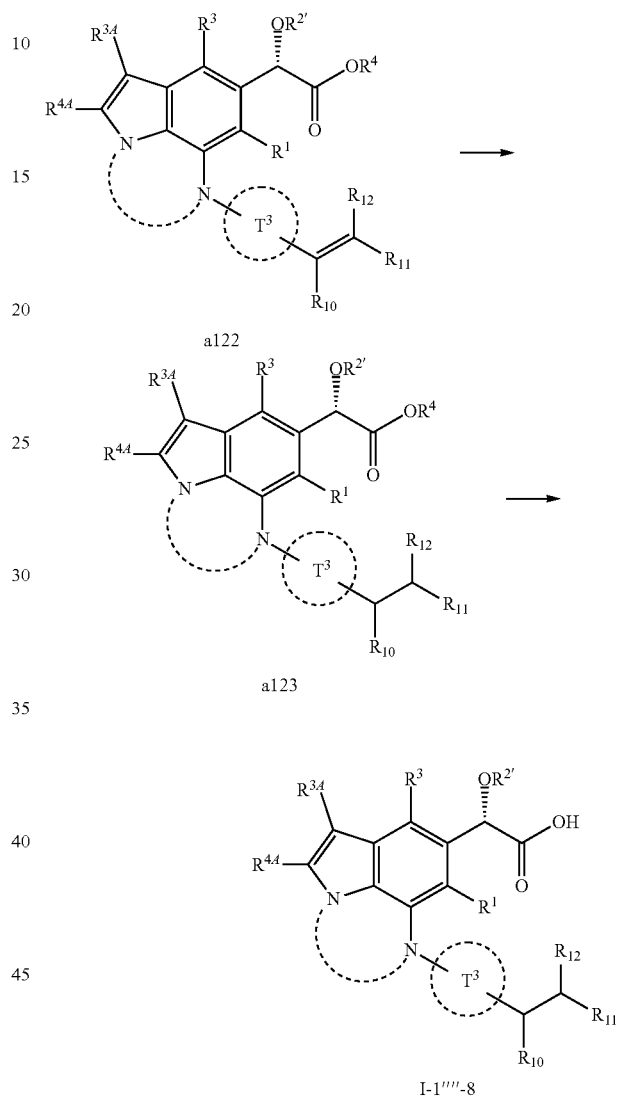

a122 a123

I-1''''-8 wherein each symbol is the same as defined above.

(Step 1)

The compound a123 can be obtained by reacting the compound a122 in a solvent such as methanol, ethanol, tetrahydrofuran, ethyl acetate, acetic acid or the like or a mixture thereof, with a catalyst such as 5% or 10% palladium on carbon, palladium hydroxide or platinum dioxide etc., at 0° C. to 50° C., preferably 15° C. to 25° C., for 0.1 hour to 48 hours, preferably 1 hour to 24 hours, udder hydrogen atmosphere, at normal pressure or increased pressure.

(Step 2)

It can be carried out according to Step 15 in the synthesis of the compound (I-1').

[2-19] Synthesis of the Compound (I-1''''-9)

[Chemical formula 114]

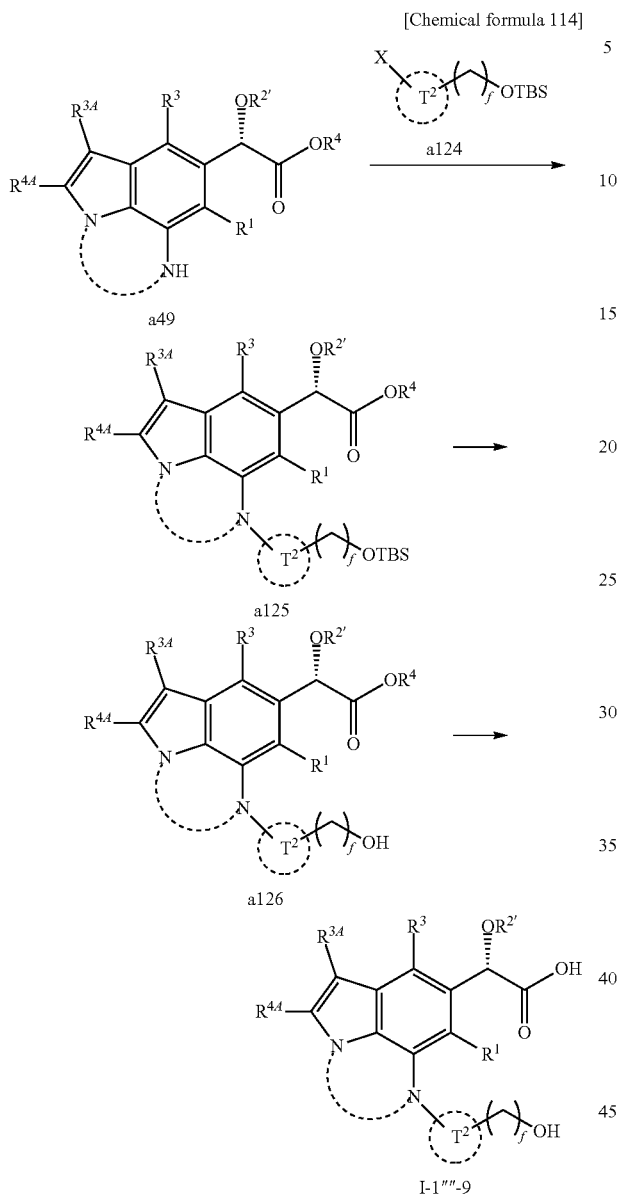

wherein f is an integer of 1 to 4, the other symbols are the same as defined above.

(Step 1)

It can be carried out according to Step 1 in the synthesis of the compound a113.

(Step 2)

The compound a126 can be obtained by reacting the compound a125 in a solvent such as THF, dioxane or the like, or a mixture thereof, with a fluorine ion such as tetrabutylammonium fluoride, Pyridine-HF etc., at 0° C. to 100° C., preferably 20° C. to 40° C., for 1 hour to 24 hours, preferably 2 hours to 6 hours.

(Step 3)

It can be carried out according to Step 15 in the synthesis of the compound (I-1').

[2-19] Synthesis of the Compound (I-1''''-9-1)

[Chemical formula 115]

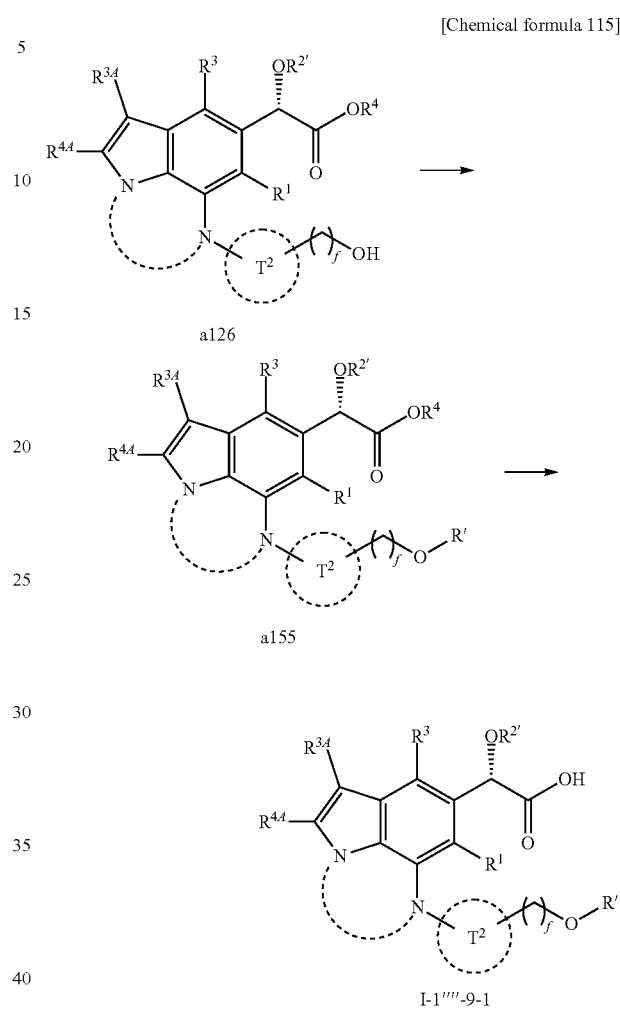

wherein each symbol is the same as defined above.

(Step 1)

The compound a155 can be obtained by reacting the compound a126 in a solvent such as DMF, DME, tetrahydrofuran, acetone, acetonitrile or the like, with a base such as potassium carbonate, sodium carbonate, cesium carbonate, sodium hydride etc. and an alkylating agent which is commercially available or synthesized in a known method, at −30° C. to 100° C., preferably −10° C. to 50° C., for 0.5 hour to 24 hours, preferably 1 hour to 5 hours. Or, the compound a155 can be obtained by reacting an alcohol represented by R'OH which is commercially available or synthesized by a known method, and is dissolved in a solvent such as THF, dichloromethane etc., or a mixture thereof, with Mitsunobu reagent such as DEAD, DIAD, or bis(2-methoxyethyl)azodicalboxylate, triphenylphosphine, tri-n-butylphosphine or tributylphosphine, and the compound a126, at −20° C. to 100° C., preferably 0° C. to 30° C., for 0.5 hour to 24 hours, preferably 1 hour to 5 hours.

(Step 2)

It can be carried out according to Step 15 in the synthesis of the compound (I-1').

[2-20] Synthesis of the Compound (I-1''''-10)

[Chemical formula 116]

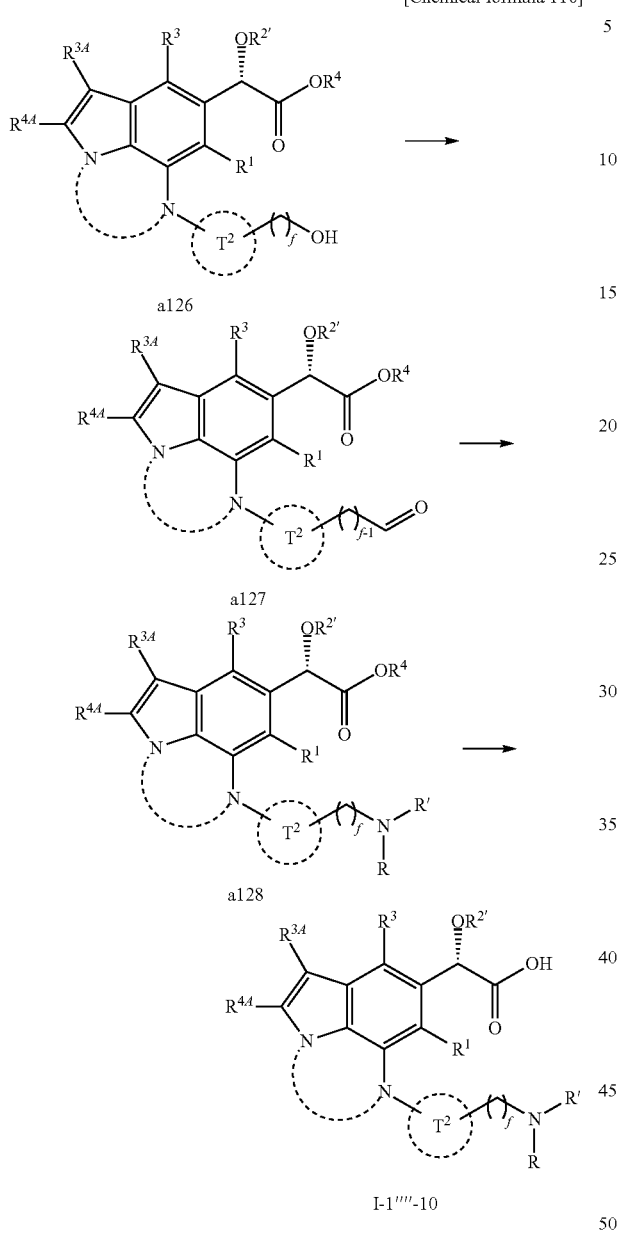

I-1''''-10 wherein each symbol is the same as defined above.

(Step 1)

The compound a127 can be obtained by reacting the compound a126 in a solvent such as methylene chloride, acetone, DMSO etc., or a mixture thereof, with an oxidant such as Dess-martin reagent, manganese dioxide, pyridinium chorochromatic etc., at 0° C. to 80° C., preferably 20° C. to 45° C., for 0.5 hour to 5 hours, preferably 1 hour to 3 hours. Or, it can be obtained by general Swern oxidation.

(Step 2)

The compound a128 can be obtained by reacting the compound a127 in a solvent such as dichloromethane, THF, methanol or the like, or a mixture thereof, with acetic acid or TFA etc. and an amine which is commercially available or synthesized in a known method to generate an imine as a reactive intermediate, then reacting the reaction solution with a reductant such as sodium cyanoborohyride or sodium triacetoxy borohydride, picoline-borane complex etc., at −30° C. to 60° C., preferably 0° C. to 20° C., for 0.1 hour to 24 hours, preferably 0.5 hour to 12 hours.

(Step 3)

It can be carried out according to Step 15 in the synthesis of the compound (I-1').

[2-21] Synthesis of the compound (I-1''''-11) and the compound (I-1''''-12)

[Chemical formula 117]

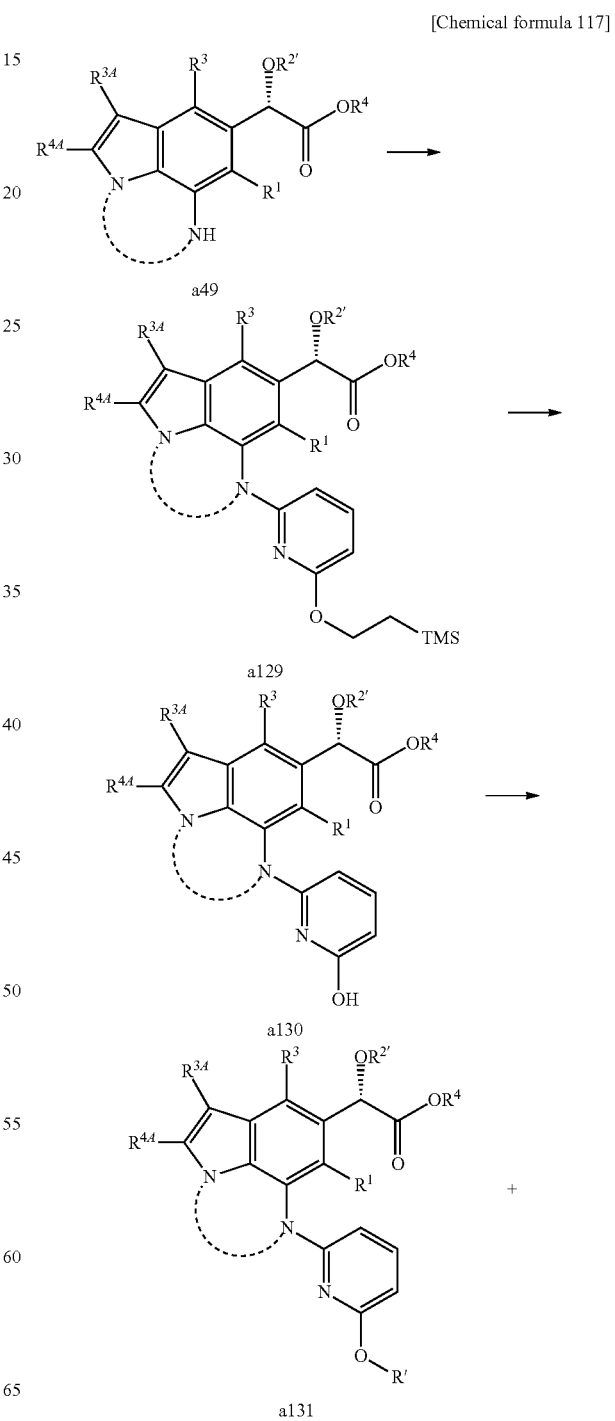

[2-22] Synthesis of the Compound (I-1''''-13)

[Chemical formula 118]

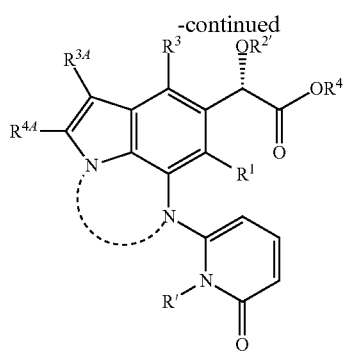
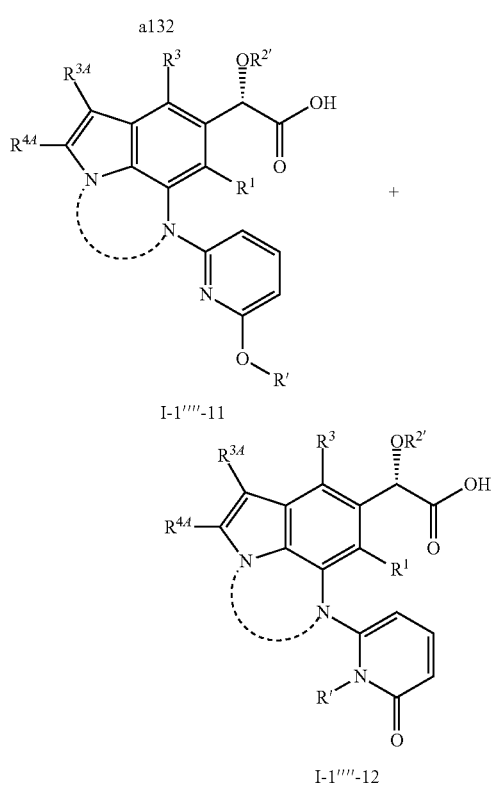

wherein each symbol is the same as defined above.

(Step 1)

It can be carried out according to Step 1 in the synthesis of the compound a113.

(Step 2)

It can be carried out according to Step 5 in the [2-7] Synthesis of the compound a40.

(Step 3)

The compound a131 and the compound a132 can be obtained by reacting the compound a130 in a solvent such as DMF, tetrahydrofuran, acetonitrile or the like, with a base such as potassium carbonate, sodium carbonate, cesium carbonate, sodium hydride or the like, and an alkylating agent which is commercially available or synthesized in a known method, at −30° C. to 100° C., preferably 0° C. to 50° C., for 0.5 hour to 24 hours, preferably 1 hour to 5 hours.

(Step 4)

It can be carried out according to Step 15 in the synthesis of the compound (I-1').

-continued

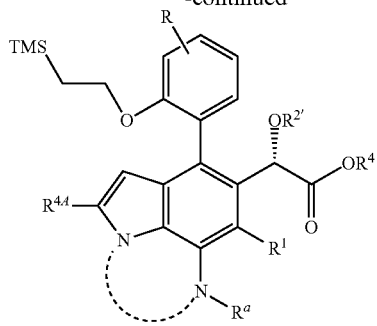
a136

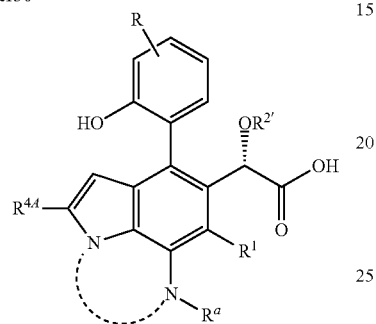
I-1''''-13 wherein each symbol is the same as defined above.

(Step 1)
It can be carried out according to Step 3 in the [2-7] Synthesis of the compound a40.

(Step 2)
It can be carried out according to Step 4 in the synthesis of the compound (I-1').

(Step 3)
It can be carried out according to Step 14 in the synthesis of the compound (I-1').

(Step 4)
It can be carried out according to Step 5 in the [2-7] Synthesis of the compound a40.

(Step 5)
It can be carried out according to Step 13 in the synthesis of the compound (I-1').

(Step 6)
The compound (I-1''''-13) can be obtained by reacting the compound a136 in a solvent such as THF, dioxane or the like, or a mixture thereof, with a fluorine ion such as tetrabutylammonium fluoride, Pyridine-HF or the like, at 0° C. to 100° C., preferably 60° C. to 80° C., for 1 hour to 24 hours, preferably 2 hours to 6 hours.

[2-23] Synthesis of the Compound (I-1''''-14)

[Chemical formula 119]

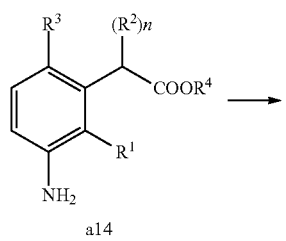
a14

-continued

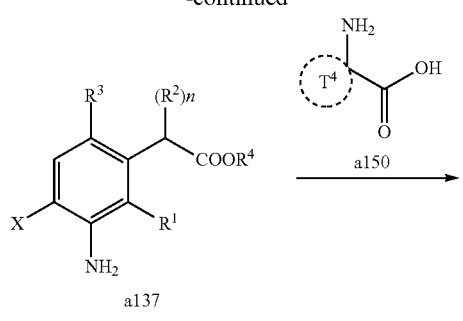
a137

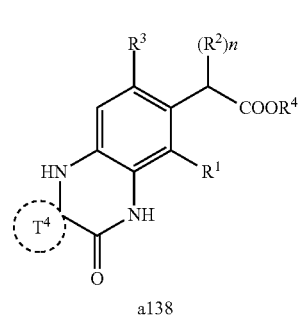
a138

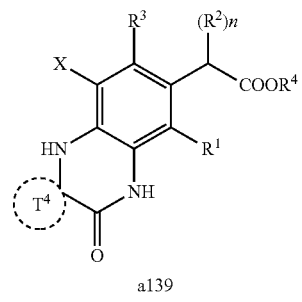
a139

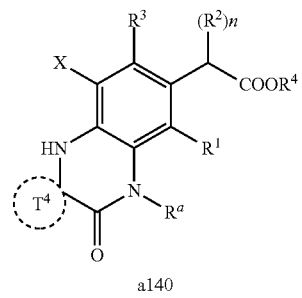
a140

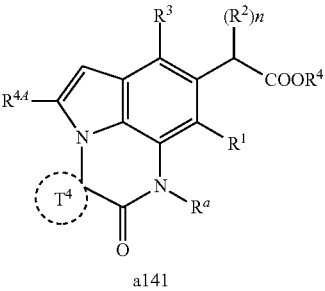
a141

-continued

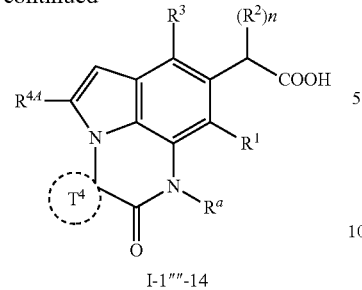

I-1''''-14 wherein T⁴ ring is substituted or unsubstituted non-aromatic carbocycle or substituted or unsubstituted non-aromatic heterocycle, the other symbols are the same as defined above.

(Step 1)

It can be carried out according to Step 4 in the synthesis of the compound (I-1'-1).

(Step 2)

The compound a138 can be obtained by reacting the compound a137 in a solvent such as toluene, xylene, DMF, DMSO or the like, with the compound a150, a base such as 2,6-lutidine, N,N-diisopropylethylamine, N,N'-dimethyl-1,2-ethylenediamine or the like, and copper(I) iodide, at 30° C. to 250° C., preferably 80° C. to 200° C., 0.1 hour to 10 hours, preferably 0.5 hour to 2 hour.

(Step 3)

It can be carried out according to Step 4 in the synthesis of the compound (I-1'-1).

(Step 4)

It can be carried out according to Step 13 in the synthesis of the compound (I-1'). Or, it can be carried out according to Step 1 in the synthesis of the compound a113.

(Step 5)

It can be carried out according to Step 10 in the synthesis of the compound (I-1'-1).

(Step 6)

It can be carried out according to Step 15 in the synthesis of the compound (I-1').

[2-24] Synthesis of the Compound (I-1''''-15)

[Chemical formula 120]

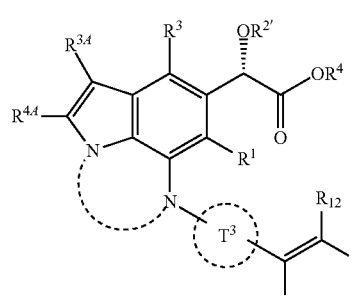

a122

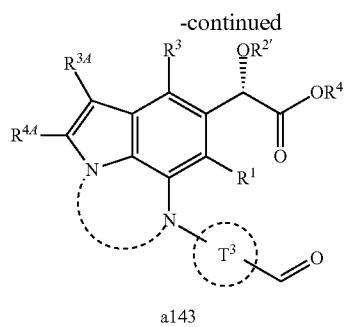

a143

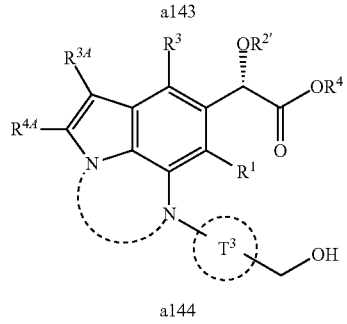

a144

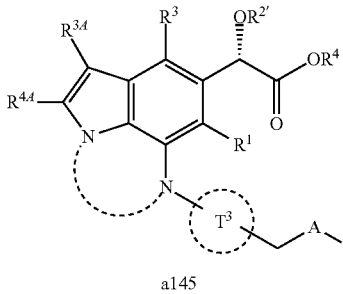

a145

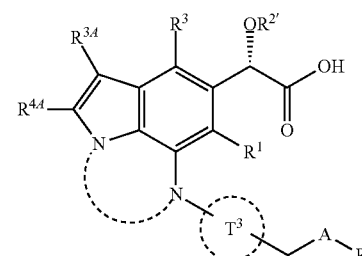

I-1''''-15 wherein each symbol is the same as defined above.

(Step 1)

It can be carried out according to Step 4, 5 in the synthesis of the compound (I-1'-2).

(Step 2)

It can be carried out according to Step 6 in the synthesis of the compound (I-1'-2).

(Step 3)

It can be carried out according to Step 4 in the synthesis of the compound (I-1''''-1).

(Step 4)

It can be carried out according to Step 15 in the synthesis of the compound (I-1').

[2-25] Synthesis of the Compound (I-1''''-16)

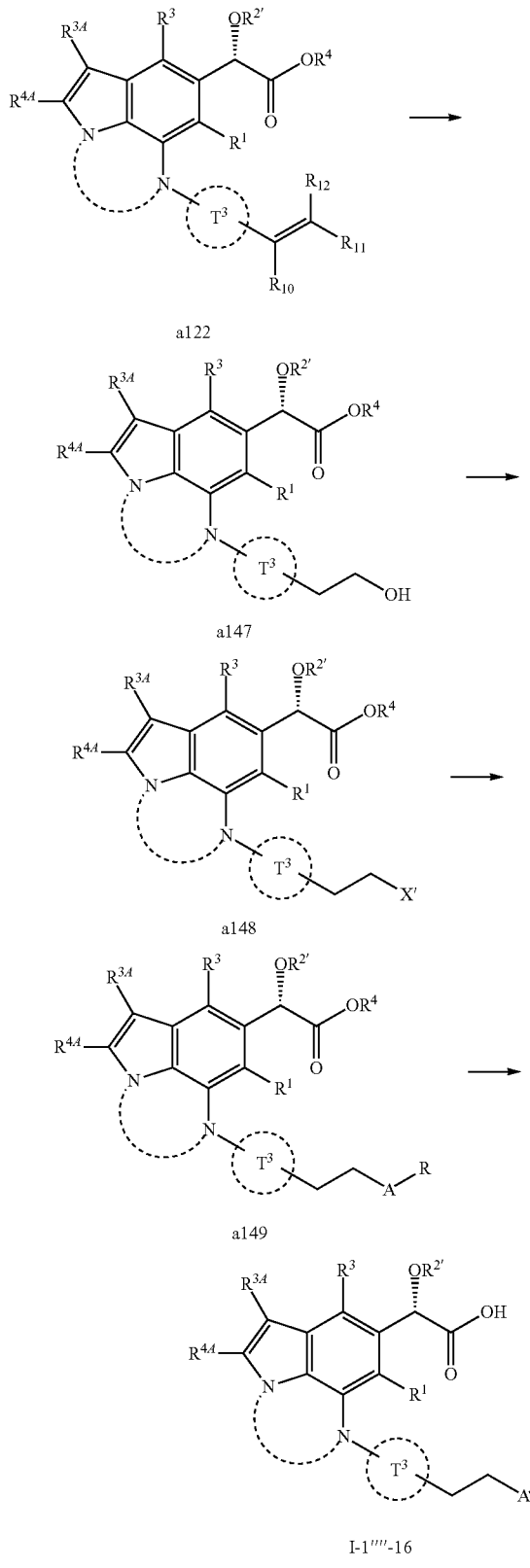

(Step 1)

The compound a147 can be obtained by reacting the compound a122 in a solvent such as THF, diethyl ether or the like, 9-borabicyclo[3.3.1]nonane, a borane compound such as disiamylborane, thexylborane or the like, at −10° C. to 50° C., preferably 0° C. to 25° C., for 0.1 hour to 10 hours, preferably 0.5 hour to 5 hours, and then reacting the mixture with water and an oxidant sodium peroxoborate tetra hydrate at 0° C. to 60° C., preferably 25° C. to 50° C., for 0.1 hour to 10 hours, preferably 0.5 hour to 5 hours.

(Step 2)

It can be carried out according to Step 3 in the synthesis of the compound (I-1''''-3).

(Step 3)

It can be carried out according to Step 4 in the synthesis of the compound (I-1''''-1).

(Step 4)

It can be carried out according to Step 15 in the synthesis of the compound (I-1').

Synthesis of the Compound (I-2)

[Chemical formula 122]

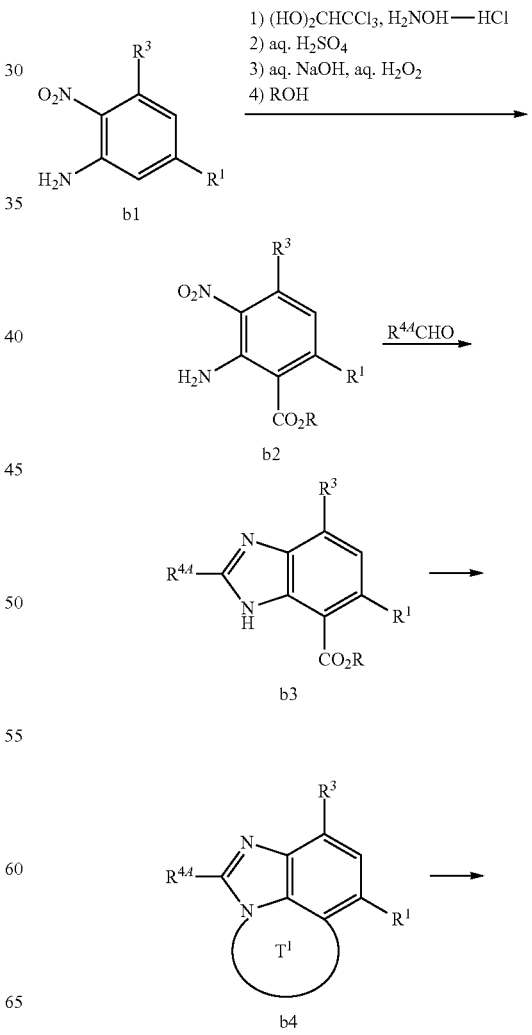

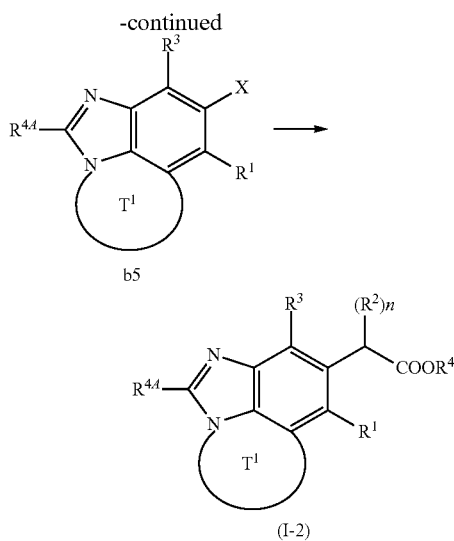

wherein R is alkyl etc.; the other symbols are the same as defined above.
(Step 1)

The compound b2 can be obtained by reacting the compound b1, for example, according to the method described in Journal of Organic Chemistry, 2013, 78(17), 8217-8231.
(Step 2)

The compound b3 can be obtained by reacting the compound b2 with $R^{4A}$—CHO, for example, according to the method described in Angewandte Chemie, International Edition, 2012, 51(46), 11589-11593.
(Step 3)

The ester group of the compound b3 can be converted to the carboxyl group by reacting it in a presence of a base (e.g.: sodium hydroxide), in a solvent (e.g.: THF, a mixture of methanol and water), at a suitable temperature (e.g.: room temperature to about 50° C.). Thereafter, its carboxyl group can be converted to the amino group by Crutius reaction using DPPA for example. Subsequently, the compound b4 can be obtained by conducting according to the formation reaction of $T^1$ ring described above.
(Step 4)

The compound b5 can be obtained by reacting the compound b4 with the halogenating agent (e.g.: NIS) in a solvent (e.g.: DMF, dichloromethane), at a suitable temperature (e.g.: under ice-cooling to reflux).
(Step 5)

It can be carried out according to Step 6, 7 in the synthesis of the compound (I-1).

The final compound obtained by the above process can be converted to a further compound of the present invention by carrying out a well-known chemical modification to a person skilled in the art. When the functional groups (e.g.: hydroxy, amino, carboxy) exist in each reaction before and after, it may be optionally conducted to protecting or deprotecting reaction for the functional groups by well-known reaction to the skilled person in the art (ref: Organic Synthesis, written by T. W. Greene, John Wiley & Sons Inc. (1991).

The compound of the present invention has an inhibitory effect on HIV replication, thus is useful as a therapeutic agent and/or prophylactic agent of viral infections such as AIDS or the like.

In HIV replication inhibition activity of the compound of the present invention, for example, in the following Experimental Example 1 and/or Experimental Example 2, preferably, EC50 value is 100 nM or less, more preferably 50 nM or less, more preferably 20 nM or less, particularly preferably 10 nM or less. EC90 value is also available in the evaluation of this activity. Also, preferred compound has strong virus mutations resistance. More preferred compound has high C24/EC50 value (C24: blood concentration after administration 24 hours).

The compound of the present invention has a utility as a pharmaceutical as well as the replication inhibitory activity against virus, especially HIV (e.g.: HIV-1), its mutant viruses, or its resistant viruses, and has one or more of the following excellent features.

a) an anti-virus activity in the presence of serum proteins (e.g.: PA-EC50, PA-EC90 etc.) is good;
b) an inhibitory activity against CYP enzymes (e.g., CYP1A2, CYP2C9, CYP3A4, CYP2D6, CYP2C19 etc.) is weak;
c) it shows good pharmacokinetics such as high concentration in the blood, high oral absorption, long-acting, low tissue migration, appropriate clearance, high bioavailability or the like;
d) it does not show the toxicity such as light toxicity (e.g.: light hemolytic activity etc.), mutagenicity, cardiac toxicity (e.g.: QTc prolongation etc.), liver toxicity, kidney toxicity, convulsion or the like;
e) it show no irreversible inhibition against CYP enzymes (e.g., CYP3A4), within the concentration range of the measurement conditions described herein, and low MBI ability;
f) a stability of the compound (e.g., solution stability, solution stability, light stability, coloration stability etc. in various liquid) and/or solubility in water is(are) high;
g) a metabolic stability is high;
h) it does not cause gastrointestinal disorders (e.g.: hemorrhagic enteritis, gastrointestinal ulceration, gastrointestinal bleeding, etc.);
i) a low frequency, probability of appearance of resistant viruses caused by the present compound itself or a combination with other drugs;
j) it shows strong efficacy against resistant viruses.

The pharmaceutical composition of the present invention can be administered orally or parenterally. Methods for parenteral administration include dermal, subcutaneous, intravenous, intra-arterial, intramuscular, intraperitneal, transmucosal, inhalation, transnasal, ophthalmic, inner ear or vaginal administration and the like.

In case of oral administration, any forms, which are usually used, such as oral solid formulations (e.g., tablets, powder, granyles, capsules, pills, films or the like), oral liquid formulations (e.g., suspension, emulsion, elixir, syrup, lemonade, spirit, aromatic water, extract, decoction, tincture or the like) or the like may prepared. The tablets can be sugar coated tablets, film coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In the case of parenteral administration, any forms, which are used usually, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) or the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrates, lubricants, diluents or the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, or 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination with a reverse transcriptase inhibitor, a protease inhibitor, an integrase inhibitor, other anti-HIV drug, or the like (hereinafter, abbreviated as concomitant drug), for the purpose of enhancement of action of the compound, reduction of the dosage amount of the compound, or the like. At this time, the time of administration of the compound of the present invention and the concomitant drug is not limited, and, these may be administered simultaneously, or may be administered with a time difference, to the administration subject. Furthermore, the compound of the present invention and the concomitant drug may be administered as two types of preparations containing each active ingredient, or may be administered as a single preparation containing both active ingredients.

The dosage amount of the concomitant drug can be appropriately selected based on the clinically used dose. In addition, the blending ratio of the compound of the present invention to the concomitant drug can be appropriately selected depending on the administration subject, administration route, target disease, symptoms, combination and the like. For example, when the administration subject in a human, 0.01 to 100 parts by weight of the concomitant dug may be used, based on 1 part by weight of the compound of the present invention.

In addition, the compound of the present invention can be used, in the field of gene therapy, to prevent infection of retroviral vectors from spreading to other parts than the object tissues when using a retroviral vector based on HIV and MLV. In particular, when a vector is transmitted to cells and the like in a test tube and then returned to the body, by administering the compound of the present invention in advance, it is possible to prevent unnecessary infection in the body.

Examples of the reverse transcriptase inhibitor include AZT, 3TC, didanosine, zalcitabine, sanirubujin, abacavir, tenofovir, emtricitabine, nebirabin, efavirenz, capravirine, etracirine, delavirdine and the like.

Examples of the protease inhibitor include indinavir, ritonavir, saquinavir, nelfinavir, amprenavir, atazanavir, lopinavir, fosamprenavir, darunavir, atanazavir, brecanavir, tipranavir and the like.

Examples of the integrase inhibitor include raltegravir, elvitegravir, JTK-656, dolutegravir (S-349572), S-265744 and the like.

Examples of the other anti-HIV drugs include entry inhibitors such as maraviroc and vicriviroc and the like, fusion inhibitors such as enfuvirtide, sifuvirtide, albuvirtide and the like.

Hereinafter, the present invention will be described in more detail with reference to examples and reference examples of the present invention and test examples, but the present invention is not limited by these examples.
(LC/MS Measurement Conditions)
(1) Column: ACQUITY UPLC (Registered trademark) BEH C18 (1.71 μm i.d.2.1×50 mm) (Waters)

Flow rate: 0.8 mL/min; UV detection wavelength: 254 nm;

Mobile phase: [A] a 0.1% formic acid-containing aqueous solution, [B] a 0.1% formic acid-containing acetonitrile solution a linear gradient of 5% to 100% solvent [B] was carried out in 3.5 minutes, and 100% solvent [B] was kept for 0.5 minutes.

(2) Column: Shim-pack XR-ODS (2.2 μm, i.d.50×3.0 mm) (Shimadzu)

Flow rate: 1.6 mL/min; UV detection wavelength: 254 nm;

Mobile phase: [A] a 0.1% formic acid-containing aqueous solution, [B] a 0.1% formic acid-containing acetonitrile solution Gradient: a linear gradient of 10% to 100% solvent [B] was carried out in 3 minutes, and 100% solvent [B] was kept for 0.5 minutes.

(3) Column: ACQUITY UPLC (Registered trademark) BEH C18 (1.7 μm i.d.2.1×50 mm) (Waters)

Flow rate: 0.8 mL/min; UV detection wavelength: 254 nm;

Mobile phase: [A] a 10 mM ammonium carbonate-containing aqueous solution, [B] an acetonitrile solution Gradient: a linear gradient of 5% to 100% solvent [B] was carried out in 3.5 minutes, and 100% solvent [B] was kept for 0.5 minutes.

ABBREVIATION

BINAP: 2,2'-bis(diphenylphosphino)-1,1'-binaphthyl
Cbz: benzyloxycarbonyl
DEAD: diethyl azodicarboxylate
DIAD: diisopropyl azodicarboxylate
DMA: N,N-dimethylacetoamide
DME: 1,2-dimethoxyethane
DMAP: N,N-dimethyl-4-aminopyridine
DMF: N,N-dimethylformamide
DMSO: dimethyl sulfoxide
dtbpf: 1,1'-di-tert-butylphosphino ferrocene
Fmoc: 9-fluorenylmethyl oxycarbonyl
HF: hydrogen fluoride
IPE: isopropyl ether
Me: methyl
Ms: methyl sulfonyl
mCPBA: metachloroperbenzoic acid
Ns: nosyl=2-nitrobenzenesulfonyl
Ph: phenyl
PdCl$_2$: palladium chloride
Pd$_2$(dba)$_3$: tris(dibenzylideneacetone)dipalladium(0)
p-Tol: p-tolyl
SEM: 2-(trimethylsilyl)ethoxymethyl
SES: 2-(trimethylsilyl) ethanesulfonyl tBu: tert-butyl
TBAF: tetra-n-butyl ammonium fluoride
TBS: tributylsilyl
THF: tetrahydrofuran
Tf: trifluoromethanesulfonyl
TFA: trifluoroacetic acid
TFAA: trifluoroacetic anhydride
TMS: trimethylsilyl
TIPS: triisopropylsilyl
Xantphos: 4,5-bis(diphenylphosphino)-9,9-dimethyl-9H-xanthene Example 1-A The Synthesis of Compound 6i

[Chemical formula 123]

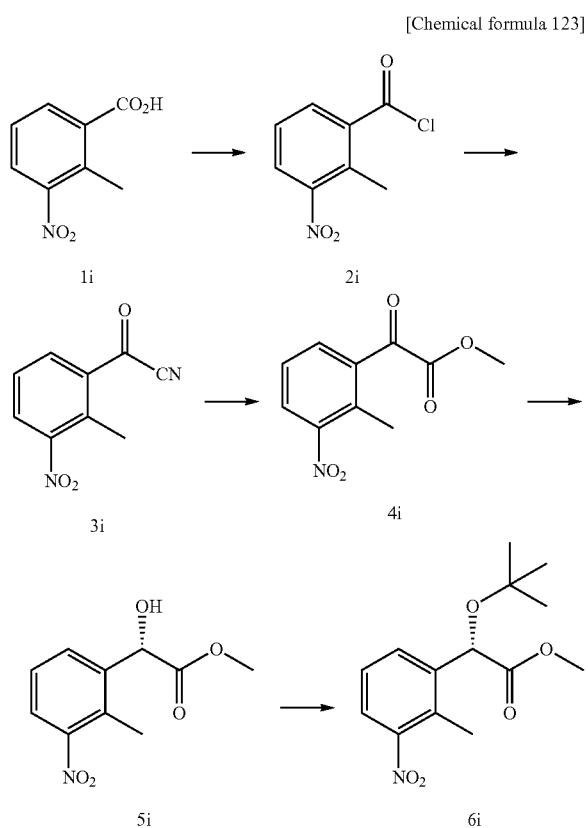

Step 1

To Compound 1i (18.4 g, 102 mmol) was added thionyl chloride (48.9 g, 411 mmol), and the mixture was refluxed for 6 hours. The reaction mixture was concentrated under reduced pressure to yield the Compound 2i (20.07 g, yield 99%) as a brown solid.

1H-NMR (CDCl$_3$) δ:2.61 (3H, s), 7.52 (1H, t, J=8.0 Hz), 7.94 (1H, d, J=8.0 Hz), 8.28 (1H, d, J=8.0 Hz).

Step 2

Copper cyanide (9.91 g, 111 mmol), acetonitrile (100 mL), sodium iodide (30.1 g, 201 mmol) was added in 4-necked flask under nitrogen atmosphere, and the mixture was stirred for 5 minutes at room temperature. Compound 2i (20.07 g, 101 mmol) in acetonitrile solution (100 mL) was added thereto, and the mixture was stirred for 1 hour at room temperature. The solvent was concentrated under reduced pressure, and dichloromethane (200 mL) was added to the resulting residue. The mixture was stirred at room temperature for 1 hour. The reaction mixture was filtered, the filtrate was concentrated under reduced pressure to yield Compound 3i (19.40 g, yield 100%) as a brown solid.

1H-NMR (CDCl$_3$) δ:2.69 (3H, s), 7.67 (1H, t, J=8.0 Hz), 8.05 (1H, d, J=8.0 Hz), 8.47 (1H, d, J=8.0 Hz).

Step 3

To Compound 3i (15.34 g, 81 mmol) were added toluene (30 mL), sodium bromide (0.83 g, 8.1 mmol) and 85 (w/w) % sulfuric acid (26.1 mL, 403 mmol), and the mixture was stirred for 1 hour at 70° C. In addition, 85 (w/w) % sulfuric acid (26.1 mL, 403 mmol) was added thereto, and the mixture was stirred for 2 hours at 70° C. After the reaction mixture was cooled in an ice bath, methanol (150 mL) was added thereto, and the mixture was refluxed for 2 hours. The reaction mixture was cooled in an ice bath, and extracted with ethyl acetate after addition of water (150 mL). The organic layer was successively washed with saturated aqueous sodium hydrocarbonate solution, water, and saturated brine, dried over anhydrous magnesium sulfate, and the solvent was concentrated under r educed pressure. The obtained residue was solidified with ethyl acetate-hexane to yield Compound 4i (11.45 g, yield 64%) as an orange solid.

1H-NMR (CDCl$_3$) δ:2.58 (3H, s), 3.96 (3H, s), 7.49 (1H, t, J=8.0 Hz), 7.84 (1H, d, J=8.0 Hz), 7.96 (1H, d, J=8.0 Hz).

Step 4

N-((1S, 2S)-2-aminocyclohexyl)-p-toluenesulfonamide (5.27 mg, 0.02 mmol), dichloro (p-cymene) ruthenium (II) dimer (6.12 mg, 0.01 mmol), DMSO (1 mL), triethylamine (6.1 mg, 0.06 mmol) were added in 3-necked flask under nitrogen atmosphere, and the mixture was stirred for 1 hour at 80° C. After the mixture was cooled to room temperature, Compound 4i (893 mg, 4.0 mmol), DMSO (3 mL), formic acid-triethylamine mixture (molar ratio of 5:2) (4 mL) was added thereto, and the mixture was stirred for 2 hours at room temperature. The reaction mixture was extracted with ethyl acetate after addition of water. The organic layer was successively washed with water, 1M hydrochloric acid, water, saturated aqueous sodium hydrocarbonate solution, water, and saturated brine, dried over anhydrous magnesium sulfate, and the solvent was concentrated under reduced pressure. The resulting residue was purified by silica gel column chromatography (hexane/ethyl acetate) to yield Compound 5i (872 mg, yield 97%) as an orange solid.

As a result of SFC chiral column analysis (IF column manufactured by Daicel: 4.6×259 mm, 3 μm), the optical purity was 90% ee.

1H-NMR (CDCl$_3$) δ:2.51 (3H, s), 3.56 (1H, d, J=4.3 Hz), 3.79 (3H, s), 5.47 (1H, d, J=4.3 Hz), 7.35 (1H, dd, J=7.8, 8.0 Hz), 7.58 (1H, dd, J=1.0, 7.8 Hz), 7.72 (1H, dd, J=1.0, 8.0 Hz).

Step 5

Compound 5i (5.04 g, 22.4 mmoL) was dissolved in acetic acid t-butyl (50.5 mL), and 70% aqueous perchloric acid solution (1.93 mL, 22.4 mmoL) was added thereto under ice-cooling. The mixture was stirred for 1 hour. The reaction mixture was poured into a 5% aqueous sodium bicarbonate solution, and the mixture was extracted with ethyl acetate. The organic layer was washed with saturated brine, and was dried over anhydrous sodium sulfate. The solvent was concentrated under reduced pressure to yield the crude Compound 6i (6.14 g, crude yield 97.4%) as a colorless oil.

$^1$H NMR (CDC$_3$) δ: 1.22 (s, 9H), 2.53 (s, 3H), 3.69 (s, 3H), 5.31 (s, 1H), 7.32-7.37 (m, 1H), 7.68 (d, J=7.6 Hz, 1H), 7.84 (d, J=7.6 Hz, 1H).

Example 1-B

The Synthesis of Compound 14i

[Chemical formula 124]

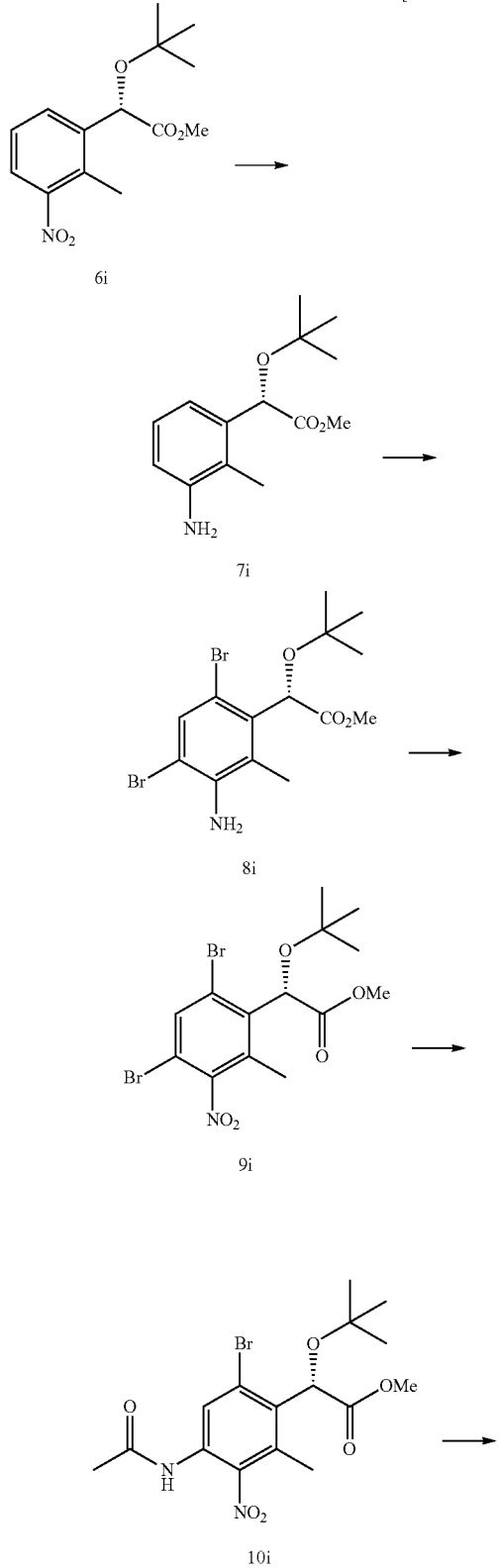

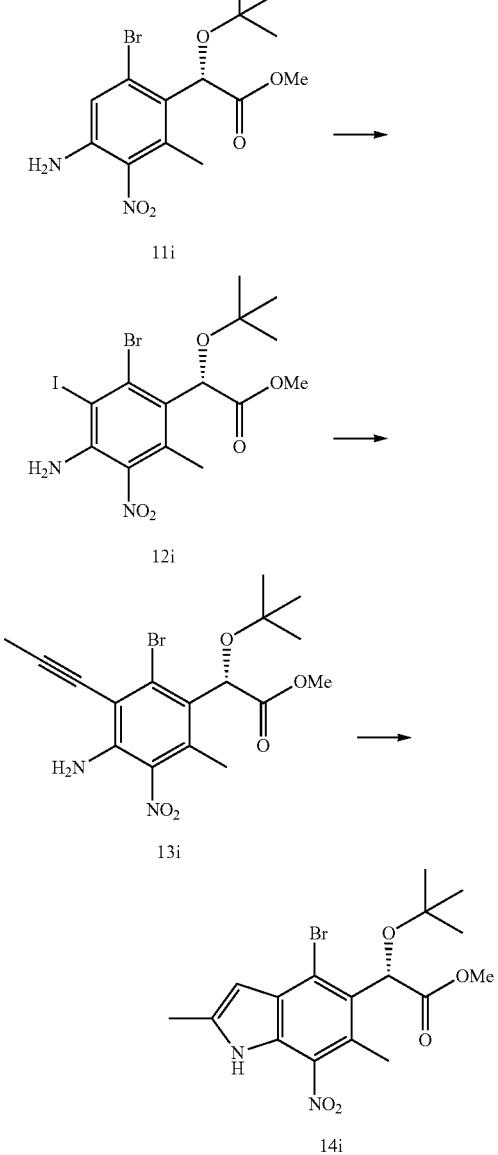

Step 1

The crude Compound 6i (30.0 g, 107 mmmol) was dissolved in ethanol (150 mL) and water (150 mL), and ammonium chloride (34.2 g, 640 mmol), iron (17.87 g, 320 mmol) were added thereto at room temperature. After the mixture was stirred for 1 hour at room temperature, the mixture was stirred for 2 hours at 60° C. The reaction mixture was filtered through Celite and the filtrate was extracted with ethyl acetate. The organic layer was washed with saturated aqueous sodium hydrogen carbonate solution, saturated brine, and dried over anhydrous magnesium sulfate. The solvent was concentrated under reduced pressure to yield the crude Compound 7i (27 g, crude yield 100%) as a brown oil.

$^1$H NMR (CDCl$_3$) δ: 1.21 (s, 9H), 2.21 (s, 3H), 3.60 (brs, 2H), 3.65 (s, 3H), 5.22 (s, 1H), 6.63-6.68 (m, 1H), 6.97-7.04 (m, 1H).

Step 2

The crude Compound 7i (2.0 g) was dissolved in DMA (10 mL), and NBS (3.12 g, 17.51 mmoL) was added thereto under water bath. The mixture was stirred for 1 hour at the same temperature. 20% aqueous sodium thiosulfate solution and 5% aqueous sodium hydrogen carbonate solution were sequentially added dropwise to the reaction mixture, and the mixture was stirred for 10 minutes at room temperature. Water was added dropwise to the mixed solution, and the mixture was stirred for 60 minutes at room temperature. The precipitated solid was filtered to yield Compound 8i (2.5 g, yield 76.8%) as a pale red solid.

$^1$H NMR (CDCl$_3$) δ: 1.21 (s, 9H), 2.26 (s, 3H), 3.67 (s, 3H), 4.13 (brs, 2H), 5.71 (s, 1H), 7.54 (s, 1H).

Step 3

To a solution of Compound 8i (0.5 g, 1.22 mmol) and potassium iodide (60.6 mg, 0.37 mmol) in acetonitrile (4 mL) was added dropwise tert-butyl hydroperoxide (0.4 mL, 4.64 mmol) over 1 hour at 60° C., and the mixture was stirred at the same temperature for 1 hour. The reaction mixture was extracted with ethyl acetate after addition of 20% aqueous sodium thiosulfate solution and 5% aqueous sodium bicarbonate solution successively. The organic layer was washed with water, and dried over anhydrous magnesium sulfate. The solvent was concentrated under reduced pressure to yield the crude Compound 9i (0.4 g, crude yield 76.2%) as a pale yellow solid.

1H-NMR (CDCl$_3$) δ: 1.22 (s, 9H), 2.37 (s, 3H), 3.71 (s, 3H), 5.77 (s, 1H), 7.77 (s, 1H)

Step 4

To a suspension of Compound 9i (2.2 g, 5.01 mmol), cesium carbonate (2.45 g, 7.52 mmol), acetamide (0.59 g, 10.0 mmol), rac-BINAP (0.23 g, 0.38 mmol) in toluene (11 mL)/DMA (5.5 mL) was added palladium(0)bis(dibenzylidene acetone) (144 mg, 0.25 mmol) at 80° C., and the mixture was stirred for 1 hour at 110° C. The reaction mixture was extracted with ethyl acetate after addition of 10% aqueous ammonium chloride solution. The organic layer was washed with water, dried over anhydrous magnesium sulfate, and concentrated under reduced pressure. The resulting residue was purified by silica gel column chromatography (hexane-acetic acid) to yield Compound 10i (1.8 g, yield 59.7%) as a pale yellow solid.

1H-NMR (CDCl$_3$) δ: 1.21 (s, 9H), 2.17 (s, 3H), 2.38 (s, 3H), 3.70 (s, 3H), 5.81 (s, 1H), 7.85 (s, 1H), 8.45 (s, 1H)

Step 5

To a solution of Compound 10i (6 g, 14.38 mmol) in methanol (60 mL) was added potassium carbonate (9.94 g, 71.9 mmol), and the mixture was heated under reflux and stirred for 3 hours. 2 mol/L hydrochloric acid was added to the reaction mixture, and the mixture was extracted with chloroform. The organic layer was washed with water, dried over anhydrous sodium sulfate, and concentrated under reduced pressure. The resulting residue was purified by silica gel column chromatography (chloroform-methanol) to yield Compound 11i (2.6 g, yield 48%) as a yellow solid.

LC/MS (ESI): m/z=374.95 [M+H]+, RT=2.21 min, LC/MS measurement conditions: (2)

Step 6

To a solution of Compound 11i (3.6 g, 9.59 mmol) in ethanol (36 mL) were added silver nitrate (3.26 g, 19.19 mmol) and iodine (4.87 g, 19.19 mmol) under ice-cooling, and the mixture was stirred for 4 hours at room temperature. The insoluble materials were filtered, and the filtrate was extracted with chloroform after addition of aqueous sodium bicarbonate solution and aqueous sodium thiosulfate solution. The organic layer was washed with water, dried over anhydrous sodium sulfate, and concentrated under reduced pressure. The resulting residue was purified by silica gel column chromatography (hexane-ethyl acetate) to yield Compound 12i (4.5 g, yield 94%) as a brown solid.

LC/MS (ESI): m/z=499.10 [M−H]−, RT=2.49 min, LC/MS measurement conditions: (2)

Step 7

To a solution of Compound 12i (5 g, 9.83 mmol) in DMF (30 mL) were added triethylamine (4.09 mL, 29.5 mmol), propyne (about 4% DMF solution, about 1.0 mol/L) (19.7 mL, 19.7 mmol), copper iodide (374 mg, 0.20 mmol), PdCl$_2$(PPh$_3$)$_2$ (690 mg, 0.983 mmol), and the mixture was stirred for 3 hours at 65° C. The reaction mixture was extracted with ethyl acetate after addition of 15% aqueous ammonium chloride solution. The organic layer was washed with water, dried over anhydrous magnesium sulfate, and concentrated under reduced pressure. Further the resulting residue was treated with activated carbon after addition of methanol. The solvent was concentrated under reduced pressure to yield the crude Compound 13i (3.7 g, crude yield 91.1%) as a brown solid.

1H-NMR (CDCl$_3$) δ:1.23 (s, 9H), 2.22 (s, 3H), 2.37 (s, 3H), 3.70 (s, 3H), 5.26 (brs, 1H), 5.85 (s, 1H), 7.85 (s, 1H), 8.45 (s, 1H)

Step 8

To a solution of Compound 13i (3.7 g, 8.93 mmol) in THF (19 mL) was added 1 mol/L-TBAF THF solution (31.2 mL, 31.2 mmol), and the mixture was heated under reflux and stirred for 12 hours. The reaction mixture was extracted with ethyl acetate after addition of 15% aqueous ammonium chloride solution. The organic layer was washed with water, dried over anhydrous magnesium sulfate, and concentrated under reduced pressure. The resulting residue was solidified by azeotropy with toluene. The resulting residue was filtered through silica gel with chloroform/toluene (1:1) (16 mL). The residue was solidified with n-hexane/toluene to yield Compound 14i (1.89 g, yield 51.2%) as a pale green solid.

1H-NMR (CDCl$_3$) δ:1.23 (s, 9H), 2.50 (s, 3H), 2.72 (s, 3H), 3.68 (s, 3H), 6.05 (s, 1H), 6.41 (s, 1H), 9.43 (brs, 1H)

Example 1-C

The Synthesis of Compound 19i

[Chemical formula 125]

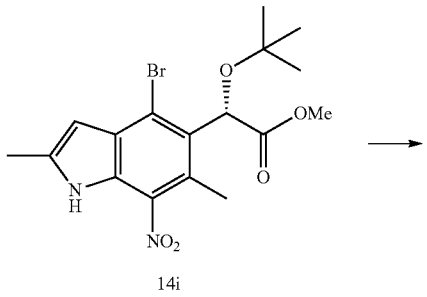

14i

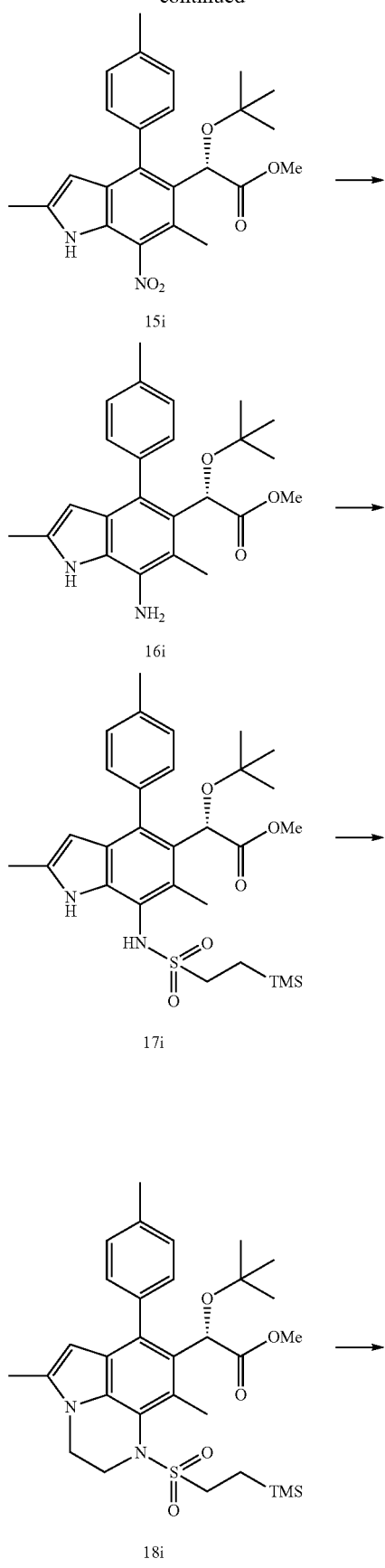

15i

16i

17i

18i

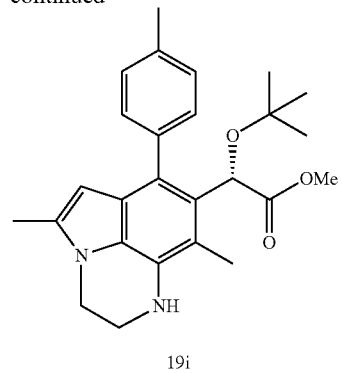

19i

Step 1

To a solution of Compound 14i (2.12 g, 5.13 mmol) in dimethylformamide (21.2 mL) were added 4-methyl phenyl boronic acid (1.40 g, 10.26 mmol), $PdCl_2$ (dtbpf) (334 mg, 0.51 mmol) and potassium carbonate (2.12 g, 5.13 mmol), and the mixture was stirred under nitrogen atmosphere for 50 minutes at 130° C. The reaction mixture was cooled to room temperature, and extracted with ethyl acetate after addition of water. The organic layer was washed with water and saturated brine, dried over anhydrous magnesium sulfate, and the solvent was concentrated under reduced pressure. The resulting residue was purified by silica gel chromatography (hexane-ethyl acetate) to yield Compound 15i as a yellow solid (2.1 g, 90%).

MS(ESI) m/z:425.27 [M+H]+, RT=3.04 min, LC/MS measurement conditions: (1)

Step 2

To a solution of Compound 15i (2.1 g, 4.95 mmol) in ethanol (21 mL) and water (4 mL) were added iron powder (1.38 g, 24.7 mmol) and ammonium chloride (2.65 g, 49.5 mmol), and the mixture was stirred for 50 minutes at 90° C. The reaction mixture was cooled to room temperature, and filtered through celite with saturated aqueous sodium bicarbonate solution and ethyl acetate. The filtrate was extracted with ethyl acetate. The organic layer was washed with water and saturated brine, dried over anhydrous magnesium sulfate, and the solvent was concentrated under reduced pressure. The resulting residue was purified by DIOL column chromatography (hexane-ethyl acetate) to yield Compound 16i as a brown solid (1.7 g, 87%).

MS(ESI) m/z:395.25 [M+H]+, RT=2.68 min, LC/MS measurement conditions: (1)

Step 3

To a solution of Compound 16i (4.9 g, 12.4 mmol) in dichloromethane (25 mL) were added pyridine (2.51 mL, 31.1 mmol) and 2-trimethylsilyl ethyl sulfonyl chloride (2.83 mL, 14.9 mmol) under ice-cooling, and the mixture was stirred for 1 hour at room temperature. The reaction solution was extracted with dichloromethane after addition of saturated aqueous sodium hydrogen carbonate solution. The organic layer was washed with 2 mol/L aqueous hydrochloric acid and saturated brine, dried over anhydrous magnesium sulfate, and the solvent was concentrated under reduced pressure. The resulting residue was purified by silica gel column chromatography (hexane-ethyl acetate) to yield Compound 17i (6.6 g, 86%, purity 90%) as colorless foam compound.

MS(ESI) m/z:559.38 [M+H]+, RT=3.01 min, LC/MS measurement conditions: (1)

Step 4

To a solution of Compound 17i (6.6 g, 10.7 mmol) in dimethylacetamide (66 mL) were added cesium carbonate (9.05 g, 27.8 mmol) and 1,2-dibromoethane (2.61 g, 13.9 mmol), and the mixture was stirred at room temperature for 18 hours. The reaction mixture was extracted with ethyl acetate after addition of 2 mol/L aqueous hydrochloric acid and water. The organic layer was washed with water and saturated brine, dried over anhydrous magnesium sulfate, and the solvent was concentrated under reduced pressure. The resulting residue was purified by silica gel column chromatography (hexane-ethyl acetate) to yield Compound 18i (6.2 g, 98%) as a colorless foam compound.

MS(ESI) m/z:602.52 [M+H$_2$O]+, RT=2.25 min, LC/MS measurement conditions: (1)

Step 5

To a solution of Compound 18i (6.2 g, 10.5 mmol) in tetrahydrofuran (15 mL) was added 1 mol/L tetrabutylammonium fluoride tetrahydrofuran solution (27 mL, 27.0 mmol), and the mixture was stirred for 1 hour at 60° C. The reaction mixture was extracted with ethyl acetate after addition of saturated aqueous sodium hydrogencarbonate solution. The organic layer was washed with saturated brine, dried over anhydrous magnesium sulfate, and the solvent was concentrated under reduced pressure. The resulting residue was purified by silica gel column chromatography (hexane-ethyl acetate) to yield Compound 19i (4.2 g, 96%) as a colorless foam compound.

MS(ESI) m/z:421.40 [M+H]+, RT=2.85 min, LC/MS measurement conditions: (1)

Example 1

[Chemical formula 126]

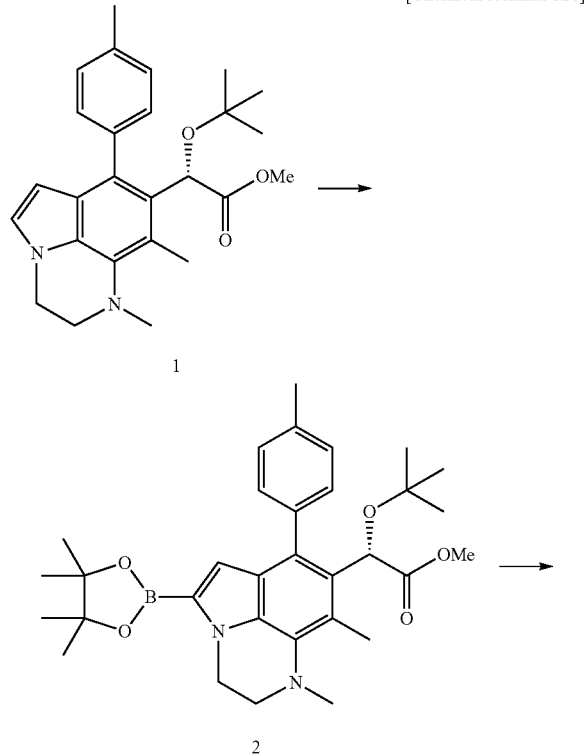

-continued

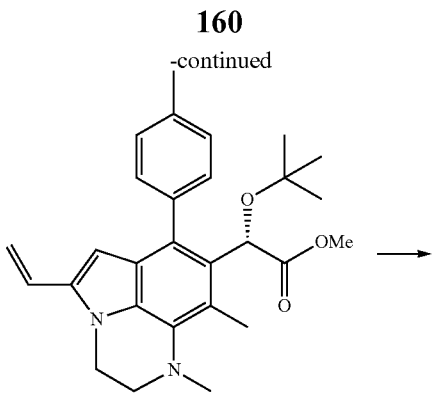

3

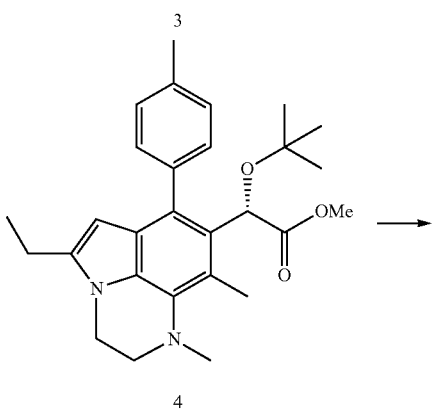

4

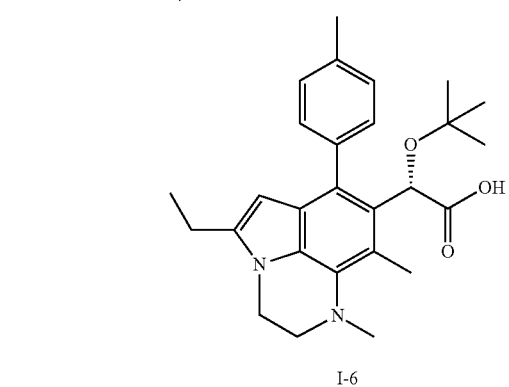

I-6

The First Step

To a solution of bis(pinacolato)diboron (136 mg, 0.535 mmol) in hexane (2 mL) were added di-tert-butyl-2,2'-bipyridine (28.7 mg, 0.107 mmol) and 1,5-cyclooctadiene methoxy iridium (23.6 mg, 0.036 mmol), and the mixture was stirred under nitrogen atmosphere for 10 minutes at 50° C. Then THF (0.4 mL) and Compound 1 (150 mg, 0.357 mmol) were added thereto, and the mixture was heated under reflux and stirred for 30 minutes. The reaction mixture was concentrated under reduced pressure, and the resulting residue was purified by silica gel column chromatography (hexane-ethyl acetate) to yield Compound 2 (154 mg, yield 79%).

LC/MS (ESI): m/z=547.00 [M+H]$^+$

The Second Step

To a solution of Compound 2 (70 mg, 0.128 mmol) in DMF (1 mL) were added 2 mol/L aqueous potassium carbonate solution (0.192 mL, 0.384 mmol), 1 mol/L vinyl bromide.THF solution (1.28 mL, 1.28 mmol), PdCl$_2$ (dtbpf) (8.35 mg, 0.013 mmol), and the mixture was stirred under nitrogen atmosphere at 60° C. for 30 minutes. The reaction mixture was extracted with ethyl acetate after addition of water. The organic layer was washed with water, dried over anhydrous sodium sulfate, and concentrated under reduced pressure. The resulting residue was purified by silica gel column chromatography (hexane-ethyl acetate) to yield Compound 3 (32.3 mg, yield 57%).

LC/MS (ESI): m/z=447.05 [M+H]+

The Third Step

To a solution of Compound 3 (30 mg, 0.067 mmol) in methanol (2 mL) was added 10% Pd/C (10 mg, 0.004 mmol), and the mixture was stirred under hydrogen atmosphere at room temperature for 30 minutes. After the reaction mixture was filtered through Celite, and the filtrate was concentrated under reduced pressure to yield Compound 4 (25 mg, yield 83%).

LC/MS (ESI): m/z=449.10 [M+H]+

The Fourth Step

To a solution of Compound 4 (25 mg, 0.056 mmol) in ethanol (2 mL) and THF (2 mL) was added 2 mol/L aqueous sodium hydroxide solution (0.279 mL, 0.58 mmol), and the mixture was heated under reflux and stirred for 4.5 hours. The reaction mixture was extracted with chloroform after addition of 2 mol/L hydrochloric acid. The organic layer was washed with water, dried over anhydrous sodium sulfate, and concentrated under reduced pressure. The resulting residue was purified by silica gel column chromatography (chloroform-methanol) to yield Compound I-6 (20 mg, yield 83%).

LC/MS (ESI): m/z=435.10 [M+H]+

1H-NMR (CDCl3) δ:0.90 (s, 9H), 1.24-1.30 (3H, m), 2.43 (6H, s), 2.67-2.74 (2H, m), 2.77 (s, 3H), 3.39-3.45 (2H, m), 3.95-4.01 (2H, m), 5.59 (1H, s), 5.92 (1H, s), 7.41 (1H, d, J=7.3 Hz), 7.58 (1H, d, J=7.3 Hz), 10.0 (1H, brs)

Example 2

[Chemical formula 127]

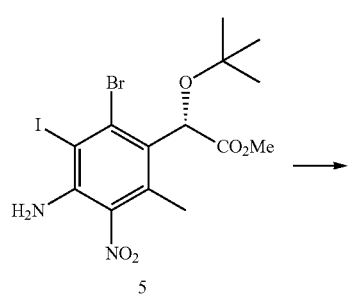

5

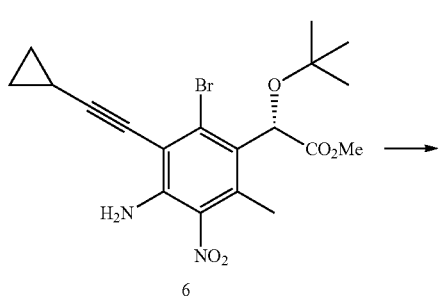

6

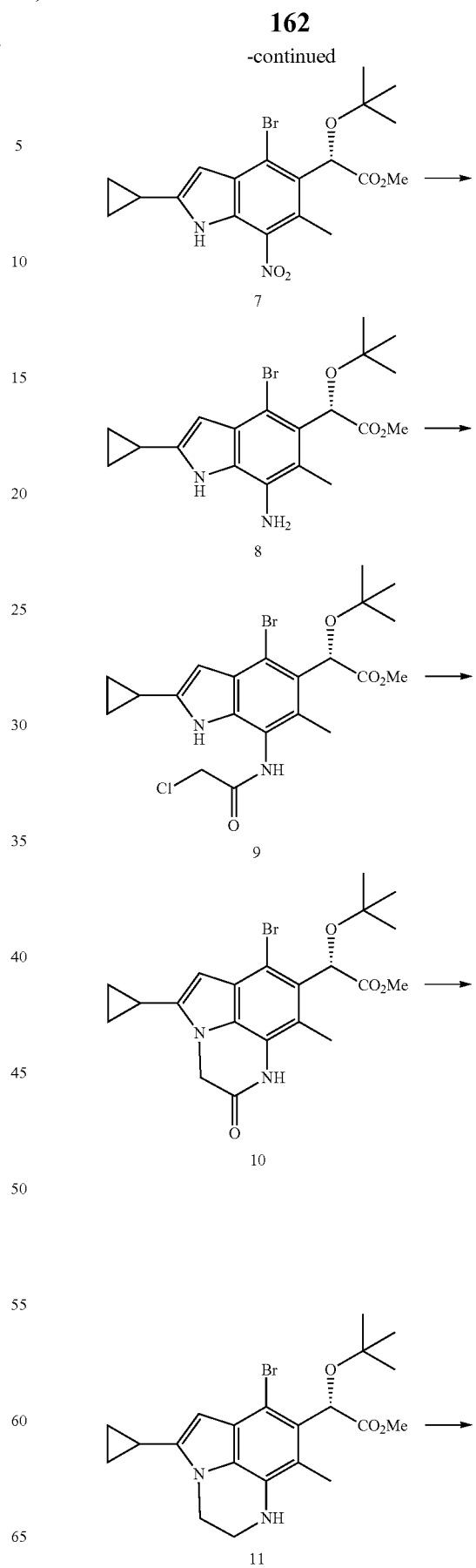

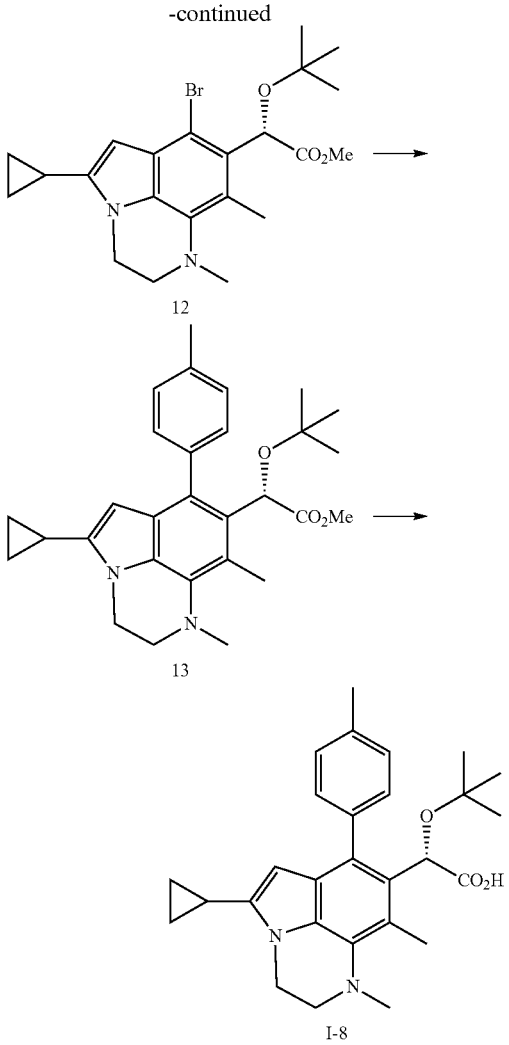

The First Step

To a solution of Compound 5 (1.00 g, 2.00 mmol) in DMF (10.0 mL) were added ethynylcyclopropane (0.339 mL, 4.00 mmol), triethylamine (0.832 mL, 6.00 mmol), bis triphenylphosphine palladium dichloride (140 mg, 0.200 mmol) and copper (I) iodide (76.0 mg, 0.400 mmol), and the mixture was stirred under nitrogen atmosphere for 1 hour and 23 minutes at 80° C. The reaction mixture was cooled to room temperature, and extracted with ethyl acetate after addition of ice water and a saturated aqueous ammonium chloride solution. The organic layer was washed with saturated brine, dried over anhydrous sodium sulfate, and the solvent was concentrated under reduced pressure. The resulting residue was purified by silica gel chromatography (hexane-ethyl acetate) to yield Compound 6 (720 mg, yield 81.9%).

MS(ESI) m/z:439.0, 441.0 [M+H]

The Second Step

To a solution of Compound 6 (718 mg, 1.63 mmol) in THF (1.63 mL) was added 1 mol/L THF solution of TBAF (2.45 mL, 2.45 mmol), and the mixture was stirred for 6 hours and 38 minutes at 75° C. The reaction mixture was cooled to room temperature, extracted with ethyl acetate after addition of ice water, saturated aqueous ammonium chloride solution and 2 mol/L aqueous hydrochloric acid solution. The organic layer was washed with saturated aqueous sodium hydrogen carbonate solution and saturated brine successively, dried over anhydrous sodium sulfate, and the solvent was concentrated under reduced pressure. The resulting residue was purified by silica gel chromatography (hexane-ethyl acetate) to yield Compound 7 (602 mg, yield 83.8%).

MS(ESI) m/z:439.0, 441.0 [M+H]$^+$

The Third Step

To a mixed solution of Compound 7 (600 mg, 1.37 mmol) in ethanol (10.0 mL) and water (2.00 mL) were added ammonium chloride (1.09 g, 20.5 mmol) and iron powder (572 mg, 10.3 mmol), and the mixture was stirred for 90 minutes at 90° C. The reaction mixture was cooled to room temperature, and filtered through celite. The filtrate was extracted with ethyl acetate after addition of ice water, a saturated aqueous ammonium chloride solution and saturated aqueous sodium bicarbonate solution. The organic layer was washed with saturated brine, dried over anhydrous sodium sulfate, and the solvent was concentrated under reduced pressure. The resulting residue was purified by silica gel chromatography (hexane-ethyl acetate) to yield Compound 8 (420 mg, yield 75.1%).

MS(ESI) m/z:409.1, 411.1 [M+H]$^+$

The Fourth Step

To a solution of Compound 8 (418 mg, 1.02 mmol) in dichloromethane (4.18 mL) were added pyridine (0.0980 mL, 1.23 mmol) and chloroacetyl chloride (0.124 mL, 1.53 mmol) under ice-cooling, and the mixture was stirred at the same temperature for 48 minutes. The reaction mixture was extracted with ethyl acetate after addition of ice water and 2 mol/L aqueous hydrochloric acid solution. The organic layer was washed with saturated aqueous sodium hydrogen carbonate solution and saturated brine successively, dried over anhydrous sodium sulfate, and the solvent was concentrated under reduced pressure. The resulting residue was purified by silica gel chromatography (hexane-ethyl acetate) to yield Compound 9 (463 mg, yield 93.3%).

MS(ESI) m/z:485.0, 487.0 [M+H]$^+$

The Fifth Step

To a solution of Compound 9 (460 mg, 0.947 mmol) in DMF (4.60 mL) was added sodium hydride (60% wt) (95.0 mg, 2.37 mmol) under ice-cooling, and the mixture was stirred at room temperature for one hour and 42 minutes. The reaction mixture was extracted with ethyl acetate after addition of ice water and 2 mol/L aqueous hydrochloric acid solution. The organic layer was washed with saturated aqueous sodium hydrogen carbonate solution and saturated brine successively, dried over anhydrous sodium sulfate, and the solvent was concentrated under reduced pressure. The resulting residue was solidified with hexane-ethyl acetate to yield Compound 10 (288 mg, yield 67.7%).

MS(ESI) m/z: 449.0, 450.9 [M+H]$^+$

The Sixth Step

To a solution of Compound 10 (287 mg, 0.639 mmoL) in THF (2.87 mL) was added borane-tetrahydrofuran complex (0.92 mol/L THF solution) (2.08 mL, 1.92 mmol) under ice-cooling, and the mixture was stirred for 1 hour and 19 minutes at 50° C. The reaction mixture was cooled to room temperature, and extracted with ethyl acetate after addition of ice water, saturated aqueous ammonium chloride solution and saturated aqueous sodium bicarbonate solution successively. The organic layer was washed with saturated brine, dried over anhydrous sodium sulfate, and the solvent was concentrated under reduced pressure. The obtained residue was purified by amino silica gel chromatography (hexane-ethyl acetate) to yield Compound 11 (234 mg, yield 84.2%).

MS(ESI) m/z:435.4, 437.4 [M+H]$^+$

The Seventh Step

To a solution of Compound 11 (232 mg, 0.533 mmol) in DMF (2.32 mL) were added potassium carbonate (147 mg, 1.07 mmol) and iodomethane (0.100 mL, 1.56 mmol), and the mixture was stirred at room temperature for 14 hours and 35 minutes. The reaction mixture was extracted with ethyl acetate after addition of ice water and saturated aqueous ammonium chloride solution. The organic layer was washed with saturated brine, dried over anhydrous sodium sulfate, and the solvent was concentrated under reduced pressure. The resulting residue was purified by silica gel chromatography (hexane-ethyl acetate) to yield Compound 12 (211 mg, yield 88.1%).

MS(ESI) m/z:449.3, 451.3 [M+H]$^+$

The Eighth Step

To a mixed solution of Compound 12 (210 mg, 0.467 mmol) in DMF (2.10 mL) and water (0.210 mL) were added 4-methyl-phenyl boronic acid (95.0 mg, 0.701 mmol), potassium carbonate (129 mg, 0.935 mmol) and PdCl$_2$ (dtbpf) (30.5 mg, 0.0470 mmol), and the mixture was stirred under nitrogen atmosphere at 100° C. 20 minutes. The reaction mixture was cooled to room temperature, extracted with ethyl acetate after addition of ice water and 2 mol/L aqueous hydrochloric acid solution. The organic layer was washed with saturated aqueous sodium hydrogen carbonate solution and saturated brine successively, dried over anhydrous sodium sulfate, and the solvent was concentrated under reduced pressure. The resulting residue was purified by silica gel chromatography (hexane-ethyl acetate) to yield Compound 13 (192 mg, yield 89.2%).

MS(ESI) m/z:461.6 [M+H]$^+$

The Ninth Step

Compound I-8 (123 mg, yield 66.8%) was obtained by reacting Compound 13 (190 mg, 0.412 mmol) in the same manner as the fourth step in Example 1.

MS(ESI) m/z:447.2 [M+H]$^+$

Example 3

[Chemical formula 128]

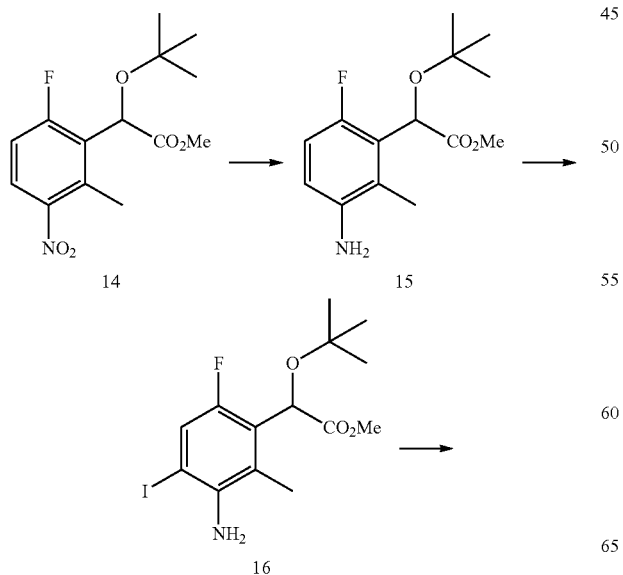

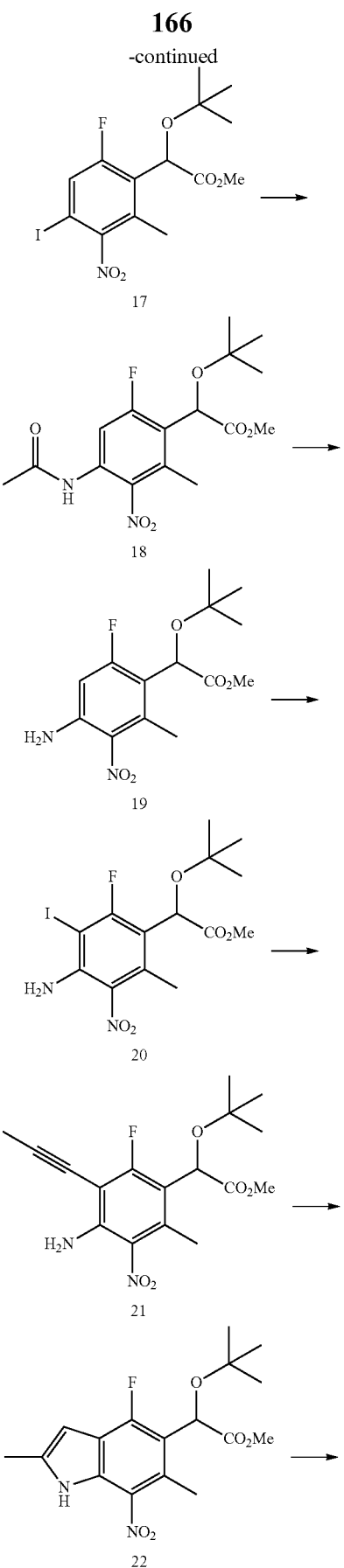

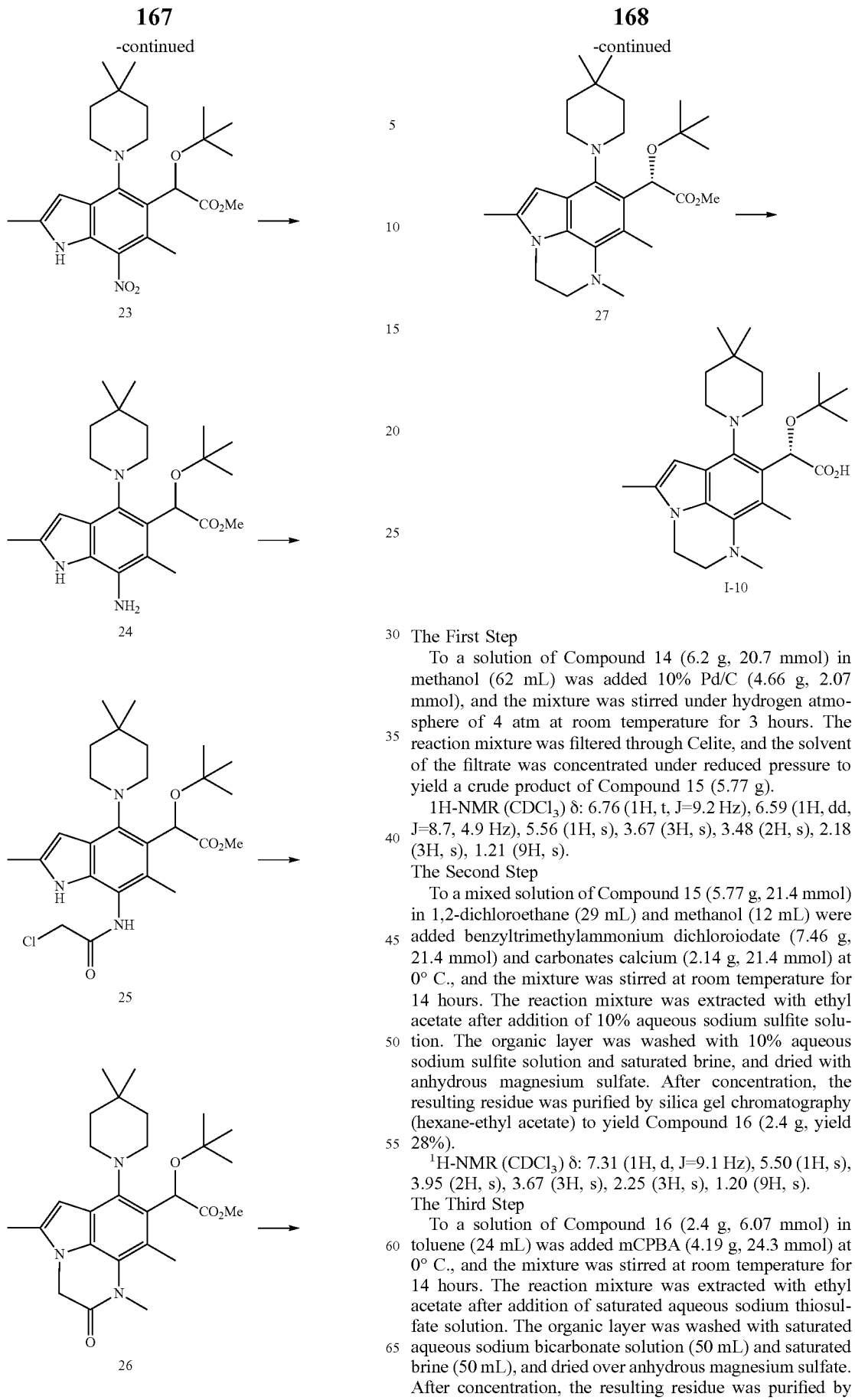

The First Step

To a solution of Compound 14 (6.2 g, 20.7 mmol) in methanol (62 mL) was added 10% Pd/C (4.66 g, 2.07 mmol), and the mixture was stirred under hydrogen atmosphere of 4 atm at room temperature for 3 hours. The reaction mixture was filtered through Celite, and the solvent of the filtrate was concentrated under reduced pressure to yield a crude product of Compound 15 (5.77 g).

1H-NMR (CDCl$_3$) δ: 6.76 (1H, t, J=9.2 Hz), 6.59 (1H, dd, J=8.7, 4.9 Hz), 5.56 (1H, s), 3.67 (3H, s), 3.48 (2H, s), 2.18 (3H, s), 1.21 (9H, s).

The Second Step

To a mixed solution of Compound 15 (5.77 g, 21.4 mmol) in 1,2-dichloroethane (29 mL) and methanol (12 mL) were added benzyltrimethylammonium dichloroiodate (7.46 g, 21.4 mmol) and carbonates calcium (2.14 g, 21.4 mmol) at 0° C., and the mixture was stirred at room temperature for 14 hours. The reaction mixture was extracted with ethyl acetate after addition of 10% aqueous sodium sulfite solution. The organic layer was washed with 10% aqueous sodium sulfite solution and saturated brine, and dried with anhydrous magnesium sulfate. After concentration, the resulting residue was purified by silica gel chromatography (hexane-ethyl acetate) to yield Compound 16 (2.4 g, yield 28%).

$^1$H-NMR (CDCl$_3$) δ: 7.31 (1H, d, J=9.1 Hz), 5.50 (1H, s), 3.95 (2H, s), 3.67 (3H, s), 2.25 (3H, s), 1.20 (9H, s).

The Third Step

To a solution of Compound 16 (2.4 g, 6.07 mmol) in toluene (24 mL) was added mCPBA (4.19 g, 24.3 mmol) at 0° C., and the mixture was stirred at room temperature for 14 hours. The reaction mixture was extracted with ethyl acetate after addition of saturated aqueous sodium thiosulfate solution. The organic layer was washed with saturated aqueous sodium bicarbonate solution (50 mL) and saturated brine (50 mL), and dried over anhydrous magnesium sulfate. After concentration, the resulting residue was purified by silica gel chromatography (hexane-ethyl acetate) to yield Compound 17 (1.56 g, yield 60%).

¹H-NMR (CDCl₃) δ: 7.47 (1H, d, J=8.6 Hz), 5.52 (1H, s), 3.71 (3H, s), 2.36 (3H, s), 1.21 (9H, s).

The Fourth Step

To a solution of Compound 17 (1.56 g, 3.67 mmol) in dioxane (15.6 mL) were added cesium carbonate (2.39 g, 7.34 mmol), acetamide (433 mg, 7.34 mmol), rac-BINAP (343 mg, 0.55 mmol), bis (dibenzylideneacetone) palladium (211 mg, 0.37 mmol), the mixture was stirred under nitrogen atmosphere at 100° C. for 4 hours. The reaction mixture was extracted with ethyl acetate after addition of 2 mol/L hydrochloric acid. The organic layer was washed with water, dried over anhydrous sodium sulfate, and concentrated under reduced pressure. The resulting residue was purified by silica gel column chromatography (hexane-ethyl acetate) to yield compound 18 (1.3 g, yield 99%).

¹H-NMR (CDCl₃) δ: 8.19 (1H, s), 8.03 (1H, d, J=11.6 Hz), 5.55 (1H, s), 3.71 (3H, s), 2.38 (3H, s), 2.20 (3H, s), 1.22 (9H, s).

The Fifth Step

To a solution of Compound 18 (1.3 g, 3.65 mmol) in methanol (13 mL) was added potassium carbonate (1.5 g, 11 mmol), and the mixture was stirred for 5 hours at 60° C. After the solvent of the reaction mixture was concentrated, 2 mol/L hydrochloric acid was added thereto, followed by extraction with ethyl acetate, dried over anhydrous sodium sulfate, and concentrated under reduced pressure. The resulting residue was dissolved in methanol (6 mL) and toluene (6 mL), and 2 mol/L trimethylsilyldiazomethane-hexane solution (1.8 mL, 3.7 mL) was added thereto. The mixture was stirred for 1 hour at room temperature, and concentrated under reduced pressure. The residue was purified by silica gel column chromatography (chloroform-methanol) to yield Compound 19 (800 g, yield 70%).

¹H-NMR (CDCl₃) δ: 6.37 (1H, d, J=11.3 Hz), 5.44 (1H, s), 4.89 (2H, s), 3.70 (3H, s), 2.39 (3H, s), 1.21 (9H, s).

The Sixth Step

To a solution of Compound 19 (800 mg, 2.55 mmol) in ethanol (8.0 mL) were added silver nitrate (865 mg, 5.1 mmol) and iodine (1.3 g, 5.1 mmol), and the mixture was stirred for 2 hours at room temperature. The insoluble materials were filtered through celite, and the filtrate was extracted with ethyl acetate after addition of aqueous sodium hydrogencarbonate solution and aqueous sodium thiosulfate solution. The organic layer was washed with water, dried over anhydrous sodium sulfate, and concentrated under reduced pressure. The resulting residue was purified by silica gel column chromatography (hexane-ethyl acetate) to yield compound 20 (477 mg, yield 43%).

¹H-NMR (CDCl₃) δ: 5.47 (1H, s), 5.33 (2H, s), 3.71 (3H, s), 2.35 (3H, s), 1.21 (9H, s).

The Seventh Step

To a solution of Compound 20 (100 mg, 0.23 mmol) in DMF (1.0 mL) were added triethylamine (0.094 mL, 0.68 mmol) and 1 mol/L propyne-dimethyl formamide solution (0.45 mL, 0.45 mmol), copper iodide (8.7 mg, 0.045 mmol) and PdCl₂(PPh₃)₂ (16 mg, 0.023 mmol), and the mixture was stirred under nitrogen atmosphere for 1 hour at 80° C. The reaction mixture was cooled to room temperature, and extracted with ethyl acetate after addition of water. The organic layer was washed with water and saturated brine, and dried over anhydrous magnesium sulfate. After concentration, the resulting residue was purified by silica gel chromatography (hexane-ethyl acetate) to yield compound 21 (471 mg, yield 72%).

1H-NMR (CDCl₃) δ: 5.49 (2H, s), 5.45 (1H, s), 3.69 (3H, s), 2.38 (3H, s), 2.19 (3H, s), 1.21 (9H, s).

The Eighth Step

To a solution of Compound 21 (243 mg, 0.69 mmol) in THF (2.4 mL) was added 1 mol/L-TBAF.THF solution (1.38 mL, 1.38 mmol), and the mixture was heated under reflux and stirred for 1 hour. The reaction mixture was extracted with ethyl acetate after addition of water. The organic layer was washed with water, dried over anhydrous sodium sulfate, and concentrated under reduced pressure. The resulting residue was purified by silica gel column chromatography (hexane-ethyl acetate) to yield Compound 22 (230 mg, yield 95%).

¹H-NMR (CDCl₃) δ: 9.56 (1H, s), 6.39 (1H, s), 5.73 (1H, s), 3.69 (3H, s), 2.73 (3H, s), 2.49 (3H, s), 1.22 (9H, s).

The Ninth Step

To a solution of Compound 22 (290 mg, 0.82 mmol) in DMSO (2.9 mL) were added potassium carbonate (455 mg, 3.29 mmol) and 4,4-dimethylpiperidine (936 mg, 6.6 mmol), and the mixture was stirred under nitrogen atmosphere for 2 hours at 120° C. The reaction mixture was extracted with ethyl acetate after addition of water. The organic layer was washed with water and saturated brine, and dried over anhydrous magnesium sulfate. After concentration, the resulting residue was purified by DNH silica gel chromatography (hexane-ethyl acetate) to yield Compound 23 (140 mg, yield 38%).

MS(ESI) m/z: 446 [M+H]⁺

The Tenth Step

To a solution of Compound 23 (140 mg, 0.31 mmol) in methanol (1.4 mL) was added 10% Pd/C (350 mg, 0.15 mmol), the mixture was stirred under 4 atm hydrogen atmosphere for 15 hours. The reaction mixture was filtered through Celite, and the filtrate was concentrated to yield Compound 24 (119 mg) as a crude product.

MS(ESI) m/z: 416 [M+H]⁺

The Eleventh Step

Compound 25 (117 mg) was obtained as a crude product by reacting Compound 24 (119 mg) in the same manner as the fourth step in Example 2.

MS(ESI) m/z: 492 [M+H]⁺

The Twelfth Step

Compound 26 (94 mg, 3 steps yield 84%) was obtained by reacting Compound 25 (117 mg, 0.24 mmol) in the same manner as the fifth and seventh step in Example 2.

MS(ESI) m/z: 470 [M+H]⁺

The Thirteenth Step

Compound 27 (23 mg, 25% yield) was obtained by reacting Compound 26 (94 mg, 0.20 mmol) in the same manner as the sixth step in Example 2.

MS(ESI) m/z: 456 [M+H]+

The Fourteenth Step

To a mixed solution of Compound 27 (23 mg, 0.050 mmol) in THF (0.23 mL), methanol (0.23 mL) and water (0.02 mL) was added 2 mmol/L aqueous sodium hydroxide solution (0.13 mL, the 0.25 mmol), and the mixture was stirred under nitrogen atmosphere for 4 hours at 70° C. The reaction mixture was extracted with chloroform after addition of 0.1 mmol/L hydrochloric acid. The organic layer was separated from the aqueous layer with the organic layer phase separator. After concentrating the organic layer, optical resolution was carried out by DIOL chromatography (chloroform-methanol) and liquid chromatography, followed by purification to yield Compound I-10 (5 mg, yield 22%).

MS(ESI) m/z: 442 [M+H]⁺

Example 4

[Chemical formula 129]

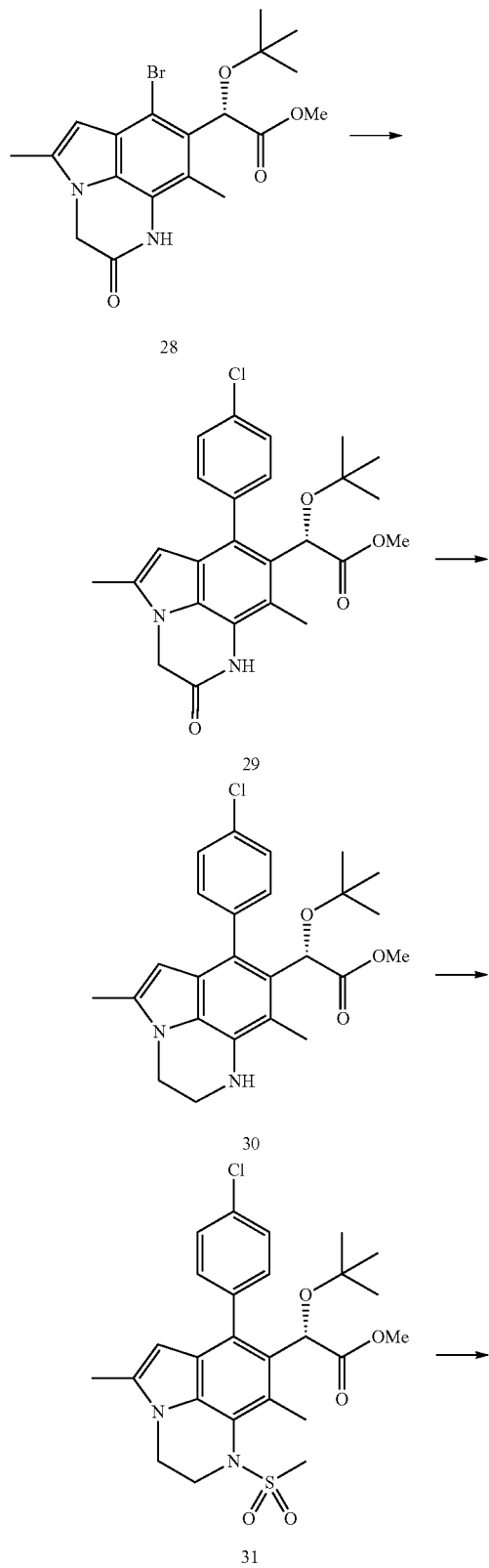

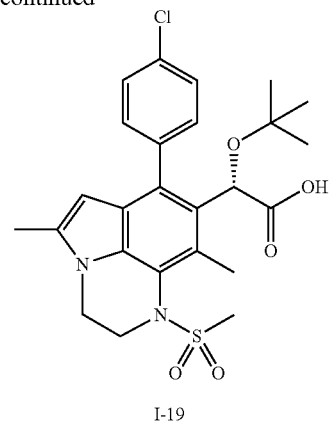

I-19

The First Step

To a solution of Compound 28 (3.1 g, 7.32 mmol) in DMF (30 mL) were added 2 mol/L aqueous potassium carbonate solution (7.32 mL, 14.65 mmol), p-chlorophenyl boronic acid (1.72 mg, 11.0 mmol) and $PdCl_2$ (dppf) (536 mg, 0.732 mmol), and the mixture was stirred under nitrogen atmosphere for 1 hour at 100° C. The reaction mixture was extracted with ethyl acetate after addition of water. The organic layer was washed with water, dried over anhydrous sodium sulfate, and concentrated under reduced pressure by an evaporator. The resulting residue was purified by silica gel column chromatography (hexane-ethyl acetate) to yield compound 29 (2.61 g, yield 78%).

LC/MS (ESI): m/z=454.90 [M+H]+

The Second Step

Compound 30 (239 mg, yield 82%) was obtained by reacting Compound 29 (300 mg, 0.659 mmol) in the same manner as the sixth step in Example 2.

LC/MS (ESI): m/z=441.00 [M+H]+

The Third Step

To a solution of Compound 30 (80 mg, 0.181 mmol) in pyridine (0.5 mL) was added methanesulfonic anhydride (63.2 mg, 0.363 mmol), and the mixture was stirred for 1 hour at room temperature. The reaction mixture was extracted with chloroform after addition of 2 mol/L hydrochloric acid. The organic layer was washed with water, dried over anhydrous sodium sulfate, and concentrated under reduced pressure by an evaporator. The resulting residue was purified by silica gel column chromatography (chloroform-methanol) to yield Compound 31 (87.1 mg, yield 93%).

LC/MS (ESI): m/z=519.00[M+H]

The Fourth Step

Compound I-19 (35 mg, yield 41%) was obtained by reacting Compound 31 (87.1 mg, 0.168 mmol) in the same manner as the fourth step in Example 1.

LC/MS (ESI): m/z=505.00 [M+H]+

1H-NMR (CDCl$_3$) δ:0.94 (s, 9H), 2.34 (s, 3H), 2.45 (s, 3H), 3.08 (s, 3H), 3.45 (brs, 1H), 4.09-4.41 (m, 3H), 5.41 (s, 1H), 5.89 (s, 1H), 7.37-7.47 (m, 3H), 7.67-7.76 (m, 1H)

Example 5

[Chemical formula 130]

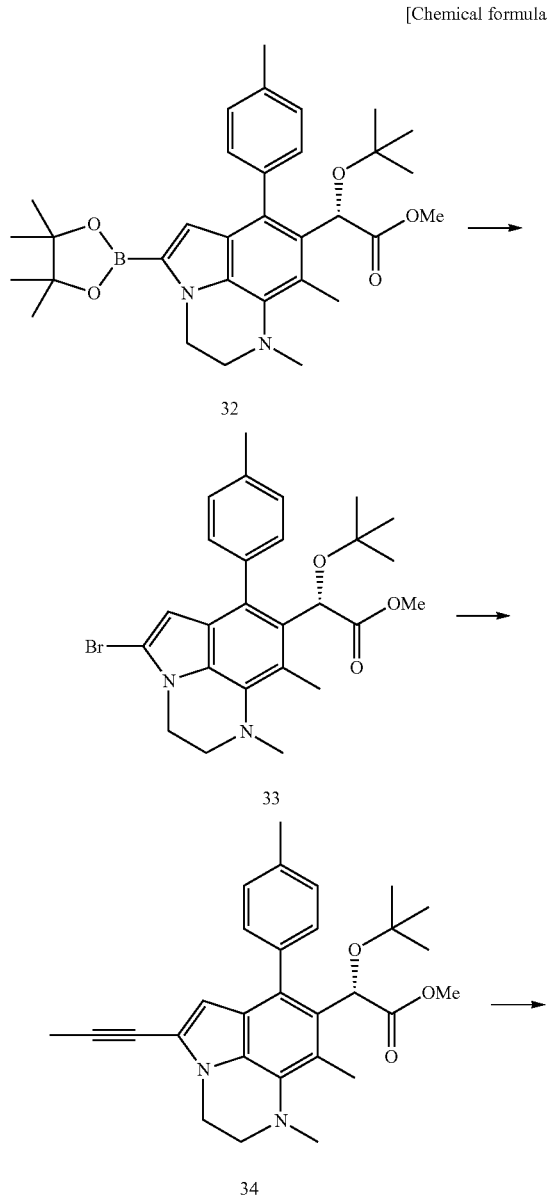

The First Step

To a mixed solution of Compound 32 (300 mg, 0.549 mmol) in methanol (8 mL) and water (2 mL) was added copper bromide (II) (368 mg, 1.65 mmol), and the mixture was heated under reflux and stirred for 30 minutes. The reaction mixture was extracted with chloroform after addition of water. The organic layer was dried over anhydrous sodium sulfate, and concentrated under reduced pressure. The resulting residue was purified by silica gel chromatography (hexane-ethyl acetate) to yield the crude product (187 mg) of Compound 33.

MS(ESI) m/z:499.00, 500.80 [M+H]$^+$

The Second Step

To a solution of the crude product of the Compound 33 (130 mg, 0.260 mmol) in DMF (2 mL) were added triethylamine (0.108 mL, 0.781 mmol), copper iodide (I) (9.91 mg, 0.052 mmol), bis (triphenylphosphine) palladium (II) dichloride (18.3 mg, 0.026 mmol) and 1 mol/L propyne DMF solution (0.521 mL, 0.521 mmol), and the mixture was stirred under nitrogen atmosphere for 3.5 hours at 60° C. The reaction mixture was extracted with ethyl acetate after addition of water. The organic layer was washed with water, dried over anhydrous sodium sulfate, and concentrated under reduced pressure. The resulting residue was purified by silica gel chromatography (ethyl acetate-hexane) to yield the crude product (83.0 mg) of Compound 34.

MS(ESI) m/z:459.2 [M+H]$^+$

The Third Step

Compound I-84 (26.0 mg, 3 steps yield 16%) was obtained by reacting the crude product of Compound 34 (80 mg, 0.174 mmol) in the same manner as the fourth step in Example 1.

$^1$H-NMR (CDCl$_3$) δ: 0.90 (s, 9H), 2.10 (s, 3H), 2.42 (s, 3H), 2.43 (s, 3H), 2.77 (s, 3H) 3.37-3.44 (m, 2H), 4.05-4.12 (m, 2H), 5.59 (s, 1H), 6.34 (s, 1H), 7.22-7.27 (m, 2H), 7.37 (d, J=7.8 Hz, 1H), 7.57 (d, J=6.8 Hz, 1H), 10.01 (s, 1H).

Example 6

[Chemical formula 131]

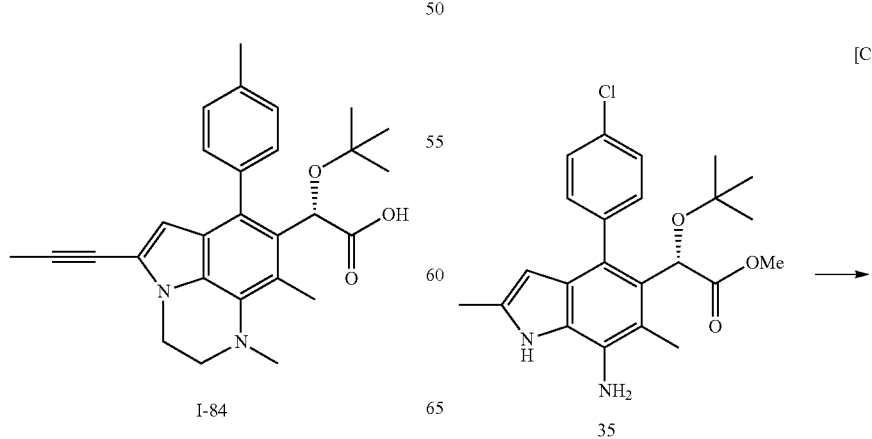

-continued

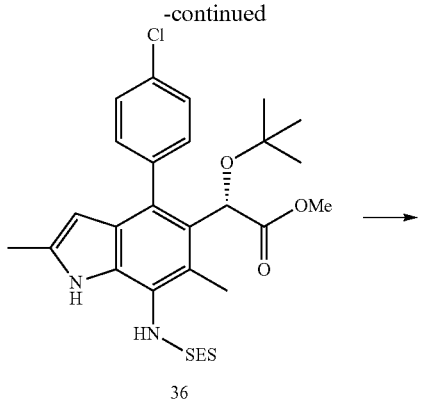
36

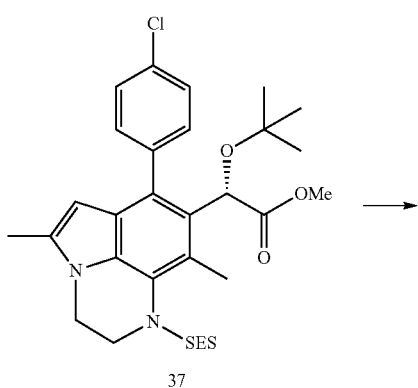
37

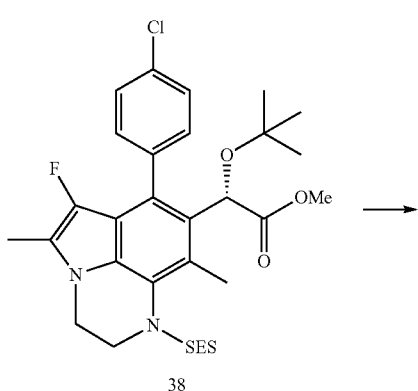
38

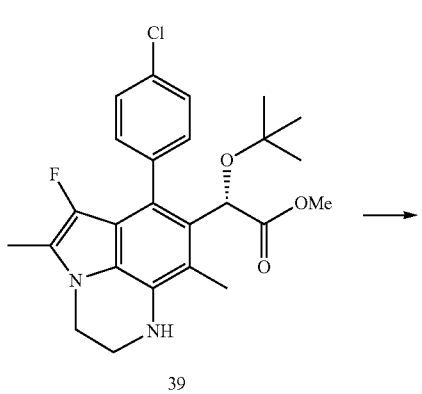
39

-continued

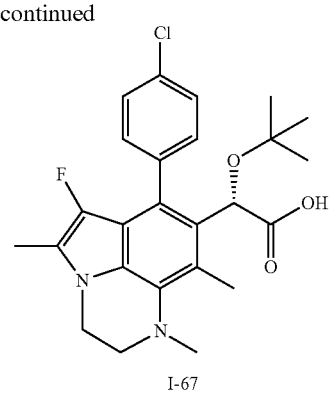
I-67

The First Step
To a solution of Compound 35 (5.92 g, 14.3 mmol) and pyridine (2.88 mL, 35.6 mmol) in dichloromethane was added dichloromethane solution of 2-(trimethylsilyl) ethane sulfonyl chloride (5.72 g, 28.5 mmol) under ice-cooling, the mixture was stirred for 16.5 hours at room temperature. The reaction mixture was extracted with chloroform after addition of saturated aqueous sodium hydrogen carbonate solution. The organic layer was washed with 1 mol/L aqueous hydrochloric acid solution and saturated brine, dried over anhydrous magnesium sulfate, and concentrated under reduced pressure. The resulting residue was purified by silica gel chromatography (hexane-ethyl acetate) to yield Compound 36 (7.03 g, yield 85%).

$^1$H-NMR (CDCl$_3$) δ: 0.00 (s, 9H), 0.92 (s, 9H), 1.05-1.12 (m, 2H), 2.37 (s, 3H), 2.48 (s, 3H), 3.02-3.10 (m, 2H), 3.71 (s, 3H), 5.27 (s, 1H), 5.75-5.79 (m, 1H), 6.15 (s, 1H), 7.35-7.39 (m, 1H), 7.43-7.50 (m, 3H), 9.04 (s, 1H).

The Second Step
To a solution of Compound 36 (1.14 g, 1.97 mmol) in DMF (12 mL) were added cesium carbonate (1.29 g, 3.95 mmol) and 1,2-dibromoethane (0.255 mL, 2.96 mmol), and the mixture was stirred at room temperature for 18.5 hours. The reaction mixture was extracted with ethyl acetate after addition of water. The organic layer was washed with water and saturated brine, dried over anhydrous magnesium sulfate, and concentrated under reduced pressure. The resulting residue was purified by silica gel chromatography (hexane-ethyl acetate) to yield Compound 37 (1.13 g, yield 95%).

MS(ESI) m/z:605.1 [M+H]$^+$

The Third Step
To a solution of Compound 37 (30.0 mg, 0.050 mmol) in acetonitrile (1 mL) was added 1-chloromethyl-4-fluoro-1,4-diazoniabicyclo [2,2,2] octane bis (tetrafluoroborate) (selectfluor (R), 26.3 mg, 0.074 mmol) under ice-cooling, and the mixture was stirred for 30 minutes under ice-cooling. The reaction mixture was extracted with chloroform after addition of saturated aqueous sodium hydrogen carbonate solution. The organic layer was dried over anhydrous sodium sulfate, and concentrated under reduced pressure. The resulting residue was purified by silica gel chromatography (hexane-ethyl acetate) to yield compound 38 (11.6 mg, yield 38%).

MS(ESI) m/z:623.0 [M+H]+

The Fourth Step
To a solution of Compound 38 (110 mg, 0.176 mmol) in THF (2 mL) was added 1 mol/L TBAF THF solution (0.353 mL, 0.353 mmol), and the mixture was stirred at room temperature for 20 hours. The reaction mixture was extracted with chloroform after addition of water. The organic layer was dried over anhydrous sodium sulfate, and concentrated under reduced pressure. The resulting residue was purified by silica gel chromatography (hexane-ethyl acetate) to yield Compound 39 (73.0 mg, yield 90%).

MS(ESI) m/z:459.0 [M+H]$^+$

The Fifth Step

Compound I-67 (31.3 mg, 2 steps yield 43%) was obtained by reacting Compound 39 (73.0 mg, 0.159 mmol) in the same manner as the seventh step in Example 2 and the fourth step of Example 1.

$^1$H-NMR (CDCl$_3$) δ: 0.93 (s, 9H), 2.30 (s, 3H), 2.42 (s, 3H), 2.76 (s, 3H), 3.39-3.48 (m, 2H), 3.87-3.94 (m, 2H), 5.43 (s, 1H), 7.38-7.44 (m, 3H), 7.67 (d, J=7.8 Hz, 1H), 9.96 (s, 1H).

Example 7

[Chemical formula 132]

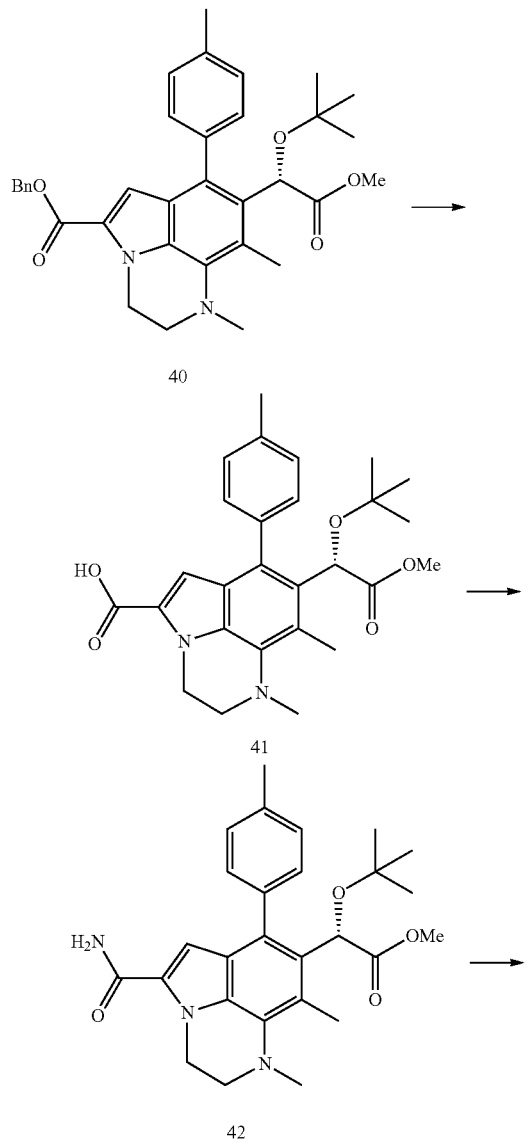

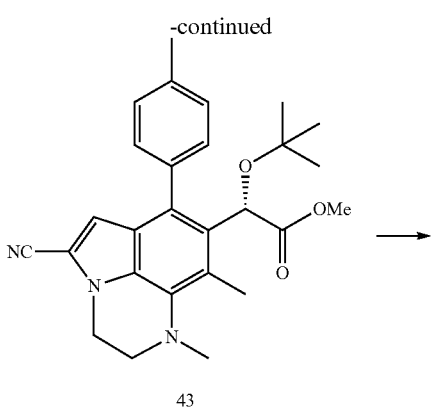

The First Step

To a mixed solution of compound 40 (1.78 g, 3.21 mmol) in methanol (10 mL)-THF (10 mL) was added 10% palladium hydroxide (451 mg, 0.321 mmol), and the mixture was stirred under hydrogen atmosphere at room temperature for 3 hours. The insoluble materials were removed by Celite filtration, and the solvent was concentrated under reduce d pressure. The resulting residue was purified by silica gel chromatography (chloroform-methanol) to yield Compound 41 (1.50 g).

$^1$H-NMR (CDCl$_3$) δ: 0.90 (s, 9H), 2.45 (s, 3H), 2.47 (s, 3H), 2.81 (s, 3H), 3.39-3.47 (m, 2H), 3.75 (s, 3H), 4.42-4.49 (m, 1H), 4.50-4.56 (m, 1H), 5.47 (s, 1H), 7.05 (s, 1H), 7.26-7.30 (m, 2H), 7.32-7.36 (m, 1H), 7.42-7.47 (m, 1H).

The Second Step

To a solution of Compound 41 (300 mg, 0.646 mmol) in DMF (2 mL) were added 0.5 mol/L ammonia in 1,4-dioxane (6.46 mL, 3.23 mmol) and O-(7-azabenzotriazol-1-yl)-N,N,N',N-tetramethyluronium hexafluorophosphate (491 mg, 1.29 mmol), and the mixture was stirred for 25 minutes at room temperature. The reaction mixture was extracted with ethyl acetate after addition of water. The organic layer was washed with water, dried over anhydrous sodium sulfate, and concentrated under reduced pressure. The resulting residue was purified by silica gel chromatography (hexane-ethyl acetate) to yield compound 42 (299 mg, yield 100%).

MS(ESI) m/z:464.1 [M+H]$^+$

The Third Step

To a solution of Compound 42 (290 mg, 0.626 mmol) in THF (3 mL) were added triethylamine (0.173 mL, 1.25 mmol) and trifluoroacetic anhydride (0.132 mL, 0.938 mmol), and the mixture was stirred at room temperature. The reaction mixture was extracted with chloroform after addition of water. The organic layer was dried over anhydrous sodium sulfate, and concentrated under reduced pressure.

The resulting residue was purified by silica gel chromatography (hexane-ethyl acetate) to yield compound 43 (270 mg, yield 97%).

$^1$H-NMR (CDCl$_3$) δ: 0.89 (s, 9H), 2.44 (s, 3H), 2.46 (s, 3H), 2.82 (s, 3H), 3.43-3.52 (m, 2H), 3.75 (s, 3H), 4.16-4.24 (m, 2H), 5.45 (s, 1H), 6.80 (s, 1H), 7.24-7.30 (m, 3H), 7.41-7.44 (m, 1H).

The Fourth Step

To a solution of Compound 43 (270 mg, 0.606 mmol) in N,N-dimethylacetamide (2 mL) was added lithium chloride (257 mg, 6.06 mmol), and the mixture was stirred for 19.5 hours at 120° C. The reaction mixture was extracted with ethyl acetate after addition of 2 mol/L aqueous hydrochloric acid solution. The organic layer was washed with water, dried over anhydrous sodium sulfate, and concentrated under reduced pressure. The resulting residue was purified by silica gel chromatography (hexane-ethyl acetate) to yield Compound I-39 (73.0 mg, yield 28%).

$^1$H-NMR (DMSO-D$_6$) δ: 0.79 (s, 9H), 2.38 (s, 3H), 2.40 (s, 3H), 2.73 (s, 3H), 3.37-3.43 (m, 2H), 4.18-4.28 (m, 2H), 5.30 (s, 1H), 6.81 (s, 1H), 7.27-7.36 (m, 3H), 7.43-7.49 (m, 1H).

Example 8

[Chemical formula 133]

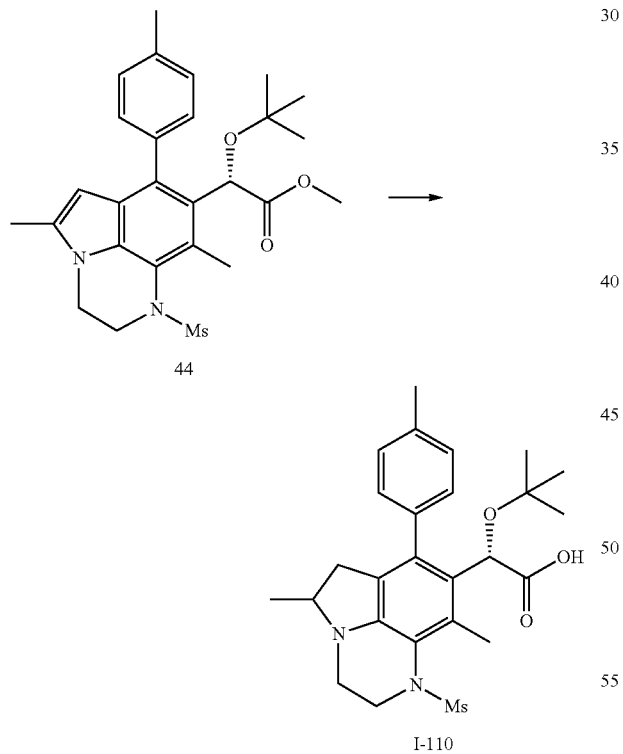

44

I-110

To a solution of Compound 44 (150 mg, 0.301 mmol) in methanol (1.5 mL) was added 10% palladium hydroxide (84.0 mg, 0.060 mmol), and the mixture was stirred under hydrogen atmosphere at room temperature for 26 hours. The insoluble materials were removed by Celite filtration, and the filtrate was concentrated under reduced pressure. The resulting residue was purified by silica gel chromatography (chloroform-methanol). Diastereomeric mixture I-110 (9.0 mg, 2 steps yield 6%) was obtained by reacting the resulting crude product (45.0 mg) in the same manner as the fourth step in Example 1.

MS(ESI) m/z:487.2 [M+H]$^+$

Example 9

[Chemical formula 134]

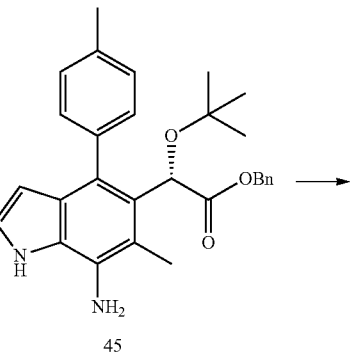

45

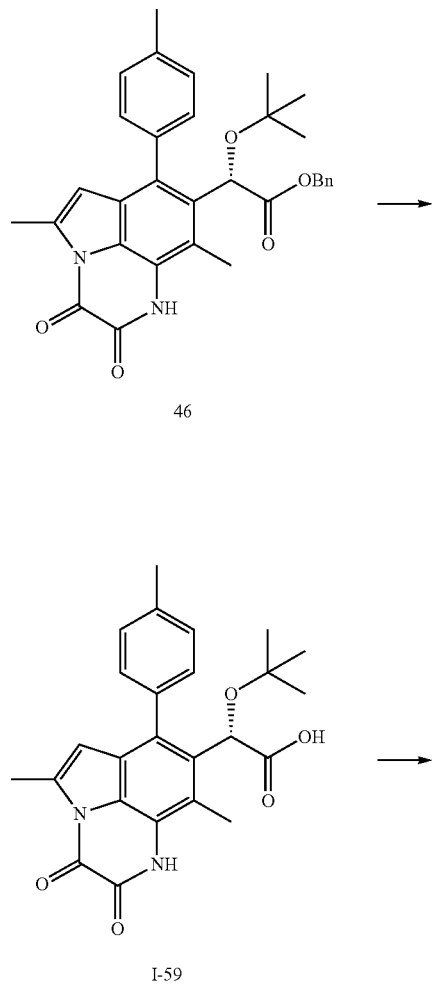

46

I-59

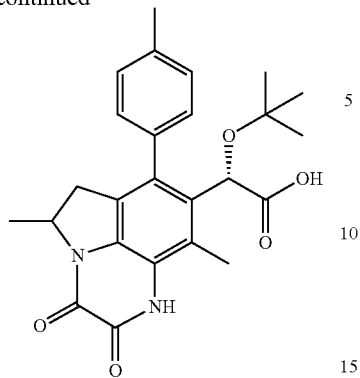

I-58

The First Step

To a solution of Compound 45 (50.0 mg, 0.106 mmol) in THF (2 mL) was added 60% sodium hydride (12.8 mg, 0.319 mmol) under ice-cooling, and the mixture was stirred under nitrogen atmosphere for 10 minutes. To the reaction mixture was added oxalyl chloride (0.211 mL, 2.417 mmol), and the mixture was stirred at room temperature overnight. The reaction mixture was poured into a saturated aqueous ammonium chloride solution, and extracted with ethyl acetate. The organic layer was washed with water and saturated brine, dried over anhydrous magnesium sulfate, and concentrated under reduced pressure. The resulting residue was purified by silica gel chromatography (hexane-ethyl acetate) to yield Compound 46 (22.3 mg, yield 40%).

$^1$H-NMR (CDCl$_3$) δ: 0.91 (s, 9H), 2.37 (s, 3H), 2.44 (s, 3H), 2.72 (s, 3H), 5.15 (d, J=12.1 Hz, 1H), 5.23 (d, J=12.1 Hz, 1H), 5.43 (s, 1H), 6.23 (s, 1H), 7.15 (d, J=7.6 Hz, 1H), 7.20-7.37 (m, 8H), 8.80 (s, 1H).

The Second Step

To a solution of Compound 46 (22.0 mg, 0.042 mmol) in ethyl acetate (2 mL) was added 5% palladium-carbon (20.0 mg, 0.009 mmol), and the mixture was stirred under hydrogen atmosphere for 1 hour at room temperature. After the insoluble materials were filtered off, the filtrate was concentrated under reduced pressure. The resulting residue was purified by high performance liquid chromatography (0.1% formic acid in water-0.1% formic acid in acetonitrile) to yield Compound I-59 (1.6 mg, yield 9%) and Compound I-58 (7.2 mg, yield 39%).

Compound I-59: MS(ESI) m/z:435 [M+H]+
Compound I-58 (Diastereomeric mixture): MS(ESI) m/z: 437 [M+H]$^+$ Example 10

[Chemical formula 135]

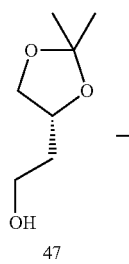

47

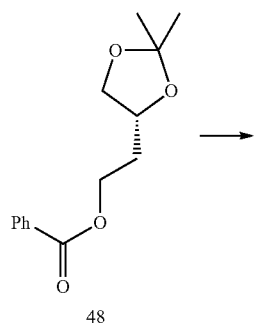

48

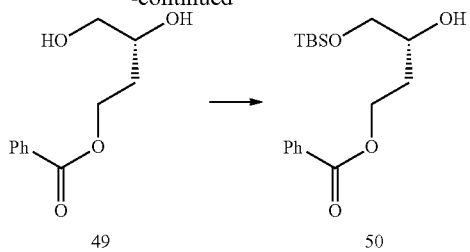

49  50

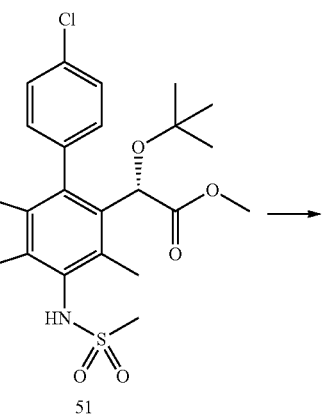

51

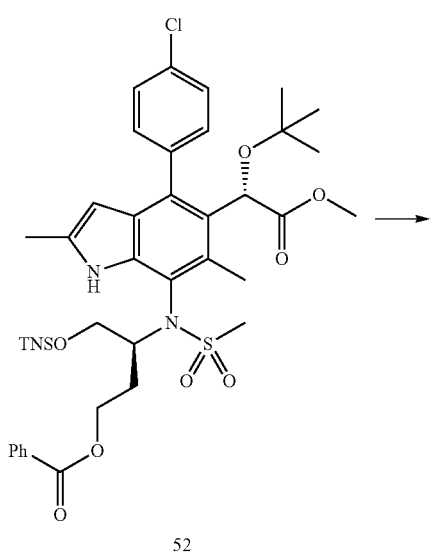

52

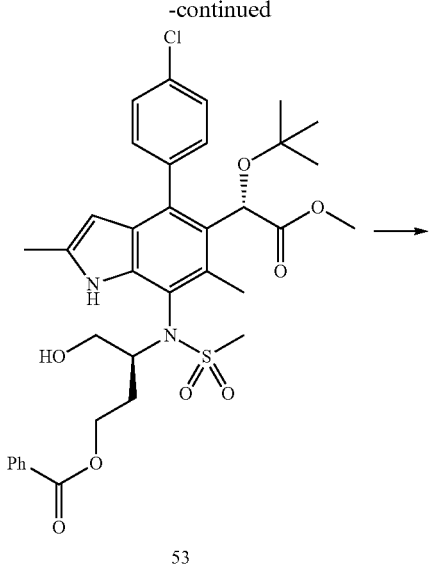

53

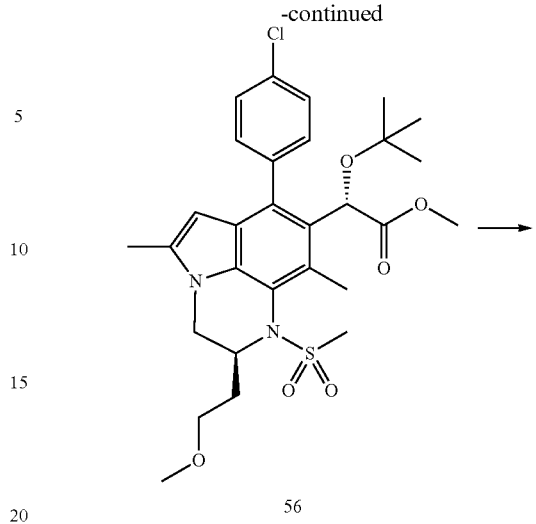

56

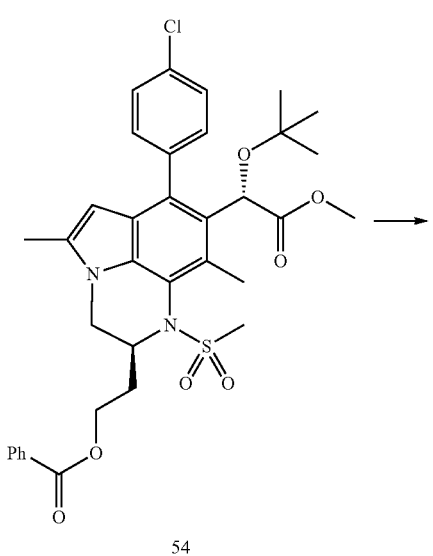

54

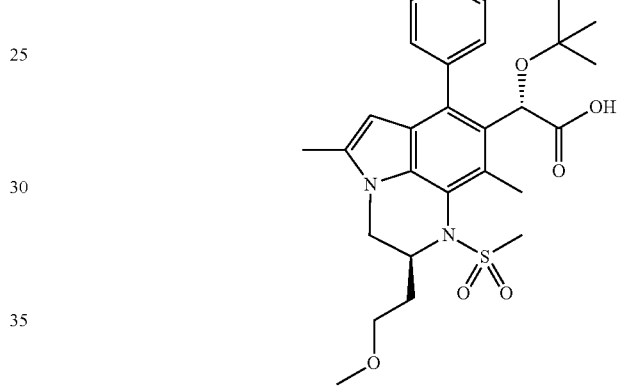

I-43

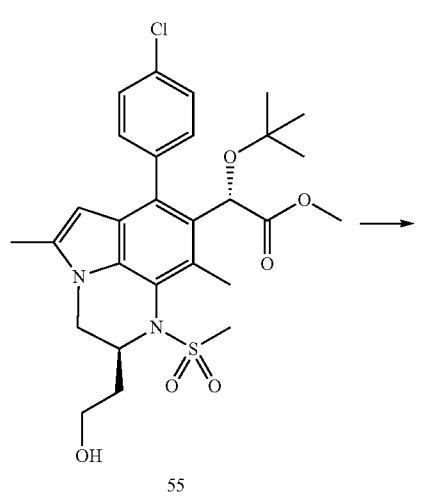

55

The First Step

To a solution of Compound 47 (4.64 mL, 33.2 mmol) in dichloromethane (50 mL) were added triethylamine (9.20 mL, 66.4 mmol), 4-(dimethylamino) pyridine (41.0 mg, 0.332 mmol) and benzoyl chloride (5.78 mL, 49.8 mmol), and the mixture was stirred for 16 hours at room temperature. The reaction mixture was extracted with ethyl acetate after addition of water. The organic layer was washed with water and saturated brine, dried over anhydrous magnesium sulfate, and concentrated under reduced pressure. The resulting residue was purified by silica gel chromatography (hexane-ethyl acetate) to yield Compound 48 (8.24 g, yield 99%).

$^1$H-NMR (CDCl$_3$) δ: 1.37 (s, 3H), 1.43 (s, 3H), 1.97-2.12 (m, 2H), 3.65 (dd, J=8.0, 7.2 Hz, 1H), 4.13 (dd, J=8.0, 5.9 Hz, 1H), 4.28 (ddd, J=11.6, 7.2, 5.9 Hz, 1H), 4.40 (ddd, J=12.4, 6.6, 4.6 Hz, 1H), 4.50 (ddd, J=12.4, 5.3, 5.3 Hz, 1H), 7.44 (dd, J=7.3, 7.3 Hz, 2H), 7.57 (dd, J=7.3, 7.3 Hz, 1H), 8.03 (d, J=7.3 Hz, 2H).

The Second Step

A mixed solution of Compound 48 (8.24 g, 32.9 mmol) in acetic acid (60 mL)-water (25 mL) was stirred for 5 hours at 60° C., and then stirred for 6 hours at 80° C. The reaction mixture was concentrated under reduced pressure, saturated aqueous sodium hydrogen carbonate solution was added thereto, followed by extraction with ethyl acetate. The organic layer was washed with water and saturated brine, dried over anhydrous magnesium sulfate, and concentrated under reduced pressure. The resulting residue was purified by silica gel chromatography (hexane-ethyl acetate) to yield Compound 49 (3.49 g, yield 51%).

$^1$H-NMR (CDCl$_3$) δ: 1.82-1.99 (m, 3H), 2.63-2.75 (m, 1H), 3.50-3.59 (m, 1H), 3.66-3.75 (m, 1H), 3.85-3.93 (m, 1H), 4.39-4.46 (m, 1H), 4.64 (ddd, J=11.1, 9.1, 5.1 Hz, 1H), 7.45 (dd, J=7.3, 7.3 Hz, 2H), 7.57 (dd, J=7.3, 7.3 Hz, 1H), 8.04 (d, J=7.3 Hz, 2H).

The Third Step

To a solution of Compound 49 (800 mg, 3.81 mmol) in dichloromethane (8 mL) were added 4-(dimethylamino) pyridine (23.3 mg, 0.190 mmol) and triethylamine (0.739 mL, 5.33 mmol), and the mixture was stirred under ice cooling for 5 minutes. A solution of tert-butyldimethylsilyl chloride (688 mg, 4.57 mmol) in dichloromethane solution (2 mL) was added dropwise thereto, and the mixture was stirred at room temperature for 24 hours. The reaction mixture was extracted with ethyl acetate after addition of water and saturated aqueous ammonium chloride solution. The organic layer was washed with water and saturated brine, dried over anhydrous magnesium sulfate, and concentrated under reduced pressure. The resulting residue was purified by silica gel chromatography (hexane-ethyl acetate) to yield Compound 50 (981 mg, yield 79%).

$^1$H-NMR (CDCl$_3$) δ: 0.08 (s, 6H), 0.91 (s, 9H), 1.80-1.97 (m, 2H), 2.52 (d, J=4.0 Hz, 1H), 3.51 (dd, J=9.9, 7.1 Hz, 1H), 3.69 (dd, J=9.9, 3.5 Hz, 1H), 3.82-3.90 (m, 1H), 4.46-4.54 (m, 2H), 7.44 (dd, J=7.3, 7.3 Hz, 2H), 7.56 (dd, J=7.3, 7.3 Hz, 1H), 8.04 (d, J=7.3 Hz, 2H).

The Fourth Step

To a solution of Compound 50 (658 mg, 2.03 mmol) and Compound 51 (500 mg, 1.01 mmol) in THF (10 mL) were added triphenylphosphine (798 mg, 3.04 mmol) and azodicarboxylic acid bis (2-methoxyethyl) (713 mg, 3.04 mmol), and the mixture was stirred for 1.5 hours at room temperature. The reaction mixture was extracted with ethyl acetate after addition of water. The organic layer was washed with water and saturated brine, dried over anhydrous magnesium sulfate, and concentrated under reduced pressure. The resulting residue was purified by silica gel chromatography (hexane-ethyl acetate) to yield Compound 52 (518 mg, yield 64%).

MS(ESI) m/z:799 [M+H]$^+$

The Fifth Step

Compound 53 (330 mg, yield 74%) was obtained by reacting Compound 52 (518 mg, 0.648 mmol) in the same manner as the fourth step in Example 6.

MS(ESI) m/z:685 [M+H]$^+$

The Sixth Step

To a solution of Compound 53 (330 mg, 0.482 mmol) in dichloromethane (4 mL) were added triethylamine (0.200 mL, 1.45 mmol) and methanesulfonyl chloride (0.113 mL, 1.45 mmol), and the mixture was stirred at room temperature for one hour. The reaction mixture was diluted with ethyl acetate, and washed with water and saturated brine. The organic layer was dried over anhydrous sodium sulfate, and concentrated under reduced pressure. The resulting residue was dissolved in DMF (4 mL), 60% sodium hydride (57.8 mg, 1.45 mmol) was added thereto under ice-cooling, and the mixture was stirred at room temperature for 14 hours. The reaction mixture was diluted with ethyl acetate, poured into a saturated aqueous ammonium chloride solution, and extracted with ethyl acetate. The organic layer was washed with water and saturated brine, dried over anhydrous magnesium sulfate, and concentrated under reduced pressure.

The resulting residue was purified by silica gel chromatography (hexane-ethyl acetate) to yield Compound 54 (103 g, yield 32%).

$^1$H-NMR (CDCl$_3$) δ: 0.90 (s, 9H), 1.52-1.59 (m, 1H), 1.79-1.88 (m, 1H), 2.32 (s, 3H), 2.48 (s, 3H), 3.11 (s, 3H), 3.77 (s, 3H), 4.00 (d, J=12.4 Hz, 1H), 4.31-4.40 (m, 2H), 4.47 (dd, J=12.4, 4.3 Hz, 1H), 4.66-4.73 (m, 1H), 5.28 (s, 1H), 5.84 (s, 1H), 7.37-7.66 (m, 7H), 8.06 (d, J=7.3 Hz, 2H).

The Seventh Step

To a mixed solution of Compound 54 (103 mg, 0.154 mmol) in methanol (1 mL)-THF (1 mL) was added 2 mol/L aqueous sodium hydroxide solution (0.500 mL, 1.00 mmol) under ice-cooling, and the mixture was stirred at room temperature for 1 hour. The reaction mixture was extracted with ethyl acetate after addition of an aqueous hydrochloric acid solution. The organic layer was washed with water and saturated brine, dried over anhydrous sodium sulfate, and concentrated under reduced pressure. The resulting residue was purified by silica gel chromatography (hexane-ethyl acetate) to yield Compound 55 (78.4 mg, yield 90%).

$^1$H-NMR (CDCl$_3$) δ: 0.90 (s, 9H), 1.30-1.37 (m, 1H), 1.41-1.49 (m, 1H), 2.32 (s, 3H), 2.45 (s, 3H), 3.21 (s, 3H), 3.64-3.72 (m, 2H), 3.75 (s, 3H), 3.96 (d, J=12.1 Hz, 1H), 4.45 (dd, J=12.1, 4.7 Hz, 1H), 4.71-4.77 (m, 1H), 5.27 (s, 1H), 5.82 (s, 1H), 7.36-7.45 (m, 3H), 7.50-7.54 (m, 1H).

The Eighth Step

To a solution of Compound 55 (73.0 mg, 0.130 mmol) in DMF (1 mL) was added 60% sodium hydride (7.8 mg, 0.194 mmol) under ice-cooling, and the mixture was stirred for 10 minutes. Iodine methyl (0.024 mL, 0.389 mmol) was added thereto, and the mixture was stirred at room temperature for 1 hour. The reaction mixture was extracted with ethyl acetate after addition of a saturated aqueous ammonium chloride solution. The organic layer was washed with water and saturated brine, dried over anhydrous sodium sulfate, and concentrated under reduced pressure. The resulting residue was purified by silica gel chromatography (hexane-ethyl acetate) to yield Compound 56 (58.3 mg, yield 78%).

$^1$H-NMR (CDCl$_3$) δ: 0.90 (s, 9H), 1.27-1.34 (m, 1H), 1.59-1.65 (m, 1H), 2.31 (s, 3H), 2.45 (s, 3H), 3.21 (s, 3H), 3.26-3.30 (m, 1H), 3.37 (s, 3H), 3.40-3.47 (m, 1H), 3.75 (s, 3H), 3.94 (d, J=12.4 Hz, 1H), 4.43 (dd, J=12.4, 4.3 Hz, 1H), 4.58-4.67 (m, 1H), 5.27 (s, 1H), 5.81 (s, 1H), 7.35-7.46 (m, 3H), 7.50-7.54 (m, 1H).

The Ninth Step

Compound I-43 (45.5 mg, 80% yield) was obtained by reacting Compound 56 (58.0 mg 0.100 mmol) in the same manner as the fourth step in Example 1.

$^1$H-NMR (CDCl$_3$) δ: 0.92 (s, 9H), 1.21-1.29 (m, 1H), 1.56-1.66 (m, 1H), 2.32 (s, 3H), 2.41 (s, 3H), 3.20-3.28 (m, 4H), 3.34-3.44 (m, 4H), 3.94 (d, J=12.4 Hz, 1H), 4.44 (dd, J=12.4, 4.4 Hz, 1H), 4.57-4.64 (m, 1H), 5.39 (s, 1H), 5.87 (s, 1H), 7.38-7.48 (m, 3H), 7.74-7.79 (m, 1H), 10.12 (s, 1H).

Example 11

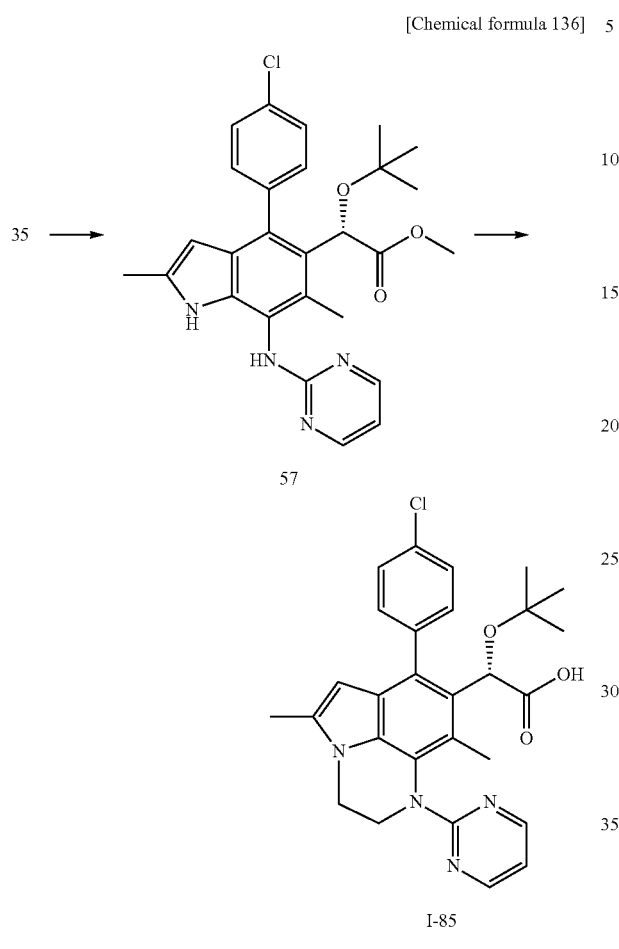

The First Step

To a solution of Compound 35 (100 mg, 0.241 mmol) in N,N-dimethylacetamide (2 mL) were added cesium carbonate (236 mL, 0.723 mmol) and 2-chloropyrimidine (55.2 mg, 0.482 mmol), and the mixture was stirred for 1 hour at 200° C. under microwave irradiation. The reaction mixture was extracted with ethyl acetate after addition of saturated aqueous sodium hydrogencarbonate solution. The organic layer was washed with water and saturated brine, dried over anhydrous magnesium sulfate, and concentrated under reduced pressure. The resulting residue was purified by silica gel chromatography (hexane-ethyl acetate) to yield Compound 57 (11.3 mg, yield 10%).

$^1$H-NMR (CDCl$_3$) δ: 0.93 (s, 9H), 2.33 (s, 3H), 2.44 (s, 3H), 3.70 (s, 3H), 5.31 (s, 1H) 5.80 (s, 1H), 6.68 (t, J=4.8 Hz, 1H), 6.90 (s, 1H), 7.37-7.47 (m, 3H), 7.50-7.55 (m, 1H), 8.36 (d, J=4.8 Hz, 2H), 8.55 (s, 1H).

The Second Step

To a solution of Compound 57 (11.0 mg, 0.022 mmol) in DMF (1 mL) were added a large excess of 60% sodium hydride and 1,2-dibromoethane under ice-cooling, and the mixture was stirred for 14 hours at room temperature. The reaction mixture was extracted with ethyl acetate after addition of a saturated aqueous ammonium chloride solution. The organic layer was washed with water and saturated brine, dried over anhydrous magnesium sulfate, and concentrated under reduced pressure. The resulting residue was purified by silica gel chromatography (ethyl acetate) to yield Compound I-85 (1.7 mg, yield 15%).

MS(ESI) m/z:505 [M+H]$^+$

Example 12

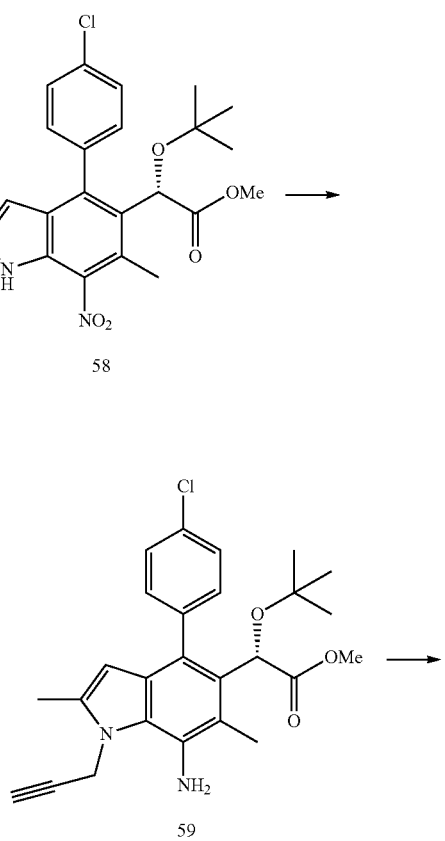

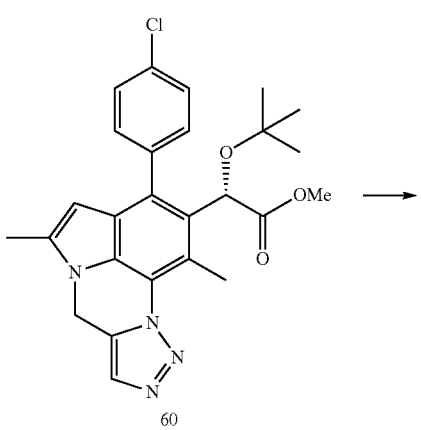

Example 13

[Chemical formula 138]

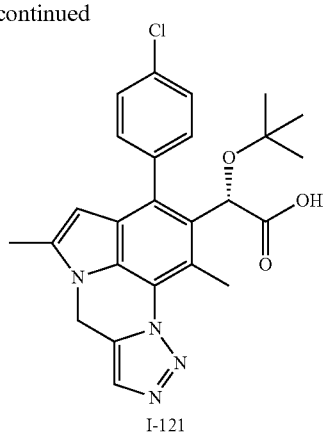

I-121

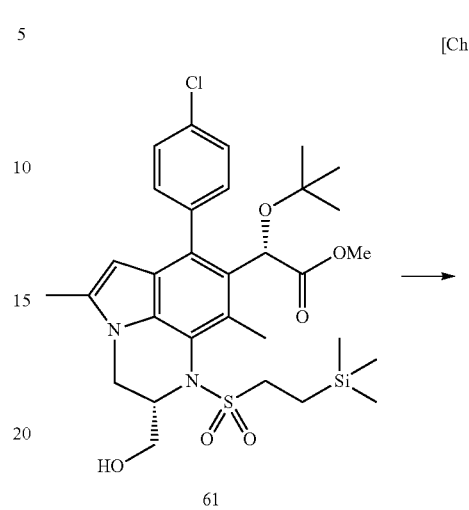

61

The First Step

To a solution of Compound 58 (850 mg, 1.91 mmol) and 3-bromoprop-1-yne (455 mg, 3.82 mmol) in DMF (5 mL) was added 60% sodium hydride (153 mg, 3.82 mmol) under ice-cooling, and the mixture was stirred for 1 hour at 0° C. After the reaction mixture was diluted with ethyl acetate, water was added thereto, and the mixture was extracted with ethyl acetate. The organic layer was washed with water, dried over anhydrous sodium sulfate, and concentrated under reduced pressure. The resulting residue was dissolved in ethanol (20 mL) and water (3 mL), ammonium chloride (1.02 g, 19.1 mmol) and iron powder (1.07 g, 19.1 mmol) was added thereto, and the mixture was stirred for 4 hours at 90° C. After the insoluble materials were removed by filtration, and the filtrate was concentrated under reduced pressure. The resulting residue was extracted with chloroform after addition of chloroform and water. The organic layer was dried over anhydrous sodium sulfate, and concentrated under reduced pressure. The resulting residue was purified by silica gel chromatography (hexane-ethyl acetate) to yield Compound 59 (251 mg, yield 29%).

MS(ESI) m/z:453 [M+H]$^+$

The Second Step

To a solution of Compound 59 (251 mg, 0.554 mmol) in acetonitrile (4 mL) were added trimethylsilylazide (77.0 mg, 0.665 mmol) and nitrite tert-butyl (86.0 mg, 0.831 mmol), the mixture was stirred at room temperature for 14 hours. The reaction mixture was extracted with ethyl acetate after addition of water. The organic layer was dried over anhydrous sodium sulfate, and concentrated under reduced pressure. The resulting residue was dissolved in toluene and stirred for 1 hour at 110° C. The reaction mixture was concentrated under reduced pressure, the resulting residue was purified by silica gel chromatography (hexane-ethyl acetate) to yield Compound 60 (139 mg, yield 52%).

MS(ESI) m/z:479 [M+H]$^+$

The Third Step

Compound I-121 (91.0 mg, yield 67%) was obtained by reacting Compound 60 (139 mg, 0.290 mmol) in the same manner as the fourth step in Example 1.

$^1$H-NMR (CDCl$_3$) δ: 0.97 (s, 9H), 2.39 (s, 3H), 3.01 (s, 3H), 5.43 (d, J=15.1 Hz, 1H), 5.49 (s, 1H), 5.54 (d, J=15.1 Hz, 1H), 6.01 (s, 1H), 7.38-7.44 (m, 1H), 7.45-7.50 (m, 2H), 7.67-7.73 (m, 1H), 7.77 (s, 1H).

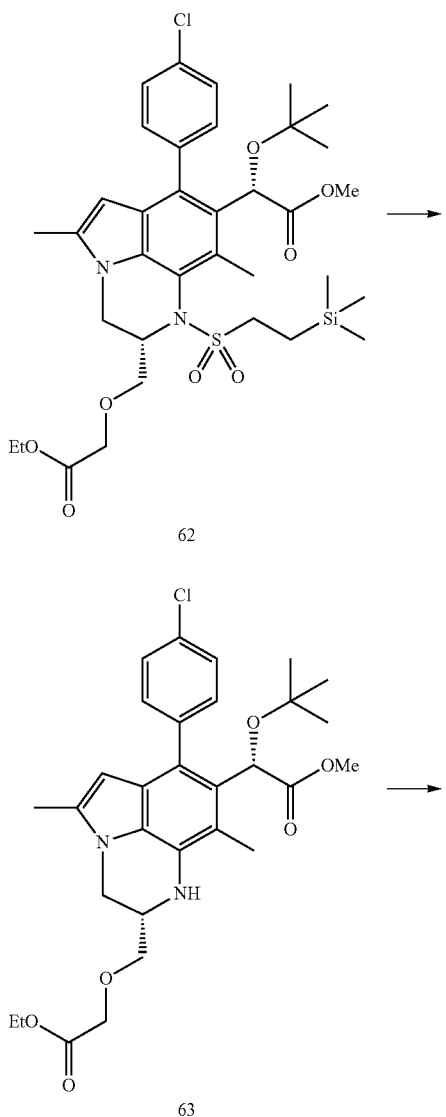

62

63

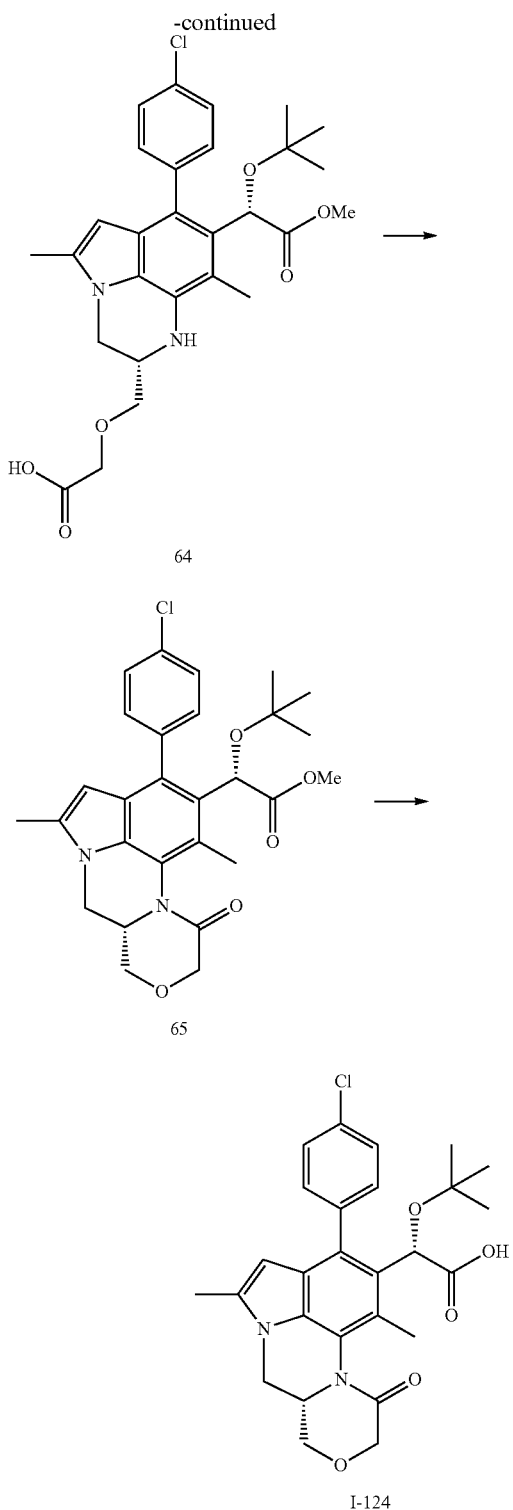

tion. The organic layer was washed with water and saturated brine, dried over anhydrous magnesium sulfate, and concentrated under reduced pressure. The resulting residue was purified by silica gel chromatography (hexane-ethyl acetate) to yield Compound 62 (66.8 mg, yield 59%).

MS(ESI) m/z:721 [M+H]$^+$

The Second Step

To a solution of Compound 62 (66.0 mg, 0.091 mmol) in THF (2 mL) was added 1 mol/L TBAF THF solution (0.500 mL, 0.500 mmol), and the mixture was stirred for 2 hours at room temperature. The reaction mixture was diluted with ethyl acetate, water was added thereto, and the mixture was extracted with ethyl acetate. The organic layer was washed with water and saturated brine, dried over anhydrous magnesium sulfate, and concentrated under reduced pressure. The resulting residue was purified by silica gel chromatography (hexane-ethyl acetate and chloroform-methanol) to yield Compound 63 (39.7 mg, yield 78%).

$^1$H-NMR (CDCl$_3$) δ: 0.90 (s, 9H), 1.30 (t, J=7.2 Hz, 3H), 2.29 (s, 3H), 2.30 (s, 3H), 3.66-3.72 (m, 4H), 3.79-3.87 (m, 2H), 3.89-3.97 (m, 1H), 4.10-4.18 (m, 3H), 4.25 (q, J=7.2 Hz, 2H), 4.46 (s, 1H), 5.31 (s, 1H), 5.81 (s, 1H), 7.38-7.42 (m, 3H), 7.49-7.53 (m, 1H).

The Third Step

Compound 64 (37.0 mg) was obtained by reacting Compound 63 (39.0 mg, 0.070 mmol) in the same manner as the seventh step in Example 10.

$^1$H-NMR (CDCl$_3$) δ: 0.91 (s, 9H), 2.30 (s, 6H), 3.67-3.76 (m, 4H), 3.81-3.88 (m, 2H), 3.90-3.97 (m, 1H), 4.10-4.16 (m, 1H), 4.21 (d, J=17.0 Hz, 1H), 4.27 (d, J=17.0 Hz, 1H), 5.32 (s, 1H), 5.81 (s, 1H), 7.37-7.43 (m, 3H), 7.48-7.53 (m, 1H).

The Fourth Step

To a solution of Compound 64 (37.0 mg, 0.070 mmol) in DMF (1 mL) were added O-(7-aza-benzotriazol-1-yl)-N,N,N'-N'-tetramethyluronium hexafluorophosphate (39.9 mg, 0.105 mmol) and N,N-diisopropylethylamine (0.018 mL, 0.105 mmol), and the mixture was stirred at room temperature for 1 hour. The reaction mixture was extracted with ethyl acetate after addition of water. The organic layer was washed with water and saturated brine, dried over anhydrous magnesium sulfate, and concentrated under reduced pressure. The resulting residue was purified by silica gel chromatography (hexane-ethyl acetate) to yield Compound 65 (34.6 mg, yield 97%).

$^1$H-NMR (CDCl$_3$) δ: 0.94 (s, 9H), 2.27 (s, 3H), 2.31 (s, 3H), 3.74 (s, 3H), 3.97-4.03 (m, 1H), 4.09-4.18 (m, 2H), 4.32-4.46 (m, 4H), 5.29 (s, 1H), 5.81 (s, 1H), 7.33-7.37 (m, 1H), 7.40-7.45 (m, 2H), 7.49-7.53 (m, 1H).

The Fifth Step

Compound I-124 (11.3 mg, 2 steps yield 35%) was obtained by reacting Compound 65 (34.0 mg, 0.067 mmol) in the same manner as the sixth step in Example 2 and the fourth step in Example 1.

$^1$H-NMR (CDCl$_3$) δ: 0.91 (s, 9H), 2.36 (s, 3H), 2.38 (s, 3H), 2.94-2.99 (m, 2H), 3.24-3.30 (m, 1H), 3.86 (dd, J=11.9, 3.5 Hz, 1H), 3.90-3.97 (m, 2H), 4.02 (d, J=11.9 Hz, 1H), 4.21 (dd, J=11.9, 3.5 Hz, 1H), 4.42 (dd, J=11.9, 11.9 Hz, 1H), 5.41 (s, 1H), 5.89 (s, 1H), 7.41-7.46 (m, 3H), 7.68 (s, 1H), 9.88 (s, 1H).

The First Step

To a solution of Compound 61 (100 mg, 0.157 mmol) in DMF (2 mL) was added 60% sodium hydride (12.6 mg, 0.315 mmol) under ice-cooling, and the mixture was stirred for 10 minutes at 0° C. Bromo ethyl acetate (0.035 mL, 0.315 mmol) was added to the reaction mixture, and the mixture was stirred for 16 hours at room temperature. The reaction mixture was extracted with ethyl acetate after addition of a saturated aqueous ammonium chloride solu-

Example 14

[Chemical formula 139]

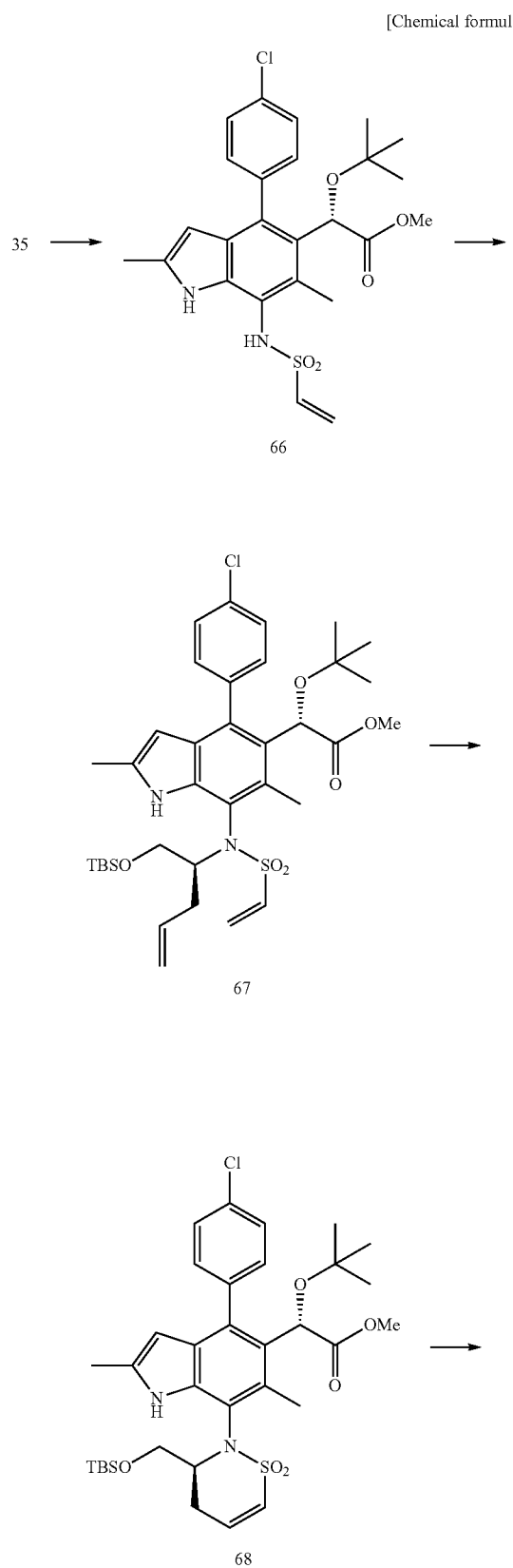

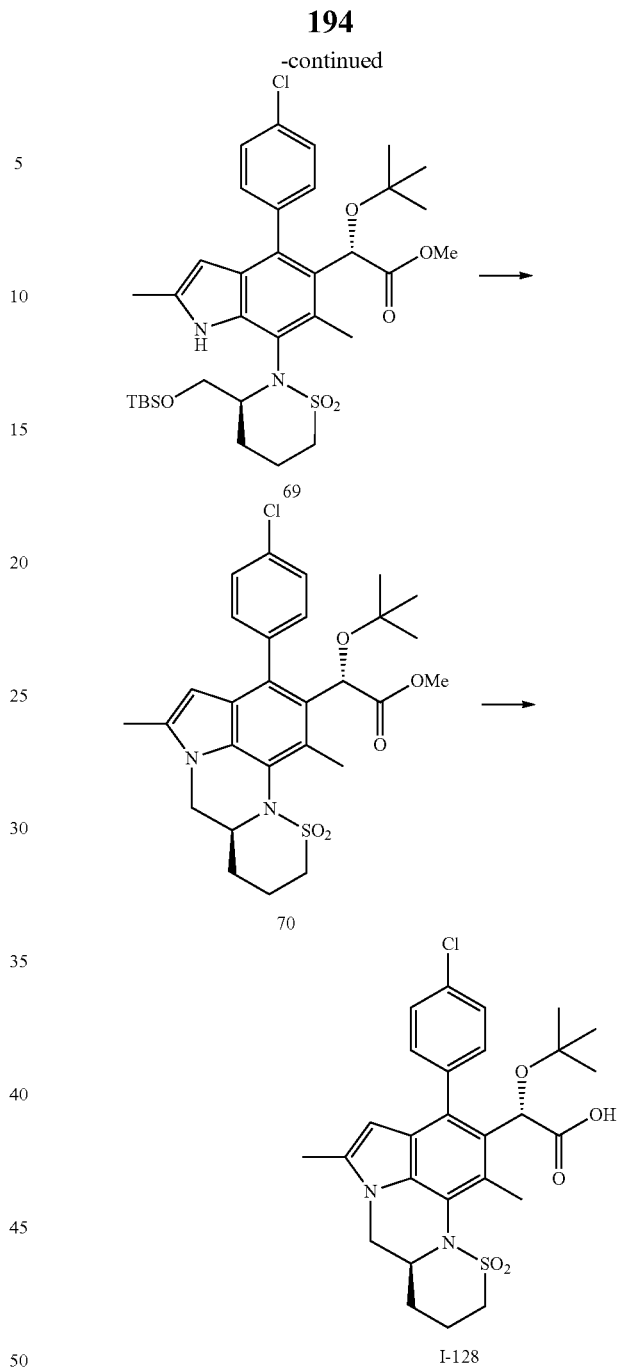

The First Step

To a solution of Compound 35 (500 mg, 1.21 mmol) and pyridine (0.292 mL, 3.62 mmol) in dichloromethane (5 mL) was added dropwise 2-chloroethane sulfonyl chloride (0.189 mL, 1.81 mmol) under ice-cooling, and the mixture was stirred for 2 hours at room temperature. The reaction mixture was extracted with ethyl acetate after addition of saturated aqueous sodium hydrogencarbonate solution. The organic layer was dried over anhydrous sodium sulfate, and concentrated under reduced pressure. The resulting residue was purified by silica gel chromatography (hexane-ethyl acetate) to yield compound 66 (342 mg, yield 56%).

$^1$H-NMR (CDCl$_3$) δ: 0.90 (s, 9H), 2.39 (s, 6H), 3.70 (s, 3H), 5.25 (s, 1H), 5.78 (s, 1H), 5.94 (d, J=9.9 Hz, 1H), 6.15-6.26 (m, 2H), 6.64 (dd, J=16.4, 9.9 Hz, 1H), 7.33-7.40 (m, 1H), 7.42-7.49 (m, 3H), 8.90 (s, 1H).

The Second Step

To a solution of Compound 66 (242 mg, 0.479 mmol), (R)-1-[(tert-butyldimethylsilyl) oxy)]penta-4-en-2-ol (311 mg, 1.44 mmol) and triphenylphosphine (377 mg, 1.44 mmol) in THF (2.42 mL) was added azodicarboxylic acid bis (2-methoxyethyl) (337 mg, 1.44 mmol) under ice-cooling, and the mixture was stirred for 1 hour at room temperature. The reaction mixture was extracted with ethyl acetate after addition of water. The organic layer was washed with water, dried over anhydrous sodium sulfate, and concentrated under reduced pressure. The resulting residue was purified by silica gel chromatography (hexane-ethyl acetate) to yield Compound 67 (179 mg, yield 53%).

MS(ESI) m/z:703 [M+H]$^+$

The Third Step

To a solution of Compound 67 (177 mg, 0.252 mmol) in dichloromethane (8.85 mL) was added Grubbs second generation catalyst (21.3 mg, 0.025 mmol), and the mixture was stirred under nitrogen atmosphere at room temperature for 2 hours. The reaction mixture was concentrated under reduced pressure, and the resulting residue was purified by silica gel chromatography (hexane-ethyl acetate) to yield compound 68 (142 mg, yield 83%).

MS(ESI) m/z:675 [M+H]$^+$

The Fourth Step

To a solution of Compound 68 (120 mg, 0.178 mmol) in methanol (1.8 mL) was added sodium borohydride (269 mg, 7.11 mmol) under ice-cooling, and the mixture was stirred at room temperature for 40 minutes. The reaction mixture was extracted with ethyl acetate after addition of saturated aqueous sodium hydrogencarbonate solution. The organic layer was washed with saturated brine, dried over anhydrous sodium sulfate, and concentrated under reduced pressure. The resulting residue was purified by silica gel chromatography (hexane-ethyl acetate) to yield Compound 69 (107 mg, yield 76%).

MS(ESI) m/z:677 [M+H]$^+$

The Fifth Step

Compound 70 (9.0 mg, 2 steps yield 10%) was obtained by reacting Compound 69 (105 mg, 0.155 mmol) in the same manner as the fourth step in Example 6 and the sixth step in Example 10.

MS(ESI) m/z:545 [M+H]$^+$

The Sixth Step

Compound I-128 (7.7 mg, yield 88%) was obtained by reacting Compound 70 (9.0 mg, 0.017 mmol) in the same manner as the ninth step in Example 2.

MS(ESI) m/z:531 [M+H]$^+$

Example 15

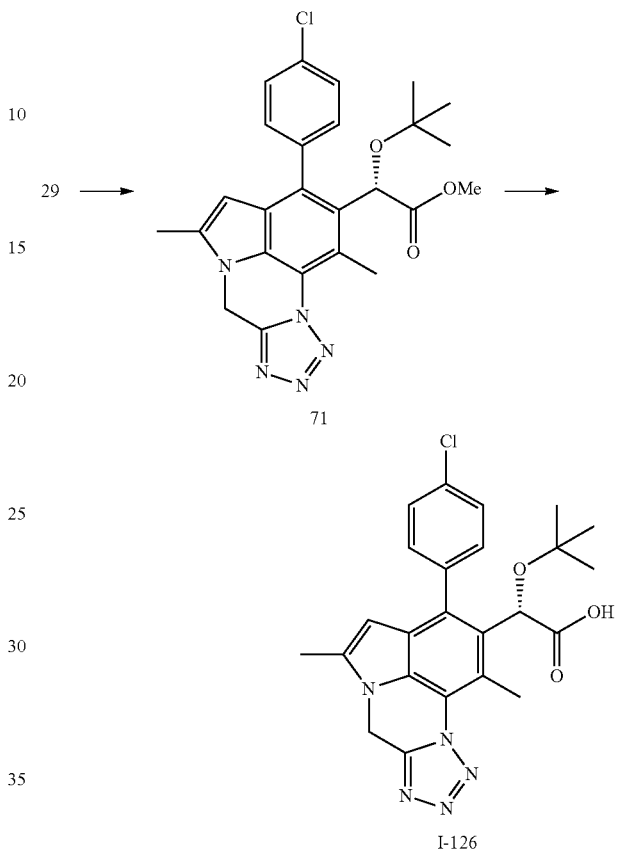

[Chemical formula 140]

The First Step

To Compound 29 (120 mg, 0.264 mmol) were added diphenyl (2-pyridyl) phosphine (259 mg, 1.06 mmol) and diisopropyl azodicarboxylate (214 mg, 1.06 mmol), and the mixture was stirred for 3 hours at 45° C. The reaction mixture was diluted with ethyl acetate, aqueous sodium bicarbonate solution was added thereto, and extracted with ethyl acetate. The organic layer was dried over anhydrous sodium sulfate, and concentrated under reduced pressure. The resulting residue was purified by silica gel chromatography (hexane-ethyl acetate) to yield compound 71 (64.0 mg, yield 51%).

$^1$H-NMR (CDCl$_3$) δ: 0.94 (s, 9H), 2.42 (s, 3H), 2.97 (s, 3H), 3.77 (s, 3H), 5.35 (s, 1H), 5.67-5.75 (m, 2H), 6.00 (s, 1H), 7.35-7.40 (m, 1H), 7.45-7.52 (m, 3H).

The Second Step

To a solution of Compound 71 (64.0 mg, 0.133 mmol) in THF (2 mL) was added 2 mol/L aqueous sodium hydroxide solution (1.00 mL, 2.00 mmol), and the mixture was heated under reflux and stirred for 2 hours. The reaction mixture was extracted with ethyl acetate after addition of water and 2 mol/L aqueous hydrochloric acid solution. The organic layer was dried over anhydrous sodium sulfate, and concentrated under reduced pressure. The resulting residue was purified by silica gel chromatography (hexane-ethyl acetate) to yield Compound I-126 (50.0 mg, yield 81%).

$^1$H-NMR (CDCl$_3$) δ: 0.97 (s, 9H), 2.43 (s, 3H), 2.97 (s, 3H), 5.47 (s, 1H), 5.70 (d, J=16.2 Hz, 1H), 5.77 (d, J=16.2 Hz, 1H), 6.05 (s, 1H), 7.37-7.43 (m, 1H), 7.45-7.51 (m, 2H), 7.65-7.71 (m, 1H).
Example 16
[Chemical formula 141]
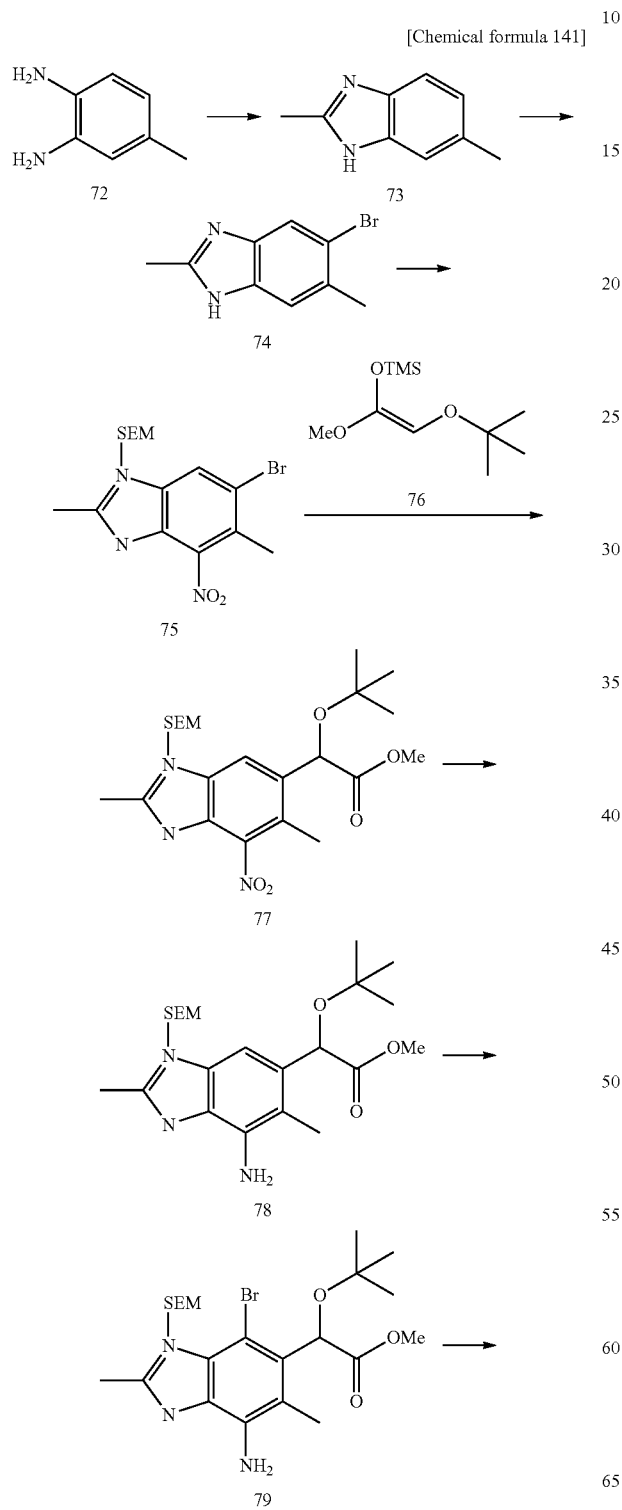
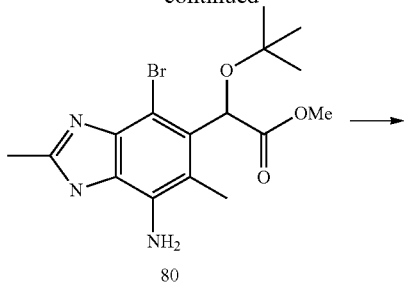
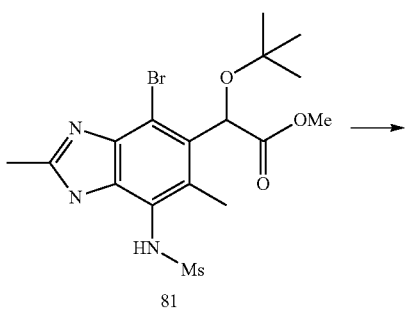

-continued

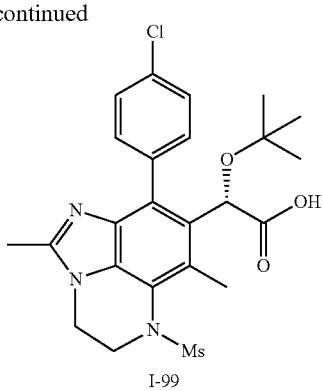

I-99

The First Step

To a suspension of Compound 72 (25.0 g, 203 mmol) in water (250 mL) were added ammonium chloride (1.86 g, 34.7 mmol) and ethyl orthoformate (50.0 g, 328 mmol), and the mixture was heated under reflux and stirred for 10.5 hours. The reaction mixture was cooled to room temperature, and extracted with chloroform. The organic layer was dried over anhydrous sodium sulfate, and concentrated under reduced pressure. The resulting residue was solidified with ethyl acetate-diisopropyl ether to yield Compound 73 (19.5 g, yield 65%).

MS(ESI) m/z:146.9 [M+H]+

The Second Step

To a solution of Compound 73 (19.1 g, 130 mmol) in chloroform (200 mL) was added N-bromosuccinimide (23.2 g, 130 mmol) under ice-cooling, and the mixture was stirred for 25 minutes at room temperature. The reaction mixture was concentrated under reduced pressure, the resulting solid was collected by filtration and washed with water to yield Compound 74 (25.4 g, yield 87%).

$^1$H-NMR (DMSO-D$_6$) δ: 2.41 (s, 3H), 2.46 (s, 3H), 7.43 (s, 1H), 7.66 (s, 1H), 11.70-12.71 (m, 1H).

The Third Step

To Compound 74 (1.00 g, 4.44 mmol) was added concentrated sulfuric acid (5.00 mL) under ice cooling, concentrated nitric acid (1.00 mL) was added dropwise thereto, and the mixture was stirred at room temperature for 35 minutes. Water was added to the reaction mixture, and the resulting solid was collected by filtration and washed with water. The resulting solid (1.04 g, 3.85 mmol) was suspended in DMF (20 mL), and 60% sodium hydride (231 mg, 5.78 mmol) and 2-(chloromethoxy) ethyl trimethylsilane (1.02 mL, 5.78 mmol) was added thereto under ice-cooling, and the mixture was stirred for 2 hours at room temperature. The reaction mixture was extracted with ethyl acetate after addition of aqueous hydrochloric acid solution. The organic layer was washed with water, dried over anhydrous sodium sulfate, and concentrated under reduced pressure. The resulting residue was purified by silica gel chromatography (hexane-ethyl acetate) to yield Compound 75 (206 mg, 2 steps yield 12%).

$^1$H-NMR (CDCl$_3$) δ: 0.00 (s, 9H), 0.94 (t, J=8.1 Hz, 2H), 2.54 (s, 3H), 2.69 (s, 3H), 3.54 (t, J=8.1 Hz, 2H), 5.47 (s, 2H), 7.81 (s, 1H).

The Fourth Step

To a solution of Compound 75 (200 mg, 0.500 mmol) in DMF (2 mL) were added zinc fluoride (155 mg, 1.50 mmol), tri-tert-butylphosphine (0.024 mL, 0.100 mmol), bis (di benzylidene acetone) palladium (0) (28.7 mg, 0.050 mmol) and Compound 76 (327 mg, 1.50 mmol) and the mixture was stirred under nitrogen atmosphere for 1.5 hours at 100° C. The reaction mixture was extracted with ethyl acetate after addition of water. The organic layer was washed with water, dried over anhydrous sodium sulfate, and concentrated under reduced pressure. The resulting residue was purified by silica gel chromatography (hexane-ethyl acetate) to yield Compound 77 (205 mg, yield 88%).

$^1$H-NMR (CDCl$_3$) δ: −0.04 (s, 9H), 0.89 (t, J=8.1 Hz, 2H), 1.24 (s, 9H), 2.51 (s, 3H), 2.68 (s, 3H), 3.52 (t, J=8.1 Hz, 2H), 3.67 (s, 3H), 5.36 (s, 1H), 5.50 (s, 2H), 7.86 (s, 1H).

The Fifth Step

Compound 78 (11.2 g, yield 92%) was obtained by reacting Compound 77 (13.0 g, 27.9 mmol) in the same manner as the third step in Example 1.

$^1$H-NMR (CDCl$_3$) δ: −0.06 (s, 9H), 0.87 (t, J=8.1 Hz, 2H), 1.24 (s, 9H), 2.30 (s, 3H), 2.61 (s, 3H), 3.51 (t, J=8.1 Hz, 2H), 3.64 (s, 3H), 4.27 (s, 2H), 5.35 (s, 1H), 5.42 (s, 2H), 7.09 (s, 1H).

The Sixth Step

To a solution of Compound 78 (10.9 g, 25.0 mmol) in dichloromethane (110 mL) was added N-bromosuccinimide (4.90 g, 27.5 mmol), and the mixture was stirred under ice cooling for 20 minutes. The reaction mixture was extracted with chloroform after addition of saturated aqueous sodium hydrogen carbonate solution. The organic layer was dried over anhydrous sodium sulfate, and concentrated under reduced pressure. The resulting residue was purified by silica gel chromatography (hexane-ethyl acetate) to yield compound 79 (6.10 g, yield 47%).

$^1$H-NMR (CDCl$_3$) δ: −0.04 (s, 9H), 0.91 (t, J=8.1 Hz, 2H), 1.22 (s, 9H), 2.29 (s, 3H), 2.63 (s, 3H), 3.58-3.68 (m, 5H), 4.28 (s, 2H), 5.82 (d, J=10.9 Hz, 1H), 5.94 (d, J=10.9 Hz, 1H), 6.01 (s, 1H).

The Seventh Step

Compound 80 (73.0 mg, yield 75%) was obtained by reacting Compound 79 (130 mg, 0.253 mmol) in the same manner as the fourth step in Example 6.

$^1$H-NMR (CDCl$_3$) δ: 1.22 (s, 9H), 2.30 (s, 3H), 2.60 (s, 3H), 3.66 (s, 3H), 4.25 (s, 2H) 5.77 (s, 1H), 8.82 (s, 1H).

The Eighth Step

To a solution of Compound 80 (300 mg, 0.781 mmol) in dichloromethane (3 mL) were added pyridine (0.252 mL, 3.12 mmol) and methanesulfonyl chloride (0.122 mL, 1.56 mmol), and the mixture was stirred at room temperature 3.5 hours. The reaction mixture was extracted with chloroform after addition of saturated aqueous sodium hydrogen carbonate solution. The organic layer was dried over anhydrous sodium sulfate, and concentrated under reduced pressure. The resulting residue was purified by silica gel chromatography (chloroform-methanol) to yield Compound 81 (300 mg, yield 83%).

MS(ESI) m/z:461.9, 463.8 [M+H]+

The Ninth Step

Compound 82 (230 mg, 2 steps yield 68%) was obtained by reacting Compound 81 (300 mg, 0.649 mmol) in the same manner as the second step in Example 6 and the first step in Example 4.

MS(ESI) m/z:520.0 [M+H]+

The Tenth Step

A carboxylic acid (140 mg, yield 63%) was obtained by reacting Compound 82 (230 mg, 0.442 mmol) in the same manner as the fourth step in Example 1. Compound I-98 and I-99 were obtained by further optical resolution.

Compound I-98: MS(ESI) m/z:506 [M+H]+
Compound I-99: MS(ESI) m/z:506 [M+H]+

Example 17

[Chemical formula 142]

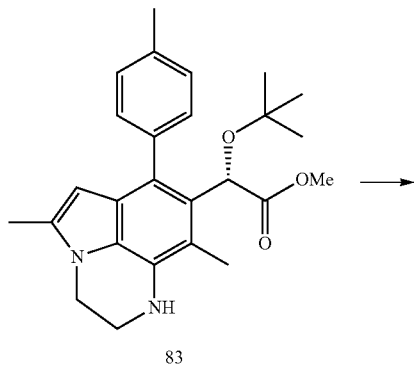
83

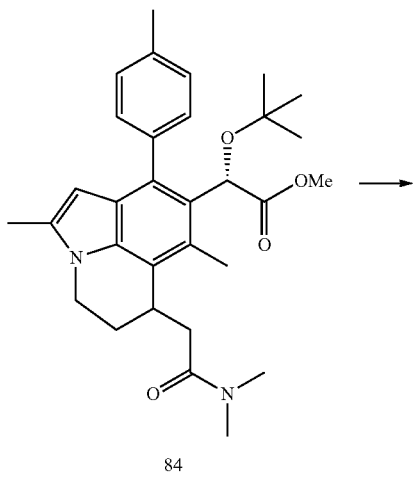
84

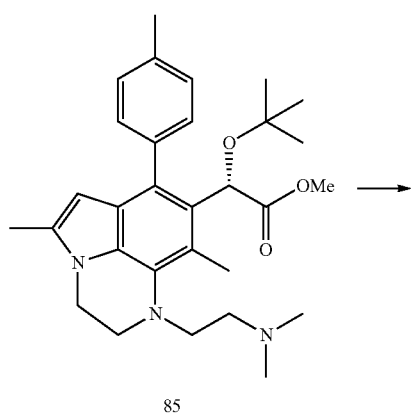
85

-continued

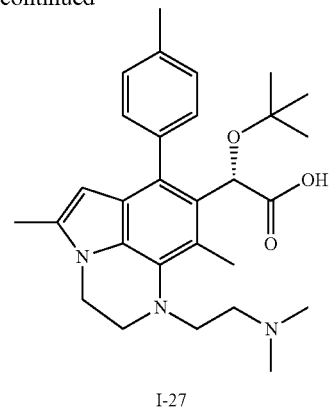
I-27

The First Step the Synthesis of Compound 84

To a solution of Compound 83 (4.24 g, 10.1 mmol) in dimethylformamide (12.7 mL) were added sodium iodide (2.27 g, 15.1 mmol), potassium carbonate (2.09 g, 15.1 mmol), 2-chloro-N,N-dimethylacetamide (1.09 mL, 10.6 mmol), and the mixture was stirred for 4 hours at 40° C. The reaction mixture was extracted with ethyl acetate after addition of water. The organic layer was washed with water and saturated brine, dried over anhydrous magnesium sulfate, and concentrated under reduced pressure. The resulting residue was purified by DIOL column chromatography (hexane-ethyl acetate (3% triethylamine)) to yield Compound 84 (4.99 g, 97%) as a yellow foam compound.

LC/MS (ESI): m/z=506.49 [M+H]+, LC/MS measurement conditions: (1)

The Second Step the Synthesis of Compound 85

To a solution of Compound 84 (4.69 g, 9.28 mmol) in tetrahydrofuran (9.4 mL) was added 0.92 mol/L borane tetrahydrofuran solution (30.2 mL, 27.8 mmol) under ice-cooling, and the mixture was stirred at 40° C. for 4 hours. The reaction mixture was extracted with ethyl acetate after addition of 10 wt % aqueous citric acid solution. The organic layer was washed with water and saturated brine, dried over anhydrous magnesium sulfate, and concentrated under reduced pressure. To the obtained residue was added methanol (50 mL), the mixture was stirred at 90° C. for 5 hours, and concentrated under reduced pressure. To the resulting residue was added ethyl acetate, and the organic layer was washed with water and saturated brine, dried over anhydrous magnesium sulfate, and concentrated under reduced pressure. The resulting residue was purified by DIOL column chromatography (hexane-ethyl acetate (3% triethylamine)) to yield Compound 85 (3.0 g, yield 65%) as a white foam compound.

LC/MS (ESI): m/z=492.38 [M+H]+, LC/MS measurement conditions: (1)

The Third Step the Synthesis of Compound I-27

To a mixed solution of Compound 85 (600 mg, 1.29 mmol) in methanol (4 mL) and THF (4 mL) was added 2 mol/L aqueous sodium hydroxide solution (2.23 mL, 4.45 mmol), and the mixture was heated under reflux and stirred for 5.5 hours. The reaction mixture was adjusted to pH7 with a 1 mol/L hydrochloric acid. After the addition of HP, the organic solvent was removed under reduced pressure. The obtained residue was purified by ODS column chromatography (water-acetonitrile) to yield Compound I-27 (195 mg, yield 46%) as a white solid.

LC/MS (ESI): m/z=478.38 [M+H]+, RT=1.70 min, LC/MS measurement conditions: (1)

¹H-NMR (CDCl₃) δ: 7.58 (1H, d, J=8.1 Hz), 7.39 (1H, d, J=7.1 Hz), 7.25-7.22 (2H, m), 5.91 (1H, s), 5.58 (1H, s), 3.94-3.89 (2H, m), 3.44-3.43 (2H, m), 3.03-2.94 (2H, m), 2.74-2.69 (2H, m), 2.42 (6H, s), 2.34-2.31 (9H, m), 0.90 (9H, s).

Example 18

[Chemical formula 143]

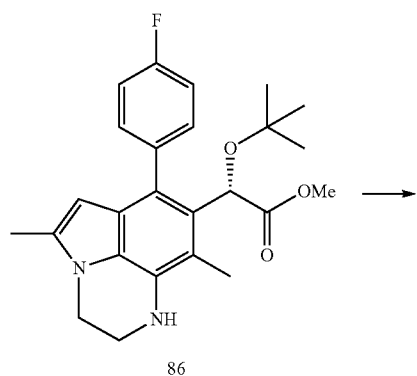

86

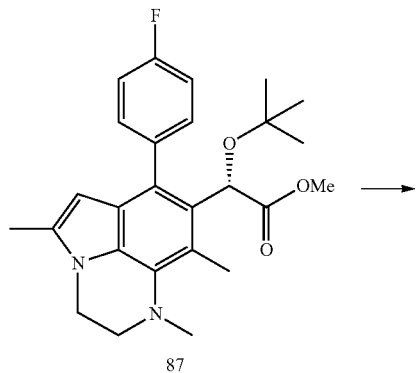

87

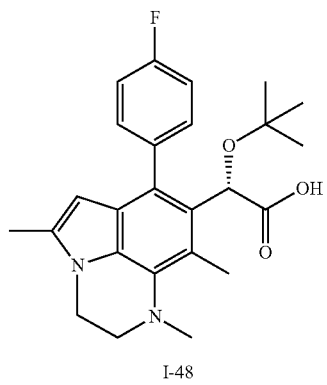

I-48

The First Step the Synthesis of Compound 87

To a solution of Compound 86 (460 mg, 1.084 mmol) in DMF (4.6 mL) were added potassium carbonate (300 mg, 2.167 mmol) and methyl iodide (60 µL, 2.167 mmol), and the mixture was stirred at 60° C. for 20 minutes. Methyl iodide (60 µL, 2.167 mmol) was added thereto, and the mixture was stirred for 20 minutes at 60° C. The reaction mixture was extracted with ethyl acetate after addition of water. The organic layer was washed with water and saturated brine successively, and dried over anhydrous magnesium sulfate. The solvent was concentrated under reduced pressure, the resulting residue was purified by silica gel column chromatography (hexane-ethyl acetate) to yield Compound 87 (433 mg, yield 91%).

LC/MS (ESI): m/z=439.3 [M+H]+, LC/MS measurement conditions: (1)

The Second Step the Synthesis of Compound I-48

To a mixed solution of Compounds 87 (430 mg, 0.961 mmol) in ethanol (8.0 mL) and THF (4 mL) was added 2 mol/L aqueous sodium hydroxide solution (4.9 mL), and the mixture was stirred at room temperature for 1 hour, and then stirred for 3 hours at 60° C. The mixture was cooled to room temperature, and extracted with ethyl acetate after addition of a 2 mol/L hydrochloric acid. The organic layer was washed with saturated brine, and dried over anhydrous magnesium sulfate. The solvent was concentrated under reduced pressure. The resulting residue was purified by silica gel column chromatography (chloroform) and purified by crystallization with methanol-IPE to yield compound I-48 (115 mg, yield 27%).

LC/MS (ESI): m/z=425.3[M+H]+, RT=2.20 min, LC/MS measurement conditions: (1)

¹H NMR (CDCl₃) δ: 0.92 (s, 9H), 2.36 (s, 3H), 2.43 (s, 3H), 2.78 (s, 3H), 3.41-3.49 (m, 2H), 3.95-4.00 (m, 2H), 5.49 (s, 1H), 5.89 (s, 1H), 7.15 (m, 3H), 7.47 (brs, 1H), 7.70 (brs, 1H)

Example 19

[Chemical formula 144]

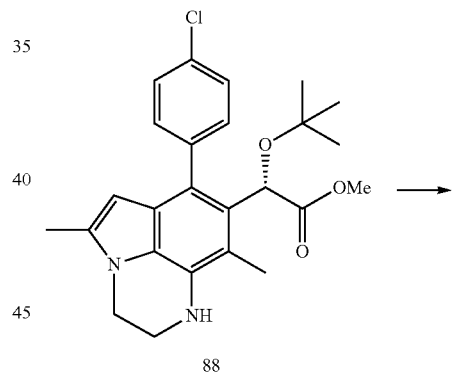

88

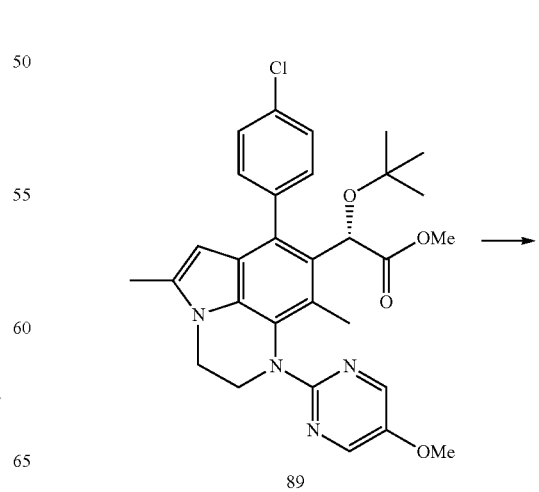

89

Example 20

[Chemical formula 145]

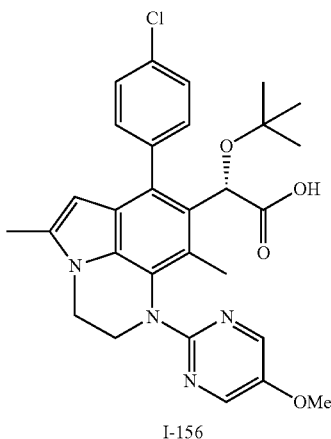

I-156

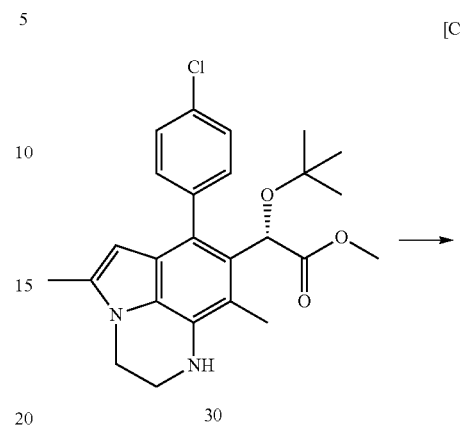

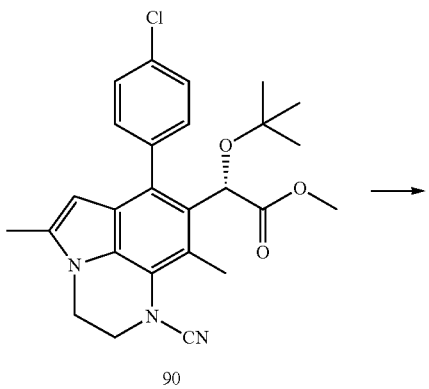

90

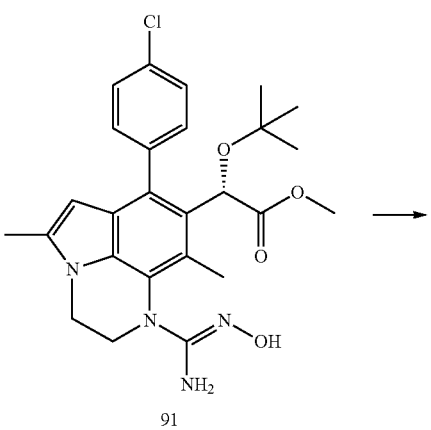

91

The First Step the Synthesis of Compound 89

To a solution of Compound 88 (1 g, 2.27 mmol) in toluene (10 mL) were added sodium tert-butoxide (327 mg, 3.4 mmol), 2-bromo-5-methoxy pyrimidine (643 mg, 3.4 mmol), 4,5-bis (diphenylphosphino)-9,9-methyl xanthene (394 mg, 0.68 mmol) and $Pd_2(dba)_3$ (623 mg, 0.68 mmol), and the mixture was stirred under nitrogen atmosphere at 60° C. for 1.5 hours. Sodium tert-butoxide (327 mg, 3.4 mmol) and 2-bromo-5-methoxy-pyrimidine (643 mg, 3.4 mmol) were added thereto, and the mixture was stirred under nitrogen atmosphere for 1.5 hours at 60° C. 2 mmol/L hydrochloric acid was added to the reaction mixture, filtered through Celite, the filtrate was extracted with chloroform. The organic layer was washed with water, dried over anhydrous sodium sulfate, and concentrated under reduced pressure by an evaporator. The resulting residue was purified by silica gel column chromatography (hexane-ethyl acetate) to yield Compound 89 (809 mg, 65%) as a yellow foam compound.

LC/MS (ESI): m/z=549.15 [M+H]+, LC/MS measurement conditions: (1)

The Second Step the Synthesis of Compound I-156

To a mixed solution of Compound 89 (795 mg, 1.45 mmol) in ethanol (4 mL) and THF (4 mL) was added 2 mol/L aqueous sodium hydroxide solution (3.62 mL, 7.24 mmol), and the mixture was heating under reflux and stirred for 2.5 hours. The reaction mixture was extracted with chloroform after addition of 2 mol/L hydrochloric acid. The organic layer was washed with water, dried over anhydrous sodium sulfate, and concentrated under reduced pressure by an evaporator. The resulting residue was purified by silica gel column chromatography (hexane-ethyl acetate) to yield compound I-156 (68.2 mg, yield 89%) as a white solid.

LC/MS (ESI): m/z=535.15 [M+H]+, RT=3.27 min, LC/MS measurement conditions: (1)

1H-NMR ($CDCl_3$) δ:0.98 (s, 9H), 2.20 (s, 3H), 2.30 (s, 3H), 3.83 (s, 3H), 3.94-4.07 (m, 3H), 4.88 (brs, 1H), 5.49 (s, 1H), 5.87 (s, 1H), 7.41-7.47 (m, 3H), 7.74 (brs, 1H), 8.15 (s, 2H)

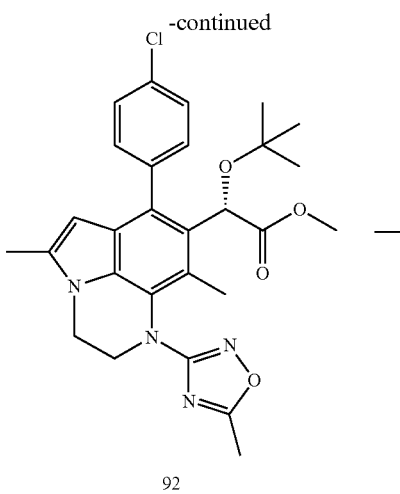

92

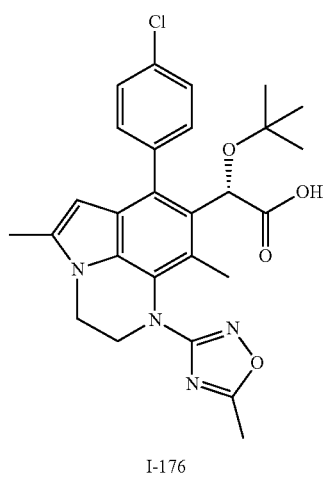 [SMILES: Cc1nc(N2CCn3c(C)cc4c(-c5ccc(Cl)cc5)c([C@H](OC(C)(C)C)C(=O)O)c(C)c2c43)no1]

I-176

The First Step the Synthesis of Compound 90

To a solution of Compound 30 (400 mg, 0.907 mmol) in DMF (8.00 mL) were added cyanogen bromide (152 mg, 1.36 mmol) and potassium carbonate (188 mg, 1.36 mmol), and the mixture was stirred at room temperature for 16 hours. Cyanogen bromide (48.0 mg, 0.454 mmol) and potassium carbonate (62.7 mg, 0.454 mmol) was added thereto, and the mixture was stirred at room temperature for 3 hours. The reaction mixture was extracted with ethyl acetate after addition of ice water. The organic layer was washed with saturated brine, and dried with anhydrous sodium sulfate. The solvent was concentrated under reduced pressure, and the resulting residue was purified by silica gel column chromatography (hexane-ethyl acetate) to yield compound 90 (346 mg, yield 82%).

LC/MS (ESI): m/z=466.24 [M+H]+, LC/MS measurement conditions: (1)

The Second Step the Synthesis of Compound 91

To a solution of Compound 90 (344 mg, 0.738 mmol) in ethanol (6.88 mL) were added hydroxylamine hydrochloride (61.6 mg, 0.886 mmol) and triethylamine (90.0 mg, 0.886 mmol), and the mixture was stirred at 60° C. for 10 minutes. THF (2.00 mL) was added thereto, and the mixture was stirred at 60° C. for 40 minutes. The reaction mixture was extracted with ethyl acetate after addition of ice water. The organic layer was washed with saturated brine, and dried with anhydrous sodium sulfate. The solvent was concentrated under reduced pressure, and the resulting residue was purified by silica gel column chromatography (hexane-ethyl acetate) to yield compound 91 (243 mg, yield 66%).

LC/MS (ESI): m/z=499.08 [M+H]+, LC/MS measurement conditions: (1)

The Third Step the Synthesis of Compound 92

To a solution of Compounds 91 (80.0 mg, 0.160 mmol) in diglyme (1.60 mL) were added pyridine (19.0 mg, 0.240 mmol) and acetyl chloride (15.1 mg, 0.192 mmol) under ice-cooling, and the mixture was stirred for 50 minutes at room temperature and stirred at 100° C. for 90 minutes. After cooling, the reaction mixture was extracted with ethyl acetate after addition of ice water and 2 mol/L hydrochloric acid. The organic layer was washed with saturated aqueous sodium hydrogen carbonate solution and saturated brine successively, and dried over anhydrous sodium sulfate. The solvent was concentrated under reduced pressure, and the resulting residue was purified by silica gel column chromatography (hexane-ethyl acetate) to yield Compound 92 (76 mg, yield 91%).

LC/MS (ESI): m/z=523.37 [M+H]+, LC/MS measurement conditions: (1)

The Fourth Step the Synthesis of Compound I-176

To a solution of Compound 92 (74.0 mg, 0.141 mmol) in ethanol (1.42 mL) was added 2 mol/L aqueous sodium hydroxide solution (0.354 mL), and the mixture was heated under reflux and stirred for 1 hour. After cooling, the reaction mixture was extracted with ethyl acetate after addition of ice water and 2 mol/L hydrochloric acid. The organic layer was washed with saturated brine, and dried over anhydrous sodium sulfate. The solvent was concentrated under reduced pressure, and the resulting residue was purified by silica gel column chromatography (hexane-ethyl acetate), and purified by crystallization with hexane to yield Compound I-176 (39.0 mg, yield 54%).

LC/MS (ESI): m/z=509.4 [M+H]+, RT=2.54 min, LC/MS measurement conditions: (1)

$^1$H NMR (DMSO-d$_6$) δ: 0.82 (s, 9H), 2.44 (s, 3H), 2.31 (s, 3H), 2.50 (s, 3H), 4.00-4.25 (m, 4H), 5.20 (s, 1H), 5.77 (s, 1H), 7.42 (m, 1H), 7.55-7.70 (m, 3H), 12.51 (brs, 1H).

Example 21

[Chemical formula 146]

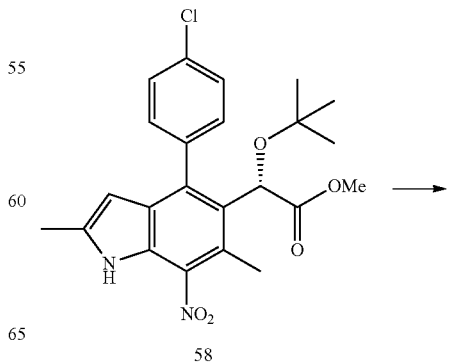

58

-continued
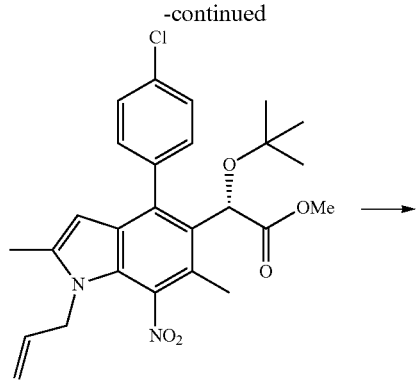
93
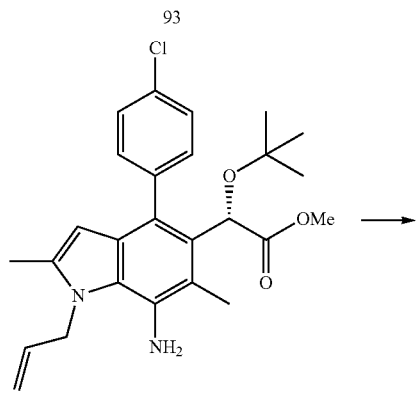
94
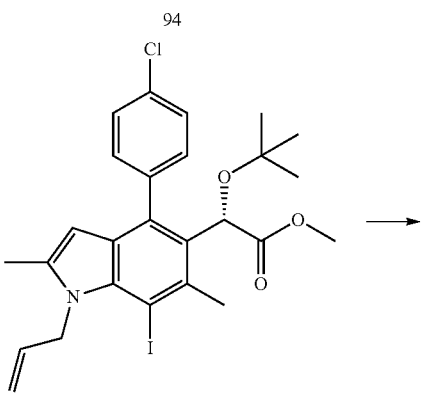
95
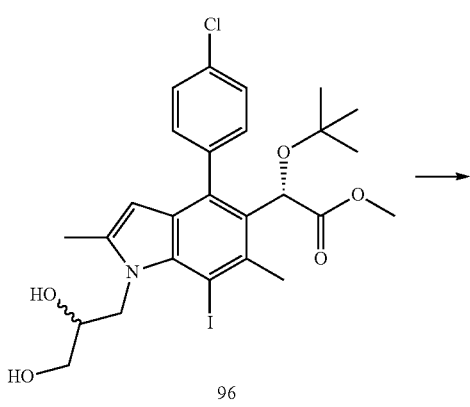
96
-continued
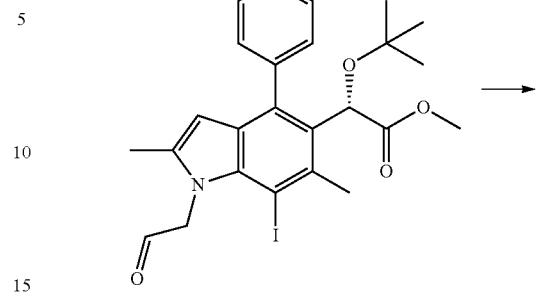
97
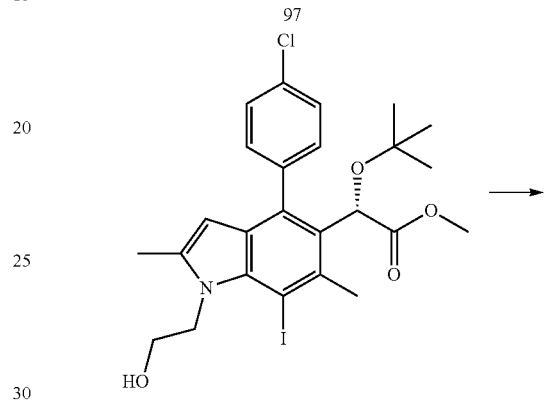
98
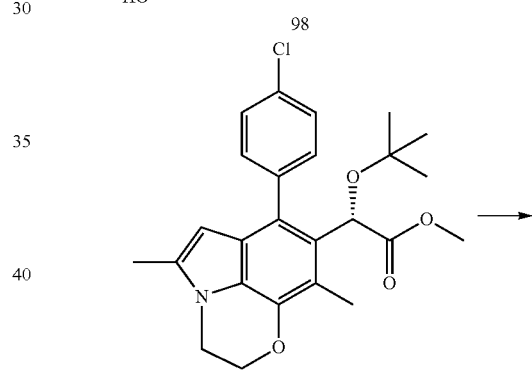
99
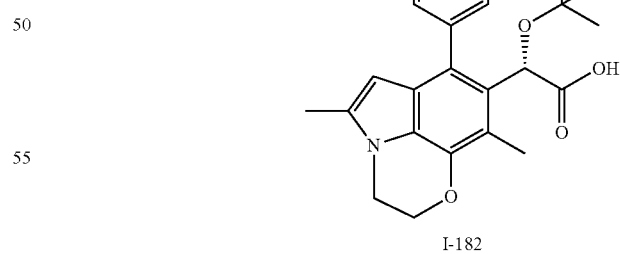
I-182
The First Step the Synthesis of Compound 93
To a solution of Compounds 58 (2.20 g, 4.90 mmol) in DMF (15.4 mL) were added allyl bromide (889 mg, 7.35 mmol) and sodium hydride (294 mg, 7.35 mmol) under ice-cooling, and the mixture was stirred for 1 hour. The reaction mixture was extracted with ethyl acetate after addition of a saturated aqueous ammonium chloride solution. The organic layer was washed with saturated aqueous ammonium chloride solution, and dried over anhydrous sodium sulfate. The solvent was concentrated under reduced pressure, and the resulting residue was purified by silica gel column chromatography (hexane-ethyl acetate) to yield Compound 93 (1.31 g, yield 73%).

LC/MS (ESI): m/z=485.22 [M+H]+, LC/MS measurement conditions: (1)

The Second Step the Synthesis of Compound 94

To a mixed solution of Compounds 93 (1.00 g, 2.06 mmol) in ethanol (20.0 mL) and water (5.00 mL) was added sodium dithionite (4.22 g, 20.6 mmol), and the mixture was heated under reflux and stirred for 1 hour. After cooling, the reaction mixture was extracted with ethyl acetate after addition of water. The organic layer was washed with water, and dried over anhydrous sodium sulfate. The solvent was concentrated under reduced pressure, and the resulting residue was purified by silica gel column chromatography (hexane-ethyl acetate) to yield Compound 94 (553 mg, yield 59%).

LC/MS (ESI): m/z=455.41 [M+H]+, LC/MS measurement conditions: (1)

The Third Step the Synthesis of Compound 95

To a mixed solution of Compounds 94 (451 mg, 0.991 mmol) in acetonitrile (8.62 mL) and water (0.862 mL) were added potassium iodide (823 mg, 4.96 mmol) and nitrous acid tert-butyl (568 mg, 4.96 mmol), and the mixture was stirred at 50° C. 40 minutes. After cooling, the reaction mixture was extracted with ethyl acetate after addition of water. The organic layer was washed with aqueous sodium thiosulfate solution and water successively, and dried over anhydrous sodium sulfate. The solvent was concentrated under reduced pressure, the resulting residue was purified by silica gel column chromatography (hexane-ethyl acetate) to yield compound 95 (202 mg, yield 36%).

LC/MS (ESI): m/z=566.24 [M+H]+, LC/MS measurement conditions: (1)

The Fourth Step the Synthesis of Compound 96

To a mixed solution of Compounds 95 (64.8 mg, 0.115 mmol) in THF (1.94 mL) and water (1.94 mL) were added potassium osmium acid dihydrate (8.44 mg, 0.0230 mmol) and sodium periodate (73.5 mg, 0.344 mmol), and the mixture was stirred for 4 hours at room temperature. The reaction mixture was extracted with ethyl acetate after addition of water. The organic layer was washed with aqueous sodium thiosulfate solution, water and saturated brine successively, and dried over anhydrous sodium sulfate. The solvent was concentrated under reduced pressure, and the resulting residue was purified by silica gel column chromatography (hexane-ethyl acetate) to yield compound 96 (38.9 mg, yield 57%).

LC/MS (ESI): m/z=600.33 [M+H]+, LC/MS measurement conditions: (1)

The Fifth Step the Synthesis of Compound 97

To a mixed solution of Compound 96 (45.0 mg, 0.0750 mmol) in THF (0.900 mL) and water (0.302 mL) was added sodium periodate (48.1 mg, 0.225 mmol), and the mixture was stirred for one hour at room temperature. Sodium periodate (16.0 mg, 0.0750 mmol) was added thereto, and the mixture was stirred for one hour. The reaction mixture was extracted with ethyl acetate after addition of water. The organic layer was washed with aqueous sodium thiosulfate solution, water, and saturated brine successively, and dried over anhydrous sodium sulfate. The solvent was concentrated under reduced pressure to yield Compound 97 (43.9 mg, yield 103%) as a crude product.

The Sixth Step the Synthesis of Compound 98

To a solution of Compound 97 (43.9 mg, 0.0750 mmol) in methanol (0.852 mL) was added sodium borohydride (2.84 mg, 0.0750 mmol) under ice-cooling, and the mixture was stirred for 50 minutes. Saturated aqueous sodium hydrogen carbonate solution was added to the reaction mixture, and the mixture was stirred for 30 minutes at room temperature. The mixture was extracted with ethyl acetate after addition of water. The organic layer was washed with saturated brine, and dried with anhydrous sodium sulfate. The solvent was concentrated under reduced pressure, the resulting residue was purified by silica gel column chromatography (hexane-ethyl acetate) to yield Compound 98 (33.2 mg, yield 78%).

LC/MS (ESI): m/z=570.27 [M+H]+, LC/MS measurement conditions: (1)

The Seventh Step the Synthesis of Compound 99

To a solution of Compounds 98 (27.5 mg, 0.0483 mmol) in toluene (1.38 mL) were added copper iodide (4.60 mg, 0.0242 mmol), N,N-dimethyl glycine (4.98 mg, 0.0483 mmol), cesium carbonate (31.4 mg, 0.0964 mmol), and the mixture was stirred for 2 hours at 160° C. under microwave irradiation. The reaction mixture was extracted with ethyl acetate after addition of water. The organic layer was washed with saturated aqueous ammonium chloride solution, and dried over anhydrous sodium sulfate. The solvent was concentrated under reduced pressure, and the resulting residue was purified by silica gel column chromatography (hexane-ethyl acetate) to yield Compound 99 (18.3 mg, yield 73%).

LC/MS (ESI): m/z=442.32 [M+H]+, LC/MS measurement conditions: (1)

The Eighth Step the Synthesis of Compound I-182

To a mixed solution of Compounds 99 (17.0 mg, 0.0385 mmol) in ethanol (0.340 mL) and THF (0.340 mL) was added 2 mol/L aqueous sodium hydroxide solution (0.350 mL), and the mixture was heated under reflux and stirred for 3 hours. After cooling, the reaction mixture was extracted with chloroform after addition of 2 mol/L aqueous hydrochloric acid solution (0.345 mL), and dried with anhydrous sodium sulfate. The solvent was concentrated under reduced pressure, and the resulting residue was purified by silica gel column chromatography (hexane-ethyl acetate) to yield Compound I-182 (12.8 mg, yield 78%).

LC/MS (ESI): m/z=428.31 [M+H]+, RT=2.59 min, LC/MS measurement conditions: (1)

Example 22

[Chemical formula 147]

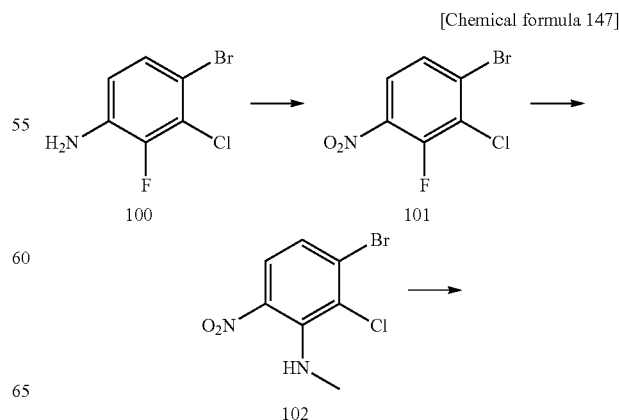

-continued
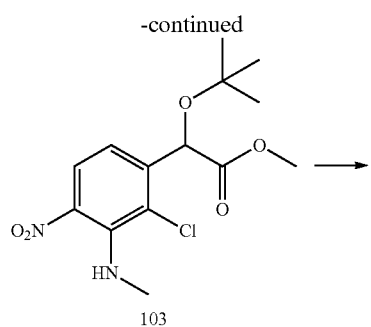
103
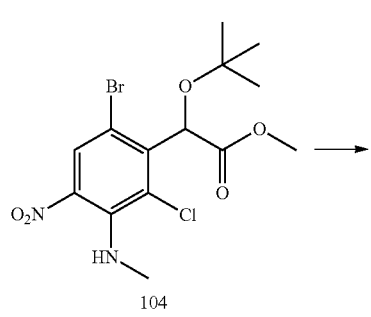
104
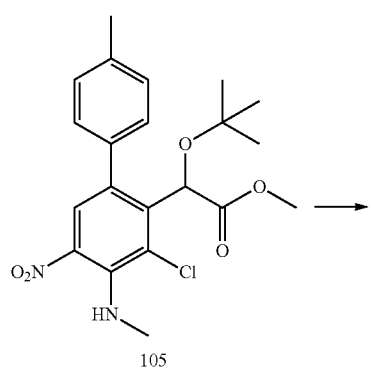
105
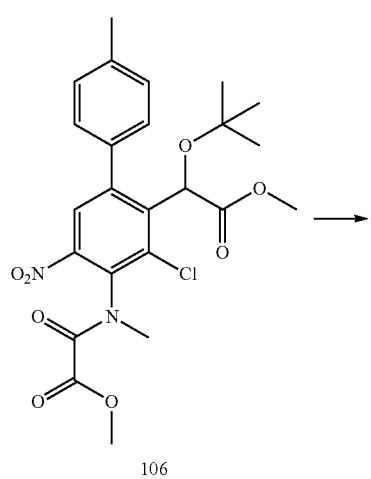
106
-continued
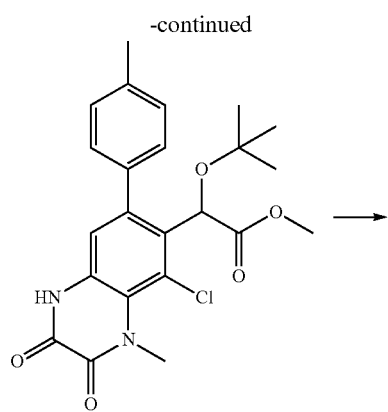
107
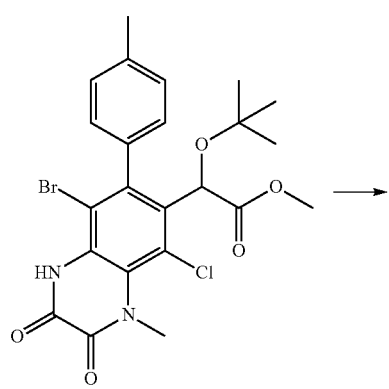
108
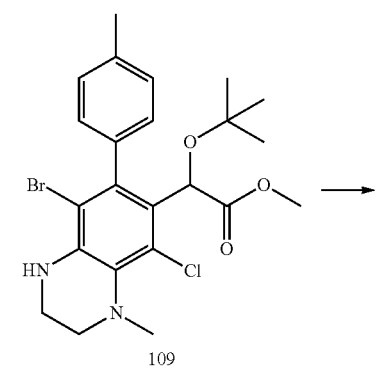
109
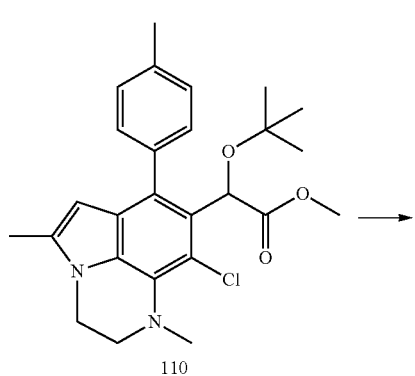
110

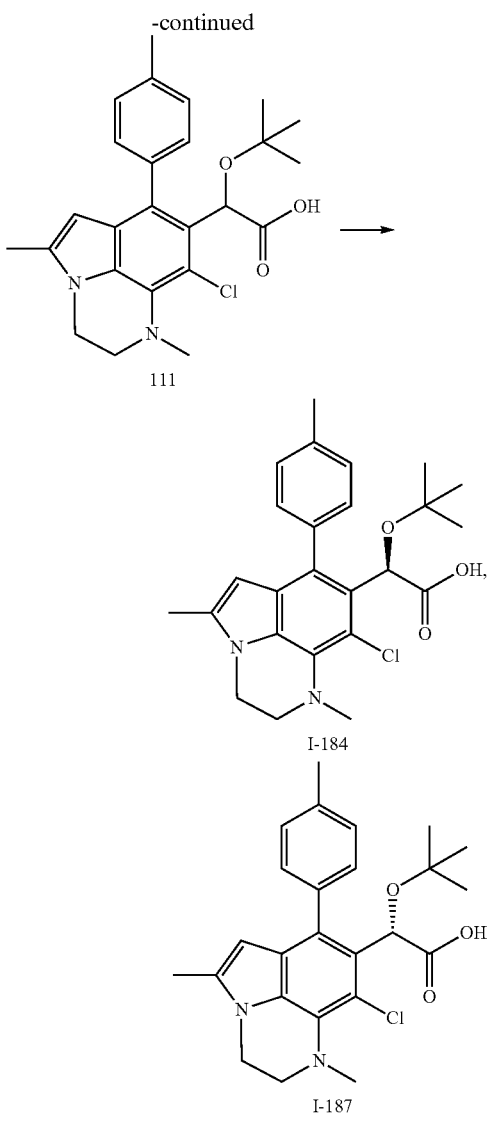

111

I-184

I-187

The First Step the Synthesis of Compound 101

To a solution of Compound 100 (10 g, 44.6 mmol) in toluene (150 mL) was added m-CPBA (43.9 mg, 178 mmol), and the mixture was stirred for 22 hours at 50° C. After cooling, chloroform was added thereto, and the mixture was filtered. The filtrate was washed with a 10% aqueous sodium thiosulfate solution, water and saturated brine successively, dried over anhydrous sodium sulfate, and concentrated under reduced pressure to yield Compound 101 (8.70 g) as a crude product.

The Second Step the Synthesis of Compound 102

To a suspension of Compound 101 (8.70 g) in dimethyl sulfoxide (113 mL) was added 40% aqueous methylamine solution (11.5 mL, 134 mmol), and the mixture was stirred for 15 hours at room temperature. The reaction mixture was extracted with ethyl acetate after addition of water. The organic layer was washed with water, and dried over anhydrous sodium sulfate. The solvent was concentrated under reduced pressure, and the resulting residue was purified by silica gel column chromatography (hexane-ethyl acetate) to yield compound 102 (1.67 g, 2 steps yield 14%).

LC/MS (ESI): m/z=264.99 [M+H]+, LC/MS measurement conditions: (1)

The Third Step the Synthesis of Compound 103

To a solution of Compound 102 (1.85 g, 7.00 mmol) in DMF (13.0 mL) were added (Z)-((2-(tert-butoxy)-1-methoxy-vinyl) oxy) trimethylsilane (3.06 g, 14.0 mmol), $ZnF_2$ (1.45 g, 14.0 mmol) and bis(tri-tert-butylphosphine) palladium (357 mg, 0.700 mmol), and the mixture was stirred under nitrogen atmosphere for 2 hours at 100° C. After cooling, ethyl acetate and water was added to the reaction mixture, and the mixture was filtered. The resulting filtrate was extracted with ethyl acetate. The organic layer was washed with water, and dried with anhydrous sodium sulfate. The solvent was concentrated under reduced pressure, the resulting residue was purified by silica gel column chromatography (hexane-ethyl acetate) to yield compound 103 (1.93 g, yield 83%).

LC/MS (ESI): m/z=331.01 [M+H]+, LC/MS measurement conditions: (1)

The Fourth Step the Synthesis of Compound 104

To a solution of Compounds 103 (1.93 g, 5.83 mmol) in DMF (19.3 mL) was added NBS (1.09 g, 6.13 mmol) under ice-cooling, and the mixture was stirred for 2.5 hours at room temperature. The reaction mixture was extracted with ethyl acetate after addition of water. The organic layer was washed with water, and dried with anhydrous sodium sulfate. The solvent was concentrated under reduced pressure to yield Compound 104 (2.38 g, yield 100%) as a crude product.

LC/MS (ESI): m/z=409.15 [M+H]+, LC/MS measurement conditions: (1)

The Fifth Step the Synthesis of Compound 105

To a mixed solution of Compound 104 (1.14 g, 2.78 mmol) in DMF (5.70 mL) and water (2.85 mL) were added p-tolyl boronic acid (568 mg, 4.17 mmol), potassium carbonate (1.15 g, 8.35 mmol) and $PdCl_2$ (dtbpf) (181 mg, 0.278 mmol), and the mixture was stirred under nitrogen atmosphere for 30 minutes at room temperature. After cooling, the reaction mixture was extracted with ethyl acetate after addition of water. The organic layer was washed with water, and dried over anhydrous sodium sulfate. The solvent was concentrated under reduced pressure, the resulting residue was purified by silica gel column chromatography (hexane-ethyl acetate) to yield compound 105 (991 mg, yield 85%).

LC/MS (ESI): m/z=421.07 [M+H]+, LC/MS measurement conditions: (1)

The Sixth Step the Synthesis of Compound 106

To a solution of Compound 105 (987 mg, 2.35 mmol) in dichloromethane (5.94 mL) were added triethylamine (475 mg, 4.69 mmol), chloro-glyoxylic acid methyl (431 mg, 3.52 mmol), DMAP (29.0 mg, 0.235 mmol) under ice-cooling, and the mixture was stirred for 20 minutes at room temperature. The reaction mixture was extracted with ethyl acetate after addition of a saturated aqueous sodium hydrogen carbonate solution. The organic layer was washed with saturated aqueous sodium hydrogen carbonate solution and water successively, and dried over anhydrous sodium sulfate. The solvent was concentrated under reduced pressure to yield Compound 106 (1.11 g, yield 93%) as a crude product.

LC/MS (ESI): m/z=507.30 [M+H]+, LC/MS measurement conditions: (1)

The Seventh Step the Synthesis of Compound 107

To a mixed solution of Compound 106 (1.11 g, 2.19 mmol) in THF (11.1 mL), methanol (5.56 mL) and water (2.78 mL) was added sodium dithionite (3.81 g, 21.9 mmol), and the mixture was heated under reflux and stirred for 6 hours. After cooling, the reaction mixture was extracted with ethyl acetate after addition of water. The organic layer was washed with saturated brine, and dried over anhydrous sodium sulfate. The solvent was concentrated under reduced pressure, the resulting residue was purified by silica gel column chromatography (hexane-ethyl acetate) to yield compound 107 (553 mg, yield 57%).

LC/MS (ESI): m/z=445.30 [M+H]+, LC/MS measurement conditions: (1)

The Eighth Step the Synthesis of Compound 108

To a solution of Compound 107 (550 mg, 1.24 mmol) in DMF (5.5 mL) was added NBS (264 mg, 1.48 mmol), and the mixture was stirred for 1 hour at room temperature and stirred for 1 hour at 60° C. NBS (264 mg, 1.48 mmol) was added thereto, and the mixture was stirred for 5 hours at 60° C. After cooling, the reaction mixture was extracted with ethyl acetate after addition of water. The organic layer was washed with water, saturated aqueous sodium hydrogen carbonate solution and water successively and dried over anhydrous sodium sulfate. The solvent was concentrated under reduced pressure to yield Compound 108 (695 mg) as a crude product.

LC/MS (ESI): m/z=523.22 [M+H]+, LC/MS measurement conditions: (1)

The Ninth Step the Synthesis of Compound 109

To a solution of Compounds 108 (695 mg) in THF (1.30 mL) was added a solution of 0.90 mol/L borane THF complex (29.0 mg, 0.235 mmol) in THF under ice-cold, and the mixture was stirred at room temperature for 70 minutes. The reaction mixture was extracted with ethyl acetate after addition of methanol, ethyl acetate and saturated aqueous sodium hydrogen carbonate solution under ice-cooling. The organic layer was washed with saturated brine, and dried over anhydrous sodium sulfate. The solvent was concentrated under reduced pressure, and the resulting residue was purified by silica gel column chromatography (hexane-ethyl acetate) to yield compound 109 (491 mg, yield 80%).

LC/MS (ESI): m/z=495.28 [M+H]+, LC/MS measurement conditions: (1)

The Tenth Step the Synthesis of Compound 110

To a solution of Compound 109 (485 mg, 0.978 mmol) in toluene (3.40 mL) were added isopropenyl acetate (294 mg, 2.93 mmol), tributyl (methoxy) tin (941, 2.93 mmol), acetic acid palladium (43.9 mg, 0.196 mmol) and tri (o-tolyl) phosphine (119 mg, 0.391 mmol), and the mixture was stirred under nitrogen atmosphere for 1 hour at 100° C. After cooling, ethyl acetate and a 4 mol/L aqueous potassium fluoride solution were added to the reaction mixture, and the mixture was stirred for 1 hour and filtered. The filtrate was extracted with ethyl acetate, and the organic layer was washed with saturated brine, and dried with anhydrous sodium sulfate. The solvent was concentrated under reduced pressure, and the resulting residue was purified by silica gel column chromatography (hexane-ethyl acetate) to yield Compound 110 (296 mg, yield 67%).

LC/MS (ESI): m/z=455.13 [M+H]+, LC/MS measurement conditions: (1)

The Eleventh Step the Synthesis of Compounds I-184 and I-187

To a mixed solution of Compound 110 (232 mg, 0.510 mmol) in ethanol (3.48 mL) and THF (1.50 mL) was added 2 mol/L aqueous sodium hydroxide solution (2.65 mL), and the mixture was heated under reflux and stirred for 2 hours. After cooling, the reaction mixture was extracted with chloroform after addition of 2 mol/L aqueous hydrochloric acid solution (2.70 mL), and dried with anhydrous sodium sulfate. The solvent was concentrated under reduced pressure, the resulting residue was crystallized with ethyl acetate, diisopropyl ether and hexane to yield Compound 111 (203 mg, yield 90%) as racemates, and carried optical resolution to yield optically active Compound I-184 (87 mg) and optically active Compound I-187 (84.7 mg).

Compound I-184: LC/MS (ESI): m/z=441 [M+H]+, RT=2.32 min, LC/MS measurement conditions: (1)

Compound I-187: LC/MS (ESI): m/z=441 [M+H]+, RT=2.32 min, LC/MS measurement conditions: (1)

Example 23

[Chemical formula 148]

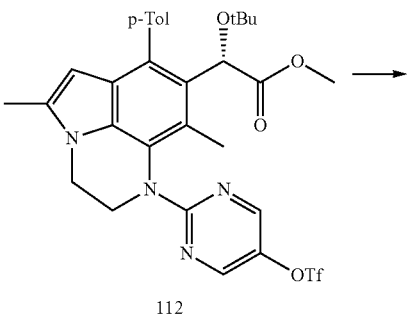

112

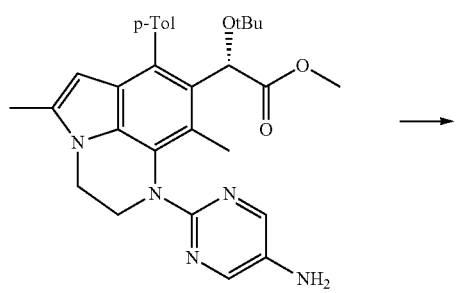

113

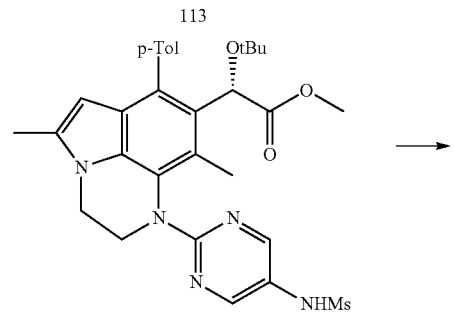

114

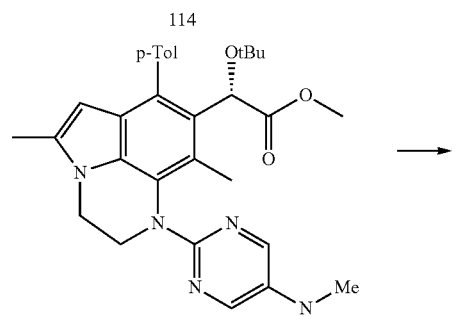

115

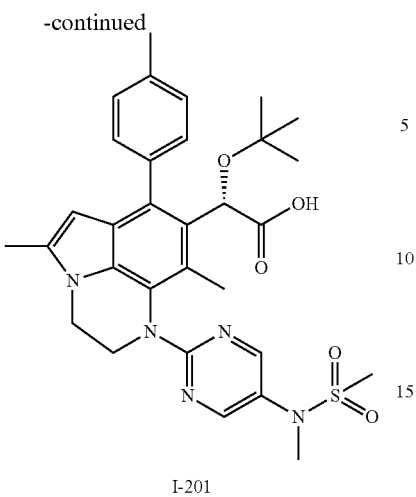

I-201

The First Step the Synthesis of Compound 113

Compound 112 (450 mg, 0.696 mmol) was dissolved in toluene (4.5 mL), then diphenyl methane imine (252 mg, 1.39 mmol), 2,2'-bis (diphenylphosphino)-1,1'-naphthyl (130 mg, 0.209 mmol), tris(dibenzylideneacetone) dipalladium (63.7 mg, 0.070 mmol) and cesium carbonate (680 mg, 2.09 mmol) were added thereto, and the mixture was stirred under nitrogen atmosphere at 100° C. for 3 hours. Tetrahydrofuran (10 mL) and 2 mol/L hydrochloric acid (5 mL) added thereto, and the mixture was stirred for 40 minutes at room temperature. The reaction mixture was extracted with ethyl acetate (30 mL) after addition of water (20 mL). The organic layer was washed with water (30 mL) and saturated brine (30 mL), and dried over anhydrous magnesium sulfate. After concentration, the resulting residue was purified by silica gel chromatography (hexane-ethyl acetate) to yield Compound 113 (271 mg, yield 76%) as orange foam.

LC/MS measurement conditions: (1): m/z=514 [M+H]+

The Second Step the Synthesis of Compound 114

Compound 113 (40 mg, 0.078 mmol) was dissolved in pyridine (0.7 mL). Methanesulfonyl chloride (0.012 mL, 0.156 mmol) was added thereto under ice-cooling, and the mixture was stirred for 40 minutes at room temperature. The reaction mixture was extracted with ethyl acetate (20 mL) after addition of water (10 mL). The organic layer was washed with 2 mol/L hydrochloric acid (10 mL), water (10 mL) and saturated brine (10 mL), and dried over anhydrous magnesium sulfate. After concentration, the resulting residue was purified by silica gel chromatography (hexane-ethyl acetate) to yield Compound 114 (41 mg, yield 81%) as yellow foam.

LC/MS measurement conditions: (1): m/z=592 [M+H]+

The Third Step the Synthesis of Compound 115 Compound 114 (37 mg, 0.063 mmol) and potassium carbonate (43 mg, 0.313 mmol) was dissolved in N,N-dimethylformamide (0.7 mL). Methyl iodide (0.020 mL, 0.313 mmol) was added thereto at room temperature, and the mixture was stirred for 1.5 hours at room temperature. The reaction mixture was extracted with ethyl acetate (20 mL) after addition of water (10 mL). The organic layer was washed with water (10 mL) and saturated brine (10 mL), and dried over anhydrous magnesium sulfate. After concentration, the resulting residue was purified by silica gel chromatography (hexane-ethyl acetate) to yield Compound 115 (34 mg, yield 89%) as yellow foam.

LC/MS measurement conditions: (1): m/z=606 [M+H]+

The Fourth Step the Synthesis of Compound I-201

Compounds 115 (34 mg, 0.056 mmol) was dissolved in tetrahydrofuran (0.5 mL) and ethanol (0.5 mL). 2 mol/L aqueous sodium hydroxide solution (0.5 mL) was added thereto, and the mixture was stirred for 3.5 hours at 80° C. 2 mol/L aqueous hydrochloric acid solution (0.5 mL) and saturated brine (30 mL) was added thereto, and the mixture was extracted with ethyl acetate (30 mL). The organic layer was dried over anhydrous magnesium sulfate. After concentration, the resulting residue was purified by silica gel chromatography (chloroform-methanol) to yield Compound I-201 (29 mg, yield 87%).

LC/MS measurement conditions: (1): m/z=592 [M+H]+, RT=2.71

Example 24

[Chemical formula 149]

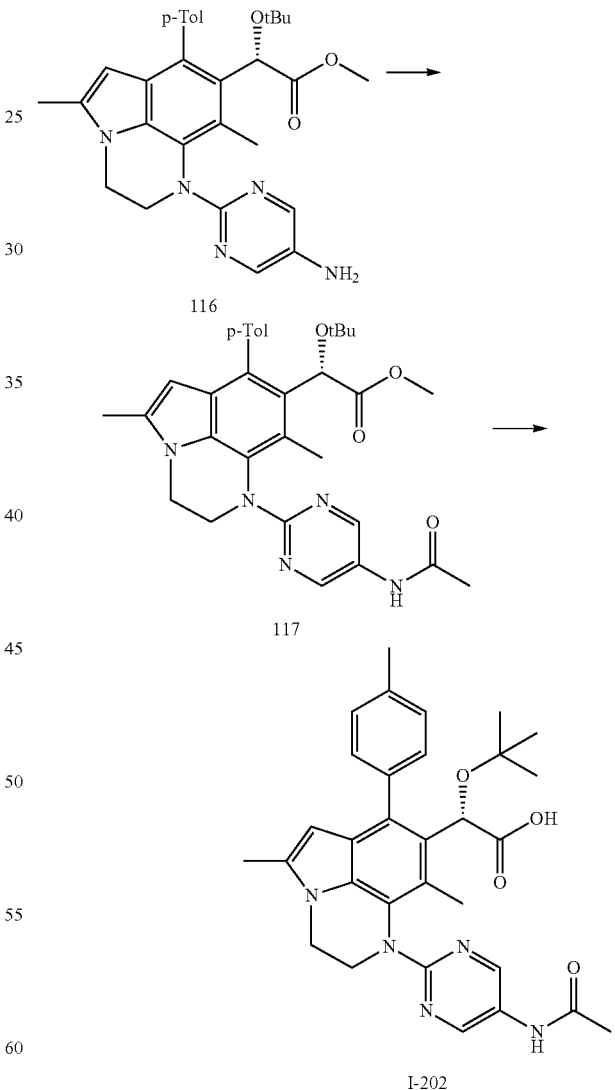

Step 1 Synthesis of Compound 117

Compound 116 (70 mg, 0.136 mmol) and pyridine (0.022 mL, 0.237 mmol) were dissolved in dichloro methane (0.7 mL). Under ice-cooling, acetyl chloride (0.015 mL, 0.204 mmol) was added dropwise thereto, and the mixture was stirred at room temperature for 50 minutes. Water (10 mL) was added thereto, and the mixture was extracted with ethyl acetate (20 mL). The organic layer was washed with water (10 mL) and saturated brine (10 mL), and dried over anhydrous magnesium sulfate. After concentration, the residue was purified by silica gel chromatography (hexane-ethyl acetate) to obtain Compound 117 (61 mg, 80% yield).

LC/MS measurement conditions: (1), m/z=556 [M+H]+.

Step 2 Synthesis of Compound I-202

Compound 117 (61 mg, 0.109 mmol) was dissolved in tetrahydrofuran (0.5 mL) and ethanol (0.5 mL). 2 mol/L aqueous sodium hydroxide solution (0.5 mL) was added thereto, and the mixture was stirred at 80° C. for 2 hours. 2 mol/L aqueous hydrochloric acid solution (0.5 mL) and saturated brine (30 mL) were added thereto, and the mixture was extracted with ethyl acetate (30 mL). The organic layer was dried over anhydrous magnesium sulfate. After concentration, the residue was purified by preparative thin layer chromatography (chloroform-methanol) to obtain Compound I-20 (18 mg, 28% yield).

LC/MS measurement conditions: (1), m/z=542 [M+H]+, RT=2.43 min.

Example 25

[Chemical formula 150]

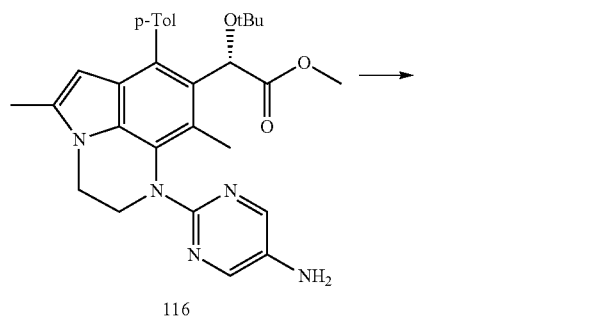

116

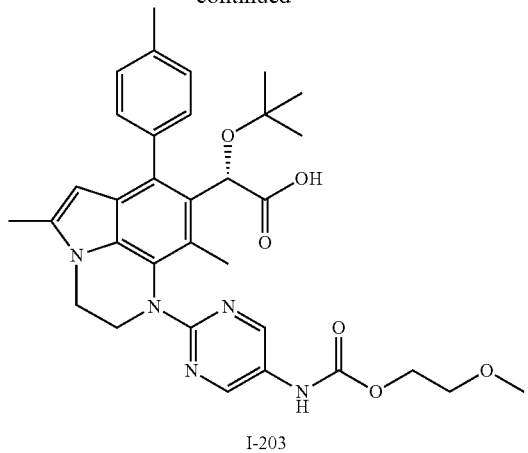

I-203

Step 1 Synthesis of Compound 118

Compound 116 (70 mg, 0.136 mmol) and pyridine (0.022 mL, 0.273 mmol) were dissolved in methylene chloride (0.7 mL). Under ice-cooling, to the mixture was added dropwise 2-methoxyethyl carbonochloridate (0.024 mL, 0.204 mmol), and was stirred at room temperature for 1.5 hours. Under ice-cooling, 2-methoxyethyl carbonochloridate (0.024 mL, 0.204 mmol) and pyridine (0.022 mL, 0.273 mmol) were added dropwise thereto, and the mixture was stirred at room temperature for 1 hour. Water (10 mL) was added thereto, and the mixture was extracted with ethyl acetate (20 mL). The organic layer was washed with water (10 mL) and saturated brine (10 mL), and dried over anhydrous magnesium sulfate. After concentration, the residue was purified by silica gel chromatography (hexane-ethyl acetate) to obtain Compound 118 (64 mg, 77% yield) as yellow foam.

LC/MS measurement conditions: (1), m/z=616 [M+H]+.

Step 2 Synthesis of Compound I-203

Compound 118 (64 mg, 0.104 mmol) was dissolved in N,N-dimethylacetamide (1.0 mL). To the mixture was added lithium chloride (88 mg, 2.079 mmol), and the mixture was stirred at 120° C. for 20 hours. 2 mol/L aqueous hydrochloric acid solution (0.5 mL) and water (20 mL) were added thereto, and the mixture was extracted with ethyl acetate (30 mL). The organic layer was dried over anhydrous magnesium sulfate. After concentration, the residue was purified by HPLC (0.1% formic acid in water-0.1% formic acid in acetonitrile) to obtain Compound I-203 (3 mg, 5% yield).

LC/MS measurement conditions: (1), m/z=602 [M+H]+, RT=2.69 min.

Example 26

[Chemical formula 151]

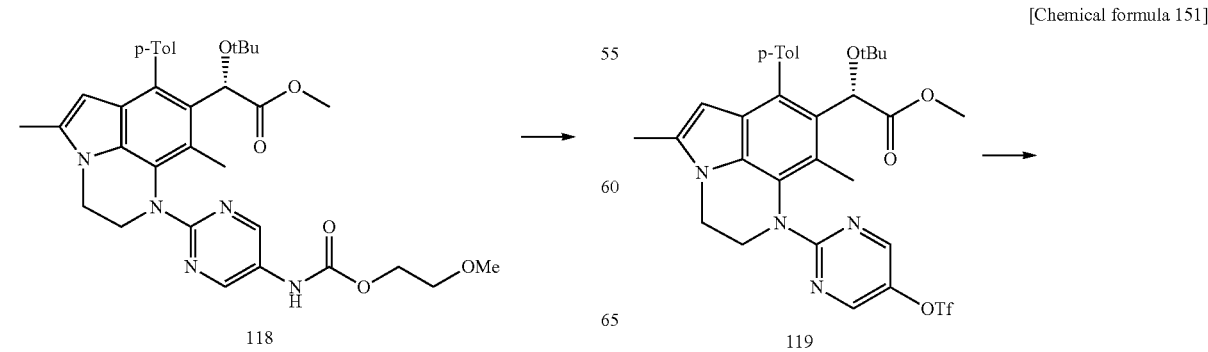

118

119

223

-continued

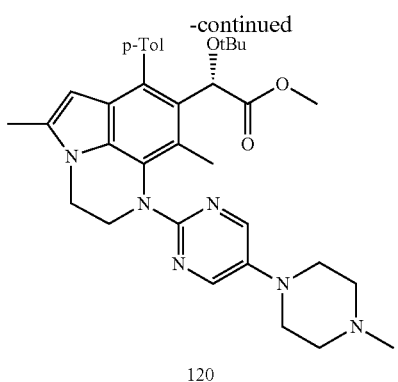

120

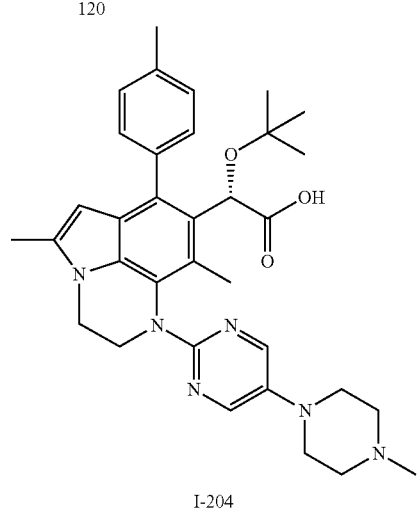

I-204

Step 1 Synthesis of Compound 120

Tris(dibenzylideneacetone)dipalladium (56.6 mg, 0.062 mmol) and 2-dicyclohexylphosphino-2',6'-diisopropoxy-1,1'-biphenyl (87 mg, 0.186 mmol) were dissolved in toluene (2 mL), and the mixture was stirred under nitrogen atmosphere at 110° C. for 2 minutes. Compound 119 (400 mg, 0.619 mmol), 1-methylpiperazine (620 mg, 6.20 mmol) and cesium carbonate (605 mg, 1.86 mmol) in toluene (2 mL) were added thereto, and the mixture was stirred under nitrogen atmosphere at 110° C. for 4 hours. Water (30 mL) was added thereto, and the mixture was extracted with ethyl acetate (50 mL). The organic layer was washed with water (30 mL) and saturated brine (30 mL), and then dried over anhydrous magnesium sulfate. After concentration, the residue was purified by diol silica gel chromatography (ethyl acetate) to obtain Compound 120 (173 mg, 47% yield) as orange foam.

LC/MS measurement conditions: (3), m/z=597 [M+H]+.

Step 2 Synthesis of Compound I-204

Compound 120 (171 mg, 0.287 mmol) was dissolved in tetrahydrofuran (1.0 mL) and ethanol (1.0 mL). 2 mol/L aqueous sodium hydroxide solution (1.5 mL) was added thereto, and stirred at 90° C. for 3.5 hours. 2 mol/L aqueous hydrochloric acid solution (1.5 mL) and saturated brine (30 mL) were added thereto, and the mixture was extracted with ethyl acetate (30 mL), the organic layer was dried over anhydrous magnesium sulfate. After concentration, the residue was purified by diol silica gel column chromatography (chloroform-methanol) to obtain Compound I-204 (120 mg, 72% yield).

LC/MS measurement conditions: (1), m/z=583 [M+H]+, RT=2.35 min.

224

Example 27

[Chemical formula 152]

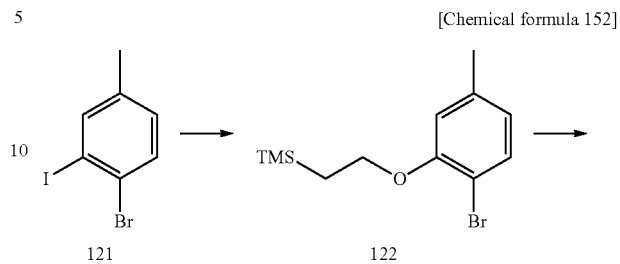

121    122

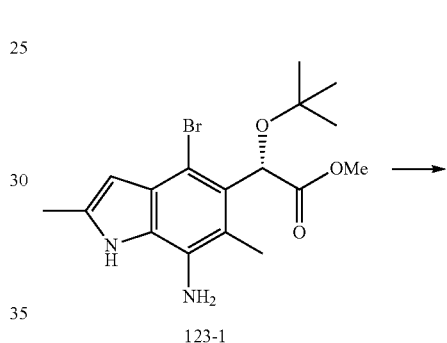

123

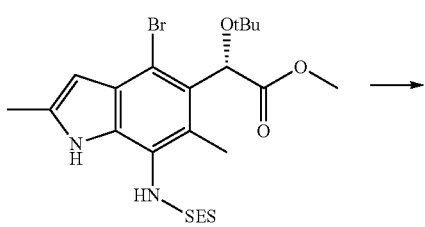

123-1

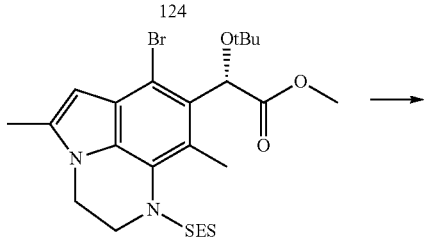

124

125

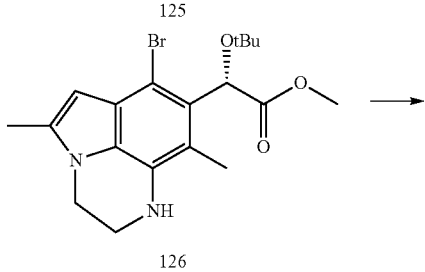

126

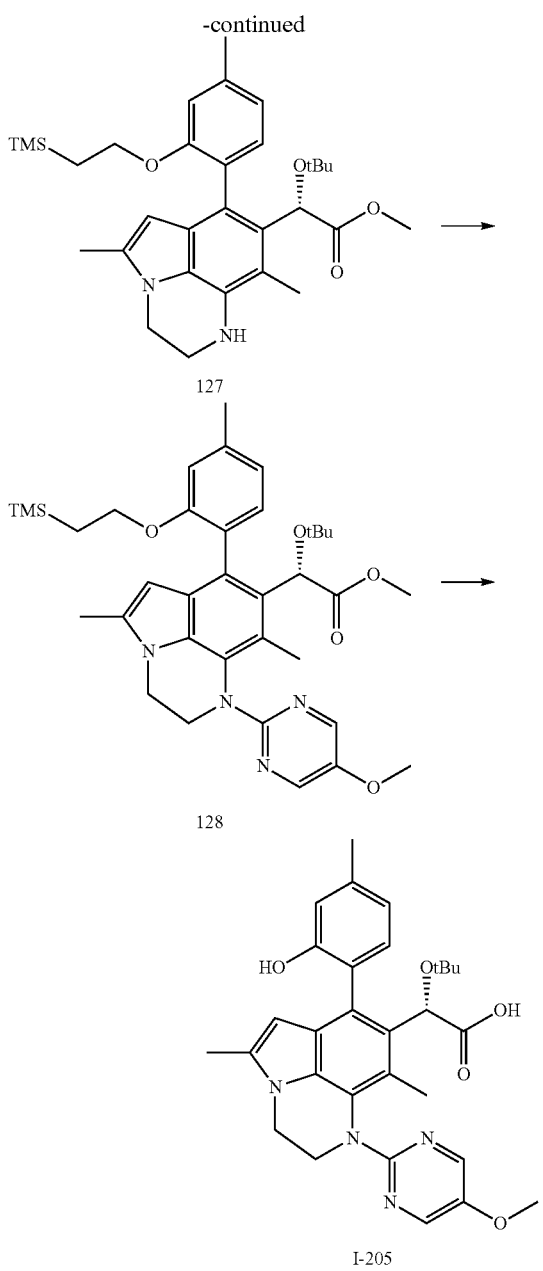

Step 1 Synthesis of Compound 122

Compound 121 (450 mg, 1.515 mmol), 2-(trimethylsilyl) ethanol (538 mg, 4.55 mmol), 1,10-phenanthroline (54.6 mg, 0.303 mmol), copper iodide (28.9 mg, 0.152 mmol) and cesium carbonate (988 mg, 2.03 mmol) were dissolved in toluene (0.75 mL), and the mixture was stirred under nitrogen atmosphere at 115° C. for 17 hours. 2 mol/L aqueous hydrochloric acid solution (30 mL) was added thereto, and the mixture was extracted with ethyl acetate (30 mL). The organic layer was washed with saturated aqueous sodium bicarbonate solution (30 mL) and water (30 mL), and dried over anhydrous magnesium sulfate. After concentration, the residue was purified by amino silica gel chromatography (hexane-ethyl acetate) to obtain Compound 122 (282 mg, 65% yield) as a colorless liquid material.

$^1$H-NMR (CDCl$_3$) δ: 7.38 (1H, d, J=8.0 Hz), 6.69 (1H, s), 6.63 (1H, d, J=8.0 Hz), 4.11 (2H, t, J=8.0 Hz), 2.31 (3H, s), 1.20 (2H, t, J=8.0 Hz), 0.01 (9H, s).

Step 2 Synthesis of Compound 123

Compound 122 (8.65 g, 30.1 mmol) was dissolved in tetrahydrofuran (87 mL), under a nitrogen atmosphere, 1.6 mol/L n-butyl lithium in hexane solution at −78° C. (19.1 mL, 49.7 mmol)) was added thereto, and the mixture was stirred for 30 minutes at −78° C. Boric acid triisopropyl ester (14.0 mL, 60.2 mmol) was added dropwise thereto, and the mixture was stirred at −78° C. for 1 hour. Saturated aqueous ammonium chloride solution (100 mL) and 2 mol/L aqueous hydrochloric acid solution (50 mL) were added thereto, and the mixture was extracted with ethyl acetate (300 mL). The organic layer was washed with water (300 mL), and dried over anhydrous magnesium sulfate. After concentration, the residue was washed with hexane to obtain Compound 123 (5.33 g, 70% yield).

$^1$H-NMR (CDCl$_3$) δ: 7.70 (1H, d, J=7.4 Hz), 6.83 (1H, d, J=7.4 Hz), 6.70 (1H, s), 5.96 (2H, s), 4.14 (2H, t, J=8.2 Hz), 2.37 (3H, s), 1.21 (2H, t, J=8.2 Hz), 0.10 (9H, s).

Step 3 Synthesis of Compound 124

Under ice-cooling, to Compound 123-1 (9.0 g, 23.5 mmol) in methylene chloride (10 mL) solution were added pyridine (4.05 mL, 50.1 mmol) and 2-trimethylsilyl chloride (4.5 mL, 23.7 mmol), the mixture was stirred at room temperature for 2 hours. To the reaction mixture was added saturated aqueous sodium hydrogen carbonate solution, and the mixture was extracted with methylene chloride. The organic layer was washed with 1 mol/L hydrochloric acid and saturated brine, and dried over anhydrous magnesium sulfate. After concentration under reduced pressure, the residue was purified by silica gel column chromatography (hexane-ethyl acetate) to obtain Compound 124 (5.6 g, 43.6% yield) as a colorless solid.

LC/MS (ESI): m/z=546.99 [MH]−, RT=2.92 min., LC/MS measurement conditions: (1).

Step 4 Synthesis of Compound 125

Compound 124 (1.5 g, 2.74 mmol) and cesium carbonate (2.68 g, 8.22 mmol) were dissolved in N,N-dimethylformamide (7.5 mL) at room temperature, 1,2-dibromoethane (0.354 mL, 4.11 mmol) was added dropwise thereto, and the mixture was stirred for 21 hours. Water (50 mL) was added thereto, and the mixture was extracted with ethyl acetate (50 mL). The organic layer was washed with water (50 mL) and saturated aqueous sodium chloride solution (50 mL), and dried over anhydrous magnesium sulfate. After concentration, the residue was washed with hexane to obtain Compound 125 (1.39 g, 88% yield).

LC/MS measurement conditions: (1), m/z=573 [M+H]+.

Step 5 Synthesis of Compound 126

Compound 125 (1.4 g, 2.44 mmol) was dissolved in tetrahydrofuran (7.0 mL). 1 mol/L tetrabutylammonium fluoride in tetrahydrofuran solution (7.32 mL, 7.32 mmol) was added dropwise thereto at room temperature, the mixture was stirred at 60° C. for 1 hour. Water (50 mL) was added thereto, and the mixture was extracted with ethyl acetate (50 mL). The organic layer was washed with water (50 mL) and saturated brine (50 mL), and dried over anhydrous magnesium sulfate. After concentration, the residue was purified by silica gel chromatography (hexane-ethyl acetate) to obtain Compound 126 (959 mg, 95% yield).

LC/MS measurement conditions: (1), m/z=409 [M+H]+.

Step 6 Synthesis of Compound 127

Compound 126 (500 mg, 1.22 mmol), Compound 123 (770 mg, 3.05 mmol), [1,1'-bis(di-tert-butylphosphino)ferrocene]palladium(II)dichloride (80 mg, 0.122 mmol) and 2 mol/L potassium carbonate aqueous solution (1.83 mL, 3.66 mmol) were dissolved in N,N-dimethylformamide (5.0 mL), and the mixture was stirred under nitrogen atmosphere at 120° C. for 1 hour. Water (30 mL) was added thereto, and the mixture was extracted with ethyl acetate (50 mL). The organic layer was washed with water (30 mL) and saturated brine (30 mL), and dried over anhydrous magnesium sulfate. After concentration, the residue was purified by silica gel column chromatography (hexane-ethyl acetate) to obtain Compound 127 (331 mg, 50% yield) as brown foam.

LC/MS measurement conditions: (1), m/z=537 [M+H]+.

Step 7 Synthesis of Compound 128

Compound 127 (50 mg, 0.093 mmol) was dissolved in toluene (0.7 mL), then 2-bromo-5-methoxy-pyrimidine (70.4 mg, 0.373 mmol), 4,5-bis(diphenyl phosphino)-9,9-dimethylxanthene (16.2 mg, 0.028 mmol), tris(dibenzylideneacetone)dipalladium (12.8 mg, 0.014 mmol), and sodium tert-butoxide (35.8 mg, 0.373 mmol) were added thereto, and the mixture was stirred under nitrogen atmosphere at 60° C. for 1 hour. 2-bromo-5-methoxy pyrimidine (70.4 mg, 0.373 mmol) and sodium tert-butoxide (35.8 mg, 0.373 mmol) were added thereto, and after stirring for 1.5 h, 2-bromo-5-methoxy pyrimidine (70.4 mg, 0.373 mmol) and sodium tert-butoxide (35.8 mg, 0.373 mmol) were added thereto, and the mixture was stirred for 1.5 hours. Water (20 mL) was added thereto, and the mixture was extracted with ethyl acetate (20 mL). The organic layer was washed with water (20 mL) and saturated brine (20 mL), and dried over anhydrous magnesium sulfate. After concentration, the residue was purified by silica gel chromatography (hexane-ethyl acetate) to obtain Compound 128 as a crude product. The resulting crude product was directly used in the next reaction without further purification.

LC/MS measurement conditions: (1), m/z=645 [M+H]+.

Step 8 Synthesis of Compound I-205

Compound 128 (128 mg, 0.198 mmol) was dissolved in tetrahydrofuran (7.0 mL). 1 mol/L tetrabutylammonium fluoride in tetrahydrofuran solution (0.595 mL, 0.595 mmol) was added dropwise thereto at room temperature, the mixture was stirred at 80° C. for 1.5 hours. 1 mol/L tetrabutylammonium fluoride in tetrahydrofuran solution (0.595 mL, 0.595 mmol) was added thereto, and the mixture was stirred for 1.5 hours, then further 1 mol/L tetrabutylammonium fluoride in tetrahydrofuran solution (0.595 mL, 0.595 mmol) was added thereto, and the mixture was stirred for 1.5 hours. Water (30 mL) was added thereto, and the mixture was extracted with ethyl acetate (30 mL). The organic layer was washed with water (30 mL) and saturated brine (30 mL), and dried over anhydrous magnesium sulfate. After concentration, the residue was purified by silica gel chromatography (chloroform-methanol) to obtain Compound I-205 (25 mg, 2 steps, 31% yield) as a brown foam.

LC/MS measurement conditions: (1), m/z=531 [M+H]+, RT=2.66 min.

Example 28

[Chemical formula 153]

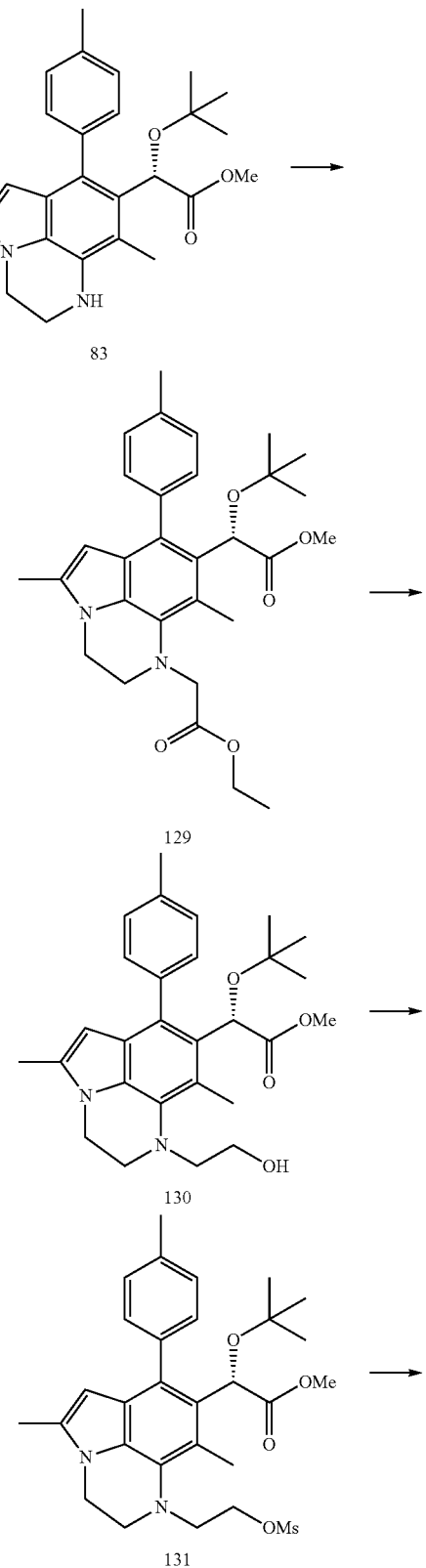

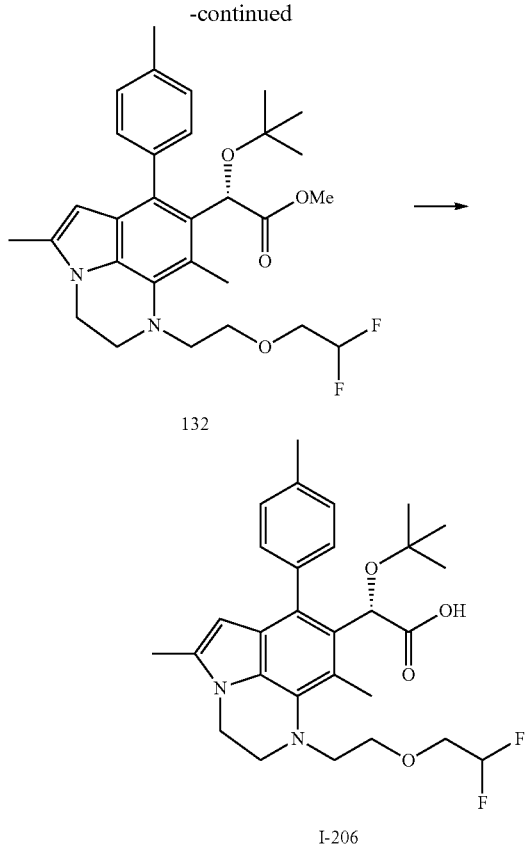

132

I-206

Step 1 Synthesis of Compound 129

To Compound 83 (400 mg, 0.951 mmol) in dimethylformamide (4.0 mL) solution were added ethyl iodoacetate (305 mg, 1.43 mmol) and cesium carbonate (620 mg, 1.90 mmol), the mixture was stirred at 70° C. for 3 hours. 1 mol/L hydrochloric acid was added thereto, and the aqueous layer was extracted with chloroform, the organic layer was washed with water and saturated brine, and dried over anhydrous magnesium sulfate. After concentration under reduced pressure, Compound 129 (572 mg, 118% yield) was obtained as a yellow solid. Compound 129 was used directly for the next reaction without further purification.

LC/MS (ESI): m/z=507.21 [M+H]+, RT=3.07 min., LC/MS measurement conditions: (1).

Step 2 Synthesis of Compound 130

Under ice-cooling, to Compound 129 (572 mg, 1.13 mmol) in ethanol (5.7 mL) solution was added 2 mol/L aqueous solution of sodium hydroxide (1.69 mL, 3.39 mmol), then and the mixture was stirred at 0° C. for 1 hour. 1 mol/L hydrochloric acid was added thereto, and the mixture was extracted with chloroform. The organic layer was washed with water and saturated brine, and dried over anhydrous magnesium sulfate. After concentration under reduced pressure, crude product was obtained as yellow foam.

Under ice-cooling, to the crude product (470 mg, 0.98 mmol) in tetrahydrofuran (6.0 mL) solution was added dropwise 0.92 mol/L borane in tetrahydrofuran solution, and the reaction mixture was heated to reflux for 1 hour. 1 mol/L hydrochloric acid was added thereto, and the mixture was extracted with chloroform. The organic layer was washed with water and saturated brine, and dried over anhydrous magnesium sulfate. After concentration under reduced pressure, the residue was purified by diol silica gel column chromatography (hexane-ethyl acetate) to obtain Compound 130 (339 mg, 64% yield) as white foam.

LC/MS (ESI): m/z=465.27 [M+H]+, RT=2.57 min., LC/MS measurement conditions: (1).

Step 3 Synthesis of Compound 131

Under ice-cooling, to Compound 130 (1.40 g, 3.01 mmol) in ethyl acetate (10 mL) solution were added triethylamine (2.09 mL, 15.1 mmol) and methanesulfonyl chloride (0.939 mL, 12.1 mmol), the mixture was stirred at room temperature for 30 minutes. Saturated aqueous sodium hydrogen carbonate solution was added thereto, and the mixture was extracted with ethyl acetate. The organic layer was washed with water and saturated brine, and dried over anhydrous magnesium sulfate. After concentration under reduced pressure, the residue was purified by diol silica gel column chromatography (hexane-ethyl acetate) to obtain Compound 131 (860 mg, 53% yield) as yellow foam.

LC/MS (ESI): m/z=545.30 [M+H]+, RT=2.87 min., LC/MS measurement conditions: (1).

Step 4 Synthesis of Compound 132

To 2,2-difluoroethane-1-ol (26.5 mg, 0.322 mmol) in dimethylformamide (0.35 mL) solution were added sequentially sodium hydride solution (12.9 mg, 0.322 mmol) and Compound 131 (35 mg, 0.064 mmol), and the mixture was stirred at 80° C. for 1 hour. 1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by diol silica gel column chromatography (hexane-ethyl acetate) to obtain Compound 132 (64 mg, 66% yield) as a yellow oily material.

LC/MS (ESI): m/z=529.25 [M+H]+, RT=3.22 min., LC/MS measurement conditions: (1).

Step 5 Synthesis of Compound I-206

To Compound 132 (74 mg, 0.14 mmol) in tetrahydrofuran (0.7 mL) and methanol (0.7 mL) solution was added 2 mol/L aqueous sodium hydroxide (0.7 mL, 1.4 mmol), the mixture was stirred at 90° C. for 2 hours. 1 mol/L hydrochloric acid was added thereto, and the aqueous layer was extracted with chloroform. After concentration under reduced pressure, the residue was purified by liquid chromatography to obtain Compound I-206 (32 mg, 49% yield) as a yellow solid.

LC/MS (ESI): m/z=515.46 [M+H]+, RT=2.82 min., LC/MS measurement conditions: (1).

$^1$H-NMR (CDCl$_3$) δ: 10.03 (1H, s), 7.57 (1H, d, J=6.7 Hz), 7.39 (1H, d, J=6.7 Hz), 7.25-7.23 (2H, br m), 5.92 (1H, s), 5.85 (1H, td, J=111.1, 4.3 Hz), 5.59 (1H, s), 3.96 (2H, dt, J=16.7, 6.4 Hz), 3.85 (2H, td, J=5.4, 2.3 Hz), 3.70 (2H, td, J=27.7, 4.1 Hz), 3.57-3.51 (2H, m), 3.12 (2H, dt, J=19.4, 7.4 Hz), 2.42 (3H, s), 2.40 (3H, s), 2.34 (3H, s), 0.90 (9H, s).

Example 29

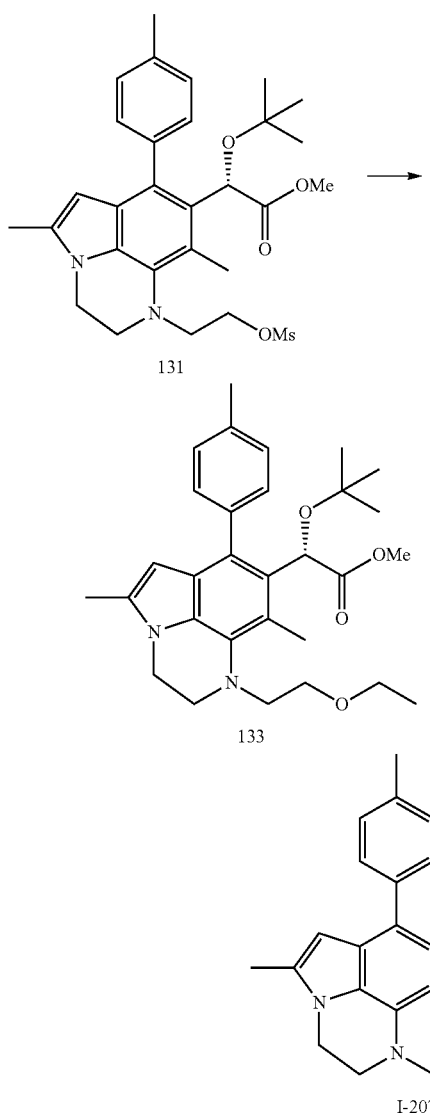

Step 1 Synthesis of Compound 133

To Compound 131 (100 mg, 0.184 mmol) in dimethylformamide (1.0 mL) solution was added sodium ethoxide (62.7 mg, 0.921 mmol), and the mixture was stirred at 80° C. for 1 hour. 1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by diol silica gel column chromatography (hexane-ethyl acetate) to obtain Compound 133 (21 mg, 23% yield) as a yellow oily material.

LC/MS (ESI): m/z=493.24 [M+H]+, RT=3.16 min., LC/MS measurement conditions: (1).

Step 2 Synthesis of Compound I-207

To Compound 133 (21 mg, 0.043 mmol) in tetrahydrofuran (0.5 mL) and methanol (0.5 mL) solution was added 2 mol/L aqueous sodium hydroxide (0.5 mL, 1.0 mmol), the mixture was stirred at 90° C. for 1 hour. 1 mol/L hydrochloric acid was added thereto, and the aqueous layer was extracted with chloroform, and the organic layer was concentrated under reduced pressure. The residue was purified by liquid chromatography to obtain Compound I-207 (3 mg, 15% yield) as a yellow solid.

LC/MS (ESI): m/z=479.20 [M+H]+, RT=2.82, LC/MS measurement conditions: (1).

$^1$H-NMR (CDCl$_3$) δ: 7.59 (1H, d, J=7.3 Hz), 7.39 (1H, d, J=7.4 Hz), 7.25-7.23 (2H, br m), 5.92 (1H, s), 5.58 (1H, s), 3.96 (2H, d, J=4.9 Hz), 3.76-3.74 (4H, m), 3.56-3.53 (2H, m), 3.26-2.91 (2H, m), 2.43-2.41 (6H, br m), 2.34 (3H, s), 1.23 (3H, t, J=6.8 Hz), 0.89 (9H, s).

Example 30

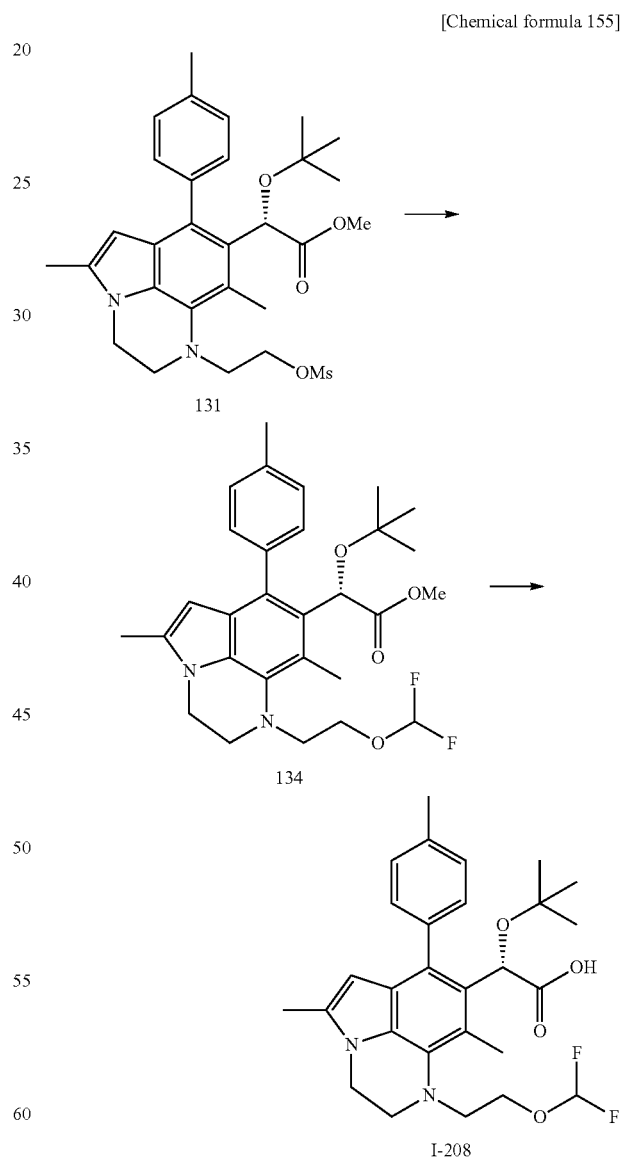

Step 1 Synthesis of Compound 134

Under ice-cooling, to Compound 131 (50 mg, 0.184 mmol) in methylene chloride (2.5 mL) solution were added 20% aqueous solution of potassium hydroxide (181 mg, 0.65 mmol) and (bromodifluoromethyl)trimethylsilane (43.7 mg, 0.21 mmol), and the mixture was stirred at 0° C. for 1 hour. Water was added thereto, and the aqueous layer was extracted with ethyl acetate. The organic layer was washed with water and saturated brine, and dried over anhydrous magnesium sulfate. After concentration under reduced pressure, the residue was purified by liquid chromatography to obtain Compound 134 (21 mg, 38% yield) as a yellow oily material.

LC/MS (ESI): m/z=515.20 [M+H]+, RT=3.24 min., LC/MS measurement conditions: (1).

Step 2 Synthesis of Compound I-208

To Compound 134 (21 mg, 0.041 mmol) in tetrahydrofuran (0.3 mL) and methanol (0.3 mL) solution was added 4 mol/L aqueous solution of lithium hydroxide (0.3 mL, 1.2 mmol), the mixture was stirred at 80° C. for 3 hours. 1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by liquid chromatography to obtain Compound I-208 (13 mg, 64% yield) as a yellow solid.

LC/MS (ESI): m/z=501.49 [M+H]+, RT=2.85 min., LC/MS measurement conditions: (1).

$^1$H-NMR (CDCl$_3$) δ: 10.03 (1H, s), 7.57 (1H, d, J=7.8 Hz), 7.39 (1H, d, J=7.1 Hz), 7.24 (2H, d, J=10.0 Hz), 6.27 (1H, t, J=74.7 Hz), 5.93 (1H, s), 5.58 (1H, s), 4.17 (2H, t, J=5.7 Hz), 3.96 (2H, d, J=4.8 Hz), 3.51-3.48 (2H, br m), 3.25-3.05 (2H, m), 2.42 (3H, s), 2.41 (3H, s), 2.34 (3H, s), 0.90 (9H, s).

Example 31

[Chemical formula 156]

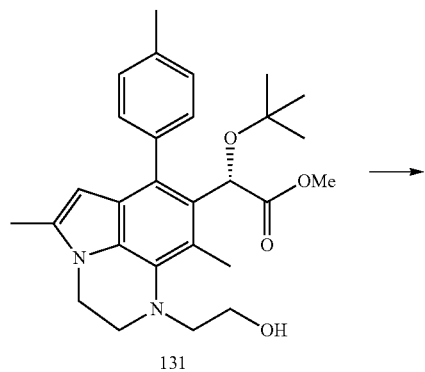

131

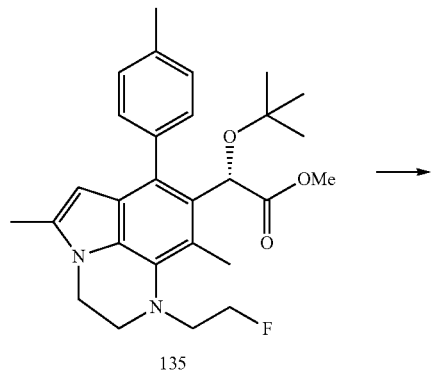

135

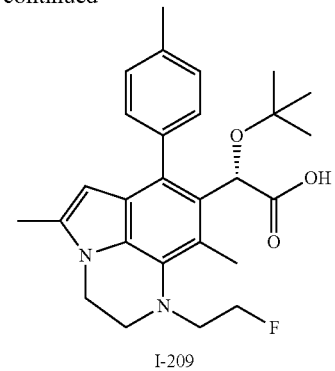

I-209

Step 1 Synthesis of Compound 135

Under ice-cooling, to Compound 131 (20 mg, 0.043 mmol) in methylene chloride (300 μL) solution was added N,N-diethylaminosulfur trifluoride (181 mg, 0.65 mmol), the mixture was stirred at 0° C. for 3 hours. Saturated aqueous solution of sodium hydrogen carbonate was added thereto, and the aqueous layer was extracted with ethyl acetate. The organic layer was washed with water and saturated brine, and dried over anhydrous magnesium sulfate. After concentration under reduced pressure, the residue was purified by liquid chromatography to obtain Compound 135 (5 mg, 25% yield) as yellow foam.

LC/MS (ESI): m/z=467.25 [M+H]+, RT=3.02 min., LC/MS measurement conditions: (1).

Step 2 Synthesis of Compound I-209

To Compound 135 (5 mg, 10 μmol) in tetrahydrofuran (50 μL) and methanol (50 μL) solution was added 2 mol/L aqueous solution of sodium hydroxide (50 μL, 0.1 mmol), the mixture wad stirred at 80° C. for 3 hours. 1 mol/L hydrochloric acid was added thereto, and the aqueous layer was extracted with methylene chloride, and the organic layer was concentrated under reduced pressure. The residue was purified by liquid chromatography to obtain Compound I-209 (1 mg, 21% yield) as a yellow solid.

LC/MS (ESI): m/z=453.17 [M+H]+, RT=2.75 min., LC/MS measurement conditions: (1).

$^1$H-NMR (CDCl$_3$) δ: 7.60 (1H, d, J=7.3 Hz), 7.40 (1H, d, J=7.3 Hz), 7.25-7.19 (2H, m), 5.93 (1H, s), 5.55 (1H, s), 4.74 (2H, dt, J=47.7, 4.4 Hz), 3.97 (2H, dd, J=11.1, 5.1 Hz), 3.53 (2H, t, J=4.9 Hz), 3.27-3.19 (2H, m), 2.42 (3H, s), 2.40 (3H, s), 2.34 (3H, s), 0.89 (9H, s).

Example 32

[Chemical formula 157]

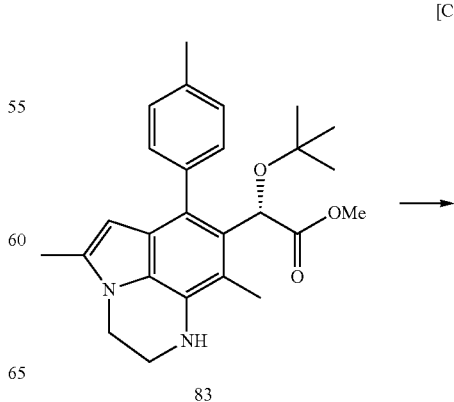

83

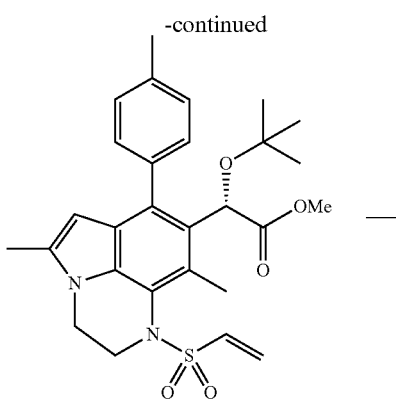

136

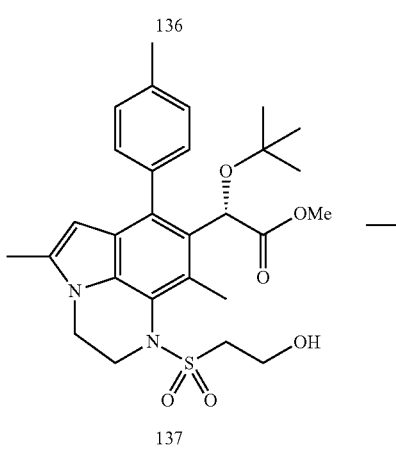

137

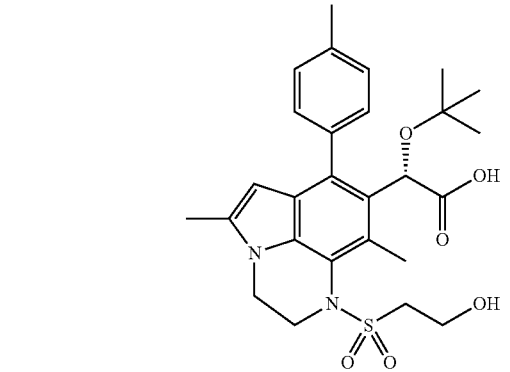

I-210

Step 1 Synthesis of Compound 136

Under ice-cooling, to Compound 83 (100 mg, 0.238 mmol) in pyridine (5 mL) solution was added 2-chloroethane-1-sulfonyl chloride (58 mg, 0.357 mmol), the mixture was stirred at room temperature for 3 hours. 1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by silica gel chromatography to obtain Compound 136 (99 mg, 82% yield) as a yellow oily material.

$^1$H-NMR (CDCl$_3$) δ: 7.42 (1H, d, J=8.6 Hz), 7.33 (1H, d, J=6.3 Hz), 7.26-7.17 (2H, m), 6.57 (1H, dd, J=16.5, 10.0 Hz), 6.32 (1H, d, J=16.4 Hz), 5.95 (1H, d, J=9.9 Hz), 5.90 (1H, s), 5.42 (1H, s), 3.73-3.71 (4H, m), 2.45 (6H, br s), 2.29 (3H, s), 0.90 (9H, s).

Step 2 Synthesis of Compound 137

To Compound 136 (90 mg, 176 μmol) in tetrahydrofuran (3 mL) solution was added 0.5 mol/L tetrabutylammonium hydroxide aqueous solution (3.42 mL, 1.76 mmol), the mixture was stirred at room temperature for 1 hour. Water was added thereto, and the aqueous layer was extracted with ethyl acetate. The organic layer was washed with water and saturated brine, and dried over anhydrous magnesium sulfate. After concentration under reduced pressure, the residue was purified by silica gel chromatography to obtain Compound 137 (45 mg, 48% yield) as colorless foam.

LC/MS (ESI): m/z=546.20 [M+H$_2$O]+, RT=2.56 min., LC/MS measurement conditions: (1).

$^1$H-NMR (CDCl$_3$) δ: 7.60 (1H, d, J=7.3 Hz), 7.40 (1H, d, J=7.3 Hz), 7.25-7.19 (2H, m), 5.93 (1H, s), 5.55 (1H, s), 4.74 (2H, dt, J=47.7, 4.4 Hz), 3.97 (2H, dd, J=11.1, 5.1 Hz), 3.53 (2H, t, J=4.9 Hz), 3.27-3.19 (2H, m), 2.42 (3H, s), 2.40 (3H, s), 2.34 (3H, s), 0.89 (9H, s).

Step 3 Synthesis of Compound I-210

To Compound 137 (45 mg, 85 μmol) in tetrahydrofuran (450 μL) and methanol (450 μL) solution was added 4 mol/L lithium hydroxide aqueous solution (450 μL, 1.8 mmol), the mixture was stirred at 80° C. for 3 hours. 1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by silica gel chromatography to obtain Compound I-210 (1 mg, 2.3% yield) as a yellow solid.

LC/MS (ESI): m/z=515.13 [M+H]+, RT=2.33 min., LC/MS measurement conditions: (1).

$^1$H-NMR (CDCl$_3$) δ: 7.61 (1H, d, J=7.0 Hz), 7.35 (1H, d, J=7.3 Hz), 7.29-7.27 (2H, m), 5.93 (1H, s), 5.52 (1H, s), 4.22-4.13 (6H, br m), 3.40-3.36 (3H, m), 2.43 (6H, br s), 2.32 (3H, s), 0.91 (9H, s).

Example 33

[Chemical formula 158]

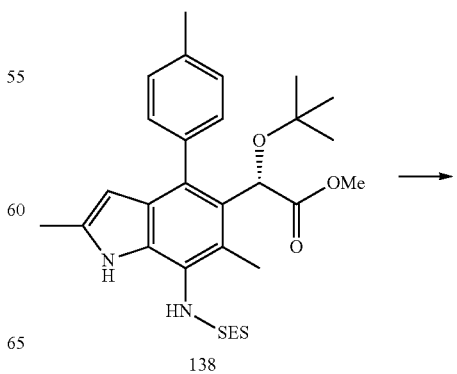

138

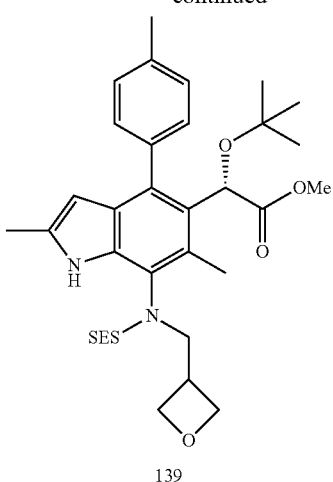

139

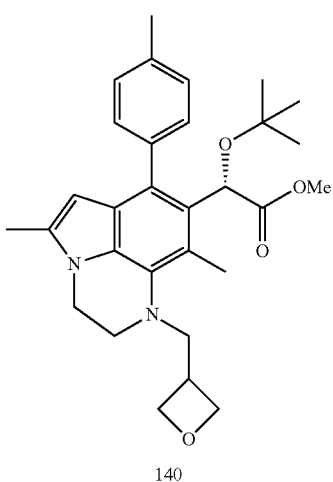

140

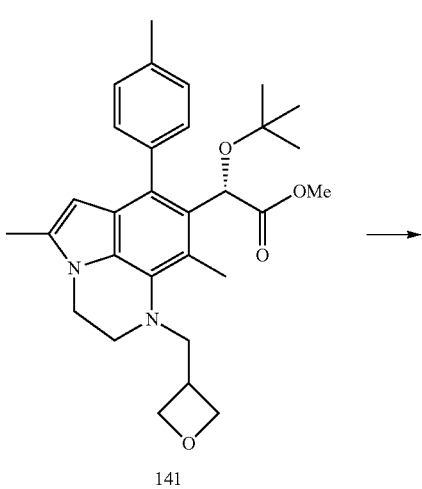

141

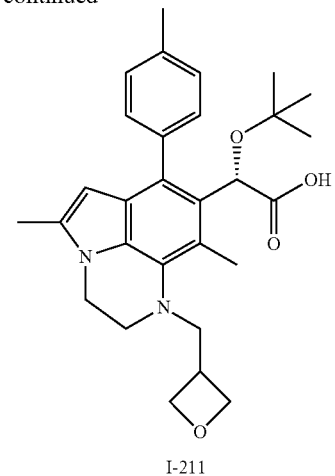

I-211

Step 1 Synthesis of Compound 139

Under ice-cooling, to Compound 138 (150 mg, 0.268 mmol) in tetrahydrofuran (1.5 mL) solution were added oxetane-3-yl methanol (35.5 mg, 0.403 mmol), triphenylphosphine (106 mg, 0.403 mmol) and bis(2-methoxyethyl) azocarboxylate (94 mg, 0.403 mmol), the mixture was stirred at room temperature for 24 hours. Water was added thereto, and the aqueous layer was extracted with ethyl acetate, and the organic layer water was washed with saturated brine, and dried over anhydrous magnesium sulfate. After concentration under reduced pressure, the residue was purified by silica gel chromatography (hexane-ethyl acetate) to obtain Compound 139 (140 mg, yield 82.9%) as a yellow oily material.

LC/MS (ESI): m/z=629.19 [M+H]+, RT=3.15 min., LC/MS measurement conditions: (1).

Step 2 Synthesis of Compound 140

To Compound 139 (140 mg, 223 μmol) in tetrahydrofuran (1.4 mL) solution was added 1.0 mol/L tetrabutylammonium fluoride solution (668 μL, 668 μmol), the mixture was stirred at 60° C. for 4 hours and at 80° C. for 1 hour. Saturated aqueous solution of sodium hydrogen carbonate was added thereto, and the aqueous layer was extracted with ethyl acetate. The organic layer was washed with water and saturated brine, and dried over anhydrous magnesium sulfate. After concentration under reduced pressure, the residue was purified by silica gel chromatography (hexane-ethyl acetate) to obtain Compound 140 (60 mg, 58% yield) as a yellow oily material.

LC/MS (ESI): m/z=465.16 [M+H]+, RT=2.45 min., LC/MS measurement conditions: (1).

Step 3 Synthesis of Compound 141

Under ice-cooling, to Compound 140 (60 mg, 129 μmol) in methylene chloride (0.6 mL) solution were added potassium hydroxide (36.2 mg, 0.65 mmol) and diphenyl(vinyl) trifluoromethanesulfonate (94 mg, 258 μmol), and the mixture was stirred at room temperature for 2 hours. 0.1 mol/L hydrochloric acid was added thereto, and the aqueous layer was extracted with ethyl acetate. The organic layer was washed with water and saturated brine, and dried over anhydrous magnesium sulfate. After concentration under reduced pressure, the residue was purified by silica gel chromatography (hexane-ethyl acetate) to obtain Compound 141 (44 mg, 86.7% yield) as a yellow oily material.

LC/MS (ESI): m/z=491.19 [M+H]+, RT=2.61 min., LC/MS measurement conditions: (1).

Step 4 Synthesis of Compound I-211

To Compound 141 (44 mg, 90 µmol) in tetrahydrofuran (440 µL) and methanol (440 µL) solution was added 4 mol/L lithium hydroxide aqueous solution (440 µL, 1.76 mmol), the mixture was stirred at 80° C. for 3 hours. 1 mol/L hydrochloric acid was added thereto, and the aqueous layer was extracted with chloroform, and the organic layer was concentrated under reduced pressure. The residue was purified by silica gel chromatography (chloroform-methanol) to obtain Compound I-211 (10 mg, 23.4% yield) as a yellow solid.

LC/MS (ESI): m/z=477.19 [M+H]+, RT=2.30 min., LC/MS measurement conditions: (3).

$^1$H-NMR (CDCl$_3$) δ: 7.57 (1H, d, J=7.3 Hz), 7.38 (1H, d, J=7.3 Hz), 7.27-7.25 (2H, m), 5.93 (1H, s), 5.59 (1H, s), 4.86 (2H, dd, J=14.3, 8.0 Hz), 4.55 (2H, q, J=5.7 Hz), 3.99-3.91 (2H, m), 3.52-3.45 (1H, m), 3.37-3.16 (4H, m), 2.42-2.40 (6H, br m), 2.34 (3H, s), 0.92 (9H, s).

Example 34

[Chemical formula 159]

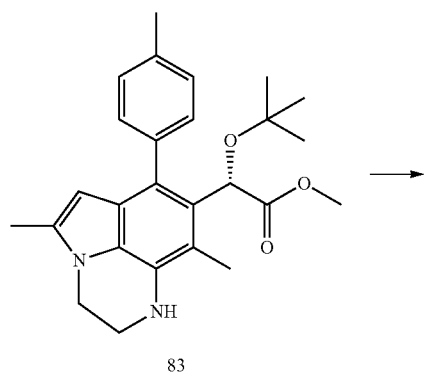
83

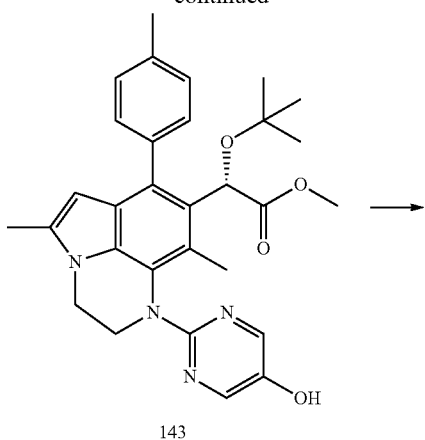
143

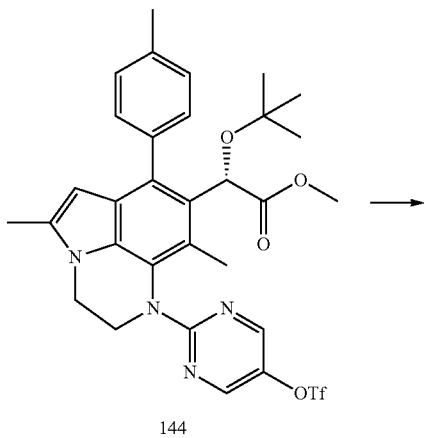
144

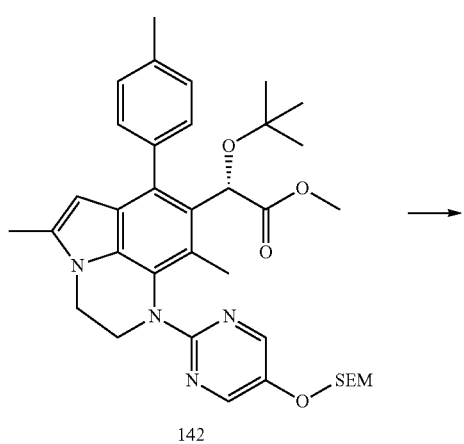
142

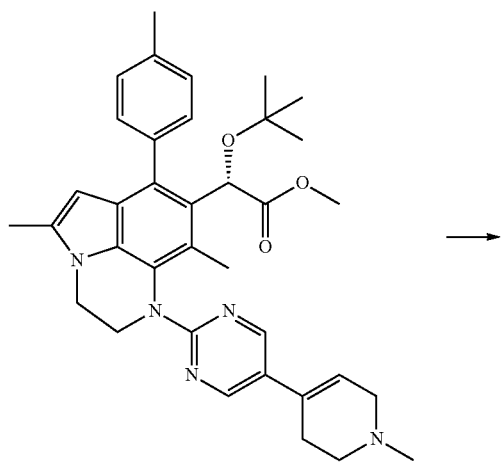
145

I-212

Step 1

To Compound 83 (9 g, 21.4 mmol) in toluene (90 mL) solution were added sodium tert-butoxide (3.09 g, 32.1 mmol), 2-bromo-5-[(2-(trimethylsilyl)ethoxy)methoxy]pyrimidine (9.8 g, 32.1 mmol), Xantphos (3.71 g, 6.42 mmol) and dibenzylideneacetone palladium (2.94 g, 3.21 mmol), the mixture was stirred under nitrogen atmosphere at 60° C. for 40 minutes. Sodium tert-butoxide (3.09 g, 32.1 mmol), 2-bromo-5-[(2-(trimethylsilyl)ethoxy)methoxy]pyrimidine (9.8 g, 32.1 mmol) were added again thereto, and the mixture was stirred under nitrogen atmosphere at 60° C. for 1 hour. The reaction mixture was added to 2 mol/L hydrochloric acid, and the aqueous layer was extracted with ethyl acetate. The organic layer was washed with water, and dried over anhydrous sodium sulfate. After concentration under reduced pressure, the residue was purified by silica gel column chromatography (hexane-ethyl acetate) to obtain Compound 142 (8.67 g, 63% yield) as yellow foam.

LC/MS (ESI): m/z=645.35 [M+H]+, RT=3.75 min., LC/MS measurement conditions: (1).

Step 2

To Compound 142 (8.67 g, 13.44 mmol) in THF (86 mL) solution was added 1 mol/L tetrabutylammonium fluoride in THF solution (40.3 mL, 40.3 mmol), the mixture was stirred under reflux at 60° C. for 16 hours. Water was added thereto, and the mixture was extracted with ethyl acetate. The organic layer was washed with water, and dried over anhydrous sodium sulfate. After concentration under reduced pressure, the residue was purified by silica gel column chromatography (hexane-ethyl acetate) to obtain Compound 143 (6.28 g, 91% yield) as yellow foam.

LC/MS (ESI): m/z=515.25 [M+H]+, RT=2.86 min., LC/MS measurement conditions: (1).

Step 3

To Compound 143 (500 mg, 0.972 mmol) in DMF (5 mL) solution was added triethylamine (0.202 mL, 1.457 mmol) and N-phenyl-bis(trifluoromethane sulfonimide) (451 mg, 1.263 mmol), the mixture was stirred under ice-cooling for 10 minutes. Water was added thereto, and extracted with ethyl acetate. The organic layer was washed with water, and dried over anhydrous sodium sulfate. After concentration under reduced pressure, the residue was purified by silica gel column chromatography (hexane-ethyl acetate) to obtain Compound 144 (567 mg, 90% yield) as yellow foam.

LC/MS (ESI): m/z=647.15 [M+H]+, RT=3.47 min., LC/MS measurement conditions: (1).

Step 4

To Compound 144 (200 mg, 0.309 mmol) in DMF (2 mL) solution were added 2 mol/L potassium carbonate aqueous solution (0.309 mL, 0.619 mmol), 1-methyl-4-(4,4,5,5-tetramethyl-1,3,2-dioxobororan-2-yl)-1,2,3,6-tetrahydropyridine (1.28 mL, 1.28 mmol) and PdCl$_2$(dtbpf) (20.16 mg, 0.031 mmol), the mixture was stirred under a nitrogen atmosphere at 100° C. for 30 minutes. Water was added thereto, and the mixture was extracted with ethyl acetate. The organic layer was washed with water, and dried over anhydrous sodium sulfate. After concentration under reduced pressure, the residue was purified by silica gel column chromatography (hexane-ethyl acetate) to obtain Compound 145 (190 mg, 100% yield) as a brown oily material.

LC/MS (ESI): m/z=594.35 [M+H]+, RT=2.43 min., LC/MS measurement conditions: (1).

Step 5

To Compound 145 (70 mg, 0.118 mmol) in ethanol (1 mL) and THF (1 mL) solution were added 2 mol/L aqueous sodium hydroxide (0.279 mL, 0.58 mmol), the mixture was stirred under reflux for 3.5 hours. 2 mol/L hydrochloric acid was added thereto, and the mixture was extracted with chloroform. The organic layer was washed with water, and dried over anhydrous sodium sulfate. After concentration under reduced pressure, the residue was purified by silica gel column chromatography (chloroform-methanol) to obtain Compound I-212 (40 mg, 59% yield) as a brown solid.

LC/MS (ESI): m/z=580.30 [M+H]+, RT=2.21 min., LC/MS measurement conditions: (1).

1H-NMR (CDCl3) δ: 0.97 (9H, s), 2.19 (3H, s), 2.29 (3H, s), 2.42 (3H, s), 2.43 (3H, s), 2.53 (2H, brs), 2.66-2.73 (2H, m), 3.13 (2H, brs), 4.04 (2H, brs), 5.59 (1H, s), 5.90 (1H, s), 6.00 (1H, s), 7.20-7.28 (2H, m), 7.39 (1H, d, J=7.1 Hz), 7.65 (1H, d, J=7.1 Hz).

Example 35

[Chemical formula 160]

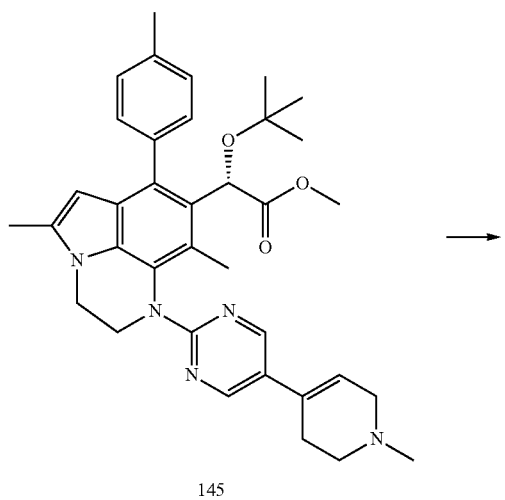

145

2.35-2.40 (1H, m), 2.43 (3H, s), 2.98 (2H, d, J=12.0 Hz), 3.94-4.08 (2H, m), 5.59 (1H, s), 5.90 (1H, s), 7.22-7.27 (2H, m), 7.35-7.41 (1H, m), 7.64-7.70 (1H, m), 8.28 (2H, s).

Example 36

[Chemical formula 161]

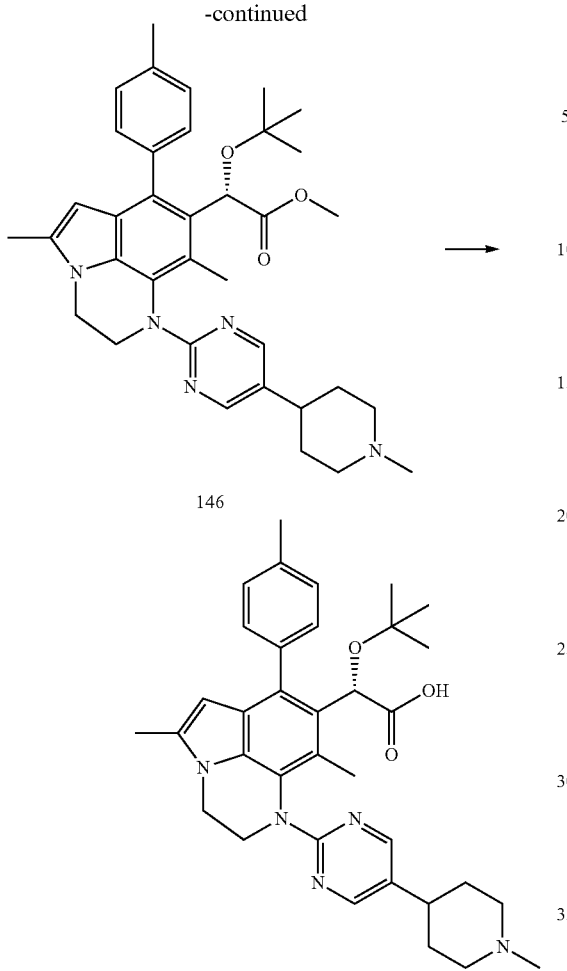

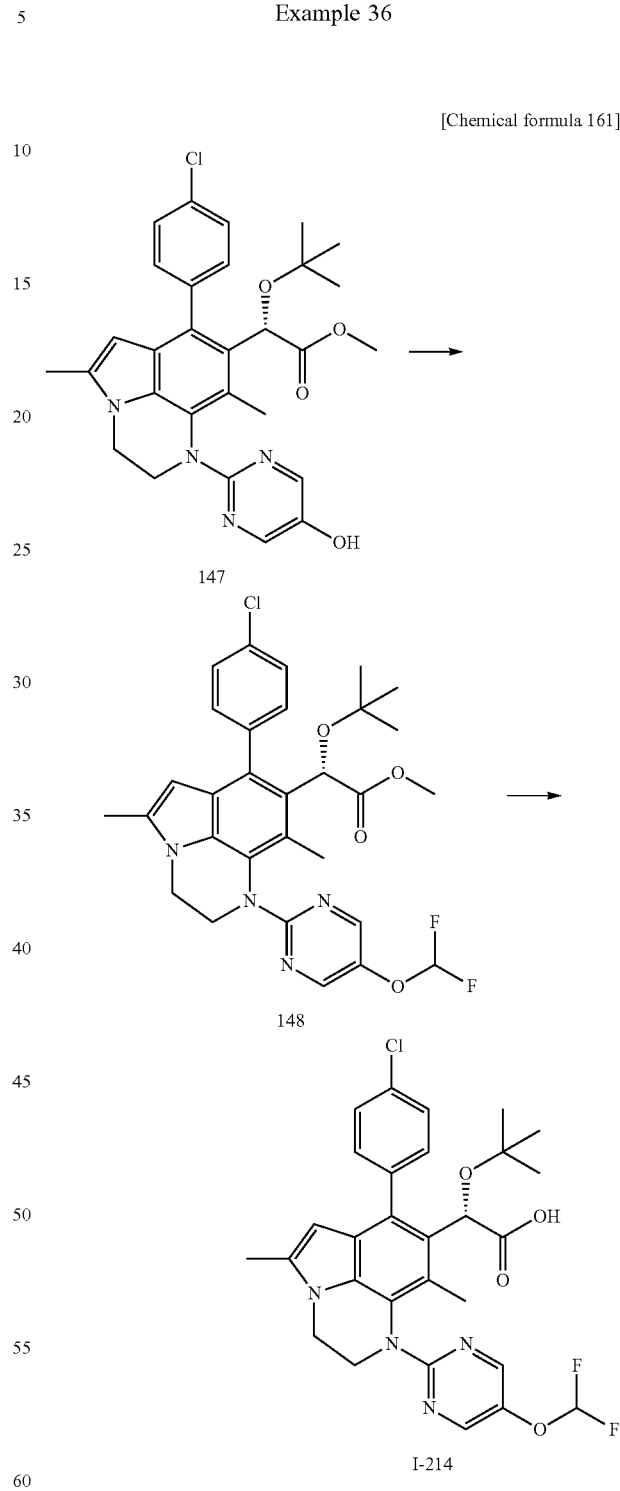

Step 1
To Compound 145 (120 mg, 0.202 mmol) in methanol (2 mL) solution was added palladium hydroxide (28.4 mg, 0.202 mmol), the mixture was stirred under hydrogen atmosphere at room temperature for 30 minutes. Then, acetic acid (2 mL) was added thereto, and the mixture was stirred under hydrogen atmosphere at room temperature for 2 hours and 30 minutes. The reaction mixture was filtered through Celite, and the filtrate was concentrated to obtain crude Compound 146 (120 mg) as a brown oily material.

LC/MS (ESI): m/z=596.35 [M+H]+, RT=2.37 min., LC/MS measurement conditions: (1).

Step 2
To Compound 146 (120 mg, 0.201 mmol) in ethanol (1 mL) and THF (1 mL) solution was added 2 mol/L aqueous sodium hydroxide solution (1.01 mL, 2.01 mmol), the mixture was stirred under reflux for 3 hours. 2 mol/L hydrochloric acid was added thereto, and the mixture was extracted with chloroform. The organic layer was washed with water, and dried over anhydrous sodium sulfate. After concentration under reduced pressure, the residue was purified by preparative liquid chromatography to obtain Compound I-213 (10 mg, 9%, two steps yield) as a brown solid.

LC/MS (ESI): m/z=582.30 [M+H]+, RT=2.21 min., LC/MS measurement conditions: (1).

1H-NMR (CDCl3) δ: 0.97 (9H, s), 1.71-1.85 (4H, m), 2.00-2.10 (2H, m), 2.22 (3H, s), 2.28 (3H, s), 2.33 (3H, s),

Step 1
To Compound 147 (220 mg, 0.411 mmol) in DMF (2 mL) solution were added cesium carbonate (268 mg, 0.823 mmol) and methyl-2-chloro-2,2-difluoro acetate (0.086 mL, 0.823 mmol), the mixture was stirred under nitrogen atmosphere at 60° C. for 15 minutes. Water was added thereto, and the mixture was extracted with ethyl acetate. The organic layer was washed with water, and dried over anhydrous sodium sulfate. After concentration under reduced pressure, the residue was purified by silica gel chromatography (hexane-ethyl acetate) to obtain Compound 148 (94 mg, 39% yield) as yellow foam.

LC/MS (ESI): m/z=585.15 [M+H]+, RT=3.33 min., LC/MS measurement conditions: (1).

Step 2

To Compound 148 (96 mg, 0.201 mmol) in ethanol (1 mL) and THF (1 mL) solution was added 2 mol/L aqueous sodium hydroxide solution (0.41 mL, 0.82 mmol), the mixture was stirred under reflux for 3 hours. 2 mol/L hydrochloric acid was added thereto, and the mixture was extracted with chloroform. The organic layer was washed with water, and dried over anhydrous sodium sulfate. After concentration under reduced pressure, the residue was purified by silica gel chromatography (hexane-ethyl acetate) to obtain Compound I-214 (36 mg, 38% yield) as a white solid.

LC/MS (ESI): m/z=571.20 [M+H]+, RT=3.07 min., LC/MS measurement conditions: (1).

1H-NMR (CDCl3) δ: 0.98 (9H, s), 2.22 (3H, s), 2.31 (3H, s), 3.96-4.15 (2H, m), 5.48 (1H, s), 5.88 (1H, s), 6.45 (1H, t, J=73 Hz), 7.39-7.49 (3H, m), 7.70-7.80 (1H, s), 8.30 (2H, s).

Example 37

[Chemical formula 162]

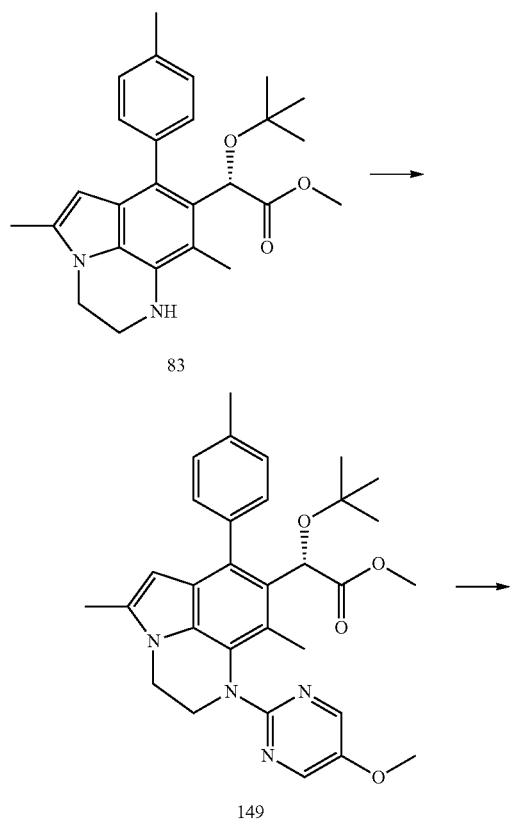

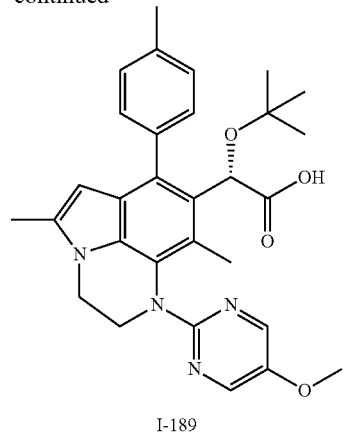

I-189

Step 1

To Compound 83 (1 g, 2.38 mmol) in toluene (10 mL) solution were added sodium tert-butoxide (343 mg, 3.57 mmol), 2-bromo-5-methoxypyrimidine (752 mg, 3.57 mmol), Xantphos (413 mg, 0.713 mmol) and dibenzylideneacetone palladium (327 mg, 0.357 mmol), the mixture was stirred under nitrogen atmosphere at 60° C. for 30 minutes. Then, sodium tert-butoxide (343 mg, 3.57 mmol) and 2-bromo-5-methoxy-pyrimidine (752 mg, 3.57 mmol) were added again thereto, and the mixture was stirred under nitrogen atmosphere at 60° C. for 30 minutes. The reaction mixture was added to 2 mol/L aqueous hydrochloric acid and was extracted with ethyl acetate. The organic layer was washed with water, and dried over anhydrous sodium sulfate. After concentration under reduced pressure, and the residue was purified by silica gel column chromatography (hexane-ethyl acetate) to obtain Compound 149 (1.12 g, 89% yield) as yellow foam.

LC/MS (ESI): m/z=529.20 [M+H]+, RT=3.17 min., LC/MS measurement conditions: (1).

Step 2

To Compound 149 (1.13 g, 2.138 mmol) in ethanol (6 mL) and THF (6 mL) solution was added 2 mol/L sodium hydroxide solution (5.34 mL, 10.69 mmol), the mixture was stirred under reflux for 3 hours. 2 mol/L hydrochloric acid was added thereto, and the mixture was extracted with chloroform. The organic layer was washed with water, and dried over anhydrous sodium sulfate. After concentration under reduced pressure, the residue was purified by silica gel chromatography (hexane-ethyl acetate) to obtain Compound I-189 (919 mg, 84% yield) as yellow foam.

LC/MS (ESI): m/z=515.20 [M+H]+, RT=2.90 min., LC/MS measurement conditions: (1).

1H-NMR (CDCl3) δ: 0.97 (9H, s), 2.20 (3H, s), 2.29 (3H, s), 2.43 (3H, s), 3.83 (3H, s), 3.94-4.15 (3H, m), 4.75-4.96 (1H, m), 5.61 (1H, s), 5.91 (1H, s), 7.22-7.28 (2H, m), 7.40 (1H, d, J=7.1 Hz), 7.66 (1H, d, J=7.1 Hz), 8.15 (2H, s).

Example 38

[Chemical formula 163]

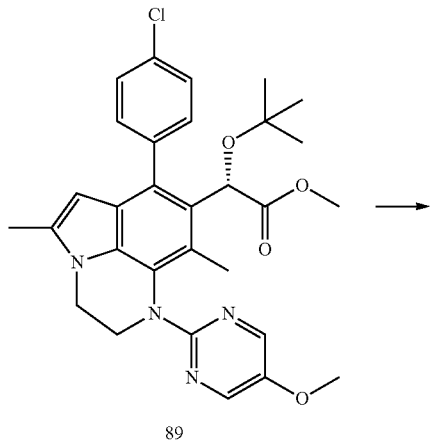

89

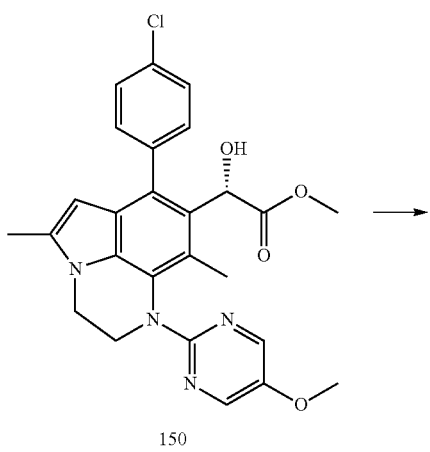

150

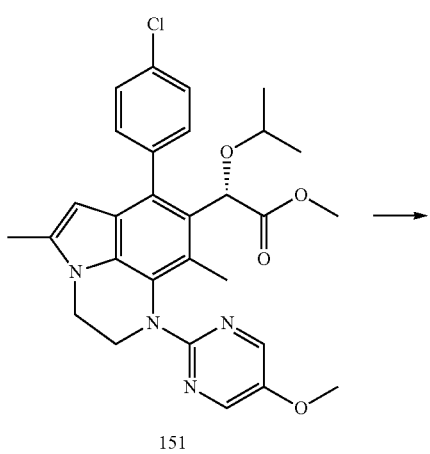

151

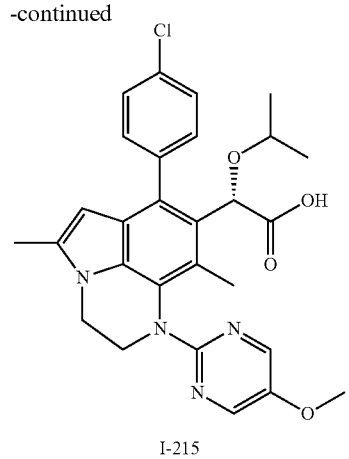

I-215

Step 1

To Compound 89 (1 g, 1.821 mmol) in dichloromethane (10 mL) solution was added trifluoroacetic acid (10 mL), the mixture was stirred at room temperature for 1 hour. Then, saturated aqueous sodium bicarbonate solution was added thereto, and the mixture was extracted with chloroform. The organic layer was washed with water, and dried over anhydrous sodium sulfate. After concentration under reduced pressure, the residue was purified by silica gel chromatography (hexane-ethyl acetate) to obtain Compound 150 (831 mg, 93% yield) as yellow foam.

LC/MS (ESI): m/z=493.10 [M+H]+, RT=2.53 min., LC/MS measurement conditions: (1).

Step 2

To Compound 150 (60 mg, 0.122 mmol) in dimethylformamide (10 mL) solution were added sodium hydride (40.0 mg, 0.96 mmol) and isopropyl iodide (0.148 mL, 1.46 mmol), the mixture was stirred at room temperature for 2 hours. Then, saturated aqueous ammonium chloride solution was added thereto, and the mixture was extracted with ethyl acetate. The organic layer was washed with water, and dried over anhydrous sodium sulfate. After concentration under reduced pressure, the residue was purified by silica gel chromatography (hexane-ethyl acetate) to obtain Compound 151 (27 mg, 42% yield) as yellow foam.

LC/MS (ESI): m/z=535.15 [M+H]+, RT=3.09 min., LC/MS measurement conditions: (1).

Step 3

To Compound 151 (25 mg, 0.047 mmol) in ethanol (0.5 mL) and THF (0.5 mL) solution was added 2 mol/L sodium hydroxide solution (0.234 mL, 0.467 mmol), the mixture was stirred under reflux for 2 hours. Then, 2 mol/L hydrochloric acid was added thereto, and the reaction mixture was extracted with chloroform. The organic layer was washed with water, and dried over anhydrous sodium sulfate. After concentration under reduced pressure, the residue was purified by silica gel chromatography (chloroform-methanol) to obtain Compound I-215 (18.8 mg, 77% yield) as a yellow solid.

LC/MS (ESI): m/z=521.15 [M+H]+, RT=2.77 min., LC/MS measurement conditions: (1).

1H-NMR (CDCl3) δ:0.84 (3H, d, J=6.0 Hz), 1.07 (3H, d, J=6.0 Hz), 2.17 (3H, s), 2.31 (3H, s), 3.48 (1H, tt, J=6.0 Hz, 6.0 Hz), 3.83 (3H, s), 3.94-4.08 (2H, m), 4.14 (1H, brs), 4.84 (1H, brs), 5.38 (1H, s), 5.85 (1H, s), 7.32-7.60 (4H, m), 8.15 (2H, s).

Example 39

[Chemical formula 164]

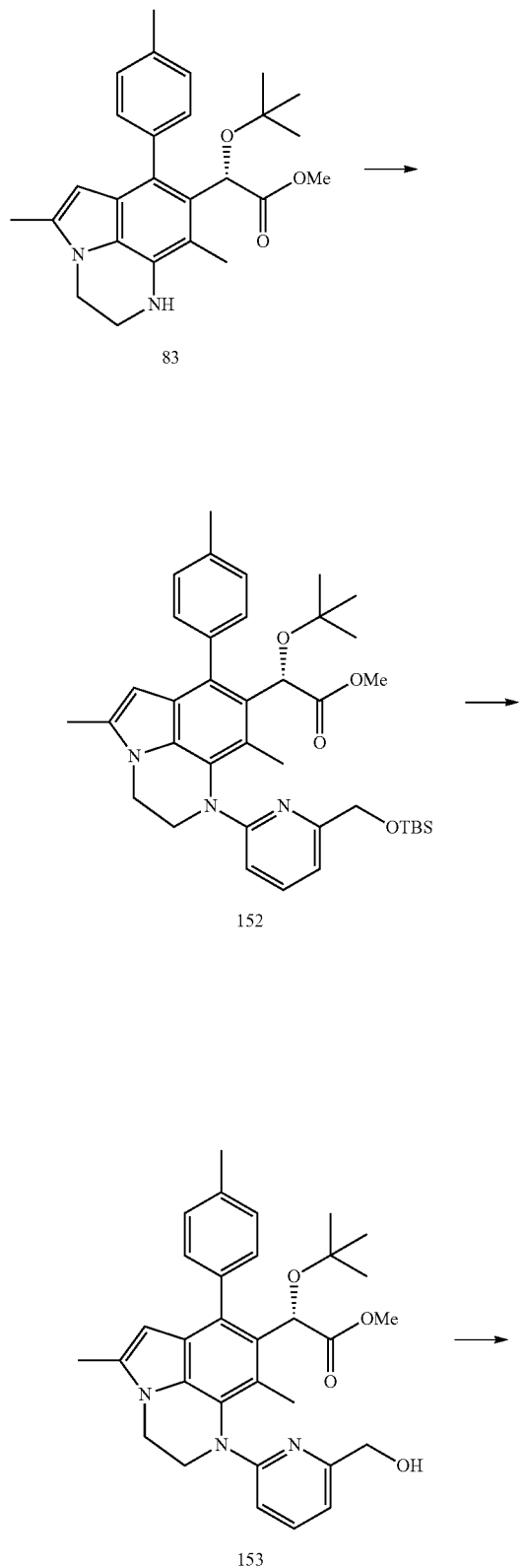

Step 1

To Compound 83 (100 mg, 0.238 mmol), 2-bromo-6-((tert-butyldimethylsiloxy)methyl)pyridine (108 mg, 0.357 mmol), dibenzylideneacetone palladium (32.7 mg, 0.036 mmol) and xantphos (41.3 mg, 0.071 mmol) in toluene (1 mL) suspension was added sodium tert-butoxide (34.3 mg, 0.357 mmol) at room temperature, the mixture was stirred under nitrogen atmosphere at 60° C. for 2 hours. Saturated aqueous solution of ammonium chloride (3 mL) and water (20 mL) was added thereto, and the mixture was extracted with ethyl acetate (30 mL). The organic layer was washed with water (20 mL) and saturated brine (20 mL), and dried over anhydrous magnesium sulfate. After concentration, the residue was purified by silica gel chromatography (hexane-ethyl acetate) to obtain Compound 152 (162 mg, 89% yield) as brown foam.

LC/MS measurement conditions: (1) LC/MS (ESI): m/z=642.8 [M+H]+.

Step 2

To Compound 152 (134 mg, 0.209 mmol) in THF solution (1.34 mL) was added 0.92 mol/L TBAF in THF solution (0.681 mL, 0.626 mmol), the mixture was stirred at room temperature for 1.5 hours. Water (20 mL) was added thereto, and the mixture was extracted with ethyl acetate (30 mL). The organic layer was washed with water (20 mL) and saturated brine (20 mL), and dried over anhydrous magnesium sulfate. After concentration, the residue was purified by silica gel chromatography (hexane-ethyl acetate) to obtain Compound 153 (106 mg, 96% yield) as brown foam.

LC/MS measurement conditions: (1), LC/MS (ESI): m/z=528.6 [M+H]+.

Step 3

To Compound 153 (50 mg, 0.095 mmol) in ethanol (1 mL) and THF (1 mL) solution was added 4 mol/L aqueous lithium hydroxide solution (0.500 mL, 2.00 mmol), the mixture was stirred under reflux for 2 hours. 1 mol/L hydrochloric acid (2 mL) and saturated brine (20 mL) were added thereto, and the mixture was extracted with ethyl acetate (30 mL). The organic layer was dried over anhydrous sodium sulfate. After concentration, the residue was purified by silica gel column chromatography (chloroform-methanol) to obtain Compound I-216 (32.0 mg, 66% yield).

LC/MS measurement conditions: (1), LC/MS (ESI): m/z=514.6 [M+H]+, RT=2.54 min.

$^1$H-NMR (CDCl$_3$) δ: 0.96 (s, 9H), 2.18 (s, 3H), 2.31 (s, 3H), 2.44 (s, 3H), 3.61-3.81 (m, 1H), 3.92-3.99 (m, 2H), 4.27-4.47 (m, 1H), 4.71 (s, 2H), 5.63 (s, 1H), 5.96 (s, 1H), 6.26-6.33 (m, 1H), 6.62-6.71 (m, 1H), 7.20-7.31 (m, 2H), 7.38-7.47 (m, 2H), 7.59-7.67 (m, 1H).

Example 40

[Chemical formula 165]

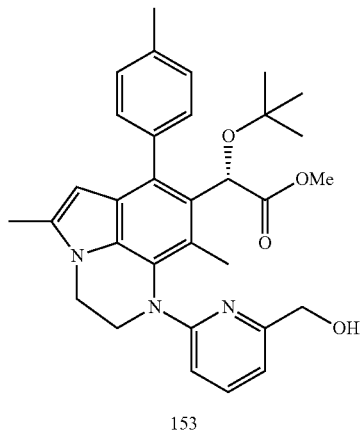

153

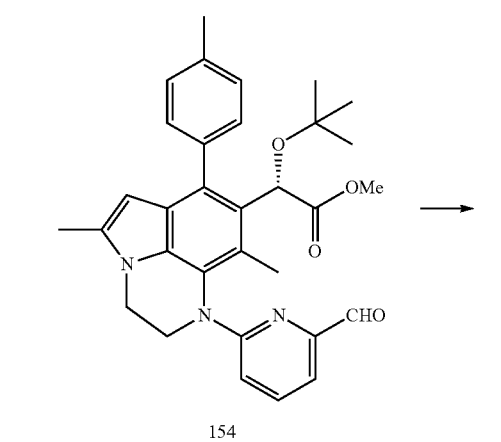

154

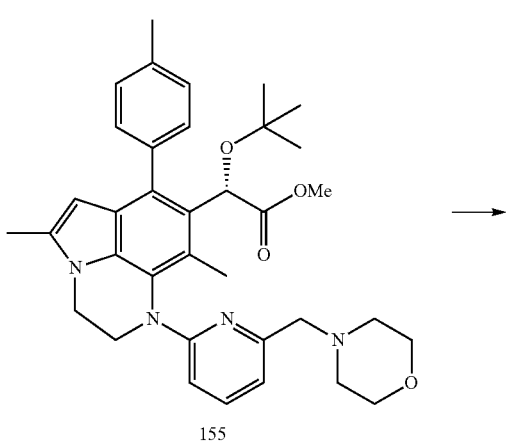

155

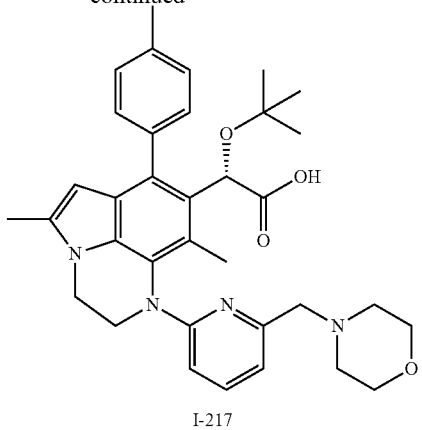

I-217

Step 1

Under ice-cooling, to Compound 153 (50.0 mg, 0.095 mmol) in dichloromethane (1 mL) was added Dess-Martin reagent (60.3 mg, 0.142 mmol), the mixture was stirred for 1 hour while elevating to room temperature. Saturated aqueous sodium hydrogen carbonate solution (20 mL) was added thereto, and the mixture was extracted with ethyl acetate (30 mL). The organic layer was washed with saturated aqueous solution of sodium hydrogen carbonate (20 mL) and saturated brine (20 mL), and dried over anhydrous magnesium sulfate. After concentration, the residue was purified by silica gel chromatography (hexane-ethyl acetate) to obtain Compound 154 (32.1 mg, 65% yield) as brown foam.

LC/MS measurement conditions: (1), LC/MS (ESI): m/z=526.4 [M+H]+.

Step 2

To Compound 154 (30 mg, 0.057 mmol) and morpholine (0.015 mL, 0.171 mmol) in dichloromethane (0.9 mL), methanol (0.9 mL) and acetic acid (0.09 mL) solution was added picoline-borane complex (9.2 mg, 0.086 mmol), the mixture was stirred at room temperature for 1 hour. Saturated aqueous sodium hydrogen carbonate solution (20 mL) was added thereto, and the mixture was extracted with ethyl acetate (30 mL). The organic layer was washed with saturated brine (20 mL), and dried over anhydrous magnesium sulfate. After concentration, the residue was purified by amino silica gel chromatography (hexane-ethyl acetate) to obtain Compound 155 (23.2 mg, 68% yield) as brown foam.

LC/MS measurement conditions: (1), LC/MS (ESI): m/z=597.8 [M+H]+.

Step 3

To Compound 155 (22.0 mg, 0.037 mmol) in ethanol (0.5 mL) and THF (0.5 mL) solution was added 4 mol/L aqueous solution of lithium hydroxide (0.500 mL, 2.00 mmol), the mixture was stirred under reflux for 3 hours. 1 mol/L hydrochloric acid (2 mL) and saturated brine (20 mL) were added thereto, and the mixture was extracted with ethyl acetate (30 mL). The organic layer was dried over anhydrous sodium sulfate. After concentration, the residue was purified by diol silica gel column chromatography (hexane-ethylacetate) to obtain Compound I-217 (9.9 mg, 46% yield).

LC/MS measurement conditions: (1), LC/MS (ESI): m/z=583.7 [M+H]+, RT=2.59 min.

$^1$H-NMR (CDCl$_3$) δ: 0.95 (s, 9H), 2.18 (s, 3H), 2.31 (s, 3H), 2.44 (s, 3H), 2.54-2.68 (m, 4H), 3.65 (s, 2H), 3.72-3.81 (m, 4H), 3.89-3.97 (m, 2H), 4.24-4.40 (m, 1H), 4.61-4.80

(m, 1H), 5.62 (s, 1H), 5.95 (s, 1H), 6.26 (d, J=8.3 Hz, 1H), 6.89 (d, J=7.1 Hz, 1H), 7.24-7.32 (m, 2H), 7.37-7.45 (m, 2H), 7.61-7.66 (m, 1H).

Example 41

[Chemical formula 166]

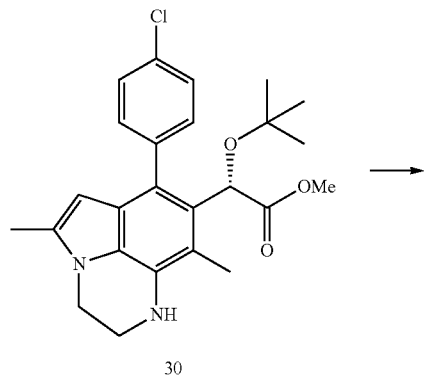

Step 1

To Compound 30 (200 mg, 0.454 mmol) in dichloromethane (2 mL) solution was added isocyanato-2-nitrobenzene (149 mg, 0.907 mmol), the mixture was stirred at 80° C. for 20 hours. Saturated aqueous ammonium chloride solution (15 mL) and water (15 mL) were added thereto, and the mixture was extracted with ethyl acetate (50 mL). The organic layer was washed with water (30 mL) and saturated brine (30 mL), and dried over anhydrous magnesium sulfate. After concentration, the residue was purified by silica gel chromatography (hexane-ethyl acetate) to obtain Compound 156 (235 mg, 86% yield) as brown foam.

LC/MS measurement conditions: (1), LC/MS (ESI): m/z=605.3 [M+H]+.

Step 2

To Compound 156 (190 mg, 0.314 mmol) in ethanol (1.9 mL) and water (0.38 mL) solution were added iron powder (88.0 mg, 1.57 mmol) and sodium chloride (168 mg, 3.14 mmol), the mixture was stirred at 90° C. for 2.5 hours. Water (30 mL) and ethyl acetate (50 mL) were added thereto, and the insoluble material was removed by filtration. The organic layer was washed with water (30 mL) and saturated brine (30 mL), and dried over anhydrous magnesium sulfate. After concentration, the residue was purified by silica gel chromatography (hexane-ethyl acetate) to obtain Compound 157 (108 mg, 60% yield) as brown foam.

LC/MS measurement conditions: (1), LC/MS (ESI): m/z=575.4 [M+H]+.

Step 3

To Compound 157 (125 mg, 0.217 mmol) in ethanol (1 mL) and THF (1 mL) solution was added 4 mol/L aqueous solution of lithium hydroxide (0.543 mL, 2.17 mmol), the mixture was stirred under reflux for 45 min. 1 mol/L hydrochloric acid (3 mL) and saturated brine (20 mL) were added thereto, and the mixture was extracted with ethyl acetate (30 mL). The organic layer was dried over anhydrous sodium sulfate. After concentration, the residue was purified by HPLC (0.1% formic acid in water-0.1% formic acid in acetonitrile) to obtain Compound I-218 (49.0 mg, 40% yield).

LC/MS measurement conditions: (1), LC/MS (ESI): m/z=561.7 [M+H]+, RT=2.42 min.

Example 42

[Chemical formula 167]

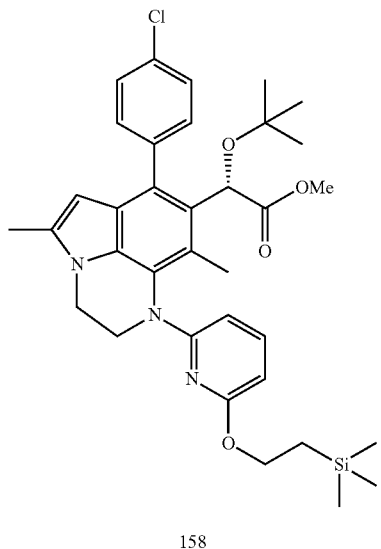

158

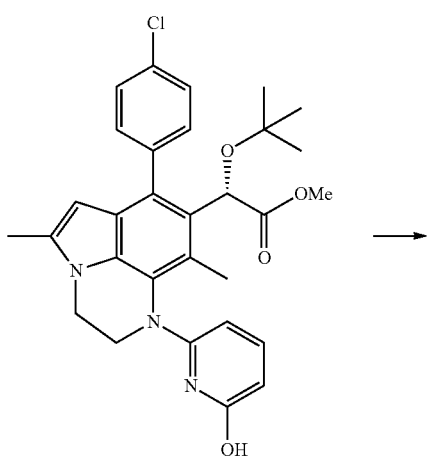

159

Step 1

To Compound 158 (135 mg, 0.213 mmol), which was synthesized by the same technique with Compound 89 of Example 19 in THF solution (0.675 mL), was added 1 mmol/L TBAF in THF solution (0.426 mL, 0.426 mmol), the mixture was stirred at room temperature for 1 day. 1 mmol/L TBAF in THF solution (0.426 mL, 0.426 mmol) was added thereto, and the mixture was stirred at room temperature for 3.5 hours and at 50° C. for 1 day. Water (20 mL) was added to the reaction mixture, and the mixture was extracted with ethyl acetate (30 mL). The organic layer was washed with water (20 mL) and saturated brine (20 mL), and dried over anhydrous magnesium sulfate. After concentration, the residue was purified by silica gel chromatography (hexane-ethyl acetate) to obtain Compound 159 (20 mg, 18% yield) as brown foam.

LC/MS measurement conditions: (1), LC/MS (ESI): m/z=534.6 [M+H]+.

Step 2

To Compound 159 (20.0 mg, 0.037 mmol) in DMF (1 mL) solution was added potassium carbonate (10.4 mg, 0.075 mmol), the mixture was stirred at room temperature for 5 minutes. Then methyl iodide (0.005 mL, 0.075 mmol) was added thereto, and the mixture was stirred at room temperature for 3.5 hours. Water (20 mL) was added to the reaction mixture, and the mixture was extracted with ethyl acetate (30 mL). The organic layer was washed with water (20 mL) and saturated brine (20 mL), and dried over anhydrous magnesium sulfate.

After concentration, the residue was dissolved (20.0 mg) in ethanol (1 mL), and 2 mol/L aqueous solution of sodium hydroxide (0.500 mL, 1.00 mmol) was added thereto, and then the mixture was stirred under reflux for 1.5 hours. 1 mol/L hydrochloric acid (1.5 mL) and saturated brine (20 mL) were added thereto, and the mixture was extracted with ethyl acetate (30 mL). The organic layer was dried over anhydrous sodium sulfate. After concentration, the residue was purified by HPLC (0.1% formic acid in water-0.1% formic acid in acetonitrile) to obtain Compound I-219 (2.6 mg, 13% yield).

LC/MS measurement conditions: (1), LC/MS (ESI): m/z=534.6 [M+H]+, RT=2.46 min.

Example 43

[Chemical formula 168]

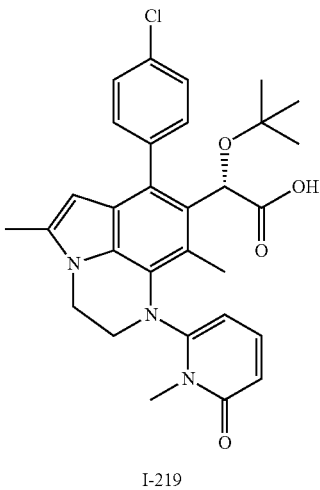

I-219

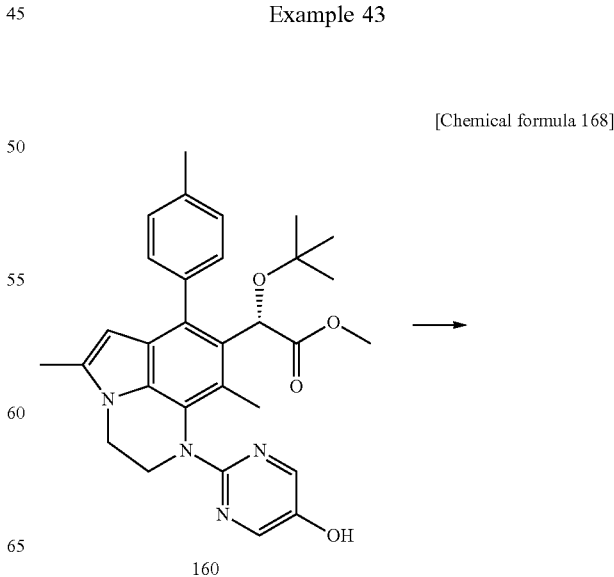

160

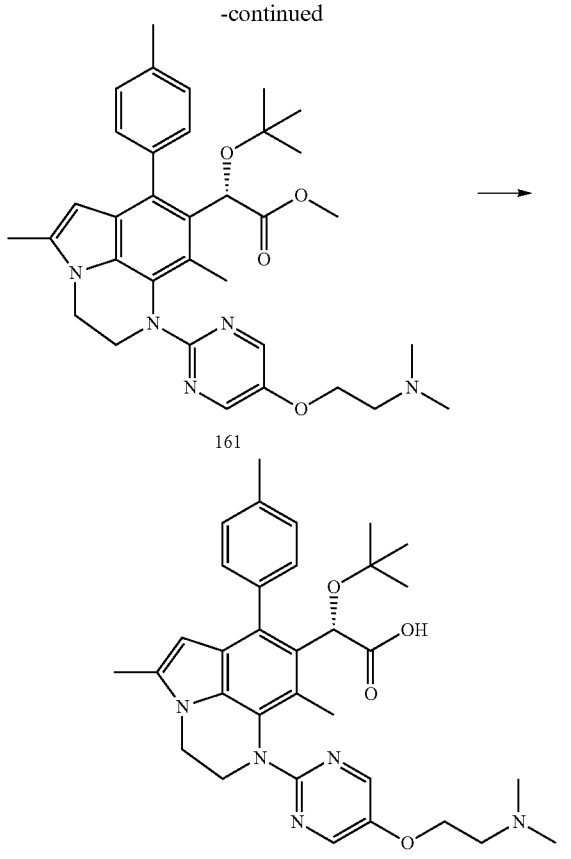

161

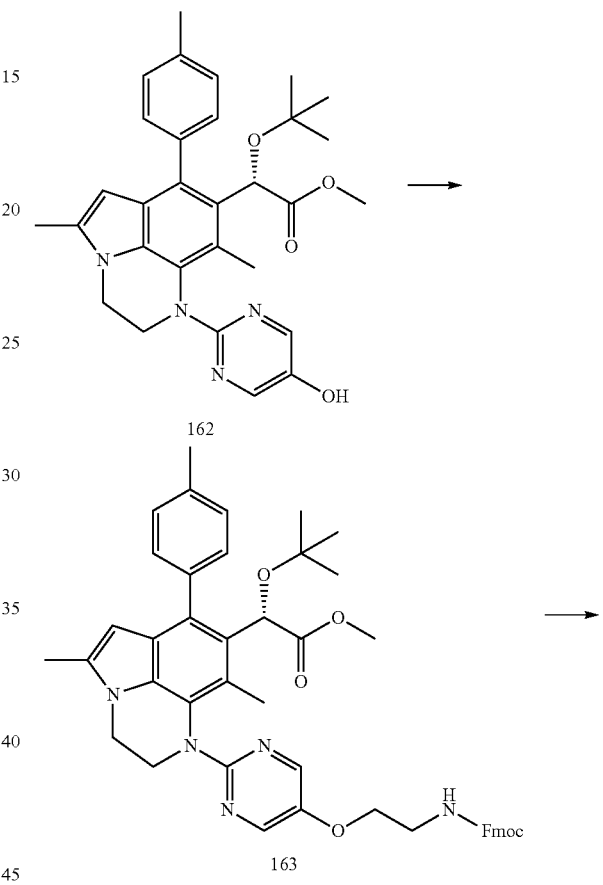

I-220

Step 1 Synthesis of Compound 161

Under ice-cooling, to Compound 160 (513 mg, 0.997 mmol) in THF (5.1 mL) solution were added 2-(dimethylamino)ethanol (267 mg, 2.99 mmol), triphenylphosphine (784 mg, 2.99 mmol) and DIAD (605 mg, 2.99 mmol), the mixture was stirred at room temperature for 40 minutes. Under ice-cooling, 2-(dimethylamino)ethanol (267 mg, 2.99 mmol), triphenylphosphine (784 mg, 2.99 mmol) and DIAD (605 mg, 2.99 mmol) were added to the reaction mixture, and the mixture was stirred at room temperature for 80 minutes. Ethyl acetate and water were added thereto, and the mixture was extracted with ethyl acetate. The organic layer was washed with saturated brine, and dried over anhydrous sodium sulfate. After concentration under reduced pressure, the residue was purified by silica gel column chromatography (chloroform-methanol) to obtain Compound 161 (476 mg, 82% yield).

LC/MS (ESI): m/z=586.27 [M+H]+, LC/MS measurement conditions: (1).

Step 2 Synthesis of Compound I-220

To Compound 161 (476 mg, 0.812 mmol) in ethanol (4.76 mL) solution was added the 2 mol/L sodium hydroxide solution (2.38 mL), and the mixture was stirred at 80° C. for 140 minutes. After cooling, 2 mol/L hydrochloric acid (2.30 mL) was added thereto, and the mixture was extracted with chloroform-methanol (10:1). After concentration under reduced pressure, the residue was purified by diol silica gel column chromatography (chloroform-methanol) to obtain Compound I-220 (250 mg, 54% yield).

LC/MS (ESI): m/z=572.27 [M+H]+, RT=2.28 min., LC/MS measurement conditions: (1).

$^1$H-NMR (CDCl$_3$) δ: 0.96 (9H, s), 2.19 (3H, s), 2.29 (3H, s), 2.34 (6H, s), 2.43 (3H, s), 2.72 (2H, t, J=5.6 Hz), 3.88-4.19 (5H, m), 4.70-5.05 (1H, m), 5.59 (1H, s), 5.90 (1H, s), 7.21-7.30 (2H, m), 7.36-7.43 (1H, m), 7.61-7.71 (1H, m), 8.17 (2H, s).

Example 44

[Chemical formula 169]

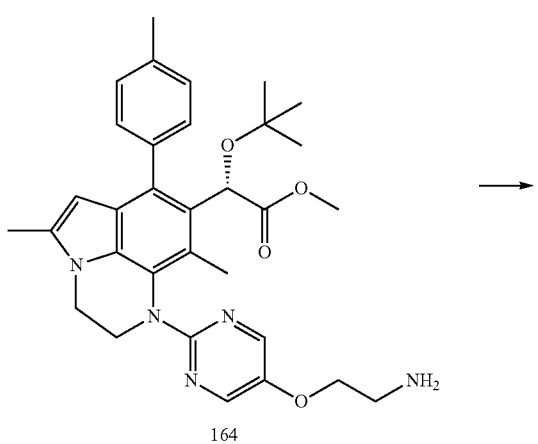

162

163

164

Example 45

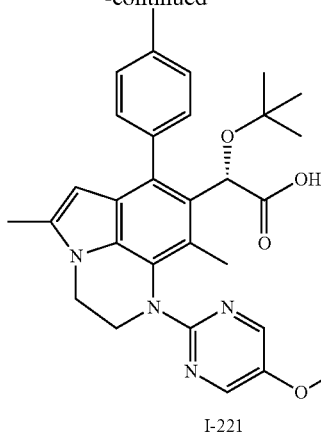

I-221

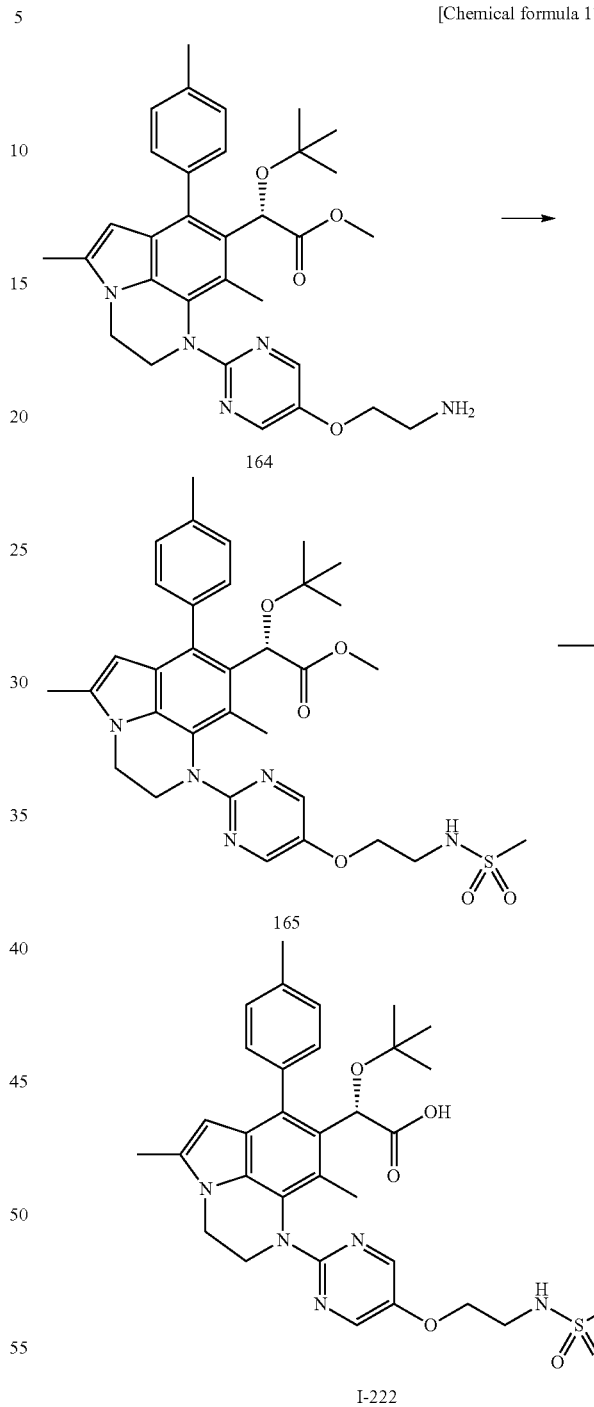

Step 1 Synthesis of Compound 163

Under ice-cooling, to Compound 162 (600 mg, 1.17 mmol) in THF (6.0 mL) solution were added N-Fmoc-ethanolamine (991 mg, 3.50 mmol), triphenylphosphine (917 mg, 3.50 mmol) and DIAD (707 mg, 3.50 mmol), and the mixture was stirred at room temperature for 40 minutes. After concentration under reduced pressure, the residue was purified by silica gel column chromatography (hexane-ethyl acetate) to obtain Compound 163 (493 mg, 54% yield).

LC/MS (ESI): m/z=780.14 [M+H]+, LC/MS measurement conditions: (1).

Step 2 Synthesis of Compound 164

To Compound 163 (493 mg, 0.632 mmol) in dichloromethane (1.7 mL) solution were added diethyl amine (1.21 g, 16.6 mmol), the mixture was stirred at room temperature for 50 minutes, at 35° C. for 30 minutes and at 40° C. for 90 minutes. After cooling, the solvent was concentrated under reduced pressure, the residue was purified by diol silica gel column chromatography (chloroform-methanol) to obtain Compound 164 (276 mg, 78% yield).

LC/MS (ESI): m/z=558.23 [M+H]+, LC/MS measurement conditions: (1).

Step 3 Synthesis of Compound I-221

In the same manner as Step 2 of Example 43, Compound I-221 (41.2 mg, 70% yield) was obtained from Compound 164 (60.0 mg, 0.108 mmol).

LC/MS (ESI): m/z=544.75 [M+H]+, RT=2.67 min., LC/MS measurement conditions: (1).

$^1$H-NMR (CDCl$_3$) δ: 0.88 (9H, s), 2.17 (3H, s), 2.31 (3H, s), 2.40 (3H, s), 2.79-4.11 (8H, m), 5.53 (1H, s), 5.96 (1H, s), 7.17-7.30 (2H, m), 7.38-7.46 (1H, m), 7.60-7.69 (1H, m), 8.01 (2H, brs).

Step 1 Synthesis of Compound 165

Under ice-cooling, to Compound 164 (150 mg, 0.269 mmol) in dichloromethane (0.75 mL) solution were added pyridine (63.8 mg, 0.807 mmol), mesyl chloride (37.0 mg, 0.323 mmol) and DMAP (3.3 mg, 0.027 mmol), and the mixture was stirred at room temperature for 20 minutes. Under ice-cooling, pyridine (21.3 mg, 0.269 mmol) and mesyl chloride (30.8 mg, 0.269 mmol) were added thereto, and the mixture was stirred for 30 minutes. Under ice-cooling, pyridine (0.75 mL) and mesyl chloride (61.6 mg, 0.538 mmol) were added thereto, and the mixture was stirred for 20 minutes. Ethyl acetate and 1 mol/L hydrochloric acid were added thereto, and the mixture was extracted with ethyl acetate. The organic layer was washed sequentially with 1 mol/L hydrochloric acid, saturated aqueous sodium hydrogen carbonate solution and saturated brine, and dried over anhydrous sodium sulfate. After concentration under reduced pressure, the residue was purified by silica gel column chromatography (hexane-ethyl acetate) to obtain Compound 165 (146 mg, 85% yield).

LC/MS (ESI): m/z=636.71 [M+H]+, LC/MS measurement conditions: (1).

Step 2 Synthesis of Compound I-222

In the same manner as Step 2 of Example 43, Compound I-222 (45.9 mg, 78% yield) was obtained from Compound 165 (60.0 mg, 0.094 mmol).

LC/MS (ESI): m/z=622.41 [M+H]+, RT=2.55 min, LC/MS measurement conditions: (1)

$^1$H-NMR (CDCl$_3$) δ: 0.96 (9H, s), 2.20 (3H, s), 2.29 (3H, s), 2.43 (3H, s), 3.02 (3H, s), 3.47-3.60 (2H, m), 3.89-4.21 (5H, m), 4.63-4.99 (2H, m), 5.61 (1H, s), 5.91 (1H, s), 7.22-7.31 (2H, m), 7.36-7.43 (1H, m), 7.61-7.69 (1H, m), 8.15 (2H, s), 9.85-10.30 (1H, brs).

Example 46

Synthesis of Compound I-223 and Compound I-224

[Chemical formula 171]

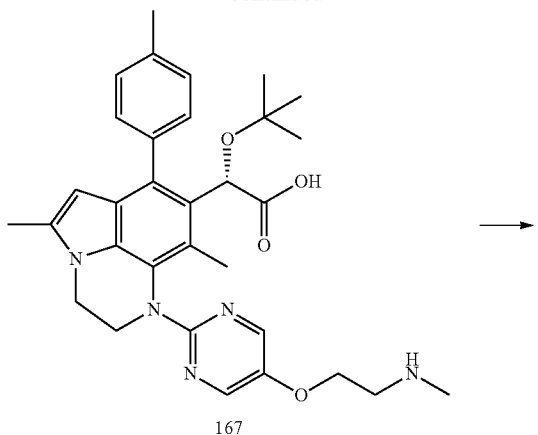
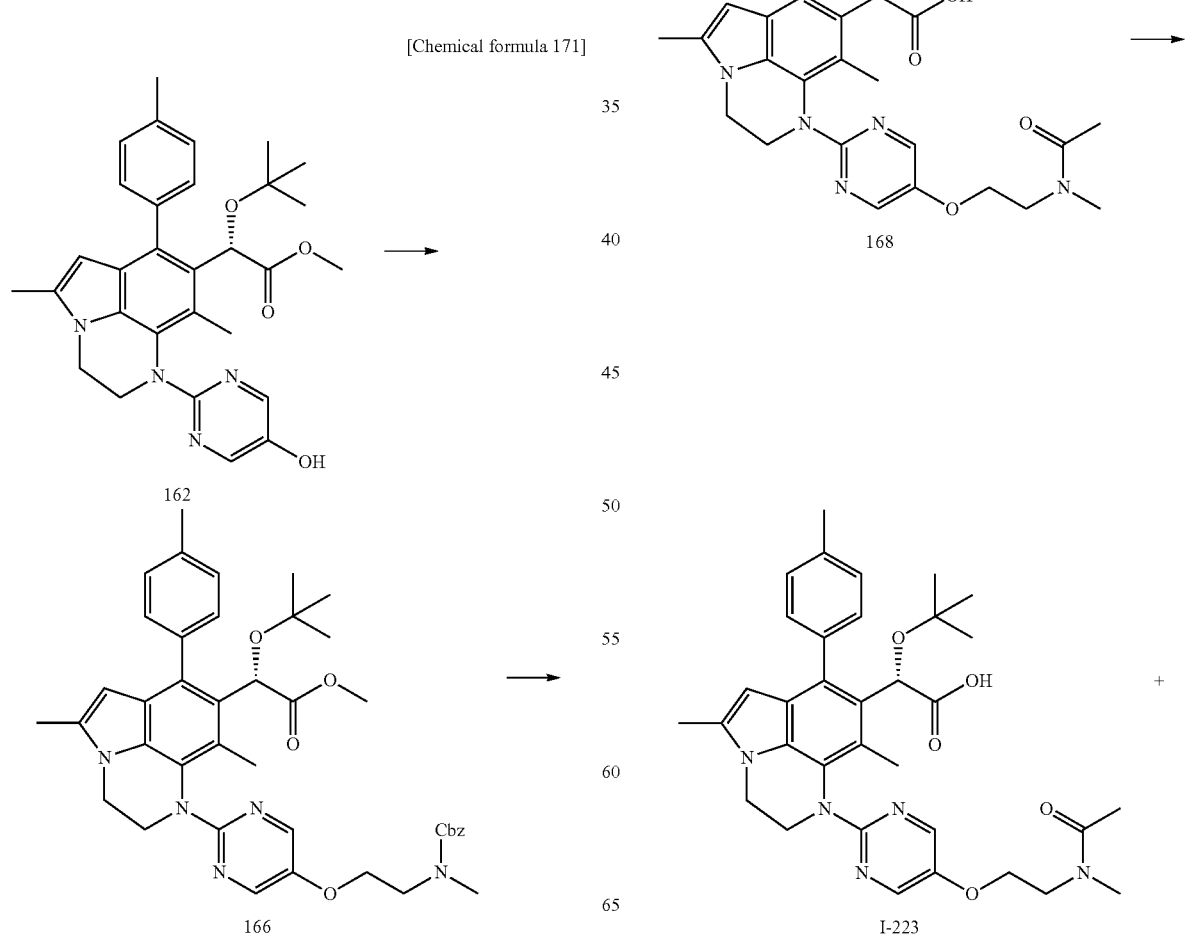

-continued

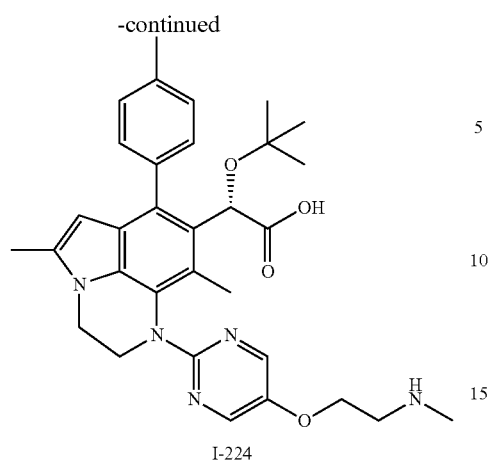

I-224

Step 1 Synthesis of Compound 166

Under ice-cooling, to Compound 162 (500 mg, 0.972 mmol) in THF (5.0 mL) solution were added N,N-Cbz-methyl-ethanolamine (610 mg, 2.91 mmol), triphenylphosphine (765 mg, 2.91 mmol) and DIAD (589 mg, 2.91 mmol), and the mixture was stirred at room temperature for 20 minutes. Then, the mixture was allowed to stand at room temperature for 14 hours. The solvent was concentrated under reduced pressure, the residue was purified by silica gel column chromatography (hexane-ethyl acetate) to obtain Compound 166 (498 mg, 73% yield).

LC/MS (ESI): m/z=706.51 [M+H]+, LC/MS measurement conditions: (1).

Step 2 Synthesis of Compound 167

To Compound 166 (250 mg, 0.354 mmol) in THF (5.00 mL) and methanol (5.00 mL) solution was added Pd—C (75.0 mg, 0.035 mmol), and the mixture was stirred under a hydrogen atmosphere at room temperature for 1 hour. The reaction mixture was filtered through Celite, the filtrate was concentrated under reduced pressure to obtain Compound 167 (192 mg, 95% yield) as a crude product.

LC/MS (ESI): m/z=572.84 [M+H]+, LC/MS measurement conditions: (1).

Step 3 Synthesis of Compound 168

Under ice-cooling, to Compound 167 (60 mg, 0.105 mmol) in methanol (0.420 mL) solution was added acetic anhydride (16.1 mg, 0.157 mmol), and the mixture was stirred at room temperature for 20 minutes. Saturated aqueous solution of sodium hydrogen carbonate was added thereto, and the mixture was stirred for 30 minutes. Ethyl acetate and water were added thereto, and the mixture was extracted with ethyl acetate. The organic layer was washed sequentially with saturated aqueous sodium hydrogen carbonate solution and saturated brine, and dried over anhydrous sodium sulfate. The solvent was concentrated under reduced pressure, to obtain Compound 168 (62.8 mg, 98% yield) as a crude product.

LC/MS (ESI): m/z=614.42 [M+H]+, LC/MS measurement conditions: (1).

Step 4 Syntheses of Compound I-223 and Compound I-224

In the same manner as step 2 of Example 43, Compound I-223 (25.2 mg, 41% yield) and Compound I-224 (26.9 mg, 47% yield) were obtained from Compound 168 (62.8 mg, 0.102 mmol).

Compound I-223: LC/MS (ESI): m/z=600.77 [M+H]+, RT=2.52 min., LC/MS measurement conditions: (1).

¹H-NMR (CDCl₃) δ: 0.97 (9H, s), 2.07-2.24 (6H, m), 2.29 (3H, s), 2.43 (3H, s), 3.01 (1H, s), 3.16 (2H, s), 3.64-3.82 (2H, m), 3.91-4.23 (5H, m), 4.75-5.05 (1H, m), 5.54-5.68 (1H, m), 5.91 (1H, s), 7.21-7.32 (2H, m), 7.36-7.44 (1H, m), 7.62-7.70 (1H, m), 8.13 (2H, s), 10.07 (1H, br s).

Compound I-224: LC/MS (ESI): m/z=558.51 [M+H]+, RT=2.35 min., LC/MS measurement conditions: (1).

¹H-NMR (CDCl₃) δ: 0.88 (9H, s), 2.16 (3H, s), 2.28 (3H, s), 2.42 (3H, s), 2.58 (3H, s), 2.80-3.07 (2H, m), 3.75-4.18 (6H, m), 4.65-5.06 (1H, m), 5.55 (1H, s), 5.95 (1H, s), 7.19-7.30 (2H, m), 7.39-7.46 (1H, m), 7.61-7.71 (1H, m), 8.07 (2H, s).

Example 47

[Chemical formula 172]

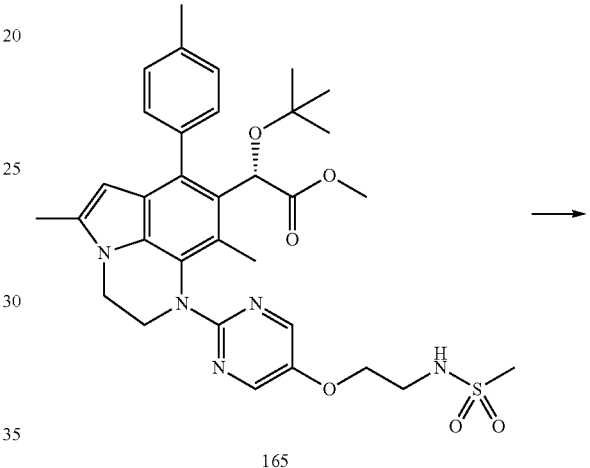

165

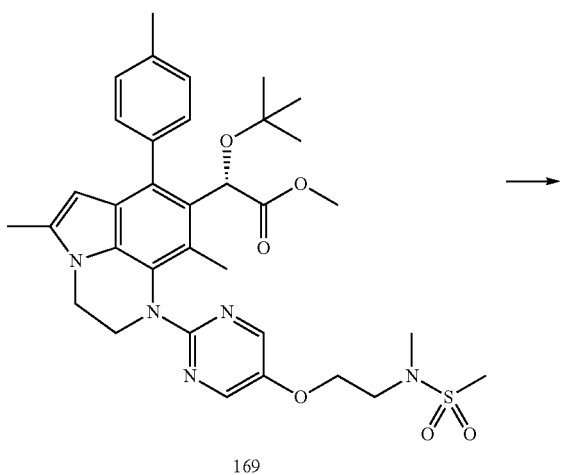

169

-continued

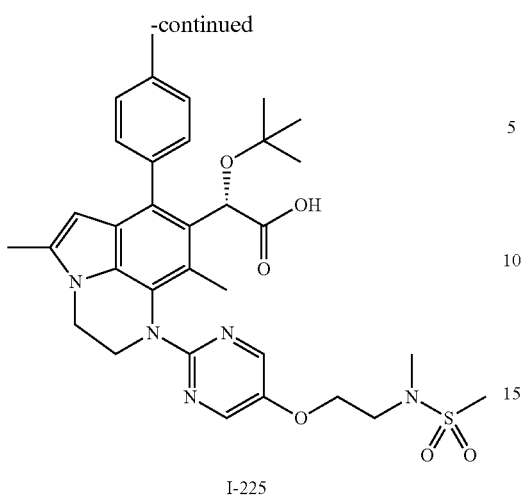

I-225

Step 1 Synthesis of Compound 169

To Compound 165 (60.0 mg, 0.094 mmol) in DMF (0.60 mL) solution were added cesium carbonate (92.0 mg, 0.283 mmol) and iodomethane (26.8 mg, 0.189 mmol), the mixture was stirred at room temperature for 20 minutes. Ethyl acetate and water were added thereto, and the mixture was extracted with ethyl acetate. The organic layer was washed with water, and dried over anhydrous sodium sulfate. The solvent was concentrated under reduced pressure to obtain Compound 169 (62.6 mg) quantitatively as a crude product.

LC/MS (ESI): m/z=650.42 [M+H]+, LC/MS measurement conditions: (1).

Step 2 Synthesis of Compound I-225

In the same manner as Step 2 of Example 43, Compound I-225 (51.6 mg, 86% yield) was obtained from Compound 169 (61.1 mg, 0.094 mmol).

LC/MS (ESI): m/z=636.42 [M+H]+, RT=2.67 min., LC/MS measurement conditions: (1).

$^1$H-NMR (CDCl$_3$) δ: 0.97 (9H, s), 2.20 (3H, s), 2.29 (3H, s), 2.43 (3H, s), 2.88 (3H, s), 3.02 (3H, s), 3.57 (2H, t, J=5.3 Hz), 3.92-4.22 (5H, m), 4.74-4.99 (1H, m), 5.61 (1H, s), 5.91 (1H, s), 7.21-7.31 (2H, m), 7.36-7.43 (1H, m), 7.60-7.70 (1H, m), 8.15 (2H, s), 10.10 (1H, brs).

Example 48

[Chemical formula 173]

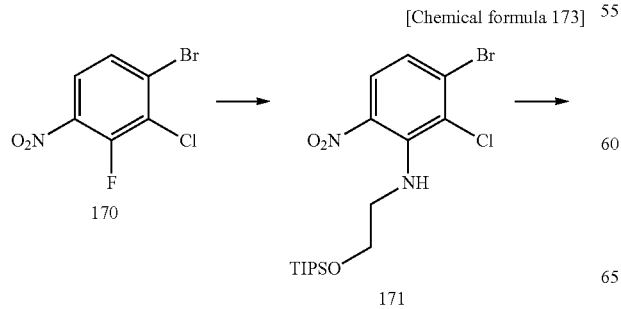

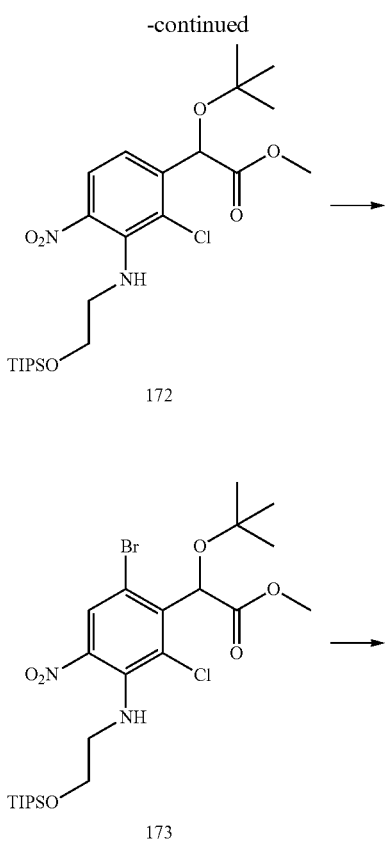

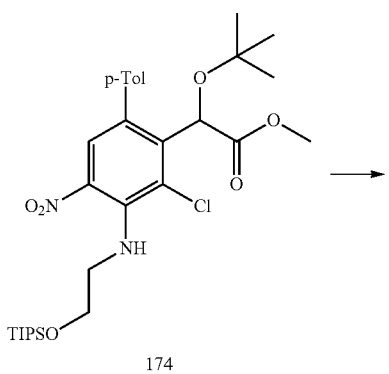

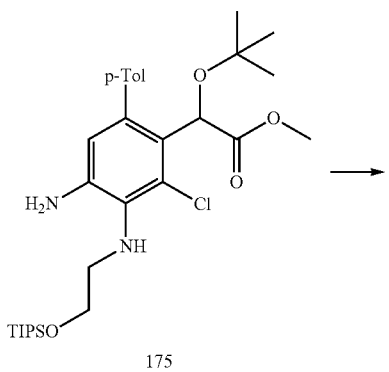

267
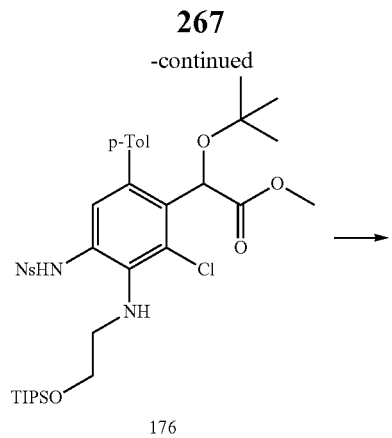
176
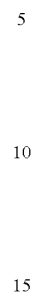
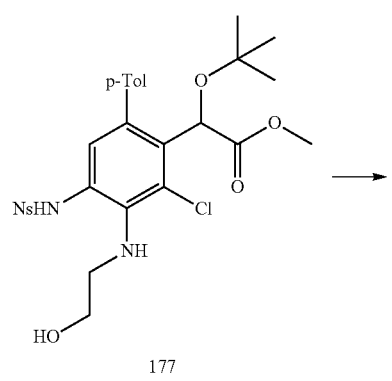
177
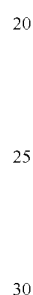
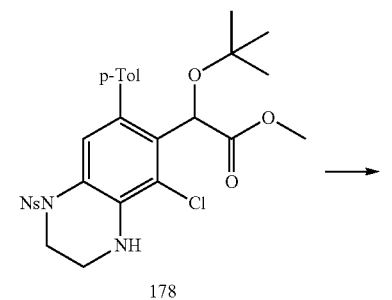
178
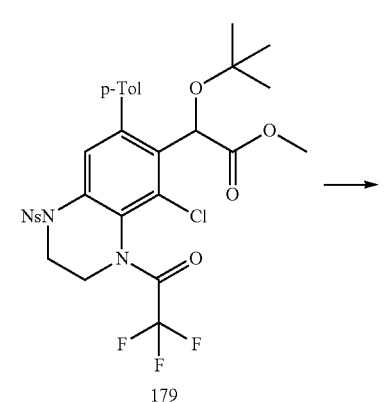
179
268
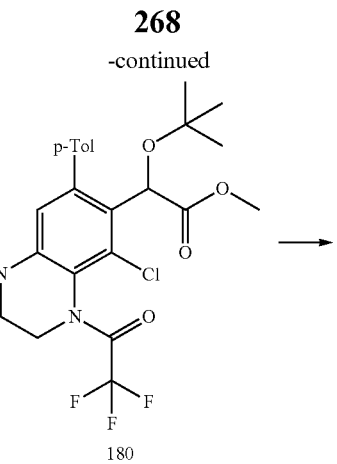
180
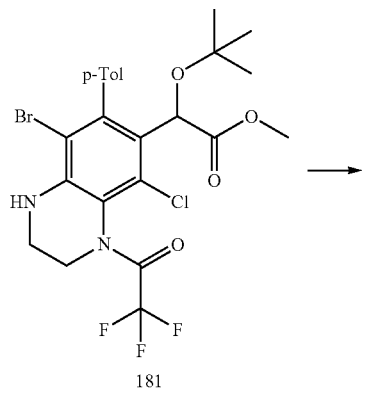
181
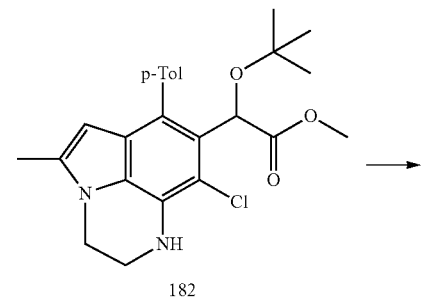
182
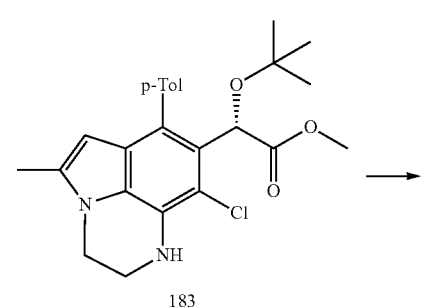
183

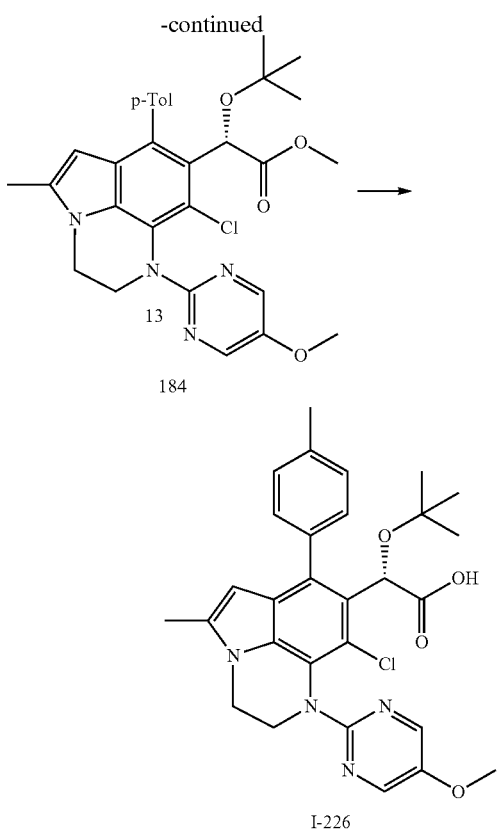

Step 1 Synthesis of Compound 171

To Compound 170 (10.0 g, 39.3 mmol) in DMF (50.0 mL) solution were added triethylamine (4.77 g, 47.2 mmol) and aminoethanol (2.40 g, 39.3 mmol), the mixture was stirred at room temperature for 30 minutes. Imidazole (6.02 g, 88.0 mmol) and triisopropylsilyl chloride (7.96 g, 41.3 mmol) were added thereto, and the mixture was stirred for 30 minutes. DMAP (240 mg, 1.97 mmol) was added thereto, and the mixture was stirred for 30 minutes. Imidazole (6.02 g, 88.0 mmol) and triisopropylsilyl chloride (7.96 g, 41.3 mmol) were added thereto, and the mixture was stirred for 10 minutes, then, allowed to stand at room temperature for 12 hours. Ethyl acetate and water were added thereto, and the mixture was extracted with ethyl acetate. The organic layer was washed with water, and dried over anhydrous sodium sulfate. After concentration under reduced pressure, the residue was purified by silica gel column chromatography (hexane-ethyl acetate) to obtain Compound 171 (15.9 g, 90% yield).

LC/MS (ESI): m/z=451.01 [M+H]+, LC/MS measurement conditions: (1).

Step 2 Synthesis of Compound 172

To Compound 171 (15.9 g, 35.2 mmol) in DMF (111 mL) solution were added (Z)-((2-(tert-butoxy)-1-methoxy-vinyl)oxy)trimethylsilane (15.4 g, 70.3 mmol), $ZnF_2$ (7.27 g, 70.3 mmol) and Bis-tri-tert-butylphosphine palladium (1.80 g, 3.52 mmol), the mixture was stirred under nitrogen atmosphere at 100° C. for 2 hours. After cooling, ethyl acetate and water were added thereto, and the mixture was filtered. After extraction with ethyl acetate, the organic layer was washed with water, and dried with anhydrous sodium sulfate. After concentration under reduced pressure, the residue was purified by silica gel column chromatography (hexane-ethyl acetate) to obtain Compound 172 (12.6 g, 69% yield).

LC/MS (ESI): m/z=517.22 [M+H]+, LC/MS measurement conditions: (1).

Step 3 Synthesis of Compound 173

Under ice-cooling, to Compound 172 (12.5 g, 24.2 mmol) in DMF (125 mL) solution was added NBS (5.16 g, 29.0 mmol), the mixture was stirred at room temperature for 4 hours and allowed to stand at room temperature for 11 hours. Ethyl acetate and water were added thereto, and the mixture was extracted with ethyl acetate. The organic layer was washed sequentially with water, saturated aqueous sodium hydrogen carbonate solution and saturated brine, and dried over anhydrous sodium sulfate. After concentration under reduced pressure, Compound 173 (15.1 g) was obtained quantitatively as a crude product.

LC/MS (ESI): m/z=595.13 [M+H]+, LC/MS measurement conditions: (1).

Step 4 Synthesis of Compound 174

To Compound 173 (9.09 g, 15.3 mmol) in DMF (45.5 mL) and water (22.7 mL) solution were added under nitrogen atmosphere p-tolyl boronic acid (3.11 g, 22.9 mmol), carbonate potassium (6.32 g, 45.8 mmol) and $PdCl_2$(dtbpf) (994 mg, 1.53 mmol), the mixture was stirred at 100° C. for 30 minutes. Ethyl acetate and water were added thereto, and the mixture was filtered. Then, the mixture was extracted with ethyl acetate, the organic layer was washed with water, and dried over anhydrous sodium sulfate. After concentration under reduced pressure, the residue was purified by silica gel column chromatography (hexane-ethyl acetate) to obtain Compound 174 (5.96 g, 64% yield).

LC/MS (ESI): m/z=607.26 [M+H]+, LC/MS measurement conditions: (1).

Step 5 Synthesis of Compound 175

To Compound 174 (117 mg, 0.193 mmol) in ethanol (1.17 mL) and water (0.29 mL) solution was added sodium dithionite (197 mg, 0.963 mmol), and the mixture was stirred at 60° C. for 1 hour. Ethyl acetate and water were added thereto, and the mixture was extracted with ethyl acetate. The organic layer was washed with water, and dried over anhydrous sodium sulfate. After extraction under reduced pressure, Compound 175 (113 mg) was obtained quantitatively as a crude product.

LC/MS (ESI): m/z=577.31 [M+H]+, LC/MS measurement conditions: (1).

Step 6 Synthesis of Compound 176

Under ice-cooling, to Compound 175 (111 mg, 0.193 mmol) in dichloromethane (0.56 mL) were added pyridine (38.2 mg, 0.483 mmol), 2-nitrobenzenesulfonyl chloride (64.2 mg, 0.290 mmol) and DMAP (2.4 mg, 0.019 mmol), and the mixture was stirred at room temperature for 30 minutes, then the mixture was allowed to stand at room temperature for 15 hours. Ethyl acetate and 1 mol/L hydrochloric acid were added thereto, and the mixture was extracted with ethyl acetate. The organic layer was washed sequentially with saturated aqueous sodium hydrogen carbonate solution and saturated brine, and dried over anhydrous sodium sulfate. After concentration under reduced pressure, the residue was purified by silica gel column chromatography (hexane-ethyl acetate) to obtain Compound 176 (68.0 mg, 46% yield).

LC/MS (ESI): m/z=762.25 [M+H]+, LC/MS measurement conditions: (1).

Step 7 Synthesis of Compound 177

To Compound 176 (1.77 g, 2.33 mmol) in THF (8.85 mL) solution was added 1 mol/L of TBAF in THF solution (6.96 mL, 6.96 mmol), and the mixture was stirred at 60° C. for 3 hours. After cooling, ethyl acetate and saturated ammonium chloride solution were added thereto, and the mixture was extracted with ethyl acetate. The organic layer was washed sequentially with aqueous saturated ammonium chloride solution and saturated brine, and dried over anhydrous sodium sulfate. After concentration under reduced pressure, the residue was purified by silica gel column chromatography (hexane-ethyl acetate) to obtain Compound 177 (1.13 g, 80% yield).

LC/MS (ESI): m/z=606.14 [M+H]+, LC/MS measurement conditions: (1).

Step 8 Synthesis of Compound 178

Under ice-cooling, to Compound 177 (1.12 g, 1.85 mmol) in THF (56.0 mL) solution were added triphenylphosphine (727 mg, 2.77 mmol) and DIAD (561 mg, 2.77 mmol), the mixture was stirred at room temperature for 20 minutes. Ethyl acetate and water were added thereto, and the mixture was extracted with ethyl acetate. The organic layer was washed with saturated brine and dried with anhydrous sodium sulfate. After concentration under reduced pressure, the residue was purified by silica gel column chromatography (hexane-ethyl acetate) to obtain Compound 178 (960 mg, 88% yield).

LC/MS (ESI): m/z=588.11 [M+H]+, LC/MS measurement conditions: (1).

Step 9 Synthesis of Compound 179

Under ice-cooling, to Compound 178 (850 mg, 1.45 mmol) in pyridine (4.23 mL) were added TFAA (911 mg, 4.34 mmol) and DMAP (530 mg, 4.34 mmol), the mixture was stirred at room temperature for 75 minutes. TFAA (455 mg, 2.17 mmol) was added thereto, and the mixture was stirred at room temperature for 40 minutes. Ethyl acetate and 1 mol/L hydrochloric acid were added thereto, and the mixture was extracted with ethyl acetate. The organic layer was washed sequentially with saturated aqueous sodium hydrogen carbonate solution and saturated brine, and dried over anhydrous sodium sulfate. After concentration under reduced pressure, the residue was purified by silica gel column chromatography (hexane-ethyl acetate) to obtain Compound 179 (966 mg, 98% yield).

LC/MS (ESI): m/z=701.65 [M+18]+, LC/MS measurement conditions: (1).

Step 10 Synthesis of Compound 180

Under ice-cooling, to Compound 179 (956 mg, 1.40 mmol) in DMF (9.57 mL) solution were added potassium carbonate (386 mg, 2.79 mmol) and thiophenol (231 mg, 2.10 mmol), and the mixture was stirred at 0° C. for 70 minutes. Ethyl acetate and 1 mol/L hydrochloric acid were added thereto, and the mixture was extracted with ethyl acetate. The organic layer was washed with water, and dried over anhydrous sodium sulfate. After concentration under reduced pressure, the residue was purified by silica gel column chromatography (hexane-ethyl acetate) to obtain Compound 180 (632 mg, 91% yield).

LC/MS (ESI): m/z=516.15 [M+18]+, LC/MS measurement conditions: (1)

Step 11 Synthesis of Compound 181

To Compound 180 (632 g, 1.27 mmol) in DMF (6.3 mL) solution was added NBS (225 mg, 1.267 mmol), the mixture was stirred at room temperature for 20 minutes. Ethyl acetate and water were added thereto, and the mixture was extracted with ethyl acetate. The organic layer was washed with water, and dried over anhydrous sodium sulfate. After concentration under reduced pressure, Compound 181 (731 mg, 99% yield) was obtained as a crude product.

LC/MS (ESI): m/z=762.60 [M+H]+, LC/MS measurement conditions: (1).

Step 12 and 13 Synthesis of Compound 182

To Compound 182 (727 mg, 1.26 mmol) in toluene (7.3 mL) solution were added isopropenyl acetate (504 mg, 5.03 mmol), tributyl(methoxy)stannane (1.62 g, 5.03 mmol), palladium acetate (56.0 mg, 0.252 mmol) and tri(o-tolyl)phosphine (153 mg, 0.503 mmol), the mixture was stirred under nitrogen atmosphere at 100° C. for 1 hour. Ethyl acetate and 4 mol/L aqueous potassium fluoride solution were added thereto, and the mixture was stirred for 1 hour and filtered. The filtrate was extracted with ethyl acetate, and the organic layer was washed with saturated brine, and dried over anhydrous sodium sulfate. After concentration under reduced pressure, to the obtained crude product in methanol (7.3 mL) and THF (7.3 mL) solution was added potassium carbonate (1.74 g, 12.6 mmol), and the mixture was stirred for 40 min. Ethyl acetate and water were added thereto, and the mixture was extracted with ethyl acetate. The organic layer was washed with saturated brine, and dried over anhydrous sodium sulfate. After concentration under reduced pressure, the residue was purified by silica gel column chromatography (hexane-ethyl acetate) to obtain Compound 182 (460 mg, 83% yield) as a racemic form. By performing further optical resolution, Compound 183 (194 mg, 35% yield) was obtained as an optically active form.

LC/MS (ESI): m/z=441.59 [M+H]+, LC/MS measurement conditions: (1).

Step 14 and 15 Synthesis of Compound 184

To Compound 183 (60.0 mg, 0.136 mmol) in toluene (0.60 mL) solution were added sodium tert-butoxide (19.6 mg, 0.204 mmol), 2-bromo-5-methoxypyrimidine (38.6 g, 0.204 mmol), Xantphos (31.5 mg, 0.054 mmol) and dibenzylideneacetone palladium (24.9 mg, 0.027 mmol), the mixture was stirred under nitrogen atmosphere at 60° C. for 70 minutes. Sodium tert-butoxide (19.6 mg, 0.204 mmol) and 2-bromo-5-methoxypyrimidine (38.6 g, 0.204 mmol) were added thereto under nitrogen atmosphere, and the mixture was stirred at 60° C. for 45 minutes. Ethyl acetate, water and chloroform were added thereto, and the mixture was filtered. The filtrate was extracted with chloroform, and dried over anhydrous sodium sulfate. After concentration under reduced pressure, the residue was purified by silica gel column chromatography (hexane-ethyl acetate) to obtain Compound 184 (72.1 mg, 97% yield).

LC/MS (ESI): m/z=549.19 [M+H]+, LC/MS measurement conditions: (1).

Step 14 Synthesis of Compound I-226

To Compound 184 (72.1 mg, 0.131 mmol) in ethanol (1.00 mL) solution was added 2 mol/L sodium hydroxide solution (0.500 mL), and the mixture was stirred at 80° C. for 160 minutes. After cooling, 2 mol/L hydrochloric acid (0.500 mL) was added under ice-cooling thereto. The precipitated crystals were collected by filtration to obtain Compound I-226 (48.1 mg, 69% yield).

LC/MS (ESI): m/z=535.15 [M+H]+, RT=2.67 min., LC/MS measurement conditions: (1).

$^1$H-NMR (CDCl$_3$) δ: 0.95 (9H, s), 2.31 (3H, s), 2.43 (3H, s), 3.84 (3H, s), 3.94-4.23 (3H, m) 4.72-4.87 (1H, m), 5.56 (1H, brs), 5.98 (1H, brs), 7.21-7.32 (2H, m), 7.37-7.48 (1H, m), 7.61-7.74 (1H, m), 8.18 (2H, s).

Example 49

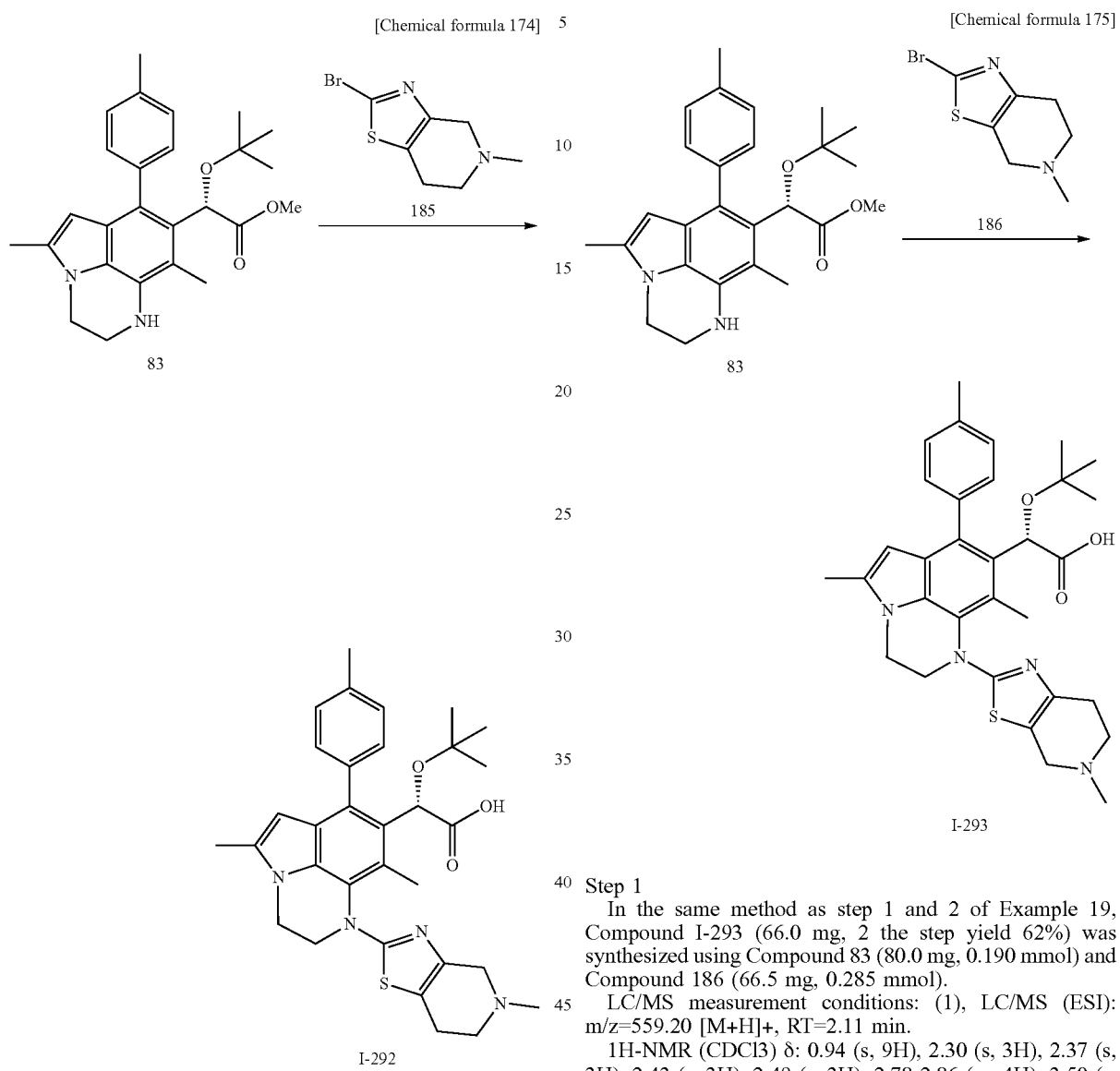

Step 1

In the same method as step 1 and 2 of Example 19, Compound I-292 (60.0 mg, 56%, 2 the step yield) was synthesized using Compound 83 (80.0 mg, 0.190 mmol) and Compound 185 (66.5 mg, 0.285 mmol).

LC/MS measurement conditions: (1), LC/MS (ESI): m/z=559.20 [M+H]+, RT=2.10 min.

1H-NMR (CDCl3) δ: 0.95 (s, 9H), 2.31 (s, 3H), 2.37 (s, 3H), 2.44 (s, 3H), 2.47 (s, 3H), 2.77-2.82 (m, 4H), 3.46 (s, 2H), 3.95-4.04 (m, 3H), 4.61-4.66 (m, 1H), 5.57 (s, 1H), 5.93 (s, 1H), 7.26-7.29 (m, 2H), 7.39 (d, J=6.6 Hz, 1H), 7.62 (d, J=7.1 Hz, 1H).

Example 50

Step 1

In the same method as step 1 and 2 of Example 19, Compound I-293 (66.0 mg, 2 the step yield 62%) was synthesized using Compound 83 (80.0 mg, 0.190 mmol) and Compound 186 (66.5 mg, 0.285 mmol).

LC/MS measurement conditions: (1), LC/MS (ESI): m/z=559.20 [M+H]+, RT=2.11 min.

1H-NMR (CDCl3) δ: 0.94 (s, 9H), 2.30 (s, 3H), 2.37 (s, 3H), 2.43 (s, 3H), 2.49 (s, 3H), 2.78-2.86 (m, 4H), 3.50 (s, 2H), 3.93-4.07 (m, 3H), 4.56-4.67 (m, 1H), 5.56 (s, 1H), 5.93 (s, 1H), 7.24-7.30 (m, 2H), 7.39 (d, J=7.2 Hz, 1H), 7.62 (d, J=7.3 Hz, 1H).

Example 51

-continued
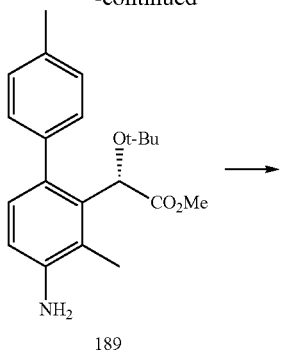
189
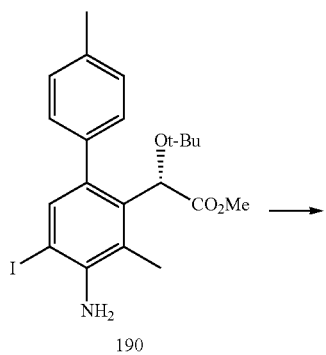
190
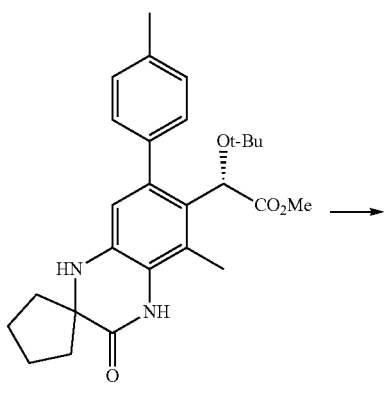
191
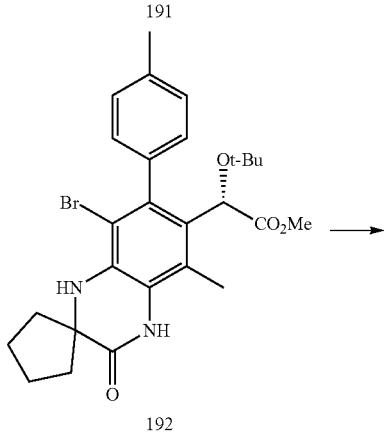
192
-continued
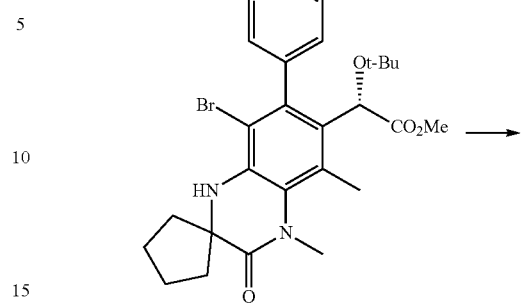
193
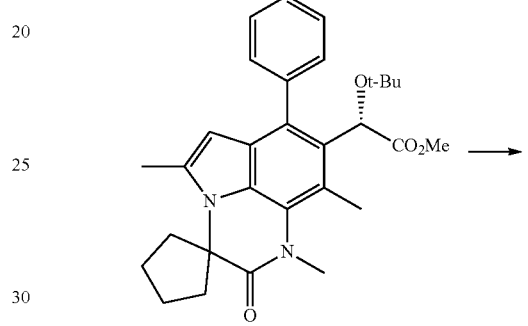
194
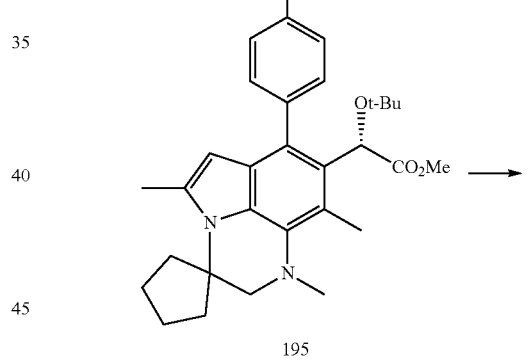
195
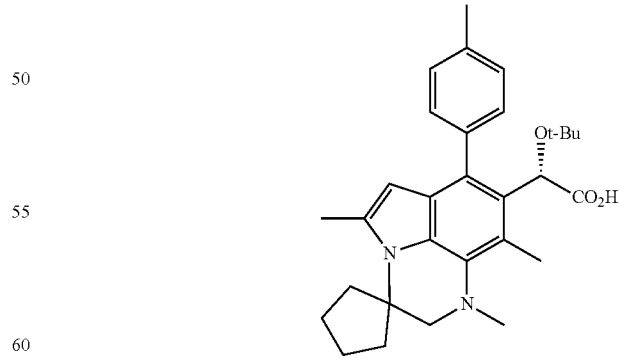
I-302
Step 1
Under cooling of dry ice-acetone bath, to Compound 187 (1.80 g, 7.16 mmol) in DMA (4 mL) solution was added dropwise N-bromosuccinimide (1.01 g, 5.66 mmol) in DMA (4 mL) solution, and the mixture was stirred for 1 hour. 10% aqueous sodium thiosulfate solution (1 mL) and saturated aqueous sodium hydrogen carbonate solution and water (10 mL) were added thereto, and the mixture was stirred at room temperature. Methanol (4 mL) and water (5 mL) were added thereto, and the mixture was stirred at room temperature. The resulting solid was collected by filtration and washed with 40% aqueous methanol solution (50 mL) to obtain Compound 188 (1.70 g, 72% yield) as a pale brown solid.

1H-NMR (CDCl3) δ: 1.22 (s, 9H), 2.20 (s, 3H), 3.63 (s, 2H), 3.68 (s, 3H), 5.78 (s, 1H), 6.51 (d, J=8.4 Hz, 1H), 7.21 (d, J=8.4 Hz, 1H).

Step 2

To Compound 188 (10.0 g, 30.3 mmol), 4-tolylboronic acid (4.32 g, 31.8 mmol) and palladium (987 mg, 1.51 mmol) in DMF (50 mL)-water (5 mL) solution was added sodium carbonate (8.37 g, 60.6 mmol), and the mixture was stirred under nitrogen atmosphere at 120° C. for 1 hour. Water (150 mL) and ethyl acetate (150 mL) were added thereto, and the insoluble material was removed by filtration. The organic layer was washed with water (100 mL×2 times) and saturated brine (100 mL). After activated carbon and anhydrous magnesium sulfate were added thereto, the insoluble were filtered off, and the filtrate was concentrated under reduced pressure. The residue was purified by silica gel chromatography (hexane-ethyl acetate) to obtain Compound 189 (9.62 g, 93% yield) as a brown oily material.

1H-NMR (CDCl3) δ: 0.89 (s, 9H), 2.20 (s, 3H), 2.40 (s, 3H), 3.65 (s, 2H), 3.75 (s, 3H), 5.32 (s, 1H), 6.69 (d, J=8.1 Hz, 1H), 6.93 (d, J=8.1 Hz, 1H), 7.18 (d, J=8.1 Hz, 2H), 7.24-7.37 (m, 2H).

Step 3

To Compound 189 (7.00 g, 20.5 mmol) in dichloromethane (35 mL) and methanol (35 mL) solution were added calcium carbonate (2.67 g, 26.7 mmol) and benzyltrimethylammonium dichloroiodate (8.56 g, 24.6 mmol), and the mixture was stirred at room temperature for 20 hours. Under ice-cooling, 10% sodium bisulfite (100 mL) and saturated aqueous sodium bicarbonate solution (100 mL) were added thereto, and the mixture was extracted with ethyl acetate (300 mL). The organic layer was washed with water (30 mL) and saturated brine (30 mL), and dried over anhydrous magnesium sulfate. After concentration, the residue was purified by silica gel chromatography (hexane ethyl acetate) to obtain Compound 190 (8.42 g, 88% yield) as a brown solid.

1H-NMR (CDCl3) δ: 0.88 (s, 9H), 2.28 (s, 3H), 2.39 (s, 3H), 3.75 (s, 3H), 4.14 (s, 2H), 5.25 (s, 1H), 7.17-7.32 (m, 4H), 7.47 (s, 1H).

Step 4

Compound 190 (3.00 g, 6.42 mmol), cyclo-leucine (1.66 g, 12.8 mmol), copper (I) chloride (64.0 mg, 0.642 mmol), N,N'-dimethylethylenediamine (0.137 mL, 1.28 mmol) and tripotassium phosphate (2.73 g, 12.8 mmol) in DMSO (30 mL) suspension were stirred at 140° C. for 1 hour. After cooling to room temperature, saturated ammonium chloride solution (25 mL), water (75 mL) and ethyl acetate (150 mL) were added thereto, and the insoluble material was removed by filtration. The organic layer was washed with saturated brine (50 mL), and dried over anhydrous magnesium sulfate. After concentration, the residue was purified by silica gel chromatography (hexane-ethyl acetate) to obtain Compound 191 (1.69 g, 58% yield) as pale brown foam.

1H-NMR (CDCl3) δ: 0.89 (s, 9H), 1.68-1.84 (m, 6H), 2.21-2.33 (m, 5H), 2.40 (s, 3H), 3.74 (s, 3H), 3.83 (s, 1H), 5.22 (s, 1H), 6.41 (s, 1H), 7.17-7.33 (m, 4H), 7.44 (s, 1H).

Step 5

Under ice cooling, to Compound 191 (1.68 g, 3.73 mmol) in DMF (21 mL) solution was added N-bromosuccinimide (796 mg, 4.47 mmol), and the mixture was stirred under ice-cooling for 30 minutes. Water (30 mL) and saturated aqueous ammonium chloride solution (30 mL) were added thereto, and the mixture was extracted with ethyl acetate (100 mL). The organic layer was washed with saturated brine (30 mL), and dried over anhydrous magnesium sulfate. After concentration, the residue was purified by silica gel chromatography (hexane-ethyl acetate) to obtain Compound 192 (1.66 g, 79% yield) as a white solid.

1H-NMR (CDCl3) δ: 0.95 (s, 9H), 1.70-1.87 (m, 6H), 2.21-2.31 (m, 5H), 2.43 (s, 3H), 3.68 (s, 3H), 4.63 (s, 1H), 4.94 (s, 1H), 7.10-7.14 (m, 1H), 7.18-7.25 (m, 3H), 7.49 (s, 1H).

Step 6

To Compound 192 (165 mg, 0.312 mmol) in DMF (1.65 mL) solution were added cesium carbonate (254 mg, 0.779 mmol) and iodomethane (0.097 mL, 1.56 mmol), the mixture was stirred at room temperature for 1.5 hours. Water (30 mL) was added thereto, and the mixture was extracted with ethyl acetate (50 mL). The organic layer was washed with water (30 mL) and saturated brine (30 mL), and dried over anhydrous magnesium sulfate. After concentration, the residue was purified by silica gel chromatography (hexane ethyl acetate) to obtain Compound 193 (148 mg, 88% yield) as white foam.

1H-NMR (CDCl3) δ: 0.96 (s, 9H), 1.58-1.87 (m, 6H), 1.87-2.02 (m, 1H), 2.32 (s, 3H), 2.40-2.50 (m, 4H), 3.34 (s, 3H), 3.70 (s, 3H), 4.62 (s, 1H), 4.98 (s, 1H), 7.09-7.14 (m, 1H), 7.20-7.25 (m, 3H).

Step 7

To Compound 193 (145 mg, 0.267 mmol), tributyl (methoxy)stannane (0.230 mL, 0.800 mmol), palladium acetate (12.0 mg, 0.053 mmol), tri-(o-tolyl)phosphine (32.5 mg, 0.107 mmol) in toluene (7 mL) suspension was added isopropenyl acetate (0.145 mL 1.33 mmol), under nitrogen atmosphere the mixture was stirred at 100° C. for 2 hours. After cooling, ethyl acetate (2 mL) and 4 mol/L aqueous potassium fluoride (1.8 mL) were added thereto, and the mixture was stirred for 1 hour, and the insoluble material was removed by filtration. Water (30 mL) was added thereto, and the mixture was extracted with ethyl acetate (50 mL). The organic layer was washed with saturated brine (30 mL), and dried over anhydrous magnesium sulfate. The concentrated residue was dissolved in acetic acid (1.45 mL), and the mixture was stirred at 60° C. for 45 minutes. After concentration under reduced pressure, the resulting mixture was diluted with ethyl acetate (30 mL). The organic layer was washed with water (20 mL), saturated aqueous sodium bicarbonate solution (20 mL) and saturated brine (20 mL), and dried over anhydrous magnesium sulfate. After concentration, the residue was purified by silica gel column chromatography (hexane-ethyl acetate) to obtain Compound 194 (112 mg, 83% yield).

1H-NMR (CDCl3) δ: 0.92 (s, 9H), 1.88-2.14 (m, 6H), 2.43 (s, 3H), 2.46 (s, 3H), 2.52-2.58 (m, 4H), 2.62-2.73 (m, 1H), 3.60 (s, 3H), 3.75 (s, 3H), 5.43 (s, 1H), 5.95 (s, 1H), 7.22-7.33 (m, 3H), 7.39-7.44 (m, 1H).

Step 8

To Compound 194 (90.0 mg, 0.179 mmol) in 0.92 mol/L borane in THF solution (0.973 mL, 0.895 mmol) was added, the mixture was stirred at room temperature for 30 hours. Water (20 mL) was added thereto, and the mixture was extracted with ethyl acetate (30 mL). The organic layer was washed with saturated brine (20 mL), and dried over anhydrous magnesium sulfate. After concentration, the residue was purified by amino silica gel chromatography (hexane-ethyl acetate) to obtain Compound 195 (63.1 mg, 72% yield) as white foam.

1H-NMR (CDCl3) δ: 0.90 (s, 9H), 1.73-1.88 (m, 2H), 1.90-2.02 (m, 4H), 2.07-2.15 (m, 1H), 2.21-2.31 (m, 1H), 2.39 (s, 3H), 2.42 (s, 3H), 2.46 (s, 3H), 3.15 (s, 3H), 3.34 (d, J=14.1 Hz, 1H), 3.40 (d, J=14.1 Hz, 1H), 3.72 (s, 3H), 5.46 (s, 1H), 5.89 (s, 1H), 7.21-7.25 (m, 2H), 7.35-7.39 (m, 1H), 7.44-7.48 (m, 1H).

Step 9

To Compound 195 (60 mg, 0.123 mmol) in ethanol (1 mL) solution was added 2 mol/L aqueous sodium hydroxide (0.5 mL, 1.00 mmol), and the mixture was stirred under reflux for 2 hours. 1 mol/L aqueous hydrochloric acid solution (1 mL) and saturated brine (20 mL) were added thereto, and the mixture was extracted with ethyl acetate (30 mL). The organic layer was dried over anhydrous magnesium sulfate. After concentration, the residue was purified by silica gel chromatography (chloroform-methanol) to obtain Compound I-302 (56.7 mg, 97% yield) as a white solid.

LC/MS measurement conditions: (1), LC/MS (ESI): m/z=475.6 [M+H]+, RT=3.10 min.

1H-NMR (CDCl3) δ: 0.91 (s, 9H), 1.72-1.89 (m, 2H), 1.90-2.04 (m, 4H), 2.05-2.13 (m, 1H), 2.23-2.33 (m, 1H), 2.37 (s, 3H), 2.42 (s, 3H), 2.47 (s, 3H), 3.13 (s, 3H), 3.35 (d, J=14.1 Hz, 1H), 3.40 (d, J=14.1 Hz, 1H), 5.58 (s, 1H), 5.93 (s, 1H), 7.23-7.26 (m, 2H), 7.37-7.42 (m, 1H), 7.53-7.57 (m, 1H).

Example 52

[Chemical formula 177]

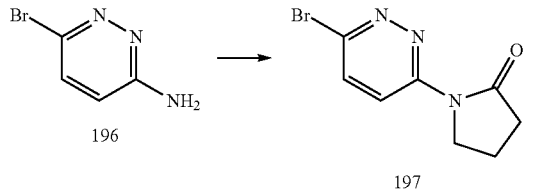

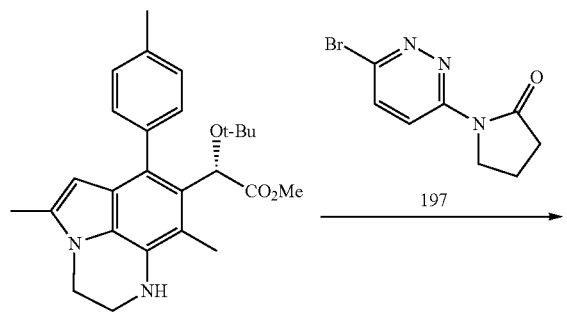

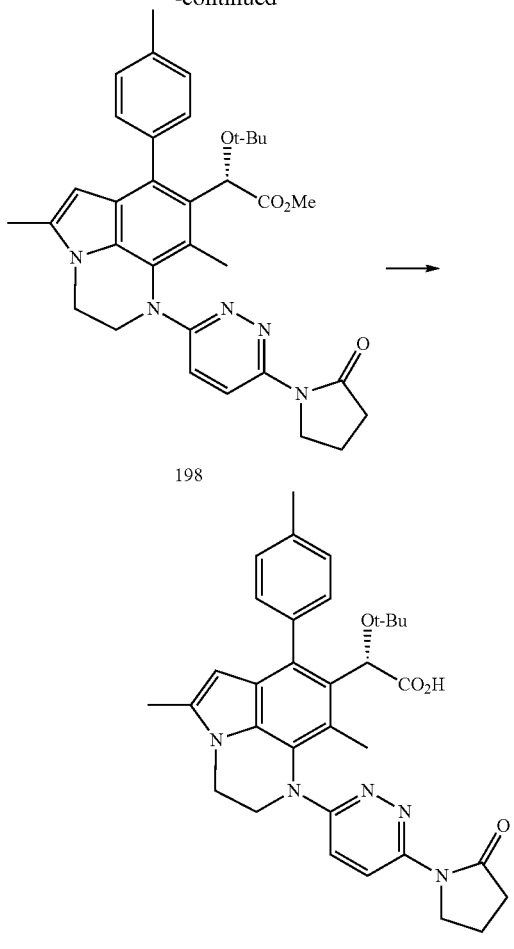

Step 1

To Compound 196 (1.00 g, 5.75 mmol) in acetonitrile (20 mL) suspension were added 4-bromobutanoyl chloride (0.798 mL, 6.90 mmol) and potassium carbonate (1.99 g, 14.4 mmol), and the mixture was stirred at room temperature for 21 hours. After the insoluble material was removed by filtration, and the filtrate solution was concentrated under reduced pressure. The concentrated residue was dissolved in chloroform (50 mL), and washed with water (30 mL). The aqueous layer was re-extracted with chloroform (50 mL), the organic layer was dried over anhydrous magnesium sulfate. After concentration, the residue was purified by silica gel chromatography (chloroform-methanol), and obtained solid was washed with hexane to obtain Compound 197 (990 mg, 71% yield) as a white solid.

1H-NMR (CDCl3) δ: 2.22 (tt, J=8.2, 7.2 Hz, 2H), 2.69 (t, J=8.2 Hz, 2H), 4.22 (t, J=7.2 Hz, 2H), 7.60 (d, J=9.4 Hz, 1H), 8.63 (d, J=9.4 Hz, 1H).

Step 2

To Compound 83 (300 mg, 0.713 mmol), Compound 197 (259 mg, 1.07 mmol), dibenzylideneacetone palladium (98.0 mg, 0.107 mmol), and RuPhos (66.6 mg, 0.143 mmol) in toluene (3 mL) suspension was added sodium tert-butoxide (103 mg, 1.07 mmol) at room temperature, and the mixture was stirred under nitrogen atmosphere at 60° C. for 20 hours. Saturated ammonium chloride solution (3 mL), water (30 mL) and ethyl acetate (50 mL) were added to the reaction mixture, and the insoluble material was removed by filtra-

281 tion. The organic layer was washed with water (30 mL) and saturated brine (30 mL), and dried over anhydrous magnesium sulfate. After concentration, the residue was purified by silica gel chromatography (hexane-ethyl acetate) to obtain Compound 198 (191 mg, 46% yield) as brown foam.

1H-NMR (CDCl3) δ: 0.93 (s, 9H), 2.15-2.24 (m, 5H), 2.31 (s, 3H), 2.45 (s, 3H), 2.66 (t, J=8.1 Hz, 2H), 3.77 (s, 3H), 3.98-4.07 (m, 2H), 4.19-4.29 (m, 2H), 4.47-4.62 (m, 1H), 4.77-4.89 (m, 1H), 5.47 (s, 1H), 5.93 (s, 1H), 6.70 (d, J=9.8 Hz, 1H), 7.25-7.29 (m, 2H), 7.37-7.40 (m, 1H), 7.43-7.46 (m, 1H), 8.45 (d, J=9.8 Hz, 1H).

Step 3

To Compound 198 (130 mg, 0.223 mmol) in dimethylacetamide (1.3 mL) solution was added lithium chloride (474 mg, 11.2 mmol), the mixture was stirred at 120° C. for 15 hours. 1 mol/L aqueous hydrochloric acid (1.5 mL) and water (20 mL) were added thereto, and the mixture was extracted with ethyl acetate (30 mL). The organic layer was washed with water (20 mL×2 times) and saturated brine (20 mL), and dried over anhydrous magnesium sulfate. After concentration, the residue was purified by HPLC (acetonitrile-ammonium formate solution) to obtain Compound I-303 (28.0 mg, 22% yield) as a brown solid.

LC/MS measurement conditions: (1), LC/MS (ESI): m/z=568.7 [M+H]+, RT=2.54 min.

1H-NMR (CDCl3) δ: 0.96 (s, 9H), 2.14-2.24 (m, 5H), 2.32 (s, 3H), 2.43 (s, 3H), 2.66 (t, J=8.0 Hz, 2H), 3.99-4.11 (m, 2H), 4.13-4.43 (m, 3H), 4.88-5.14 (m, 1H), 5.60 (s, 1H), 5.95 (s, 1H), 6.69 (d, J=9.8 Hz, 1H), 7.24-7.30 (m, 2H), 7.40 (d, J=6.8 Hz, 1H), 7.63 (d, J=6.8 Hz, 1H), 8.46 (d, J=9.8 Hz, 1H).

Example 53

[Chemical formula 178]

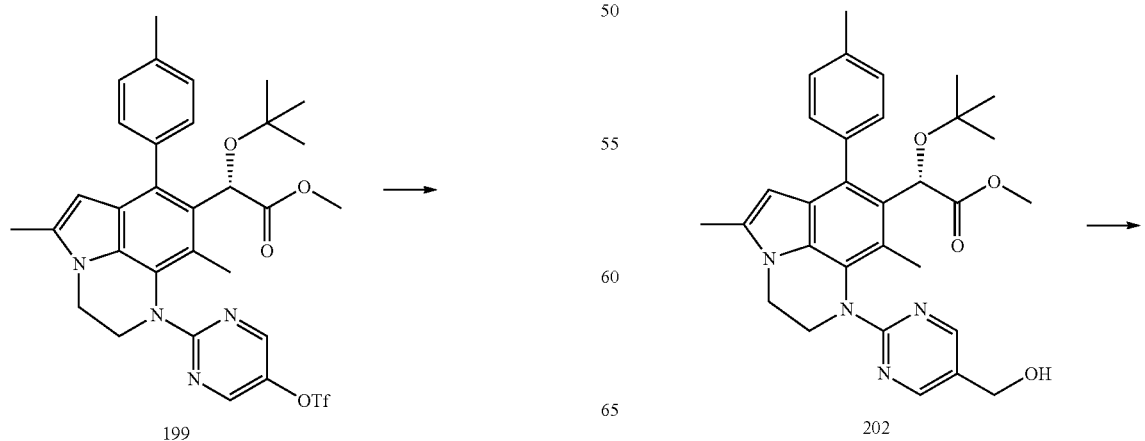

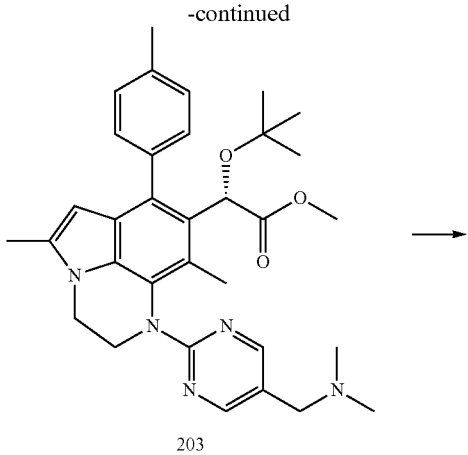

203

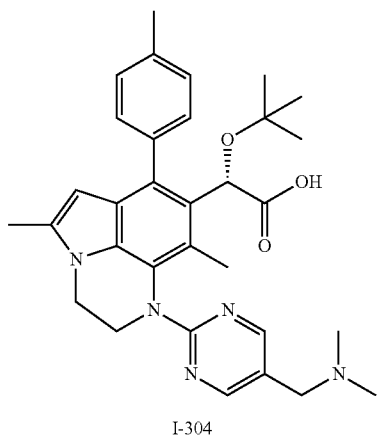

I-304

Step 1

To Compound 199 (3.7 g, 5.72 mmol) in DMF (37 mL) solution were added tributylvinyltin (3.33 mL, 11.44 mmol), lithium chloride (485 mg, 11.44 mmol), and dichlorobistriphenylphosphine triphenylphosphine palladium (402 mg, 0.572 mmol), and the mixture was stirred under nitrogen atmosphere at 60° C. for 30 minutes. Aqueous potassium fluoride was added to the mixture and the precipitated solid was filtered, and the filtrate solution was extracted with ethyl acetate. The organic layer was washed with water and dried over anhydrous sodium sulfate. After concentration under reduced pressure, the residue was purified by silica gel column chromatography (hexane-ethyl acetate) to obtain Compound 200 (2.64 g, 88% yield) as yellow foam.

LC/MS measurement conditions: (1), LC/MS (ESI): m/z=525.25 [M+H]+, RT=3.30 min.

Step 2

To Compound 200 (2 g, 3.81 mmol) in THF (20 mL) and water (4 mL) solution were added osmium (VI) potassium dihydrate (70.2 mg, 0.191 mmol) and sodium periodate (3.26 g, 15.2 mmol), and the mixture was stirred at room temperature for 2.5 hours. Water was added thereto, and the mixture was extracted with chloroform. The organic layer was washed with water, and dried over anhydrous sodium sulfate. After concentration under reduced pressure, the residue was purified by silica gel column chromatography (hexane-ethyl acetate) to obtain Compound 201 (991 mg, 49% yield) as yellow foam.

LC/MS measurement conditions: (1), LC/MS (ESI): m/z=527.20 [M+H]+, RT=3.07 min.

Step 3

Under ice-cooling, to Compound 201 (990 mg, 1.88 mmol) in methanol (10 mL) was added sodium borohydride (71.1 mg, 1.88 mmol), and the mixture was stirred at 0° C. for 20 min. 2 mol/L hydrochloric acid was added thereto, and the mixture was extracted with ethyl acetate. The organic layer was washed with water, and dried over anhydrous sodium sulfate. The solvent was concentrated under reduced pressure, the residue was purified by silica gel column chromatography (hexane-ethyl acetate) to obtain Compound 202 (790 mg, 71% yield) as a pink solid.

LC/MS measurement conditions: (1), LC/MS (ESI): m/z=529.25 [M+H]+, RT=2.77 min.

Step 4

Under ice-cooling, to Compound 202 (100 mg, 0.189 mmol) in dichloromethane (2 mL) solution were added triphenylphosphine (99 mg, 0.378 mmol) and carbon tetrabromide (125 mg, 0.378 mmol), the mixture was stirred under nitrogen atmosphere at room temperature for 50 minutes. Then, 2 mol/L dimethylamine in THF solution (0.946 mL, 1.89 mmol) was added thereto, and the mixture was stirred at room temperature for 20 minutes. Water was added thereto, and the mixture was extracted with ethyl acetate. The organic layer was washed with water and dried over anhydrous sodium sulfate. After concentration under reduced pressure, the residue was purified by amino silica gel column chromatography (hexane-ethyl acetate) to obtain Compound 203 (95.6 mg, 91% yield) as yellow foam.

LC/MS measurement conditions: (1), LC/MS (ESI): m/z=556.25 [M+H]+, RT=2.45 min.

Step 5

To Compound 203 (90 mg, 0.162 mmol) in ethanol (1 mL) and THF (1 mL) solution was added 2 mol/L aqueous sodium hydroxide solution (0.81 mL, 1.62 mmol), the mixture was stirred under reflux for 7 hours. 2 mol/L hydrochloric acid was added thereto, and the mixture was extracted with chloroform. The organic layer was washed with water, and dried over anhydrous sodium sulfate. After concentration under reduced pressure, the residue was purified by diol silica gel chromatography (chloroform-methanol) to obtain Compound I-304 (56.1 mg, 64% yield) as a brown solid.

LC/MS measurement conditions: (1), LC/MS (ESI): m/z=542.20 [M+H]+, RT=2.22 min.

1H-NMR (CDCl3) δ: 0.97 (9H, s), 1.12 (3H, s), 2.23 (3H, s), 2.29 (3H, s), 2.29 (3H, s), 2.43 (3H, s), 3.25-3.35 (2H, m), 3.59-3.69 (1H, m), 3.97-4.10 (2H, m), 5.59 (1H, s), 5.90 (1H, s), 7.22-7.29 (2H, m), 7.34-7.43 (1H, m), 7.62-7.71 (1H, m), 8.33 (2H, s).

Example 54

[Chemical formula 179]

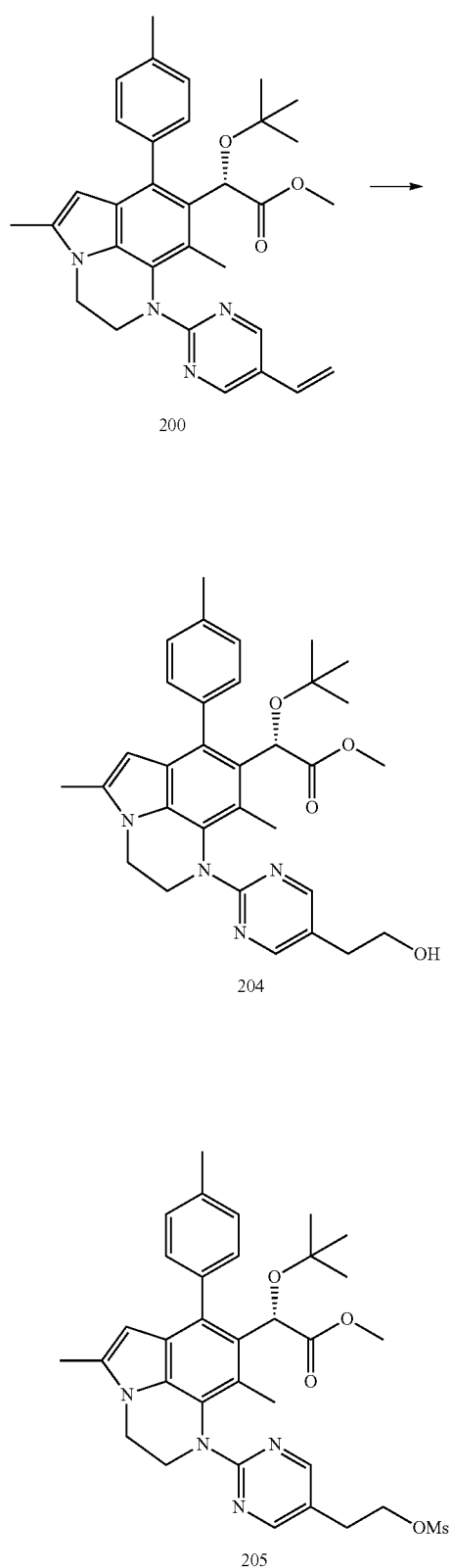

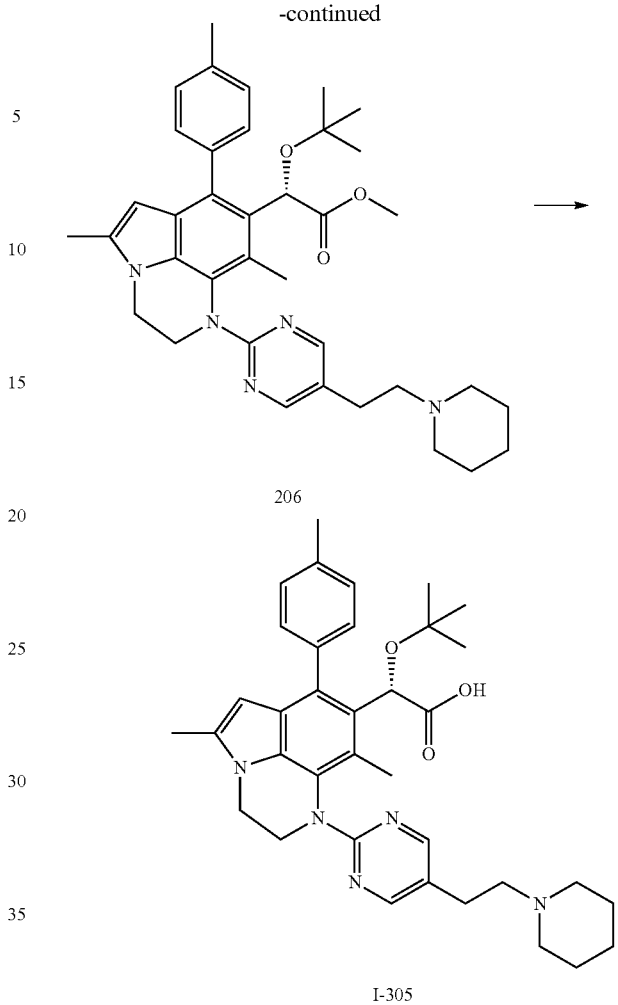

Step 1

Under ice-cooling, to Compound 200 (550 mg, 1.05 mmol) in THF (5 mL) solution was added 0.5 mol/L 9-borabicyclo[3.3.1]nonane in THF solution (3.14 mL, 1.57 mmol), and the mixture was stirred under nitrogen atmosphere at 0° C. for 4 hours. Then water (5 mL) and sodium perborate tetrahydrate (484 mg, 3.14 mmol) were added thereto, and the mixture was stirred at room temperature for 4.5 hours. Water was added thereto, and the mixture was extracted with chloroform. The organic layer was washed with water, and dried over anhydrous sodium sulfate. After concentration under reduced pressure, the residue was purified by silica gel column chromatography (hexane-ethyl acetate) to obtain Compound 204 (490 mg, 86% yield) as yellow foam.

LC/MS measurement conditions: (1), LC/MS (ESI): m/z=543.25 [M+H]+, RT=2.80 min.

Step 2

To Compound 204 (270 mg, 0.498 mmol) in dichloromethane (3 mL) solution were added triethylamine (0.103 mL, 0.746 mmol) and mesyl chloride (0.05 mL, 0.647 mmol), the mixture was stirred under nitrogen atmosphere at room temperature for 10 minutes. Water was added thereto, and the mixture was extracted with chloroform. The organic layer was washed with water, and dried over anhydrous sodium sulfate. After concentration under reduced pressure, the residue was purified by silica gel column chromatography (hexane-ethyl acetate) to obtain Compound 205 (490 mg, 86% yield) as yellow foam.

LC/MS measurement conditions: (1), LC/MS (ESI): m/z=621.2 [M+H]+, RT=3.00 min.

Step 3

To Compound 205 (100 mg, 0.161 mmol) in DMF (1 mL) solution were added piperidine (0.159 mL, 1.61 mmol) and mesyl chloride (0.05 mL, 0.647 mmol), the mixture was stirred 80° C. for 1.5 hours. Water was added thereto, and the mixture was extracted with ethyl acetate. The organic layer was washed with water, and dried over anhydrous sodium sulfate. After concentration under reduced pressure, the residue was purified by amino silica gel column chromatography (hexane-ethyl acetate) to obtain Compound 206 (86.3 mg, 88% yield) as yellow foam.

LC/MS measurement conditions: (1), LC/MS (ESI): m/z=610.30 [M+H]+, RT=2.86 min.

Step 4

To Compound 206 (85 mg, 0.139 mmol) in ethanol (1 mL) and THF (1 mL) solution was added 2 mol/L aqueous sodium hydroxide solution (0.70 mL, 1.39 mmol), the mixture was stirred under reflux for 4.5 hours. 2 mol/L hydrochloric acid was added thereto, and the mixture was extracted with chloroform. The organic layer was washed with water, and dried over anhydrous sodium sulfate. After concentration under reduced pressure, the residue was purified by diol silica gel chromatography (chloroform-methanol) to obtain Compound I-305 (77.6 mg, 93% yield) as a yellow solid.

LC/MS measurement conditions: (1), LC/MS (ESI): m/z=542.20 [M+H]+, RT=2.22 min.

1H-NMR (CDCl3) δ:0.97 (9H, s), 1.23-1.28 (2H, m), 1.40-1.52 (2H, m), 1.54-1.69 (4H, m), 2.21 (3H, s), 2.29 (3H, s), 2.36-2.57 (4H, m), 2.43 (3H, s), 2.62-2.74 (2H, m), 3.95-4.07 (2H, m), 5.59 (1H, s), 5.90 (1H, s), 7.23-7.28 (2H, m), 7.34 (1H, f, J=7.2 Hz), 7.67 (1H, d, J=7.23 Hz), 8.27 (2H, s).

Example 55

-continued

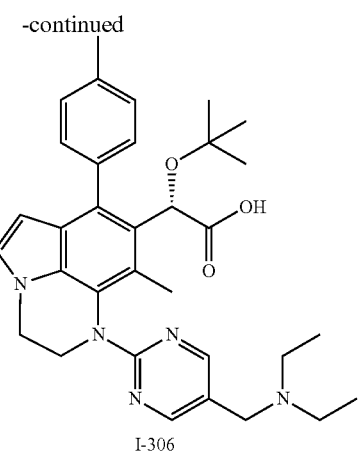

I-306

Step 1

In the same manner as steps 4 and 5 of Example 53, Compound I-306 (66.9 mg, 0.117 mmol, 62% yield) was obtained as a yellow solid from Compound 202 (100 mg, 0.189 mmol) and Compound 207 (0.197 mL, 1.892 mmol).

LC/MS measurement conditions: (1), LC/MS (ESI): m/z=570.30 [M+H]+, RT=2.41 min.

1H-NMR (CDCl3) δ: 0.96 (9H, s), 0.97-1.88 (10H, m), 2.22 (3H, s), 2.29 (3H, s), 2.42 (3H, s), 2.46-2.86 (2H, m), 3.39-3.74 (1H, m), 4.05 (2H, brs), 5.61 (1H, s), 5.91 (1H, s), 7.22-7.29 (2H, m), 7.35-7.42 (1H, m), 7.62-7.69 (1H, m), 8.41 (2H, brs).

Example 56

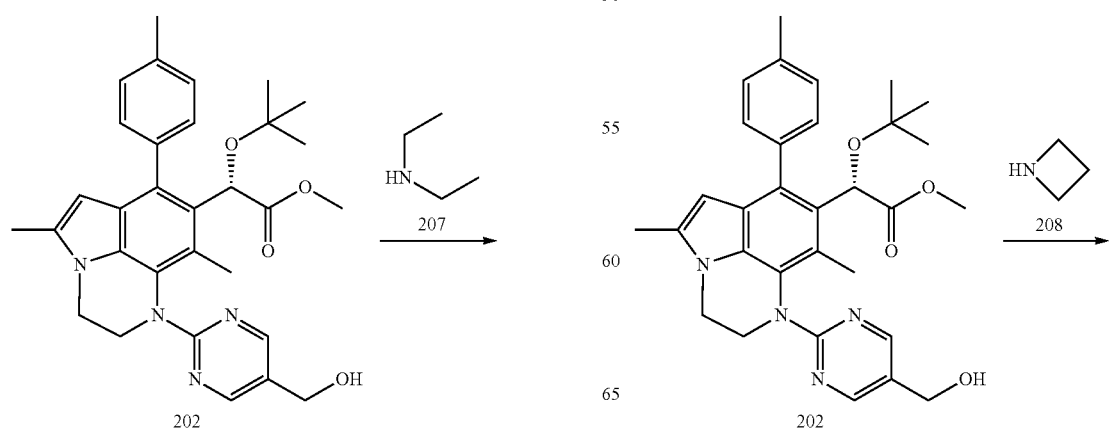

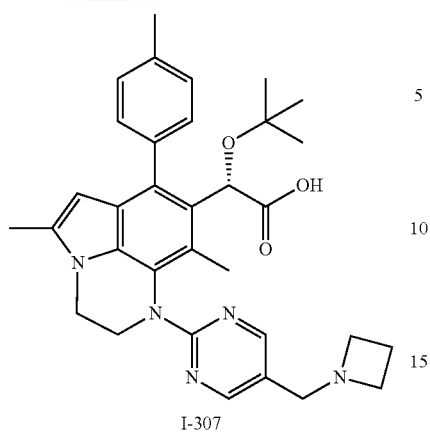

I-307

I-308

Step 1

In the same manner as steps 4 and 5 of Example 53, Compound I-307 (56 mg, 0.105 mmol, 56% yield) was obtained as a yellow solid from Compound 202 (100 mg, 0.189 mmol) and Compound 208 (0.128 mL, 1.892 mmol).

LC/MS measurement conditions: (1), LC/MS (ESI): m/z=554.25 [M+H]+, RT=2.35 min.

1H-NMR (CDCl3) δ: 0.96 (9H, s), 2.04-2.12 (2H, m), 2.20 (3H, s), 2.29 (3H, s), 2.43 (3H, s), 3.16-3.23 (4H, m), 3.39-3.47 (2H, m), 3.95-4.08 (2H, m), 5.59 (1H, s), 5.90 (1H, s), 7.22-7.29 (2H, m), 7.35-7.40 (1H, m), 7.63-7.69 (1H, m), 8.32 (2H, s).

Example 57

Step 1

In the same manner as steps 4 and 5 of Example 53, Compound I-308 (71.6 mg, 0.123 mmol, 65% yield) was obtained as a yellow solid from Compound 202 (100 mg, 0.189 mmol) and Compound 209 (0.128 mL, 1.892 mmol).

LC/MS measurement conditions: (1), LC/MS (ESI): m/z=582.30 [M+H]+, RT=2.48 min.

1H-NMR (CDCl3) δ: 0.98 (9H, s), 1.38-1.48 (2H, m), 1.52-1.60 (4H, m), 2.22 (3H, s), 2.28 (3H, s), 2.36 (4H, brs), 2.43 (3H, s), 3.35 (2H, s), 3.96-4.09 (2H, m), 5.59 (1H, s), 5.90 (1H, s), 7.23-7.29 (2H, m), 7.35-7.41 (1H, m), 7.63-7.70 (1H, m), 8.33 (2H, s).

Example 58

[Chemical formula 182]

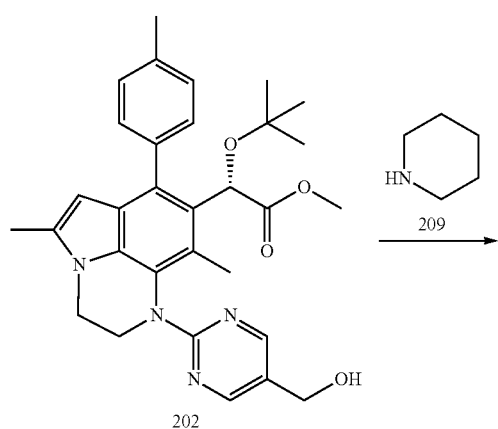

202

[Chemical formula 183]

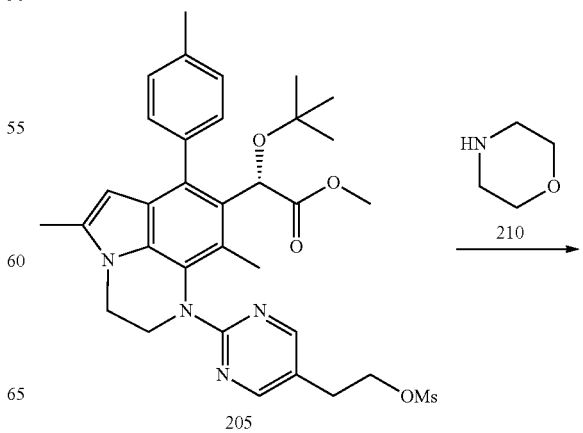

205

-continued

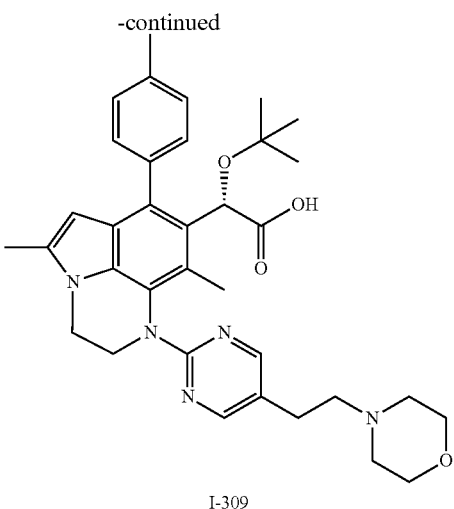

I-309

Step 1

In the same manner as steps 3 and 4 of Example 54, Compound I-309 (75.6 mg, 0.126 mmol, 80% yield) was obtained as a yellow solid from Compound 205 (100 mg, 0.161 mmol) and Compound 210 (0.139 mL, 1.611 mmol).

LC/MS measurement conditions: (1), LC/MS (ESI): m/z=598.30 [M+H]+, RT=2.35 min.

1H-NMR (CDCl3) δ: 0.97 (9H, s), 2.21 (3H, s), 2.29 (3H, s), 2.43 (3H, s), 2.47-2.56 (6H, m), 2.61-2.68 (2H, m), 3.72 (4H, brs), 3.96-4.09 (2H, m), 5.60 (1H, s), 5.90 (1H, s), 7.23-7.29 (2H, m), 7.39 (1H, d, J=7.5 Hz), 7.66 (1H, d, J=7.5 Hz), 8.28 (2H, s).

The following compounds were synthesized using commercially available compounds or the above intermediates according to the above Examples or the above General methods.

In the table, "Comp. No." means a compound number, "Struct" means chemical structure formula, "Ms cond." means the above measurement condition of LC/MS (liquid chromatography/mass spectrometry), "RT(min)" means retention time (minute).

TABLE 1

| Comp. No. | Struct | Ms cond. | RT(min) | MS | Comment |
|---|---|---|---|---|---|
| I-001 | | (1) | 2.37 | 421 [M + H]+ | |
| I-002 | | (1) | 2.64 | 455 [M + H]+ | |
| I-003 | | (1) | 2.53 | 485 [M + H]+ | |

TABLE 1-continued
| Comp. No. | Struct | Ms cond. | RT(min) | MS | Comment |
|---|---|---|---|---|---|
| I-004 | 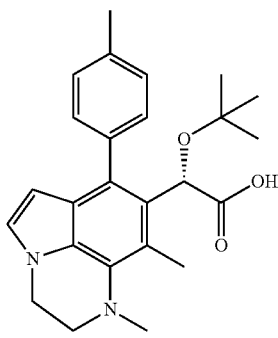 [SMILES: Cc1ccc(-c2c([C@H](OC(C)(C)C)C(=O)O)c(C)c3c4c2ccn4CCN3C)cc1] | (2) | 2.18 | 407 [M + H]+ | |
| I-005 | 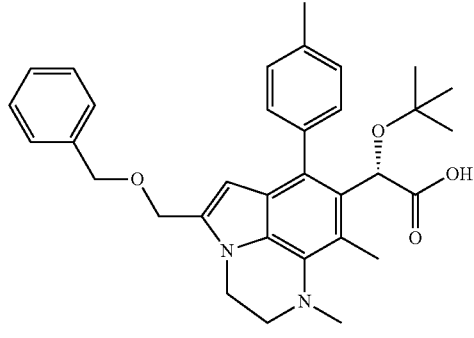 [SMILES: Cc1ccc(-c2c([C@H](OC(C)(C)C)C(=O)O)c(C)c3c4c2cc(COCc2ccccc2)n4CCN3C)cc1] | (1) | 2.92 | 527 [M + H]+ | |
| I-007 | 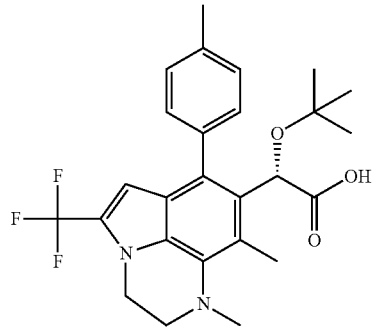 [SMILES: Cc1ccc(-c2c([C@H](OC(C)(C)C)C(=O)O)c(C)c3c4c2cc(C(F)(F)F)n4CCN3C)cc1] | (2) | 2.78 | 475 [M + H]+ | |
TABLE 2
| Comp. No. | Struct | Ms cond. | RT(min) | MS | Comment |
|---|---|---|---|---|---|
| I-009 | 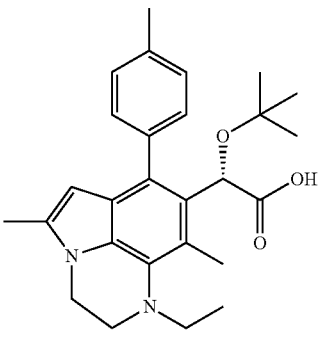 [SMILES: CCN1CCn2c(C)cc3c(-c4ccc(C)cc4)c([C@H](OC(C)(C)C)C(=O)O)c(C)c1c32] | (1) | 2.61 | 435 [M + H]+ | |

TABLE 2-continued

| Comp. No. | Struct | Ms cond. | RT(min) | MS | Comment |
|---|---|---|---|---|---|
| I-011 | | (1) | 2.34 | 451 | [M + H]+ |
| I-012 | | (2) | 2.43 | 441 | [M + H]+ |
| I-013 | | (2) | 2.65 | 449 | [M + H]+ |
| I-014 | | (2) | 2.31 | 449 | [M + H]+ |

TABLE 2-continued
| Comp. No. | Struct | Ms cond. | RT(min) | MS | Comment |
|---|---|---|---|---|---|
| I-015 | 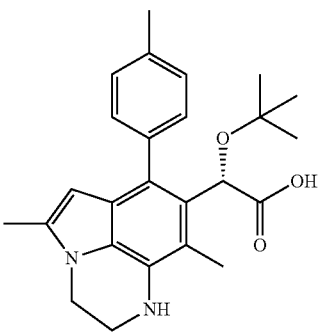 [SMILES: Cc1ccc(-c2c([C@H](OC(C)(C)C)C(=O)O)c(C)c3c4c2cc(C)n4CCN3)cc1] | (2) | 2.35 | 407 | [M + H]+ |
TABLE 3
| Comp. No. | Struct | Ms cond. | RT(min) | MS | Comment |
|---|---|---|---|---|---|
| I-016 | 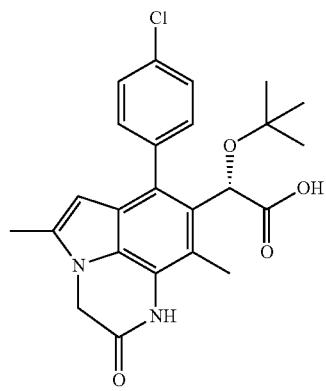 [SMILES: Cc1c([C@H](OC(C)(C)C)C(=O)O)c(-c2ccc(Cl)cc2)c2cc(C)n3c2c1NC(=O)C3] | (2) | 2.27 | 441 | [M + H]+ |
| I-017 | 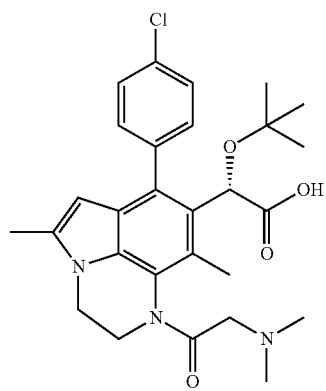 | (2) | 1.56 | 512 | [M + H]+ |

TABLE 3-continued

| Comp. No. | Struct | Ms cond. | RT(min) | MS | Comment |
|---|---|---|---|---|---|
| I-018 | | (2) | 1.60 | 498 | [M + H]+ |
| I-020 | | (1) | 2.53 | 435 | [M + H]+ |
| I-021 | | (1) | 2.30 | 451 | [M + H]+ |
| I-022 | | (1) | 1.85 | 437 | [M + H]+ |

TABLE 4
| Comp. No. | Struct | Ms cond. | RT(min) | MS | Comment |
|---|---|---|---|---|---|
| I-023 | 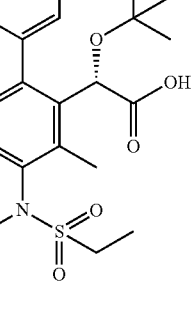 | (1) | 2.53 | 519 | [M + H]+ |
| I-024 | 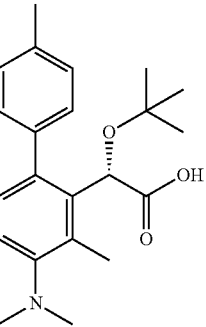 | (1) | 2.55 | 457 | [M + H]+ |
| I-025 | 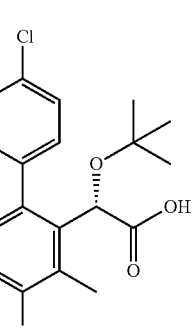 | (2) | 2.34 | 469 | [M + H]+ |
| I-026 | 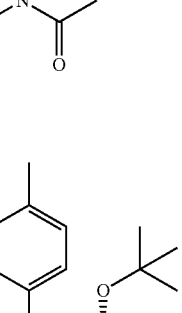 | (1) | 2.28 | 465 | [M + H]+ |

TABLE 4-continued
| Comp. No. | Struct | Ms cond. | RT(min) | MS | Comment |
|---|---|---|---|---|---|
| I-028 | 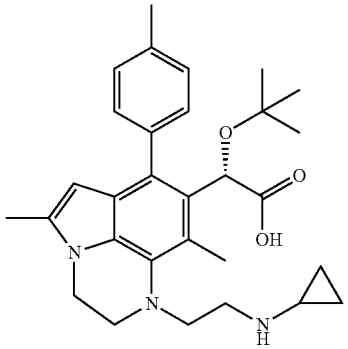 [SMILES: Cc1ccc(-c2c([C@H](OC(C)(C)C)C(=O)O)c(C)c3c4c2cc(C)n4CCN3CCNC2CC2)cc1] | (1) | 1.75 | 490 | [M + H]+ |
TABLE 5
| Comp. No. | Struct | Ms cond. | RT(min) | MS | Comment |
|---|---|---|---|---|---|
| I-029 | 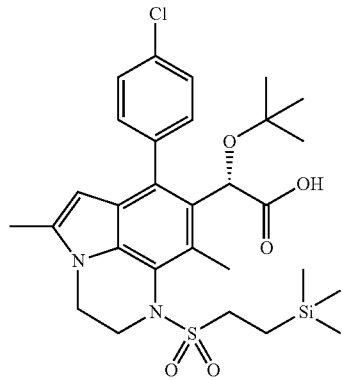 | (1) | 2.98 | 591 | [M + H]+ |
| I-030 | 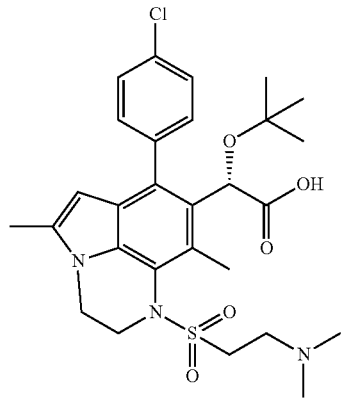 | (1) | 2.11 | 562 | [M + H]+ |

TABLE 5-continued

| Comp. No. | Struct | Ms cond. | RT(min) | MS | Comment |
|---|---|---|---|---|---|
| I-031 | | (1) | 2.55 | 485 | [M + H]+ |
| I-032 | | (2) | 2.45 | 529 | [M − H]− |
| I-033 | | (2) | 2.20 | 466 | [M + H]+ |
| I-034 | | (2) | 2.36 | 509 | [M + H]+ |

TABLE 6

| Comp. No. | Struct | Ms cond. | RT(min) | MS | Comment |
|---|---|---|---|---|---|
| I-035 | | (1) | 2.80 | 491 | [M + H]+ |
| I-036 | | (1) | 2.52 | 519 | [M + H]+ |
| I-037 | | (1) | 2.79 | 475 | [M + H]+ |
| I-038 | | (2) | 2.38 | 496 | [M − H]− |

TABLE 6-continued
| Comp. No. | Struct | Ms cond. | RT(min) | MS | Comment |
|---|---|---|---|---|---|
| I-040 | 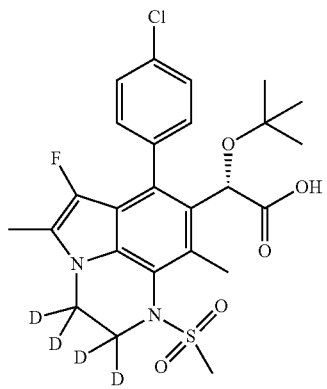 [SMILES: [2H]C1([2H])N(S(C)(=O)=O)c2c(C)c([C@H](OC(C)(C)C)C(=O)O)c(-c3ccc(Cl)cc3)c3c(F)c(C)n(c23)C1([2H])[2H]] | (2) | 2.35 | 525 | [M − H]− |
TABLE 7
| Comp. No. | Struct | Ms cond. | RT(min) | MS | Comment |
|---|---|---|---|---|---|
| I-041 | 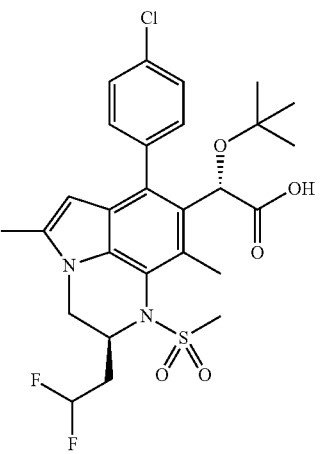 [SMILES: Cc1c([C@H](OC(C)(C)C)C(=O)O)c(-c2ccc(Cl)cc2)c2cc(C)n3c2c1N(S(C)(=O)=O)[C@@H](CC(F)F)C3] | (1) | 2.62 | 569 | [M + H]+ |
| I-042 | 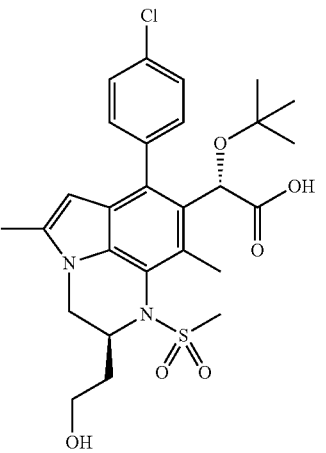 [SMILES: Cc1c([C@H](OC(C)(C)C)C(=O)O)c(-c2ccc(Cl)cc2)c2cc(C)n3c2c1N(S(C)(=O)=O)[C@@H](CCO)C3] | (1) | 2.30 | 549 | [M + H]+ |

TABLE 7-continued

| Comp. No. | Struct | Ms cond. | RT(min) | MS | Comment |
|---|---|---|---|---|---|
| I-044 | | (1) | 2.15 | 588 | [M + H]+ |
| I-045 | | (1) | 2.13 | 618 | [M + H]+ |

TABLE 8

| Comp. No. | Struct | Ms cond. | RT(min) | MS | Comment |
|---|---|---|---|---|---|
| I-046 | | (1) | 2.45 | 483 | [M + H]+ |

TABLE 8-continued

| Comp. No. | Struct | Ms cond. | RT(min) | MS | Comment |
|---|---|---|---|---|---|
| I-047 | | (2) | 2.39 | 477 | [M − H]− |
| I-048 | | (1) | 2.20 | 425 | [M + H]+ |
| I-049 | | (1) | 2.22 | 457 | [M + H]+ |
| I-050 | | (1) | 2.52 | 475 | [M + H]+ |

TABLE 8-continued
| Comp. No. | Struct | Ms cond. | RT(min) | MS | Comment |
|---|---|---|---|---|---|
| I-051 | 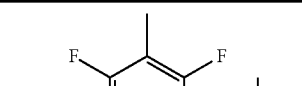 | (1) | 0.04 | 457 | [M + H]+ |
TABLE 9
| I-052 | | (2) | 2.36 | 521 | [M − H]− |
| I-053 | | (2) | 2.53 | 455 | [M + H]+ |
| I-054 | | (1) | 2.49 | 455 | [M + H]+ enantiomer |

TABLE 9-continued
| | | | | | |
|---|---|---|---|---|---|
| I-055 | 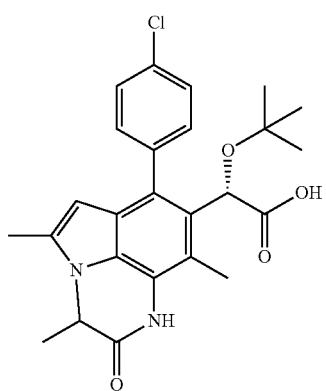 [SMILES: Cc1c([C@H](OC(C)(C)C)C(=O)O)c(-c2ccc(Cl)cc2)c2cc(C)n3c2c1NC(=O)C3C] | (1) | 2.54 | 455 | [M + H]+ diastereomer of I-054 |
| I-056 | 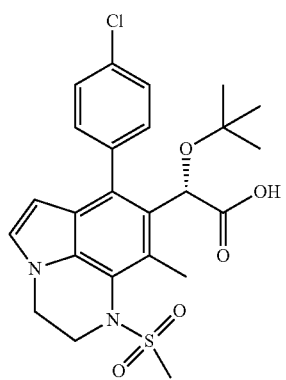 [SMILES: Cc1c([C@H](OC(C)(C)C)C(=O)O)c(-c2ccc(Cl)cc2)c2ccn3c2c1N(S(C)(=O)=O)CC3] | (1) | 2.41 | 489 | [M − H]− |
| I-057 | 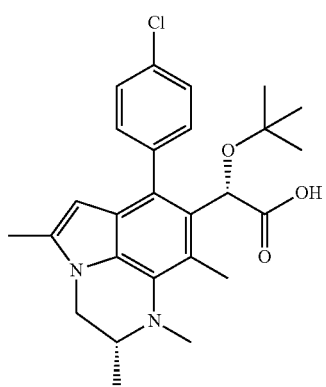 | (2) | 2.51 | 455 | [M + H]+ |

TABLE 10

| | | | | | |
|---|---|---|---|---|---|
| I-060 | [structure] | (1) | 2.61 | 519 | [M + H]+ |
| I-061 | [structure] | (1) | 2.49 | 483 | [M + H]+ |
| I-062 | [structure] | (1) | 2.63 | 519 | [M + H]+ enantiomer |
| I-063 | [structure] | (1) | 2.69 | 519 | [M + H]+ diastereomer of I-062 |

TABLE 10-continued

| Comp. No. | Struct | Ms cond. | RT(min) | MS | Comment |
|---|---|---|---|---|---|
| I-064 | | (1) | 2.74 | 499 | [M + H]+ |

TABLE 11

| Comp. No. | Struct | Ms cond. | RT(min) | MS | Comment |
|---|---|---|---|---|---|
| I-065 | | (1) | 2.70 | 499 | [M + H]+ |
| I-066 | | (2) | 2.40 | 445 | [M + H]+ |

TABLE 11-continued

| Comp. No. | Struct | Ms cond. | RT(min) | MS | Comment |
|---|---|---|---|---|---|
| I-068 | | (2) | 2.68 | 441 | [M + H]+ |
| I-069 | | (1) | 2.64 | 497 | [M + H]+ |
| I-070 | | (1) | 2.73 | 509 | [M + H]+ |
| I-071 | | (1) | 2.39, 2.50 | 505 | [M + H]+ |

TABLE 12

| Comp. No. | Struct | Ms cond. | RT(min) | MS | Comment |
|---|---|---|---|---|---|
| I-072 | | (1) | 2.48 | 491 | [M + H]+ |
| I-073 | | (1) | 2.72 | 477 | [M + H]+ |
| I-074 | | (1) | 2.11 | 437 | [M + H]+ |
| I-075 | | (1) | 1.98 | 498 | [M + H]+ |

TABLE 12-continued

| Comp. No. | Struct | Ms cond. | RT(min) | MS | Comment |
|---|---|---|---|---|---|
| I-076 | | (1) | 2.75 | 485 | [M + H]+ |
| I-077 | | (1) | 2.46 | 443 | [M + H]+ |

TABLE 13

| Comp. No. | Struct | Ms cond. | RT(min) | MS | Comment |
|---|---|---|---|---|---|
| I-078 | | (1) | 2.52, 2.61 | 519 | [M + H]+ |
| I-079 | | (1) | 2.86 | 456 | [M + H]+ |

TABLE 13-continued

| Comp. No. | Struct | Ms cond. | RT(min) | MS | Comment |
|---|---|---|---|---|---|
| I-080 | | (2) | 2.45 | 455 | [M + H]+ |
| I-081 | | (2) | 2.73 | 485 | [M + H]+ |
| I-082 | | (1) | 2.54 | 435 | [M + H]+ |
| I-083 | | (1) | 2.96 | 495 | [M + H]+ |

TABLE 14
| | | | | | |
|---|---|---|---|---|---|
| I-086 | 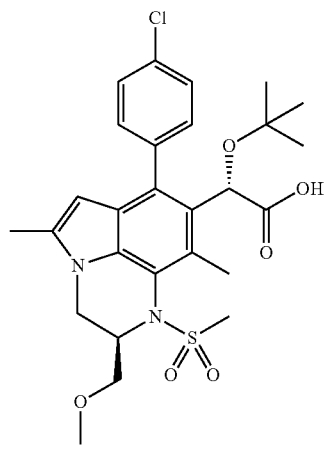 [SMILES: COC[C@H]1Cn2c(C)cc3c(-c4ccc(Cl)cc4)c([C@H](OC(C)(C)C)C(=O)O)c(C)c(c32)N1S(C)(=O)=O] | (1) | 2.49 | 549 | [M + H]+ |
| I-087 | 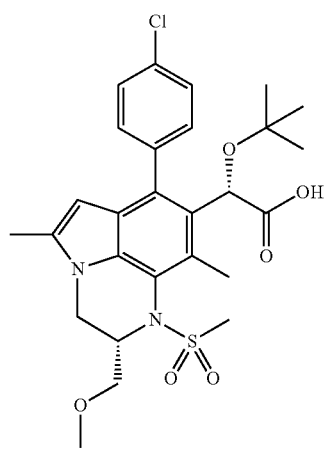 [SMILES: COC[C@@H]1Cn2c(C)cc3c(-c4ccc(Cl)cc4)c([C@H](OC(C)(C)C)C(=O)O)c(C)c(c32)N1S(C)(=O)=O] | (1) | 2.51 | 549 | [M + H]+ |
| I-088 | 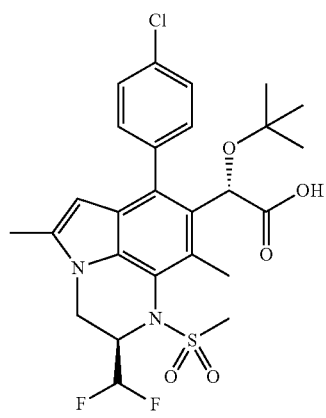 [SMILES: Cc1c([C@H](OC(C)(C)C)C(=O)O)c(-c2ccc(Cl)cc2)c2cc(C)n3c2c1N(S(C)(=O)=O)[C@@H](C(F)F)C3] | (1) | 2.53 | 555 | [M + H]+ |

TABLE 14-continued

| I-089 | (structure) | (1) | 2.56 | 469 | [M + H]+ | |
| I-090 | (structure) | (1) | 2.79 | 456 | [M + H]+ | enantiomer |

TABLE 15

| I-091 | (structure) | (1) | 2.84 | 455 | [M + H]+ | diastereomer of I-090 |
| I-092 | (structure) | (2) | 2.31 | 439 | [M + H]+ | |

TABLE 15-continued
| | | | | |
|---|---|---|---|---|
| I-093 | 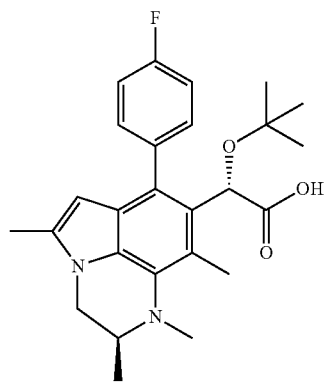 [SMILES: Cc1c([C@H](OC(C)(C)C)C(=O)O)c(-c2ccc(F)cc2)c2cc(C)n3c2c1N(C)[C@@H](C)C3] | (2) | 2.33 | 439 [M + H]+ |
| I-094 | 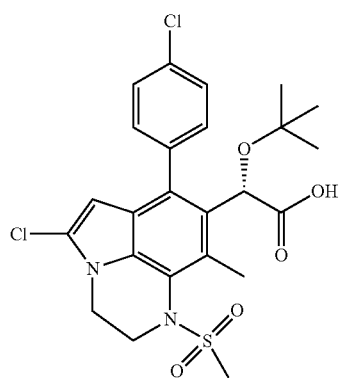 [SMILES: Cc1c([C@H](OC(C)(C)C)C(=O)O)c(-c2ccc(Cl)cc2)c2cc(Cl)n3c2c1N(S(C)(=O)=O)CC3] | (2) | 2.56 | 523 [M − H]− |
| I-095 | 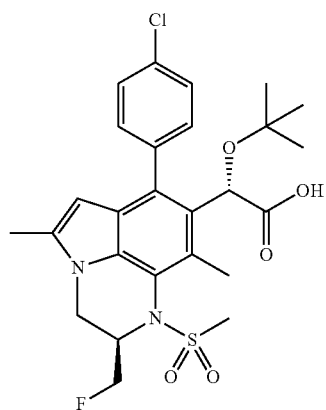 [SMILES: Cc1c([C@H](OC(C)(C)C)C(=O)O)c(-c2ccc(Cl)cc2)c2cc(C)n3c2c1N(S(C)(=O)=O)[C@@H](CF)C3] | (1) | 2.54 | 537 [M + H]+ |
| I-096 | 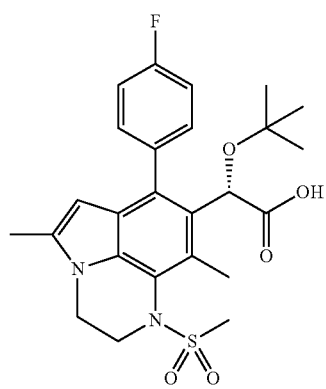 [SMILES: Cc1c([C@H](OC(C)(C)C)C(=O)O)c(-c2ccc(F)cc2)c2cc(C)n3c2c1N(S(C)(=O)=O)CC3] | (1) | 2.35 | 489 [M + H]+ |

TABLE 16
| | | | | | |
|---|---|---|---|---|---|
| I-097 | 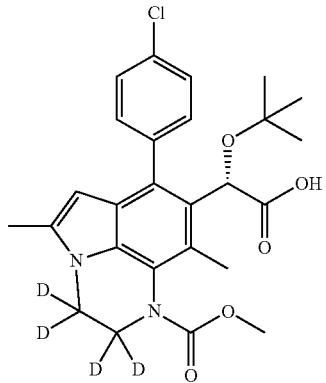 [SMILES: [2H]C1([2H])N(C(=O)OC)c2c(C)c([C@H](OC(C)(C)C)C(=O)O)c(-c3ccc(Cl)cc3)c3cc(C)n(c23)C1([2H])[2H]] | (1) | 2.64 | 489 | [M + H]+ |
| I-100 | 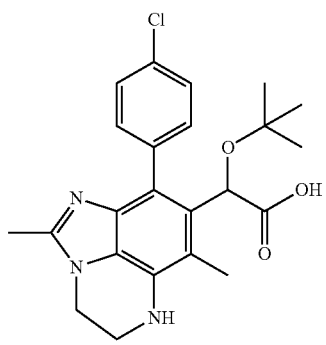 [SMILES: Cc1c(C(OC(C)(C)C)C(=O)O)c(-c2ccc(Cl)cc2)c2nc(C)n3c2c1NCC3] | (2) | 1.27 | 428 | [M + H]+ racemate |
| I-102 | 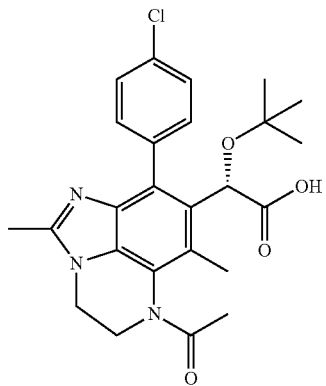 [SMILES: CC(=O)N1CCn2c(C)nc3c(-c4ccc(Cl)cc4)c([C@H](OC(C)(C)C)C(=O)O)c(C)c1c32] | (2) | 1.28 | 470 | [M + H]+ |
| I-103 | 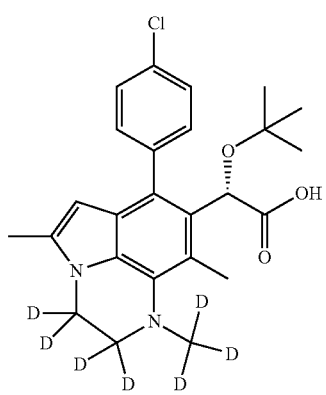 [SMILES: [2H]C([2H])([2H])N1c2c(C)c([C@H](OC(C)(C)C)C(=O)O)c(-c3ccc(Cl)cc3)c3cc(C)n(c23)C([2H])([2H])C1([2H])[2H]] | (2) | 2.39 | 448 | [M + H]+ |

TABLE 16-continued
| Comp. No. | Struct | Ms cond. | RT(min) | MS | Comment |
|---|---|---|---|---|---|
| I-104 | | (2) | 2.41 | 444 | [M + H]+ |
TABLE 17
| Comp. No. | Struct | Ms cond. | RT(min) | MS | Comment |
|---|---|---|---|---|---|
| I-105 | | (2) | 2.20 | 429 | [M + H]+ |
| I-106 | 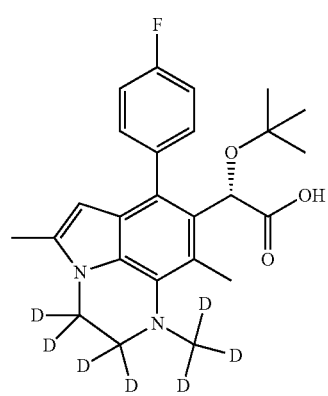 [SMILES: [2H]C([2H])([2H])N1c2c(C)c([C@H](OC(C)(C)C)C(=O)O)c(-c3ccc(F)cc3)c3cc(C)n(c23)C([2H])([2H])C1([2H])[2H]] | (2) | 2.18 | 432 | [M + H]+ |

TABLE 17-continued

| Comp. No. | Struct | Ms cond. | RT(min) | MS | Comment |
|---|---|---|---|---|---|
| I-107 | | (2) | 2.93 | 517 | [M + H]+ |
| I-108 | | (1) | 2.56 | 563 | [M + H]+ |
| I-109 | | (1) | 2.76 | 499 | [M + H]+ |

TABLE 18

| Comp. No. | Struct | Ms cond. | RT (min) | MS | Comment |
|---|---|---|---|---|---|
| I-111 | | (1) | 2.74 | 499 [M + H]+ | |
| I-112 | | (1) | 2.10 | 512 [M + H]+ | |
| I-113 | | (1) | 2.00 | 512 [M + H]+ | |
| I-114 | | (2) | 2.56 | 445 [M + H]+ | |

TABLE 18-continued

| Comp. No. | Struct | Ms cond. | RT (min) | MS | Comment |
|---|---|---|---|---|---|
| I-115 | | (2) | 2.71 | 465 [M + H]+ | |

TABLE 19

| I-116 | | (2) | 2.41 | 519 [M + H]+ | |

| I-117 | | (2) | 2.10 | 518 [M + H]+ | |

TABLE 19-continued
| | | | | | | |
|---|---|---|---|---|---|---|
| I-118 | F 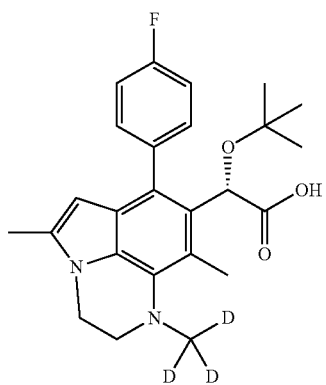 | (2) | 2.20 | 428 | [M + H]+ | |
| I-119 | Cl 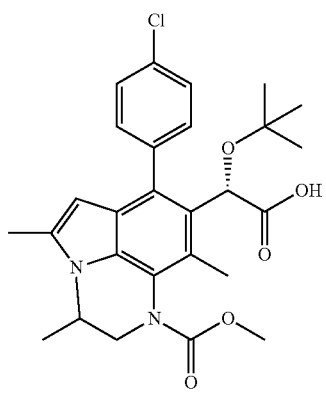 | (1) | 2.62 | 499 | [M + H]+ | enantiomer |
| I-120 | Cl 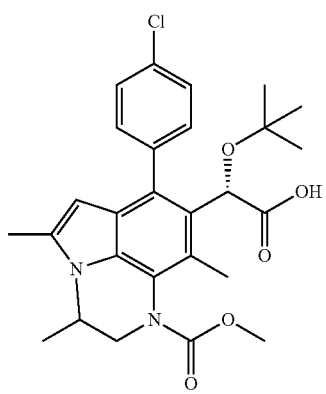 | (1) | 2.61 | 499 | [M + H]+ | diastereomer of I-119 |

TABLE 20

| Comp. No. | Struct | Ms cond. | RT (min) | MS | Comment |
|---|---|---|---|---|---|
| I-122 | | (1) | 2.77 | 523 [M + H]+ | |
| I-123 | | (1) | 2.47 | 489 [M + H]+ | |
| I-125 | | (2) | 2.57 | 504 [M + H]+ | |
| I-127 | | (1) | 3.00 | 469 [M + H]+ | |

TABLE 20-continued

| Comp. No. | Struct | Ms cond. | RT (min) | MS | Comment |
|---|---|---|---|---|---|
| I-129 | | (1) | 2.44 | 495 | [M − H]− |

TABLE 21

| | | | | | |
|---|---|---|---|---|---|
| I-130 | | (4) | 1.96 | 504 | [M + H]+ |
| I-131 | | (1) | 1.97 | 520 | [M + H]+ |

TABLE 21-continued
| I-132 | 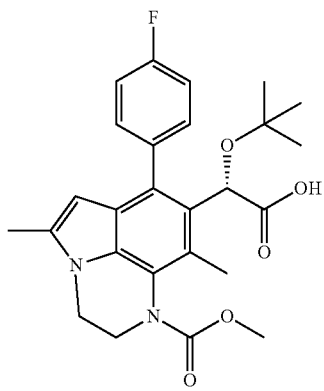 [SMILES: COC(=O)N1CCn2c(C)cc3c(-c4ccc(F)cc4)c([C@H](OC(C)(C)C)C(=O)O)c(C)c1c32] | (1) | 2.47 | 467 | [M − H]− | |
| --- | --- | --- | --- | --- | --- | --- |
| I-133 | 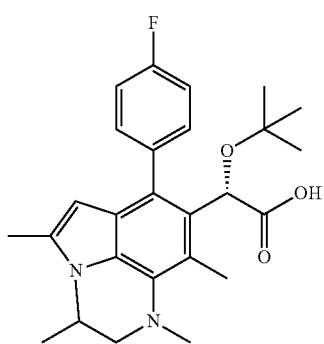 [SMILES: Cc1c([C@H](OC(C)(C)C)C(=O)O)c(-c2ccc(F)cc2)c2cc(C)n3c2c1N(C)CC3C] | (1) | 2.60 | 440 | [M + H]+ | enantiomer |
| I-134 | 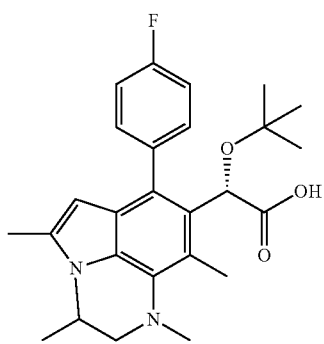 [SMILES: Cc1c([C@H](OC(C)(C)C)C(=O)O)c(-c2ccc(F)cc2)c2cc(C)n3c2c1N(C)CC3C] | (1) | 2.63 | 439 | [M + H]+ | diastereomer of I-133 |

TABLE 22
| I-135 | 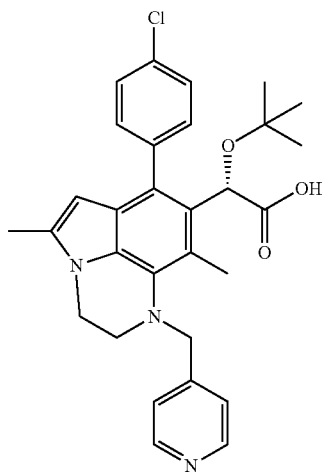 [SMILES: Cc1c([C@H](OC(C)(C)C)C(=O)O)c(-c2ccc(Cl)cc2)c2cc(C)n3c2c1N(Cc1ccncc1)CC3] | (2) | 1.90 | 518 [M + H]+ | |
|---|---|---|---|---|---|
| I-136 | 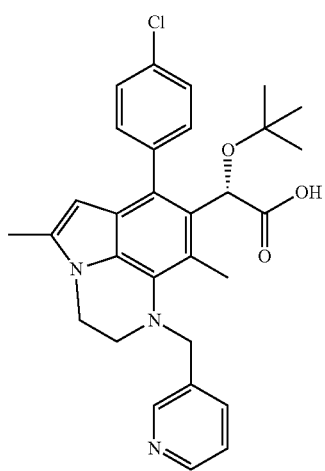 [SMILES: Cc1c([C@H](OC(C)(C)C)C(=O)O)c(-c2ccc(Cl)cc2)c2cc(C)n3c2c1N(Cc1cccnc1)CC3] | (2) | 2.01 | 518 [M + H]+ | |
| I-137 | 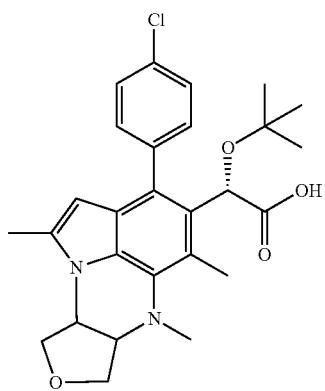 [SMILES: Cc1c([C@H](OC(C)(C)C)C(=O)O)c(-c2ccc(Cl)cc2)c2cc(C)n3c2c1N(C)C1COCC13] | (2) | 2.47 | 483 [M + H]+ | enantiomer |

TABLE 22-continued
| I-138 | 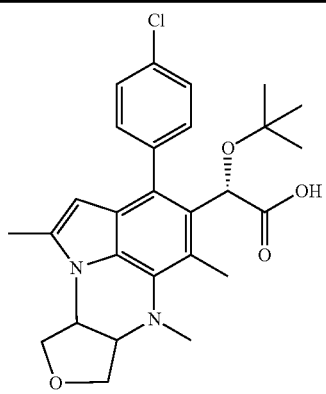 | (2) | 2.42 | 483 [M + H]+ | diasteromer of I-137 |
| I-139 | 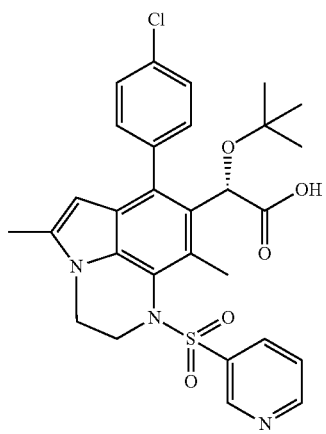 [SMILES: Cc1c([C@H](OC(C)(C)C)C(=O)O)c(-c2ccc(Cl)cc2)c2cc(C)n3c2c1N(S(=O)(=O)c1cccnc1)CC3] | (2) | 2.39 | 568 [M + H]+ | |
TABLE 23
| I-140 | 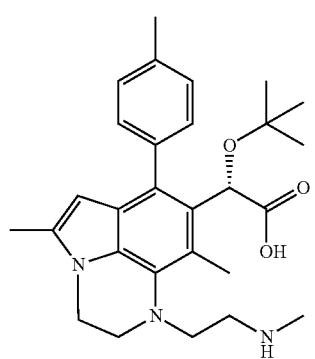 | (4) | 2.43 | 464 [M + H]+ | |

TABLE 23-continued
| | | | | | |
|---|---|---|---|---|---|
| I-141 | 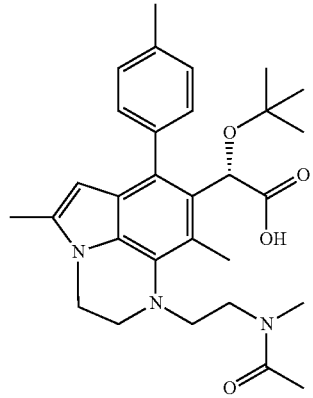 [SMILES: CC(=O)N(C)CCN1CCn2c(C)cc3c(-c4ccc(C)cc4)c([C@H](OC(C)(C)C)C(=O)O)c(C)c1c32] | (4) | 2.76 | 506 | [M + H]+ |
| I-142 | 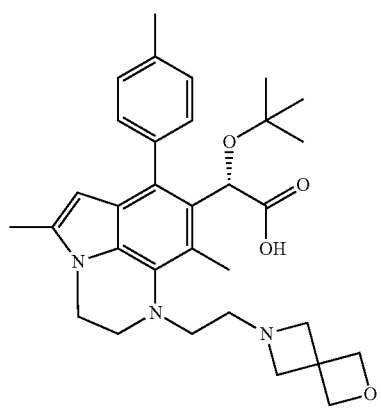 [SMILES: Cc1ccc(-c2c([C@H](OC(C)(C)C)C(=O)O)c(C)c3c4c2cc(C)n4CCN3CCN2CC3(COC3)C2)cc1] | (4) | 2.42 | 532 | [M + H]+ |
| I-143 | 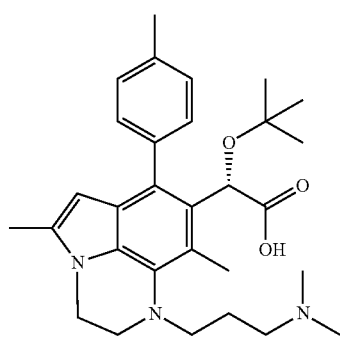 | (4) | 2.50 | 492 | [M + H]+ |
| I-144 | 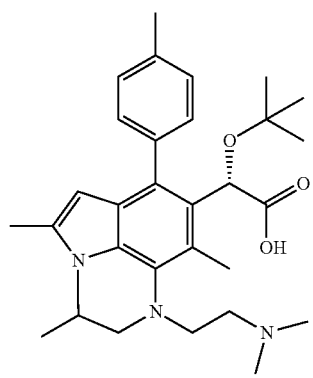 | (4) | 2.04 | 492 | [M + H]+ a mixture of diastereomers |

TABLE 23-continued

| Comp. No. | Struct | Ms cond. | RT (min) | MS | Comment |
|---|---|---|---|---|---|
| I-145 | | (1) | 2.47 | 481 [M − H]− | |

TABLE 24

| Comp. No. | Struct | Ms cond. | RT (min) | MS | Comment |
|---|---|---|---|---|---|
| I-146 | | (1) | 2.44 | 481 [M − H]− | |
| I-147 | | (1) | 2.86 | 524 [M + H]+ | |

TABLE 24-continued

| Comp. No. | Struct | Ms cond. | RT (min) | MS | Comment |
|---|---|---|---|---|---|
| I-148 | | (1) | 2.11 | 492 [M + H]+ | |
| I-149 | | (1) | 2.72 | 511 [M + H]+ | |
| I-150 | | (1) | 2.67 | 508 [M + H]+ | |

TABLE 25
| Comp. No. | Struct | Ms cond. | RT (min) | MS | Comment |
|---|---|---|---|---|---|
| I-151 | 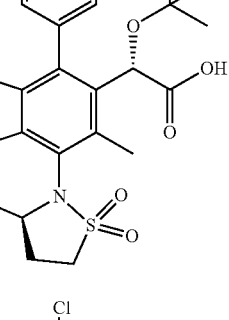 | (1) | 2.51 | 517 [M + H]+ | |
| I-152 | 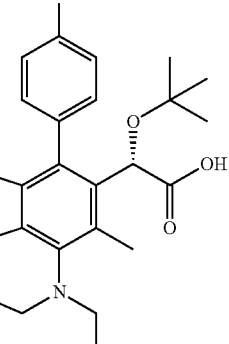 | (2) | 2.49 | 519 [M + H]+ | |
| I-153 | 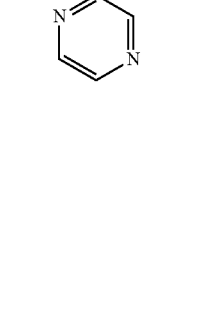 | (2) | 2.41 | 519 [M + H]+ | |

TABLE 25-continued

| Comp. No. | Struct | Ms cond. | RT (min) | MS | Comment |
|---|---|---|---|---|---|
| I-154 | | (2) | 2.81 | 522 [M + H]+ | |
| I-155 | | (2) | 1.65 | 504 [M + H]+ | |

TABLE 26

| Comp. No. | Struct | Ms cond. | RT (min) | MS | Comment |
|---|---|---|---|---|---|
| I-156 | | (1) | 3.27 | 535 [M + H]+ | |

TABLE 26-continued

| Comp. No. | Struct | Ms cond. | RT (min) | MS | Comment |
|---|---|---|---|---|---|
| I-157 | | (1) | 3.41 | 555 [M + H]+ | |
| I-158 | | (1) | 2.08 | 534 [M + H]+ | |
| I-159 | | (1) | 2.30 | 495 [M + H]+ | |
| I-160 | | (1) | 1.85 | 478 [M + H]+ | |

TABLE 27
| | | | | | |
|---|---|---|---|---|---|
| I-161 | 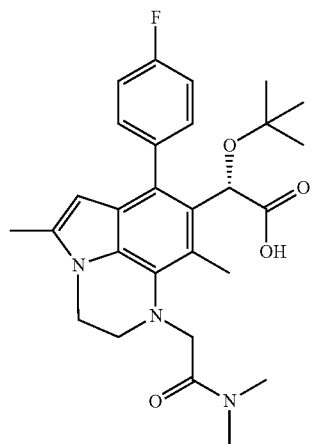 [SMILES: Cc1c([C@H](OC(C)(C)C)C(=O)O)c(-c2ccc(F)cc2)c2cc(C)n3c2c1N(CC(=O)N(C)C)CC3] | (1) | 2.24 | 496 [M + H]+ | |
| I-162 | 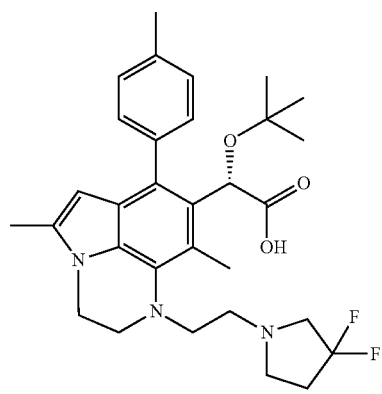 [SMILES: Cc1ccc(-c2c([C@H](OC(C)(C)C)C(=O)O)c(C)c3c4c2cc(C)n4CCN3CCN2CCC(F)(F)C2)cc1] | (1) | 2.2 | 540 [M + H]+ | |
| I-163 | 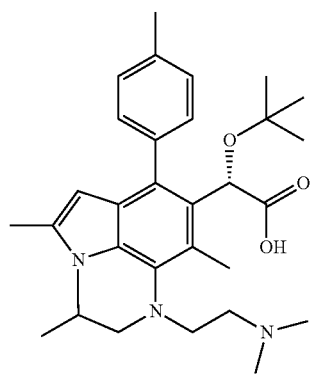 | (1) | 2.08 | 492 [M + H]+ | enantiomer |
| I-164 | 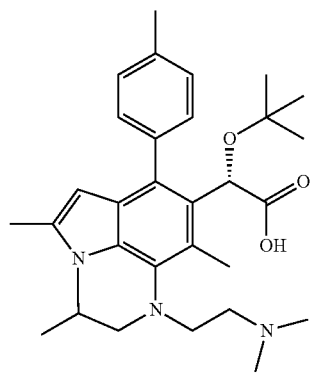 | (1) | 1.94 | 492 [M + H]+ | diastereomer of I-163 |

TABLE 28
| I-165 | 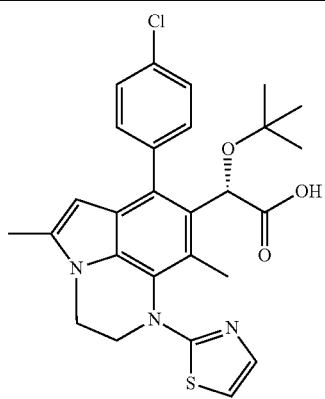 | (1) | 2.77 | 510 [M + H]+ |
| I-168 | 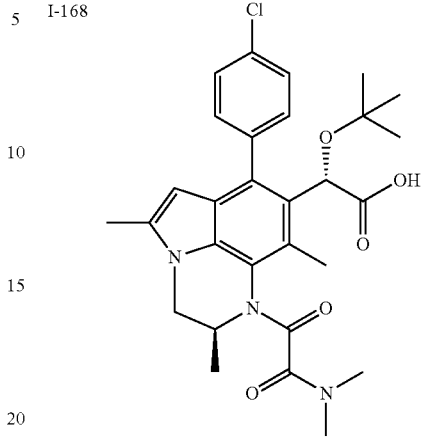 | (1) | 2.39 | 540 [M + H]+ |
| I-166 | 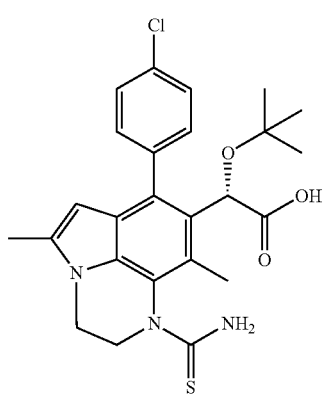 [SMILES: Cc1c([C@H](OC(C)(C)C)C(=O)O)c(-c2ccc(Cl)cc2)c2cc(C)n3c2c1N(C(N)=S)CC3] | (1) | 2.5 | 486 [M + H]+ |
| I-167 | 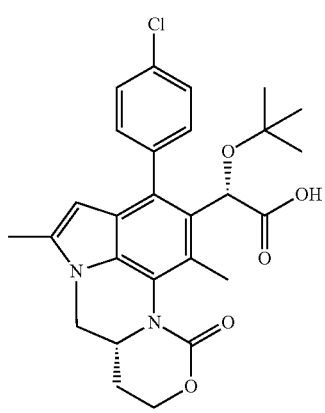 [SMILES: Cc1c([C@H](OC(C)(C)C)C(=O)O)c(-c2ccc(Cl)cc2)c2cc(C)n3c2c1N1C(=O)OCC[C@@H]1C3] | (1) | 2.38 | 495 [M − H]− |
| I-169 | 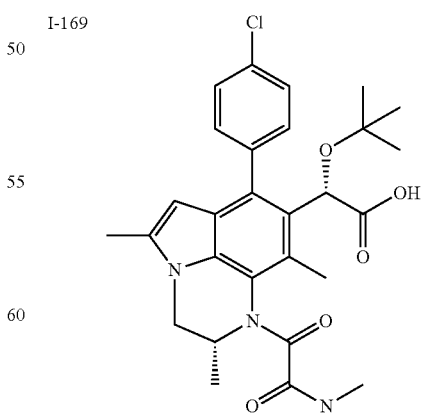 | (1) | 2.31 | 540 [M + H]+ |

TABLE 29
I-170 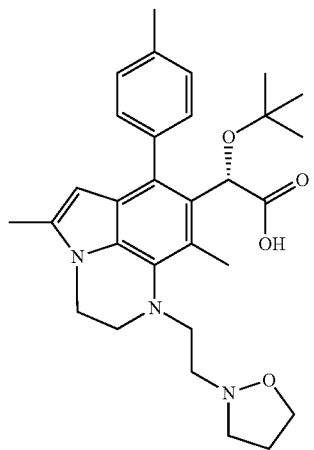 [SMILES: Cc1ccc(-c2c([C@H](OC(C)(C)C)C(=O)O)c(C)c3c4c2cc(C)n4CCN3CCN2CCCO2)cc1] (1) 2.18 506 [M + H]+
I-171 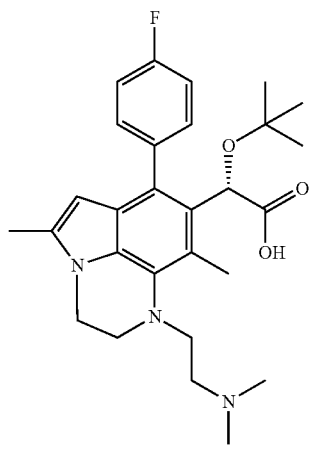 [SMILES: Cc1c([C@H](OC(C)(C)C)C(=O)O)c(-c2ccc(F)cc2)c2cc(C)n3c2c1N(CCN(C)C)CC3] (1) 1.89 482 [M + H]+
I-172 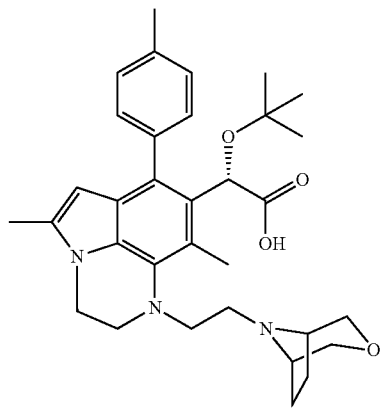 [SMILES: Cc1ccc(-c2c([C@H](OC(C)(C)C)C(=O)O)c(C)c3c4c2cc(C)n4CCN3CCN2C3CCC2COC3)cc1] (1) 1.74 546 [M + H]+

TABLE 29-continued
| | | | | | |
|---|---|---|---|---|---|
| I-173 | Cl 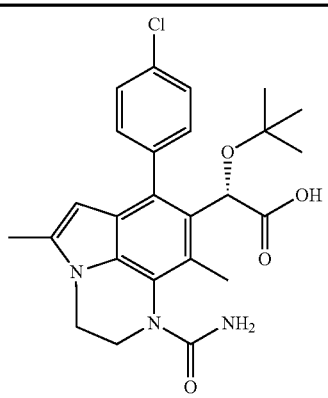 | (1) | 2.29 | 470 [M + H]+ | |
| I-174 | Cl 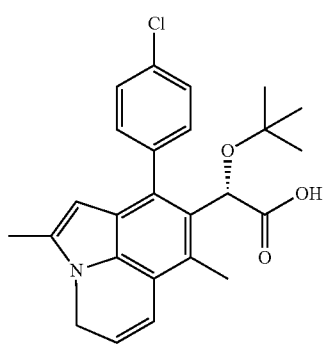 [SMILES: Cc1c([C@H](OC(C)(C)C)C(=O)O)c(-c2ccc(Cl)cc2)c2cc(C)n3c2c1C=CC3] | (1) | 2.75 | 424 [M + H]+ | including 15% of I-175 |
TABLE 30
| | | | | | |
|---|---|---|---|---|---|
| I-175 | Cl 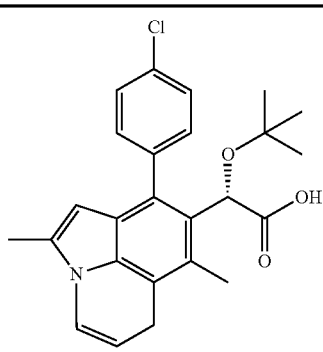 | (1) | 2.84 | 424 [M + H]+ | including 35% of I-174 |
| I-177 | F 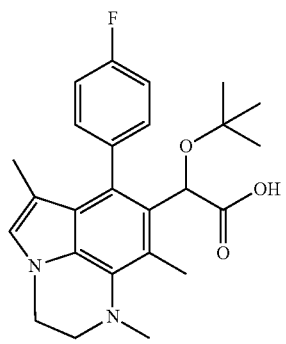 [SMILES: Cc1c(C(OC(C)(C)C)C(=O)O)c(-c2ccc(F)cc2)c2c(C)cn3c2c1N(C)CC3] | (1) | 2.13 | 425 [M + H]+ | racemate purity 90% |

TABLE 30-continued
| I-179 | 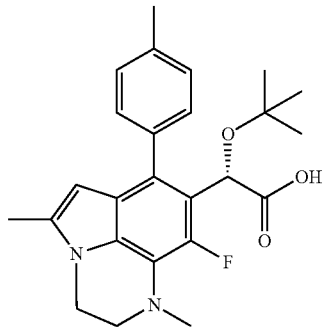 [SMILES: Cc1ccc(-c2c([C@H](OC(C)(C)C)C(=O)O)c(F)c3c4c2cc(C)n4CCN3C)cc1] | (1) | 2.62 | 425 | [M + H]+ |
TABLE 31
| I-180 | 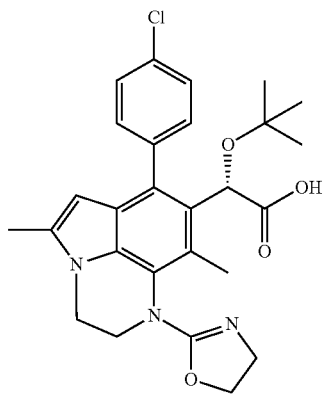 [SMILES: Cc1c([C@H](OC(C)(C)C)C(=O)O)c(-c2ccc(Cl)cc2)c2cc(C)n3c2c1N(C1=NCCO1)CC3] | (1) | 1.93 | 496 | [M + H]+ |
| I-181 | 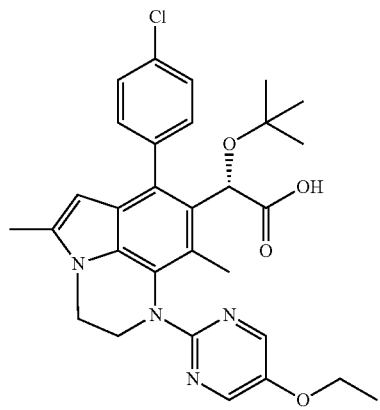 [SMILES: CCOc1cnc(N2CCn3c(C)cc4c(-c5ccc(Cl)cc5)c([C@H](OC(C)(C)C)C(=O)O)c(C)c2c43)nc1] | (1) | 3.09 | 549 | [M + H]+ |

TABLE 31-continued
| I-183 | Cl 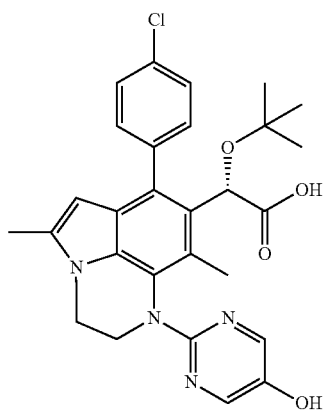 [SMILES: Cc1c([C@H](OC(C)(C)C)C(=O)O)c(-c2ccc(Cl)cc2)c2cc(C)n3c2c1N(c1ncc(O)cn1)CC3] | (1) | 2.67 | 521 | [M + H]+ |
| I-185 | F 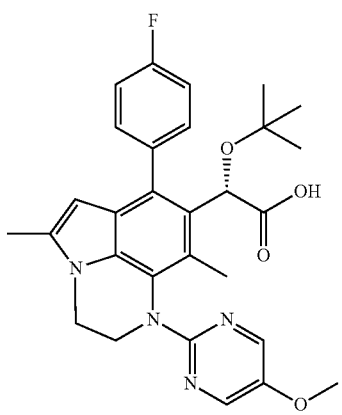 | (1) | 2.5 | 519 | [M + H]+ |
| I-186 | 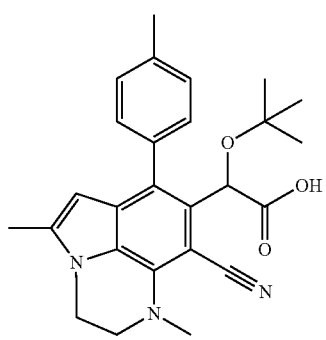 [SMILES: Cc1ccc(-c2c(C(OC(C)(C)C)C(=O)O)c(C#N)c3c4c2cc(C)n4CCN3C)cc1] | (1) | 2.45 | 432 | [M + H]+ |
| I-188 | Cl 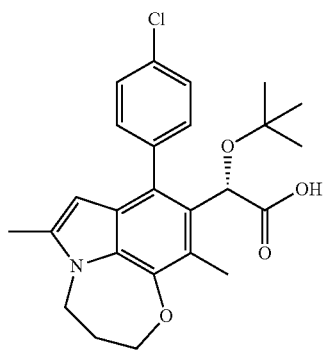 [SMILES: Cc1c([C@H](OC(C)(C)C)C(=O)O)c(-c2ccc(Cl)cc2)c2cc(C)n3c2c1OCCC3] | (1) | 2.83 | 442.2 | [M + H]+ |

TABLE 32
| | | | | | |
|---|---|---|---|---|---|
| I-189 | 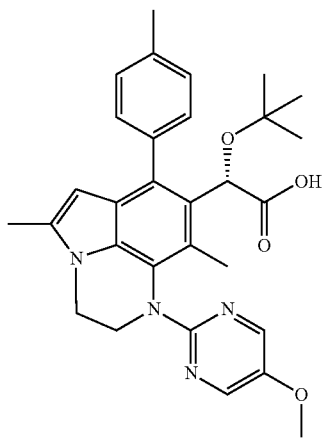 | (1) | 2.9 | 515.2 | [M + H]+ |
| I-190 | 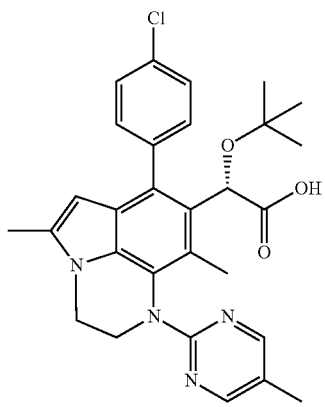 | (1) | 2.98 | 519.2 | [M + H]+ |
| I-191 | 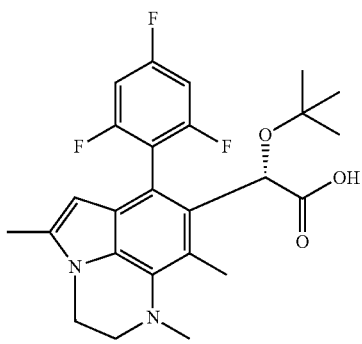 [SMILES: Cc1c([C@H](OC(C)(C)C)C(=O)O)c(-c2c(F)cc(F)cc2F)c2cc(C)n3c2c1N(C)CC3] | (1) | 2.31 | 461 | [M + H]+ |
| I-192 | 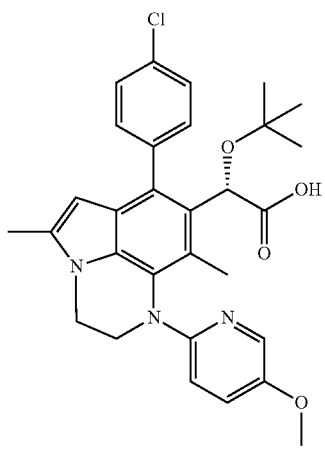 | (1) | 2.99 | 534.2 | [M + H]+ |

TABLE 32-continued
| | | | | | | |
|---|---|---|---|---|---|---|
| I-193 | 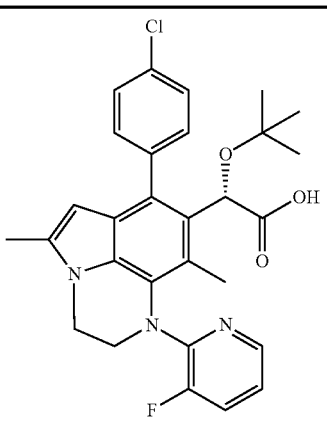 | (1) | 2.96 | 522.1 | [M + H]+ | |
TABLE 33
| | | | | | | |
|---|---|---|---|---|---|---|
| I-194 | 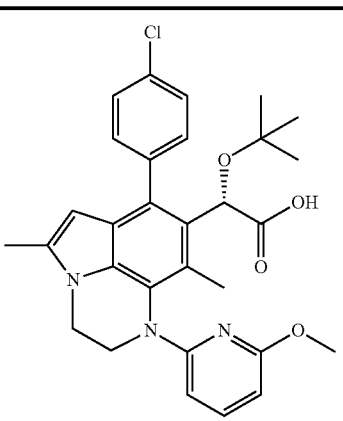 | (2) | 3.3 | 534 | [M + H]+ | |
| I-195 | 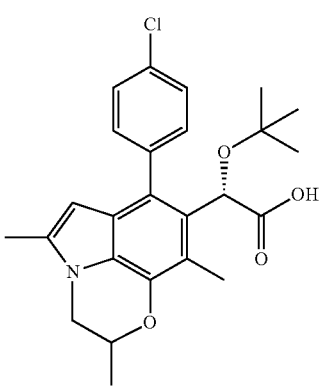 [SMILES: Cc1c([C@H](OC(C)(C)C)C(=O)O)c(-c2ccc(Cl)cc2)c2cc(C)n3c2c1OC(C)C3] | (1) | 2.89 | 442 | [M + H]+ | enantiomer |

TABLE 33-continued
| | | | | | | |
|---|---|---|---|---|---|---|
| I-196 | 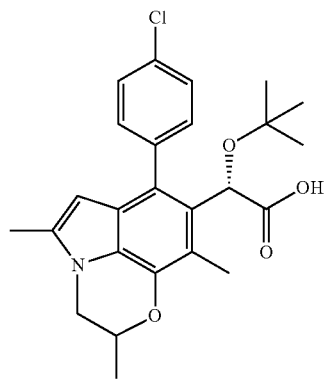 | (1) | 2.85 | 442 | [M + H]+ | diastereomer of I-195 |
| I-197 | 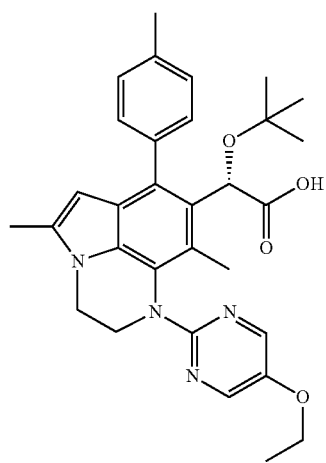 [SMILES: CCOc1cnc(N2CCn3c(C)cc4c(-c5ccc(C)cc5)c([C@H](OC(C)(C)C)C(=O)O)c(C)c2c43)nc1] | (2) | 3.05 | 529 | [M + H]+ | |
| I-198 | 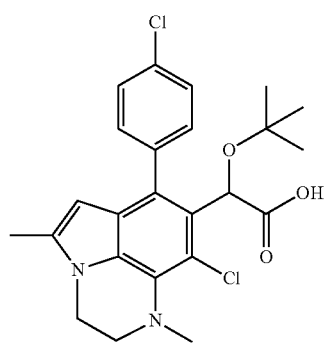 [SMILES: Cc1cc2c(-c3ccc(Cl)cc3)c(C(OC(C)(C)C)C(=O)O)c(Cl)c3c2n1CCN3C] | (1) | 2.66 | 461 | [M + H]+ | racemate |

TABLE 34

| Comp. No. | Struct | MS cond. | RT (min) | MS |
|---|---|---|---|---|
| I-199 | | (1) | 2.68 | 408 [M + H]+ |

TABLE 35

| Comp. No. | Struct | MS cond. | RT (min) | MS |
|---|---|---|---|---|
| I-227 | | (1) | 2.78 | 487 [M − H]− |
| I-228 | | (1) | 2.65 | 461 [M + H]+ |
| I-229 | | (1) | 2.32 | 457 [M + H]+ |

TABLE 35-continued
| Comp. No. | Struct | MS cond. | RT (min) | MS |
|---|---|---|---|---|
| I-230 | | (1) | 2.58 | 551 [M + H]+ |
TABLE 36
| I-231 | | (1) | 2.76 | 501 [M + H]+ |
|---|---|---|---|---|
| I-232 | 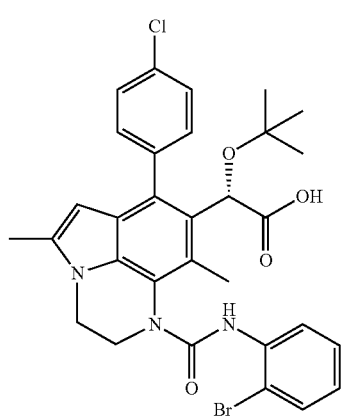 [SMILES: Cc1c([C@H](OC(C)(C)C)C(=O)O)c(-c2ccc(Cl)cc2)c2cc(C)n3c2c1N(C(=O)Nc1ccccc1Br)CC3] | (1) | 3.11 | 622 [M − H]− |

TABLE 36-continued
| | | | | |
|---|---|---|---|---|
| I-233 | 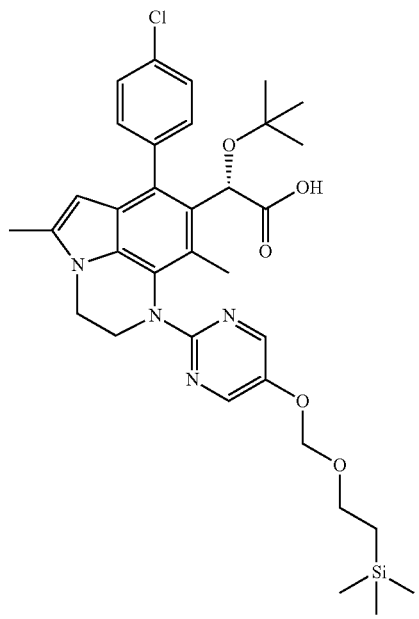 | (1) | 3.5 | 651 [M + H]+ |
| I-234 | 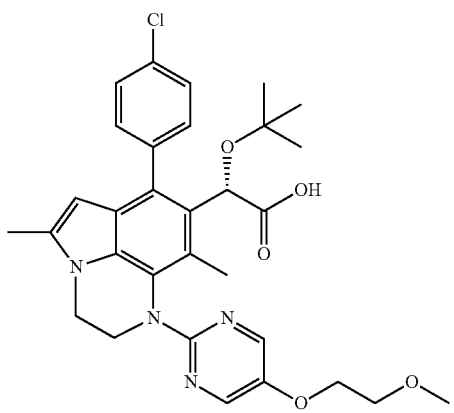 | (1) | 2.87 | 579 [M + H]+ |
TABLE 37
| | | | | |
|---|---|---|---|---|
| I-235 | 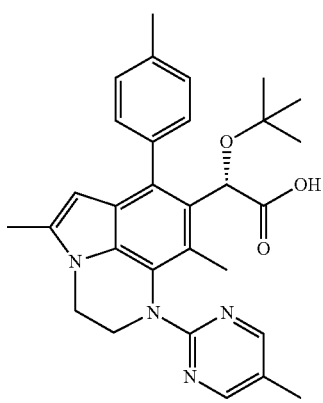 | (1) | 2.91 | 499 [M + H]+ |

TABLE 37-continued
| I-236 | 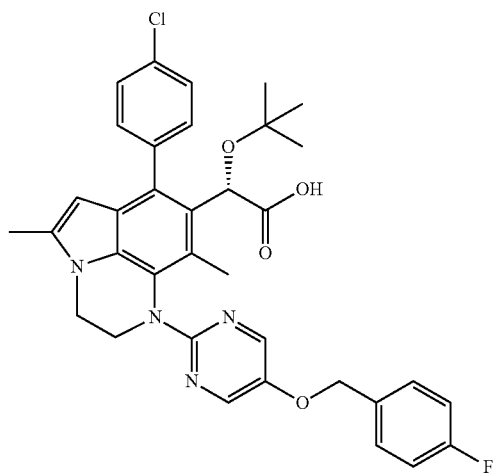 [SMILES: Cc1c([C@H](OC(C)(C)C)C(=O)O)c(-c2ccc(Cl)cc2)c2cc(C)n3c2c1N(c1ncc(OCc2ccc(F)cc2)cn1)CC3] | (2) | 3.23 | 629 | [M + H]+ | |
| I-237 | 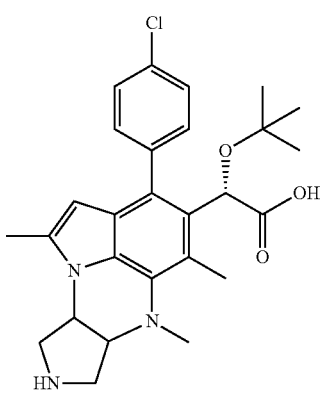 [SMILES: Cc1c([C@H](OC(C)(C)C)C(=O)O)c(-c2ccc(Cl)cc2)c2cc(C)n3c2c1N(C)C1CNCC13] | (2) | 1.88 | 482 | [M + H]+ | enantiomer |
| I-238 | 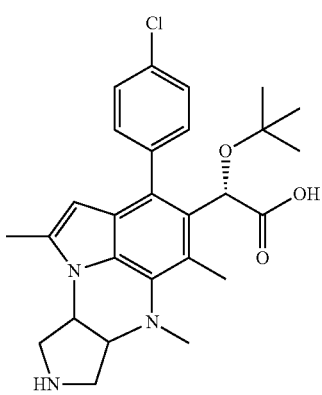 [SMILES: Cc1c([C@H](OC(C)(C)C)C(=O)O)c(-c2ccc(Cl)cc2)c2cc(C)n3c2c1N(C)C1CNCC13] | (2) | 2.06 | 482 | [M + H]+ | diastereomer of I-237 |

TABLE 38
| I-239 | 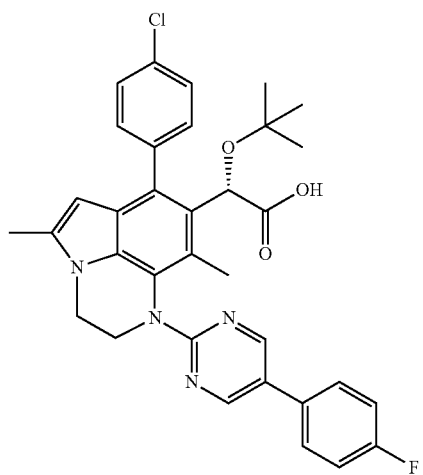 [SMILES: Cc1c([C@H](OC(C)(C)C)C(=O)O)c(-c2ccc(Cl)cc2)c2cc(C)n3c2c1N(c1ncc(-c2ccc(F)cc2)cn1)CC3] | (1) | 3.05 | 599 | [M + H]+ |
| I-240 | 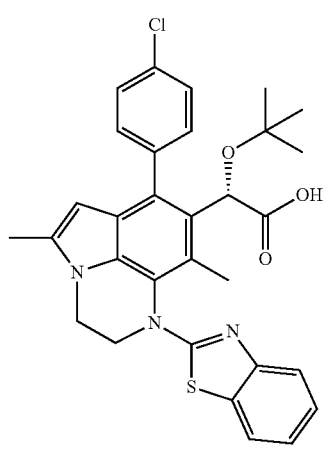 [SMILES: Cc1c([C@H](OC(C)(C)C)C(=O)O)c(-c2ccc(Cl)cc2)c2cc(C)n3c2c1N(c1nc2ccccc2s1)CC3] | (1) | 2.96 | 560 | [M + H]+ |
| I-241 | 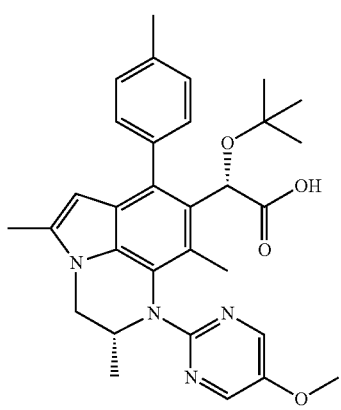 | (1) | 2.91 | 527 | [M − H]− |

TABLE 38-continued
| I-242 | 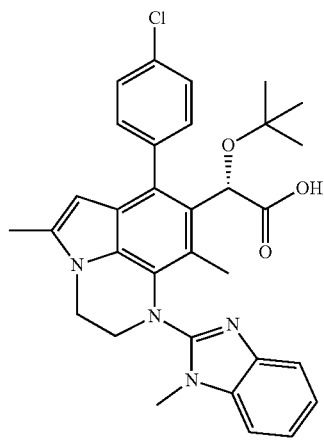 [SMILES: Cc1c([C@H](OC(C)(C)C)C(=O)O)c(-c2ccc(Cl)cc2)c2cc(C)n3c2c1N(c1nc2ccccc2n1C)CC3] | (1) | 2.42 | 558 | [M + H]+ |
| I-243 | 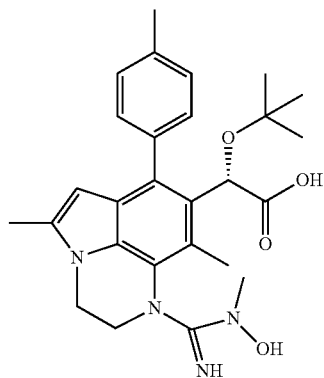 [SMILES: Cc1ccc(-c2c([C@H](OC(C)(C)C)C(=O)O)c(C)c3c4c2cc(C)n4CCN3C(=N)N(C)O)cc1] | (1) | 2.13 | 479 | [M + H]+ |
TABLE 39
| I-244 | 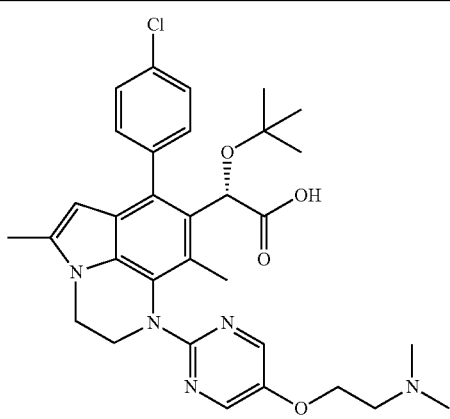 | (1) | 2.2 | 592 | [M + H]+ |

TABLE 39-continued
| I-245 | 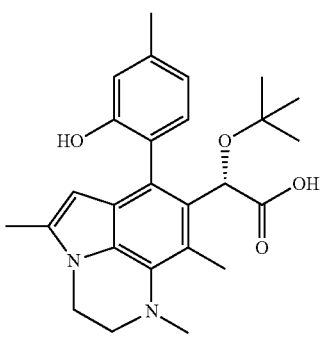 [SMILES: Cc1ccc(-c2c([C@H](OC(C)(C)C)C(=O)O)c(C)c3c4c2cc(C)n4CCN3C)c(O)c1] | (1) | 2.2 | 437 | [M + H]+ | a mixture of diastereomers |
| I-246 | 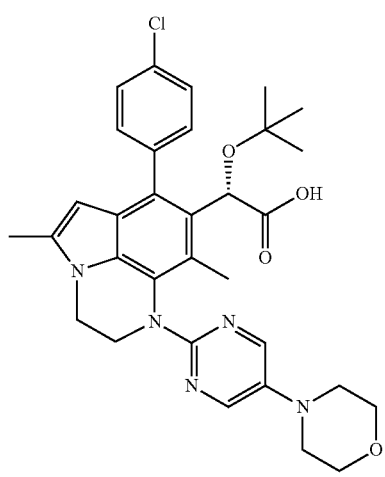 [SMILES: Cc1c([C@H](OC(C)(C)C)C(=O)O)c(-c2ccc(Cl)cc2)c2cc(C)n3c2c1N(c1ncc(N2CCOCC2)cn1)CC3] | (1) | 2.61 | 590 | [M + H]+ | |
| I-247 | 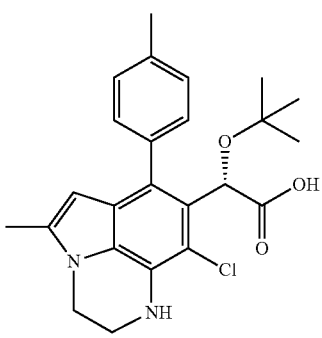 [SMILES: Cc1ccc(-c2c([C@H](OC(C)(C)C)C(=O)O)c(Cl)c3c4c2cc(C)n4CCN3)cc1] | (1) | 2.49 | 427 | [M + H]+ | |

TABLE 40
| | | | | | |
|---|---|---|---|---|---|
| I-248 | 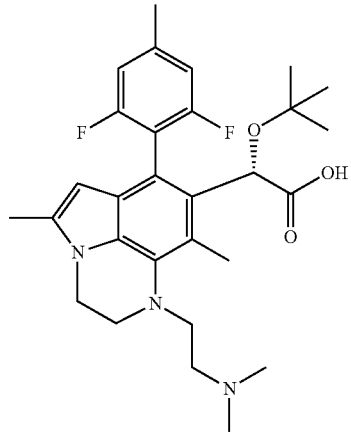 [SMILES: Cc1cc(F)c(-c2c([C@H](OC(C)(C)C)C(=O)O)c(C)c3c4c2cc(C)n4CCN3CCN(C)C)c(F)c1] | (1) | 2.12 | 514 | [M + H]+ |
| I-249 | 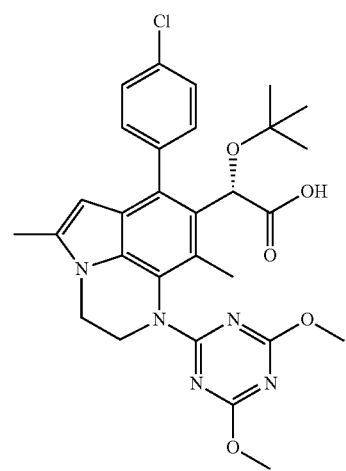 | (1) | 2.44 | 566 | [M + H]+ |
| I-250 | 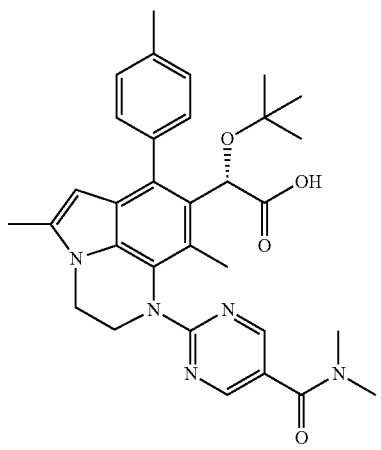 | (1) | 2.5 | 556 | [M + H]+ |

TABLE 40-continued
| I-251 | 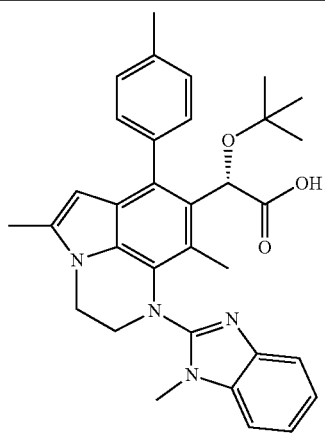 | (1) | 2.43 | 537 | [M + H]+ | |
TABLE 41
| I-252 | 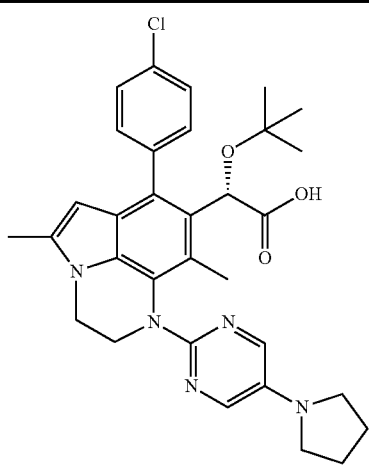 | (1) | 3.03 | 574 | [M + H]+ | |
| I-253 | 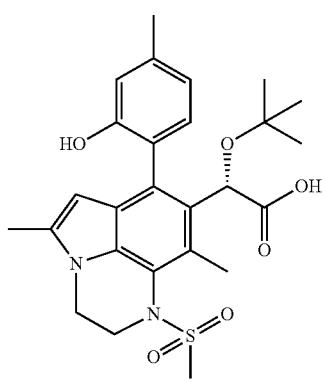 [SMILES: Cc1ccc(-c2c([C@H](OC(C)(C)C)C(=O)O)c(C)c3c4c2cc(C)n4CCN3S(C)(=O)=O)c(O)c1] | (1) | 2.38 | 501 | [M + H]+ | a mixture of diastereomers |

TABLE 41-continued
| | | | | | |
|---|---|---|---|---|---|
| I-254 | 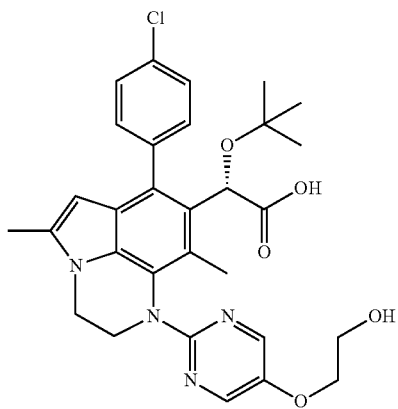 [SMILES: Cc1c([C@H](OC(C)(C)C)C(=O)O)c(-c2ccc(Cl)cc2)c2cc(C)n3c2c1N(c1ncc(OCCO)cn1)CC3] | (1) | 2.5 | 565 | [M + H]+ |
| I-255 | 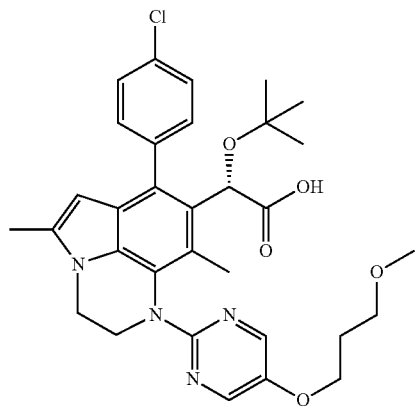 | (1) | 2.9 | 593 | [M + H]+ |
TABLE 42
| | | | | | |
|---|---|---|---|---|---|
| I-256 | 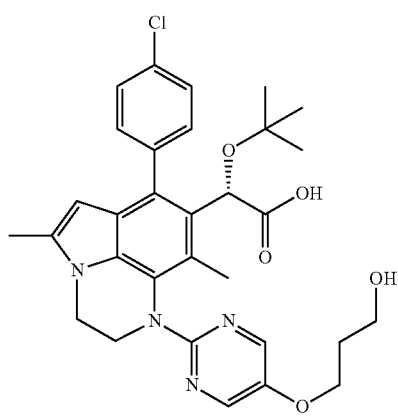 [SMILES: Cc1c([C@H](OC(C)(C)C)C(=O)O)c(-c2ccc(Cl)cc2)c2cc(C)n3c2c1N(c1ncc(OCCCO)cn1)CC3] | (1) | 2.58 | 579 | [M + H]+ |

TABLE 42-continued
| | | | | | |
|---|---|---|---|---|---|
| I-257 | 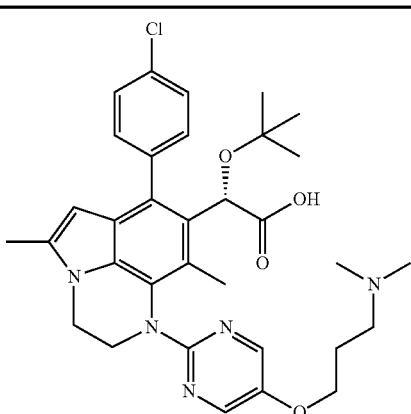 | (1) | 2.43 | 606 | [M + H]+ |
| I-258 | 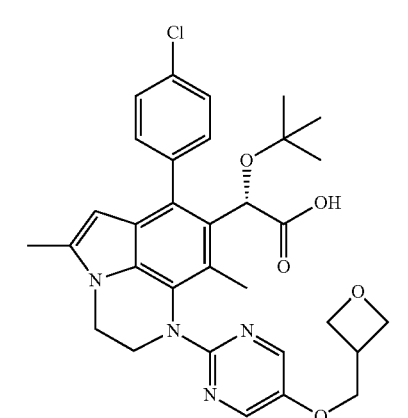 [SMILES: Cc1c([C@H](OC(C)(C)C)C(=O)O)c(-c2ccc(Cl)cc2)c2cc(C)n3c2c1N(c1ncc(OCC2COC2)cn1)CC3] | (1) | 2.7 | 591 | [M + H]+ |
| I-259 | 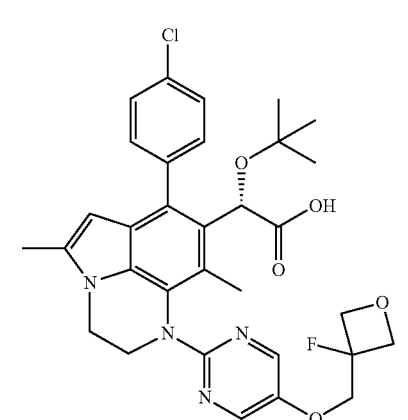 | (1) | 2.78 | 607 | [M − H]− |
| I-260 | 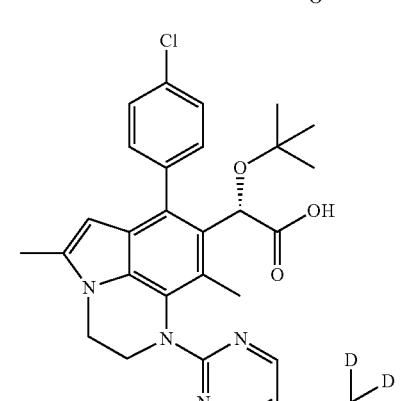 | (1) | 2.81 | 538 | [M + H]+ |

TABLE 43
| I-261 | 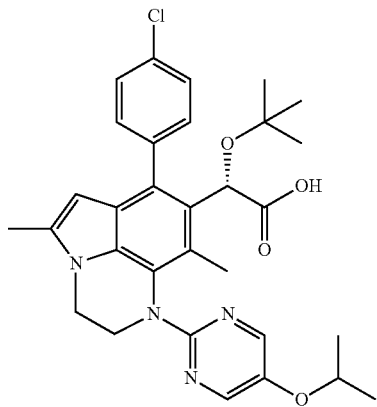 [SMILES: Cc1c([C@H](OC(C)(C)C)C(=O)O)c(-c2ccc(Cl)cc2)c2cc(C)n3c2c1N(c1ncc(OC(C)C)cn1)CC3] | (1) | 3.04 | 563 | [M + H]+ |
| I-262 | 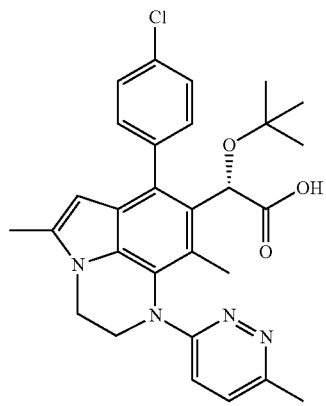 | (1) | 2.39 | 519 | [M + H]+ |
| I-263 | 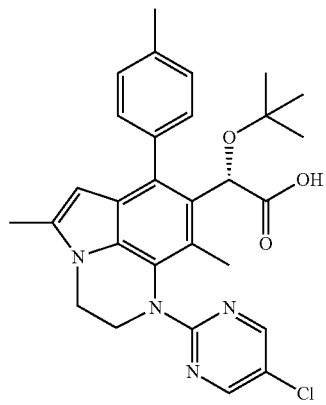 [SMILES: Cc1ccc(-c2c([C@H](OC(C)(C)C)C(=O)O)c(C)c3c4c2cc(C)n4CCN3c2ncc(Cl)cn2)cc1] | (1) | 3.15 | 519 | [M + H]+ |
| I-264 | 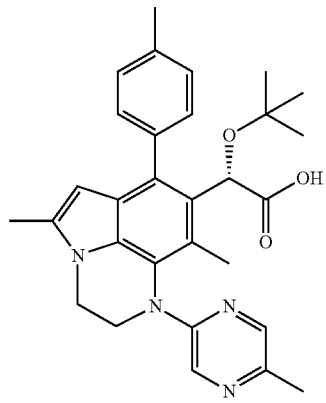 | (1) | 2.74 | 500 | [M + H]+ |

TABLE 43-continued
| | | | | |
|---|---|---|---|---|
| I-265 | 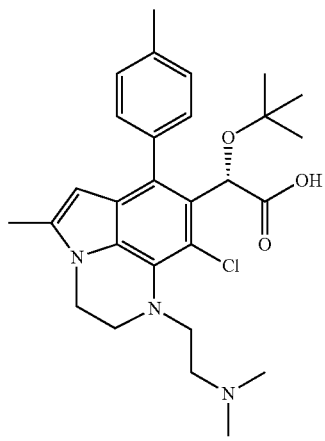 [SMILES: Cc1ccc(-c2c([C@H](OC(C)(C)C)C(=O)O)c(Cl)c3c4c2cc(C)n4CCN3CCN(C)C)cc1] | (1) | 2.13 | 498 [M + H]+ |
TABLE 44
| | | | | |
|---|---|---|---|---|
| I-266 | 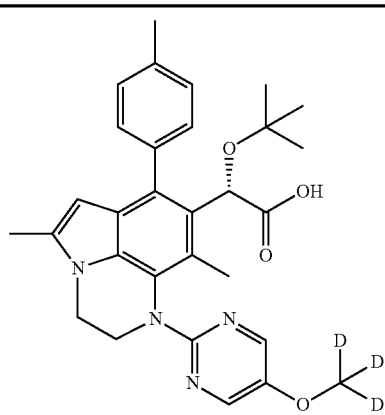 | (1) | 2.77 | 518 [M + H]+ |
| I-267 | 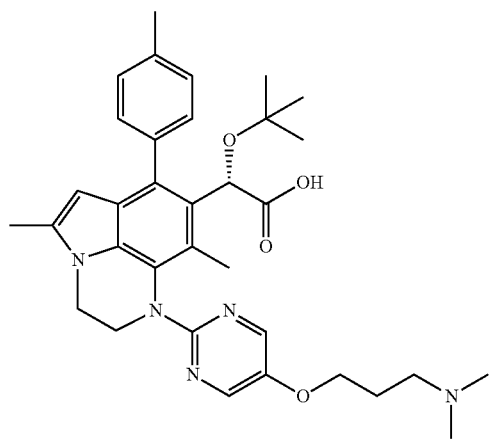 | (1) | 2.29 | 586 [M + H]+ |

TABLE 44-continued
| I-268 | 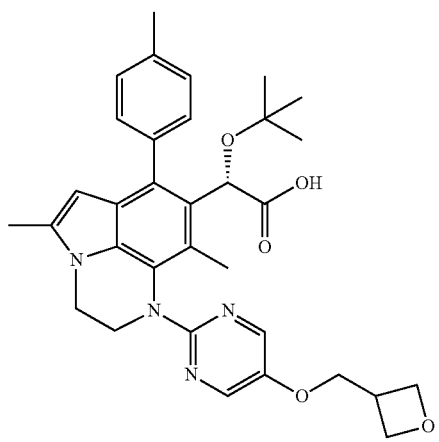 [SMILES: Cc1ccc(-c2c([C@H](OC(C)(C)C)C(=O)O)c(C)c3c4c2cc(C)n4CCN3c2ncc(OCC3COC3)cn2)cc1] | (1) | 2.66 | 571 [M + H]+ |
| I-269 | 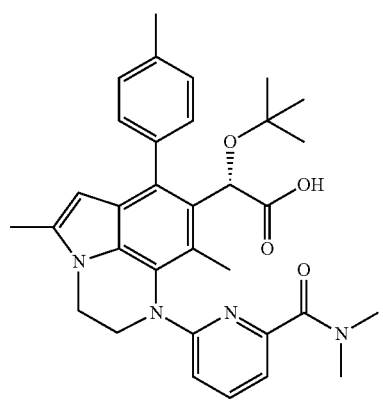 | (1) | 2.62 | 556 [M + H]+ |
| I-270 | 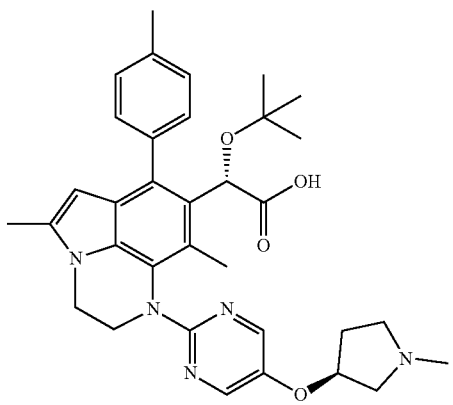 | (1) | 2.27 | 584 [M + H]+ |

TABLE 45
| I-271 | 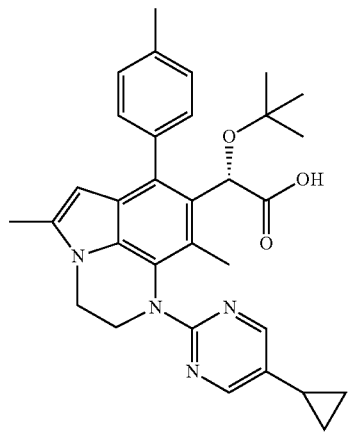 [SMILES: Cc1ccc(-c2c([C@H](OC(C)(C)C)C(=O)O)c(C)c3c4c2cc(C)n4CCN3c2ncc(C3CC3)cn2)cc1] | (1) | 2.92 | 525 | [M + H]+ |
| I-272 | 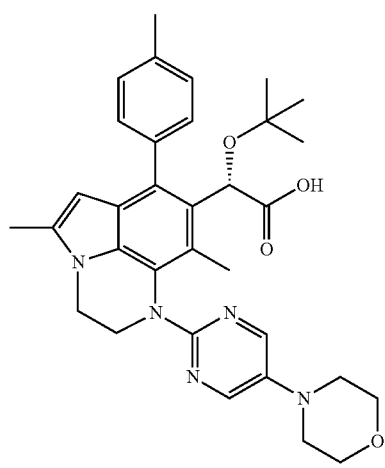 [SMILES: Cc1ccc(-c2c([C@H](OC(C)(C)C)C(=O)O)c(C)c3c4c2cc(C)n4CCN3c2ncc(N3CCOCC3)cn2)cc1] | (1) | 2.63 | 570 | [M + H]+ |
| I-273 | 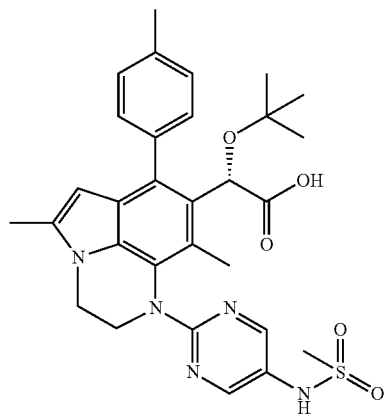 [SMILES: Cc1ccc(-c2c([C@H](OC(C)(C)C)C(=O)O)c(C)c3c4c2cc(C)n4CCN3c2ncc(NS(C)(=O)=O)cn2)cc1] | (1) | 2.49 | 578 | [M + H]+ |

TABLE 45-continued
| | | | | |
|---|---|---|---|---|
| I-274 | 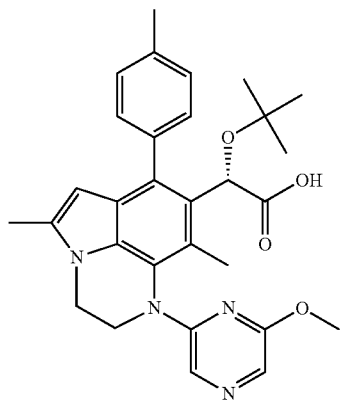 | (1) | 2.97 | 515 [M + H]+ |
| I-275 | 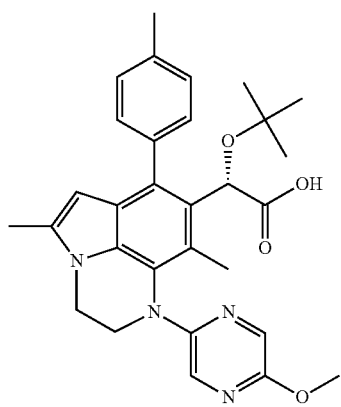 | (1) | 3.08 | 515 [M + H]+ |
TABLE 46
| | | | | |
|---|---|---|---|---|
| I-276 | 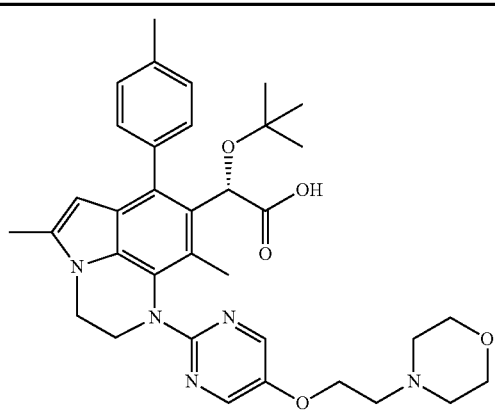 | (1) | 2.24 | 614 [M + H]+ |

TABLE 46-continued
| | | | | |
|---|---|---|---|---|
| I-277 | 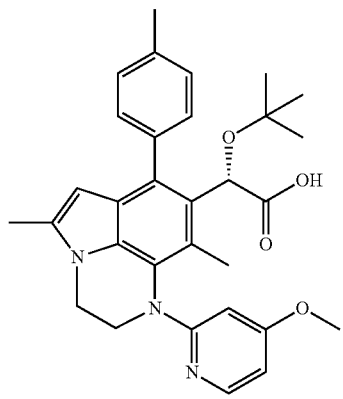 | (1) | 2.33 | 514 [M + H]+ |
| I-278 | 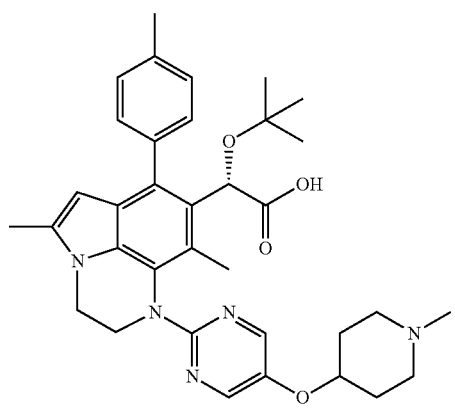 | (1) | 2.33 | 598 [M + H]+ |
| I-279 | 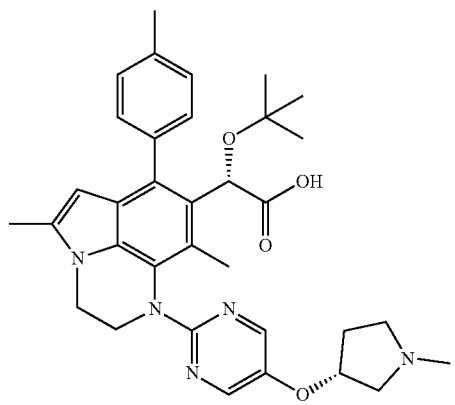 | (1) | 2.21 | 584 [M + H]+ |

TABLE 47
| I-280 | 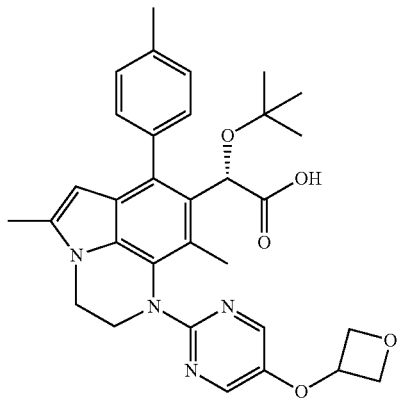 [SMILES: Cc1ccc(-c2c([C@H](OC(C)(C)C)C(=O)O)c(C)c3c4c2cc(C)n4CCN3c2ncc(OC3COC3)cn2)cc1] | (1) | 2.67 | 557 [M + H]+ |
| I-281 | 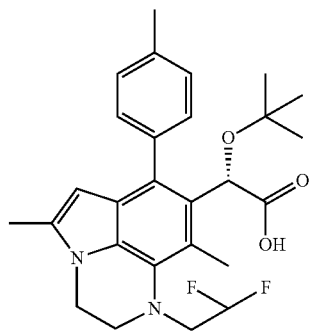 [SMILES: Cc1ccc(-c2c([C@H](OC(C)(C)C)C(=O)O)c(C)c3c4c2cc(C)n4CCN3CC(F)F)cc1] | (1) | 2.84 | 471 [M + H]+ |
| I-282 | 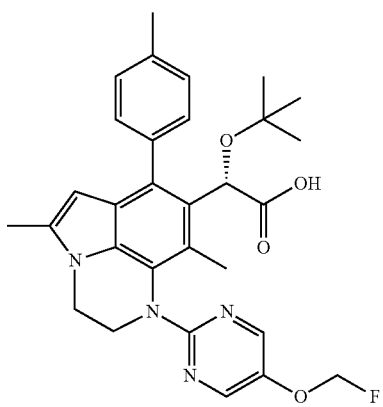 [SMILES: Cc1ccc(-c2c([C@H](OC(C)(C)C)C(=O)O)c(C)c3c4c2cc(C)n4CCN3c2ncc(OCF)cn2)cc1] | (1) | 2.78 | 533 [M + H]+ |
| I-283 | 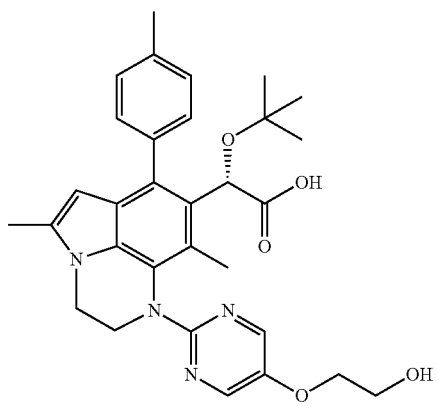 [SMILES: Cc1ccc(-c2c([C@H](OC(C)(C)C)C(=O)O)c(C)c3c4c2cc(C)n4CCN3c2ncc(OCCO)cn2)cc1] | (1) | 2.43 | 546 [M + H]+ |

TABLE 48
| I-284 | 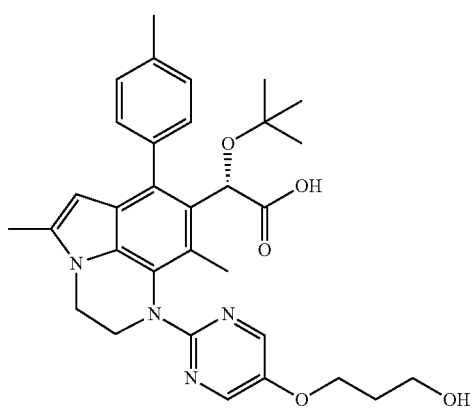 [SMILES: Cc1ccc(-c2c([C@H](OC(C)(C)C)C(=O)O)c(C)c3c4c2cc(C)n4CCN3c2ncc(OCCCO)cn2)cc1] | (1) | 2.51 | 560 [M + H]+ |
| I-285 | 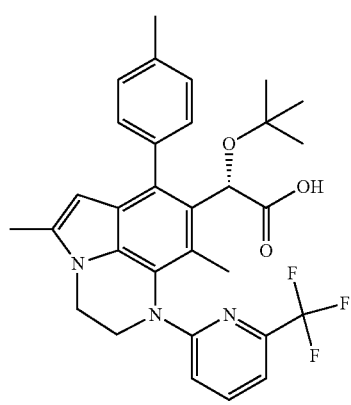 [SMILES: Cc1ccc(-c2c([C@H](OC(C)(C)C)C(=O)O)c(C)c3c4c2cc(C)n4CCN3c2cccc(C(F)(F)F)n2)cc1] | (1) | 3.35 | 552 [M + H]+ |
| I-286 | 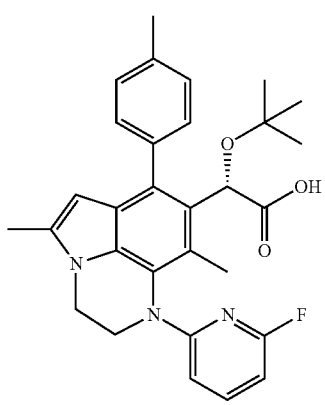 [SMILES: Cc1ccc(-c2c([C@H](OC(C)(C)C)C(=O)O)c(C)c3c4c2cc(C)n4CCN3c2cccc(F)n2)cc1] | (1) | 3.18 | 502 [M + H]+ |
| I-287 | 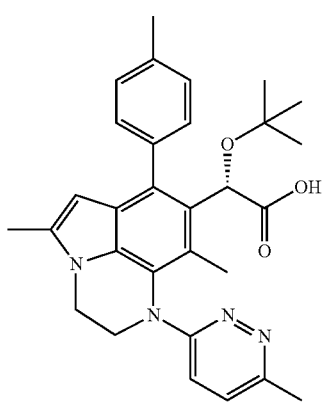 | (1) | 2.41 | 500 [M + H]+ |

TABLE 49
| I-288 | 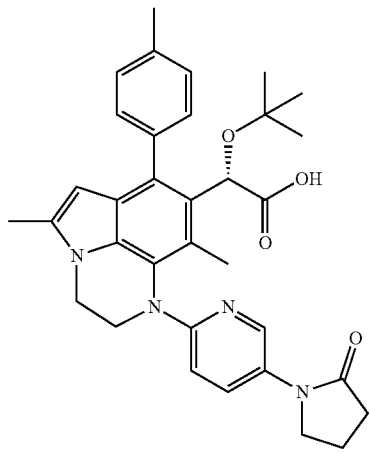 [SMILES: Cc1ccc(-c2c([C@H](OC(C)(C)C)C(=O)O)c(C)c3c4c2cc(C)n4CCN3c2ccc(N3CCCC3=O)cn2)cc1] | (1) | 2.65 | 568 | [M + H]+ |
| I-289 | 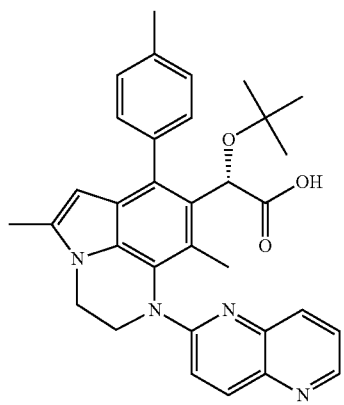 [SMILES: Cc1ccc(-c2c([C@H](OC(C)(C)C)C(=O)O)c(C)c3c4c2cc(C)n4CCN3c2ccc3ncccc3n2)cc1] | (1) | 2.77 | 535 | [M + H]+ |
| I-290 | 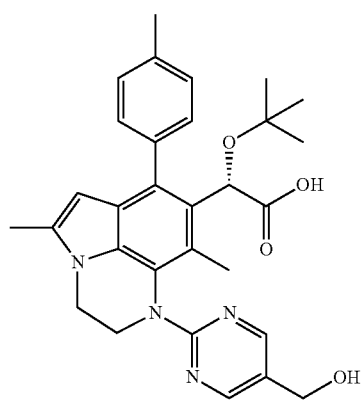 [SMILES: Cc1ccc(-c2c([C@H](OC(C)(C)C)C(=O)O)c(C)c3c4c2cc(C)n4CCN3c2ncc(CO)cn2)cc1] | (1) | 2.51 | 515 | [M + H]+ |

TABLE 49-continued
| I-291 | 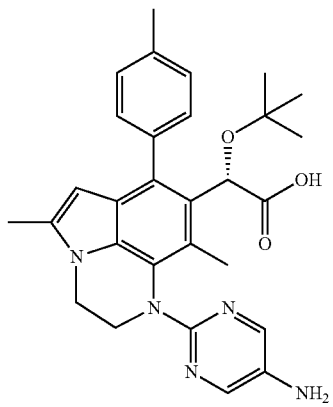 [SMILES: Cc1ccc(-c2c([C@H](OC(C)(C)C)C(=O)O)c(C)c3c4c2cc(C)n4CCN3c2ncc(N)cn2)cc1] | (1) | 2.41 | 500 | [M + H]+ |
TABLE 50
| I-292 | 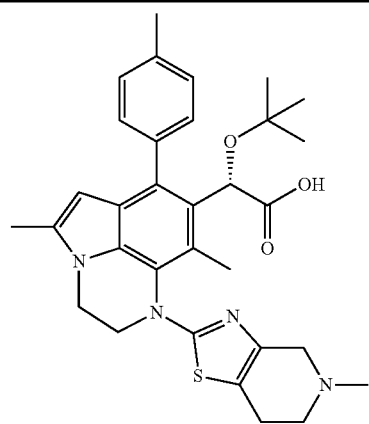 | (1) | 2.1 | 559 | [M + H]+ |
| I-293 | 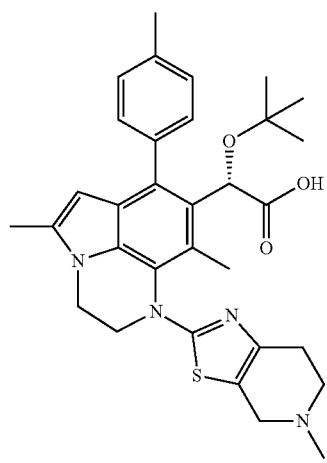 | (1) | 2.1 | 559 | [M + H]+ |

TABLE 50-continued
| I-294 | 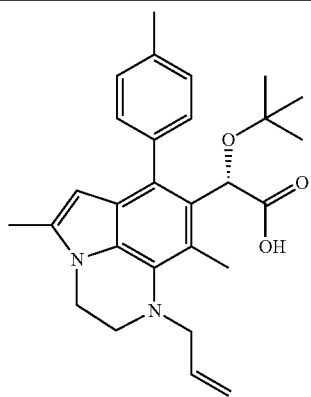 | (1) | 2.93 | 447 | [M + H]+ |
| I-295 | 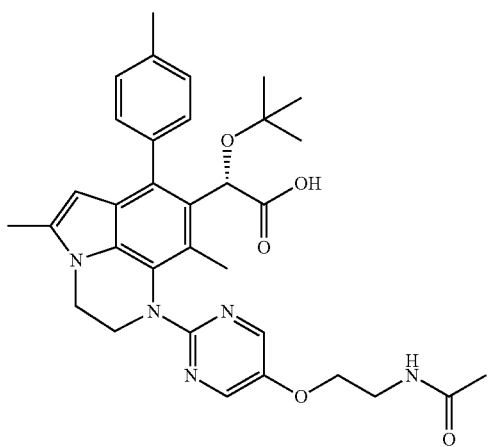 [SMILES: CC(=O)NCCOc1cnc(N2CCn3c(C)cc4c(-c5ccc(C)cc5)c([C@H](OC(C)(C)C)C(=O)O)c(C)c2c43)nc1] | (1) | 2.52 | 586 | [M + H]+ |
TABLE 51
| I-296 | 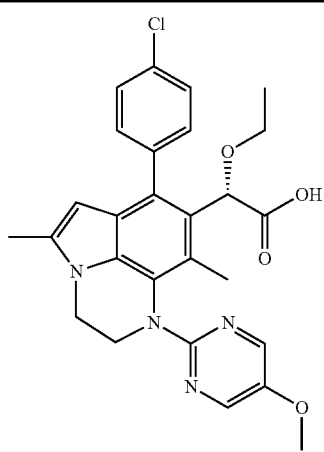 | (1) | 2.65 | 507 | [M + H]+ |

TABLE 51-continued
| | | | | | |
|---|---|---|---|---|---|
| I-297 | 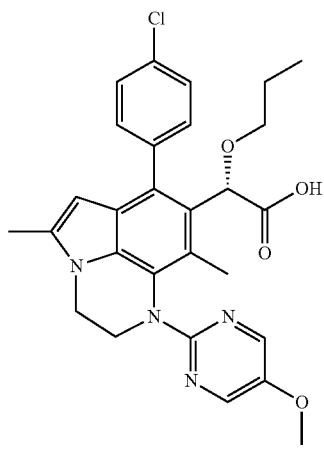 [SMILES: CCCO[C@H](C(=O)O)c1c(C)c2c3c(cc(C)n3CCN2c2ncc(OC)cn2)c1-c1ccc(Cl)cc1] | (1) | 2.81 | 521 | [M + H]+ |
| I-298 | 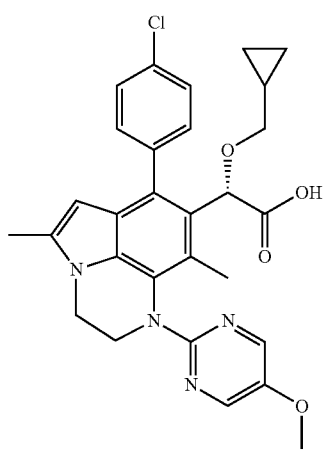 | (1) | 2.79 | 533 | [M + H]+ |
| I-299 | 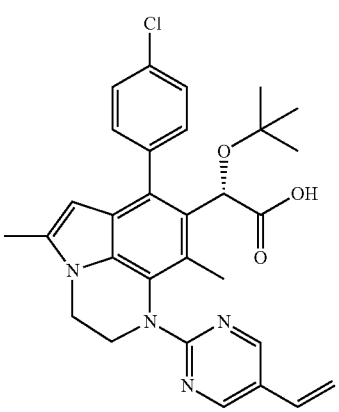 | (1) | 3.09 | 521 | [M + H]+ |

TABLE 52

| I-300 | [structure] | (1) | 2.98 | 587 | [M + H]+ |
|---|---|---|---|---|---|
| I-301 | [structure] | (1) | 2.66 | 519 | [M + H]+ |

TABLE 53

| Comp. No. | Struct. | Ms cond. | RT (min) | MS | Comment |
|---|---|---|---|---|---|
| I-310 | [structure] | (1) | 1.99 | 552 | [M + H]+ enantiomer |

TABLE 53-continued
| Comp. No. | Struct. | Ms cond. | RT (min) | MS | Comment |
|---|---|---|---|---|---|
| I-311 | 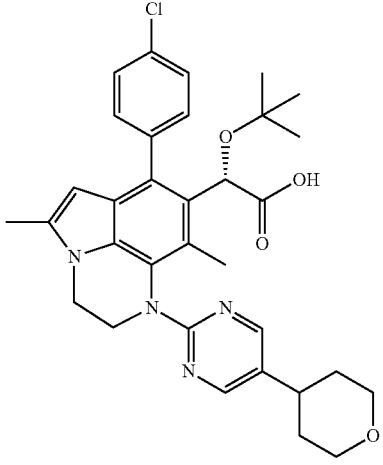 [SMILES: Cc1c([C@H](OC(C)(C)C)C(=O)O)c(-c2ccc(Cl)cc2)c2cc(C)n3c2c1N(c1ncc(C2CCOCC2)cn1)CC3] | (1) | 2.92 | 589 | [M + H]+ |
| I-312 | 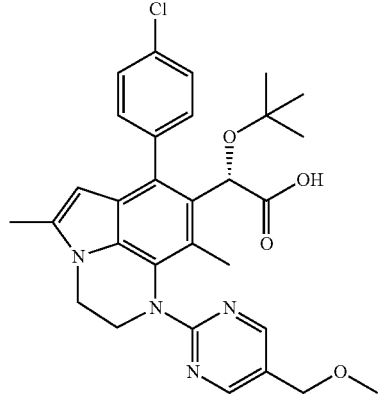 | (1) | 2.88 | 549 | [M + H]+ |
| I-313 | 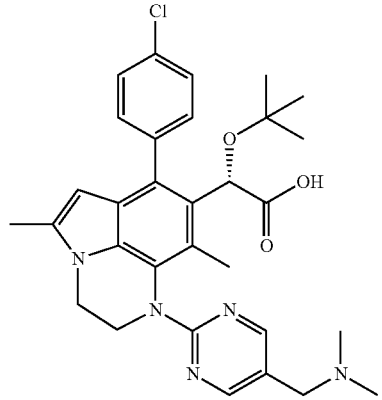 | (1) | 2.2 | 562 | [M + H]+ |

TABLE 54
I-314 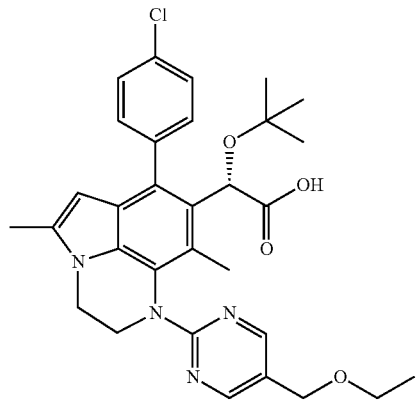 [SMILES: CCOCc1cnc(N2CCn3c(C)cc4c(-c5ccc(Cl)cc5)c([C@H](OC(C)(C)C)C(=O)O)c(C)c2c43)nc1] (1) 3.01 563 [M + H]+
I-315 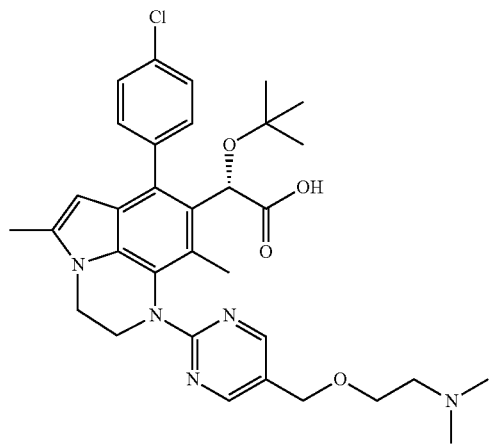 (1) 2.27 606 [M + H]+
I-316 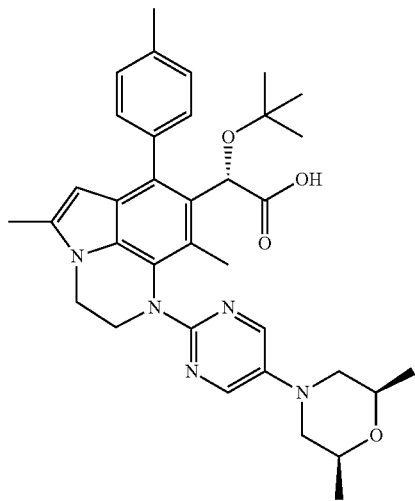 (1) 2.85 598 [M + H]+

TABLE 54-continued
| | | | | | |
|---|---|---|---|---|---|
| I-317 | 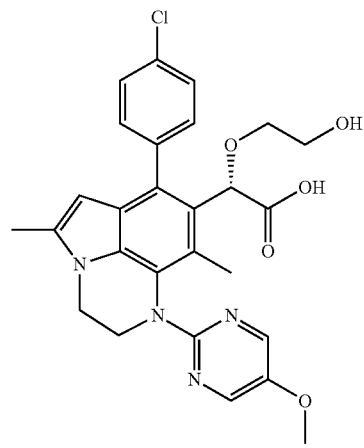 [SMILES: COc1cnc(N2CCn3c(C)cc4c(-c5ccc(Cl)cc5)c([C@H](OCCO)C(=O)O)c(C)c2c43)nc1] | (1) | 2.25 | 523 | [M + H]+ |
| I-318 | 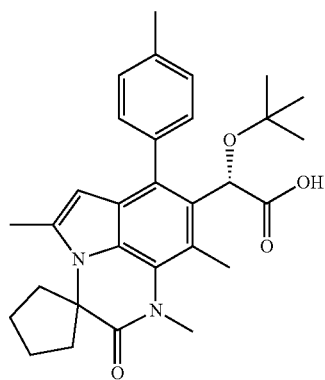 [SMILES: Cc1ccc(-c2c([C@H](OC(C)(C)C)C(=O)O)c(C)c3c4c2cc(C)n4C2(CCCC2)C(=O)N3C)cc1] | (1) | 2.99 | 490 | [M + H]+ |
TABLE 55
| | | | | | |
|---|---|---|---|---|---|
| I-319 | 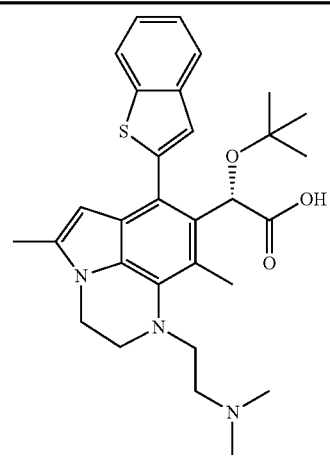 | (1) | 2.15 | 520 | [M + H]+ |

TABLE 55-continued
| I-320 | 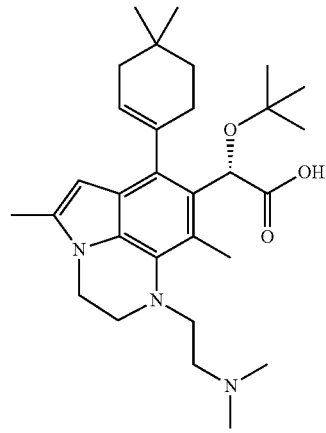 [SMILES: Cc1c([C@H](OC(C)(C)C)C(=O)O)c(C2=CCC(C)(C)CC2)c2cc(C)n3c2c1N(CCN(C)C)CC3] | (1) | 2.43 | 496 [M + H]+ | |
| --- | --- | --- | --- | --- | --- |
| I-321 | 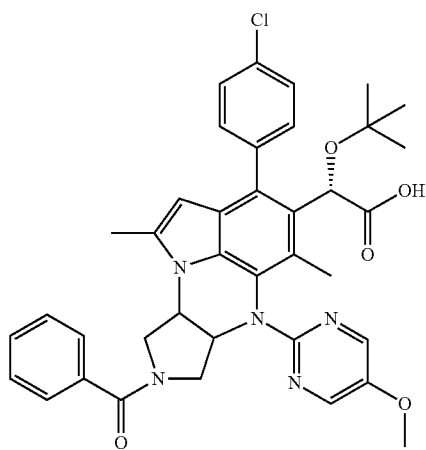 [SMILES: COc1cnc(N2c3c(C)c([C@H](OC(C)(C)C)C(=O)O)c(-c4ccc(Cl)cc4)c4cc(C)n(c34)C3CN(C(=O)c4ccccc4)CC32)nc1] | (1) | 2.82 | 680 [M + H]+ | diastereomer of I-322 |
| I-322 | 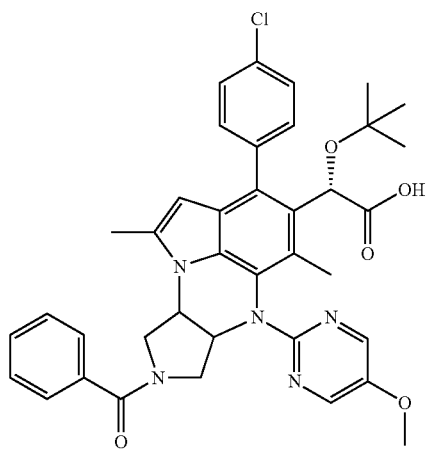 [SMILES: COc1cnc(N2c3c(C)c([C@H](OC(C)(C)C)C(=O)O)c(-c4ccc(Cl)cc4)c4cc(C)n(c34)C3CN(C(=O)c4ccccc4)CC32)nc1] | (1) | 2.71 | 680 [M + H]+ | enantiomer |

TABLE 56
| | | | | | |
|---|---|---|---|---|---|
| I-323 | 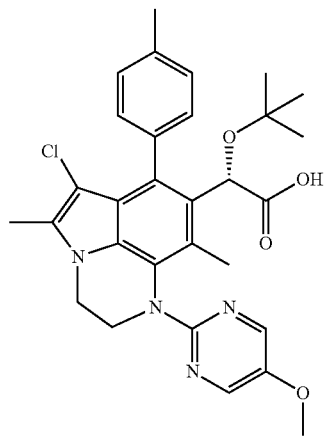 | (1) | 2.99 | 549 | [M + H]+ |
| I-324 | 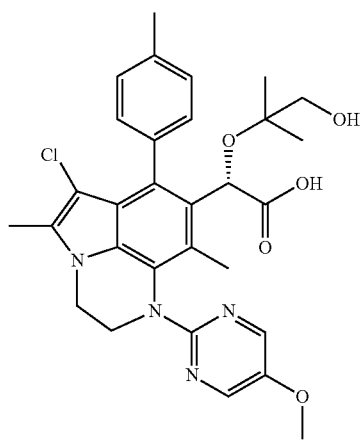 [SMILES: COc1cnc(N2CCn3c(C)c(Cl)c4c(-c5ccc(C)cc5)c([C@H](OC(C)(C)CO)C(=O)O)c(C)c2c43)nc1] | (1) | 2.63 | 565 | [M + H]+ |
| I-325 | 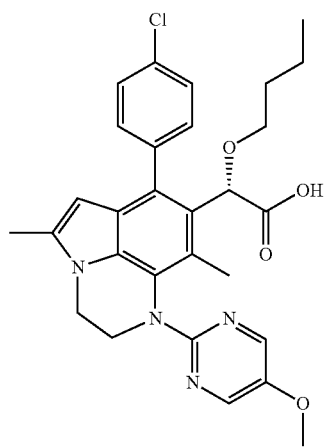 | (1) | 2.95 | 535 | [M + H]+ |

TABLE 56-continued
| | | | | | |
|---|---|---|---|---|---|
| I-326 | 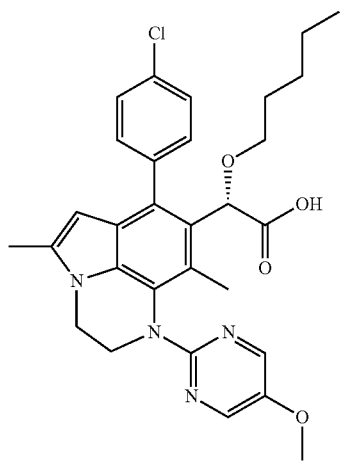 [SMILES: CCCCCO[C@H](C(=O)O)c1c(C)c2c3c(cc(C)n3CCN2c2ncc(OC)cn2)c1-c1ccc(Cl)cc1] | (1) | 3.09 | 549 | [M + H]+ |
| I-327 | 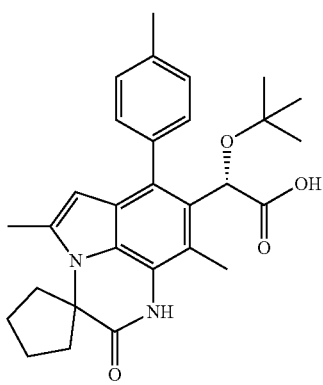 [SMILES: Cc1ccc(-c2c([C@H](OC(C)(C)C)C(=O)O)c(C)c3c4c2cc(C)n4C2(CCCC2)C(=O)N3)cc1] | (1) | 2.8 | 476 | [M + H]+ |
TABLE 57
| | | | | | |
|---|---|---|---|---|---|
| I-328 | 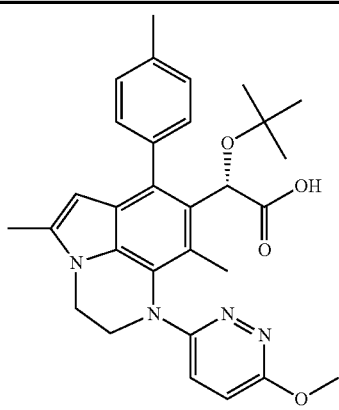 | (1) | 2.46 | 515 | [M + H]+ |

TABLE 57-continued
| | | | | | |
|---|---|---|---|---|---|
| I-329 | 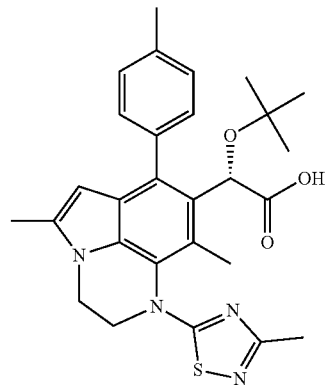 [SMILES: Cc1ccc(-c2c([C@H](OC(C)(C)C)C(=O)O)c(C)c3c4c2cc(C)n4CCN3c2nc(C)ns2)cc1] | (1) | 2.75 | 505 | [M + H]+ |
| I-330 | 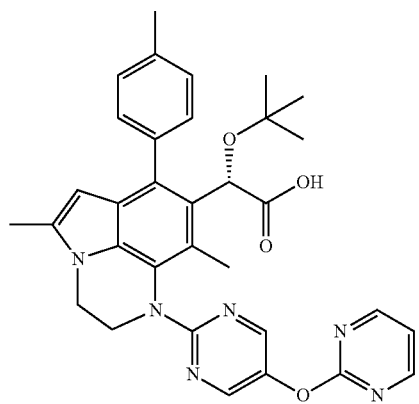 [SMILES: Cc1ccc(-c2c([C@H](OC(C)(C)C)C(=O)O)c(C)c3c4c2cc(C)n4CCN3c2ncc(Oc3ncccn3)cn2)cc1] | (1) | 2.62 | 580 | [M + H]+ |
| I-331 | 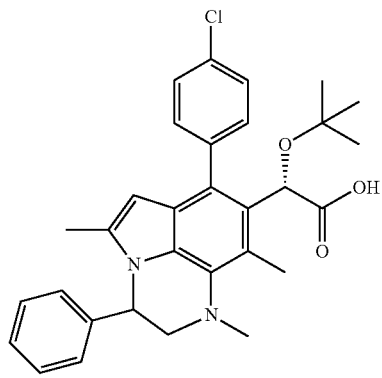 [SMILES: Cc1c([C@H](OC(C)(C)C)C(=O)O)c(-c2ccc(Cl)cc2)c2cc(C)n3c2c1N(C)CC3c1ccccc1] | (1) | 3.21 | 517 | [M + H]+ diastereomer of I-332 |
| I-332 | 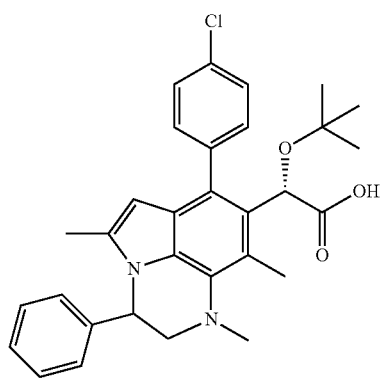 [SMILES: Cc1c([C@H](OC(C)(C)C)C(=O)O)c(-c2ccc(Cl)cc2)c2cc(C)n3c2c1N(C)CC3c1ccccc1] | (1) | 3.11 | 517 | [M + H]+ enantiomer |

TABLE 58
| I-333 | 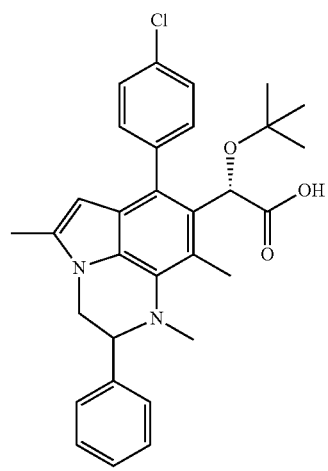 [SMILES: Cc1c([C@H](OC(C)(C)C)C(=O)O)c(-c2ccc(Cl)cc2)c2cc(C)n3c2c1N(C)C(c1ccccc1)C3] | (1) 3.24 517 [M + H]+ diastereomaer of I-334 |
| I-334 | 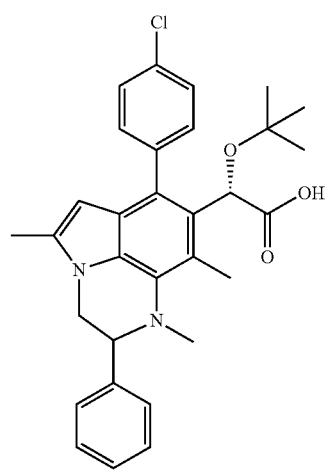 [SMILES: Cc1c([C@H](OC(C)(C)C)C(=O)O)c(-c2ccc(Cl)cc2)c2cc(C)n3c2c1N(C)C(c1ccccc1)C3] | (1) 3.34 517 [M + H]+ enantiomer |
| I-335 | 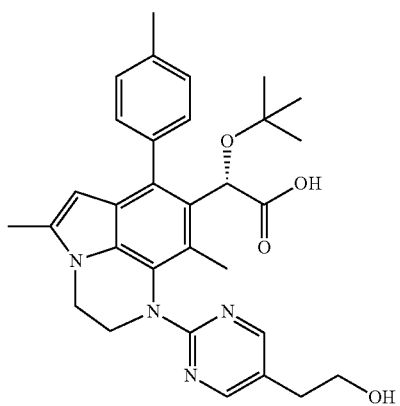 [SMILES: Cc1ccc(-c2c([C@H](OC(C)(C)C)C(=O)O)c(C)c3c4c2cc(C)n4CCN3c2ncc(CCO)cn2)cc1] | (1) 2.53 529 [M + H]+ |

TABLE 58-continued
| | | | | |
|---|---|---|---|---|
| I-336 | 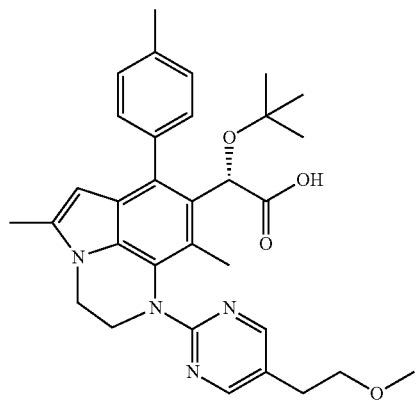 | (1) | 2.87 | 543 [M + H]+ |
| I-337 | 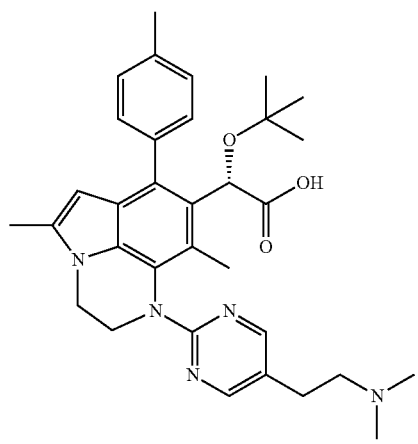 | (1) | 2.23 | 556 [M + H]+ |
TABLE 59
| | | | | |
|---|---|---|---|---|
| I-338 | 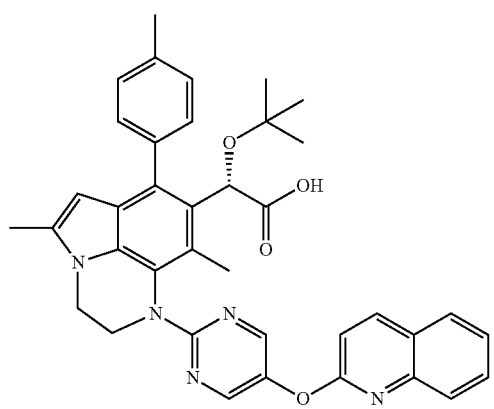 [SMILES: Cc1ccc(-c2c([C@H](OC(C)(C)C)C(=O)O)c(C)c3c4c2cc(C)n4CCN3c2ncc(Oc3ccc4ccccc4n3)cn2)cc1] | (1) | 3.326 | 628 [M + H]+ |

TABLE 59-continued
I-339 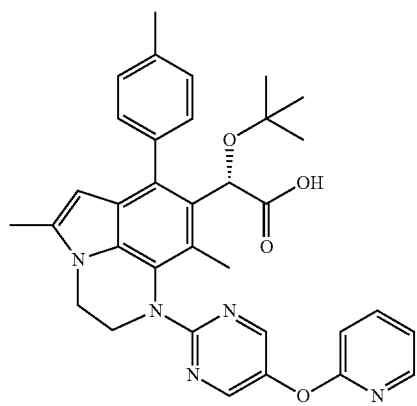 [SMILES: Cc1ccc(-c2c([C@H](OC(C)(C)C)C(=O)O)c(C)c3c4c2cc(C)n4CCN3c2ncc(Oc3ccccn3)cn2)cc1] (1) 3.042 578 [M + H]+
I-340 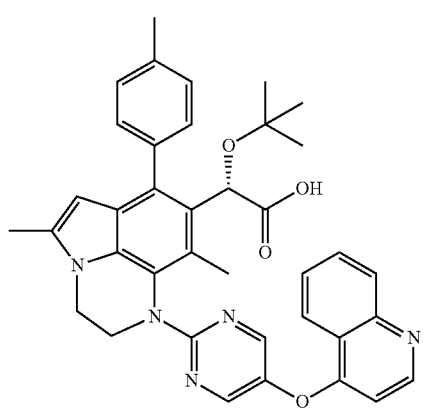 [SMILES: Cc1ccc(-c2c([C@H](OC(C)(C)C)C(=O)O)c(C)c3c4c2cc(C)n4CCN3c2ncc(Oc3ccnc4ccccc34)cn2)cc1] (1) 2.399 628 [M + H]+
I-341 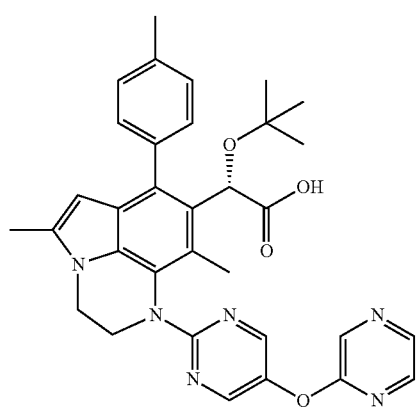 [SMILES: Cc1ccc(-c2c([C@H](OC(C)(C)C)C(=O)O)c(C)c3c4c2cc(C)n4CCN3c2ncc(Oc3cnccn3)cn2)cc1] (1) 2.889 579 [M + H]+
I-342 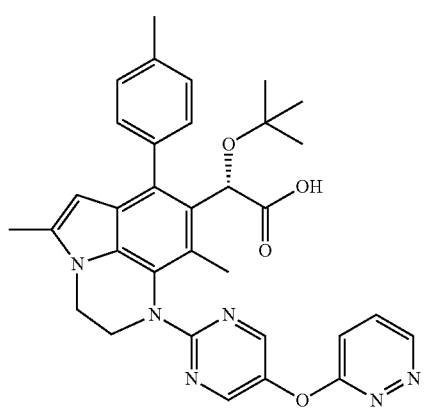 [SMILES: Cc1ccc(-c2c([C@H](OC(C)(C)C)C(=O)O)c(C)c3c4c2cc(C)n4CCN3c2ncc(Oc3cccnn3)cn2)cc1] (1) 2.71 579 [M + H]+

TABLE 60
I-343 (1) 3.081 643 [M + H]+
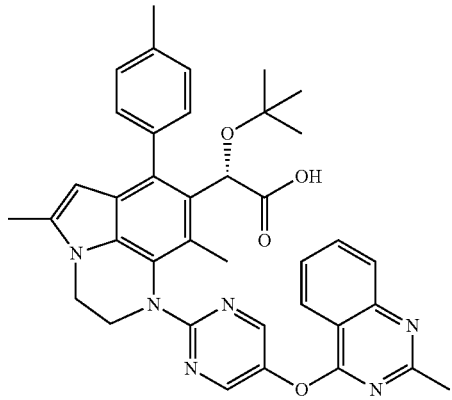
I-344 (1) 3.366 628 [M + H]+
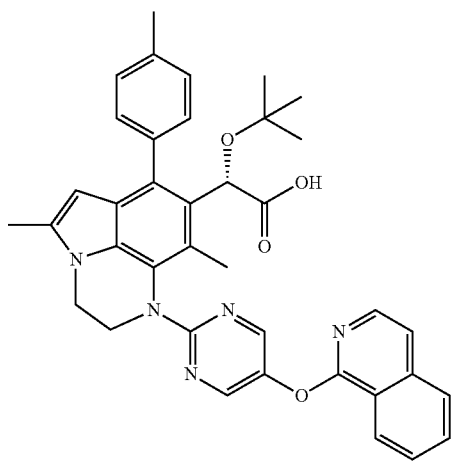 [SMILES: Cc1ccc(-c2c([C@H](OC(C)(C)C)C(=O)O)c(C)c3c4c2cc(C)n4CCN3c2ncc(Oc3nccc4ccccc34)cn2)cc1]
I-345 (1) 3.215 618 [M + H]+
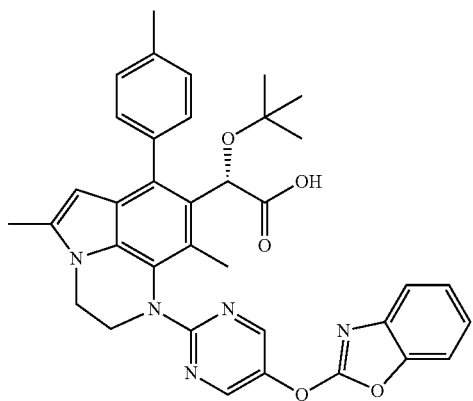 [SMILES: Cc1ccc(-c2c([C@H](OC(C)(C)C)C(=O)O)c(C)c3c4c2cc(C)n4CCN3c2ncc(Oc3nc4ccccc4o3)cn2)cc1]

TABLE 60-continued
| I-346 | 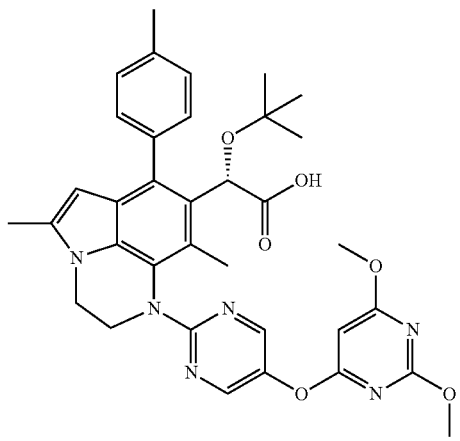 | (1) | 3.15 | 639 | [M + H]+ |
| I-347 | 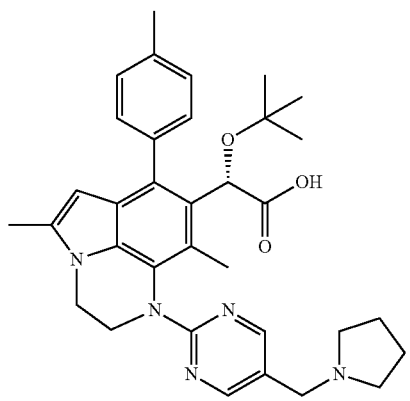 [SMILES: Cc1ccc(-c2c([C@H](OC(C)(C)C)C(=O)O)c(C)c3c4c2cc(C)n4CCN3c2ncc(CN3CCCC3)cn2)cc1] | (1) | 2.39 | 568 | [M + H]+ |
TABLE 61
| I-348 | 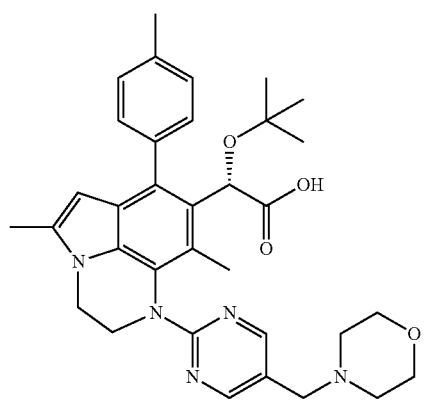 [SMILES: Cc1ccc(-c2c([C@H](OC(C)(C)C)C(=O)O)c(C)c3c4c2cc(C)n4CCN3c2ncc(CN3CCOCC3)cn2)cc1] | (1) | 2.37 | 584 | [M + H]+ |

TABLE 61-continued
| I-349 | 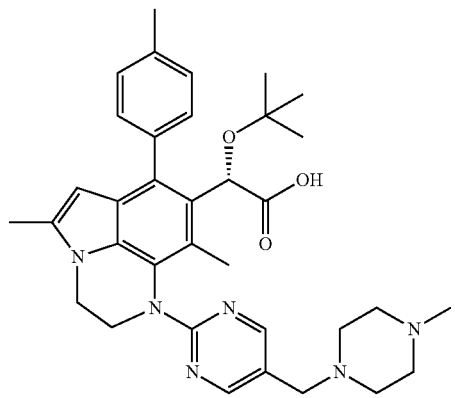 | (3) | 1.96 | 597 [M + H]+ |
| I-350 | 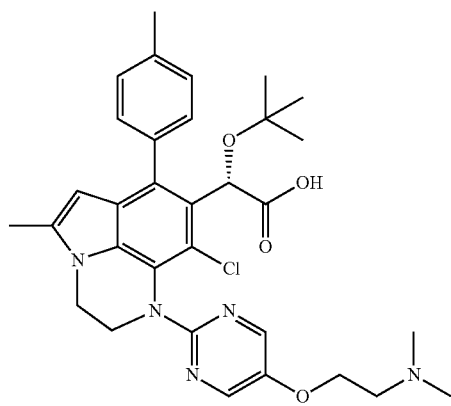 | (1) | 2.11 | 592 [M + H]+ |
| I-351 | 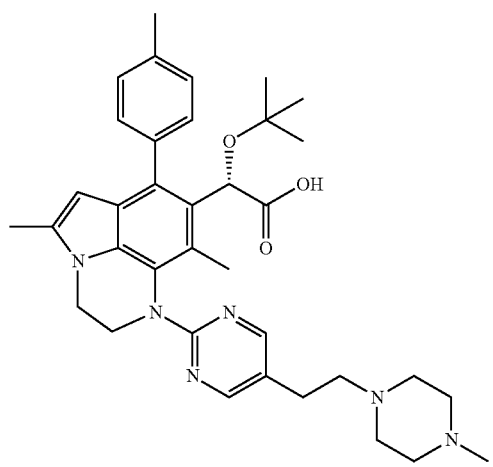 | (3) | 1.77 | 611 [M + H]+ |

TABLE 61-continued
| | | | | |
|---|---|---|---|---|
| I-352 | 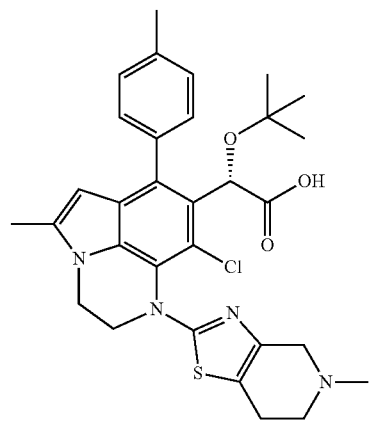 | (1) | 2.26 | 579 [M + H]+ |
TABLE 62
| | | | | |
|---|---|---|---|---|
| I-353 | 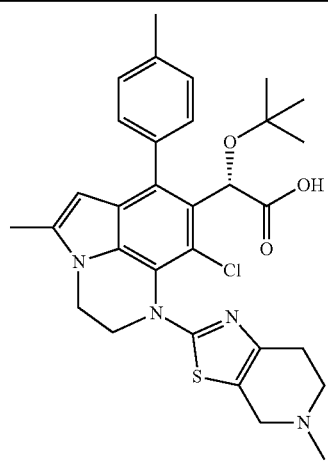 | (1) | 2.21 | 579 [M + H]+ |
| I-354 | 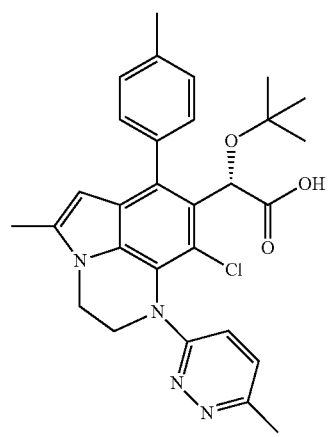 [SMILES: Cc1ccc(-c2c([C@H](OC(C)(C)C)C(=O)O)c(Cl)c3c4c2cc(C)n4CCN3c2ccc(C)nn2)cc1] | (1) | 2.41 | 519 [M + H]+ |

TABLE 62-continued

| | | | | | |
|---|---|---|---|---|---|
| I-355 | [structure] | (1) | 3.14 | 611 | [M + H]+ |
| I-356 | [structure] | (1) | 3.14 | 611 | [M + H]+ |

The biology assays of the compound of the present invention are described below.

Test Example 1: HIV Replication Inhibition Assay

HIV (HTLV-IIIB strain) persistent infected human T cell strain Molt-4 clone8 was cultured in RPMI-1640 medium supplemented with 10% fetal bovine serum and the supernatant was filtered, then the virus titer was measured and stored at −80° C. Each anti-human immunodeficiency virus active substance was diluted with the above culture medium to the designated concentration, which was dispensed into 96-well microtiter plate by 50 μL. Next, 100 μL of MT-4 cell suspension ($2.5 \times 10^4$ cells) was dispensed into each well, then 50 μl of the above HIV-containing supernatant diluted with the above culture medium was added thereto (60 pfu (plaque forming unit)).

Cell mixture was cultured at 37° C. in $CO_2$ incubator for four days, then 30 μL of MTT (3-(4,5-dimethylthiazole-2-yl)-2,5-diphenyltetrazolyum bromide) reagent (5 mg/mL in PBS) was added to all wells followed by incubation for 1 hour. In this step, MTT was reduced to insoluble formazan in living cells. To elute generated formazan 150 μL of the culture supernatant was removed from all wells, then 150 μL of cell lysis solution (10% Triton X-100 and 0.4% (v/v)-HCl containing isopropanol) was added thereto, followed by shaking with a plate mixer. The formazan was measured with micro plate reader at OD: 560 nm and 690 nm (reference wavelength) and the result was compared with the reference wells. $EC_{50}$ and $EC_{90}$ mean the compound concentration at which cytotoxicity caused by virus infection is inhibited 50% and 90%, respectively.

(Result) The EC50 are shown below.

TABLE 63

| Comp. No. | EC50 (nM) |
|---|---|
| I-001 | 0.69 |
| I-002 | 2.2 |
| I-003 | 1.3 |
| I-004 | 4.1 |
| I-005 | 31 |
| I-006 | 1 |
| I-007 | 2 |
| I-008 | 1.3 |
| I-009 | 0.98 |
| I-011 | 16 |
| I-012 | 0.77 |
| I-013 | 9.7 |
| I-014 | 1.6 |
| I-015 | 27 |
| I-016 | 8.7 |
| I-017 | 20 |
| I-018 | 83 |
| I-019 | 1.2 |
| I-020 | 9.5 |
| I-021 | 5.2 |
| I-022 | 17 |
| I-023 | 1 |
| I-024 | 1.6 |

TABLE 63-continued

| Comp. No. | EC50 (nM) |
|---|---|
| I-025 | 2.3 |
| I-026 | 0.99 |
| I-027 | 9.9 |
| I-028 | 74 |
| I-029 | 8.6 |

TABLE 64

| Comp. No. | EC50 (nM) |
|---|---|
| I-164 | 11 |
| I-167 | 7.6 |
| I-170 | 3.1 |
| I-171 | 15 |
| I-172 | 3.5 |
| I-176 | 2.3 |
| I-181 | 1.4 |
| I-182 | 1.6 |
| I-187 | 1 |

TABLE 65

| Comp. No. | EC50 (nM) |
|---|---|
| I-204 | 4.1 |
| I-205 | 16 |
| I-213 | 12 |
| I-220 | 6 |
| I-226 | 1.2 |
| I-227 | 1 |
| I-229 | 2.4 |
| I-230 | 1.8 |
| I-235 | 1.6 |
| I-244 | 4.8 |
| I-245 | 27 |
| I-246 | 2.3 |
| I-254 | 7.9 |
| I-255 | 1.6 |
| I-257 | 7.4 |
| I-258 | 2.1 |
| I-260 | 1.1 |
| I-265 | 13 |
| I-266 | 1.3 |
| I-267 | 11 |
| I-268 | 1.5 |
| I-270 | 4.5 |
| I-272 | 1.6 |
| I-276 | 1.5 |
| I-278 | 5.5 |
| I-279 | 5.1 |
| I-282 | 1.4 |
| I-287 | 1.4 |

TABLE 66

| Comp. No. | EC50 (nM) |
|---|---|
| I-041 | 1.5 |
| I-043 | 1.4 |
| I-048 | 1.2 |
| I-085 | 0.54 |
| I-112 | 4.9 |
| I-122 | 1.3 |
| I-156 | 0.85 |
| I-189 | 1.6 |
| I-190 | 0.83 |
| I-197 | 1.3 |
| I-262 | 3.2 |
| I-292 | 2.5 |
| I-293 | 3.1 |
| I-303 | 1.5 |

TABLE 66-continued

| Comp. No. | EC50 (nM) |
|---|---|
| I-304 | 4.1 |
| I-305 | 3.7 |
| I-306 | 3.4 |
| I-307 | 9.3 |
| I-308 | 1.6 |
| I-309 | 2.2 |

(Result) The EC90 are shown below.

TABLE 67

| Comp. No. | EC90 (nM) |
|---|---|
| I-001 | 1.1 |
| I-002 | 3.5 |
| I-003 | 1.7 |
| I-004 | 6 |
| I-005 | 46 |
| I-006 | 1.7 |
| I-007 | 3.6 |
| I-008 | 1.6 |
| I-009 | 1.6 |
| I-011 | 24 |
| I-012 | 1.1 |
| I-013 | 15 |
| I-014 | 2.2 |
| I-015 | 40 |
| I-016 | 13 |
| I-017 | 31 |
| I-018 | 100 |
| I-019 | 1.6 |
| I-020 | 12 |
| I-021 | 7.5 |
| I-022 | 25 |
| I-023 | 2.6 |
| I-024 | 2.1 |
| I-025 | 3.1 |
| I-026 | 1.6 |
| I-027 | 16 |
| I-028 | 93 |
| I-029 | 12 |
| I-041 | 2.3 |
| I-043 | 2.3 |
| I-048 | 1.5 |
| I-085 | 0.58 |
| I-112 | 11 |
| I-122 | 2.9 |
| I-156 | 1.2 |
| I-164 | 20 |
| I-167 | 18 |
| I-170 | 5.2 |
| I-171 | 24 |
| I-172 | 5.4 |
| I-176 | 5.6 |
| I-181 | 2.3 |
| I-182 | 2.6 |
| I-187 | 2.2 |
| I-189 | 3.2 |
| I-190 | 1.3 |
| I-197 | 2.2 |
| I-204 | 5.8 |
| I-205 | 35 |
| I-213 | 19 |
| I-220 | 11 |
| I-226 | 1.6 |
| I-227 | 1.4 |
| I-229 | 5.5 |
| I-230 | 3.3 |
| I-244 | 8 |
| I-245 | 42 |
| I-246 | 2.5 |
| I-254 | 13 |
| I-255 | 2.4 |
| I-257 | 8.1 |
| I-258 | 2.9 |
| I-260 | 1.5 |

TABLE 67-continued

| Comp. No. | EC90 (nM) |
|---|---|
| I-262 | 5.1 |
| I-265 | 30 |
| I-266 | 2.1 |
| I-267 | 18 |
| I-268 | 2.1 |
| I-270 | 7.5 |
| I-272 | 2 |
| I-276 | 2.5 |
| I-278 | 11 |
| I-279 | 7.7 |
| I-282 | 2.1 |
| I-287 | 2.2 |
| I-292 | 5.1 |
| I-293 | 5.5 |
| I-303 | 4 |
| I-305 | 4.9 |
| I-306 | 12 |
| I-307 | 45 |
| I-308 | 4.8 |
| I-309 | 1.5 |

Test Example 2: HIV Replication Inhibition Assay

Persistently HIV (HTLV-IIIB strain) infected human T cell strain Molt-4 clone8 was cultured in RPMI-1640 medium supplemented with 10% fetal bovine serum and the supernatant was filtered, then the virus titer was measured and stored at −80° C. Polymorphic mutations in HIV-1-infected patients have been observed in amino acids 124 and 125 on the HIV-1 integrase (IN) gene. A point mutation was introduced on the amino acids 124 and/or 125 of IN gene of the HIV-1 NL-432 recombinant molecular clone to generate a mutant virus plasmid construct. These mutant virus plasmids were transfected into 293T cells, and after two days, the supernatant was filtered and then the virus titer was measured and stored at −80° C. Each anti-HIV active substance was diluted with culture medium described above to the designated concentration, which was dispensed into 96-well microtiter plate by 50 μL. Next, 100 μL of MT-4 cell suspension (2.5×104 cells) was dispensed into each well, then 50 μl of HIV-containing supernatant diluted with culture medium described above was added thereto (60 pfu (plaque forming unit)).

Cells were cultured at 37° C. in CO2 incubator for four days, then 30 μL of MTT (3-(4,5-dimethylthiazole-2-yl)-2,5-diphenyltetrazolyum bromide) reagent (5 mg/mL in PBS) was added to all wells followed by incubation for 1 hour. In this step, MTT was reduced to insoluble formazan in living cells. To elute generated formazan, 150 μL of the culture supernatant was removed from all wells, then 150 μL of cell lysis solution (10% Triton X-100 and 0.4% (v/v)-HCl containing isopropanol) was added thereto, followed by shaking with a plate mixer. The formazan was measured with micro plate reader at OD: 560 nm and 690 nm (reference wavelength) and the result was compared with the reference wells. EC50 means the compound concentration at which 50% of cytotoxicity caused by virus infection is inhibited. (Result) The EC50 against T125A mutant virus about 125 amino acids are shown below.

TABLE 68

| Comp. No. | EC50 (nM) |
|---|---|
| I-001 | 4.7 |
| I-002 | 21 |

TABLE 68-continued

| Comp. No. | EC50 (nM) |
|---|---|
| I-003 | 8.9 |
| I-004 | 48 |
| I-006 | 17 |
| I-007 | 18 |
| I-008 | 16 |
| I-009 | 14 |
| I-012 | 3.8 |
| I-014 | 15 |
| I-016 | 42 |
| I-017 | 94 |
| I-019 | 6.6 |
| I-021 | 22 |
| I-023 | 5.5 |
| I-024 | 7.7 |
| I-025 | 13 |
| I-026 | 13 |
| I-027 | 26 |
| I-029 | 89 |
| I-030 | 23 |
| I-031 | 11 |
| I-032 | 5 |
| I-034 | 9.6 |
| I-035 | 14 |
| I-036 | 6.5 |
| I-037 | 30 |
| I-038 | 45 |
| I-039 | 70 |
| I-040 | 11 |
| I-041 | 13 |
| I-043 | 11 |
| I-045 | 58 |
| I-046 | 18 |
| I-047 | 46 |
| I-048 | 11 |
| I-049 | 22 |
| I-050 | 49 |
| I-051 | 22 |
| I-052 | 9 |
| I-053 | 5.6 |
| I-054 | 48 |
| I-055 | 24 |
| I-056 | 59 |
| I-057 | 2.7 |
| I-060 | 14 |
| I-061 | 9.6 |
| I-062 | 34 |
| I-063 | 4.5 |
| I-064 | 19 |
| I-065 | 12 |
| I-066 | 4 |
| I-067 | 7.4 |
| I-068 | 6.8 |
| I-069 | 16 |
| I-070 | 43 |
| I-071 | 45 |
| I-072 | 13 |
| I-073 | 39 |
| I-074 | 27 |
| I-075 | 24 |
| I-076 | 16 |
| I-078 | 21 |
| I-079 | 17 |
| I-080 | 33 |
| I-081 | 9.6 |
| I-082 | 6.1 |
| I-083 | 15 |
| I-085 | 3.7 |
| I-086 | 11 |
| I-087 | 20 |
| I-088 | 27 |
| I-089 | 18 |
| I-090 | 39 |
| I-091 | 2 |
| I-092 | 7.6 |
| I-093 | 16 |
| I-094 | 12 |
| I-095 | 14 |
| I-096 | 19 |

TABLE 68-continued

| Comp. No. | EC50 (nM) |
|---|---|
| I-097 | 9.7 |
| I-103 | 3.4 |
| I-104 | 4.1 |
| I-105 | 11 |
| I-106 | 11 |
| I-107 | 25 |
| I-108 | 19 |
| I-109 | 15 |
| I-111 | 4.2 |
| I-112 | 18 |
| I-113 | 22 |
| I-114 | 18 |
| I-115 | 11 |
| I-116 | 6.7 |
| I-117 | 8.6 |
| I-118 | 10 |
| I-119 | 2.8 |
| I-120 | 52 |
| I-121 | 65 |
| I-122 | 5.1 |
| I-123 | 14 |
| I-124 | 13 |
| I-125 | 8.2 |
| I-126 | 88 |
| I-127 | 16 |
| I-128 | 42 |
| I-129 | 89 |
| I-130 | 27 |
| I-131 | 15 |
| I-132 | 28 |
| I-133 | 96 |
| I-134 | 8.4 |
| I-135 | 8.2 |
| I-136 | 8.4 |
| I-137 | 86 |
| I-138 | 1.5 |
| I-139 | 6.8 |
| I-141 | 41 |
| I-144 | 37 |
| I-146 | 16 |
| I-147 | 16 |
| I-148 | 22 |
| I-149 | 15 |
| I-150 | 15 |
| I-152 | 11 |
| I-153 | 11 |
| I-154 | 13 |
| I-155 | 58 |
| I-156 | 3.6 |
| I-157 | 12 |
| I-158 | 4.6 |
| I-159 | 16 |
| I-160 | 70 |

TABLE 69

| Comp. No. | EC50 (nM) |
|---|---|
| I-162 | 35 |
| I-163 | 38 |
| I-164 | 42 |
| I-165 | 6.9 |
| I-166 | 62 |
| I-167 | 49 |
| I-169 | 50 |
| I-170 | 18 |
| I-171 | 62 |
| I-172 | 16 |
| I-173 | 71 |
| I-174 | 55 |
| I-176 | 4.6 |
| I-179 | 83 |
| I-180 | 13 |
| I-181 | 3.5 |
| I-182 | 7.3 |

TABLE 69-continued

| Comp. No. | EC50 (nM) |
|---|---|
| I-183 | 31 |
| I-185 | 7.1 |
| I-186 | 20 |
| I-187 | 4.8 |
| I-188 | 14 |
| I-189 | 3.1 |
| I-190 | 2.1 |
| I-191 | 13 |
| I-192 | 4.6 |
| I-193 | 2.8 |
| I-194 | 12 |
| I-195 | 15 |
| I-196 | 18 |

TABLE 70

| Comp. No. | EC50 (nM) |
|---|---|
| I-201 | 14 |
| I-202 | 56 |
| I-203 | 13 |
| I-204 | 9.5 |
| I-205 | 63 |
| I-206 | 71 |
| I-207 | 19 |
| I-208 | 24 |
| I-209 | 16 |
| I-210 | 65 |
| I-211 | 20 |
| I-212 | 6.8 |
| I-213 | 31 |
| I-214 | 4 |
| I-215 | 47 |
| I-216 | 20 |
| I-217 | 39 |
| I-218 | 20 |
| I-219 | 43 |
| I-220 | 14 |
| I-221 | 81 |
| I-222 | 89 |
| I-223 | 15 |
| I-224 | 79 |
| I-225 | 11 |
| I-226 | 3.6 |
| I-227 | 4.1 |
| I-228 | 2.6 |
| I-229 | 7.3 |
| I-230 | 6.7 |
| I-231 | 10 |
| I-232 | 34 |
| I-234 | 3.6 |
| I-235 | 2.8 |
| I-236 | 9.9 |
| I-239 | 22 |
| I-240 | 51 |
| I-241 | 2.2 |
| I-242 | 6.4 |
| I-244 | 12 |
| I-245 | 63 |
| I-246 | 4.5 |
| I-247 | 8.3 |
| I-248 | 67 |
| I-250 | 9.9 |
| I-251 | 4.2 |
| I-252 | 8.5 |
| I-254 | 17 |
| I-255 | 5.1 |
| I-256 | 5.6 |
| I-257 | 28 |
| I-258 | 4.9 |
| I-259 | 4.4 |
| I-260 | 3.6 |
| I-261 | 3.7 |
| I-262 | 5 |
| I-263 | 7.2 |

TABLE 70-continued

| Comp. No. | EC50 (nM) |
| --- | --- |
| I-264 | 4.4 |
| I-265 | 44 |
| I-266 | 3.7 |
| I-267 | 26 |
| I-268 | 4.8 |
| I-269 | 29 |
| I-270 | 13 |
| I-271 | 4.2 |
| I-272 | 4.3 |
| I-274 | 14 |
| I-275 | 13 |
| I-276 | 5.1 |
| I-277 | 14 |
| I-278 | 13 |
| I-279 | 13 |
| I-280 | 5.3 |
| I-281 | 17 |
| I-282 | 4 |
| I-283 | 12 |
| I-284 | 3.6 |
| I-286 | 15 |
| I-287 | 5.1 |
| I-288 | 5.3 |
| I-289 | 35 |
| I-290 | 22 |
| I-292 | 6.3 |
| I-293 | 9.3 |
| I-294 | 16 |
| I-295 | 62 |
| I-299 | 5.1 |
| I-300 | 4.6 |
| I-301 | 3.3 |

TABLE 71

| Comp. No. | EC50 (nM) |
| --- | --- |
| I-302 | 43 |
| I-303 | 4.3 |
| I-304 | 7.2 |
| I-305 | 12 |
| I-306 | 5.3 |
| I-307 | 15 |
| I-308 | 4.3 |
| I-309 | 4.7 |
| I-310 | 68 |
| I-311 | 3.1 |
| I-312 | 4.6 |
| I-313 | 8.8 |
| I-314 | 5.3 |
| I-315 | 80 |
| I-316 | 6.6 |
| I-319 | 87 |
| I-320 | 16 |
| I-322 | 44 |
| I-323 | 16 |
| I-324 | 63 |
| I-328 | 51 |
| I-329 | 19 |
| I-330 | 7.7 |
| I-331 | 92 |
| I-332 | 13 |
| I-334 | 93 |
| I-335 | 14 |
| I-336 | 2.7 |
| I-337 | 28 |
| I-338 | 21 |
| I-339 | 11 |
| I-340 | 15 |
| I-341 | 4.1 |
| I-342 | 13 |
| I-343 | 21 |
| I-344 | 17 |
| I-345 | 38 |
| I-346 | 10 |

TABLE 71-continued

| Comp. No. | EC50 (nM) |
| --- | --- |
| I-347 | 10 |
| I-348 | 5 |
| I-349 | 30 |
| I-350 | 22 |
| I-351 | 17 |
| I-352 | 14 |
| I-353 | 15 |
| I-354 | 5.3 |

Test Example 3: Calculation of Potency Shift Value

To confirm the influence of human serum on anti-HIV activity as necessary, human serum was added and determined EC50 in this condition. Human serum (100 µL/well) was dispensed into each anti-HIV active substance at a designated concentration dispensed 50 µL each in advance into a 96-well microtiter plate, and the plate was incubate at room temperature for 1 hour. To the serum-free plate, only culture medium (100 µL/well) was dispensed into 96-well microtiter plate. MT-4 cells (3×104 cells/well) was infected with 3 µL/well of HIV solution diluted to an appropriate concentration (600 pfu/50 µL) by the required number of wells and incubated at 37° C. for 1 hour. The infected cells were centrifuged at 1200 rpm for 5 minutes, the supernatant was discarded, and the infected cells were dispersed into culture medium for the required number of wells at 50 µL/well. Infected cell suspension was dispensed into a 96-well microtiter plate of which anti-HIV active substance and human serum prepared in advance. The cell mixture was mixed with a plate mixer and cultured in a $CO_2$ incubator for 4 days. The $EC_{50}$ in the presence of human serum was calculated in the same manner as in Test Example 1 and the ratio of $EC_{50}$ in the presence of human serum and $EC_{50}$ in the absence of human serum was calculated as the potency shift value. (Result) The potency shift value at the time of addition of 25% human serum $EC_{50}$ are as described below.

TABLE 72

| Comp. No. | Potency shift value (e0) |
| --- | --- |
| I-001 | 13 |
| I-012 | 13 |
| I-027 | 1.4 |
| I-048 | 9.2 |
| I-085 | 22 |
| I-122 | 23 |
| I-130 | 2.7 |
| I-138 | 5.8 |
| I-152 | 6.9 |
| I-156 | 12 |
| I-159 | 8.8 |

TABLE 73

| Comp. No. | Potency shift value (e0) |
| --- | --- |
| I-161 | 1.9 |
| I-162 | 7.5 |
| I-164 | 2.6 |
| I-165 | 8.3 |
| I-166 | 3.5 |
| I-168 | 2.9 |
| I-169 | 30 |

TABLE 73-continued

| Comp. No. | Potency shift value (e0) |
|---|---|
| I-173 | 4 |
| I-174 | 14 |
| I-176 | 12 |
| I-179 | 23 |
| I-180 | 7.8 |
| I-181 | 17 |
| I-182 | 8.3 |
| I-183 | 7.6 |
| I-185 | 15 |
| I-186 | 15 |
| I-187 | 11 |
| I-188 | 11 |
| I-189 | 22 |
| I-190 | 21 |
| I-191 | 7.4 |
| I-192 | 11 |
| I-193 | 21 |
| I-194 | 13 |
| I-195 | 12 |
| I-196 | 11 |

TABLE 74

| Comp. No. | Potency shift value (e0) |
|---|---|
| I-203 | 30 |
| I-204 | 3.6 |
| I-206 | 9.7 |
| I-207 | 8.1 |
| I-208 | 11 |
| I-209 | 24 |
| I-210 | 5.4 |
| I-211 | 7.5 |
| I-212 | 3.9 |
| I-213 | 3.9 |
| I-216 | 9.2 |
| I-217 | 9.1 |
| I-218 | 5.5 |
| I-219 | 7.6 |
| I-220 | 3.7 |
| I-221 | 3.7 |
| I-223 | 11 |
| I-224 | 3.3 |
| I-225 | 9.7 |
| I-226 | 26 |
| I-227 | 15 |
| I-228 | 9.1 |
| I-229 | 16 |
| I-230 | 24 |
| I-231 | 22 |
| I-232 | 8.6 |
| I-233 | 12 |
| I-234 | 19 |
| I-237 | 2.4 |
| I-239 | 16 |
| I-240 | 12 |
| I-241 | 8.4 |
| I-242 | 11 |
| I-244 | 3.4 |
| I-245 | 12 |
| I-246 | 23 |
| I-247 | 7.6 |
| I-248 | 1.5 |
| I-250 | 19 |
| I-251 | 9.6 |
| I-252 | 23 |
| I-254 | 10 |
| I-255 | 22 |
| I-256 | 10 |
| I-258 | 11 |
| I-259 | 15 |
| I-260 | 15 |
| I-262 | 13 |

TABLE 74-continued

| Comp. No. | Potency shift value (e0) |
|---|---|
| I-264 | 26 |
| I-265 | 2.5 |
| I-266 | 23 |
| I-268 | 19 |
| I-269 | 7.4 |
| I-270 | 3.8 |
| I-272 | 16 |
| I-274 | 16 |
| I-275 | 18 |
| I-276 | 5.9 |
| I-278 | 3.6 |
| I-279 | 3.5 |
| I-280 | 21 |
| I-281 | 23 |
| I-283 | 9.5 |
| I-284 | 17 |
| I-285 | 5.1 |
| I-286 | 14 |
| I-287 | 12 |
| I-288 | 11 |
| I-289 | 15 |
| I-292 | 4.5 |
| I-293 | 4.8 |
| I-295 | 5.3 |
| I-296 | 2.1 |
| I-297 | 7.6 |
| I-298 | 11 |
| I-299 | 20 |

TABLE 75

| Comp. No. | Potency shift value (e0) |
|---|---|
| I-303 | 15 |
| I-304 | 6.8 |
| I-305 | 3.6 |
| I-306 | 4.1 |
| I-307 | 4.7 |
| I-308 | 11 |
| I-309 | 13 |
| I-310 | 1.2 |
| I-311 | 15 |
| I-312 | 37 |
| I-313 | 7.7 |
| I-314 | 41 |
| I-315 | 3.9 |
| I-316 | 17 |
| I-317 | 1.3 |
| I-319 | 3.4 |
| I-320 | 2.6 |
| I-322 | 15 |
| I-325 | 5.4 |
| I-326 | 5.8 |
| I-328 | 4.2 |
| I-329 | 15 |
| I-330 | 39 |
| I-331 | 7 |
| I-332 | 25 |
| I-333 | 6.4 |
| I-335 | 36 |
| I-337 | 3.6 |
| I-338 | 18 |
| I-340 | 18 |
| I-343 | 11 |
| I-344 | 33 |
| I-345 | 41 |
| I-347 | 7.4 |
| I-348 | 21 |
| I-349 | 3.6 |
| I-350 | 4.3 |
| I-351 | 5.5 |
| I-352 | 10 |
| I-353 | 10 |

TABLE 75-continued

| Comp. No. | Potency shift value (e0) |
|---|---|
| I-354 | 27 |

TABLE 76

| Comp. No. | Potency shift value (e0) |
|---|---|
| I-003 | 14 |
| I-005 | 7.8 |
| I-006 | 44 |
| I-007 | 49 |
| I-008 | 45 |
| I-009 | 38 |
| I-011 | 21 |
| I-013 | 49 |
| I-014 | 8.7 |
| I-015 | 11 |
| I-016 | 8.6 |
| I-017 | 4.5 |
| I-018 | 6.8 |
| I-019 | 16 |
| I-020 | 41 |
| I-021 | 5.4 |
| I-022 | 4.5 |
| I-023 | 12 |
| I-024 | 22 |
| I-025 | 11 |
| I-026 | 13 |
| I-028 | 2.5 |
| I-029 | 28 |
| I-041 | 4.1 |
| I-043 | 3.2 |
| I-112 | 3.5 |
| I-157 | 12 |
| I-167 | 4.1 |
| I-170 | 3.5 |
| I-171 | 1.4 |
| I-172 | 2.3 |
| I-197 | 32 |
| I-205 | 32 |
| I-235 | 46 |
| I-257 | 4 |
| I-267 | 4 |
| I-282 | 36 |

In human plasma, the compound binds to serum proteins, the amount of free active compound in plasma was decreases and anti-viral activity may decrease. In the field of HIV, it is known that if the trough concentration in plasma exceeds the PA-EC90 (protein adjusted-EC90) value, the clinical efficacy would be obtained. In order to predict the clinical antiviral activity more accurately, PA-EC50 and/or PA-EC90 in the presence of 100% human serum was extrapolated from the following formula using the calculated potency shift value in the presence of 25% human serum.

PA-EC$_{50}$=EC$_{50}$×(potency shift value in the presence of 25% human serum)×4

PA-EC$_{90}$=EC$_{90}$×(potency shift value in the presence of 25% human serum)×4

As a result, the compound of the present invention showed preferable PA-EC$_{50}$ value and/or PA-EC$_{90}$ value.

Test Example 4: CYP Inhibition Assay

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4) an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, and a test drug in 50 mmol/L Hepes buffer as a reaction solution was added to a 96-well plate as the composition ad described above, NADPH, as a coenzyme was added to initiate metabolism reactions as markers and, after the incubation at 37° C. for 15 minutes, a methanol/acetonitrile=1/1 (V/V) solution was added to stop the reaction. After the centrifugation at 3000 rpm for 15 minutes, resorufin (CYP1A2 metabolite) in the supernatant was quantified by a fluorescent multilabel counter and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

A reaction system containing only DMSO which is a solvent for dissolving a drug was adopted as a control (100%), and the remaining activity (%) was calculated, then IC$_{50}$ was calculated by reverse presumption with a logistic model using a concentration and an inhibition rate.

(Result)

The results of the CYP2C9 inhibition test are that the every compounds of I-026, I-027, I-041, I-043, I-048, I-112, I-122, I-156, I-157, I-164, I-181, I-189, I-190, I-197, I-220, I-244, I-257, I-258, I-260, I-262, I-267, I-270, I-278, I-292, I-293, I-303, I-304, I-305, I-306, I-307, I-308, and I-309 were IC50>20 μM.

Test Example 5: CYP3A4 Fluorescent MBI Test

The CYP3A4 fluorescent MBI test is to investigate the enhancement of CYP3A4 inhibition of a compound by a metabolism reaction. 7-Benzyloxytrifluoromethylcoumarin (7-BFC) is debenzylated by the CYP3A4 enzyme to produce 7-hydroxytrifluoromethylcoumarin (HFC), a metabolite emitting fluorescent light. The test was performed using 7-HFC-producing reaction as an index.

The reaction conditions were as follows: substrate 5.6 μmol/L 7-BFC; pre-reaction time, 0 or 30 minutes; reaction time, 15 minutes; reaction temperature, 25° C. (room temperature); CYP3A4 content (expressed in *Eschericha coli*), at pre-reaction 62.5 μmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate so that it was 1/10 siluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1(V/V) was added to stop the reaction. In addition, NADPH was added to a remaining preincubation solution to initiate a preincubation (with preincubation) and, after a predetermined time of a preincubation, a part was transferred to another plate so that it was 1/10 siluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm) Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. A case where the difference of $IC_{50}$ values was 5 µmol/L or more was defined as (+) and, a case where the difference was 3 µmol/L or less was defined as (−).

As a result, the present compounds showed good results.

Test Example 6: CYP3A4 (MDZ) MBI Test

CYP3A4 (MDZ) MBI test is a test of investigating mechanism based inhibition (MBI) ability on CYP3A4 inhibition of a compound by enhancement of a metabolism reaction. CYP3A4 inhibition was evaluated using 1-hydroxylation reaction of midazolam (MDZ) by pooled human liver microsomes as an index.

The reaction conditions are as follows: substrate, 10 µmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, 1, 5, 10, 20 µmol/L (four points).

Pooled human liver microsomes in K-Pi buffer (pH 7.4) and a solution of the compound of the present invention as a pre-reaction solution were added to a 96-well plate at the composition of the pre-reaction. A part of pre-reaction solution was transferred to another 96-well plate, and 1/10 diluted by a substrate in K-Pi buffer NADPH as a co-factor was added in order to initiate a reaction as an index (without preincubation). After a predetermined time of a reaction, methanol/acetonitrile=1/1 (V/V) solution was added in order to stop the reaction. On the other hand, NADPH was also added to a remaining pre-reaction solution in order to initiate a preincubation (with preincubation). After a predetermined time of a preincubation, a part was transferred to another 96-well plate, and 1/10 diluted by a substrate in K-Pi buffer in order to initiate a reaction as an index. After a predetermined time of a reaction, methanol/acetonitrile=1/1 (V/V) solution was added in order to stop the reaction. After centrifuged at 3000 rpm for 15 minutes, 1-hydroxymidazolam in the supernatant was quantified by LC/MS/MS.

The sample adding DMSO to a reaction system instead of a solution of the compound of the present invention was adopted as a control (100%) because DMSO was used as a solvent to dissolve the compound of the present invention. Remaining activity (%) was calculated at each concentration of the compound of the present invention added as the solution, and IC-value is calculated by reverse-presumption by a logistic model using a concentration and an inhibition rate. Shifted IC value was calculated as "IC of preincubation at 0 min/IC of preincubation at 30 min". When a shifted IC was 1.5 or more, this was defined as positive. When a shifted IC was 1.0 or less, this was defined as negative.

(Result)

The compounds of I-003, I-019, I-027, I-041, I-043, I-122, I-156, I-157, I-164, I-176, I-181, I-187, I-189, I-190, I-220, I-244, I-257, I-258, I-260, I-262, I-267, I-270, I-278, I-292, I-293, I-303, I-304, I-305, I-306, I-307, I-308, and I-309 were (−).

Test Example 7: Metabolism Stability Test

Commercially available pooled human hepatic microsomes and a test compound were reacted for a constant time, then a remaining rate was calculated by comparing a reacted sample and an unreacted sample, thereby a degree of metabolism of the test compound in liver was assessed.

A reaction was performed (oxidative reaction) at 37° C. for 0 minute or 30 minutes in the presence of 1 mmol/L NADPH in 0.2 mL of a buffer (50 mmol/L Tris-HCl, pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

As a result, the present compounds showed good metabolism stability.

Test Example 8: Solubility Test

The solubility of the compound of the present invention was determined under 1% DMSO addition conditions. A 10 mmol/L solution of the compound was prepared with DMSO, and 6 µL of the solution was added to 594 µL of an artificial intestinal juice (: water and a 118 mL solution of 0.2 mol/L NaOH reagent are added to 250 mL of 0.2 mol/L potassium dihydrogen phosphate reagent to reach 1000 mL) with a pH of 6.8. The mixture was left standing for 16 hours at 25° C., and the mixture was vacuum-filtered. The filtrate was two-fold diluted with methanol/water=1/1(v/v), and the compound concentration in the filtrate was measured with HPLC or LC/MS/MS by the absolute calibration method.

As a result, the present compounds showed good solubility.

Test Example 9: Fluctuation Ames Test

The mutagenicity of the compound of the present invention was assayed. 20 µL of freezing-stored rat typhoid bacillus (*Salmonella typhimurium* TA98 strain, TA 100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000× g, 10 minutes) to remove a culturing solution. The bacteria was suspended in F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of an Exposure medium (Micro F buffer containing Biotin: 8 µg/mL, histidine: 0.2 µg/mL, glucose: 8 mg/mL). The TA100 strain was added to 120 mL of the Exposure medium per 3.16 mL of the bacterial solution to prepare a test bacterial solution. Each 12 µL of a test substance DMSO solution (several stage dilution from maximum dose 50 mg/mL at 2 to 3-fold ratio), DMSO as a negative control, 50 µg/mL of 4-nitroquinoline-1-oxide DMSO solution for the TA98 strain, 0.25 µg/mL of 2-(2-furyl)-3-(5-nitro-2-furyl) acrylamide DMSO solution for the TA100 strain each under the non-metabolism activating condition, 40 µg/mL of 2-aminoanthracene DMSO solution for the TA98 strain, 20 µg/mL of 2-aminoanthracene DMSO solution for the TA100 strain each under the metabolism condition all as a positive control, and 588 µL of the test bacterial solution (a mixed solution of 498 µl of the test bacterial solution and 90 µL of S9 mix under the metabolism activating condition) were mixed, and this was shaking-cultured at 37° C. for 90 minutes. 460 µL of the bacterial solution exposed to the test substance was mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turner to yellow in 48 wells per dose is counted, and was assessed by comparing with a negative control group. (−) means that mutagenicity is negative and (+) is positive.

As a result, the present compounds did not show mutagenicity.

Test Example 10: BA Test

Materials and methods for studies an oral absorption
(1) Animal: mouse or SD rats were used.
(2) Breeding conditions: mouse or SD rats were allowed to freely take solid feed and sterilized tap water.
(3) Dose and grouping: orally or intravenously administered at a predetermined dose; grouping was as follows (Dose depends on the compound)
Oral administration: 1 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state.
(5) Administration method: in oral administration, forcedly administer into ventriculus with oralprobe; in intravenous administration, administer from caudal vein with a needle-equipped syringe.
(6) Evaluation items: blood was collected over time, and the plasma concentration of drug was measured by LC/MS/MS.
(7) Statistical analysis: regarding the transition of the plasma concentration, the area under the plasma concentration-time curve (AUC) was calculated by non-linear least squares program WinNonlin (Registered trademark), and the bioavailability (BA) was calculated from the AUCs of the oral administration group and intravenous administration group.

As a result, the present compounds showed good BA.

Experimental Example 11: hERG Test

For the purpose of assessing risk of an electrocardiogram QT interval prolongation, effects on delayed rectifier K+ current ($I_{Kr}$), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid, 4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using analysis software (DataXpress ver. 1, Molecular Devices Corporation). Further, the inhibition relative to the tail peak current before application of the test substance was calculated, and compared with the vehicle-applied group (0.1% dimethyl sulfoxide solution) to access influence of the test substance on $I_{Kr}$.

As a result, the risk of an electrocardiogram QT interval prolongation of the present compounds was low.

Test Example 12: Powder Solubility Test

Appropriate amounts of the test substances are put into appropriate containers. To the respective containers are added 200 µL of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µL of 20 mmol/L TCA (sodium taurocholate)/JP-2 fluid (TCA 1.08 g and JP-2 fluid to reach 100 µL). IN the case that all amount of the test compound is dissolved after the addition of the test fluid, the test compound is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

As a result, the present compounds showed good solubility.

Test Example 13: Photohemolysis Test

Aliquots of sheep red blood cells (RBC) suspension prepared with medium to make a 2.5 v/v % concentration are dispensed into microplates. The compound of the present invention was desolved with a vehicle to make target concentrations and then these solutions were immediately added (in concentrations of 0.0008 to 0.1 w/v %) into the microplates. The mixtures on the microplates were exposed to 10 J/cm2 of UV-irradiation (UV-A and UV-B, 290-400 nm) with a GL20SE lamp (SANKYO DENKI) and a FL20S-BLB lamp (Panasonic). After the UV-irradiation, the mixtures were centrifuged. Aliquots of supernatant were transferred to a microplate. Absorbance of the supernatants was measured at 540 nm and 630 nm for judgement of the potential of phototoxicity. In the study, two endpoints were evaluated in biomembrane impairment (% of photohemolysis index; PI) and hyperoxidation of lipid membrane (methemoglobin formation; met-Hb) with the absorbance at 540 nm and 630 nm, respectively. PI and met-Hb were assessed based on the negative criteria (−), PI<10% and changes in absorbance at 630 nm<0.05, respectively. All else was judged as positive (+).

(Result)

The compounds of I-001, I-003, I-012, I-027, I-041, I-043, I-048, I-085, I-112, I-122, I-156, I-164, I-176, I-181, I-189, I-190, I-197, I-220, I-244, I-257, I-258, I-260, I-262, I-267, I-270, I-278, I-292, I-293, I-303, I-304, I-305, I-306, I-307, I-308, and I-309 were (−).

Test Example 14: Resistant Virus Isolation Study

A certain concentration of the present invention compound or in combination with multiple drugs is added to the culture medium of HIV infected cells and continuously cultured in the presence of the drug. Cells or culture supernatant are collected periodically and mutation on the viral genome was determined compared with initial sequence.

INDUSTRIAL APPLICABILITY

The compound of the present invention is useful as a medicament used as a therapeutic or prophylactic agent for virus infectious disease such as AIDS, or an intermediate thereof.

The invention claimed is:

1. A compound of formula (I')

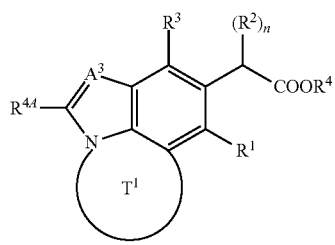

(I')

or a pharmaceutically acceptable salt thereof,
wherein
$A^3$ is $CR^{3A}$, or N;
$R^{3A}$ is hydrogen or halogen;
$R^{4A}$ is halogen, cyano, substituted or unsubstituted alkyl, substituted or unsubstituted alkynyl, or substituted or unsubstituted non-aromatic carbocyclyl, where a substituent or substituents of $R^{4A}$ are same or different 1 to 4 substituents selected from alkyloxy, hydroxy, halogen, haloalkyl, haloalkyloxy, amino, alkylamino, and aromatic carbocyclylalkyloxy;
a ring $T^1$ is substituted or unsubstituted nitrogen-containing non-aromatic heterocycle, where a substituent or substituents of $T^1$ ring are each independently oxo, hydroxy, halogen, amino, alkylamino, substituted or unsubstituted alkyl, substituted or unsubstituted alkenyl, substituted or unsubstituted alkynyl, —COR$^{a1}$, —SOR$^{a2}$, —SO$_2$R$^{a3}$, or —NR$^{a4}$R$^{a5}$ or same or different 1 to 4 substituents selected from R$^a$, R$^b$, and R$^c$, where a substituent or substituents of the substituent or substituents on the $T^1$ ring are same or different 1 to 4 substituents selected from alkyl, alkenyl, alkynyl, alkyloxy, hydroxy, alkyloxy alkyl, hydroxyalkyl, halogen, haloalkyl, haloalkyloxy, amino, alkylamino, dialkylamino, trialkylsilyl, non-aromatic carbocycle amino, substituted or unsubstituted phenyl where a substituent or substituents are selected from alkyl, alkyloxy, hydroxy, and halogen, substituted or unsubstituted phenyloxy where a substituent or substituents are selected from alkyl, alkyloxy, hydroxy, and halogen, substituted or unsubstituted benzyloxy where a substituent or substituents are selected from alkyl, alkyloxy, hydroxy, and halogen, substituted or unsubstituted aromatic heterocyclyl where a substituent or substituents are selected from alkyl, alkyloxy, hydroxy, and halogen, substituted or unsubstituted non-aromatic heterocyclyl where a substituent or substituents are selected from alkyl, alkyloxy, hydroxy, and halogen, and non-aromatic heterocycle amino;
$R^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —COR$^{a1}$, —SOR$^{a2}$, —SO$_2$R$^{a3}$, —CONR$^{a4}$R$^{a5}$, —CSNR$^{a4}$R$^{a5}$, —COCONR$^{a4}$R$^{a5}$, or —C(NR$^{a6}$)NR$^{a4}$R$^{a5}$, where a substituent or substituents of R$^a$ are same or different 1 to 4 substituents selected from alkyl, alkenyl, alkynyl, alkyloxy, hydroxy, alkyloxyalkyl, hydroxyalkyl, halogen, haloalkyl, haloalkyloxy, amino, alkylamino, dialkylamino, aminoalkyl, alkyloxyalkyl, alkylsulfonyl aminoalkyl, alkylcarbonylamino, alkylcarbonyl aminoalkyl, alkyloxyalkyloxycarbonylamino, alkylaminoalkyl, dialkyl aminoalkyl, amino alkyloxy, alkylamino alkyloxy, dialkylaminoalkyloxy, dialkylaminoalkyloxyalkyl, alkylcarbonylamino, carbamoyl, alkylcarbamoyl, dialkylcarbamoyl, benzyl, halogenated benzyl, aromatic carbocyclyl which is optionally substituted with halogen, alkyl, alkyloxy, cycloalkyl and/or haloalkyl, non-aromatic carbocyclyl which is optionally substituted with halogen, alkyl, alkyloxy, oxo and/or haloalkyl, aromatic heterocyclyl which is optionally substituted with halogen, alkyl, alkenyl, hydroxyalkyl, alkyloxy, cycloalkyl, non-aromatic carbocyclyl, non-aromatic heterocyclyl, and/or haloalkyl, non-aromatic heterocyclyl which is optionally substituted with halogen, alkyl, alkyloxy, oxo and/or haloalkyl, aromatic carbocyclylalkyl which is optionally substituted with halogen, alkyl, and/or haloalkyl, non-aromatic carbocycle which is optionally substituted with halogen, alkyl, and/or haloalkyl, aromatic heterocyclylalkyl which is optionally substituted with halogen, alkyl, and/or haloalkyl, non-aromatic heterocyclylalkyl which is optionally substituted with halogen, alkyl, and/or haloalkyl, non-aromatic heterocyclyl which is optionally substituted with alkylhalogen, non-aromatic carbocycle amino, non-aromatic heterocyclylalkyl which is optionally substituted with oxo, halogen, and/or alkyl, and trialkylsilyl;
$R^{a1}$, $R^{a2}$ and $R^{a3}$ are each independently alkyl optionally substituted with one or more groups selected from Substituent Group A, alkenyl, alkyloxy, amino, aromatic carbocyclyl, non-aromatic carbocyclyl optionally substituted with one or more groups selected from Substituent Group B, aromatic heterocyclyl optionally substituted with one or more groups selected from the Substituent Group B, or non-aromatic heterocyclyl;

the Substituent Group A is each independently halogen, amino, hydroxy, carboxy, oxo, monoalkyl amino, dialkyl amino, carbamoyl, monoalkyl carbamoyl, dialkyl carbamoyl, alkyloxy, haloalkyloxy, sulfamoyl, monoalkyl sulfamoyl, dialkyl sulfamoyl, alkyloxyalkyloxy, haloalkyloxyalkyloxy, alkylcarbonyl, alkylsulfonyl, alkylcarbonylamino, alkylcarbonyl(alkyl)amino, alkylsulfonylamino, alkylsulfonyl(alkyl)amino, trialkylsilyl, alkyl and/or halogeno aromatic carbocyclyl, non-aromatic carbocyclyl optionally substituted with oxo, alkyl and/or halogen, alkyl and/or halogeno aromatic heterocyclyl, non-aromatic heterocyclyl optionally substituted with oxo, alkyl and/or halogen, alkyl and/or halogeno aromatic carbocyclyloxy, non-aromatic carbocyclyloxy optionally substituted with oxo, alkyl and/or halogen, alkyl and/or halogeno aromatic heterocyclyloxy, or non-aromatic heterocyclyloxy optionally substituted with oxo, alkyl and/or halogen;

the Substituent Group B is each independently halogen, amino, hydroxy, carboxy, oxo, monoalkyl amino, dialkyl amino, carbamoyl, monoalkyl carbamoyl, dialkyl carbamoyl, alkyl, haloalkyl, alkyloxy, haloalkyloxy, hydroxyalkyl, amino alkyl, monoalkyl amino alkyl, dialkyl amino alkyl, sulfamoyl, monoalkyl sulfamoyl, dialkyl sulfamoyl, alkyl oxy alkyl, alkyl oxy alkyl oxy, haloalkyloxyalkyl, haloalkyloxyalkyloxy, alkylcarbonylamino, alkylcarbonyl(alkyl)amino, alkylsulfonylamino, alkylsulfonyl(alkyl)amino, alkyl and/or halogeno aromatic carbocyclyl, non-aromatic carbocyclyl optionally substituted with oxo, alkyl and/or halogen, alkyl and/or halogeno aromatic heterocyclyl, non-aromatic heterocyclyl optionally substituted with oxo, alkyl and/or halogen, alkyl and/or halogeno aromatic carbocyclyloxy, non-aromatic carbocyclyloxy optionally substituted with oxo, alkyl and/or halogen, alkyl and/or halogeno aromatic heterocyclyloxy, non-aromatic heterocyclyloxy optionally substituted with oxo, alkyl and/or halogen, alkyl and/or halogeno aromatic carbocyclylalkyl, non-aromatic carbocyclylalkyl optionally substituted with oxo, alkyl and/or halogen, alkyl and/or halogeno aromatic heterocyclylalkyl, non-aromatic heterocyclylalkyl optionally substituted with oxo, alkyl and/or halogen, alkyl and/or halogeno aromatic carbocyclylalkyloxy, non-aromatic carbocyclylalkyloxy optionally substituted with oxo, alkyl and/or halogen, alkyl and/or halogeno aromatic heterocyclylalkyloxy, or non-aromatic heterocyclylalkyloxy optionally substituted with oxo, alkyl and/or halogen;

$R^{a4}$ and $R^{a5}$ are each independently hydrogen, hydroxy, alkyl optionally substituted with one or more groups selected from the Substituent Group A, alkenyl, alkynyl, alkyloxy, aromatic carbocyclyl optionally substituted with amino or halogen, non-aromatic carbocyclyl optionally substituted with one or more groups selected from the Substituent Group B, aromatic heterocyclyl optionally substituted with one or more groups selected from the Substituent Group B, or non-aromatic heterocyclyl;

$R^{a6}$ is hydrogen, hydroxy, alkyl, alkenyl, alkynyl, alkyloxy, aromatic carbocyclyl, non-aromatic carbocyclyl, aromatic heterocyclyl, or non-aromatic heterocyclyl;

$R^b$ is each independently hydrogen, halogen, substituted or unsubstituted alkyl or aromatic carbocyclyl, where a substituent or substituents of $R^b$ are each independently halogen, hydroxy, alkyloxy, haloalkyl, haloalkyloxy, amino, alkylamino, carbamoyl, alkylcarbamoyl, phenyl, halogenated phenyl, aromatic carbocyclyl, non-aromatic carbocyclyl, aromatic heterocyclyl, or non-aromatic heterocyclyl;

$R^c$ is each independently hydrogen, halogen, substituted or unsubstituted alkyl or aromatic carbocyclyl, where a substituent or substituents of $R^c$ are each independently halogen, hydroxy, alkyloxy, haloalkyl, haloalkyloxy, amino, alkylamino, carbamoyl, alkyl carbamoyl, phenyl, halogenated phenyl, aromatic carbocyclyl, non-aromatic carbocyclyl, aromatic heterocyclyl, or non-aromatic heterocyclyl;

$R^b$ and $R^c$ on the same carbon atom may be taken together with the bonding carbon atom to form carbonyl, non-aromatic carbocycle, or non-aromatic heterocycle;

two $R^b$s on adjacent carbon atoms may be taken together with the each bonded carbon atoms to form substituted or unsubstituted monocyclic non-aromatic carbocycle or substituted or unsubstituted monocyclic non-aromatic heterocycle where a substituent or substituents of the monocyclic non-aromatic carbocycle or monocyclic non-aromatic heterocycle are each independently halogen, alkyl, hydroxy, alkyloxy, haloalkyl, or haloalkyloxy;

$R^a$ on a nitrogen atom and $R^b$ on a carbon atom which is adjacent to the nitrogen atom may be taken together with each bonded annular atoms to form substituted or unsubstituted monocyclic aromatic heterocycle or substituted or unsubstituted monocyclic non-aromatic heterocycle where a substituent or substituents of the monocyclic aromatic heterocycle or monocyclic non-aromatic heterocycle are each independently halogen, alkyl, alkyloxy, haloalkyl, haloalkyloxy, or oxo;

two $R^b$s on two carbon atoms which are not adjacent to each other may be taken together to form alkylene, alkylene containing one or more groups selected from —O—, —NR$^a$—, —S—, —CO—, —SO—, and —SO$_2$—, alkenylene, or alkenylene containing one or more groups selected from —O—, —NR$^a$—, —S—, —CO—, —SO—, and —SO$_2$—;

$R^a$ and $R^b$ on the nitrogen atom and carbon atom which are not adjacent may be taken together to form alkylene, alkylene containing one or more groups selected from —O—, —NR$^a$—, —S—, —CO—, —SO—, and —SO$_2$—, alkenylene, or alkenylene containing one or more groups selected from —O—, —NR$^a$—, —S—, —CO—, —SO—, and —SO$_2$—;

two $R^b$s on adjacent carbon atoms may be taken together to form a bond;

$R^a$ on a nitrogen atom and $R^b$ on a carbon atom which is adjacent to the nitrogen atom may be taken together to form a bond;

$R^1$ is hydrogen, halogen, cyano, or alkyl;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, or substituted or unsubstituted non-aromatic carbocyclyloxy, where a substituent or substituents of $R^2$ are each independently hydroxy, alkyloxy, halogen, haloalkyl, haloalkyloxy, or amino, alkylamino;

n is 1 or 2;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, where a substituent or substituents on rings are each independently $R^{31}$ to $R^{35}$ or oxo;

$R^{31}$, $R^{32}$, $R^{33}$, $R^{34}$ and $R^{35}$ are each independently hydrogen atom, halogen, hydroxy, amino, alkyl, cycloalkyl, alkenyl, alkynyl, haloalkyl, alkyloxy, alkenyloxy, alkynyloxy haloalkyl, haloalkyloxy, carboxy, carbamoyl, or alkylamino; and $R^4$ is hydrogen or a carboxyl protecting group;

the aromatic carbocyclyl is C6 to C14 monocyclic, or two or three ring;

the non-aromatic carbocyclyl is a cyclic saturated hydrocarbon group or a cyclic unsaturated non-aromatic hydrocarbon, which is C3 to C16 monocyclic or C8 to C13 polycyclic having two or more rings, wherein non-aromatic carbocyclyl which is polycyclic having two or more rings may be a fused cyclic group where a non-aromatic carbocyclyl, which is monocyclic or polycyclic having two or more rings, is fused with a ring of the aromatic carbocyclyl, or non-aromatic carbocyclyl, may be a group having a bridge or a group to form a spiro ring;

the aromatic heterocyclyl is a 5 to 26-membered aromatic cyclic group, which is monocyclic or polycyclic having two or more rings, containing one or more and same or different heteroatoms selected from O, S, and N;

the non-aromatic heterocyclyl is a 3 to 20-membered non-aromatic cyclic group, which is monocyclic or polycyclic having two or more rings, containing one or more and same or different heteroatoms selected from O, S and N, where non-aromatic heterocyclyl which is polycyclic having two or more rings may be a fused cyclic group wherein a non-aromatic heterocyclyl, which is monocyclic or polycyclic having two or more rings, is fused with a ring of the above aromatic carbocyclyl, non-aromatic carbocyclyl, and/or aromatic heterocyclyl, or may be rings bridged by alkylene, alkylene containing one or more groups selected from —O—, —$NR^a$—, —S—, —CO—, —SO—, and —$SO_2$—, alkenylene, alkenylene containing one or more groups selected from —O—, —$NR^a$—, —S—, —CO—, —SO—, and —$SO_2$—, alkynylene or alkynylene containing one or more groups selected from —O—, —$NR^a$—, —S—, —CO—, —SO—, and —$SO_2$—, and rings which are formed spiro ring with alkylene, alkylene containing one or more groups selected from —O—, —$NR^a$—, —S—, —CO—, —SO—, and —$SO_2$—, alkenylene, alkenylene containing one or more groups selected from —O—, —$NR^a$—, —S—, —CO—, —SO—, and —$SO_2$—, alkynylene or alkynylene containing one or more groups selected from —O—, —$NR^a$—, —S—, —CO—, —SO—, and —$SO_2$—; and the nitrogen-containing non-aromatic heterocycle is 5 to 20-membered cyclic non-aromatic ring, which is monocyclic or polycyclic having two or more rings, having at least one nitrogen atom as an annular atom and may have same or different one or more hetero atoms selected from oxygen atom, sulfur atom, and nitrogen atom in the ring, where nitrogen-containing non-aromatic heterocycle may be nitrogen-containing non-aromatic heterocycle which is monocyclic or polycyclic having two or more rings fused each ring in aromatic carbocycle, non-aromatic carbocycle, and/or aromatic heterocycle, or may be ring having a bridged structure or ring formed a spiro ring.

2. The compound or pharmaceutically acceptable salt according to claim 1, wherein a substructure

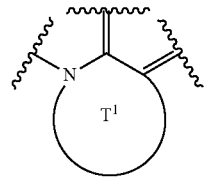 [SMILES: *NC(=*)C=*]

in the formula (I') is formula ($T^1$-I-1)

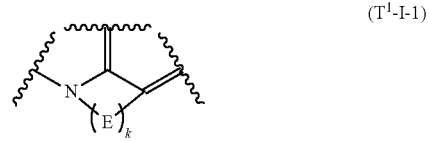

($T^1$-I-1)

where E is each independently —$NR^a$—, —O—, —S—, —$SO_2$—, —SO—, or —$CR^bR^c$—;

$R^a$ is each independently hydrogen, substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, —$COR^{a1}$, —$COOR^{a1}$, —$SOR^{a2}$, —$SO_2R^{a3}$, —$CONR^{a4}R^{a5}$, —$CSNR^{a4}R^{a5}$, —$COCONR^{a4}R^{a5}$, or —$C(NR^{a6})NR^{a4}R^{a5}$;

$R^{a1}$, $R^{a2}$, and $R^{a3}$ are each independently substituted or unsubstituted alkyl, alkenyl, alkyloxy, amino, aromatic carbocyclyl, substituted or unsubstituted non-aromatic carbocyclyl, substituted or unsubstituted aromatic heterocyclyl, or non-aromatic heterocyclyl;

$R^{a4}$ and $R^{a5}$ are each independently hydrogen, hydroxy, substituted or unsubstituted alkyl, alkenyl, alkynyl, alkyloxy, substituted or unsubstituted aromatic carbocyclyl, substituted or unsubstituted non-aromatic carbocyclyl, substituted or unsubstituted aromatic heterocyclyl, or non-aromatic heterocyclyl;

$R^{a6}$ is hydrogen, hydroxy, alkyl, alkenyl, alkynyl, alkyloxy, aromatic carbocyclyl, non-aromatic carbocyclyl, aromatic heterocyclyl, or non-aromatic heterocyclyl;

$R^b$ is each independently hydrogen, halogen, substituted or unsubstituted alkyl, or aromatic carbocyclyl;

$R^c$ is each independently hydrogen, halogen, substituted or unsubstituted alkyl, or aromatic carbocyclyl; or $R^b$ and $R^c$ on the same carbon atom may be taken together with the bonded carbon atom to form carbonyl, non-aromatic carbocycle, or non-aromatic heterocycle; and/or two $R^b$s on adjacent carbon atoms may be taken together with each bonded carbon atom to form substituted or unsubstituted monocyclic non-aromatic carbocycle or substituted or unsubstituted monocyclic non-aromatic heterocycle; or two $R^b$s on adjacent carbon atoms may be taken together to form a bond; and/or $R^a$ on a nitrogen atom and $R^b$ on a carbon atom which is adjacent to the nitrogen atom may be taken together with the nitrogen atom and the carbon atom to form substituted or unsubstituted monocyclic aromatic heterocycle or substituted or unsubstituted monocyclic non-aromatic heterocycle; or $R^a$ on a nitrogen atom and $R^b$ on a carbon atom which is adjacent to the nitrogen atom may be taken together to form a bond;

two $R^b$s on two carbon atoms which are not adjacent to each other may be taken together to form alkylene, alkylene containing one or more groups selected from —O—, —$NR^a$—, —S—, —CO—, —SO—, and —$SO_2$—, alkenylene, or alkenylene containing one or more groups selected from —O—, —$NR^a$—, —S—, —CO—, —SO—, and —$SO_2$—; or $R^a$ on a nitrogen atom and $R^b$ on a carbon atom which is not adjacent to the nitrogen atom may be taken together to form alkylene, alkylene containing one or more groups selected form —O—, —$NR^a$—, —S—, —CO—, —SO—, and —$SO_2$—, alkenylene, or alkenylene containing one or more groups selected from —O—, —$NR^a$—, —S—, —CO—, —SO—, —$SO_2$—; and k is an integer of 2 to 7.

3. The compound or pharmaceutically acceptable salt according to claim 2, wherein a substructure

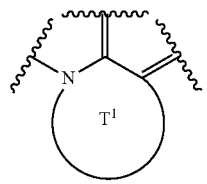 [SMILES: *NC(=*)C=*]

in the formula (I') is one of formula ($T^1$-3) and formula ($T^1$-4)

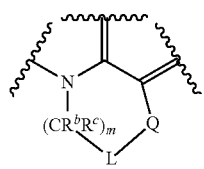
($T^1$-3)

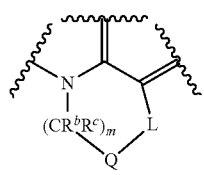
($T^1$-4)

where

Q is —$NR^a$—, —O—, —S— or —$CR^bR^c$—,

L is —$SO_2$—, —SO—, or —$CR^bR^c$—; and m is an integer of 0 to 5.

4. The compound or pharmaceutically acceptable salt according to claim 3, wherein the formula (I') is formula (I-1-1) or (I-2-1)

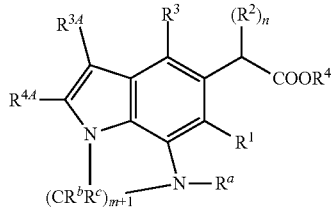
(I-1-1)

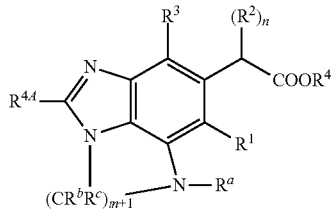
(I-2-1)

where $R^{3A}$ is hydrogen.

5. The compound or pharmaceutically acceptable salt according to claim 1, wherein $R^1$ is alkyl, cyano, or halogen.

6. The compound or pharmaceutically acceptable salt according to claim 1, wherein n is 1; $R^2$ is alkyloxy.

7. The compound or pharmaceutically acceptable salt according to claim 1, wherein $R^4$ is hydrogen.

8. The compound or pharmaceutically acceptable salt according to claim 1, wherein $R^1$ is alkyl or halogen; n is 1; $R^2$ is alkyloxy; and $R^4$ is hydrogen.

9. The compound or pharmaceutically acceptable salt according to claim 2, wherein $R^1$ is alkyl or halogen; n is 1; $R^2$ is alkyloxy; $R^4$ is hydrogen; $R^3$ is substituted or unsubstituted aromatic carbocyclyl, or substituted or unsubstituted non-aromatic heterocyclyl; $R^a$ is hydrogen, substituted or unsubstituted alkyl, —$COR^{a1}$, —$CONR^{a4}R^{a5}$, —$SO_2R^{a3}$, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; $R^b$ is each independently hydrogen, halogen, substituted or unsubstituted alkyl, or aromatic carbocyclyl; $R^c$ is each independently hydrogen, halogen, substituted or unsubstituted alkyl, or aromatic carbocyclyl; or $R^a$ on a nitrogen atom and $R^b$ on a carbon atom which is adjacent to the nitrogen atom may be taken together with the nitrogen atom and the carbon atom to form substituted or unsubstituted monocyclic aromatic heterocycle or substituted or unsubstituted monocyclic non-aromatic heterocycle, or two $R^b$s on adjacent carbon atoms may be taken together with each bonded carbon atom to form substituted or unsubstituted monocyclic non-aromatic carbocycle or substituted or unsubstituted monocyclic non-aromatic heterocycle; and k is an integer of 3 to 5.

10. The compound or pharmaceutically acceptable salt according to claim 3, wherein $R^a$ is hydrogen, substituted or unsubstituted alkyl, —$COR^{a1}$, —$CONR^{a4}R^{a5}$, or —$SO_2R^{a3}$; $R^b$ is each independently hydrogen, halogen, or substituted or unsubstituted alkyl; $R^c$ is each independently hydrogen, halogen, or substituted or unsubstituted alkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

11. The compound or pharmaceutically acceptable salt according to claim 3, wherein m is an integer of 1 to 3; $R^1$ is alkyl or halogen; n is 1; $R^2$ is alkyloxy; $R^4$ is hydrogen; $R^3$ is substituted or unsubstituted aromatic carbocyclyl or substituted or unsubstituted non-aromatic heterocyclyl; $R^a$ on a nitrogen atom and $R^b$ on a carbon atom which is adjacent to the nitrogen atom are taken together with each bonded atom to form substituted or unsubstituted monocyclic aromatic heterocycle or substituted or unsubstituted monocyclic non-aromatic heterocycle, two $R^b$ on adjacent carbon atoms are taken together with each bonded carbon atom to form substituted or unsubstituted monocyclic non-aromatic carbocycle or substituted or unsubstituted monocyclic non-aromatic heterocycle, or $R^b$ and $R^c$ on the same carbon atom are taken together with the bonded carbon atom to form carbonyl, non-aromatic carbocycle or non-aromatic heterocycle.

12. The compound or pharmaceutically acceptable salt according to claim 3, wherein $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl or halogen; n is 1; $R^2$ is alkyloxy; $R^3$ is substituted or unsubstituted aromatic carbocyclyl or substituted or unsubstituted non-aromatic heterocyclyl; and $R^4$ is hydrogen.

13. The compound or pharmaceutically acceptable salt according to claim 3, wherein $R^{4A}$ is halogen, cyano, alkyl, or haloalkyl; $R^a$ is hydrogen, substituted or unsubstituted alkyl, —$COR^{a1}$, —$CONR^{a4}R^{a5}$, —$SO_2R^{a3}$; $R^b$s are each independently hydrogen, halogen, or substituted or unsubstituted alkyl; $R^c$s are each independently hydrogen, halogen, or substituted or unsubstituted alkyl; m is an integer of 1 to 3; $R^1$ is alkyl or halogen; n is 1; $R^2$ is alkyloxy; $R^3$ is substituted or unsubstituted aromatic carbocyclyl or substituted or unsubstituted non-aromatic heterocyclyl; and $R^4$ is hydrogen.

14. The compound or pharmaceutically acceptable salt according to claim 3, wherein $R^{4A}$ is halogen, cyano, alkyl, or haloalkyl; $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

15. The compound or pharmaceutically acceptable salt according to claim 1, wherein the formula (I') is one of

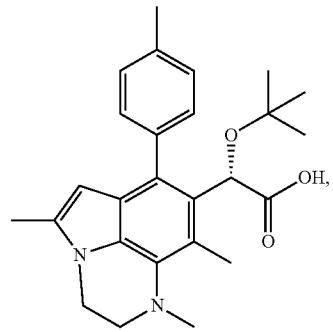

I-001

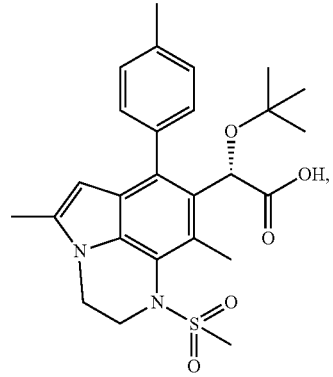

I-003

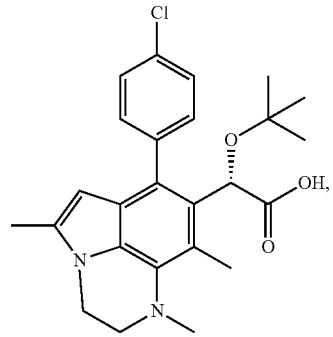

I-012

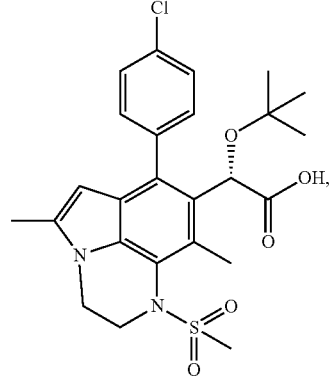

I-019

-continued
I-026
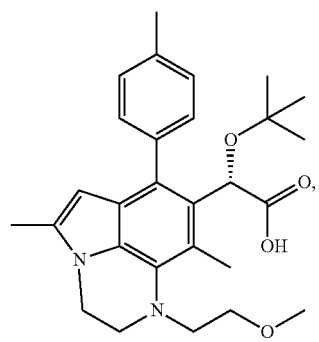
I-027
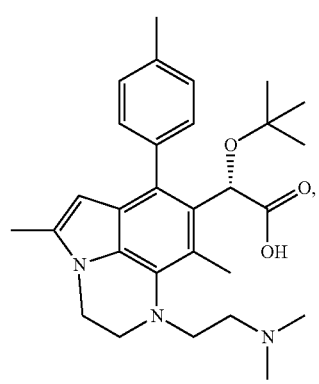
I-041
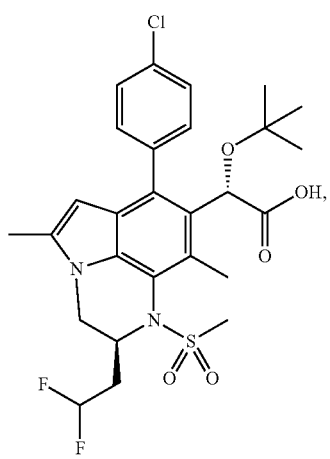
I-043
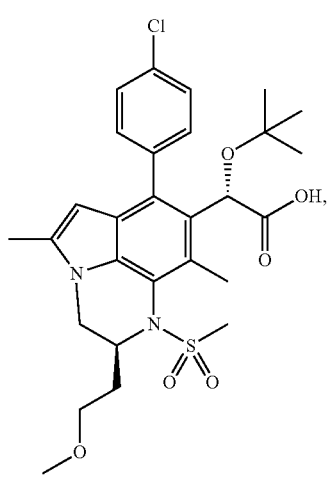
-continued
I-048
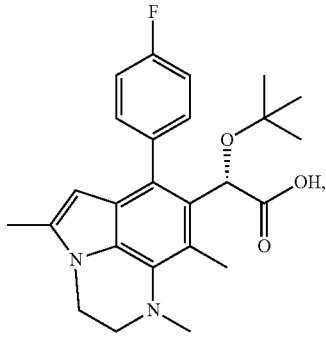
I-085
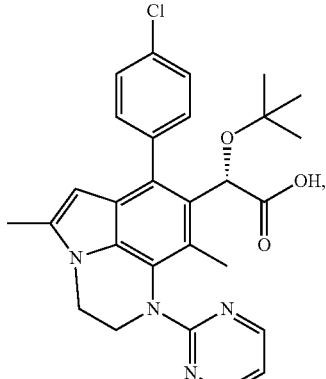
I-112
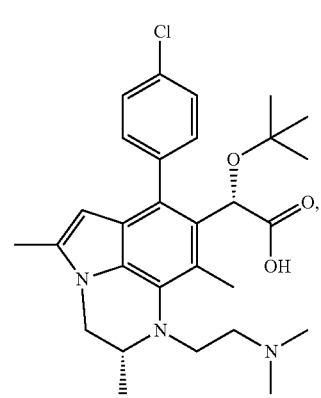
I-122
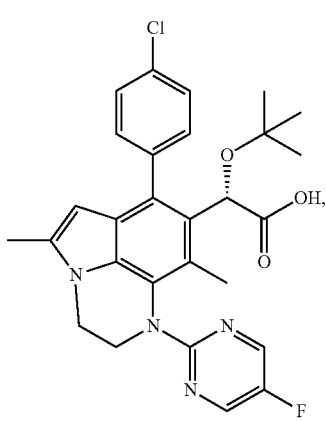

I-156
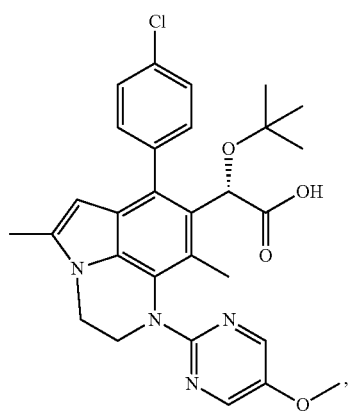
I-157
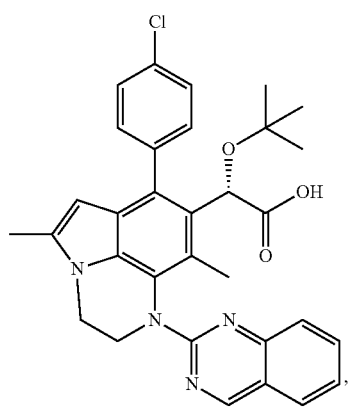
I-164
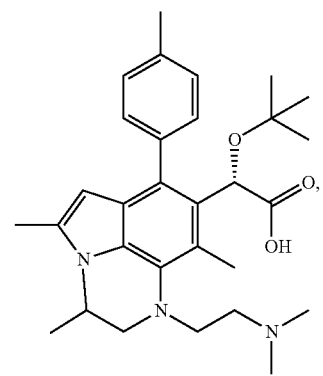
I-176
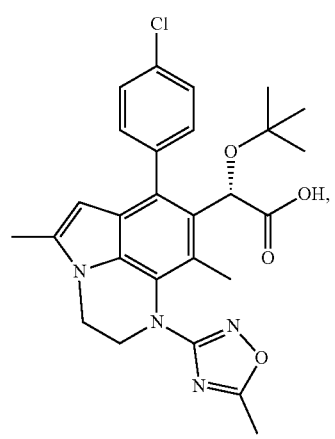
I-181
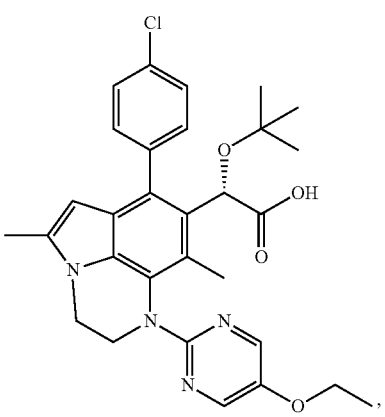
I-187
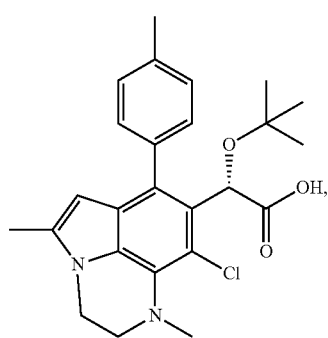
I-189
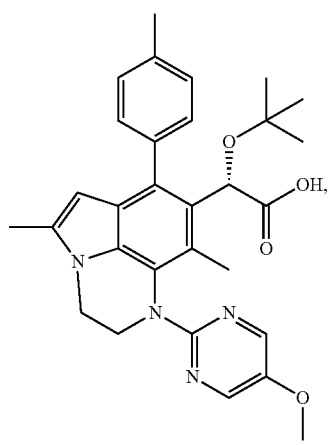
I-190
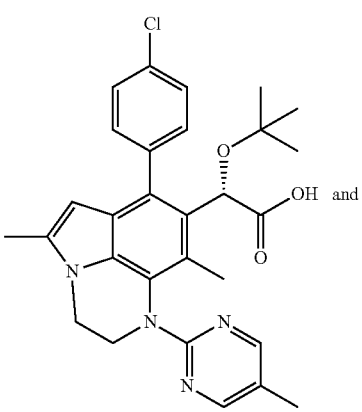
and I-197
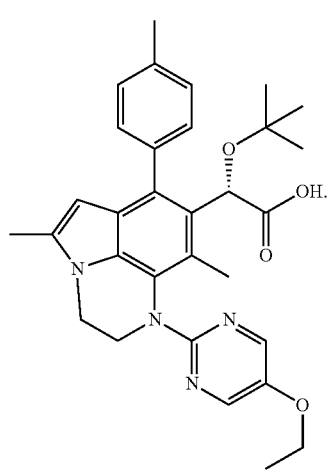
16. The compound or pharmaceutically acceptable salt according to claim 1, wherein the formula (I') is one of
I-220
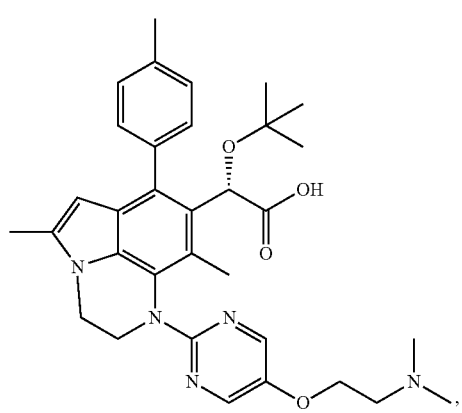
I-244
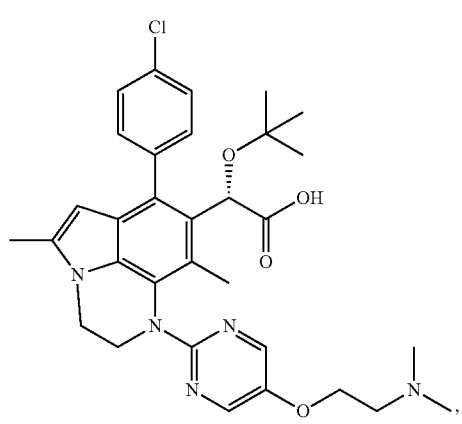
I-257
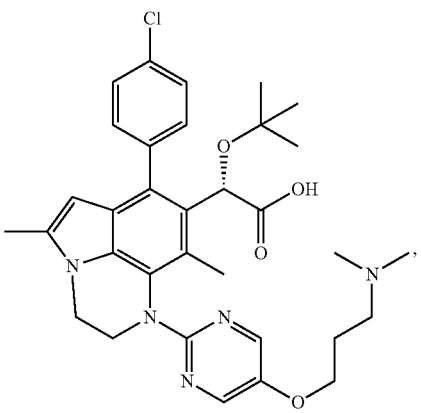
I-258
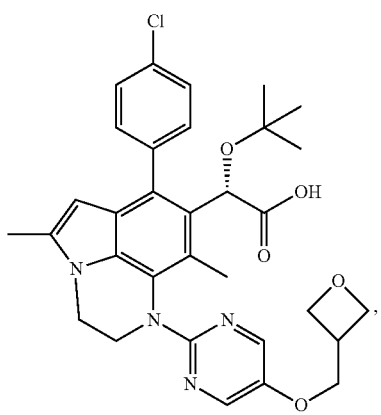
I-260
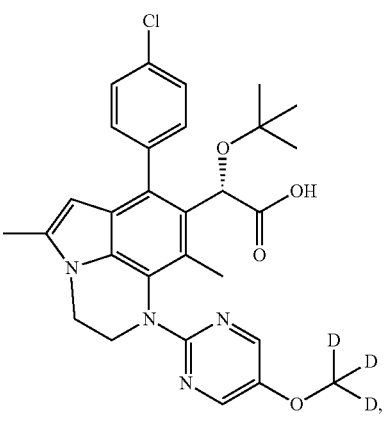
I-262
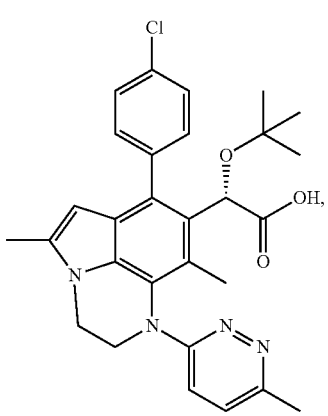

I-267
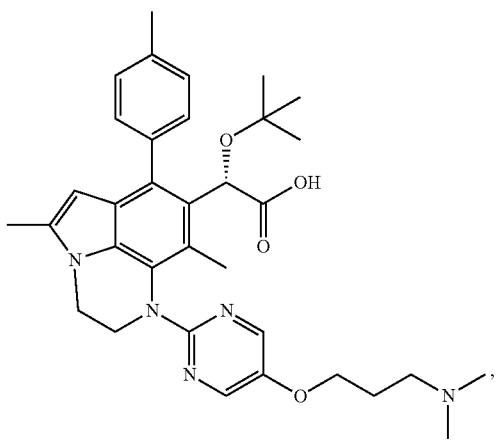
I-270
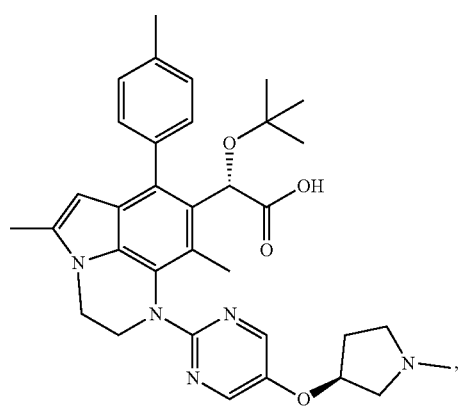
I-278
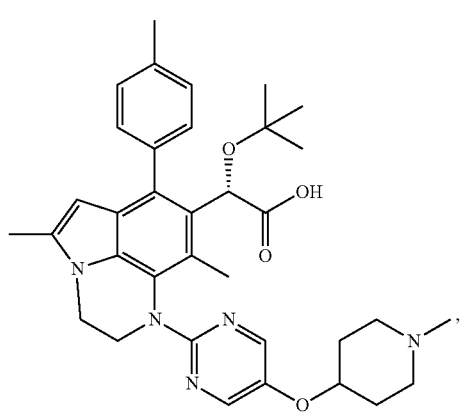
I-292
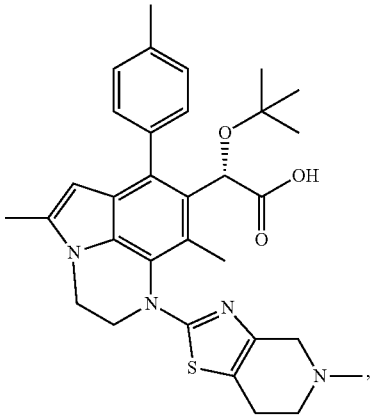
I-293
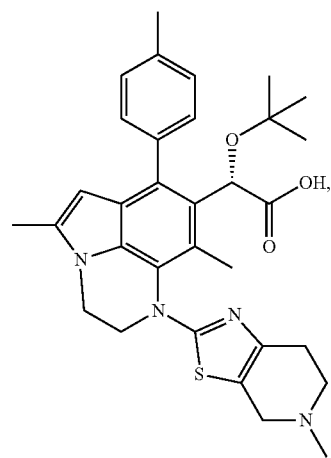
I-303
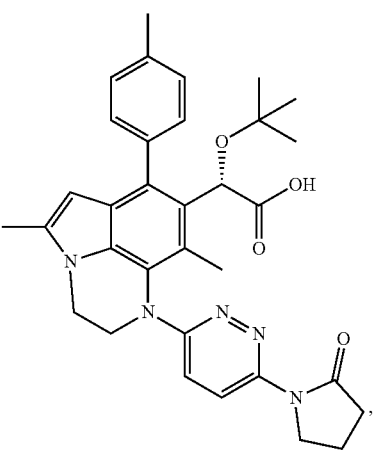

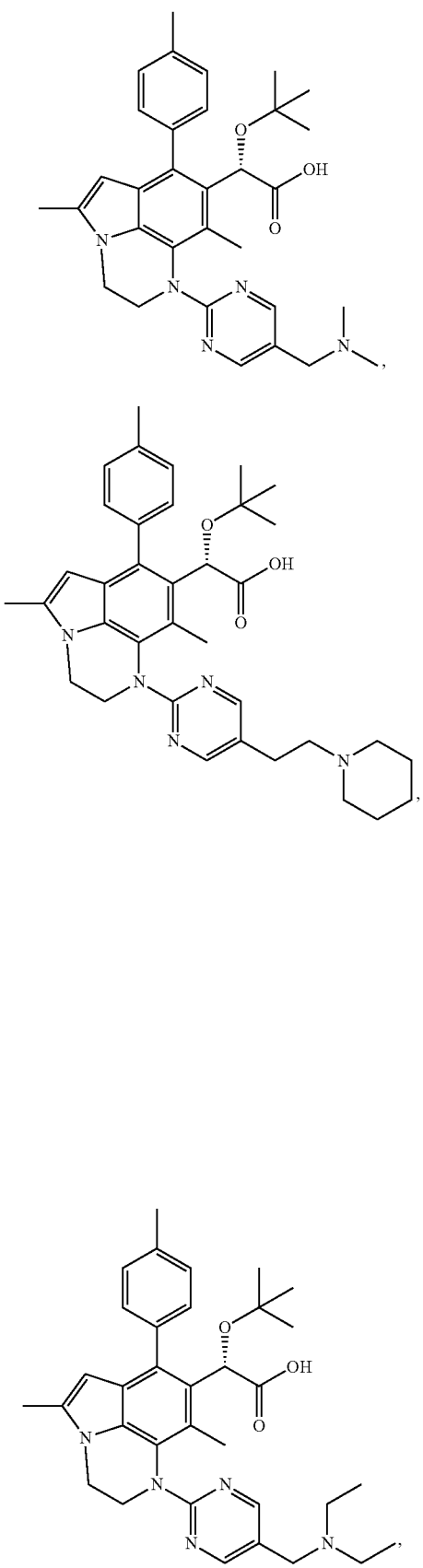

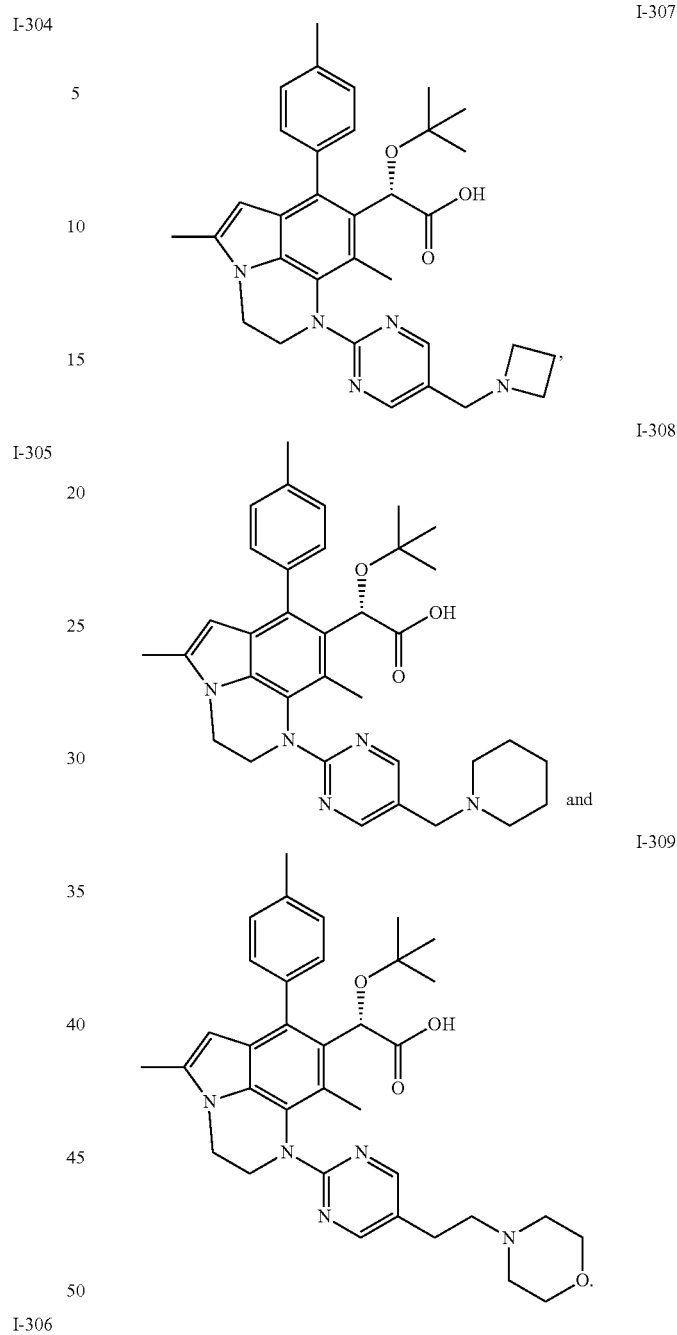

17. A pharmaceutical composition, comprising:
the compound or pharmaceutically acceptable salt according to claim 1 in an effective amount; and
a pharmaceutically acceptable carrier.

18. The pharmaceutical composition according to claim 17, wherein the effective amount of the compound or pharmaceutically acceptable salt according to claim 1 is an effective amount having anti-virus activity.

19. The pharmaceutical composition according to claim 17, wherein the effective amount of the compound or pharmaceutically acceptable salt according to claim 1 is an effective amount having anti-HIV activity.

20. A method of treating or preventing a HIV infectious disease, comprising:

administering the compound or pharmaceutically acceptable salt according to claim 1 to a patient in need thereof.

21. A method of treating or preventing a HIV infectious disease, comprising:
administering the compound or pharmaceutically acceptable salt according to claim 2 to a patient in need thereof.

22. A method of treating or preventing a HIV infectious disease, comprising:
administering the compound or pharmaceutically acceptable salt according to claim 3 to a patient in need thereof.

23. A method of treating or preventing a HIV infectious disease, comprising:
administering the compound or pharmaceutically acceptable salt according to claim 4 to a patient in need thereof.

24. The compound or pharmaceutically acceptable salt according to claim 1, wherein the formula (I') is formula (I-1-1)

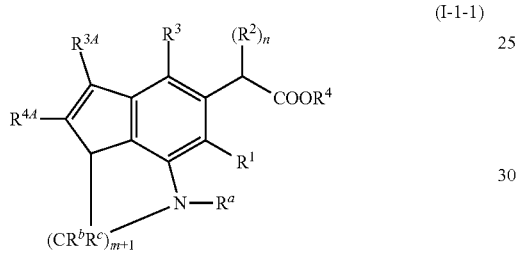

where $R^{3A}$ is hydrogen; $R^{4A}$ is halogen, cyano, alkyl, or haloalkyl; $R^a$ is hydrogen, substituted or unsubstituted alkyl, —$COR^{a1}$, —$CONR^{a4}R^{a5}$, —$SO_2R^{a3}$; $R^b$s are each independently hydrogen, halogen, or substituted or unsubstituted alkyl; $R^c$s are each independently hydrogen, halogen, or substituted or unsubstituted alkyl; m is an integer of 1 to 3; $R^1$ is alkyl or halogen; n is 1; $R^2$ is alkyloxy; $R^3$ is substituted or unsubstituted aromatic carbocyclyl or substituted or unsubstituted non-aromatic heterocyclyl; and $R^4$ is hydrogen.

25. The compound or pharmaceutically acceptable salt according to claim 1, wherein the formula (I') is formula (I-1-1)

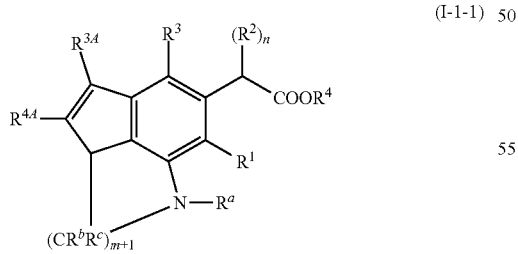

where $R^{3A}$ is hydrogen; $R^{4A}$ is halogen, cyano, alkyl, or haloalkyl; $R^a$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, or substituted or unsubstituted non-aromatic heterocyclylalkyl; m is an integer of 1 to 3; $R^1$ is alkyl or halogen; n is 1; $R^2$ is alkyloxy; $R^3$ is substituted or unsubstituted aromatic carbocyclyl, or substituted or unsubstituted non-aromatic heterocyclyl; and $R^4$ is hydrogen.

26. A compound of formula (I-001)

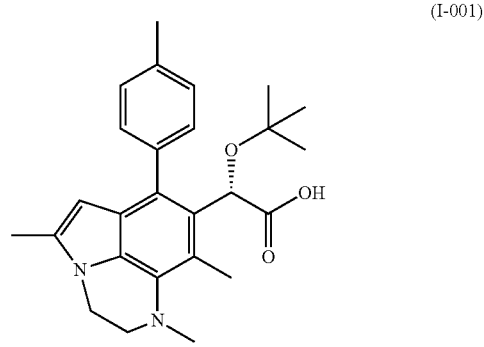 [SMILES: Cc1ccc(-c2c([C@H](OC(C)(C)C)C(=O)O)c(C)c3c4c2cc(C)n4CCN3C)cc1]

or a pharmaceutically acceptable salt thereof.

27. A compound of formula (I-027)

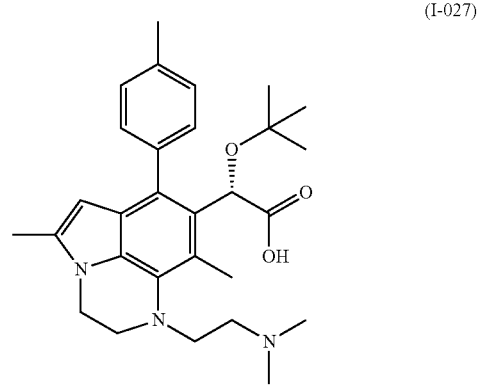

or a pharmaceutically acceptable salt thereof.

28. A compound of formula (I-220)

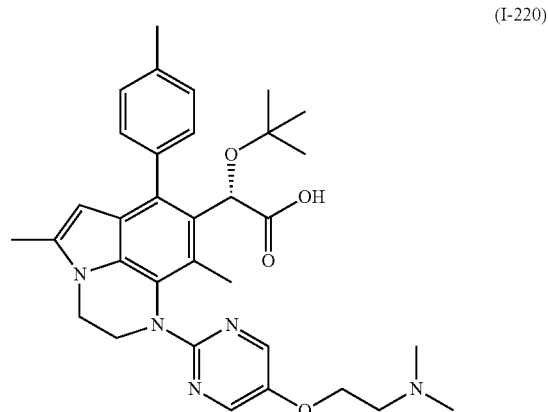

or a pharmaceutically acceptable salt thereof.

29. A compound of formula (I-292)

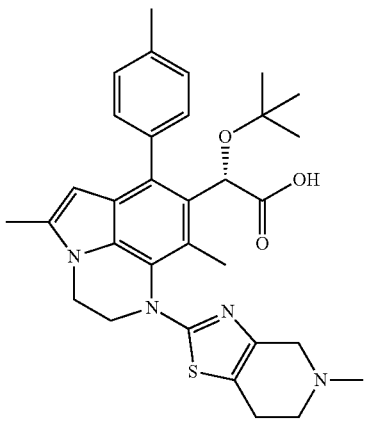
(I-292)

or a pharmaceutically acceptable salt thereof.

30. A compound of formula (I-304)

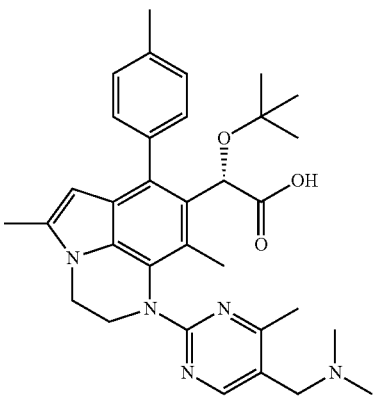
(I-304)

or a pharmaceutically acceptable salt thereof.

31. A method of treating or preventing a HIV infectious disease, comprising:
administering the compound or pharmaceutically acceptable salt according to claim 24 to a patient in need thereof.

32. A method of treating or preventing a HIV infectious disease, comprising:
administering the compound or pharmaceutically acceptable salt according to claim 25 to a patient in need thereof.

33. A method of treating or preventing a HIV infectious disease, comprising:
administering the compound or pharmaceutically acceptable salt according to claim 26 to a patient in need thereof.

34. A method of treating or preventing a HIV infectious disease, comprising:
administering the compound or pharmaceutically acceptable salt according to claim 27 to a patient in need thereof.

35. A method of treating or preventing a HIV infectious disease, comprising:
administering the compound or pharmaceutically acceptable salt according to claim 28 to a patient in need thereof.

36. A method of treating or preventing a HIV infectious disease, comprising:
administering the compound or pharmaceutically acceptable salt according to claim 29 to a patient in need thereof.

37. A method of treating or preventing a HIV infectious disease, comprising:
administering the compound or pharmaceutically acceptable salt according to claim 30 to a patient in need thereof.

* * * * *